United States Patent
Itai et al.

(10) Patent No.: US 8,097,610 B2
(45) Date of Patent: Jan. 17, 2012

(54) DERIVATIVE HAVING PPAR AGONISTIC ACTIVITY

(75) Inventors: Akiko Itai, Bunkyo-ku (JP); Susumu Muto, Bunkyo-ku (JP); Ryuko Tokuyama, Bunkyo-ku (JP); Hiroshi Fukasawa, Bunkyo-ku (JP); Takafumi Ohara, Osaka (JP); Terukazu Kato, Osaka (JP)

(73) Assignees: Shionogi & Co., Ltd., Osaka (JP); Institute of Medicinal Molecular Design, Inc., Tokyo (JP)

( * ) Notice: Subject to any disclaimer, the term of this patent is extended or adjusted under 35 U.S.C. 154(b) by 917 days.

(21) Appl. No.: 11/990,977

(22) PCT Filed: Aug. 24, 2006

(86) PCT No.: PCT/JP2006/316564
§ 371 (c)(1), (2), (4) Date: Apr. 8, 2008

(87) PCT Pub. No.: WO2007/023882
PCT Pub. Date: Mar. 1, 2007

(65) Prior Publication Data
US 2009/0286974 A1    Nov. 19, 2009

(30) Foreign Application Priority Data

Aug. 26, 2005 (JP) ................. 2005-246297
Jun. 2, 2006 (JP) ................. 2006-154607

(51) Int. Cl.
*A61K 31/55* (2006.01)
*A61K 31/5377* (2006.01)
*A61K 31/4535* (2006.01)
*C07D 401/04* (2006.01)
*C07D 413/14* (2006.01)
*C07D 417/04* (2006.01)

(52) U.S. Cl. ............ 514/217.04; 514/233.8; 514/321; 540/597; 544/129; 546/198

(58) Field of Classification Search ............ 540/575; 544/368, 353, 231
See application file for complete search history.

(56) References Cited

U.S. PATENT DOCUMENTS

| | | |
|---|---|---|
| 5,786,479 A | 7/1998 | Hashiba et al. |
| 5,789,409 A | 8/1998 | Ogata et al. |
| 6,121,288 A | 9/2000 | Masui et al. |
| 6,300,364 B1 | 10/2001 | Shimokawa et al. |
| 2003/0109533 A1 | 6/2003 | Lavielle et al. |
| 2004/0077689 A1 | 4/2004 | Sugiyama et al. |
| 2004/0110945 A1 | 6/2004 | Nakayama et al. |
| 2004/0214870 A1 | 10/2004 | Xin et al. |
| 2004/0224997 A1 | 11/2004 | Smith et al. |
| 2005/0239854 A1 | 10/2005 | Sugiyama et al. |
| 2006/0100261 A1 | 5/2006 | Hamamura et al. |
| 2006/0154944 A1 | 7/2006 | Ohmoto et al. |
| 2007/0078120 A1 | 4/2007 | Ban et al. |
| 2007/0105959 A1 | 5/2007 | Kusuda et al. |
| 2007/0135402 A1 | 6/2007 | Habashita et al. |
| 2007/0190079 A1 | 8/2007 | Shiau et al. |

FOREIGN PATENT DOCUMENTS

| | | |
|---|---|---|
| EP | 0 398 425 | 3/1994 |
| EP | 1 029 872 | 8/2000 |
| JP | 3-47174 | 2/1991 |
| JP | 5-345765 | 12/1993 |
| JP | 9-208570 | 8/1997 |
| JP | 2003/64055 | 3/2003 |
| JP | 2005-119998 | 5/2005 |
| WO | 95/00510 | 1/1995 |
| WO | 97/31907 | 9/1997 |
| WO | 98/00134 | 1/1998 |
| WO | 98/00401 | 1/1998 |
| WO | 99/50247 | 10/1999 |
| WO | 00/06558 | 2/2000 |
| WO | 01/05763 | 1/2001 |
| WO | 01/66098 | 9/2001 |
| WO | 02/46158 | 6/2002 |
| WO | 03/088908 | 10/2003 |
| WO | 2004/000789 | 12/2003 |
| WO | 2004/033427 | 4/2004 |
| WO | 2004/054974 | 7/2004 |
| WO | 2004/063166 | 7/2004 |
| WO | 2004/091604 | 10/2004 |
| WO | 2004/092117 | 10/2004 |
| WO | 2004/099170 | 11/2004 |
| WO | 2005/018642 | 3/2005 |

(Continued)

OTHER PUBLICATIONS

Vippagunta et al., Crystalline solids, 2001, Advanced Drug Delivery Reviews, 48, pp. 3 and 18.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Maria L. López-Rodriguez et al., "*Benzimidazole derivatives. Part 5: Design and synthesis of new benzimidazole-arylpiperazine derivatives acting as mixed 5-HT$_{1A}$/5-HT$_3$ ligands*", Bioorganic & Medicinal Chemistry, vol. 12, pp. 5181-5191 (2004).
Maria L. López-Rodriguez et al., "*Design and Synthesis of New Benzimidazole-Arylpiperazine Derivatives Acting as Mixed 5-HT$_{1A}$/5-HT$_3$ Ligands*", Bioorganic & Medicinal Chemistry Letters, vol. 13, pp. 3177-3180 (2003).

(Continued)

*Primary Examiner* — Kamal Saeed
*Assistant Examiner* — Kristin Bianchi
(74) *Attorney, Agent, or Firm* — Wendroth, Lind & Ponack, L.L.P.

(57) ABSTRACT

A compound of the formula (I):

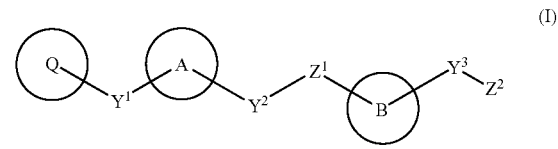

or a pharmaceutically acceptable salt thereof.

14 Claims, No Drawings

FOREIGN PATENT DOCUMENTS

| | | |
|---|---|---|
| WO | 2005/019151 | 3/2005 |
| WO | 2005/086661 | 9/2005 |
| WO | 2005/115983 | 12/2005 |
| WO | 2006/024517 | 3/2006 |
| WO | 2006/060461 | 6/2006 |
| WO | 2006/130986 | 12/2006 |
| WO | 2007/030567 | 3/2007 |

OTHER PUBLICATIONS

Frank J. Urban et al., "*A Novel Synthesis of the Antipsychotic Agent Ziprasidone*", Synthetic Communications, vol. 26(8), pp. 1629-1638 (1996).

Jan H. Van Maarseveen et al., "*Design and Synthesis of an Orally Active GPIIb/IIIa Antagonist Based on a Phenylpiperazine Scaffold*", Bioorganic & Medicinal Chemistry Letters, vol. 8, pp. 1531-1536 (1998).

Barry G. Shearer et al., "*Recent Advances in Peroxisome Proliferator-Activated Receptor Science*", Current Medicinal Chemistry, vol. 10, pp. 267-280 (2003).

Karl D. Hargrave et al., "*N-(4-Substituted-thiazolyl)oxamic Acid Derivatives, a New Series of Potent, Orally Active Antiallergy Agents*", J. Med. Chem., vol. 26, pp. 1158-1163 (1983).

* cited by examiner

DERIVATIVE HAVING PPAR AGONISTIC ACTIVITY

FIELD OF THE INVENTION

The present invention relates to compounds which have an agonistic activity of a peroxisome proliferator-activated receptor (referred to below as PPAR) and which are useful as a medicine.

BACKGROUND ART

Peroxisome which is an intracellular granule is a small granule in the cytoplasm containing catalase and a group of oxidases. Peroxisome proliferators which proliferate peroxisome are thought as important controlling elements of lipid metabolism in the body. A nuclear receptor, PPAR, which is activated by the peroxisome proliferator has turned out to be a multifunctional receptor concerning incretion, metabolism, inflammation or the like. Therefore, the ligand is thought to be able to apply as various medicines and the number of researches is recently increasing.

The subtype genes of PPARs are found from various animal organs and formed a family. In mammals, PPARs are classified into three subtypes of PPARα, PPARδ (also referred to as PPARγ and PPARγ.

The drugs of the fibrate group used as an antihyperlipemic drug are thought to show the activity by PPARα activation-mediated transcriptional enhancement of the gene group which improves serum lipid. Additionally, it is suggested that PPARα may relate to bone metabolism and expression of the activity of non-steroidal anti-inflammatory drugs.

The thiazolidindion compounds, which are improving drugs for insulin resistance, are ligands of PPARγ. As these compounds show hypoglycemic action, hypolipidemic action, adipocyte differentiation-inducing action or the like, PPARγ agonists are expected to develop as therapeutic agents for diabetes, hyperlipidemia, obesity or the like. Furthermore, PPARγ agonists are expected to be therapeutic agents for chronic pancreatitis, inflammatory colitis, glomerulosclerosis, Alzheimer's disease, psoriasis, parkinsonism, Basedow's disease, chronic rheumatoid arthritis, cancer (breast cancer, colonic cancer, prostatic cancer or the like), sterility or the like.

It was reported that transgenic mice in which PPARδ is overexpressed specifically in adipocyte were difficult to get fat or the like. Therefore, PPARδ agonists can be used as an antiobesity or antidiabetic drug. Additionally, PPARδ agonists are suggested the possibility as therapeutic agents for colonic cancer, osteoporosis, sterility, psoriasis, multiple sclerosis or the like.

Based on these findings, PPAR agonists are expected to be useful for treatment or prevention of hyperlipidemia, diabetes, hyperglycosemia, insulin resistance, obesity, arteriosclerosis, atherosclerosis, hypertension, syndrome X, inflammation, allergic disease (inflammatory colitis, chronic rheumatoid arthritis, chronic pancreatitis, multiple sclerosis, glomerulosclerosis, psoriasis or the like), osteoporosis, sterility, cancer, Alzheimer's disease, parkinsonism, Basedow's disease or the like (Non-Patent Document 1).

Patent Document 1 disclosed benzothiazole derivatives containing piperazine which can be used as antiobesity drugs or the like. However, it did not disclose the PPAR agonistic activity at all.

Patent Document 2 disclosed benzothiazole or benzoxazole derivatives containing piperazine or piperidine as antiviral drugs. However, it did not disclose the PPAR agonistic activity at all.

Patent Document 3 disclosed benzoxazole derivatives containing pyrrolidine as PPARγ agonists. However, it did not disclose a compound containing piperazine or piperidine.

Patent Document 4 and 5 disclosed that compounds containing piperazine have antiallergic action or the like. Non-patent Document 2 disclosed compounds containing piperazine as glycoprotein IIb/IIIa antagonists. Patent Document 6 disclosed compounds containing piperazine as CB1 antagonists. However, they did not disclose the PPAR agonistic activity at all.

Patent Document 7 and 8 disclosed compounds containing piperazine or piperidine as PPAR modulators. However, these compounds are characterized by having a sulfonyl group between piperazine and a phenyl group as a linker.

[Patent Document 1] WO 00/006558
[Patent Document 2] EP 398425
[Patent Document 3] WO 97/31907
[Patent Document 4] JP1992-345765
[Patent Document 5] JP1997-208570
[Patent Document 6] WO 2006/060461
[Patent Document 7] WO 2004/092117
[Patent Document 8] WO 2005/115983
[Non-patent Document 1]
Current Medicinal Chemistry, 2003, Vol. 10, p.p. 267-280
[Non-patent Document 2]
Bioorganic & Medical Chemistry Letters, 1998, Vol. 8, p.p. 1531-1536

DISCLOSURE OF INVENTION

Problems to be solved by the Invention

The objection of the present invention is to provide good PPAR agonists.

Means for Solving the Problem

The present inventors have intensively studied to synthesize excellent PPAR agonists and carried out search for compounds having desired pharmacological activities by using computerized molecular design technology as a means to discover candidate compounds. The inventors carried out an automatic search program of a compound from a three-dimensional compound database based on the three-dimensional structure of peroxisome proliferator-activated receptors whose structures are registered in PDB (Protein Data Bank), and by virtual screenings, they selected compounds having potentials as PPAR agonists from compounds registered in databases of commercial compounds. The inventors synthesized a lot of derivatives on the basis of the skeletons of the selected compounds and carried out tests of the synthesized derivatives such as assays for transcriptional activation of PPAR δ, α and ≡, assays for cell toxicity and the like. The inventors selected compounds having strong and desired pharmacological activities, and further prepared their derivatives to achieve the present invention. Additionally, the inventors found that compounds of the present invention have PPAR transcriptional activity, less inhibition of drug-metabolizing enzymes and good metabolic stability and solubility. Furthermore, compounds of the present invention are less toxic and thought to be safe enough for pharmaceutical use.

The present invention includes the followings.
(1) A compound of the formula (I):

[Formula 1]

$$Q-Y^1-A-Y^2-Z^1-B-Y^3-Z^2 \quad (I)$$

a pharmaceutically acceptable salt or solvate thereof,
wherein
Ring Q is optionally substituted monocyclic aryl, optionally substituted monocyclic heteroaryl, optionally substituted fused aryl or optionally substituted fused heteroaryl provided that Ring Q is not unsubstituted 11H-dibenz[b,e]-azepine-6-yl, $Y^1$ is a bond, —$NR^6$— or —$NR^6$—CO— wherein $R^6$ is hydrogen or optionally substituted lower alkyl, provided that $Y^1$ is —$NR^6$—CO— when Ring Q is unsubstituted monocyclic aryl, and Ring Q is phenyl substituted with alkyl halide when Ring Q is monocyclic aryl and $Y^1$ is a bond, Ring A is optionally substituted nonaromatic heterocyclediyl, provided that Ring Q binds with a nitrogen atom of Ring A when $Y^1$ is a bond, a group of the formula: —$Y^2Z^1$— is a group of the formula:

[Formula 2]

provided that a group of the formula: —$Y^2Z^1$— is not —$SO_2$— and, a group of the formula: —$Y^2Z^1$— is not —$CH_2$—$CH_2$—O— or —O— when Ring Q is unsubstituted benzothiazole-2-yl or unsubstituted benzoxazole-2-yl, $R^7$ are each independently hydrogen, optionally substituted lower alkyl or optionally substituted cycloalkyl, $R^8$ and $R^9$ are each independently hydrogen or optionally substituted lower alkyl, n is an integer between 0 and 3, $Z^1$ is a bond, —O—, —S— or —$NR^9$— wherein $R^9$ is hydrogen, optionally substituted lower alkyl, optionally substituted acyl, optionally substituted lower alkylsulfonyl or optionally substituted arylsulfonyl, Ring B is optionally substituted aromatic carbocyclediyl or optionally substituted aromatic heterocyclediyl, $Y^3$ is a bond, optionally substituted lower alkylene optionally intervened by —O—, cycloalkylene optionally intervened by —O— or optionally substituted lower alkenylene, $Z^2$ is $COOR^3$, $C(=NR^1)NR^{14}OR^{15}$, CONHCN or a group of the formula:

[Formula 3]

$R^3$, $R^{14}$ and $R^{15}$ are each independently hydrogen, optionally substituted lower alkyl, optionally substituted lower alkenyl, optionally substituted aryl or optionally substituted heteroaryl, and provided that a compound wherein a group of the formula: —$Y^2Z^1$— is a group of the formula:

[Formula 4]

n is 0 and $Z^1$ is a bond is excluded.

(2) The compound, pharmaceutically acceptable salt or solvate thereof according to (1),
wherein
Ring A is a group of the formula:

[Formula 5]

-continued

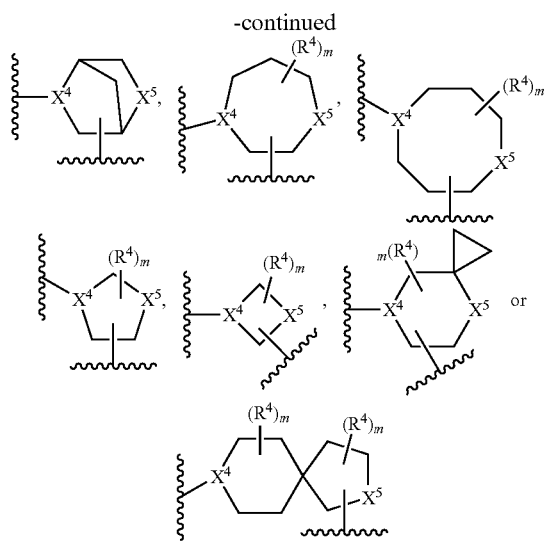

wherein
$X^4$ is N or $CR^5$ wherein $R^5$ is hydrogen or optionally substituted lower alkyl,
$X^5$ is O, S, $NR^{16}$ or $CR^{17}R^{18}$ wherein $R^{16}$ to $R^{18}$ are each independently hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, provided that a compound wherein $X^4$ is $CR^5$ and $X^5$ is $CR^{17}R^{18}$ is excluded,
$R^4$ are each independently halogen, optionally substituted lower alkyl, optionally substituted lower alkenyl, optionally substituted lower alkynyl, optionally substituted lower alkoxy or optionally substituted aryl,
m is an integer between 0 and 2,
the bond from $X^4$ binds with $Y^1$ and the other bond binds with $Y^2$, and the other bond can bind with $X^5$ when $X^5$ is $NR^{16}$ or $CR^{17}R^{18}$.

(3) The compound, pharmaceutically acceptable salt or solvate thereof according to (1), wherein
Ring A is a group of the formula:

[Formula 6]

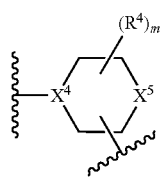

$X^4$ is N or $CR^5$ wherein $R^5$ is hydrogen or optionally substituted lower alkyl,
$X^5$ is $NR^{16}$ or $CR^{17}R^{18}$ wherein $R^{16}$ to $R^{18}$ are each independently hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl,
$R^4$ are each independently halogen, optionally substituted lower alkyl, optionally substituted lower alkenyl, optionally substituted lower alkynyl, optionally substituted lower alkoxy or optionally substituted aryl,
m is an integer between 0 and 2,
the bond from $X^4$ binds with $Y^1$ and the other bond binds with $Y^2$, and the other bond can bind with $X^5$.

(4) The compound, pharmaceutically acceptable salt or solvate thereof according to (1), wherein
Ring A is a group of the formula:

[Formula 7]

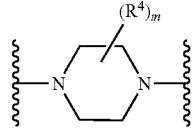

$R^4$ are each independently halogen, optionally substituted lower alkyl, optionally substituted lower alkenyl, optionally substituted lower alkynyl or optionally substituted lower alkoxy, and
m is an integer of 1 or 2.

(5) The compound, pharmaceutically acceptable salt or solvate thereof according to (1), wherein
Ring A is a group of the formula:

[Formula 8]

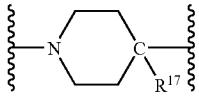

$R^{17}$ is optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, the bond from N binds with $Y^1$ and the bond from C binds with $Y^2$.

(6) The compound, pharmaceutically acceptable salt or solvate thereof according to (1), wherein
Ring A is a group of the formula:

[Formula 9]

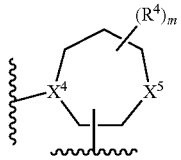

$X^4$ is N or $CR^5$ wherein $R^5$ is hydrogen or optionally substituted lower alkyl,
$X^5$ is $NR^{16}$ or $CR^{17}R^{18}$ wherein $R^{16}$ to $R^{18}$ are each independently hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, provided that a compound wherein $X^4$ is $CR^5$ and $X^5$ is $CR^{17}R^{18}$ is excluded,
$R^4$ are each independently halogen, optionally substituted lower alkyl, optionally substituted lower alkenyl, optionally substituted lower alkynyl, optionally substituted lower alkoxy or optionally substituted aryl,
m is an integer between 0 and 2,
the bond from $X^4$ binds with $Y^1$ and the other bond binds with $Y^2$, and the other bond can bind with $X^5$.

(7) The compound, pharmaceutically acceptable salt or solvate thereof according to (1) or (2), wherein Ring Q is substituted fused heteroaryl.

(8) The compound, pharmaceutically acceptable salt or solvate thereof according to (1) or (2), wherein Ring Q is substituted benzofuryl, substituted benzothienyl, substituted benzopyrolyl, substituted benzoxazolyl, substituted benzoisoxazolyl, substituted benzothiazolyl, substituted benzoisothiazolyl, substituted benzoimidazolyl or substituted benzopyrazolyl.

(9) The compound, pharmaceutically acceptable salt or solvate thereof according to (1) or (2), wherein
a group of the formula:

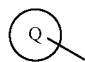

[Formula 10]

is a group of the formula:

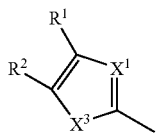

[Formula 11]

R$^1$ is hydrogen, halogen, hydroxy, optionally substituted lower alkyl, optionally substituted lower alkenyl, optionally substituted lower alkynyl, optionally substituted lower alkoxy or optionally substituted aryl, R$^2$ is halogen, optionally substituted alkyl, optionally substituted aryl, optionally substituted aryloxy, optionally substituted arylthio or optionally substituted heteroaryl, or R$^1$ and R$^2$ can be taken together with the neighboring carbon atom and 5-membered ring including X$^1$ and X$^3$ as the constructive atoms to form a substituted fused heteroaryl, X$^1$ is N or CR$^{10}$, and X$^3$ is NR$^{11}$, O or S wherein R$^{10}$ and R$^{11}$ are each independently hydrogen or optionally substituted lower alkyl.

(11) The compound, pharmaceutically acceptable salt or solvate thereof according to (1) or (2), wherein
a group of the formula:

[Formula 12]

is a group of the formula:

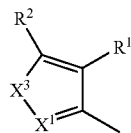

[Formula 13]

R$^1$ is hydrogen, halogen, hydroxy, optionally substituted lower alkyl, optionally substituted lower alkenyl, optionally substituted lower alkynyl or optionally substituted lower alkoxy, R$^2$ is halogen, optionally substituted alkyl, optionally substituted aryl, optionally substituted aryloxy, optionally substituted arylthio or optionally substituted heteroaryl, or R$^1$ and R$^2$ can be taken together with the neighboring carbon atom and 5-membered ring including X$^1$ and X$^3$ as the constructive atoms to form a substituted fused heteroaryl, X$^1$ is N or CR$^{12}$, and X$^3$ is NR$^{13}$, O or S wherein R$^{12}$ and R$^{13}$ are each independently hydrogen or optionally substituted lower alkyl.

(12) The compound, pharmaceutically acceptable salt or solvate thereof according to (1) or (2), wherein
a group of the formula:

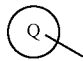

[Formula 14]

is a group of the formula:

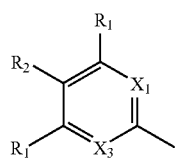

[Formula 15]

R$^1$ are each independently hydrogen, halogen, hydroxy, optionally substituted lower alkyl, optionally substituted lower alkenyl, optionally substituted lower alkynyl or optionally substituted lower alkoxy, R$^2$ is halogen, optionally substituted alkyl, optionally substituted aryl, optionally substituted aryloxy, optionally substituted arylthio or optionally substituted heteroaryl, X$^1$ is N or CR$^{19}$, and X$^3$ is N or CR$^{20}$ wherein R$^{19}$ and R$^{20}$ are each independently hydrogen or optionally substituted lower alkyl, provided that either X$^1$ or X$^3$ is N.

(13) The compound, pharmaceutically acceptable salt or solvate thereof according to (1) or (2), wherein
a group of the formula: —Y$^2$Z$^1$— is a group of the formula:

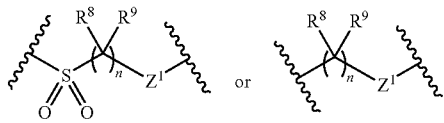

[Formula 16]

R$^8$ and R$^9$ are each independently hydrogen or lower alkyl,
n is an integer between 0 and 2, and
Z$^1$ is a bond, —O— or —S—.

(14) The compound, pharmaceutically acceptable salt or solvate thereof according to (1) or (2), wherein Ring B is optionally substituted phenylene, optionally substituted indolediyl, optionally substituted benzofurandiyl, optionally substituted benzothiophenediyl, optionally substituted furandiyl or optionally substituted thiophenediyl.

(15) The compound, pharmaceutically acceptable salt or solvate thereof according to (1) or (2), wherein Y$^3$ is a bond, optionally substituted lower alkylene, —O-optionally substituted lower alkylene or optionally substituted lower alkenylene.

(16) The compound, pharmaceutically acceptable salt or solvate thereof according to (1) or (2), wherein Z$^2$ is COOR$^3$ wherein R$^3$ is hydrogen or optionally substituted lower alkyl.

(17) The compound, pharmaceutically acceptable salt or solvate thereof according to (1), wherein
a group of the formula:

[Formula 17]

is a group of the formula:

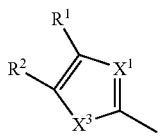

[Formula 18]

R$^1$ is hydrogen,
R$^2$ is optionally substituted aryl or
R$^1$ and R$^2$ can be taken together with the neighboring carbon atom and 5-membered ring including X$^1$ and X$^3$ as the constructive atoms to form a substituted fused heteroaryl,
X$^1$ is N or CR$^{10}$ wherein R$^{10}$ is hydrogen,
X$^3$ is O or S,
Y$^1$ is a bond,
Ring A is a group of the formula:

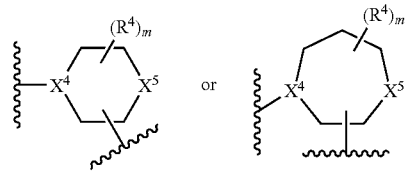

[Formula 19]

X$^4$ is N,
X$^5$ is NR$^{16}$ or CR$^{17}$R$^{18}$ wherein R$^{16}$ to R$^{18}$ are each independently hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl,
R$^4$ are each independently halogen, optionally substituted lower alkyl, optionally substituted lower alkenyl, optionally substituted lower alkynyl, optionally substituted lower alkoxy or optionally substituted aryl,
m is an integer between 0 and 2,
the bond from X$^4$ binds with Y$^1$ and the other bond binds with Y$^2$, and the other bond can bind with X$^5$,
a group of the formula: —Y$^2$Z$^1$— is a group of the formula:

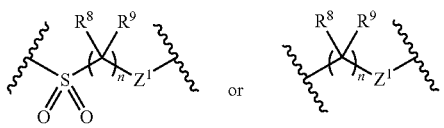

[Formula 20]

R$^8$ and R$^9$ are each independently hydrogen or lower alkyl,
n is an integer between 0 and 2,
Z$^1$ is a bond, —O— or —S—, Ring B is optionally substituted phenylene, optionally substituted furandiyl or optionally substituted thiophendiyl,
the substituent(s) of said phenylene, furandiyl or thiophendiyl of Ring B is/are selected from a group consisting of halogen, lower alkyl and lower alkoxy,
Y$^3$ is a bond, optionally substituted lower alkylene, —O— optionally substituted lower alkylene or optionally substituted lower alkenylene,
the substituent(s) of said lower alkylene or lower alkenylene of Y$^3$ is/are selected from a group consisting of halogen and lower alkylene, and
Z$^2$ is COOR$^3$ wherein R$^3$ is hydrogen or lower alkyl.
(18) The compound, pharmaceutically acceptable salt or solvate thereof according to (1), wherein
a group of the formula:

[Formula 21]

is a group of the formula:

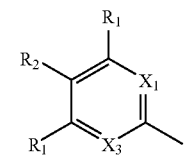

[Formula 22]

R$^1$ are each independently hydrogen, halogen, hydroxy, optionally substituted lower alkyl, optionally substituted lower alkenyl, optionally substituted lower alkynyl or optionally substituted lower alkoxy,
R$^2$ is optionally substituted alkyl or optionally substituted aryl,
X$^1$ is N or CR$^{19}$,
X$^3$ is N or CR$^{20}$ wherein R$^{19}$ and R$^{20}$ are each independently hydrogen or optionally substituted lower alkyl, provided that either X$^1$ or X$^3$ is N,
Y$^1$ is a bond,
Ring A is a group of the formula:

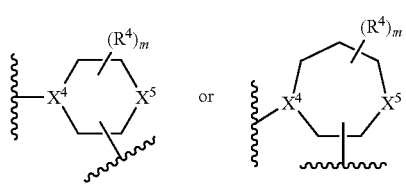

[Formula 23]

X$^4$ is N,
X$^5$ is NR$^{16}$ or CR$^{17}$R$^{18}$ wherein R$^{16}$ to R$^{18}$ are each independently hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl,
R$^4$ are each independently halogen, optionally substituted lower alkyl, optionally substituted lower alkenyl, optionally substituted lower alkynyl, optionally substituted lower alkoxy or optionally substituted aryl, m is an integer between 0 and 2, the bond from $X^4$ binds with $Y^1$ and the other bond binds with $Y^2$, and the other bond can bind with $X^5$, a group of the formula: —$Y^2Z^1$— is a group of the formula:

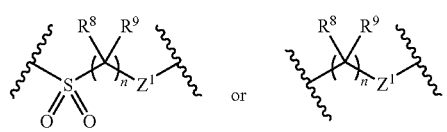

[Formula 24]

$R^8$ and $R^9$ are each independently hydrogen or lower alkyl, n is an integer between 0 and 2, $Z^1$ is a bond, —O— or —S—, Ring B is optionally substituted phenylene, optionally substituted furandiyl or optionally substituted thiophendiyl, the substituent(s) of said phenylene, furandiyl or thiophendiyl of Ring B is/are selected from a group consisting of halogen, lower alkyl and lower alkoxy, $Y^3$ is a bond, optionally substituted lower alkylene, —O— optionally substituted lower alkylene or optionally substituted lower alkenylene, the substituent(s) of said lower alkylene or lower alkenylene of $Y^3$ is/are selected from a group consisting of halogen and lower alkylene, and $Z^2$ is $COOR^3$ wherein $R^3$ is hydrogen or lower alkyl.

(19) The compound, pharmaceutically acceptable salt or solvate thereof according to (1), wherein $Y^1$ is a bond, Ring A is a group of the formula:

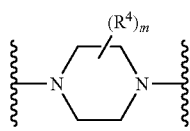

[Formula 25]

$R^4$ are each independently halogen, optionally substituted lower alkyl, optionally substituted lower alkenyl, optionally substituted lower alkynyl or optionally substituted lower alkoxy, m is an integer of 1 or 2, a group of the formula: —$Y^2Z^1$— is a group of the formula:

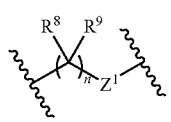

[Formula 26]

$R^8$ and $R^9$ are each independently hydrogen or lower alkyl, n is an integer of 1 or 2, $Z^1$ is a bond or —O—, Ring B is optionally substituted phenylene, $Y^3$ is optionally substituted lower alkylene or —O— optionally substituted lower alkylene, the substituent(s) of said lower alkylene of $Y^3$ is/are selected from a group consisting of halogen and lower alkylene, and $Z^2$ is $COOR^3$ wherein $R^3$ is hydrogen or lower alkyl.

(20) The compound, pharmaceutically acceptable salt or solvate thereof according to (1), wherein $Y^1$ is a bond, Ring A is a group of the formula:

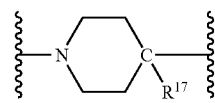

[Formula 27]

$R^{17}$ is optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, the bond from N binds with $Y^1$ and the bond from C binds with $Y^2$, a group of the formula: —$Y^2Z^1$— is a group of the formula:

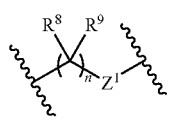

[Formula 28]

$R^8$ and $R^9$ are each independently hydrogen or lower alkyl, n is 2, $Z^1$ is —O—, Ring B is optionally substituted phenylene, $Y^3$ is optionally substituted lower alkylene or —O— optionally substituted lower alkylene, and the substituent(s) of said lower alkylene of $Y^3$ is/are selected from a group consisting of halogen and lower alkylene, and $Z^2$ is $COOR^3$ wherein $R^3$ is hydrogen or lower alkyl.

(21) A pharmaceutical composition comprising the compound, pharmaceutically acceptable salt or solvate thereof according to any one of (1) to (20) as an active ingredient.

(22) A pharmaceutical composition for prevention and/or treatment for a disease concerning peroxisome proliferator-activated receptor(s), which comprises the compound, pharmaceutically acceptable salt or solvate thereof according to any one of (1) to (20) as active ingredient.

(23) A compound of the formula:

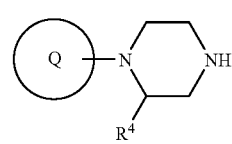

[Formula 29]

a salt or solvate thereof, wherein

Ring Q has the same meaning as defined in (1), and $R^4$ is halogen, optionally substituted lower alkyl, optionally substituted lower alkenyl, optionally substituted lower alkynyl or optionally substituted lower alkoxy.

(24) A compound of the formula:

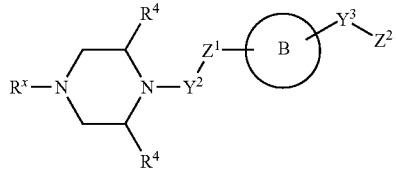

[Formula 30]

salt or solvate thereof,
wherein $Y^2$, $Z^1$, Ring B, $Y^3$ and $Z^2$ have the same meanings as defined in (1), $R^4$ are each independently halogen, optionally substituted lower alkyl, optionally substituted lower alkenyl, optionally substituted lower alkynyl, optionally substituted lower alkoxy or optionally substituted aryl, and $R^x$ is hydrogen or amino protecting group.

(25) A compound of the formula:

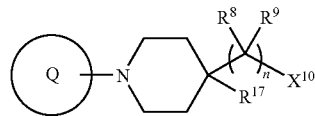

[Formula 31]

a salt or solvate thereof,
wherein

Ring Q has the same meaning as defined in (1), $R^{17}$ is optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, $R^8$ and $R^9$ are each independently hydrogen or lower alkyl, n is an integer between 1 and 3, and $X^{10}$ is halogen or hydroxy.

(26) A compound of the formula:

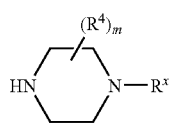

[Formula 32]

a salt or solvate thereof,
wherein $R^4$ are each independently halogen, optionally substituted lower alkyl, optionally substituted lower alkenyl, optionally substituted lower alkynyl or optionally substituted lower alkoxy, m is 1 or 2, and $R^x$ is hydrogen or amino protecting group.

(27) A compound of the formula:

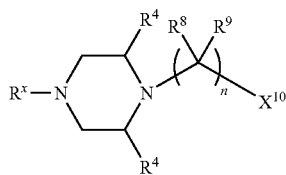

[Formula 33]

a salt or solvate thereof,
wherein $R^4$ are each independently halogen, optionally substituted lower alkyl, optionally substituted lower alkenyl, optionally substituted lower alkynyl or optionally substituted lower alkoxy, $R^8$ and $R^9$ are each independently hydrogen or lower alkyl, n is an integer between 1 and 3, $R^X$ is hydrogen or amino protecting group, and $X^{10}$ is hydroxy or halogen.

(28) A compound of the formula:

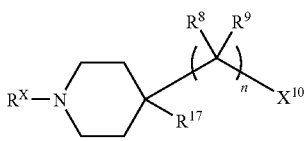

[Formula 34]

a salt or solvate thereof,
wherein $R^{17}$ is optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, $R^8$ and $R^9$ are each independently hydrogen or lower alkyl, n is an integer between 1 and 3, $X^{10}$ is halogen or hydroxy, and $R^X$ is hydrogen or amino protecting group.

Furthermore, the present invention provides a process for PPAR activation characterized by administrating the above compound, pharmaceutically acceptable salt or solvate thereof. In details, it is the treatment process and/or prevention process for hyperlipidemia, diabetes, obesity, arteriosclerosis, atherosclerosis, hyperglycemia and/or syndrome X.

As the other embodiment, the present invention provides use of the above compound, pharmaceutically acceptable salt or solvate thereof to produce medicines for PPAR activation, for example, medicines for treatment and/or prevention for hyperlipidemia, diabetes, obesity, arteriosclerosis, atherosclerosis, hyperglycemia and/or syndrome X.

Effect of the Invention

As the following test results show, compounds of the present invention have PPAR agonistic activity and are very useful as medicine and especially medicine for treatment and/or prevention for hyperlipidemia, diabetes, obesity, arteriosclerosis, atherosclerosis, hyperglycemia and/or syndrome X.

BEST MODE FOR CARRYING OUT THE INVENTION

Each term used in this description is explained below. The each term has the same meaning in this description both when it is used alone each term and when it is used with the other term.

The term "monocyclic aryl" means C6 to C12 monocyclic aromatic carbon ring. Examples include phenyl and the like.

The term "fused aryl" means aromatic carbon ring which 1 to 4 monocyclic aromatic carbon ring(s) (C6 to C12 monocyclic aromatic carbon ring(s)) is condensed with C6 to C12 monocyclic aromatic carbon ring. Examples include naphthyl, anthryl, phenanthryl and the like. The bonds can be attached to any of the rings. Naphthyl is preferable.

The term "aryl" means the above "monocyclic aryl" and "fused aryl".

The term "aralkyl" means the above "alkyl" substituted with 1 to 3 of the above "aryl". Examples include benzyl, phenethyl, phenylpropyl, trityl and the like.

The term "monocyclic heteroaryl" means 4- to 8-membered monocyclic aromatic heterocycle having 1 or more hetero atom(s) selected from O, S and N in the ring. Examples include pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like. 5- or 6-membered monocyclic aromatic heterocycle is especially preferable.

The term "fused heteroaryl" means a group derived from condensed aromatic heterocycle which aromatic carbon ring (aromatic carbon ring derived from the above "aryl") or aromatic heterocycle (4- to 8-membered aromatic heterocycle having 1 or more hetero atom(s) selected from O, S and N in the ring) is condensed with monocyclic aromatic heterocycle derived from the above "monocyclic heteroaryl". Examples include indolyl, isoindolyl, indazolyl, indolizinyl, quinolyl, isoquinolyl, cinnolinyl, phthalazinyl, quinazolinyl, naphthyridinyl, quinoxalinyl, prinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyradinopyridazinyl, quinazolinyl, tetrahydroquinolyl, tetrahydrobenzothienyl, carbazolyl, acridinyl, xanthenyl, phenothiazinyl, phenoxathiinyl, phenoxazinyl, dibenzofuryl and the like. In case of "fused heteroaryl", the bonds can be attached to any of the rings. A condensed fused heteroaryl which benzene ring is condensed with 5- or 6-membered monocyclic aromatic heterocycle is especially preferable.

The term "heteroaryl" means the above "monocyclic heteroaryl" and "fused heteroaryl".

The term "heteroaralkyl" means the above "alkyl" substituted with 1 to 3 of the above "heteroaryl".

The term "nonaromatic heterocycle" means a condensed nonaromatic heterocycle which aromatic carbon ring (aromatic carbon ring derived from the above "aryl"), aromatic heterocycle (4- to 8-membered aromatic heterocycle having 1 or more hetero atom(s) selected from O, S and N in the ring), monocyclic nonaromatic heterocycle (monocyclic nonaromatic heterocycle derived from the above "monocyclic nonaromatic heterocycle") or cycloalkane (a ring derived from the below "cycloalkyl") is condensed with 4- to 8-membered monocyclic nonaromatic heterocycle having 1 or more hetero atom(s) selected from O, S and N in the ring or the above "monocyclic nonaromatic heterocycle". Examples include indolinyl, dioxanyl, thiiranyl, oxyranyl, oxathiolanyl, azetidinyl, thianyl, pyrrolidinyl, pyrrolinyl, imidazolidinyl, imidazolinyl, pyrazolidinyl, pyrazolinyl, piperidyl, piperidino, piperazinyl, piperadino, morpholinyl, morpholino, oxadiadinyl, dihydropyridyl and the like.

The term "heterocycle" include the above "heteroaryl" and "nonaromatic heterocycle". Examples include morpholino, piperidino, piperadino, furyl, thienyl, pyridyl and the like.

The term "nonaromatic heterocyclediyl" includes a bivalent group derived by removing 2 hydrogen atoms from 4- to 10-membered nonaromatic heterocycle having 1 or more hetero atom(s) selected from O, S and N in the ring. The nonaromatic heterocycle can be bridged by alkylene. The preferable examples include piperidinediyl, piperadinediyl, morpholinediyl, dioxanediyl, pyrrolidinediyl, pyrrolinediyl, imidazolinediyl, imidazolidinediyl and the like. Examples of "nonaromatic heterocyclediyl" of Ring A include the following groups.

A group of the formula:

[Formula 35]

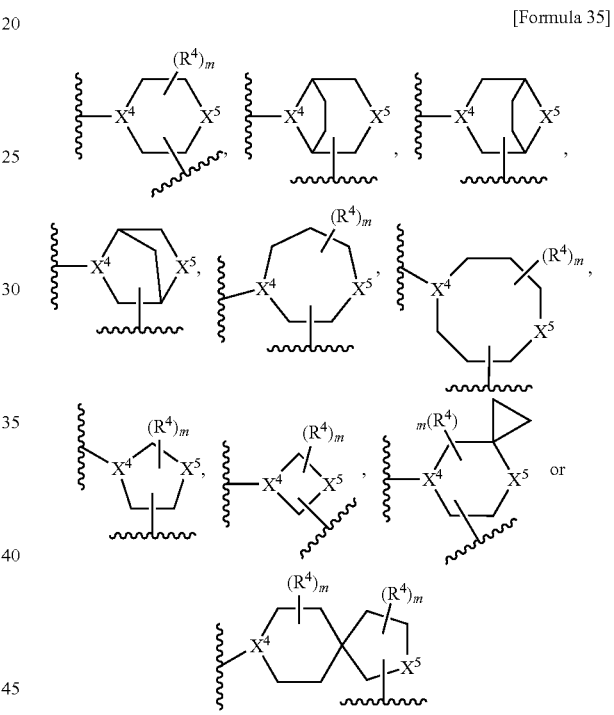

wherein $X^4$ is N or $CR^5$ wherein $R^5$ is hydrogen or optionally substituted lower alkyl, $X^5$ is O, S, $NR^{16}$ or $CR^{17}R^{18}$ wherein $R^{16}$ to $R^{18}$ are each independently hydrogen, optionally substituted lower alkyl, optionally substituted nonaromatic heterocycle, optionally substituted heteroaryl, optionally substituted amino, optionally substituted lower alkoxy, aryl lower alkyl or optionally substituted cycloalkyl, provided that a compound wherein $X^4$ is $CR^5$ and $X^5$ is $CR^{17}R^{18}$ is excluded, $R^4$ are each independently halogen, optionally substituted lower alkyl, optionally substituted lower alkenyl, optionally substituted lower alkynyl, optionally substituted lower alkoxy or optionally substituted aryl, and m is an integer between 0 and 2, the bond from $X^4$ binds with $Y^1$ and the other bond binds with $Y^2$, and the other bond can bind with $X^5$ when $X^5$ is $NR^{16}$ or $CR^{17}R^{18}$. The other bond preferably binds with $X^5$.

"The other bond can bind with $X^5$ when $X^5$ is $NR^{16}$" means the below.

[Formula 36]

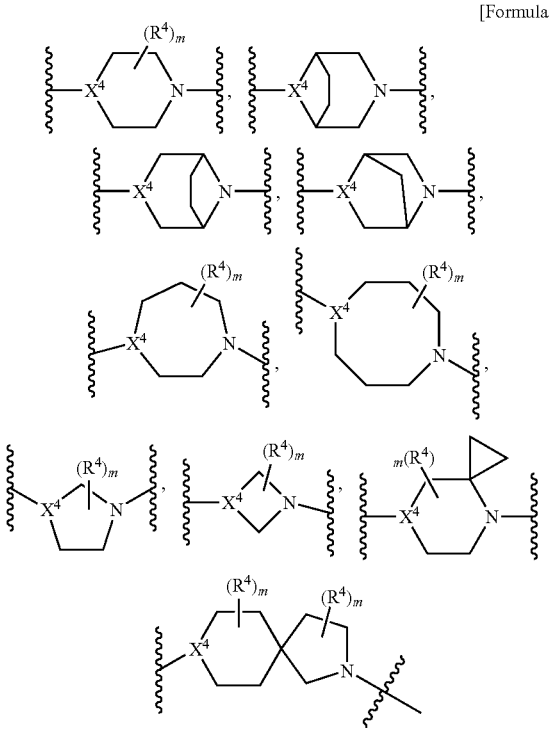

wherein each symbol has the same meaning as defined above.

"The other bond can bind with $X^5$ when $X^5$ is $CR^{17}R^{18}$" means the below.

[Formula 37]

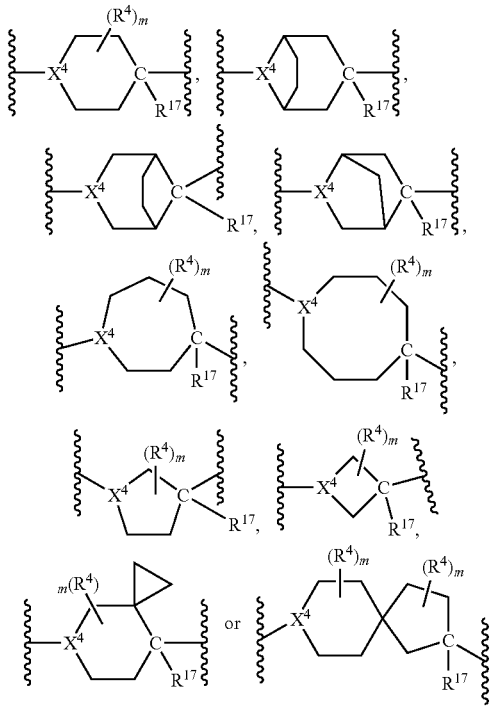

wherein each symbol has the same meaning as defined above.

The term "aromatic carbocyclediyl" includes a bivalent group derived by removing a hydrogen atom from the above "aryl". Examples include phenylene, naphthylene and the like. Phenylene is preferable.

The term "aromatic heterocyclediyl" includes a bivalent group derived by removing a hydrogen atom from the above "heteroaryl". Examples includes pyrroldiyl, imidazolediyl, pyrazolediyl, pyridinediyl, pyridazinediyl, pyrimidinediyl, pyrazinediyl, triazolediyl, triazinediyl, isoxazolediyl, oxazolediyl, oxadiazolediyl, isothiazolediyl, thiazolediyl, thiadiazolediyl, furandiyl, thiophenediyl, indolediyl, benzofurandiyl, benzothiophenediyl and the like. Indolediyl, benzofurandiyl, benzothiophenediyl, furandiyl or thiophenediyl is preferable. Monocyclic aromatic heterocyclediyl is especially preferable. Furandiyl (especially furan-2,5-diyl) or thiophenediyl (especially thiophene-2,5-diyl) is more preferable.

The term "lower alkyl" means C1 to C10, preferably C1 to C6 and more preferably C1 to C4 straight or branched alkyl group. Examples include methyl, ethyl, n-propyl, isopropyl, n-butyl, isobutyl, sec-buthyl, tert-butyl, n-pentyl, isopentyl, neopentyl, hexyl, isohexyl, n-heptyl, isoheptyl, n-octyl, isooctyl, n-nonyl, n-decyl and the like.

The term "lower alkenyl" means C2 to C10, preferably C2 to C6 and more preferably C2 to C4 straight or branched alkenyl having one or more double bond(s) at arbitrary position(s). Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

The term "lower alkynyl" means C2 to C10, preferably C2 to C6 and more preferably C2 to C4 straight or branched alkynyl. Examples include ethynyl, propynyl, butynyl, pentynyl, hexynyl, heptynyl, octynyl, nonynyl, decynyl and the like. These have one or more triple bond(s) at arbitrary position(s) and can have double bond(s).

The term "cycloalkyl" includes C3 to C9 and preferably C3 to C6 cycloalkyl. Examples include cyclopropyl, cyclobutyl, cyclopentyl, cyclohexyl, cycloheptyl, cyclooctyl and the like.

The term "cycloalkylene" includes C3 to C9 and preferably C3 to C6 cycloalkylene. Examples include cyclopropylene, cyclobutylene, cyclopenthylene, cyclohexylene, cycloheptylene, cycloethylene and the like. Cyclopropylene is especially preferable.

"Cycloalkylene optionally intervened by —O—" means cycloalkylene which is the above "cycloalkylene" optionally intervened by 1 or 2-O—. Examples include a group of the formula:

[Formula 38]

The term "acyl" includes (a) carbonyl substituted with the above "alkyl" or "alkenyl", (b) carbonyl substituted with the above "cycloalkyl", (c) carbonyl substituted with the above "aryl" or (d) formyl. Examples include formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl and the like.

The term "lower alkylene" includes C1 to 10, preferably C1 to 6 and more preferably C1 to 3 straight or branched alkylene. Examples include methylene, ethylene, trimethylene, tetramethylene, pentamethylene, hexamethylene, methylmethylene, propylene, dimethylmethylene, 1,1-dimethylethylene, 1,2-dimethylethylene and the like. Methylene, ethylene or dimethylmethylene is especially preferable.

"Lower alkylene optionally intervened by —O—" means alkylene which is the above "alkylene" optionally intervened by 1 to 3-O—. Alkylene which —O— is intervened at the end is also included. Examples include —O—CH$_2$—, —CH$_2$—O—, —CH$_2$—O—CH$_2$—, —O—CH$_2$—CH$_2$—, —CH$_2$—CH$_2$—O—, —O—CH(CH$_3$)—, —O—C(CH$_3$)$_2$—, —O—CH$_2$—CH$_2$—O—, —O—CH(CH$_3$)—O—, —O—C(CH$_3$)$_2$—O— and the like.

"—O-optionally substituted lower alkylene" means alkylene which —O— is intervened at the end.

The term "lower alkenylene" includes C2 to 10, preferably C2 to C6 and more preferably C2 to C4 straight or branched alkenylene having one or more double bond(s) at arbitrary position(s). Examples include vinylene, propenylene and the like.

The term "halogen" means fluorine, chlorine, bromine or iodine. Especially, fluorine, chlorine or bromine is preferable.

An alkyl part of "lower alkoxy" is the same as the above "lower alkyl".

Examples of the substituent of "optionally substituted lower alkyl", "optionally substituted lower alkylsulfonyl", "optionally substituted lower alkenyl", "optionally substituted lower alkynyl", "optionally substituted lower alkylene", "optionally substituted lower alkenylene", "optionally substituted lower alkoxy" or "optionally substituted acyl" include halogen, hydroxy, optionally substituted lower alkoxy, optionally substituted lower alkynyloxy, optionally substituted amino, mercapto, optionally substituted lower alkylthio, acyl, acyloxy, optionally substituted imino, carboxy, optionally substituted lower alkoxycarbonyl, optionally substituted carbamoyl, optionally substituted thiocarbamoyl, optionally substituted carbamoyloxy, optionally substituted thiocarbamoyloxy, optionally substituted sulfamoyl, optionally substituted lower alkylsulfonyl, optionally substituted lower alkylsulfonyloxy, cyano, nitro, optionally substituted cycloalkyl, optionally substituted cycloalkyloxy, optionally substituted aryl, optionally substituted aryloxy, optionally substituted arylthio, optionally substituted arylsulfonyl, optionally substituted arylsulfonyloxy, optionally substituted heterocycle, optionally substituted heterocycleoxy, optionally substituted lower alkylene, optionally substituted lower alkylenedioxy and oxo. They can be substituted at arbitrary position(s) with one or more group(s) selected from the above. In case that optionally substituted lower alkylene or optionally substituted lower alkylenedioxy is the substituent, the two bonds bind with one carbon atom to form a spiro ring, or bind with different atoms and are taken together with the neighboring carbon atom to form a ring.

A heterocycle part of "heterocycleoxy" is the same as the above "heterocycle".

Examples of the substituent of "optionally substituted monocyclic aryl", "optionally substituted monocyclic heteroaryl", "optionally substituted aryl", "optionally substituted aralkyl", "optionally substituted aryloxy", "optionally substituted arylthio", "optionally substituted heteroaryl", "optionally substituted hetroaralkyl", "optionally substituted heteroaryloxy", "optionally substituted heteroarylthio", "substituted fused aryl", "substituted fused heteroaryl", "optionally substituted arylsulfonyl", "optionally substituted aromatic carbocyclediyl", "optionally substituted aromatic heterocyclediyl" or "optionally substituted nonaromatic heterocyclediyl" include optionally substituted lower alkyl, optionally substituted lower alkenyl, optionally substituted lower alkenyl, optionally substituted lower alkenyloxy, halogen, hydroxy, optionally substituted lower alkoxy, optionally substituted lower alkynyloxy, optionally substituted amino, mercapto, optionally substituted lower alkylthio, acyl, acyloxy, optionally substituted imino, carboxy, optionally substituted lower alkoxycarbonyl, optionally substituted carbamoyl, optionally substituted thiocarbamoyl, optionally substituted carbamoyloxy, optionally substituted thiocarbamoyloxy, optionally substituted sulfamoyl, optionally substituted lower alkylsulfonyl, optionally substituted lower alkylsulfonyloxy, cyano, nitro, optionally substituted cycloalkyl, optionally substituted cycloalkyloxy, optionally substituted aryl, optionally substituted aryloxy, optionally substituted arylthio, optionally substituted arylsulfonyl, optionally substituted arylsulfonyloxy, optionally substituted heterocycle, optionally substituted heterocycleoxy, optionally substituted lower alkylene and optionally substituted lower alkylenedioxy. They can be substituted at arbitrary position(s) with one or more group(s) selected from the above. In case that optionally substituted lower alkylene or optionally substituted lower alkylenedioxy is the substituent, the bonds can bind with different atoms and be taken together with the neighboring carbon atom to form a ring.

Preferable examples in the above substituents include halogen, hydroxy, optionally substituted lower alkyl (the substituent is halogen or hydroxy), optionally substituted lower alkenyl (the substituent is halogen or hydroxy), optionally substituted lower alkoxy (the substituent is halogen or aryl), carboxy, lower alkoxycarbonyl, optionally substituted carbamoyl (the substituent is lower alkyl or aryl), optionally substituted amino (the substituent is acyl or lower alkyl), mercapto, lower alkylthio, acyl, acyloxy, cyano, nitro, aryl, heterocycle, lower alkylene and lower alkylenedioxy. Halogen or optionally substituted lower alkyl (the substituent is halogen) is especially preferable.

A substituent of "substituted benzofuryl", "substituted benzothienyl", "substituted benzopyronyl", "substituted benzoxazolyl", "substituted benzisoxazolyl", "substituted benzothiazolyl", "substituted benzisothiazolyl", "substituted benzimidazolyl" or "substituted benzopyrazolyl" is the same as the substituent of the above "substituted fused heteroaryl".

A substituent of "optionally substituted phenylene" is the same as the substituent of "optionally substituted aromatic carbocyclediyl".

A substituent of "optionally substituted indolediyl", "optionally substituted benzofurandiyl", "optionally substituted benzothiophenediyl", "optionally substituted furandiyl" or "optionally substituted thiophenediyl" is the same as the substituent of the above "optionally substituted aromatic heterocyclediyl".

Examples of a substituent of "optionally substituted nonaromatic heterocyclediyl" include halogen, hydroxy, optionally substituted lower alkoxy, optionally substituted lower alkynyloxy, optionally substituted amino, mercapto, optionally substituted lower alkylthio, acyl, acyloxy, optionally substituted imino, carboxy, optionally substituted lower alkoxycarbonyl, optionally substituted carbamoyl, optionally substituted thiocarbamoyl, optionally substituted carbamoyloxy, optionally substituted thiocarbamoyloxy, optionally substituted sulfamoyl, optionally substituted lower alkylsulfonyl, optionally substituted lower alkylsulfonyloxy, cyano, nitro, optionally substituted cycloalkyl, optionally substituted cycloalkyloxy, optionally substituted aryl, optionally substituted aryloxy, optionally substituted arylthio, optionally substituted arylsulfonyl, optionally substituted arylsulfonyloxy, optionally substituted heterocycle, optionally substituted heterocycleoxy, optionally substituted lower alkylene, optionally substituted lower alkylenedioxy and oxo. It can be optionally substituted at arbitrary position(s) with one or more group(s) selected from the above. In case that optionally substituted lower alkylene or optionally substituted lower alkylenedioxy is a substituent, the two bonds bind with one carbon atom to form a spiro ring, or bind with different atoms and are taken together to with the neighboring carbon atom to form a ring.

A substituent of "optionally substituted lower alkynyloxy", "optionally substituted lower alkylthio", "optionally substituted lower alkoxycarbonyl", "optionally substituted lower alkylsulfonyloxy", "optionally substituted cycloalkyl", "optionally substituted cycloalkyloxy", "optionally substituted arylsulfonyl", "optionally substituted arylsulfonyloxy", "optionally substituted heterocycle", "optionally substituted heterocycleoxy" or "optionally substituted lower alkylenedioxy" is the same as the substituent of the above "optionally substituted lower alkyl".

A substituent of "optionally substituted amino", "optionally substituted imino", "optionally substituted carbamoyl", "optionally substituted thiocarbamoyl", "optionally substituted carbamoyloxy", "optionally substituted thiocarbamoyloxy" or "optionally substituted sulfamoyl" is the same as the substituent of the above "optionally substituted lower alkyl". These substituents can be mono- or di-substituted on a nitrogen atom. Lower alkyl, aryl, heterocycle, acyl, lower alkoxycarbonyl, lower alkylsulfonyl or arylsulfonyl is especially preferable.

Preferable embodiments of each substituent for a compound of the formula (I) are explained below.

Ring Q is optionally substituted monocyclic aryl, optionally substituted monocyclic heteroaryl, optionally substituted fused aryl or optionally substituted fused heteroaryl. Preferable examples include monocyclic aryl substituted with one or more of $R^2$ and optionally substituted with other group(s), monocyclic heteroaryl substituted with one or more of $R^2$ and optionally substituted with other group(s) wherein each $R^2$ is halogen, optionally substituted alkyl, optionally substituted aryl, optionally substituted aralkyl, optionally substituted aryloxy, optionally substituted arylthio, optionally substituted heteroaryl, optionally substituted heteroaralkyl, optionally substituted heteroaryloxy or optionally substituted heteroarylthio, substituted fused aryl or substituted fused heteroaryl. Monocyclic heteroaryl substituted with one of $R^2$ and optionally substituted with other group(s) wherein $R^2$ is halogen, optionally substituted alkyl or optionally substituted aryl, substituted fused aryl or substituted fused heteroaryl is especially preferable.

"and optionally substituted with other group(s)" means to be optionally substituted except for the substituent, $R^2$. The substituent(s) can be the same substituent as $R^2$.

Examples of substituted fused heteroaryl include substituted benzofuryl, substituted benzothienyl, substituted benzopyronyl, substituted benzoxazolyl, substituted benzisoxazolyl, substituted benzothiazolyl, substituted benzisothiazolyl, substituted benzimidazolyl, substituted benzopyrazolyl and the like. Substituted benzothiazolyl wherein the substituent is halogen, optionally substituted lower alkyl, optionally substituted lower alkoxy, aryl, lower alkylsulfonyl or optionally substituted carbamoyl is especially preferable.

Especially preferable examples of Ring Q include below.
A group of the formula:

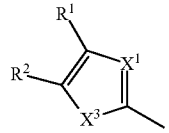

[Formula 39]

$R^1$ is hydrogen, halogen, hydroxy, optionally substituted lower alkyl, optionally substituted lower alkenyl, optionally substituted lower alkynyl, optionally substituted lower alkoxy or optionally substituted aryl, $R^2$ is halogen, optionally substituted alkyl, optionally substituted aryl, optionally substituted aryloxy, optionally substituted arylthio or optionally substituted heteroaryl, or $R^1$ and $R^2$ can be taken together with the neighboring carbon atom to form optionally substituted ring, $X^1$ is N or $CR^{10}$, and $X^3$ is $NR^{11}$, O or S wherein $R^{10}$ and $R^{11}$ are each independently hydrogen or optionally substituted lower alkyl, a group of the formula:

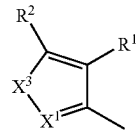

[Formula 40]

$R^1$ is hydrogen, halogen, hydroxy, optionally substituted lower alkyl, optionally substituted lower alkenyl, optionally substituted lower alkynyl or optionally substituted lower alkoxy, $R^2$ is halogen, optionally substituted alkyl, optionally substituted aryl, optionally substituted aryloxy, optionally substituted arylthio or optionally substituted heteroaryl, or $R^1$ and $R^2$ can be taken together with the neighboring carbon atom to form optionally substituted ring, $X^1$ is N or $CR^{12}$, and $X^3$ is $NR^{13}$, O or S wherein $R^{12}$ and $R^{13}$ are each independently hydrogen or optionally substituted lower alkyl, or a group of the formula:

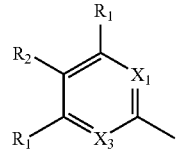

[Formula 41]

$R^1$ are each independently hydrogen, halogen, hydroxy, optionally substituted lower alkyl, optionally substituted lower alkenyl, optionally substituted lower alkynyl or optionally substituted lower alkoxy, $R^2$ is halogen, optionally substituted alkyl, optionally substituted aryl, optionally substituted aryloxy, optionally substituted arylthio or optionally substituted heteroaryl, $X^1$ is N or $CR^{19}$, and $X^3$ is N or $CR^{20}$ wherein $R^{19}$ and $R^{20}$ are each independently hydrogen or optionally substituted lower alkyl, provided that either $X^1$ or $X^3$ is N.

The following embodiments are preferable as "substituted fused heteroaryl" of Ring Q.

[Formual 42]

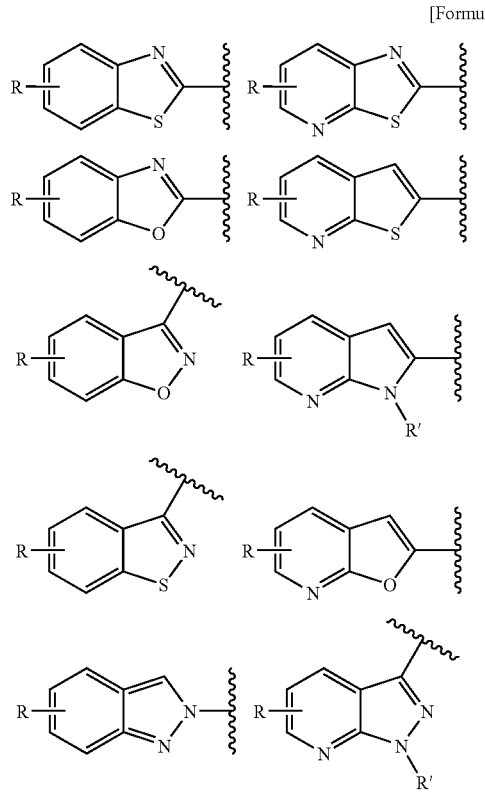

R is optionally substituted lower alkyl, optionally substituted lower alkenyl, optionally substituted lower alkenyl, optionally substituted lower alkenyloxy, halogen, hydroxy, optionally substituted lower alkoxy, optionally substituted lower alkynyloxy, optionally substituted amino, mercapto, optionally substituted lower alkylthio, acyl, acyloxy, optionally substituted imino, carboxy, optionally substituted lower alkoxycarbonyl, optionally substituted carbamoyl, optionally substituted thiocarbamoyl, optionally substituted carbamoyloxy, optionally substituted thiocarbamoyloxy, optionally substituted sulfamoyl, optionally substituted lower alkylsulfonyl, optionally substituted lower alkylsulfonyloxy, cyano, nitro, optionally substituted cycloalkyl, optionally substituted cycloalkyloxy, optionally substituted aryl, optionally substituted aryloxy, optionally substituted arylthio, optionally substituted arylsulfonyl, optionally substituted arylsulfonyloxy, optionally substituted heterocycle, optionally substituted heterocycleoxy, R' is hydrogen or has the same meaning as the above R, and provided that R can be hydrogen when R' has the same meaning as the above R.

The following embodiments are also preferable as "monocyclic heteroaryl substituted with one or more of $R^2$ and optionally substituted with other group(s)" for ring Q.

[Formula 43]

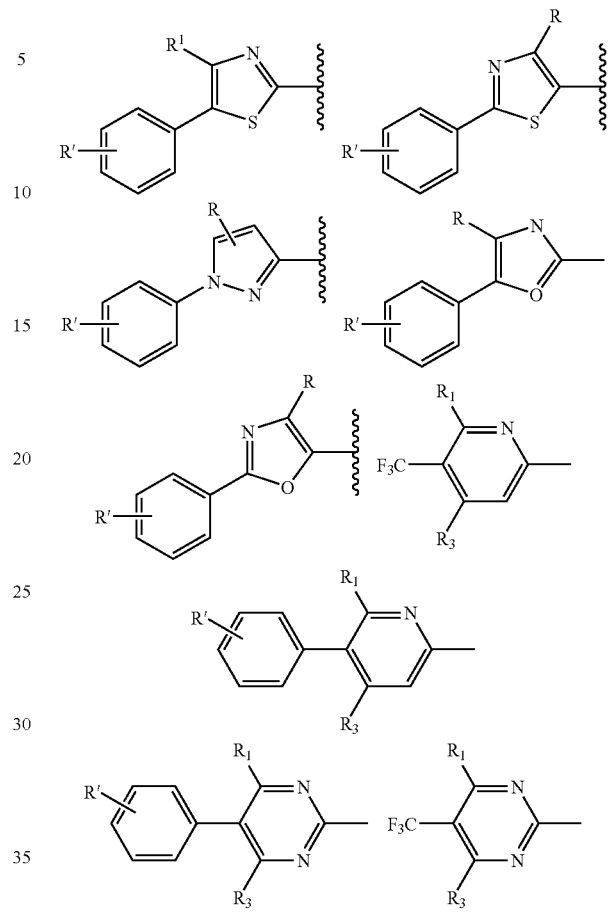

$R^1$ is hydrogen, halogen, hydroxy, optionally substituted lower alkyl, optionally substituted lower alkenyl, optionally substituted lower alkynyl, optionally substituted lower alkoxy or optionally substituted aryl, and R and R' are each independently hydrogen, halogen, hydroxy, optionally substituted lower alkoxy, optionally substituted lower alkynyl oxy, optionally substituted amino, mercapto, optionally substituted lower alkylthio, acyl, acyloxy, optionally substituted imino, carboxy, optionally substituted lower alkoxycarbonyl, optionally substituted carbamoyl, optionally substituted thiocarbamoyl, optionally substituted carbamoyloxy, optionally substituted thiocarbamoyloxy, optionally substituted sulfamoyl, optionally substituted lower alkylsulfonyl, optionally substituted lower alkylsulfonyloxy, cyano, nitro, optionally substituted cycloalkyl, optionally substituted cycloalkyloxy, optionally substituted aryl, optionally substituted aryloxy, optionally substituted arylthio, optionally substituted arylsulfonyl, optionally substituted arylsulfonyloxy, optionally substituted heterocycle, optionally substituted heterocyclyloxy or the like.

$Y^1$ is a bond, —$NR^6$— or —$NR^6$—CO— wherein $R^6$ is hydrogen or optionally substituted lower alkyl. A bond is especially preferable.

Ring A is optionally substituted nonaromatic heterocyclediyl, provided that Ring Q binds with a nitrogen atom of Ring A when $Y^1$ is a bond. Especially preferable examples include a group of the formula:

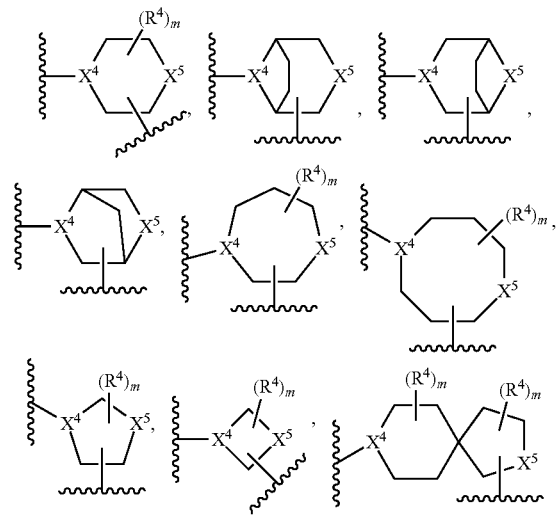

[Formula 44]

wherein
X$^4$ is N or CR$^5$ wherein R$^5$ is hydrogen or optionally substituted lower alkyl,
X$^5$ is O, S, NR$^{16}$ or CR$^{18}$R$^{18}$ wherein R$^{16}$ to R$^{18}$ are each independently hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, provided that a compound wherein X$^4$ is CR$^5$ and X$^5$ is CR$^{17}$R$^{18}$ is excluded,
R$^4$ are each independently halogen, optionally substituted lower alkyl, optionally substituted lower alkenyl, optionally substituted lower alkynyl, optionally substituted lower alkoxy or optionally substituted aryl, and
m is an integer between 0 and 2,
the bond from X$^4$ binds with Y$^1$ and the other bond binds with Y$^2$, and the other bond can bind with X$^5$ when X$^5$ is NR$^{16}$ or CR$^{17}$R$^{18}$.

More preferable examples include a group of the formula:

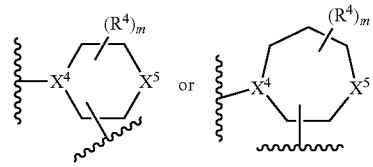

[Formula 45]

wherein
X$^4$ is N or CR$^5$ wherein R$^5$ is hydrogen or optionally substituted lower alkyl,
X$^5$ is NR$^{16}$ or CR$^{17}$R$^{18}$ wherein R$^{16}$ to R$^{18}$ are each independently hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, provided that a compound wherein X$^4$ is CR$^5$ and X$^5$ is CR$^{17}$R$^{18}$ is excluded,
R$^4$ are each independently halogen, optionally substituted lower alkyl, optionally substituted lower alkenyl, optionally substituted lower alkynyl, optionally substituted lower alkoxy or optionally substituted aryl,
m is an integer between 0 and 2,
the bond from X$^4$ binds with Y$^1$ and the other bond binds with Y$^2$, and the other bond can bind with X$^5$ when X$^5$ is NR$^{16}$ or CR$^{17}$R$^{18}$.

Much more preferable examples include a group of the formula:

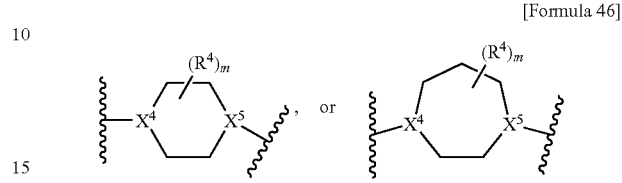

[Formula 46]

wherein
X$^4$ is N,
X$^5$ is NR$^{16}$ or CR$^{17}$R$^{18}$ wherein R$^{16}$ to R$^{18}$ are each independently hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl,
R$^4$ are each independently halogen, optionally substituted lower alkyl, optionally substituted lower alkenyl, optionally substituted lower alkynyl, optionally substituted lower alkoxy or optionally substituted aryl,
m is an integer between 0 and 2,
the bond from X$^4$ binds with Y$^1$ and the other bond binds with Y$^2$.

Especially preferable examples of m include 1 and 2. R$^4$ are especially each independently optionally substituted lower alkyl and the preferable examples include C1 to C4 straight or branched alkyl. Much more preferable examples include a group of the formula:

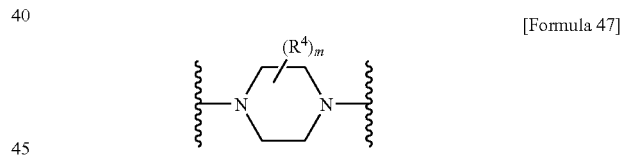

[Formula 47]

R$^4$ are each independently halogen, optionally substituted lower alkyl, optionally substituted lower alkenyl, optionally substituted lower alkynyl or optionally substituted lower alkoxy, and
m is an integer of 1 or 2, or
a group of the formula:

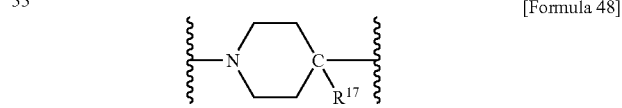

[Formula 48]

R$^{17}$ is optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl,
the bond from N binds with Y$^1$ and the bond from C binds with Y$^2$.

A group of the formula: —Y²Z¹— is a group of the formula:

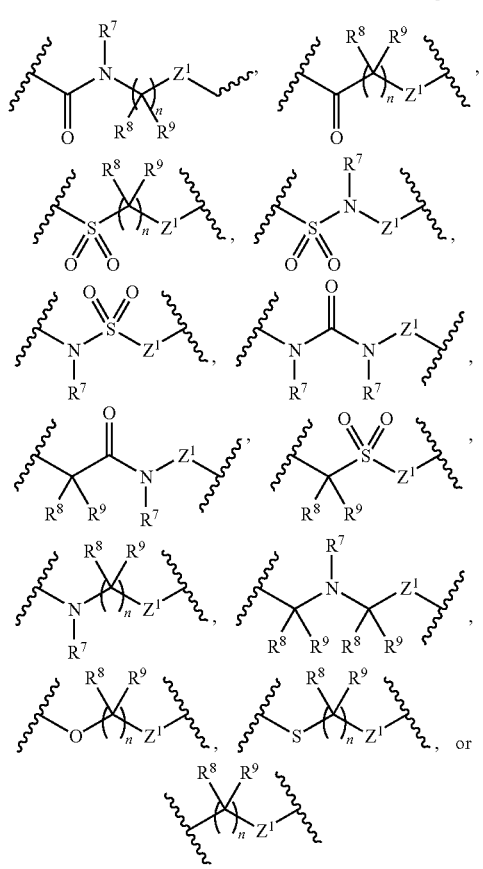

[Formula 49]

R⁷ are each independently hydrogen, optionally substituted lower alkyl or optionally substituted cycloalkyl, R⁸ and R⁹ are each independently hydrogen or optionally substituted lower alkyl, n is an integer between 0 and 3, Z¹ is a bond, —O—, —S— or —NR⁹— wherein R⁹ is hydrogen, optionally substituted lower alkyl, optionally substituted acyl, optionally substituted lower alkylsulfonyl or optionally substituted arylsulfonyl. Especially preferable examples include a group of the formula:

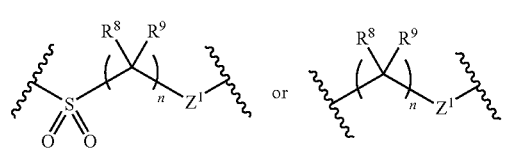

[Formula 50]

R⁸ and R⁹ are each independently hydrogen or lower alkyl, n is an integer between 0 and 2, and Z¹ is a bond, —O— or —S—.

The following embodiments are also preferable as a group of the formula: —Y¹-Ring A-Y²—Z¹—.

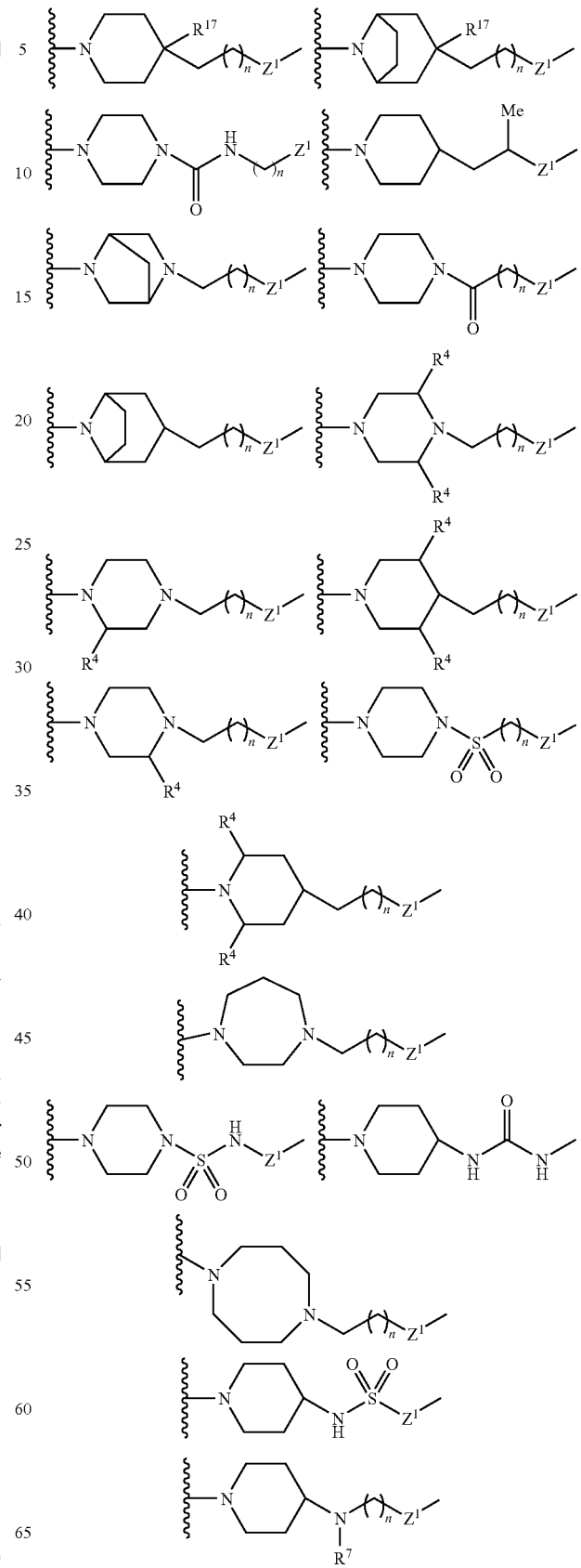

[Formula 51]

-continued

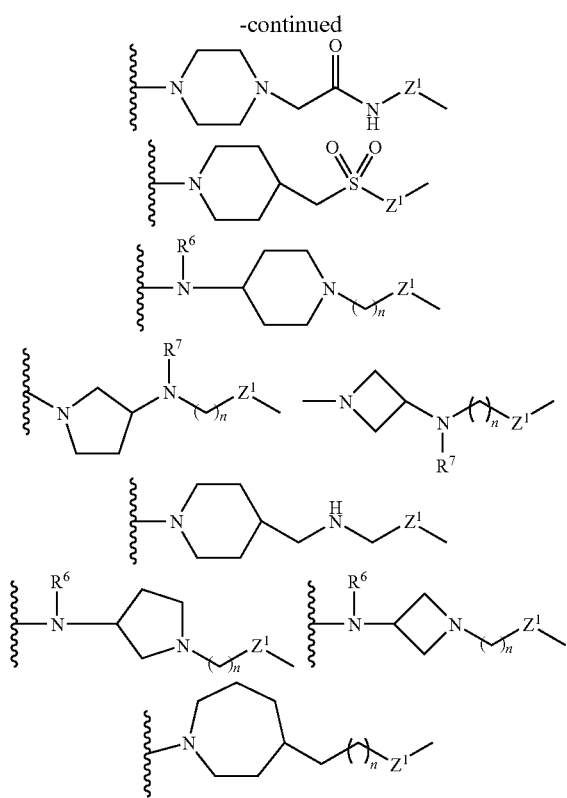

R[17] is hydrogen, optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl, R[6] is hydrogen or optionally substituted lower alkyl, R[7] is hydrogen, optionally substituted lower alkyl or optionally substituted cycloalkyl, R[4] are each independently halogen, optionally substituted lower alkyl, optionally substituted lower alkenyl, optionally substituted lower alkynyl, optionally substituted lower alkoxy or optionally substituted aryl, Z[1] is a bond, O, S or NR[9] wherein R[9] is hydrogen, optionally substituted lower alkyl, optionally substituted acyl, optionally substituted lower alkylsulfonyl or optionally substituted arylsulfonyl, n is an integer between 0 and 3.

R[17] is especially nonaromatic heterocycle. Preferable examples include pyrrolidinyl, piperidyl, azepanyl, morpholinyl and the like.

Ring B is optionally substituted aromatic carbocyclediyl or optionally substituted aromatic heterocyclediyl. Especially preferable examples include optionally substituted phenylene, optionally substituted furandiyl and optionally substituted thiophenediyl, and the substituent(s) of said phenylene, furandiyl or thiophendiyl is/are selected from a group consisting of halogen, lower alkyl and lower alkoxy.

Y[3] is a bond, optionally substituted lower alkylene optionally intervened by —O—, cycloalkylene optionally intervened by —O— or optionally substituted lower alkenylene. Especially preferable examples include a bond, optionally substituted lower alkylene, —O-optionally substituted lower alkylene and optionally substituted lower alkenylene, and the substituent(s) of said lower alkylene or lower alkenylene is/are selected from a group consisting of lower alkylene and halogen.

Z[2] is COOR[3], C(=NR[3])NR[14]OR[15], CONHCN or a group of the formula:

[Formula 52]

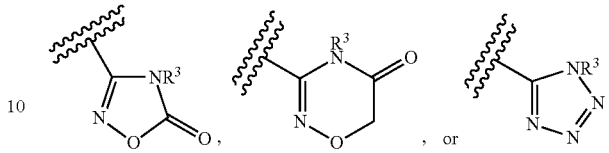

R[3], R[14] and R[15] are each independently hydrogen, optionally substituted lower alkyl, optionally substituted lower alkenyl, optionally substituted aryl or optionally substituted heteroaryl. Especially preferable examples include COORS wherein R[3] is hydrogen or optionally substituted lower alkyl.

The following embodiments are also preferable as a group of the formula: —Z[1]-Ring B—Y[3]—Z[2].

[Formula 53]

Z[1] is a bond, —O—, —S— or —NR[9]— wherein R[9] is hydrogen, optionally substituted lower alkyl, optionally substituted acyl, optionally substituted lower alkylsulfonyl or optionally substituted arylsulfonyl, and R, R' and R'' are each independently hydrogen, halogen, hydroxy, optionally substituted lower alkoxy, optionally substituted lower alkynyloxy, optionally substituted amino, mercapto, optionally substituted lower alkylthio, acyl, acyloxy, optionally substituted imino, carboxy, optionally substituted lower alkoxycarbonyl, optionally substituted carbamoyl, optionally substituted thiocarbamoyl, optionally substituted carbamoyloxy, optionally substituted thiocarbamoyloxy, optionally substituted sulfamoyl, optionally substituted lower alkylsulfonyl, optionally substituted lower alkylsulfonyloxy, cyano, nitro, optionally substituted cycloalkyl, optionally substituted cycloalkyloxy, optionally substituted aryl, optionally substituted aryloxy, optionally substituted arylthio, optionally substituted arylsulfonyl, optionally substituted arylsulfonyloxy, optionally substituted heterocycle, optionally substituted heterocyclyloxy, optionally substituted lower alkylene, optionally substituted lower alkylenedioxy or oxo.

A compound of the present invention includes producible and pharmaceutically acceptable salts of each compound. Examples of "a pharmaceutically acceptable salt" include salts of inorganic acid such as hydrochloric acid, sulfuric acid, nitric acid, phosphoric acid or the like; salts of organic acid such as paratoluenesulfonic acid, methanesulfonic acid, oxalic acid, citric acid or the like; salts of organic salt group such as ammonium, trimethylammonium or triethylammonium; salts of alkali metal such as sodium or potassium; and alkaline-earth metal salts such as calcium, magnesium or the like.

A compound of the present invention includes a solvate thereof and can be coordinate any number of solvent molecules to Compound (I). Hydrate is preferable.

When Compound (I) of the present invention has an asymmetric carbon atom, it contained racemic body and all stereoisomers (a diastereoisomer, an antipode or the like). When Compound (I) of the present invention has a double bond and there is geometrical isomer at a substituent position of the double bond, it includes both type of the isomers.

The popular methods for production of compounds of the present invention are described below.

Step A

[Formula 54]

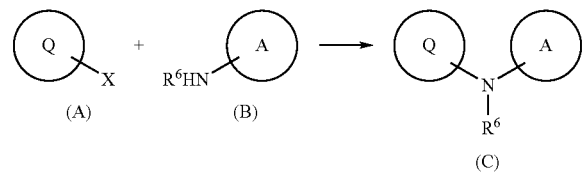

wherein X is halogen or the like, and the other symbols have the same meaning as defined in the above (1).

This step is a method for production of Compound (C) by reacting Compound (A) and (B).

This step is especially preferably carried out especially under the presence of base. Examples of the base include potassium carbonate, sodium carbonate, sodium hydrogencarbonate, sodium hydroxide, sodium hydride, triethylamine, N,N-diisopropylethylamine and the like. Examples of the reaction solvent include N,N-dimethylformamide, tetrahydrofuran, dioxane, methylene chloride, acetonitrile, dimethylsulfoxide and the like. The reaction can be performed at room temperature to 100° C.

The acid addition salt can be used as Compound (B). In that case, the value of the base used in the reaction is increased.

Step B

[Formula 55]

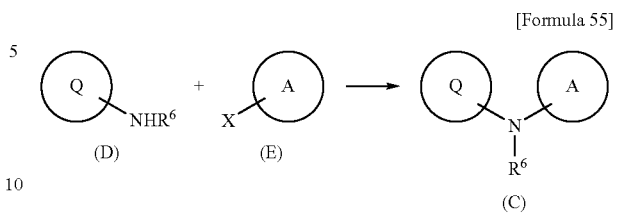

wherein X is halogen or the like, and the other symbols have the same meaning as defined in the above (1).

This step is a method for production of Compound (C) by reacting Compound (D) and (E).

This step can be carried out under the same conditions as Step B.

Step C

[Formula 56]

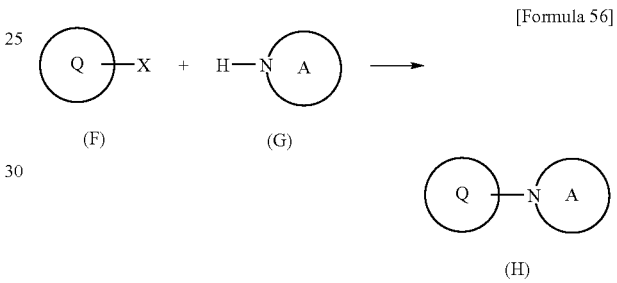

wherein X is halogen or the like, and the other symbols have the same meaning as defined in the above (1).

This step is a method for production of Compound (H) by reacting Compound (F) and (G).

This step can be carried out under the same conditions as Step A and B.

Step D

[Formula 57]

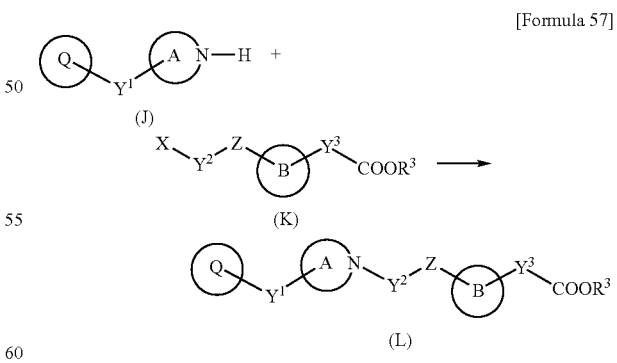

wherein X is halogen or the like, and the other symbols have the same meaning as defined in the above (1).

This step is a method for production of Compound (L) by reacting Compound (J) and (K).

This step can be carried out under the same conditions as Step A, B and C.

Step E

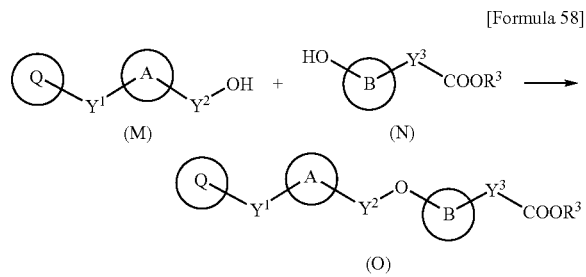

[Formula 58]

wherein each symbol has the same meaning as defined in the above (1).

This step is a method for production of Compound (O) by reacting Compound (M) and (N).

This step can be carried out by Mitsunobu reaction under the presence of azodicarboxylate and triphenylphosphine. Instead of azodicarboxylate, 1,1-azodicarbonyldipiperidine, N,N,N'N'-tetramethylazodicarboxamide or the like can be used. Instead of triphenylphosphine, tributyl phosphine or the like can be used. Examples of the reaction solvent include tetrahydrofuran, toluene, benzene and the like. The reaction can be carried out at room temperature.

Step F

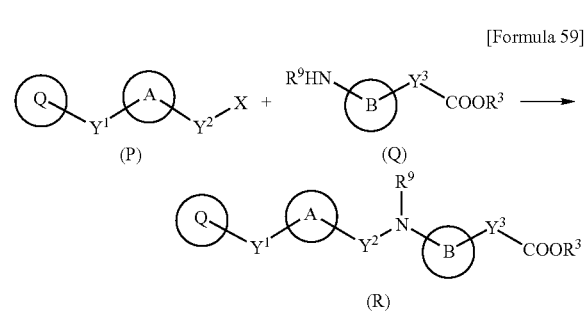

[Formula 59]

wherein X is halogen or the like, and the other symbols have the same meaning as defined in the above (1).

This step is a method for production of Compound (R) by reacting Compound (P) and (Q).

This step can be carried out under the same conditions as Step A, B, C and D.

Step G

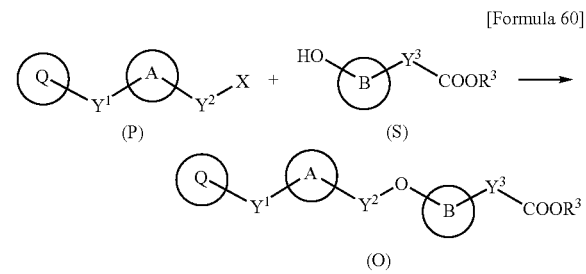

[Formula 60]

wherein X is halogen or the like, and the other symbols have the same meaning as defined in the above (1).

This step is a method for production of Compound (O) by reacting Compound (P) and (S).

This step can be carried out under the same conditions as Step A, B, C, D and F.

When the compound obtained by the above any step is ester of $COOR^3$, this compound is hydrolyze by the usual method to give carboxylic acid of COOH.

If necessary, at an appropriate step in the above method for production, any substituent can be transform to a different substituent by the well-known organic synthesized reaction.

For example, when any compound has halogen, it is reacted with alcohol in a solvent such as DMF, tetrahydrofuran or the like under the presence of base such as sodium hydride, potassium hydride or the like and deacid reagent such as alkali metal hydroxide, alkali metal hydrogencarbonate, alkali metal carbonate, organic base or the like at −20° C. to 100° C. to give a compound whose substituent is transformed to lower alkoxy.

When any compound has alkyl hydroxy, it is reacted with oxidizing agent such as pyridinium dichromate, Jones reagent, manganese dioxide, potassium permanganate, ruthenium tetroxide or the like in a solvent such as dimethyl formamide, tetrahydrofuran, dichloromethane, benzene, acetone or the like to give a compound whose substituent is transformed to carboxy.

If necessary, after amino or hydroxy of a compound is protected by the usual process at an appropriate step, it is subjected to the reaction and then deprotected by treatment with acid or base at an appropriate step.

As an amino protecting group, phthalimide, lower alkoxycarbonyl (e.g., butoxycarbonyl (Boc)), lower alkenyloxycarbonyl, halogenoalkoxycarbonyl, aryl lower alkoxycarbonyl, trialkylsilyl, lower alkylsulfonyl, halogeno lower alkylsulfonyl, arylsulfonyl, lower alkylcarbonyl, arylcarbonyl, aryl lower alkyl (e.g., benzyl) or the like can be used.

As a hydroxy protecting group, alkyl (e.g., t-butyl), aralkyl (triphenylmethyl or benzyl), trialkylsilyl (e.g., t-butyldimethylsilyl or triisopropylsilyl), alkyldiarylsilyl (e.g., t-butyl-diphenylsilyl), triaralkylsilyl (e.g., tribenzylsilyl), alkoxyalkyl (e.g., methoxymethyl, 1-ethoxyethyl or 1-methyl-1-methoxyethyl), alkoxyalkoxyalkyl (e.g., methoxyethoxymethyl), alkylthioalkyl (e.g., methylthiomethyl), tetrahydropyranyl (e.g., tetrahydropyran-2-yl or 4-methoxytetrahydropyran-4-yl), tetrahydrothiopyranyl (e.g., tetrahydrothiopyran-2-yl), tetrahydrofuranyl (e.g., tetrahydrofuran-2-yl), tetrahydrothiofuranyl (e.g., tetrahydrothiofuran-2-yl), aralkyloxyalkyl (e.g., benzyloxymethyl) alkylsulfonyl, acyl, p-toluenesulfonyl or the like can be used.

Deprotection reaction is carried out in a solvent such as tetrahydrofuran, dimethylformamide, diethylether, dichloromethane, toluene, benzene, xylene, cyelohexane, hexane, chloroform, ethyl acetate, butyl acetate, pentane, heptane, dioxane, acetone, acetonitrile or a mixed solvent thereof, by using base such as hydrazine, pyridine, sodium hydroxide, potassium hydroxide or the like or acid such as hydrochloric acid, trifluoroacetic acid, hydrofluoric acid or the like.

Step H

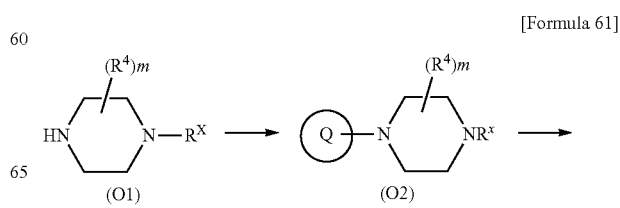

[Formula 61]

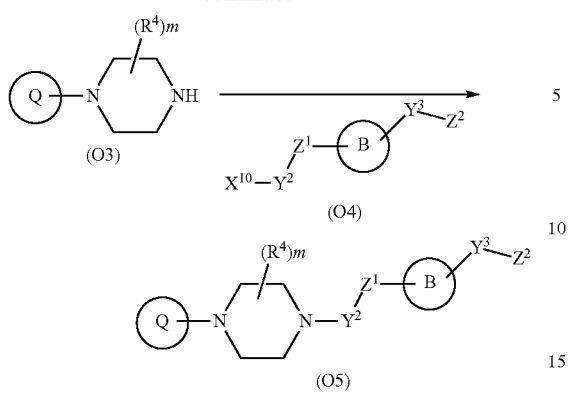

wherein $R^X$ is an amino protecting group (e.g., benzyl or tert-butoxycarbonyl) or the like, $X^{10}$ is halogen, and the other symbols have the same meanings as above.

Compound (O1) is reacted with a derivative having Ring Q under the presence of a base to give Compound (O2). The protecting group of the obtained Compound (O2) is removed and the compound is reacted with Compound (O4) to give Compound (O5).

Step I

[Formula 62]

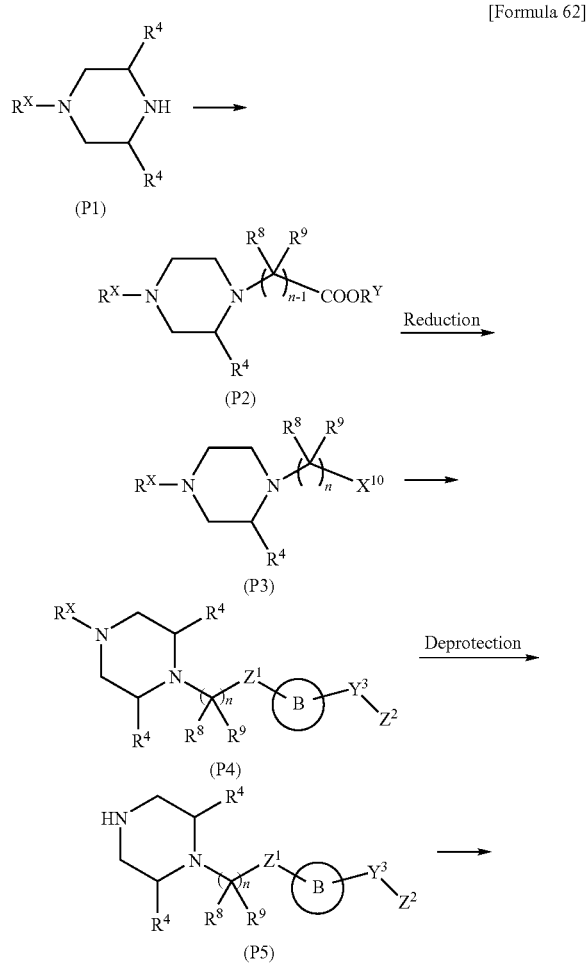

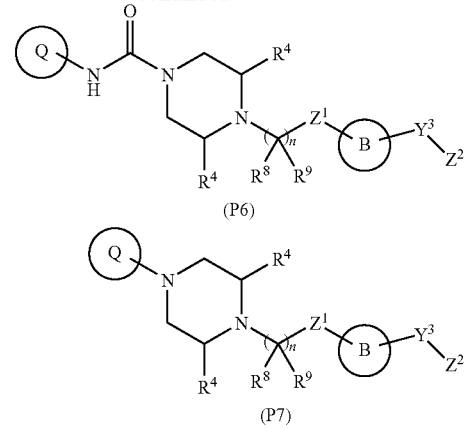

wherein $R^X$ is an amino protecting group (e.g., benzyl or tert-butoxycarbonyl) or the like, $R^Y$ is lower alkyl or the like, $X^{10}$ is hydroxy, $Z^1$ is O, S or $NR^9$, and the other symbols have the same meanings as above.

A compound of the formula: $X-C(R^8R^9)_{n-1}-COOR^Y$ is reacted to Compound (P1) under the presence of the base (e.g., potassium carbonate) to give Compound (P2). As the solvent, dimethylformamide or the like can be used.

The obtained Compound (P2) is reduced to give Compound (P3). The reduction can be used with lithium aluminium hydride or the like.

The obtained Compound (P3) is reacted with mesyl chloride or the like to transform $X^{10}$ to a leaving group and coupled with a compound having Ring B.

After that, Compound (P5) is obtained by deprotection of $R^X$ and reacted with phenylisocyanate derivatives or the like to give Compound (P6).

Compound (P7) can be also obtained by reacting with a compound having Ring Q.

A compound wherein $Z^1$ is —S— or —$NR^9$— can be obtained by transforming $X^{10}$ of Compound (P3) to halogen and reacting with a compound having Ring B.

Step J

[Formula 63]

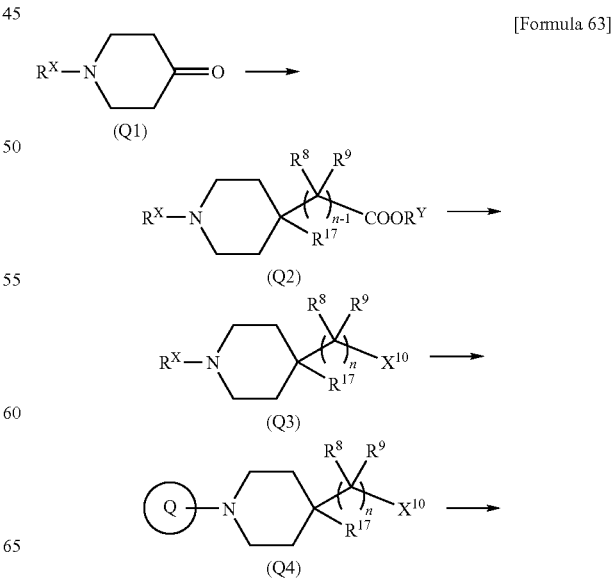

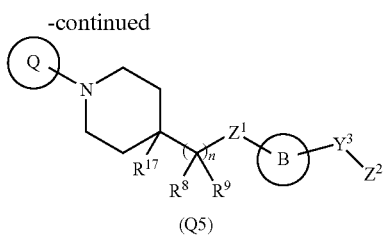

(Q5)

wherein $R^X$ is an amino protecting group (e.g., benzyl or tert-butoxycarbonyl) or the like, $R^Y$ is lower alkyl or the like, $X^{10}$ is hydroxy or halogen, $Z^1$ is —O—, —S— or —NR$^9$—, and the other symbols have the same meanings as above.

COOR$^Y$ is reduced by introducing from Compound (Q1) to Compound (Q2). The reduction can be carried out with lithium aluminium hydride or the like. Next, the deprotection of $R^X$ is carried out. When the protecting group is benzyl, the deprotection is carried out by a catalytic reduction or the like. After the deprotection, a compound having Ring Q is reacted under the presence of base (e.g., potassium carbonate) to give Compound (Q4). Next, a compound having Ring B is reacted to the obtained Compound (Q4) to give Compound (Q5). A compound wherein $Z^1$ is —S— or —NR$^9$— can be also obtained by transforming $X^{10}$ of Compound (Q4) to halogen and reacting with a compound having Ring B.

A pharmaceutical composition for PPAR agonist of the present invention can be effectively acted on all diseases concerning PPAR and especially for prevention and/or treatment of hyperlipidemia, dyslipidosis, disorder of lipid metabolism, Low HDL, High LDL, High VLDL, High TG, diabetes, hyperglycosemia, insulin resistance, obesity, bulimia, arteriosclerosis, atherosclerosis, hypertension, syndrome X, ischemic disease, inflammation, allergic disease (e.g., inflammatory bowel disease, rheumatoid arthritis, chronic pancreatitis, multiple sclerosis, glomerulosclerosis, psoriasis or eczema), osteoporosis, sterility, cancer (e.g., breast cancer, colonic cancer, colon cancer, ovarian cancer or lung cancer), Alzheimer's disease, parkinsonism or Basedow's disease. Especially, a compound having PPARδ selective agonistic activity in compounds of the present invention having PPAR agonistic activity can be a good medicine. The reason is, for example, that it can be expected to have a high HDL increasing activity or that the side effect can be lightened.

Furthermore, a compound of the present invention has the good characters, for example,
a) weak CYP enzyme inhibition
b) high water solubility
c) good drug disposition such as high bioavailability
d) low toxicity of anemia-inducing activity or the like, or
e) high metabolic stability.

When administering a compound of the present invention as a pharmaceutical composition for PPAR agonist, it can be administered orally or parenterally. For oral administration, the compound of the present invention can be used in any form of usual formulations, for example, tablets, granules, powders, capsules, pills, solutions, syrup, buccals, sublingual tablets or the like which are made by the usual process. For parenteral administration, the compound of the present invention can be used in any form of usual formulations, for example, injections such as intramuscular administration and intravenous administration, suppository, transdermal therapeutic agent, insufflation or the like. A compound of the present invention can be preferably used as an oral agent because it has high oral bioavailability.

The formulation according to the present invention may be manufactured by combining a curatively effective amount of a compound of the present invention with various pharmaceutically acceptable excipients such as binder, moistening agent, disintegrating agents, lubricant, diluents or the like, if necessary. When the formulation is injection, the compound of the present invention may be manufactured by sterilization treatment with an appropriate carrier.

For example, the excipient is lactose, saccharose, glucose, starch, calcium carbonate, crystalline cellulose or the like. The binder is methylcellulose, carboxy methylcellulose, hydroxy propylcellulose, gelatin, polyvinylpyrrolidone or the like. The disintegrating agent is carboxy methyl cellulose, carboxymethylcellulose sodium, starch, sodium alginate, powdered agar, sodium lauryl sulfate or the like. The lubricant is talc, magnesium stearate, macrogol or the like. As a basis for suppository, cocoa butter, macrogol, methylcellulose or the like can be used. When the present invention is manufactured as liquid medicine, emulsion injection or suspension injection, solubilizing agent, suspending agent, emulsifying agent, stabilizing agent, preservatives, isotonic agent or the like which is usually used can be appropriately added. In case of oral administration, sweetening agent, flavoring agent or the like can be added.

The dose as a pharmaceutical composition for PPAR agonist of a compound of the present invention is preferably established depending on age, body weight, kind of disease, conditions of the patient, the administration route or the like. In case of the oral administration for an adult, it is usually 0.05 to 100 mg/kg/day and preferably 0.1 to 10 mg/kg/day. In case of the parenteral administration, although it is very different depending on route of administration, it is usually 0.005 to 10 mg/kg/day and preferably 0.01 to 1 mg/kg/day. This can be separated and administrated at 1 time to few times a day.

EXAMPLE

The following examples are provided to explain in more detail and do not restrict the present invention.

Compounds in Reference Examples 1 to 6 were obtained by the methods described in US patent application publication no. US2004-0224997 or WO 95/22531.

Reference Example 1

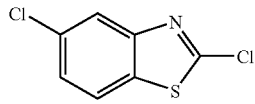

[Formula 64]

Yield: 88%, $^1$H-NMR (CDCl$_3$): δ7.41 (1H, dd, J=8.5, 2.0 Hz), 7.45 (1H, d, J=8.5 Hz), 7.95 (1H, d, J=2.0 Hz).

Reference Example 2

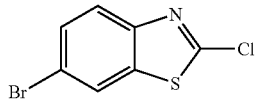

[Formula 65]

Yield: 90%, $^1$H-NMR (CDCl$_3$): δ7.60 (1H, dd, J=8.5, 2.0 Hz), 7.82 (1H, d, J=8.5 Hz), 7.93 (1H, d, J=2.0 Hz).

Reference Example 3

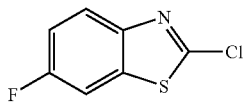

[Formula 66]

Yield: 76%, 1H-NMR (CDCl₃): δ7.23 (1H, td, J=8.0, 2.5 Hz), 7.48 (1H, dd, J=8.0, 2.5 Hz), 7.91 (1H, dd, J=8.0, 4.0 Hz).

Reference Example 4

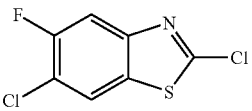

[Formula 67]

Yield: 65%, 1H-NMR (CDCl3): δ7.73 (1H, d, J=7.0 Hz), 7.82 (1H, d, J=9.0 Hz).

Reference Example 5

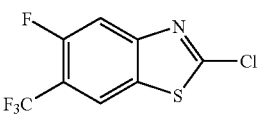

[Formula 68]

Yield: 89%, 1H-NMR (CDCl3): δ7.78 (1H, d, J=6.5 Hz), 8.06 (1H, d, J=10.5 Hz).

Reference Example 6

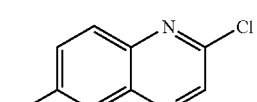

[Formula 69]

Yield: 66%, 1H-NMR (CDCl3): δ8.00 (1H, d, J=8.5 Hz), 8.17 (1H, d, J=8.5 Hz), 8.45 (1H, s), 8.89 (1H, s).

Reference Example 7

Preparation of 2-chloro-5-phenylthiazole

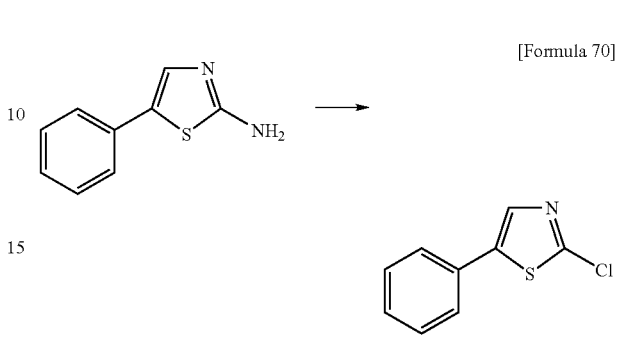

[Formula 70]

To a mixture of 2-amino-5-phenylthiazole described in Journal of Medicinal Chemistry, 1983, Vol. 26 (8), 1158-1163, (1.00 g; 5.67 mmol), copper (II) chloride dihydrate (1.94 g; 11.3 mmol), concentrated hydrochloric acid (8 ml) and acetic acid (8 ml) was added sodium nitrite (0.47 g; 6.80 mmol) under ice-cooling. The mixture was stirred at 40° C. for 1 hour. After returning the reaction solution to room temperature, water and chloroform were added and extracted. The organic layer was washed with brine, dried over anhydrous sodium sulphate, and evaporated under reduced pressure. The residue was purified by column chromatograph on silica gel (methylene chloride) to give 2-chloro-5-phenylthiazole as pale yellow crystal (0.68 g; 62%).

¹H-NMR (CDCl₃): δ7.32-7.53 (5H, m), 7.71 (1H, s).

Reference Example 8

Preparation of [3-(methoxymethoxy)-4-methylphenyl]acetonitrile

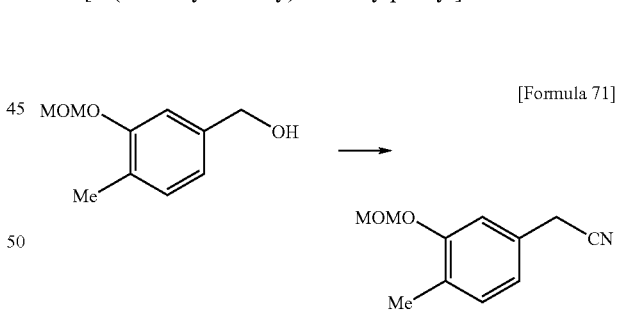

[Formula 71]

To a mixture of 3-(methoxymethoxy)-4-methylbenzyl alcohol described in WO2004/022551 (9.80 g; 53.78 mmol), triethylamine (7.90 ml; 56.47 mmol) and anhydrous THF (50 ml) was added dropwise methanesulfonyl chloride (4.40 ml; 56.47 mmol) under ice-cooling. The mixture was stirred at the same temperature for 1.5 hours. The precipitate was collected and condensed under reduced pressure. Then, to the residue were added sodium cyanide (7.91 g; 0.161 mol) and anhydrous N,N-dimethylformamide (50 ml). The mixture was stirred at room temperature for 3 days. Water and ethyl acetate were added to the reaction solution. The organic layer was separated, washed with brine, dried over anhydrous sodium sulphate, and evaporated under reduced pressure. The residue was purified by column chromatograph on silica gel (hexane: ethyl acetate=3:1) to give [3-(methoxymethoxy)-4-methylphenyl]acetonitrile as blackish brown oil (7.87 g; 77%).

$^1$H-NMR (CDCl$_3$): δ2.23 (3H, s), 3.49 (3H, s), 3.70 (2H, s), 5.21 (2H, s), 6.89 (1H, dd, J=7.5, 1.5 Hz), 6.98 (1H, d, J=1.5 Hz), 7.14 (1H, d, J=7.5 Hz).

Reference Example 9

Preparation of 3-(methoxymethoxy)-4-methylphenylacetate

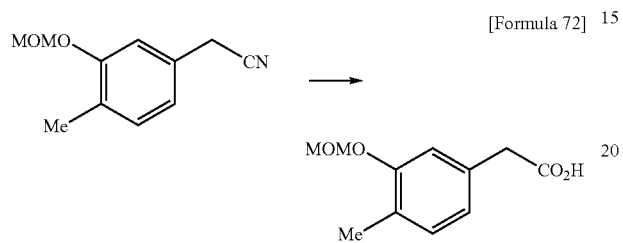

[Formula 72]

A mixture of [3-(methoxymethoxy)-4-methylphenyl]acetonitrile (7.87 g; 41.2 mmol), sodium hydroxide (8.30 g; 210 mmol), water (30 ml) and ethanol (70 ml) was refluxed for 5 hours. The reaction solution was condensed under reduced pressure. Water and ethyl acetate were added thereto and back-extracted. The water layer became pH=7 by adding 2N-aqueous hydrochloric acid. Ethyl acetate was added thereto and extracted. The organic layer was washed with brine, dried over anhydrous sodium sulphate, and evaporated under reduced pressure to give 3-(methoxymethoxy)-4-methylphenylacetate as pale blackish brown oil (5.52 g; 64%).

$^1$H-NMR (CDCl$_3$): δ2.22 (3H, s), 3.48 (3H, s), 3.59 (2H, s), 5.19 (2H, s), 6.83 (1H, dd, J=7.5, 1.5 Hz), 6.95 (1H, d, J=1.5 Hz), 7.13 (1H, d, J=7.5 Hz), 9.83 (1H, brs).

Reference Example 10

Preparation of [3-hydroxy-4-methylphenyl]ethyl acetate

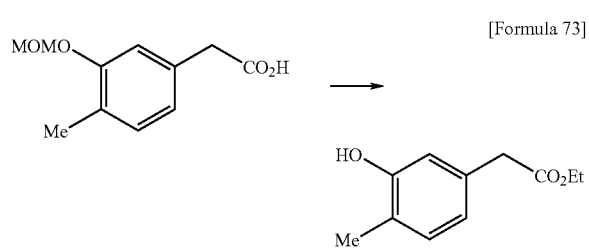

[Formula 73]

A mixture of [3-(methoxymethoxy)-4-methyl]phenylacetate (5.52 g; 26.3 mmol), concentrated hydrochloric acid (2 ml) and ethanol (20 ml) was refluxed for 3 hours. After cooling, the reaction solution was concentrated under reduced pressure. To the residue was added saturated aqueous sodium hydrogencarbonate to become pH=7. Ethyl acetate was added thereto and extracted. The organic layer was washed with brine, dried over anhydrous sodium sulphate, and evaporated under reduced pressure. The residue was purified by column chromatograph on silica gel (hexane:ethyl acetate=3:1) to give 3-hydroxy-4-methylphenylethyl acetate as pale yellow oil (2.40 g; 47%).

$^1$H-NMR (CDCl$_3$): δ1.26 (3H, t, J=7 Hz), 2.21 (3H, s), 3.53 (2H, s), 4.14 (2H, q, J=7 Hz), 5.13 (1H, s), 6.72 (1H, s), 6.74 (1H, d, J=7.5 Hz), 7.05 (1H, d, J=7.5 Hz).

Reference Example 11

Preparation of 2-chloro-5-(methoxyethoxy)toluene

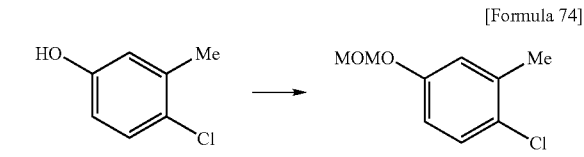

[Formula 74]

To a mixture of 4-chloro-3-methylcresol (15.0 g; 0.105 mol), N,N-diisopropylethylamine (23.3 ml; 0.137 mol) and THF (150 ml), was added dropwise chloromethylmethyl ether (9.50 ml; 0.126 mol) at room temperature. The mixture was stirred at 60° C. for 27.5 hours. The reaction solution was poured into ice water and extracted with ethyl acetate. The organic layer was washed with brine, dried over anhydrous sodium sulphate, and evaporated under reduced pressure. The residue was purified by column chromatograph on silica gel (hexane:ethyl acetate=5:1) to give 2-chloro-5-(methoxyethoxy)toluene as dark reddish-brown oil (17.7 g; 90%).

$^1$H-NMR (CDCl$_3$): δ2.34 (3H, s), 3.47 (3H, s), 5.13 (2H, s), 6.81 (1H, dd, J=8.5, 3.0 Hz), 6.92 (1H, d, J=3.0 Hz), 7.22 (1H, d, J=8.5 Hz).

Reference Example 12

Preparation of [2-chloro-5-(methoxymethoxy)phenyl]acetonitrile

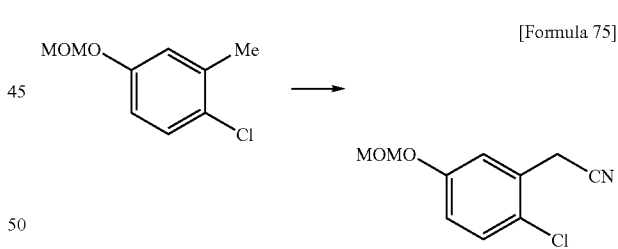

[Formula 75]

A mixture of 2-chloro-5-(methoxyethoxy)toluene (5.00 g; 26.8 mmol), N-bromosuccinimide (4.77 g; 26.8 mmol) and 2,2-azobis(isobutyronitrile) (0.09 g; 0.53 mmol) in carbon tetrachloride (25 ml) was refluxed for 2 hours. After air cooling and filtration the precipitate, the filtrate was condensed under reduced pressure. To the residue were added sodium cyanide (2.77 g; 80.4 mol) and anhydrous N,N-dimethylformamide (30 ml). The mixture was stirred at room temperature for 2 hours. Water and ethyl acetate were added to the reaction solution and extracted. The organic layer was washed with brine, dried over anhydrous sodium sulphate, and evaporated under reduced pressure. The residue was purified by column chromatograph on silica gel (hexane:ethyl acetate=6:1→4:1) to give [2-chloro-5-(methoxymethoxy)phenyl]acetonitrile as colorless oil (2.64 g; 47%).

¹H-NMR (CDCl₃): δ3.48 (3H, s), 3.80 (2H, s), 5.17 (2H, s), 6.99 (1H, dd, J=9.0, 3.0 Hz), 7.19 (1H, d, J=3.0 Hz), 7.32 (1H, d, J=9.0 Hz).

Reference Example 13

Preparation of [2-chloro-5-hydroxyphenyl]ethyl acetate

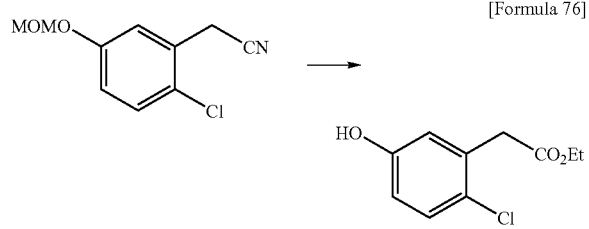

[Formula 76]

To a mixture of [2-chloro-5-(methoxymethoxy)phenyl]acetonitrile (2.60 g; 12.3 mmol), sodium hydroxide (2.46 g; 61.5 mmol), water (10.4 ml) and ethanol (33.8 ml) was stirred at 80° C. for 3 hours. After cooling, the solvent was evaporated under reduced pressure. To the residue was added water and 2N-aqueous hydrochloric acid to become acid and extracted with ethyl acetate. The organic layer was washed with brine, dried over anhydrous sodium sulphate, and evaporated under reduced pressure. To the residue, were added concentrated hydrochloric acid (0.65 ml) and ethanol (15 ml). The mixture was stirred at 80° C. for 8 hours. After cooling, the reaction solution was condensed under reduced pressure. The residue was purified by column chromatograph on silica gel (hexane:ethyl acetate=2:1) to give [2-chloro-5-hydroxyphenyl]ethyl acetate as colorless oil (0.69 g; 26%).

¹H-NMR (CDCl₃): δ1.28 (3H, t, J=7.0 Hz), 3.70 (2H, s), 4.20 (2H, q, J=7.0 Hz), 5.66 (1H, s), 6.64 (1H, dd, J=8.5, 3.0 Hz), 6.73 (1H, d, J=3.0 Hz), 7.18 (1H, d, J=8.5 Hz).

Reference Example 14

Preparation of [3-bromomethyl-5-methyl]phenoxy acetate

[Formula 77]

It was synthesized by the method described in Reference Example 77 of WO2004/022551.

¹H-NMR (CDCl₃); δ2.29 (3H, s), 2.35 (3H, s), 4.44 (2H, s), 6.85 (1H, s), 6.94 (1H, s), 7.08 (1H, s).

Reference Example 15

Preparation of 3-bromomethyl-5-methylmethyl benzoate

[Formula 78]

A mixture of 3,5-dimethylmethyl benzoate (5.00 g; 30.5 mmol), N-bromosuccinimide (5.69 g; 32.0 mmol) and 2,2-azobis(isobutyronitrile) (0.10 g; 0.61 mmol) in carbon tetrachloride (25 ml) was refluxed for 1 hour. After cooling and filtration of the precipitate, the filtrate was concentrated under reduced pressure. The residue was purified by column chromatograph on silica gel (hexane:ethyl acetate=10:1) to give 3-bromomethyl-5-methylmethyl benzoate as colorless oil (3.78 g; 51%).

¹H-NMR (CDCl₃): δ2.40 (3H, s), 3.92 (3H, s), 4.49 (2H, s), 7.40 (1H, s), 7.79 (1H, s), 7.89 (1H, s).

Compounds in Reference Examples 16 and 17 were obtained by similar methods as Reference Example 15.

Reference Example 16

[Formula 79]

Yield: 56%, ¹H-NMR (CDCl₃): δ3.93 (3H, s), 4.61 (2H, s), 7.47 (1H, d, J=8.5 Hz), 7.91 (1H, dd, J=8.5, 2 Hz), 8.11 (1H, d, J=2 Hz).

Reference Example 17

[Formula 80]

Yield: 75%, ¹H-NMR (CDCl₃): δ2.33 (3H, s), 4.40 (2H, s), 7.08 (1H, s), 7.10 (1H, s), 7.18 (1H, s).

Reference Example 18

Preparation of [(3-chloro-5-methyl)phenyl]acetonitrile

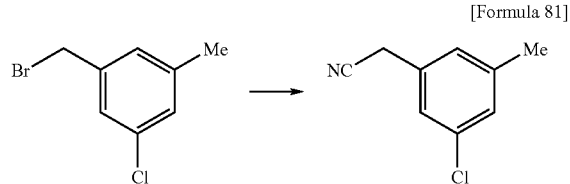

[Formula 81]

A mixture of (3-bromomethyl-5-chloro) toluene (1.67 g; 7.62 mmol), sodium cyanide (0.42 g; 8.51 mmol) and anhydrous N,N-dimethylformamide (15 ml) were stirred at 40° C. for 2 hours. Water and ethyl acetate were added to the reaction solution and extracted. The organic layer was washed with brine, dried over anhydrous sodium sulphate, and evaporated under reduced pressure. The residue was purified by column chromatograph on silica gel (methylene chloride) to give [(3-chloro-5-methyl)phenyl]acetonitrile as pale yellow oil (0.75 g; 59%).

$^1$H-NMR (CDCl$_3$): δ2.35 (3H, s), 3.69 (2H, s), 7.04 (1H, s), 7.12 (1H, s), 7.14 (1H, s).

Reference Example 19

Preparation of (3-chloro-5-methyl)phenylethyl acetate

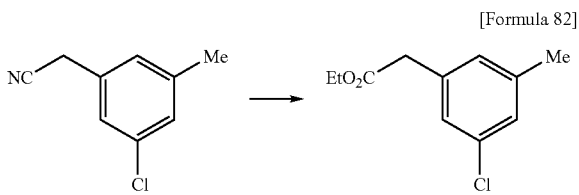

[Formula 82]

To [(3-chloro-5-methylphenyl)]acetonitrile (0.38 g; 2.29 mmol) were added 2N aqueous sodium hydroxide solution (2.1 ml) and ethanol (5 ml). The mixture was stirred at 80° C. for 1 hour. The reaction solution was concentrated under reduced pressure. To the residue were added water and 2N-aqueous HCl to become neutral. Ethyl acetate was added thereto and extracted. The organic layer was washed with brine, dried over anhydrous sodium sulphate, and evaporated under reduced pressure to give colorless crystal. Concentrated sulfuric acid (0.02 ml) and ethanol (2 ml) were added thereto, and the mixture was refluxed for 5 hours. The reaction solution was concentrated under reduced pressure. To the residue were added water and 2N-aqueous sodium hydroxide solution to become neutral. Ethyl acetate was added thereto and extracted. The organic layer was washed with brine, dried over anhydrous sodium sulphate, and evaporated under reduced pressure. The residue was purified by column chromatograph on silica gel (hexane:ethyl acetate=6:1) to give 3-chloro-5-methylphenylethyl acetate as colorless oil (0.31 g; 63%).

$^1$H-NMR (CDCl$_3$): δ1.26 (3H, t, J=7.2 Hz), 2.32 (3H, s), 3.53 (2H, s), 4.16 (2H, q, J=7.2 Hz), 6.97 (1H, s), 7.08 (2H, s).

Reference Example 20

Preparation of [3-bromomethyl-5-chloro]phenylethyl acetate

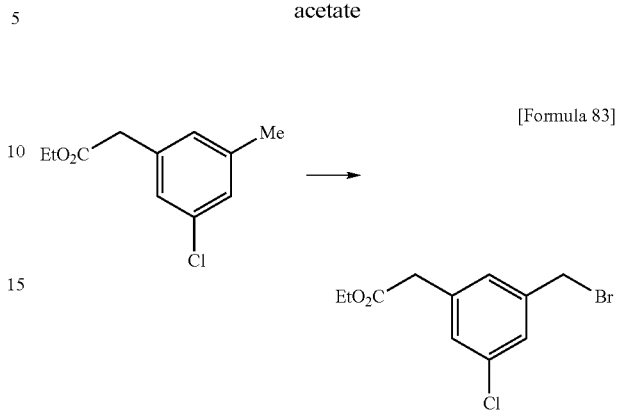

[Formula 83]

A mixture of 3-chloro-5-methylphenylethyl acetate (0.20 g; 0.958 mol), N-bromosuccinimide (0.21 g; 1.21 mmol) and 2,2-azobis(isobutyronitrile) (0.01 g; 0.037 mmol) in carbon tetrachloride (2 ml) were refluxed for 2 hours. After cooling and filtration of the precipitate, the filtrate was condensed under reduced pressure. The residue was purified by column chromatograph on silica gel (hexane:ethyl acetate=20:1) to give 3-bromomethyl-5-chlorophenylethyl acetate as colorless oil (0.16 g; 57%).

$^1$H-NMR (CDCl3): δ1.27 (3H, t, J=7.2 Hz), 3.58 (2H, s), 4.17 (2H, t, J=7.2 Hz), 4.42 (2H, s), 7.20 (1H, s), 7.22 (1H, s), 7.30 (1H, s).

Compounds in Reference Examples 21 and 22 were synthesized as above.

Reference Example 21

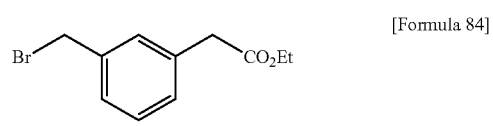

[Formula 84]

Yield: 56%, 1H-NMR (CDCl3): δ1.26 (3H, t, J=7.0 Hz), 3.61 (2H, s), 4.16 (2H, q, J=7.0 Hz), 4.48 (2H, s), 7.18-7.38 (4H, m).

Reference Example 22

[Formula 85]

Yield: 70%, 1H-NMR (CDCl3): δ1.28 (3H, t, J=7 Hz), 3.51 (3H, s), 3.59 (2H, s), 4.17 (2H, q, J=7 Hz), 4.45 (2H, s), 7.04 (1H, s), 7.12 (2H, s).

Reference Example 23

Preparation of 4-hydroxy-3-methylethyl benzoate

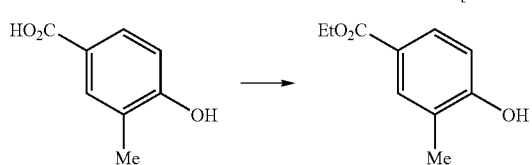

[Formula 86]

A mixture of 4-hydroxy-3-methyl benzoic acid (3.01 g; 19.78 mmol), concentrated sulfuric acid (0.20 ml) and ethanol (40 ml) was refluxed for 6 hours. The reaction solution was concentrated under reduced pressure. To the residue were added water and 2N-aqueous sodium hydroxide solution to become neutral. Ethyl acetate was added and extracted. The organic layer was washed with brine, dried over anhydrous sodium sulphate, and evaporated under reduced pressure to give 4-hydroxy-3-methylethyl benzoate as yellow crystal (3.40 g; 95

$^1$H-NMR (CDCl$_3$): δ1.38 (3H, t, J=7.2 Hz), 2.28 (3H, s), 4.35 (2H, q, J=7.2 Hz), 5.75 (1H, s), 6.81 (1H, d, J=8.1 Hz), 8.40 (1H, d, J=8.1 Hz), 7.84 (1H, s).

Reference Example 24

Preparation of 4-(methoxymethoxy)-3-methylethyl benzoate

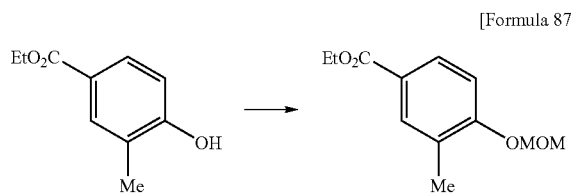

[Formula 87]

A mixture of 4-hydroxy-3-methylethyl benzoate (2.15 g; 11.93 mmol), methoxymethoxychloride (1.60 ml; 21.2 mmol), diisopropylethylamine (4.10 ml; 23.9 mmol) and THF (40 ml) was refluxed at 60° C. for 9 hours. After cooling, water and ethyl acetate were added to the reaction solution and extracted. The organic layer was washed with brine, dried over anhydrous sodium sulphate, and evaporated under reduced pressure. The residue was purified by column chromatograph on silica gel (hexane:ethyl acetate=20:1) to give 4-(methoxymethoxy)-3-methylethyl benzoate as colorless oil (1.94 g; 73%).

$^1$H-NMR (CDCl$_3$): δ1.38 (3H, t, J=7.2 Hz), 2.27 (3H, s), 3.49 (3H, s), 4.34 (2H, q, J=7.2 Hz), 5.26 (2H, s), 7.05 (1H, d, J=9.3 Hz), 7.84-7.86 (2H, m).

Reference Example 25

Preparation of [4-(methoxymethoxy)-3-methyl]benzyl alcohol

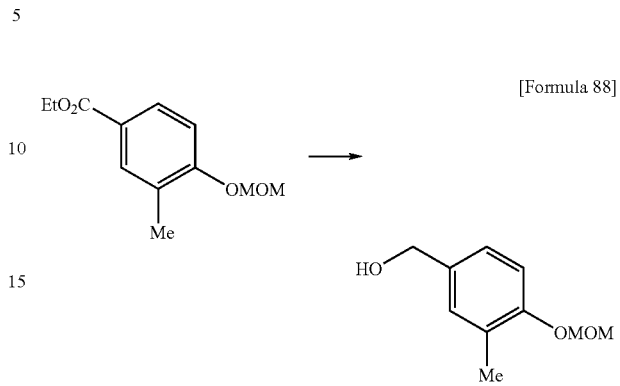

[Formula 88]

To a suspension of lithium aluminium hydride (0.26 g; 6.76 mmol) in anhydrous THF (5 ml) were added dropwise a mixture of 4-(methoxymethoxy)-3-methylethyl benzoate (1.02 g; 4.55 mmol) and anhydrous THF (10 ml) at 0° C. After stirring at the same temperature for 1 hour, 2N-aqueous sodium hydroxide solution was added dropwise to the reaction solution. The residue was filtrated. To the filtrate were added ethyl acetate and brine. The organic layer was separated and dried over anhydrous sodium sulphate and the solvent was evaporated under reduced pressure. The residue was purified by column chromatograph on silica gel (hexane:ethyl acetate=3:1) to give [4-(methoxymethoxy)-3-methyl]benzyl alcohol as colorless oil (0.80 g; 97%).

$^1$H-NMR (CDCl$_3$): δ1.63 (1H, brs), 2.25 (3H, s), 3.48 (3H, s), 4.59 (2H, d, J=3.9 Hz), 5.20 (2H, s), 7.01-7.17 (3H, m)

Reference Example 26

Preparation of 5-chloromethyl-2-(methoxymethoxy)toluene

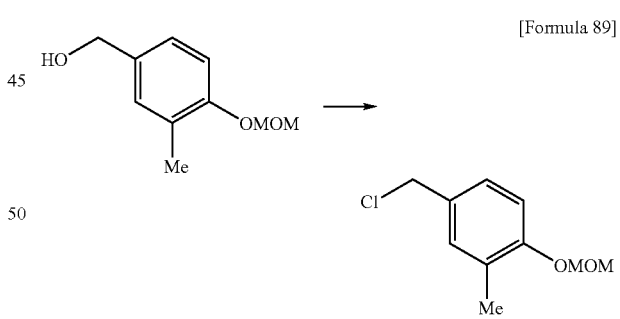

[Formula 89]

To a mixture of [4-(methoxymethoxy)-3-methyl]benzyl alcohol (0.49 g; 2.69 mmol), triethylamine (0.42 ml; 3.01 mmol) and methylene chloride (14 ml) was added dropwise methanesulfonyl chloride (0.23 ml; 2.97 mmol) under ice-cooling. The mixture was stirred for 4.5 hours. The reaction solution was concentrated under reduced pressure. The residue was purified by column chromatograph on silica gel (hexane:ethyl acetate=6:1) to give 5-chloromethyl-2-(methoxymethoxy)toluene as pale blackish brown oil (0.53 g; 99%).

$^1$H-NMR (CDCl$_3$): δ2.25 (3H, s), 3.48 (3H, s), 4.54 (2H, s), 5.20 (2H, s), 7.02 (1H, d, J=8.4 Hz), 7.14-7.18 (2H, m).

Reference Example 27

The following compound was synthesized by referring to Synthetic Communications, 2004, Vol. 34, 4111 to 4118.

Synthesis of 2-(N-chloroacetamide)methyl butanoate

[Formula 90]

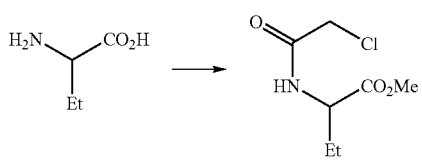

To a solution of 2-aminobutanoic acid (10.0 g; 96.97 mmol) in methanol (65 ml) was added dropwise thionyl chloride (30 ml; 411.28 mmol) under ice-cooling. The mixture was stirred at room temperature for 18 hours. The reaction solution was concentrated under reduced pressure. Diisopropyl ether (20 ml) was added to the residue. The mixture was azeotroped under reduced pressure to give colorless crystal.

To the above crystal (5.00 g) were added water (15 ml) and sodium hydrogencarbonate (6.66 g; 79.28 mmol) and added dropwise a solution of chloroacetylchloride (2.6 ml; 32.64 mmol) in toluene (10 ml) under ice-cooling. The mixture was stirred at room temperature for 18 hours. The reaction solution was separated and the organic layer was dried over anhydrous sodium sulphate. The solvent was evaporated under reduced pressure. The residue was purified by column chromatograph on silica gel (hexane:ethyl acetate=2:1) to give 2-(N-chloroacetamide)methyl butanoate as colorless oil (4.75 g; 75%).

1H-NMR (CDCl3): δ0.94 (3H, t, J=7.2 Hz), 1.74-1.86 (1H, m), 1.8-2.02 (1H, m), 3.78 (3H, s), 4.08 (2H, s), 4.59 (1H, q, J=6.6 Hz), 7.07 (1H, s).

Compounds in Reference Examples 28 to 37 were obtained as above.

Reference Example 28

[Formula 91]

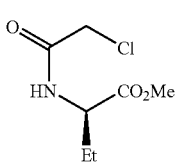

Yield: 74%, 1H-NMR (CDCl3): δ0.94 (3H, t, J=7.5 Hz), 1.70-2.00 (2H, m), 3.78 (3H, s), 4.09 (2H, s), 4.54-4.63 (1H, m), 7.10 (1H, brs).

Reference Example 29

[Formula 92]

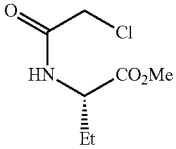

Yield: 70%, 1H-NMR (CDCl3): δ0.94 (3H, t, J=7.5 Hz), 1.65-2.00 (2H, m), 3.78 (3H, s), 4.11 (2H, s) 4.50-4.65 (1H, m), 7.09 (1H, brs).

Reference Example 30

[Formula 93]

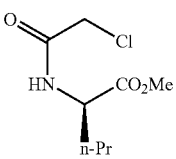

Yield: 97%, 1H-NMR (CDCl3): δ0.95 (3H, t, J=7.2 Hz), 1.26-1.41 (2H, m), 1.66-1.78 (1H, m), 1.81-1.89 (1H, m), 3.77 (3H, s), 4.08 (2H, s), 4.62 (1H, dt, J=7.8 Hz), 7.03 (1H, s)

Reference Example 31

[Formula 94]

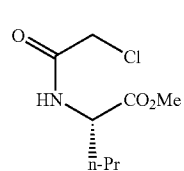

Yield: 91%, 1H-NMR (CDCl3): δ0.95 (3H, t, J=7.5 Hz), 1.24-1.43 (2H, m), 1.66-1.78 (1H, m), 1.81-1.93 (1H, m), 3.77 (3H, s), 4.08 (2H, s), 4.62 (1H, q, J=7.5 Hz), 7.02 (1H, s)

Reference Example 32

[Formula 95]

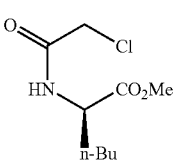

Yield: 99%, 1H-NMR (CDCl3): δ0.91 (3H, t, J=7 Hz), 1.23-1.40 (4H, m), 1.67-1.80 (1H, m), 1.81-1.96 (1H, m), 3.77 (3H, s), 4.08 (2H, s), 4.57-4.65 (1H, m), 7.03 (1H, brs).

Reference Example 33

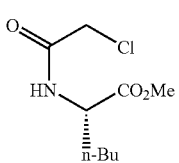
[Formula 96]

Yield: 86%, 1H-NMR (CDCl3): δ0.91 (3H, t, J=7 Hz), 1.23-1.40 (4H, m), 1.65-1.80 (1H, m), 1.82-1.95 (1H, m), 3.77 (3H, s), 4.08 (2H, s), 4.55-4.65 (1H, m), 7.02 (1H, brs).

Reference Example 34

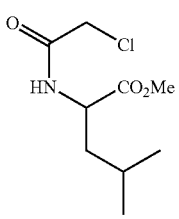
[Formula 97]

Yield: 93%, 1H-NMR (CDCl3): δ0.96 (6H, d, J=6.0 Hz), 1.58-1.74 (3H, m), 3.76 (3H, s), 4.08 (2H, s), 4.66 (1H, t, J=8.4 Hz), 6.90 (1H, br)

Reference Example 35

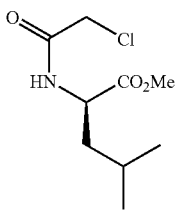
[Formula 98]

Yield: quant. %, 1H-NMR (CDCl3): δ0.96 (6H, d, J=6.0 Hz), 1.54-1.78 (3H, m), 3.76 (3H, s), 4.08 (2H, s), 4.60-4.70 (1H, m), 6.83-6.95 (1H, m).

Reference Example 36

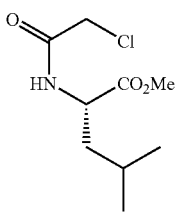
[Formula 99]

Yield: 93%, 1H-NMR (CDCl3): δ0.95 (6H, d, J=6 Hz), 1.56-1.75 (3H, m), 3.76 (3H, s), 4.08 (2H, s), 4.60-4.70 (1H, m), 6.93 (1H, brs).

Reference Example 37

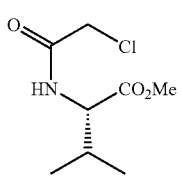
[Formula 100]

Yield: 90%, 1H-NMR (CDCl3): δ0.96 (6H, t, J=6.5 Hz), 2.16-2.30 (1H, m), 3.77 (3H, s), 4.10 (2H, s), 4.51-4.60 (1H, m), 7.04 (1H, brs).

Reference Example 38

Synthesis of 1-benzyl-3-ethylpiperazine-2,5-dion

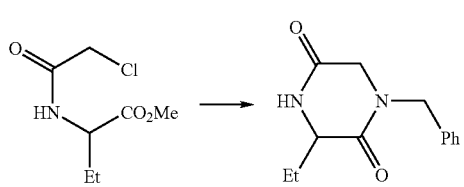
[Formula 101]

A mixture of 2-(N-chloroacetamide)methyl butanoate (4.00 g; 20.71 mmol), triethylamine (8.8 ml; 63.14 mmol), benzylamine (2.8 ml; 25.64 mmol) and methanol (45 ml) was refluxed for 16 hours. The reaction solution was concentrated under reduced pressure. Water and ethyl acetate were added to the residue and extracted. To the organic layer was added 1N aqueous hydrochloric acid to separate. To the organic layer was added aqueous sodium hydrogencarbonate water solution to become neutral. The organic layer was washed with brine, dried over anhydrous sodium sulphate, and evaporated under reduced pressure. The residue was washed with diisopropyl ether to give 1-benzyl-3-ethylpiperazine-2,5-dion as colorless crystal (1.58 g; 33%).

1H-NMR (CDCl3): δ0.98 (3H, t, J=7.2 Hz), 1.71-2.02 (2H, m), 3.84 (2H, dd, J=0.9, 5.1 Hz), 4.03-4.08 (1H, m), 4.51 (1H, d, J=14.4 Hz), 4.71 (1H, d, J=14.4 Hz), 7.25-7.36 (5H, m)

Compounds in Reference Examples 39 to 48 were obtained as above.

Reference Example 39

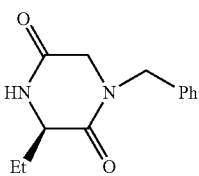
[Formula 102]

Yield: 44%, 1H-NMR (CDCl3): δ0.98 (3H, t, J=7.5 Hz), 1.83-2.03 (2H, m), 3.83 (2H, d, J=5.5 Hz), 4.00-4.10 (1H, m), 4.50 (1H, d, J=14.5 Hz), 4.71 (1H, d, J=14.5 Hz), 7.05 (1H, brs), 7.23-7.40 (5H, m).

Reference Example 40

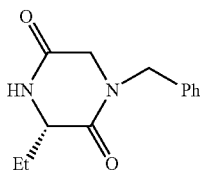

[Formula 103]

Yield: 32%, 1H-NMR (CDCl3): δ0.98 (3H, t, J=7.5 Hz), 1.85-2.05 (2H, m), 3.83 (2H, dd, J=6, 1 Hz), 4.02-4.10 (1H, m), 4.50 (1H, d, J=14.5 Hz), 4.71 (1H, d, J=14.5 Hz), 6.95 (1H, brs), 7.20-7.40 (5H, m).

Reference Example 41

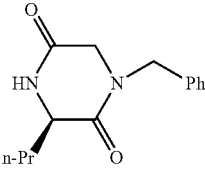

[Formula 104]

Yield: 41%, 1H-NMR (CDCl3): δ0.97 (3H, t, J=7.2 Hz), 1.36-1.48 (2H, m), 1.82-1.90 (2H, m), 3.83 (2H, dd, J=0.9, 5.4 Hz), 4.07 (1H, td, J=2.6, 5.7 Hz), 4.60 (2H, dd, J=14.1, 39.9 Hz), 7.24-7.38 (5H, m)

Reference Example 42

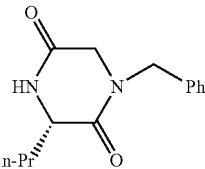

[Formula 105]

Yield: 45%, 1H-NMR (CDCl3): δ0.97 (3H, t, J=7.2 Hz), 1.36-1.48 (2H, m), 1.82-1.90 (2H, m), 3.83 (2H, dd, J=0.9, 5.4 Hz), 4.04-4.09 (1H, m), 4.53 (1H, d, J=14.4 Hz), 4.67 (1H, d, J=14.4 Hz), 7.24-7.39 (5H, m)

Reference Example 43

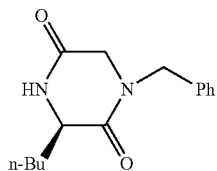

[Formula 106]

Yield: 49%, 1H-NMR (CDCl3): δ0.85-1.00 (3H, m), 1.24-1.45 (4H, m), 1.80-1.96 (2H, m), 3.83 (2H, d, J=6 Hz), 4.02-4.12 (1H, m), 4.53 (1H, d, J=14.5 Hz), 4.67 (1H, d, J=14.5 Hz), 6.68 (1H, brs), 7.21-7.40 (5H, m).

Reference Example 44

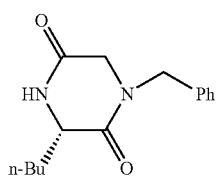

[Formula 107]

Yield: 43%, 1H-NMR (CDCl3): δ0.85-0.95 (3H, m), 1.30-1.50 (4H, m), 1.80-1.98 (2H, m), 3.72-3.91 (2H, m), 4.04-4.10 (1H, m), 4.53 (1H, d, J=14.5 Hz), 4.67 (1H, d, J=14.5 Hz), 6.45 (1H, brs), 7.23-7.40 (5H, m).

Reference Example 45

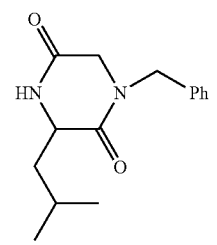

[Formula 108]

Yield: 34%, 1H-NMR (CDCl3): δ0.97 (6H, dd, J=6.0, 8.1 Hz), 1.61-1.73 (2H, m), 1.76-1.88 (1H, m), 3.83 (2H, d, J=6.3 Hz), 4.02-4.07 (1H, m), 4.59 (2H, q, J=14.7 Hz), 6.65 (1H, s), 7.23-7.35 (5H, m)

Reference Example 46

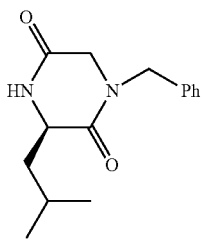

[Formula 109]

Yield: 55%, 1H-NMR (CDCl3): δ0.96 (3H, d, J=6.5 Hz), 0.98 (3H, d, J=6.5 Hz), 1.58-1.89 (3H, m), 3.80 (1H, d, J=17.5 Hz), 3.83 (1H, d, J=17.5 Hz), 4.01-4.10 (1H, m), 4.55 (1H, d, J=14.5 Hz), 4.65 (1H, d, J=14.5 Hz), 6.66 (1H, s), 7.21-7.40 (5H, m).

Reference Example 47

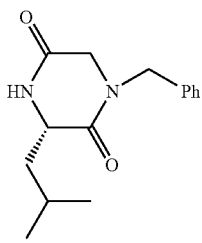

[Formula 110]

Yield: 50%, 1H-NMR (CDCl3): δ0.90-1.05 (6H, m), 1.58-1.90 (3H, m), 3.83 (2H, d, J=6.5 Hz), 4.02-4.10 (1H, m), 4.54 (1H, d, J=14.5 Hz), 4.65 (1H, d, J=14.5 Hz), 6.75 (1H, brs), 7.20-7.40 (5H, m).

Reference Example 48

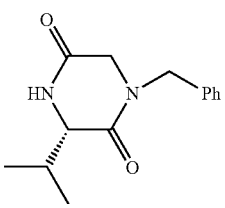

[Formula 111]

Yield: 12%, 1H-NMR (CDCl3): δ0.88 (3H, d, J=6.5 Hz), 1.02 (3H, d, J=6.5 Hz), 2.42-2.55 (1H, m), 3.83 (2H, d, J=11 Hz), 3.90-3.96 (1H, m), 4.45 (1H, d, J=14 Hz), 4.77 (1H, d, J=14 Hz), 6.43 (1H, brs), 7.21-7.45 (5H, m).

Reference Example 49

Synthesis of 1-benzyl-3-ethylpiperazine

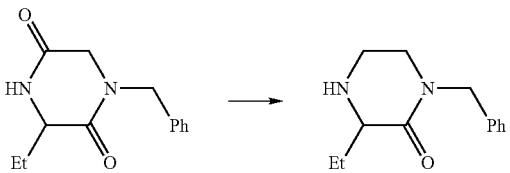

[Formula 112]

To a suspension of lithium aluminium hydride (0.87 g; 22.9 mmol) in anhydrous THF (20 ml) was added dropwise a solution of 1-benzyl-3-ethylpiperazine-2,5-dion (1.50 g; 6.46 mmol) in anhydrous THF (10 ml) under ice-cooling. After stirring at room temperature for 18 hours, a mixture of water (0.25 ml) and THF (5 ml) and 2N-aqueous sodium hydroxide solution (0.5 ml) were added dropwise sequentially under ice-cooling. The mixture was stirred at room temperature for 1 hour. After filtration of aluminium hydroxide, the filtrate was condensed under reduced pressure. To the residue were added ethyl acetate and brine to separate. The organic layer was dried over anhydrous sodium sulphate. The solvent was evaporated under reduced pressure to give 1-benzyl-3-ethylpiperazine as pale yellow oil (1.29 g; 98%).

1H-NMR (CDCl3): δ0.90 (3H, t, J=7.5 Hz), 1.30-1.40 (2H, m), 1.70 (1H, t, J=10.8 Hz), 2.01 (1H, dt, J=3.6, 10.8 Hz), 2.61-2.70 (1H, m), 2.73-2.89 (2H, m), 2.92-3.00 (1H, m), 3.49 (2H, dt, J=6.9 Hz), 3.68 (1H, t, J=5.7 Hz), 7.23-7.31 (5H, m)

Compounds in Reference Examples 50 to 60 were obtained as above.

Reference Example 50

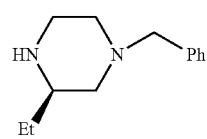

[Formula 113]

Yield: 96%, 1H-NMR (CDCl3): δ0.90 (3H, t, J=7.5 Hz), 1.29-1.36 (2H, m), 1.70 (1H, t, J=10.5 Hz), 2.01 (1H, td, J=11, 3.5 Hz), 2.60-3.00 (5H, m), 3.46 (1H, d, J=13 Hz), 3.53 (1H, d, J=13 Hz), 7.20-7.40 (5H, m).

Reference Example 51

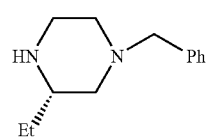

[Formula 114]

Yield: 89%, 1H-NMR (CDCl3): δ0.90 (3H, t, J=7.5 Hz), 1.35 (2H, quant, J=7.5 Hz), 1.70 (1H, t, J=10.5 Hz), 2.01 (1H, td, J=11, 3.5 Hz), 2.60-3.00 (5H, m), 3.46 (1H, d, J=13 Hz), 3.53 (1H, d, J=13 Hz), 7.20-7.40 (5H, m).

Reference Example 52

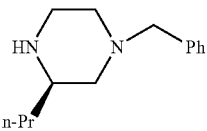

[Formula 115]

Yield: 73%, 1H-NMR (CDCl3): δ0.89 (3H, t, J=6.9 Hz), 1.29-1.40 (4H, m), 1.69 (1H, t, J=9.9 Hz), 2.00 (1H, td, J=3.6, 10.5 Hz), 2.73-2.99 (5H, m), 3.49 (2H, d, J=5.4 Hz), 7.21-7.35 (5H, m)

Reference Example 53

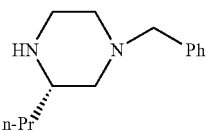

[Formula 116]

Yield: 68%, 1H-NMR (CDCl3): δ0.89 (3H, t, J=6.8 Hz), 1.26-1.40 (4H, m), 1.69 (1H, t, J=9.9 Hz), 2.00 (1H, td, J=3.6, 10.8 Hz), 2.72-2.95 (5H, m), 3.49 (2H, d, J=5.1 Hz), 7.23-7.32 (5H, m)

Reference Example 54

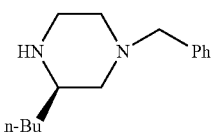

[Formula 117]

Yield: quant. %, 1H-NMR (CDCl3): δ0.88 (3H, t, J=6.5 Hz), 1.20-1.40 (6H, m), 1.50 (1H, brs), 1.70 (1H, t, J=10 Hz), 2.00 (1H, td, J=11, 4 Hz), 2.65-3.00 (5H, m), 3.46 (1H, d, J=13 Hz), 3.52 (1H, d, J=13 Hz), 7.20-7.40 (5H, m).

Reference Example 55

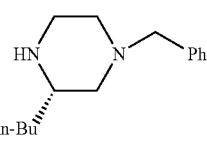

[Formula 118]

Yield: quant. %, 1H-NMR (CDCl3): δ0.88 (3H, d, J=6.5 Hz), 1.20-1.39 (6H, m), 1.70 (1H, t, J=10 Hz), 2.00 (1H, td, J=11, 4 Hz), 2.65-3.00 (5H, m), 3.46 (1H, d, J=13 Hz), 3.52 (1H, d, J=13 Hz), 7.20-7.40 (5H, m).

Reference Example 56

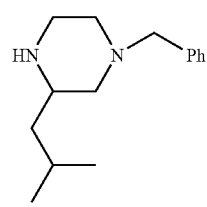

[Formula 119]

Yield: 88%, 1H-NMR (CDCl3): δ0.88 (6H, dd, J=5.1, 6.6 Hz), 1.09-1.26 (2H, m), 1.59-1.72 (3H, m), 2.00 (1H, dt, J=3.9, 10.8 Hz), 2.74-2.84 (3H, m), 2.88-2.94 (2H, m), 3.49 (2H, d, J=7.5 Hz), 7.31 (3H, s), 7.32 (2H, s)

Reference Example 57

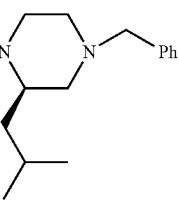

[Formula 120]

Yield: quant. %, 1H-NMR (CDCl3): δ0.87 (3H, d, J=6.5 Hz), 0.89 (3H, d, J=6.5 Hz), 1.05-1.29 (2H, m), 1.57-1.74 (2H, m), 2.00 (1H, td, J=10.5, 4.0 Hz), 2.70-2.99 (5H, m), 3.43 (1H, d, J=13.0 Hz), 3.50 (1H, d, J=13.0 Hz), 7.20-7.38 (5H, m).

Reference Example 58

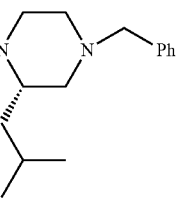

[Formula 121]

Yield: 90%, 1H-NMR (CDCl$_3$): δ0.87 (3H, d, J=5 Hz), 0.89 (3H, d, J=5 Hz), 1.16-1.30 (2H, m), 1.58-1.74 (2H, m), 2.00 (1H, td, J=11, 4 Hz), 2.70-3.00 (5H, m), 3.45 (1H, d, J=13 Hz), 3.52 (1H, d, J=13 Hz), 7.20-7.40 (5H, m).

Reference Example 59

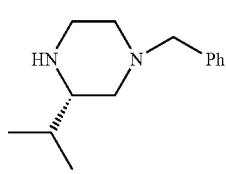

[Formula 122]

Yield: 92%, 1H-NMR (CDCl3): δ0.88 (3H, d, J=6.5 Hz), 0.93 (3H, d, J=6.5 Hz), 1.55 (1H, sextet, J=6.5 Hz), 1.78 (1H, t, J=10.5 Hz), 1.97 (1H, td, J=11, 3.5 Hz), 2.67-3.03 (5H, m), 3.44 (1H, d, J=13 Hz), 3.56 (1H, d, J=13 Hz), 7.20-7.40 (5H, m).

Reference Example 60

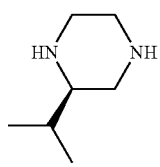

[Formula 123]

Yield: 80%, 1H-NMR (CDCl3): δ0.91 (3H, d, J=7.0 Hz), 0.94 (3H, d, J=7.0 Hz), 1.43-1.60 (1H, m), 2.27-2.37 (1H, m), 2.38-2.48 (1H, m), 2.65-2.85 (2H, m), 2.86-2.94 (1H, m), 2.96-3.06 (2H, m).

Reference Example 61

Synthesis of 3-ethylpiperazine ditrifluoroacetate

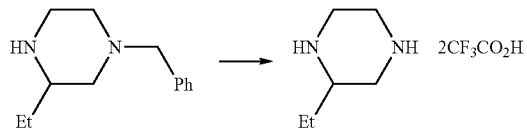

[Formula 124]

A mixture of 1-benzyl-3-ethylpiperazine (1.16 g; 5.68 mmol), 5% palladium carbon (0.11 g), trifluoroacetic acid (1.1 ml; 14.8 mmol) and methanol (30 ml) was stirred at room temperature under the presence of hydrogen gas for 17 hours. The reaction solution was filtrated and the filtrate was condensed under reduced pressure. The residue was washed with diisopropyl ether to give 3-ethylpiperazine ditrifluoroacetate as colorless crystal (1.65 g; 85%).

1H-NMR (D2O): δ0.74 (3H, t, J=7.5 Hz), 1.44-1.54 (2H, m), 2.90 (1H, dd, J=12.0 Hz), 3.07-3.15 (2H, m), 3.20-3.34 (1H, m), 3.43-3.51 (3H, m)

Compounds in Reference Examples 62 to 71 were obtained as above.

Reference Example 62

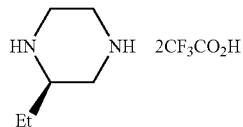

[Formula 125]

Yield: 88%, 1H-NMR (DMSO-d6): δ0.94 (3H, t, J=7.5 Hz), 1.60 (2H, quant, J=7.5 Hz), 2.93 (1H, t, J=12.5 Hz), 3.00-3.65 (6H, m), 9.24 (2H, brs).

Reference Example 63

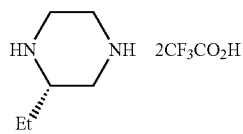

[Formula 126]

Yield: 80%, 1H-NMR (DMSO-d6): δ0.94 (3H, t, J=7.5 Hz), 1.61 (2H, quant, J=7.5 Hz), 2.93 (1H, t, J=12.5 Hz), 3.00-3.60 (6H, m), 9.27 (2H, brs).

Reference Example 64

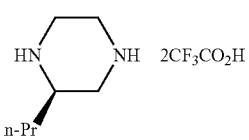

[Formula 127]

Yield: 59%, 1H-NMR (D2O): δ0.76 (3H, t, J=7.5 Hz), 1.25 (2H, m), 1.53 (2H, q, J=7.5 Hz), 3.00 (1H, t, J=12.9 Hz), 3.13-3.29 (2H, m), 3.39-3.48 (1H, m), 3.52-3.59 (3H, m)

Reference Example 65

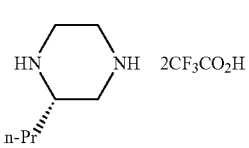

[Formula 128]

Yield: 61%, 1H-NMR (D2O): δ0.79 (3H, t, J=7.2 Hz), 1.22-1.35 (2H, m), 1.52-1.60 (2H, m), 3.03 (1H, dd, J=12.2 Hz), 3.16-3.32 (2H, m), 3.40-3.51 (1H, m), 3.55-3.63 (3H, m)

Reference Example 66

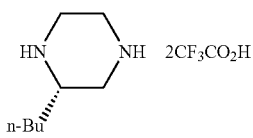

[Formula 129]

Yield: 76%, 1H-NMR (DMSO-d6): δ0.88 (3H, t, J=7 Hz), 1.20-1.40 (4H, m), 1.48-1.70 (2H, m), 2.96 (1H, t, J=12.5 Hz), 3.05-3.28 (2H, m), 3.30-3.44 (1H, m), 3.45-3.60 (3H, m), 9.39 (2H, brs).

Reference Example 67

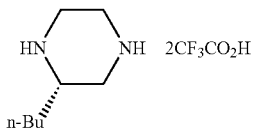

[Formula 130]

Yield: 74%, 1H-NMR (DMSO-d6): δ0.87 (3H, t, J=7.5 Hz), 1.20-1.40 (4H, m), 1.45-1.67 (2H, m), 2.94 (1H, t, J=7 Hz), 3.16 (2H, quant, J=12.5 Hz), 3.29-2.65 (4H, m), 9.35 (2H, brs).

Reference Example 68

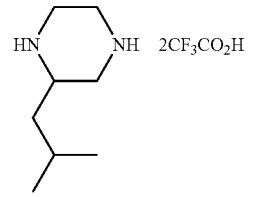

[Formula 131]

Yield: 78%, 1H-NMR (D2O): δ0.82 (6H, dd, J=1.8, 6.0 Hz), 1.49 (2H, t, J=6.9 Hz), 1.54-1.65 (1H, m), 3.06 (1H, dd, J=11.7 Hz), 3.20-3.37 (2H, m), 3.48-3.55 (1H, m), 3.57-3.66 (3H, m)

Reference Example 69

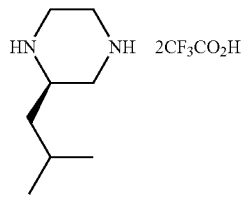

[Formula 132]

1H-NMR (CDCl3): δ0.87 (3H, d, J=6.5 Hz), 0.89 (3H, d, J=6.5 Hz), 1.44 (2H, t, J=7.0 Hz), 1.61-1.78 (1H, m), 2.85-3.00 (1H, m), 3.03-3.32 (2H, m), 3.35-3.59 (4H, m), 9.34 (2H, brs).

Reference Example 70

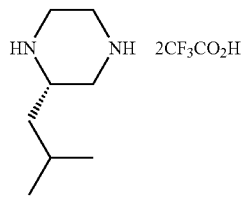

[Formula 133]

Yield: 82%, 1H-NMR (DMSO-d6): 0.88 (6H, t, J=6.5 Hz), 1.43 (2H, t, J=6.5 Hz), 1.70 (1H, quant, J=6.5 Hz), 2.90 (1H, t, J=13 Hz), 3.00-3.28 (2H, m), 3.35-3.55 (4H, m), 9.17 (2H, brs).

Reference Example 71

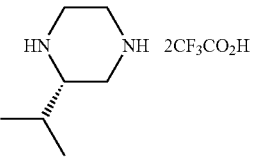

[Formula 134]

Yield: 49%, 1H-NMR (DMSO-d6): 0.94 (3H, d, J=7 Hz), 0.98 (3H, d, J=7 Hz), 1.84-1.98 (1H, m), 2.94 (1H, t, J=12.5 Hz), 3.05-3.25 (3H, m), 3.47 (2H, d, J=10.5 Hz), 3.52 (1H, d, J=15 Hz), 9.12 (2H, brs).

Reference Example 72

Synthesis of 1-tert-butoxycarbonyl-3-ethylpiperazine

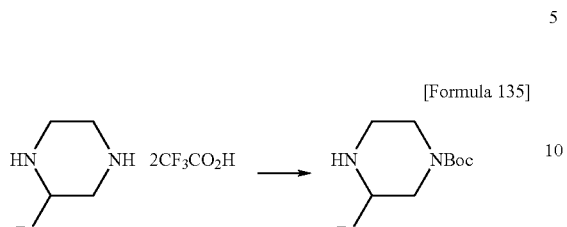

[Formula 135]

To a mixture of 3-ethylpiperazine ditrifluoroacetate (0.51 g; 1.47 mmol) and acetonitrile (10 ml) were added triethylamine (0.62 ml; 4.45 mmol) and di-t-butyldicarbonate (0.35 g; 1.59 mmol) under ice-cooling. The mixture was stirred at room temperature for 17 hours. The reaction solution was concentrated under reduced pressure. To the residue were added ethyl acetate and water and extracted. The organic layer was washed with brine, dried over anhydrous sodium sulphate, and evaporated under reduced pressure. The residue was purified by column chromatograph on silica gel (chloroform:methanol=20:1) to give 1-tert-butoxycarbonyl-3-ethylpiperazine as colorless crystal (0.27 g; 85%).

1H-NMR (CDCl3): δ 1.03 (3H, t, J=7.5 Hz), 1.47 (9H, s), 1.60-1.81 (2H, m), 2.96 (3H, br), 3.26 (2H, d, J=12.6 Hz), 4.08 (2H, d, J=14.1 Hz)

Compounds in Reference Examples 73 to 83 were obtained as above.

Reference Example 73

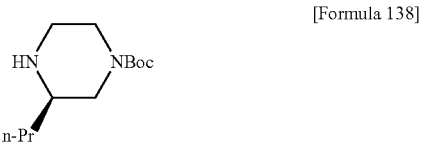

[Formula 136]

Yield: 99%, 1H-NMR (CDCl3): 0.95 (3H, t, J=7.5 Hz), 1.30-1.45 (2H, m), 1.46 (9H, s), 1.67 (1H, brs), 2.30-2.55 (2H, m), 2.68-2.90 (2H, m), 2.91-3.01 (1H, m), 3.80-4.05 (2H, m).

Reference Example 74

[Formula 137]

Yield: 80%, 1H-NMR (CDCl3): 0.95 (3H, t, J=7.5 Hz), 1.30-1.45 (2H, m), 1.46 (9H, s), 1.69 (1H, brs), 2.30-2.55 (2H, m), 2.68-2.88 (2H, m), 2.90-3.00 (1H, m), 3.85-4.02 (2H, m).

Reference Example 75

[Formula 138]

Yield: quant. %, 1H-NMR (CDCl3, 328K): 0.94 (3H, t, J=6.9 Hz), 1.29-1.46 (4H, m), 1.46 (9H, s), 2.64-2.86 (3H, m), 2.96-3.14 (2H, m), 3.64-4.04 (2H, m)

Reference Example 76

[Formula 139]

Yield: quant. %, 1H-NMR (CDCl3, 328K): 0.94 (3H, t, J=6.9 Hz), 1.36-1.60 (4H, m), 1.47 (9H, s), 2.82-2.93 (3H, m), 3.12-3.21 (2H, m), 3.99-4.10 (2H, m) R eference Example 77

[Formula 140]

Yield: 96%, 1H-NMR (CDCl3): 0.90 (3H, t, J=6 Hz), 1.25-1.40 (6H, m), 1.46 (9H, s), 1.54 (1H, brs), 2.30-2.60 (2H, m), 2.67-2.86 (2H, m), 2.90-2.99 (1H, m), 3.80-4.05 (2H, m).

Reference Example 78

[Formula 141]

Yield: 94%, 1H-NMR (CDCl3): 0.85-0.95 (3H, m), 1.25-1.40 (6H, m), 1.46 (9H, s), 1.56 (1H, brs), 2.30-3.00 (5H, m), 3.80-4.05 (2H, m).

Reference Example 79

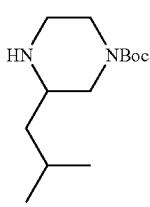

[Formula 142]

Yield: 90%, 1H-NMR (CDCl3): 0.94 (6H, dd, J=3.3, 6.3 Hz), 1.47 (9H, s), 1.43-1.54 (2H, m), 1.68-1.79 (1H, m), 2.97 (2H, dt, J=3.3, 12.3 Hz), 3.08 (1H, br), 3.22-3.28 (2H, m), 4.08 (2H, d, J=13.8 Hz)

Reference Example 80

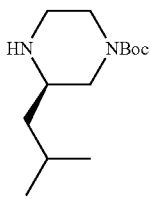

[Formula 143]

Yield: 74%, 1H-NMR (CDCl3): 0.90 (3H, d, J=6.5 Hz), 0.93 (3H, d, J=6.5 Hz), 1.11-1.30 (2H, m), 1.47 (9H, s), 1.60-1.78 (1H, m), 2.41 (1H, brs), 2.56-2.87 (3H, m), 2.90-3.00 (1H, m), 3.82-4.03 (2H, m).

Reference Example 81

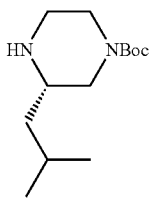

[Formula 144]

Yield: 99%, 1H-NMR (CDCl3): 0.92 (6H, t, J=7 Hz), 1.15-1.30 (2H, m), 1.46 (9H, s), 1.47 (1H, brs), 1.62-1.76 (1H, m), 2.30-2.52 (1H, m), 2.58-3.00 (4H, m), 3.82-4.04 (2H, m).

Reference Example 82

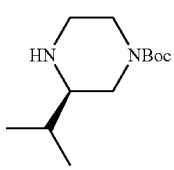

[Formula 145]

Yield: 59%, 1H-NMR (CDCl3): 0.95 (3H, d, J=13.5 Hz), 0.96 (3H, d, J=13.5 Hz), 1.46 (9H, s), 1.47-1.69 (1H, m), 2.22-2.35 (1H, m), 2.38-2.63 (1H, brs), 2.65-2.86 (2H, m), 2.93-3.04 (1H, m), 3.80-4.17 (2H, m).

Reference Example 83

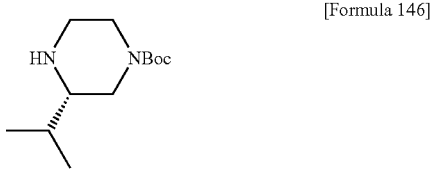

[Formula 146]

Yield: 75%, 1H-NMR (CDCl3): 0.94 (3H, d, J=2.5 Hz), 0.96 (3H, d, J=2.5 Hz), 1.46 (9H, s), 1.53-1.70 (2H, m), 2.24-2.35 (1H, m), 2.36-2.65 (1H, m), 2.66-2.86 (2H, m), 2.93-3.04 (1H, m), 3.80-4.16 (2H, m).

Reference Example 84

Preparation of 4-(6-chlorobenzothiazole-2-yl)piperazine-1-carboxylic acid tert-butyl ester

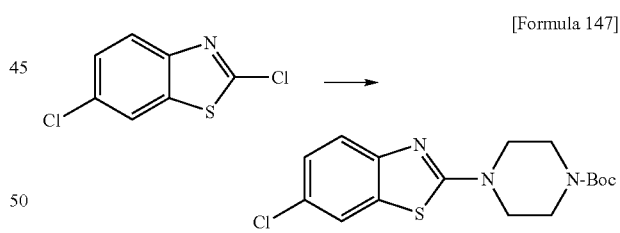

[Formula 147]

A mixture of 2,6-dichlorobenzothiazole (1.00 g; 4.90 mmol), 1-piperazine-tert-butyl ester (0.96 g; 5.15 mmol), potassium carbonate (0.71 g; 5.15 mmol) and anhydrous N,N-dimethylformamide (10 ml) was stirred at room temperature for 14 hours and at 50° C. for 3 hours. Water was added to the reaction solution. The precipitate was collected and washed with diisopropyl ether to give 4-(6-chlorobenzothiazole-2-yl)piperazine-1-carboxylic acid tert-butyl ester as pale blackish brown crystal (1.50 g; 87%).

$^1$H-NMR (DMSO-$d_6$): δ1.43 (9H, s), 3.44-3.53 (4H, m), 3.55-3.60 (4H, m), 7.30 (1H, dd, J=8, 2 Hz), 7.44 (1H, d, J=8 Hz), 7.93 (1H, d, J=2 Hz)

Compounds in Reference Examples 85 to 154 were obtained by similar methods as Reference Example 84. .

Reference Example 85

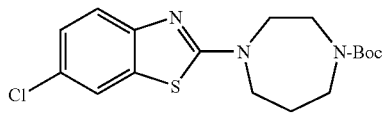
[Formula 148]

Yield: 97%, ¹H-NMR (CDCl₃); δ1.42 (9H, d, J=8.4 Hz), 2.01-2.07 (2H, m), 3.36 (1H, t, J=6.0 Hz), 3.44 (1H, t, J=5.7 Hz) 3.63-3.76 (6H, m) 7.24 (1H, dd, J=8.7, 2.1 Hz), 7.43 (1H, d, J=8.4 Hz), 7.55 (1H, d, J=2.4 Hz).

Reference Example 86

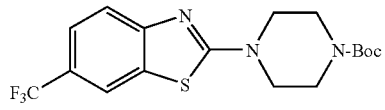
[Formula 149]

Yield: 51%, ¹H-NMR (DMSO-d₆): δ1.43 (9H, s), 3.44-3.53 (4H, m), 3.55-3.65 (4H, m), 7.58 (2H, s), 8.27 (1H, s)

Reference Example 87

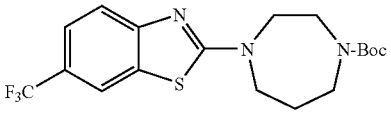
[Formula 150]

Yield: 47%, ¹H-NMR (CDCl3): δ1.44 (9H, s), 2.06 (2H, quant, J=6 Hz), 3.35-3.50 (2H, m), 3.60-3.85 (6H, m), 7.50-7.60 (2H, m), 7.85 (1H, s).

Reference Example 88

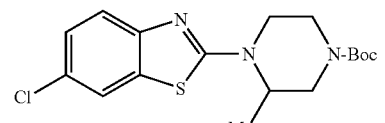
[Formula 151]

Yield: 43%, ¹H-NMR (CDCl₃): δ1.29 (3H, d, J=7 Hz), 1.49 (9H, s), 2.85-3.10 (1H, m), 3.10-3.30 (1H, m), 3.40 (1H, td, J=13, 3.5 Hz), 3.75-4.25 (4H, m), 7.24 (1H, dd, J=8.5, 2 Hz), 7.44 (1H, d, J=8.5 Hz), 7.56 (1H, d, J=2 Hz).

Reference Example 89

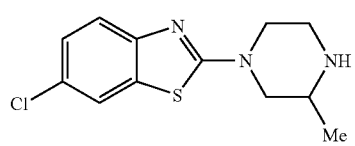
[Formula 152]

Yield: 69%, ¹H-NMR (CDCl₃): δ1.16 (3H, d, J=6 Hz), 1.76 (1H, brs), 2.80 (1H, dd, J=12, 12 Hz), 2.90-2.95 (1H, m), 3.00 (1H, dd, J=12, 3 Hz), 3.15 (1H, td, J=12, 3 Hz), 3.21 (1H, dd, J=12, 3 Hz), 3.84-4.00 (2H, m), 7.24 (1H, dd, J=8.5, 2.5 Hz), 7.44 (1H, d, J=8.5 Hz), 7.56 (1H, d, J=2.5 Hz).

Reference Example 90

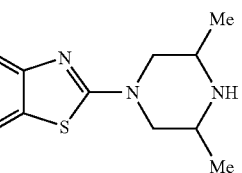
[Formula 153]

Yield: 90%, ¹H-NMR (CDCl₃): δ1.15 (6H, d, J=6 Hz), 1.61 (1H, brs), 2.73 (2H, dd, J=12.5, 10 Hz), 2.95-3.10 (2H, m), 3.94 (2H, dd, J=12.5, 2.5 Hz), 7.23 (1H, dd, J=8.5, 2 Hz), 7.42 (1H, d, J=2 Hz), 7.55 (1H, d, J=8.5 Hz).

Reference Example 91

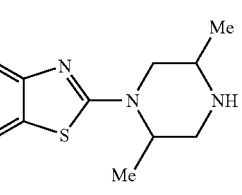
[Formula 154]

Yield: 40%, ¹H-NMR (CDCl₃): δ1.27 (3H, d, J=7 Hz), 1.37 (3H, d, J=7 Hz), 2.64 (1H, dd, J=12, 2.5 Hz), 3.20-3.35 (1H, m), 3.42 (1H, dd, J=12, 4.5 Hz), 3.50-3.65 (2H, m), 4.10-4.25 (1H, m), 7.23 (1H, dd, J=8.5, 2 Hz), 7.42 (1H, d, J=8.5 Hz), 7.54 (1H, d, J=2 Hz).

Reference Example 92

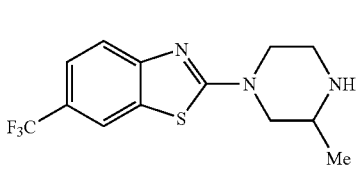
[Formula 155]

Yield: 87%, 1H-NMR (CDCl3): δ1.16 (3H, d, J=6 Hz), 1.62 (1H, brs), 2.84 (1H, t, J=10.5 Hz), 2.90-3.00 (1H, m), 3.01 (1H, dd, J=12, 3 Hz), 3.14 (1H, dt, J=12, 2.5 Hz), 3.25 (1H, td, J=12, 3.5 Hz), 4.01 (2H, t, J=12 Hz), 7.52 (1H, d, J=8.5 Hz), 7.57 (1H, d, J=8.5 Hz), 7.85 (1H, s).

Reference Example 93

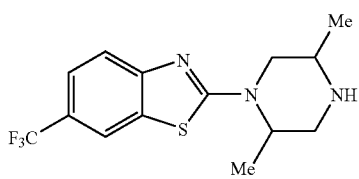

[Formula 156]

Yield: 8%, 1H-NMR (CDCl3): δ1.27 (3H, d, J=6.5 Hz), 1.40 (3H, d, J=6.5 Hz), 1.65 (1H, brs), 2.66 (1H, dd, J=13, 2 Hz), 3.25-3.40 (1H, m), 3.43 (1H, dd, J=13, 4.5 Hz), 3.61 (2H, d, J=3 Hz), 4.20-4.28 (1H, m), 7.51 (1H, d, J=8.5 Hz), 7.56 (1H, d, J=8.5 Hz), 7.84 (1H, s).

Reference Example 94

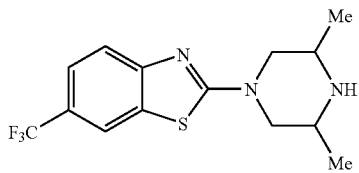

[Formula 157]

Yield: 38%, 1H-NMR (CDCl3): δ1.16 (6H, d, J=6.5 Hz), 1.54 (1H, brs), 2.76 (1H, d, J=12.5 Hz), 2.80 (1H, d, J=12.5 Hz), 2.95-3.08 (2H, m), 3.95-4.03 (2H, m), 7.52 (1H, d, J=8.5 Hz), 7.57 (1H, d, J=8.5 Hz), 7.85 (1H, s).

Reference Example 95

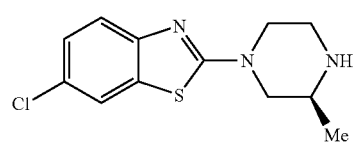

[Formula 158]

Yield: 71%, 1H-NMR (CDCl3): δ1.15 (3H, d, J=6.3 Hz), 2.80 (1H, dd, J=12.3 Hz), 2.88-3.02 (2H, m), 3.08-3.23 (2H, m), 3.94 (2H, dd, J=12.3 Hz), 7.24 (1H, dd, J=2.1, 8.7 Hz), 7.43 (1H, d, J=8.7 Hz), 7.56 (1H, d, J=2.1 Hz)

Reference Example 96

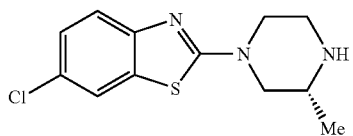

[Formula 159]

Yield: 77%, 1H-NMR (CDCl3): δ1.15 (3H, d, J=6.0 Hz), 2.80 (1H, dd, J=12.3 Hz), 2.89-3.02 (2H, m), 3.10-3.23 (2H, m), 3.95 (2H, t, J=12.3 Hz), 7.24 (1H, dd, J=2.4, 8.4 Hz), 7.44 (1H, d, J=8.4 Hz), 7.56 (1H, d, J=2.4 Hz)

Reference Example 97

[Formula 160]

Yield: 48%, 1H-NMR (CDCl3): δ1.16 (3H, d, J=6.0 Hz), 2.86 (1H, d, J=12.0 Hz), 2.88-3.03 (2H, m), 3.11-3.16 (1H, m), 3.23 (1H, dt, J=3.3, 12.0 Hz), 4.01 (2H, t, J=12.6 Hz), 7.51-7.59 (2H, m), 7.85 (1H, s)

Reference Example 98

[Formula 161]

Yield: 63%, 1H-NMR (CDCl3): δ1.01 (3H, t, J=7.2 Hz), 1.44-1.53 (2H, m), 2.67-2.76 (1H, m), 2.80-2.88 (1H, m), 2.91-3.00 (1H, m), 3.10-3.20 (2H, m), 3.91-4.01 (2H, m), 7.24 (1H, dd, J=2.1, 8.7 Hz), 7.43 (1H, d, J=8.7 Hz), 7.55 (1H, d, J=2.1 Hz), 8.02 (1H, s)

Reference Example 99

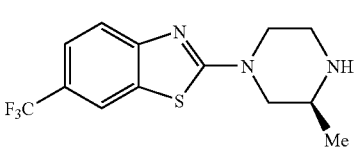

[Formula 162]

Yield: quant. %, 1H-NMR (CDCl3): δ1.16 (3H, d, J=6 Hz), 1.75 (1H, brs), 2.80-3.05 (3H, m), 3.08-3.18 (1H, m), 3.25 (1H, dd, J=12, 3.5 Hz), 4.00 (2H, t, J=12 Hz), 7.53 (1H, d, J=8.5 Hz), 7.55 (1H, d, J=8.5 Hz), 7.85 (1H, s).

Reference Example 100

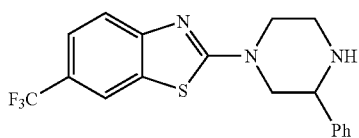

[Formula 163]

Yield: quant. %, 1H-NMR (CDCl3): δ1.98 (1H, brs), 3.06-3.30 (3H, m), 3.38 (1H, dd, J=12, 3.5 Hz), 3.93 (1H, dd, J=10.5, 3 Hz), 4.05-4.18 (2H, m), 7.30-7.60 (7H, m), 7.86 (1H, s).

Reference Example 101

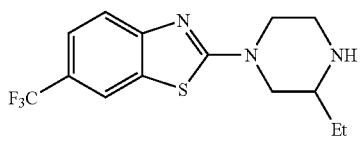

[Formula 164]

Yield: quant. %, 1H-NMR (CDCl3): δ1.02 (3H, t, J=7.5 Hz), 1.38-1.60 (2H, m), 1.75 (1H, brs), 2.65-2.80 (1H, m), 2.85-3.00 (2H, m), 3.10-3.20 (1H, m), 3.25 (1H, td, J=12, 3.5 Hz), 3.95-4.10 (2H, m), 7.52 (1H, dd, J=8.5, 1.5 Hz), 7.57 (1H, d, J=8.5 Hz), 7.85 (1H, d, J=1.5 Hz).

Reference Example 102

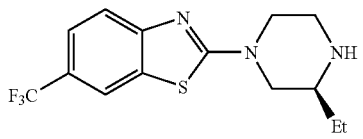

[Formula 165]

Yield: 93%, 1H-NMR (CDCl3): δ1.02 (3H, t, J=7.5 Hz), 1.38-1.60 (2H, m), 1.78 (1H, brs), 2.67-2.78 (1H, m), 2.82-3.03 (2H, m), 3.09-3.32 (2H, m), 3.95-4.10 (2H, m), 7.52 (1H, d, J=8.5 Hz), 7.70 (1H, d, J=8.5 Hz), 7.85 (1H, s).

Reference Example 103


[Formula 166]

Yield: quant. %, 1H-NMR (CDCl3): δ1.02 (3H, t, J=7.5 Hz), 1.38-1.60 (2H, m), 1.83 (1H, brs), 2.65-2.78 (1H, m), 2.85-3.03 (2H, m), 3.10-3.18 (1H, m), 3.24 (1H, td, J=12, 3.5 Hz), 3.93-4.10 (2H, m), 7.52 (1H, dd, J=8.5, 1.5 Hz), 7.57 (1H, d, J=8.5 Hz), 7.85 (1H, d, J=1.5 Hz).

Reference Example 104

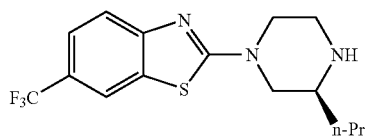

[Formula 167]

Yield: 84%, 1H-NMR (CDCl3): δ0.90-1.05 (3H, m), 1.35-1.54 (4H, m), 1.55-1.66 (2H, m), 2.75-3.02 (3H, m), 3.14 (1H, dt, J=12, 2 Hz), 3.25 (1H, td, J=12.5, 3.5 Hz), 4.01 (1H, t, J=11.5 Hz), 7.52 (1H, dd, J=8.5, 1.5 Hz), 7.57 (1H, d, J=8.5 Hz), 7.85 (1H, d, J=1.5 Hz).

Reference Example 105

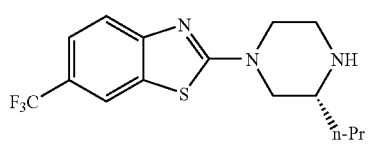

[Formula 168]

Yield: 87%, 1H-NMR (CDCl3): δ0.96-0.99 (3H, m), 1.42-1.50 (4H, m), 2.83-3.01 (3H, m), 3.12-3.29 (2H, m), 4.01 (2H, t, J=9.9 Hz), 7.51-7.59 (2H, m), 7.85 (1H, s), 8.02 (1H, s)

Reference Example 106

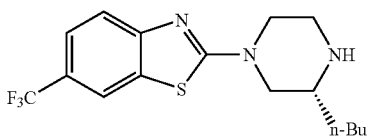

[Formula 169]

Yield: quant. %, 1H-NMR (CDCl3): δ0.94 (3H, t, J=7.5 Hz), 1.29-1.54 (6H, m), 1.56-1.70 (2H, m), 2.73-3.05 (3H, m), 3.13 (1H, dt, J=12, 2 Hz), 3.25 (1H, td, J=12, 3.5 Hz), 4.01 (1H, t, J=10 Hz), 7.52 (1H, dd, J=8.5, 1.5 Hz), 7.57 (1H, d, J=8.5 Hz), 7.85 (1H, d, J=1.5 Hz).

Reference Example 107

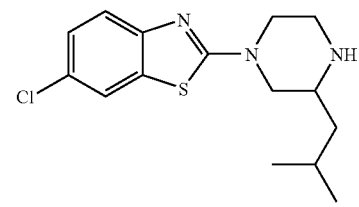

[Formula 170]

Yield: 56%, 1H-NMR (CDCl3): δ0.95 (6H, dd, J=6.6, 8.4 Hz), 1.25-1.33 (2H, m), 1.71-1.80 (1H, m), 2.77-2.92 (2H, m), 2.96-3.00 (1H, m), 3.10-3.24 (2H, m), 3.95 (2H, d, J=10.5 Hz), 7.24 (1H, dd, J=2.1, 8.4 Hz), 7.44 (1H, d, J=8.4 Hz), 7.56 (1H, d, J=2.1 Hz)

Reference Example 108

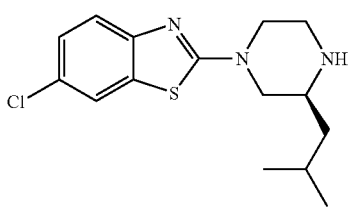

Yield: quant. %, 1H-NMR (CDCl3): δ0.93 (3H, d, J=6.5 Hz), 0.96 (3H, d, J=6.5 Hz), 1.26-1.35 (2H, m), 1.68 (1H, brs), 1.69-1.83 (1H, m), 2.73-3.03 (3H, m), 3.07-3.25 (2H, m), 3.90-4.00 (2H, m), 7.23 (1H, dd, J=8.5, 2 Hz), 7.44 (1H, d, J=8.5 Hz), 7.55 (1H, d, J=2 Hz).

Reference Example 109

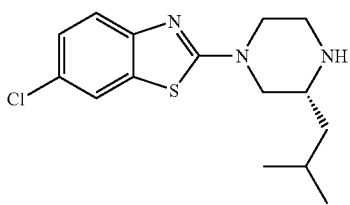

Yield: quant. %, 1H-NMR (CDCl3): δ0.93 (3H, d, J=6.5 Hz), 0.96 (3H, d, J=6.5 Hz), 1.20-1.38 (2H, m), 1.60-1.84 (2H, m), 2.72-3.03 (2H, m), 3.05-3.26 (2H, m), 3.87-4.02 (2H, m), 7.23 (1H, dd, J=8.5, 2.0 Hz), 7.43 (1H, d, J=8.5 Hz), 7.55 (1H, d, J=2.0 Hz).

Reference Example 110

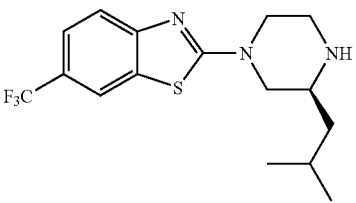

Yield: quant. %, 1H-NMR (CDCl3): δ0.94 (3H, d, J=6.5 Hz), 0.97 (3H, d J=6.5 Hz), 1.27-1.37 (2H, m), 1.66 (1H, brs), 1.70-1.83 (1H, m), 2.80-3.03 (3H, m), 3.09-3.30 (2H, m), 3.95-4.05 (2H, m), 7.52 (1H, d, J=8.5 Hz), 7.57 (1H, d, J=8.5 Hz), 7.85 (1H, s).

Reference Example 111

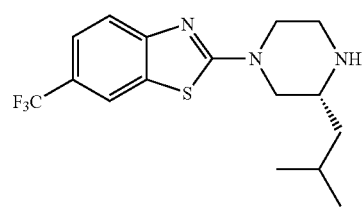

Yield 91%, 1H-NMR (CDCl3): δ0.94 (3H, d, J=6.5 Hz), 0.97 (3H, d, J=6.5 Hz), 1.27-1.36 (2H, m), 1.62-1.84 (2H, m), 2.81-3.03 (2H, m), 3.09-3.30 (2H, m), 3.94-4.07 (2H, m), 7.52 (1H, d, J=8.5 Hz), 7.57 (1H, d, J=8.5 Hz), 7.85 (1H, s).

Reference Example 112

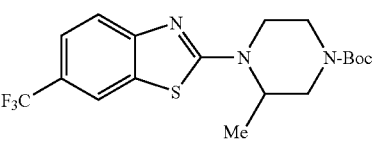

Yield: 91%, 1H-NMR (CDCl3): δ1.16 (3H, d, J=6 Hz), 1.58 (1H, brs), 2.80-3.03 (3H, m), 3.07-3.17 (1H, m), 3.24 (1H, td, J=12, 3.5 Hz), 3.99 (2H, t, J=11 Hz), 7.26 (1H, d, J=12 Hz), 7.75 (1H, d, J=6.5 Hz).

Reference Example 113

Yield: 91%, 1H-NMR (CDCl$_3$): δ1.02 (3H, t, J=7.5 Hz), 1.37-1.62 (2H, m), 1.90 (1H, brs), 2.64-2.78 (1H, m), 2.84-3.03 (2H, m), 3.10-3.20 (1H, m), 3.21-3.32 (1H, m), 3.92-4.09 (2H, m), 7.27 (1H, d, J=12.5 Hz), 7.76 (1H, d, J=6.5 Hz).

Reference Example 114

Yield: 75%, 1H-NMR (CDCl3): δ1.32 (3H, d, J=6.5 Hz), 1.50 (9H, s), 2.90-3.30 (2H, m), 3.44 (1H, td, J=12.5, 3.5 Hz), 3.80-4.40 (4H, m), 7.53 (1H, dd, J=8.5, 1.5 Hz), 7.57 (1H, d, J=8.5 Hz), 7.86 (1H, d, J=1.5 Hz).

Reference Example 115

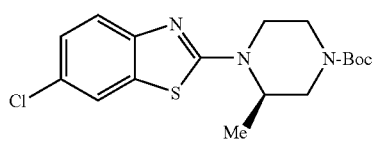

[Formula 178]

Yield: 61%, 1H-NMR (CDCl3): δ1.29 (3H, d, J=6 Hz), 1.49 (9H, s), 2.90-3.30 (2H, m), 3.34-3.48 (1H, m), 3.80-4.30 (4H, m), 7.25 (1H, dd, J=8.5, 2 Hz), 7.44 (1H, d, J=8.5 Hz), 7.57 (1H, d, J=2 Hz).

Reference Example 116

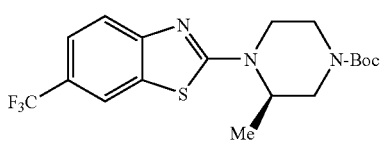

[Formula 179]

Yield: 31%, 1H-NMR (CDCl3): δ1.30 (3H, d, J=6.5 Hz), 1.49 (9H, s), 2.91-3.29 (2H, m), 3.33-3.47 (1H, m), 3.76-4.34 (4H, m), 7.25 (1H, dd, J=8.5, 2.0 Hz), 7.44 (1H, d, J=8.5 Hz), 7.57 (1H, d, J=2.0 Hz).

Reference Example 117

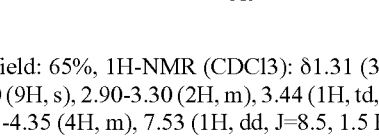

[Formula 180]

Yield: 65%, 1H-NMR (CDCl3): δ1.31 (3H, d, J=6.5 Hz), 1.50 (9H, s), 2.90-3.30 (2H, m), 3.44 (1H, td, J=12.5, 3.5 Hz), 3.85-4.35 (4H, m), 7.53 (1H, dd, J=8.5, 1.5 Hz), 7.58 (1H, d, J=8.5 Hz), 7.86 (1H, d, J=1.5 Hz).

Reference Example 118

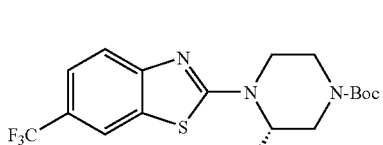

[Formula 181]

Yield: 50%, 1H-NMR (CDCl3): δ1.32 (3H, d, J=6.5 Hz), 1.50 (9H, s), 2.85-3.27 (2H, m), 3.32-3.52 (1H, m), 3.82-4.38 (4H, m), 7.54 (1H, d, J=8.5 Hz), 7.58 (1H, d, J=8.5 Hz), 7.86 (1H, s).

Reference Example 119

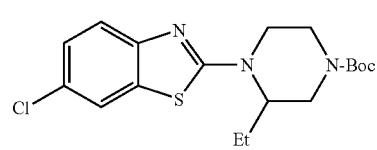

[Formula 182]

Yield: 22%, 1H-NMR (CDCl3): δ1.00 (3H, t, J=7.5 Hz), 1.49 (9H, s), 1.63-1.78 (2H, m), 2.83-3.17 (2H, m), 3.26-3.41 (1H, m), 3.82-4.31 (4H, m), 7.23 (1H, dd, J=8.5, 2.0 Hz), 7.41 (1H, d, J=8.5 Hz), 7.53 (1H, d, J=2.0 Hz).

Reference Example 120

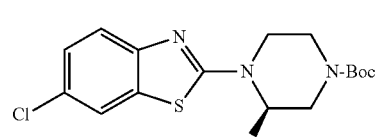

[Formula 183]

Yield: 41%, 1H-NMR (CDCl3): δ1.00 (3H, t, J=7.5 Hz), 1.49 (9H, s), 1.72 (2H, quant, J=7.5 Hz), 2.90-3.20 (3H, m), 3.26-3.42 (1H, m), 3.85-4.00 (2H, m), 4.10-4.30 (1H, m), 7.24 (1H, dd, J=8.5, 2 Hz), 7.41 (1H, d, J=8.5 Hz), 7.55 (1H, d, J=2 Hz).

Reference Example 121

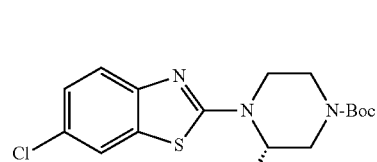

[Formula 184]

Yield: 25%, 1H-NMR (CDCl3): δ1.00 (3H, t, J=7.5 Hz), 1.49 (9H, s), 1.63-1.78 (2H, m), 2.82-3.19 (2H, m), 3.26-3.43 (1H, m), 3.80-4.30 (4H, m), 7.23 (1H, dd, J=8.5, 2.0 Hz), 7.41 (1H, d, J=8.5 Hz), 7.54 (1H, d, J=2.0 Hz).

Reference Example 122

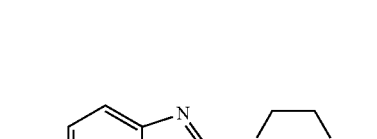

[Formula 185]

Yield: 67%, 1H-NMR (CDCl3): δ1.01 (3H, t, J=7.5 Hz), 1.49 (9H, s), 1.68-1.80 (2H, m), 2.90-3.20 (2H, m), 3.32-3.46

(1H, m), 3.90-4.32 (4H, m), 7.54 (1H, d, J=8.5 Hz), 7.55 (1H, d, J=8.5 Hz), 7.85 (1H, s).

Reference Example 123

[Formula 186]

Yield: 60%, 1H-NMR (CDCl3): δ1.01 (3H, t, J=7.5 Hz), 1.49 (9H, s), 1.74 (2H, quant, J=7.5 Hz), 2.90-3.20 (2H, m), 3.33-3.46 (1H, m), 3.92-4.31 (4H, m), 7.50-7.58 (2H, m), 7.85 (1H, s).

Reference Example 124

[Formula 187]

Yield: 43%, 1H-NMR (CDCl3): δ0.96 (3H, t, J=7.0 Hz), 1.25-1.75 (4H, m), 1.49 (9H, s), 2.84-3.18 (2H, m), 3.36 (1H, td, J=12.5, 3.0 Hz), 3.85-4.32 (4H, m), 7.24 (1H, dd, J=8.5, 2.0 Hz), 7.41 (1H, d, J=8.5 Hz), 7.55 (1H, d, J=2.0 Hz).

Reference Example 125

[Formula 188]

Yield: 33%, 1H-NMR (CDCl3, 328K): δ0.96 (3H, t, J=7.2 Hz), 1.36-1.49 (2H, m), 1.49 (9H, s), 1.59-1.71 (2H, m), 2.98 (1H, t, J=11.1 Hz), 3.10 (1H, d, J=11.1 Hz), 3.36 (1H, dt, J=3.3, 13.2 Hz), 3.93-4.12 (4H, m), 7.22 (1H, s), 7.41 (1H, d, J=8.4 Hz), 7.54 (1H, s)

Reference Example 126

[Formula 189]

Yield: 40%, 1H-NMR (CDCl3): δ0.97 (3H, t, J=7.0 Hz), 1.20-1.55 (2H, m), 1.50 (9H, s), 1.56-1.77 (2H, m), 2.83-3.21 (2H, m), 3.40 (1H, td, J=13.0, 3.0 Hz), 3.88-4.35 (4H, m), 7.52 (1H, d, J=8.5 Hz), 7.56 (1H, d, J=8.5 Hz), 7.84 (1H, s).

Reference Example 127

[Formula 190]

Yield: 64%, 1H-NMR (CDCl3, 328K): δ0.97 (3H, t, J=7.2 Hz), 1.27-1.49 (2H, m), 1.49 (9H, s), 1.69 (2H, br), 2.99 (1H, t, J=11.7 Hz), 3.11 (1H, d, J=12.6 Hz), 3.39 (1H, td, J=12.6 Hz), 3.97-4.14 (4H, m), 7.53 (2H, s, J=Hz), 7.83 (1H, s)

Reference Example 128

[Formula 191]

Yield: 18%, 1H-NMR (CDCl3): δ0.85-0.97 (3H, m), 1.30-1.45 (4H, m), 1.49 (9H, s), 1.59-1.75 (2H, m), 2.86-3.19 (2H, m), 3.30-3.43 (1H, m), 3.90-4.30 (4H, m), 7.24 (1H, dd, J=8.5, 2 Hz), 7.42 (1H, d, J=8.5 Hz), 7.55 (1H, d, J=2 Hz).

Reference Example 129

[Formula 192]

Yield: 50%, 1H-NMR (CDCl3): δ0.84-0.98 (3H, m), 1.25-1.75 (15H, m), 2.85-3.20 (2H, m), 3.30-3.45 (1H, m), 3.90-4.30 (4H, m), 7.24 (1H, dd, J=9, 2 Hz), 7.42 (1H, d, J=9 Hz), 7.55 (1H, d, J=2 Hz).

Reference Example 130

[Formula 193]

Yield: 58%, 1H-NMR (CDCl3): δ0.85-0.97 (3H, m), 1.30-1.45 (4H, m), 1.50 (9H, s), 1.63-1.78 (2H, m), 2.85-3.20 (2H, m), 3.33-3.43 (1H, m), 3.95-4.35 (4H, m), 7.50-7.58 (2H, m), 7.85 (1H, s).

Reference Example 131

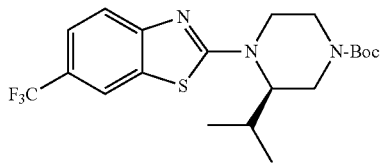

[Formula 194]

Yield: 11%, 1H-NMR (CDCl3): δ0.92 (3H, d, J=6.5 Hz), 1.13 (3H, d, J=6.5 Hz), 1.49 (9H, s), 2.07-2.27 (1H, m), 2.70-3.15 (2H, m), 3.25-3.44 (1H, m), 3.59-3.75 (1H, m), 3.95-4.46 (3H, m), 7.52 (1H, s), 7.53 (1H, s), 7.83 (1H, s).

Reference Example 132

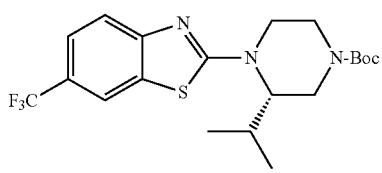

[Formula 195]

Yield: 31%, 1H-NMR (CDCl3): δ0.91 (3H, d, J=6.5 Hz), 1.13 (3H, d, J=6.5 Hz), 1.49 (9H, s), 2.12-2.24 (1H, m), 2.84-3.13 (2H, m), 3.27-3.43 (1H, m), 3.60-3.75 (1H, m), 4.02-4.40 (3H, m), 7.53 (2H, s), 7.83 (1H, s).

Reference Example 133

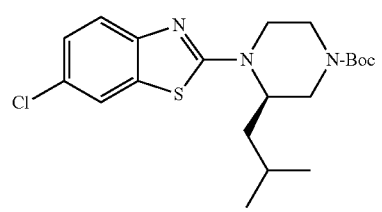

[Formula 196]

Yield: 26%, 1H-NMR (CDCl3): δ0.98 (3H, d, J=6.5 Hz), 1.00 (3H, d, J=6.5 Hz), 1.33-1.75 (3H, m), 1.49 (9H, s), 2.84-3.22 (2H, m), 3.37 (1H, td, J=13.0, 3.5 Hz), 3.88-4.32 (4H, m), 7.24 (1H, dd, J=8.5, 2.0 Hz), 7.42 (1H, d, J=8.5 Hz), 7.56 (1H, d, J=2.0 Hz).

Reference Example 134

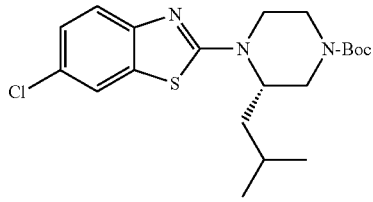

[Formula 197]

Yield: 54%, 1H-NMR (CDCl3): δ0.90-1.05 (6H, m), 1.35-1.48 (2H, m), 1.49 (9H, s), 1.58-1.73 (1H, m), 2.85-3.20 (2H, m), 3.30-3.43 (1H, m), 3.90-4.30 (4H, m), 7.35 (1H, dd, J=8.5, 2 Hz), 7.41 (1H, d, J=8.5 Hz), 7.57 (1H, d, J=2 Hz).

Reference Example 135

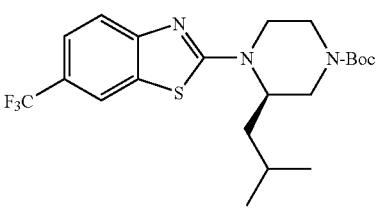

[Formula 198]

Yield: 43%, 1H-NMR (CDCl3): δ0.99 (3H, d, J=6.5 Hz), 1.00 (3H, d, J=6.5 Hz), 1.37-1.52 (1H, m), 1.49 (9H, s), 1.57-1.75 (2H, m), 2.84-3.23 (2H, m), 3.40 (1H, td, J=13.0, 3.5 Hz), 3.94-4.35 (4H, m), 7.48-7.58 (2H, m), 7.85 (1H, s).

Reference Example 136

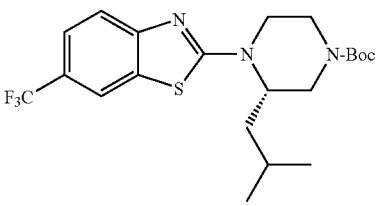

[Formula 199]

Yield: 57%, 1H-NMR (CDCl3, 328K): δ1.00 (6H, t, J=6.0 Hz), 1.40-1.52 (1H, m), 1.49 (9H, s), 1.60-1.69 (2H, m), 2.99 (1H, t, J=10.8 Hz), 3.12 (1H, d, J=10.8 Hz), 3.40 (1H, dt, J=3.6, 12.9 Hz), 3.98-4.13 (4H, m), 7.49-7.56 (2H, m), 7.84 (1H, s)

Reference Example 137

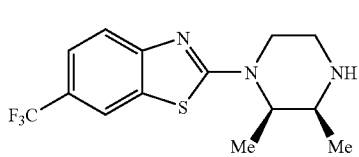

Yield: 46%, 1H-NMR (CDCl3): δ1.10 (3H, d, J=7.0 Hz), 1.26 (3H, d, J=7.0 Hz), 2.98 (1H, td, J=12.5, 3.5 Hz), 3.06-3.17 (2H, m), 3.35 (1H, td, J=12.5, 3.5 Hz), 3.75-3.93 (1H, m), 4.00-4.18 (1H, m), 7.46-7.62 (2H, m), 7.85 (1H, s).

Reference Example 138

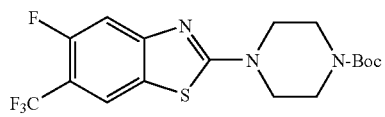

Yield: 96%, 1H-NMR (CDCl3): δ1.49 (9H, s), 3.54-3.70 (8H, m), 7.29 (1H, d, J=7.0 Hz), 7.78 (1H, d, J=11.5 Hz).

Reference Example 139

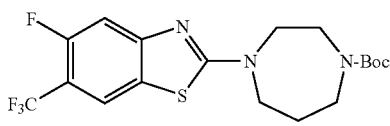

Yield: 90%, 1H-NMR (CDCl3): δ1.43 (9H, s), 2.00-2.13 (2H, m), 3.32-3.54 (2H, m), 3.62-3.89 (6H, m), 7.28 (1H, d, J=7.0 Hz), 7.75 (1H, d, J=11.5 Hz).

Reference Example 140

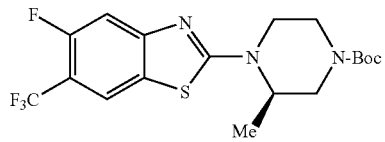

Yield: 64%, 1H-NMR (CDCl3): δ1.32 (3H, d, J=7.0 Hz), 1.50 (9H, s), 2.94-3.15 (2H, m), 3.44 (1H, td, J=12.5, 3.5 Hz), 3.77-4.42 (4H, m), 7.28 (1H, d, J=12.0 Hz), 7.77 (1H, d, J=7.0 Hz).

Reference Example 141

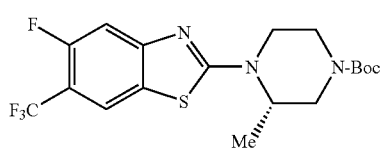

Yield: 57%, 1H-NMR (CDCl3): δ1.32 (3H, d, J=7.0 Hz), 1.50 (9H, s), 2.88-3.32 (2H, m), 3.45 (1H, td, J=12.5, 3.5 Hz), 3.75-4.36 (4H, m), 7.29 (1H, d, J=12.0 Hz), 7.77 (1H, d, J=7.0 Hz).

Reference Example 142

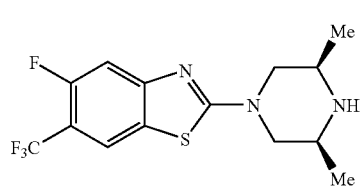

Yield: 93%, 1H-NMR (CDCl3): δ1.17 (6H, d, J=6.0 Hz), 2.76 (1H, d, J=12.5 Hz), 2.81 (1H, d, J=12.5 Hz), 2.94-3.08 (2H, m), 3.97 (2H, d, J=12.5 Hz), 7.27 (1H, d, J=11.5 Hz), 7.75 (1H, d, J=7.0 Hz).

Reference Example 143

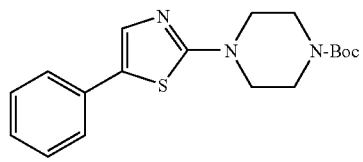

Yield: 55%, 1H-NMR (CDCl3): δ1.49 (9H, s), 3.43-3.66 (8H, m), 7.22 (1H, t, J=7.5 Hz), 7.33 (2H, t, J=7.5 Hz), 7.41 (1H, s), 7.43 (2H, d, J=7.5 Hz).

Reference Example 144

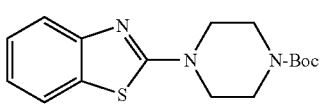

Yield: 78%, 1H-NMR (CDCl$_3$): δ1.49 (9H, s), 3.55-3.67 (8H, m), 7.10 (1H, td, J=8.0, 1.0 Hz), 7.31 (1H, td, J=8.0, 1.0 Hz), 7.57 (1H, dd, J=8.0, 1.0 Hz), 7.61 (1H, dd, J=8.0, 1.0 Hz).

Reference Example 145

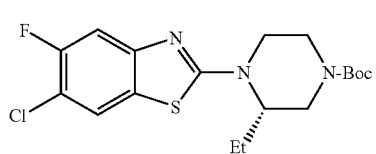
[Formula 208]

Yield: 42%, H-NMR (CDCl3): δ1.00 (3H, t, J=7.5 Hz), 1.49 (9H, s), 1.64-1.79 (2H, m), 2.85-3.19 (2H, m), 3.28-3.44 (1H, m), 3.83-4.33 (4H, m), 7.27 (1H, d, J=10.0 Hz), 7.55 (1H, d, J=7.0 Hz).

Reference Example 146

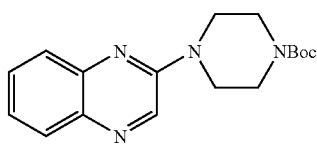
[Formula 209]

Yield: 60%, 1H-NMR (CDCl3): δ1.50 (9H, s), 3.55-3.68 (4H, m), 3.73-3.85 (4H, m), 7.37-7.47 (1H, m), 7.59 (1H, td, J=8.0, 1.0 Hz), 7.69 (1H, dd, J=8.0, 1.0 Hz), 7.89 (1H, dd, J=8.0, 1.0 Hz), 8.58 (1H, s).

Reference Example 147

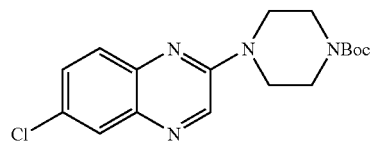
[Formula 210]

Yield: 60%, 1H-NMR (CDCl3): δ1.50 (9H, s), 3.56-3.67 (4H, m), 3.73-3.84 (4H, m), 7.53 (1H, dd, J=9.0, 2.0 Hz), 7.62 (1H, d, J=9.0 Hz), 7.88 (1H, d, J=2.0 Hz), 8.57 (1H, s).

Reference Example 148

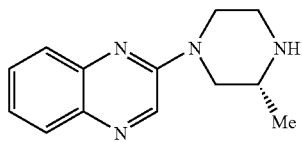
[Formula 211]

Yield: 70%, 1H-NMR (CDCl3): δ1.20 (3H, d, J=6.5 Hz), 2.68 (1H, dd, J=13.0, 10.5 Hz), 2.86-3.22 (4H, m), 4.37-4.48 (2H, m), 7.35-7.44 (1H, m), 7.53-7.62 (1H, m), 7.68 (1H, dd, J=8.5, 1.5 Hz), 7.88 (1H, dd, J=8.5, 1.5 Hz), 8.58 (1H, s).

Reference Example 149

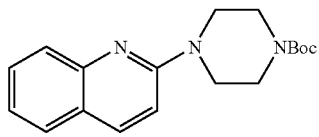
[Formula 212]

Yield: 27%, 1H-NMR (CDCl3): δ1.50 (9H, s), 3.53-3.64 (4H, m), 3.68-3.78 (4H, m), 6.98 (1H, d, J=9.0 Hz), 7.25 (1H, td, J=8.0, 1.5 Hz), 7.55 (1H, td, J=8.0, 1.5 Hz), 7.61 (1H, d, J=8.0 Hz), 7.71 (1H, d, J=8.0 Hz), 7.92 (1H, d, J=9.0 Hz)

Reference Example 150

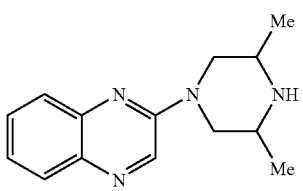
[Formula 213]

Yield: 51%, 1H-NMR (CDCl3): δ1.20 (6H, d, J=6.0 Hz), 2.58 (1H, d, J=12.5 Hz), 2.62 (1H, d, J=12.5 Hz), 2.93-3.07 (2H, m), 4.43 (2H, dd, J=12.5, 2.0 Hz), 7.38 (1H, td, J=8.5, 1.5 Hz), 7.57 (1H, td, J=8.5, 1.5 Hz), 7.68 (1H, dd, J=8.5, 1.5 Hz), 7.87 (1H, dd, J=8.5, 1.5 Hz), 8.58 (1H, s).

Reference Example 151

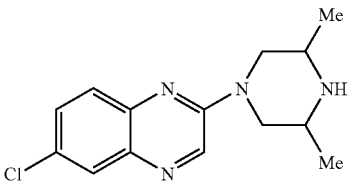
[Formula 214]

Yield: 88%, 1H-NMR (CDCl3): δ1.20 (6H, d, J=6.5 Hz), 2.58 (1H, d, J=13.0 Hz), 2.62 (1H, d, J=13.0 Hz), 2.92-3.07 (2H, m), 4.42 (2H, dd, J=13.0, 2.0 Hz), 7.50 (1H, dd, J=9.0, 2.0 Hz), 7.60 (1H, d, J=9.0 Hz), 7.85 (1H, d, J=2.0 Hz), 8.57 (1H, s).

Reference Example 152

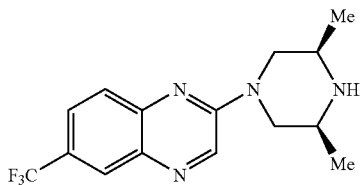
[Formula 215]

Yield: quant. %, 1H-NMR (CDCl3): δ1.21 (6H, d, J=6.0 Hz), 2.62 (1H, d, J=12.5 Hz), 2.66 (1H, d, J=12.5 Hz), 2.92-3.06 (2H, m), 4.49 (2H, dd, J=12.5, 2.0 Hz), 7.71-7.75 (2H, m), 8.14 (1H, s), 8.63 (1H, s).

Reference Example 153

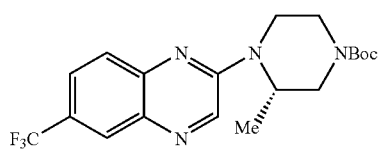
[Formula 216]

Yield: 52%, 1H-NMR (CDCl3): δ1.31 (3H, d, J=6.5 Hz), 1.51 (9H, s), 2.95-3.19 (1H, m), 3.21-3.31 (1H, m), 3.32-3.45 (1H, m), 3.92-4.41 (3H, m), 4.68-4.82 (1H, m), 7.72 (1H, s), 7.73 (1H, s), 8.17 (1H, s), 8.60 (1H, s).

Reference Example 154

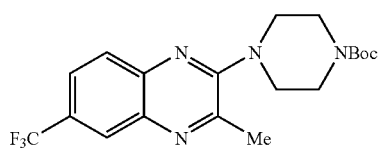
[Formula 217]

Yield: 72%, 1H-NMR (CDCl3): δ1.50 (9H, s), 2.73 (3H, s), 3.37-3.46 (4H, m), 3.62-3.70 (4H, m), 7.76 (1H, d, J=9.0 Hz), 7.89 (1H, d, J=9.0 Hz), 8.19 (1H, s).

Reference Example 155

Preparation of 4-(6-chlorobenzothiazole-2-yl)piperazine dihydrochloride

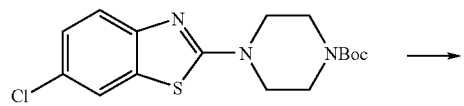
[Formula 218]

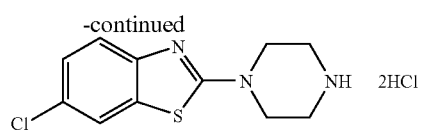

To 4N solution of hydrochloric acid-dioxane was added 4-(6-chlorobenzothiazole-2-yl)piperazine-1-carboxylic acid tert-butyl ester (1.50 g; 4.239 mmol). The mixture was stirred at 60° C. for 1 hour. The reaction solution was concentrated under reduced pressure and the residue was washed with ethyl acetate to give 4-(6-chlorobenzothiazole-2-yl)piperazine dihydrochloride as colorless crystal (1.40 g; 100%).

1H-NMR (DMSO-d6): δ3.15-3.25 (4H, m), 3.84 (4H, t, J=5 Hz), 6.88 (1H, brs), 7.34 (1H, dd, J=8.5, 2 Hz), 7.50 (1H, d, J=8.5 Hz), 7.99 (1H, d, J=2 Hz), 9.71 (2H, brs).

Compounds in Reference Examples 156 to 194 were obtained by similar methods as Reference Example 155.

Reference Example 156

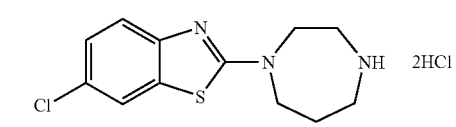
[Formula 219]

Yield: 100%, 1H-NMR (DMSO-d6): δ2.13-2.20 (2H, m), 3.20-3.22, (2H, m), 3.33-3.35 (2H, m), 3.68-3.72 (2H, m), 3.98-4.00 (2H, m), 7.33 (1H, dd, J=8.7 Hz, 2.4 Hz), 7.47 (1H, d, J=9.0 Hz), 7.97 (1H, d, J=2.1 Hz), 9.35 (2H, br-s).

Reference Example 157

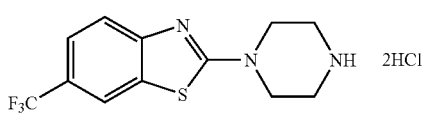
[Formula 220]

Yield: 99%, 1H-NMR (DMSO-d6): δ3.26 (4H, t, J=5 Hz), 3.90 (4H, t, J=5 Hz), 7.64 (2H, s), 8.34 (1H, s), 8.65 (1H, brs), 9.77 (2H, s).

Reference Example 158

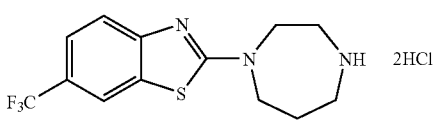
[Formula 221]

Yield: 99%, 1H-NMR (DMSO-d6): δ2.10-2.25 (2H, m), 3.20-3.30 (2H, m), 3.30-3.40 (2H, m), 3.70-3.80 (2H, m), 4.00-4.10 (2H, m), 6.64 (1H, brs), 7.60 (2H, s), 8.30 (1H, s), 9.47 (2H, s).

Reference Example 159

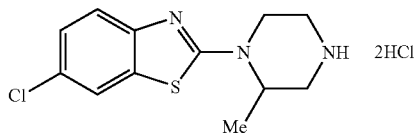
[Formula 222]

Yield: 91%, ¹H-NMR (DMSO-d₆): δ1.39 (3H, d, J=7 Hz), 3.03-3.18 (1H, m), 3.25-3.40 (4H, m), 3.95-4.05 (1H, m), 4.44-4.55 (1H, m), 7.34 (1H, dd, J=8.5, 2 Hz), 7.49 (1H, d, J=8.5 Hz), 7.96 (1H, d, J=2 Hz), 9.09 (1H, brs), 9.55 (2H, brs).

Reference Example 160

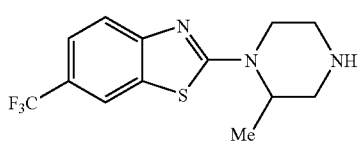
[Formula 223]

Yield: 82%, 1H-NMR (CDCl₃): δ1.40 (3H, d, J=6.5 Hz), 1.67 (1H, brs), 2.77-2.95 (2H, m), 3.05-3.15 (2H, m), 3.40 (1H, td, J=12.5, 3.5 Hz), 3.87 (1H, dd, J=12.5, 3.5 Hz), 4.15-4.30 (1H, m), 7.51 (1H, dd, J=8.5, 1 Hz), 7.56 (1H, d, J=8.5 Hz), 7.84 (1H, d, J=1 Hz).

Reference Example 161

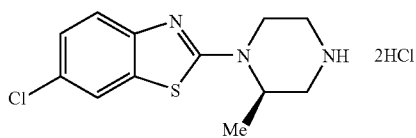
[Formula 224]

Yield: quant. %, 1H-NMR (DMSO-d6): δ1.42 (3H, d, J=7 Hz), 2.95-3.15 (1H, m), 3.15-3.40 (3H, m), 3.48-3.65 (1H, m), 3.95 (1H, m), 4.40-4.55 (1H, m), 7.33 (1H, dd, J=8.5, 2 Hz), 7.48 (1H, d, J=8.5 Hz), 7.98 (1H, d, J=2 Hz), 8.16 (1H, brs), 9.51 (1H, brs), 9.94 (1H, brs).

Reference Example 162

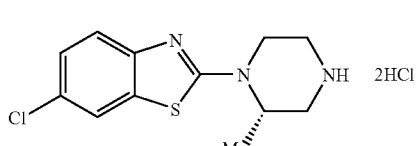
[Formula 225]

Yield: 94%, 1H-NMR (DMSO-d6): δ1.42 (3H, d, J=7.0 Hz), 2.98-3.15 (1H, m), 3.16-3.38 (3H, m), 3.47-3.63 (1H, m), 3.96-4.08 (1H, m), 4.40-4.53 (1H, m), 5.10 (1H, s), 7.33 (1H, dd, J=8.5, 2.0 Hz), 7.49 (1H, d, J=8.5 Hz), 7.97 (1H, d, J=2.0 Hz), 9.35-9.53 (1H, br), 9.82-9.98 (1H, br).

Reference Example 163

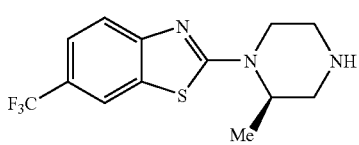
[Formula 226]

Yield: 100%, 1H-NMR (CDCl3): δ1.40 (3H, d, J=7 Hz), 2.84-2.96 (2H, m), 3.05-3.15 (2H, m), 3.39 (1H, dt, J=12.5, 3.5 Hz), 3.88 (1H, dd, J=12.5, 2.5 Hz), 4.15-4.25 (1H, m), 7.52 (1H, dd, J=8.5, 1.5 Hz), 7.56 (1H, d, J=8.5 Hz), 7.85 (1H, d, J=1.5 Hz).

Reference Example 164

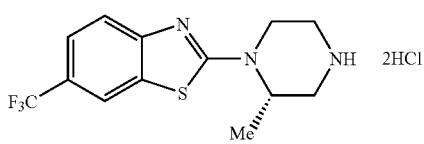
[Formula 227]

Yield: 80%, 1H-NMR (DMSO-d6): δ1.41 (3H, d, J=7.0 Hz), 3.00-3.17 (1H, m), 3.18-3.38 (3H, m), 3.49-3.64 (1H, m), 4.05-4.14 (1H, m), 4.45-4.58 (1H, m), 6.03 (1H, brs) 7.61 (2H, m), 8.31 (1H, s), 9.25-9.50 (1H, m), 9.73-9.92 (1H, m).

Reference Example 165

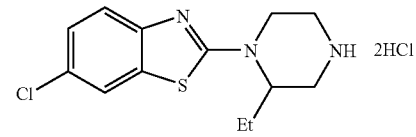
[Formula 228]

Yield: 71%, 1H-NMR (DMSO-d6): δ0.91 (3H, t, J=7.5 Hz), 1.80-1.96 (2H, m), 3.01-3.16 (1H, m), 3.17-3.42 (3H, m), 3.43-3.59 (1H, m), 4.08-4.27 (2H, m), 4.43 (1H, s), 7.33 (1H, dd, J=8.5, 2.0 Hz), 7.46 (1H, d, J=8.5 Hz), 7.94 (1H, d, J=2.0 Hz), 9.22-9.44 (1H, m), 9.60-9.75 (1H, m).

Reference Example 166

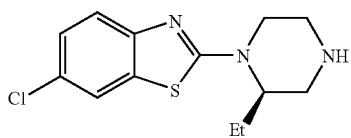

[Formula 229]

Yield: 99%, 1H-NMR (CDCl3): δ 0.98 (3H, t, J=7.5 Hz), 1.63 (1H, brs), 1.88 (2H, quant, J=7.5 Hz), 2.88 (1H, td, J=12, 3.5 Hz), 2.95-3.10 (3H, m), 3.34 (1H, td, J=12.5, 3.5 Hz), 3.77-3.86 (1H, m), 3.90-4.00 (1H, m), 7.22 (1H, dd, J=8.5, 2 Hz), 7.40 (1H, d, J=8.5 Hz), 7.53 (1H, d, J=2 Hz).

Reference Example 167

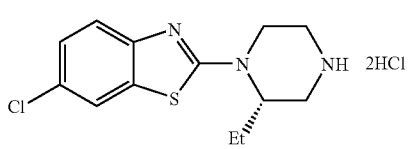

[Formula 230]

Yield: quant. % 1H-NMR (DMSO-d6): δ 0.90 (3H, t, J=7.5 Hz), 1.84-2.05 (2H, m), 2.94-3.62 (5H, m), 4.07-4.26 (2H, m), 6.71 (1H, brs), 7.32 (1H, dd, J=8.5, 2.0 Hz), 7.46 (1H, d, J=8.5 Hz), 7.96 (1H, d, J=2.0 Hz), 9.35-9.58 (1H, m), 9.73-9.95 (1H, m).

Reference Example 168

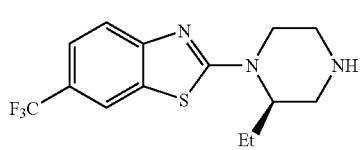

[Formula 231]

Yield: quant. %, 1H-NMR (CDCl3): δ 0.98 (3H, t, J=7.5 Hz), 1.61 (1H, brs), 1.90 (2H, quant, J=7.5 Hz), 2.89 (1H, td, J=12, 3.5 Hz), 2.95-3.13 (3H, m), 3.37 (1H, td, J=12.5, 3.5 Hz), 3.83-3.94 (1H, m), 3.95-4.06 (1H, m), 7.45-7.56 (2H, m), 7.83 (1H, s).

Reference Example 169

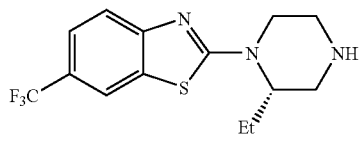

[Formula 232]

Yield: quant. %, 1H-NMR (CDCl3): δ 0.98 (3H, t, J=7.5 Hz), 1.72 (1H, brs), 1.91 (2H, quant, J=7.5 Hz), 2.89 (1H, td, J=12.5, 3.5 Hz), 2.95-3.13 (3H, m), 3.38 (1H, td, J=12.5, 3.5 Hz), 3.84-3.95 (1H, m), 3.95-4.08 (1H, m), 7.50 (1H, d, J=8.5 Hz), 7.54 (1H, d, J=8.5 Hz), 7.83 (1H, s).

Reference Example 170

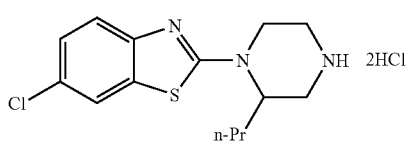

[Formula 233]

Yield: quant. %, 1H-NMR (DMSO-d6): δ 0.92 (3H, t, J=7.0 Hz), 1.20-1.45 (2H, m), 1.78-1.92 (2H, q, J=7.5 Hz), 2.97-3.38 (4H, m), 3.42-3.59 (1H, m), 4.04-4.17 (1H, m), 4.22-4.34 (1H, m), 5.64 (1H, br), 7.31 (1H, dd, J=8.5, 2.5 Hz), 7.45 (1H, d, J=8.5 Hz), 7.96 (1H, d, J=2.5 Hz), 9.04-9.20 (1H, m), 9.50-9.64 (1H, m).

Reference Example 171

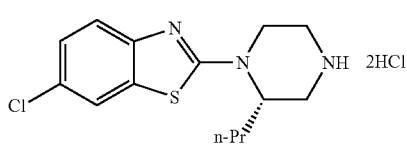

[Formula 234]

Yield: quant. %, 1H-NMR (CDCl3): δ 0.99 (3H, t, J=6.6 Hz), 1.26-1.49 (4H, m), 2.11 (2H, br), 3.63-3.83 (3H, m), 4.10 (1H, br), 4.51 (1H, br), 4.64 (1H, br), 7.22 (1H, s), 7.56-7.63 (2H, m)

Reference Example 172

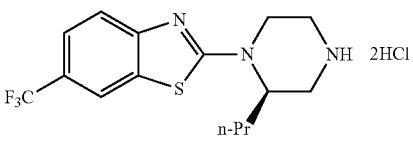

[Formula 235]

Yield: quant. %, 1H-NMR (DMSO-d6): δ 0.93 (3H, t, J=7.5 Hz), 1.18-1.46 (2H, m), 1.80-1.95 (2H, m), 3.00-3.40 (4H, m), 3.45-3.62 (1H, m), 4.12-4.24 (1H, m), 4.29-4.42 (1H, m), 7.54-7.65 (2H, m), 8.31 (1H, s), 9.14-9.32 (1H, m), 9.60-9.72 (1H, m).

Reference Example 173

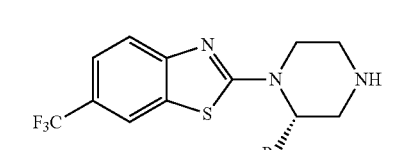

[Formula 236]

Yield: quant. %, 1H-NMR (CDCl3): δ 1.00 (3H, t, J=6.0 Hz), 1.26-1.54 (4H, m), 2.17 (2H, br), 3.63-3.86 (3H, m), 4.11 (1H, br), 4.54 (1H, br), 4.70 (1H, br), 7.50 (1H, d, J=7.5 Hz), 7.72 (1H, d, J=7.5 Hz), 7.91 (1H, s)

Reference Example 174

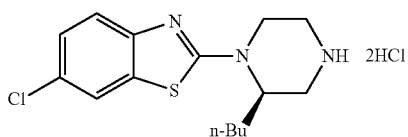

[Formula 237]

Yield: quant. %, 1H-NMR (DMSO-d6): δ0.87 (3H, t, J=7 Hz), 1.20-1.39 (4H, m), 1.78-1.95 (2H, m), 3.00-3.15 (1H, m), 3.15-3.40 (3H, m), 3.42-3.55 (1H, m), 4.07-4.20 (1H, m), 4.20-4.30 (1H, m), 4.55 (1H, brs), 7.31 (1H, dd, J=8.5, 2 Hz), 7.44 (1H, d, J=8.5 Hz), 7.95 (1H, d, J=2 Hz), 9.00 (1H, brs), 9.48 (1H, brs).

Reference Example 175

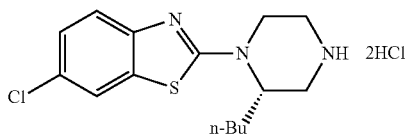

[Formula 238]

Yield: quant. %, 1H-NMR (DMSO-d6): δ0.87 (3H, t, J=7 Hz), 1.18-1.40 (4H, m), 1.77-1.98 (2H, m), 2.95-3.14 (1H, m), 3.14-3.37 (3H, m), 3.40-3.51 (1H, m), 4.08-4.20 (1H, m), 4.20-4.31 (1H, m), 6.89 (1H, brs), 7.31 (1H, dd, J=8.5, 2 Hz), 7.44 (1H, d, J=8.5 Hz), 7.95 (1H, d, J=2 Hz), 9.25 (1H, brs), 9.62 (1H, brs).

Reference Example 176

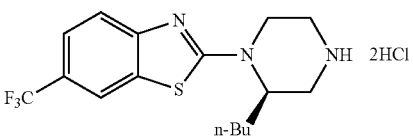

[Formula 239]

Yield: quant. %, 1H-NMR (DMSO-d6): δ0.85-0.90 (3H, m), 1.20-1.40 (4H, m), 1.85-2.00 (2H, m), 3.00-3.59 (5H, m), 4.15-4.23 (1H, m), 4.24-4.35 (1H, m), 7.60 (2H, s), 8.29 (1H, s), 9.36 (2H, brs), 9.75 (1H, s).

Reference Example 177

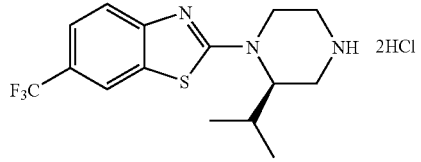

[Formula 240]

Yield: quant. %, 1H-NMR (DMSO-d6): δ0.86 (3H, d, J=6.5 Hz), 1.04 (3H, d, J=6.5 Hz), 3.00-3.35 (4H, m), 3.38-3.60 (2H, m), 3.87-4.02 (1H, m), 4.16-4.31 (1H, m), 5.20 (1H, br), 7.57 (1H, d, J=8.5 Hz), 7.61 (1H, d, J=8.5 Hz), 8.29 (1H, s), 9.05-9.22 (1H, m), 9.37-9.50 (1H, m).

Reference Example 178

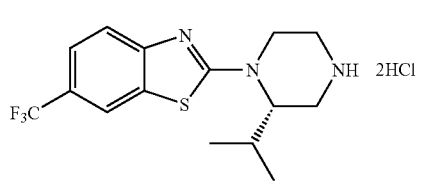

[Formula 241]

Yield: 93%, H-NMR (DMSO-d6): δ0.86 (3H, d, J=6.5 Hz), 1.00 (3H, d, J=6.5 Hz), 2.50-2.60 (1H, m), 3.03-3.31 (3H, m), 3.44-3.60 (2H, m), 3.90-4.00 (1H, m), 4.20-4.30 (1H, m), 7.54-7.63 (2H, m), 8.29 (1H, s), 9.23 (1H, brs), 9.48 (2H, brs).

Reference Example 179

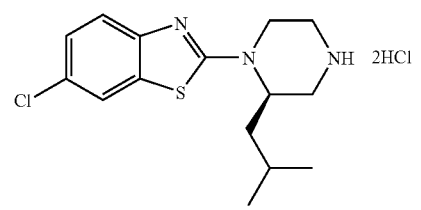

[Formula 242]

Yield: 96%, 1H-NMR (DMSO-d6): δ0.95 (6H, d, J=6.5 Hz), 1.50-1.90 (3H, m), 2.96-3.37 (4H, m), 3.40-3.60 (1H, m), 4.03-4.16 (1H, m), 4.27-4.40 (1H, m), 6.30 (1H, br), 7.32 (1H, dd, J=8.5, 2.0 Hz), 7.45 (1H, d, J=8.5 Hz), 7.97 (1H, d, J=2.0 Hz), 9.10-9.32 (1H, m), 9.52-9.75 (1H, m).

Reference Example 180

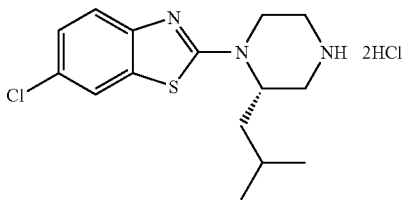

[Formula 243]

Yield: quant. %, 1H-NMR (DMSO-d6): δ0.94 (6H, d, J=6.5 Hz), 1.52-1.94 (3H, m), 2.95-3.35 (4H, m), 3.45-3.57 (1H, m), 4.04-4.16 (1H, m), 4.29-4.40 (1H, m), 7.32 (1H, dd, J=8.5, 2 Hz), 7.45 (1H, d, J=8.5 Hz), 7.97 (1H, d, J=2 Hz), 9.45 (1H, brs), 9.81 (1H, brs), 9.84 (1H, brs).

Reference Example 181

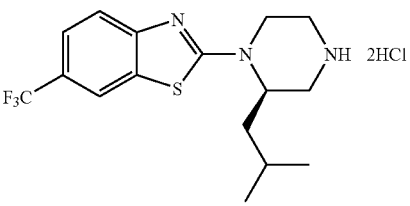

[Formula 244]

Yield: quant. %, 1H-NMR (DMSO-d6): δ0.96 (6H, d, J=6.5 Hz), 1.50-1.90 (3H, m), 2.99-3.39 (4H, m), 3.46-3.63 (1H, m), 4.08-4.22 (1H, m), 4.35-4.48 (1H, m), 6.11 (1H, brs), 7.60 (2H, s), 8.31 (1H, s), 9.10-9.29 (1H, m), 9.54-9.67 (1H, m).

Reference Example 182

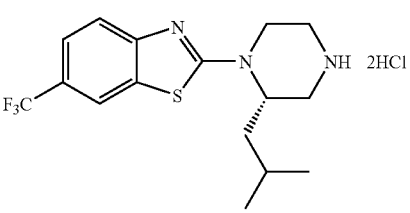

[Formula 245]

Yield: 97%, 1H-NMR (CDCl3): δ1.04 (6H, s), 1.68 (1H, br), 1.98 (1H, br), 2.07 (1H, br), 3.54 (3H, br), 3.71 (1H, br), 3.98 (1H, s), 4.46 (2H, br), 7.52 (1H, d, J=7.5 Hz), 7.65 (1H, d, J=7.5 Hz), 7.90 (1H, s)

Reference Example 183

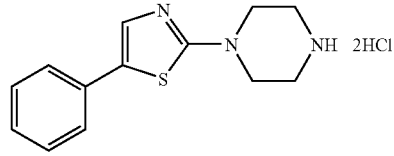

[Formula 246]

Yield: 94%, 1H-NMR (DMSO-d6): δ3.24 (4H, t, J=5.0 Hz), 3.74 (4H, t, J=5.0 Hz), 5.12 (1H, s), 7.26 (1H, t, J=7.5 Hz), 7.39 (2H, t, J=7.5 Hz), 7.51 (2H, d, J=7.5 Hz), 7.71 (1H, s), 9.58 (2H, s).

Reference Example 184

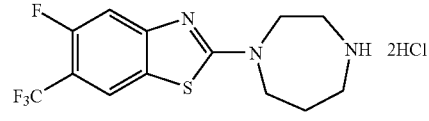

[Formula 247]

Yield: 96%, 1H-NMR (DMSO-d6): δ3.17-3.34 (4H, m), 3.83-3.96 (4H, m), 5.12 (1H, brs), 7.55 (1H, d, J=12.5 Hz), 8.36 (1H, d, J=7.5 Hz), 9.69 (2H, brs).

Reference Example 185

[Formula 248]

Yield: 92%, 1H-NMR (DMSO-d6): δ2.14-2.27 (2H, m), 3.16-3.30 (2H, m), 3.31-3.43 (2H, m), 3.66-3.84 (2H, m), 3.97-4.13 (2H, m), 4.78 (1H, brs), 7.53 (1H, d, J=12.5 Hz), 8.32 (1H, d, J=7.5 Hz), 9.53 (2H, brs).

Reference Example 186

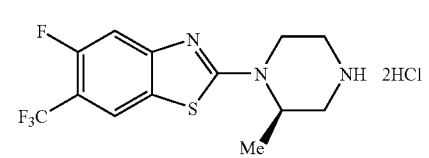

[Formula 249]

Yield: 89%, 1H-NMR (CDCl3): δ1.44 (3H, d, J=7.0 Hz), 3.00-3.13 (1H, m), 3.14-3.40 (3H, m), 3.53-3.69 (1H, m), 4.02-4.15 (1H, m), 4.46-4.60 (1H, m), 6.90 (1H, brs), 7.55 (1H, d, J=12.5 Hz), 8.35 (1H, d, J=7.0 Hz), 9.50 (1H, br), 9.94 (1H, br).

Reference Example 187

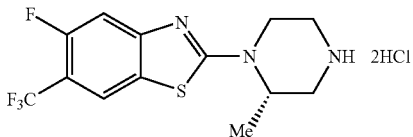
[Formula 250]

Yield: 83%, 1H-NMR (DMSO-d6): δ1.44 (3H, d, J=7.0 Hz), 3.01-3.19 (1H, m), 3.20-3.45 (3H, m), 3.51-3.70 (1H, m), 4.01-4.16 (1H, m), 4.45-4.62 (1H, m), 5.95 (1H, brs), 7.55 (1H, d, J=12.5 Hz), 8.35 (1H, d, J=7.5 Hz), 9.49 (1H, br), 9.89 (1H, br).

Reference Example 188

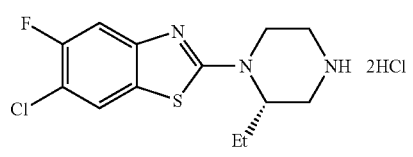
[Formula 251]

Yield: 83%, 1H-NMR (DMSO-d6): δ0.90 (3H, t, J=7.5 Hz), 1.80-2.00 (2H, m), 2.97-3.40 (4H, m), 3.41-3.56 (1H, m), 4.06-4.26 (2H, m), 7.49 (1H, d, J=10.5 Hz), 8.10 (1H, d, J=7.5 Hz), 9.02-9.25 (1H, m), 9.43-9.65 (1H, m).

Reference Example 189

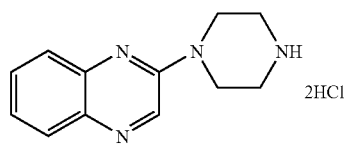
[Formula 252]

Yield: quant. %, 1H-NMR (DMSO-d6): δ3.16-3.32 (4H, m), 3.98-4.12 (4H, m), 7.42-7.51 (1H, m), 7.60-7.72 (2H, m), 7.88 (1H, d, J=8.0 Hz), 8.90 (1H, s), 9.54 (2H, s).

Reference Example 190

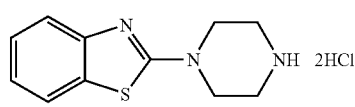
[Formula 253]

Yield: 92%, 1H-NMR (DMSO-d6): δ2.19-3.32 (4H, m), 3.80-3.90 (4H, m), 7.15 (1H, td, J=8.0, 1.0 Hz), 7.34 (1H, td; J=8.0, 1.0 Hz), 7.54 (1H, dd, J=8.0, 1.0 Hz), 7.85 (1H, dd, J=8.0, 1.0 Hz), 9.65 (2H, s).

Reference Example 191

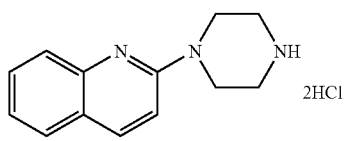
[Formula 254]

Yield: 91%, 1H-NMR (DMSO-d6): δ3.30 (4H, s), 3.80 (1H, br), 4.16 (4H, s), 7.38-7.60 (2H, m), 7.68-7.81 (1H, m), 7.84-7.97 (1H, m), 8.16 (1H, br), 8.32-8.52 (1H, m), 9.57 (2H, brs).

Reference Example 192

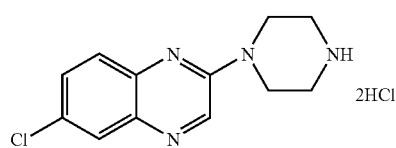
[Formula 255]

Yield: 63%, 1H-NMR (DMSO-d6): δ3.24 (4H, s), 3.87 (1H, brs), 4.03 (4H, s), 7.66 (2H, s), 7.93 (1H, s), 8.92 (1H, s), 9.38 (2H, brs).

Reference Example 193

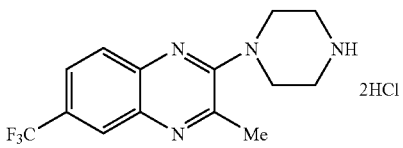
[Formula 256]

Yield: 82%, 1H-NMR (DMSO-d6): δ2.71 (3H, s), 3.24-3.35 (4H, m), 3.62-3.73 (4H, m), 7.91 (1H, d, J=9.0 Hz), 7.97 (1H, d, J=9.0 Hz), 8.23 (1H, s), 9.32 (2H, brs).

Reference Example 194

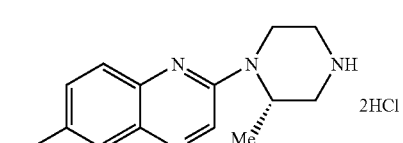
[Formula 257]

Yield: 80%, 1H-NMR (DMSO-d6): δ1.39 (3H, d, J=7.0 Hz), 3.00-3.16 (1H, m), 3.18-3.54 (5H, m), 4.68 (1H, d, J=14.0 Hz), 5.05-5.17 (1H, m), 7.79 (1H, d, J=8.5 Hz), 7.89 (1H, d, J=8.5 Hz), 8.20 (1H, s), 8.97 (1H, s), 9.19 (1H, brs), 9.53 (1H, brs).

Example 1

Preparation of 3-[[4-(6-chlorobenzothiazole-2-yl)piperazine-1-yl]methyl]benzoic acid methyl ester

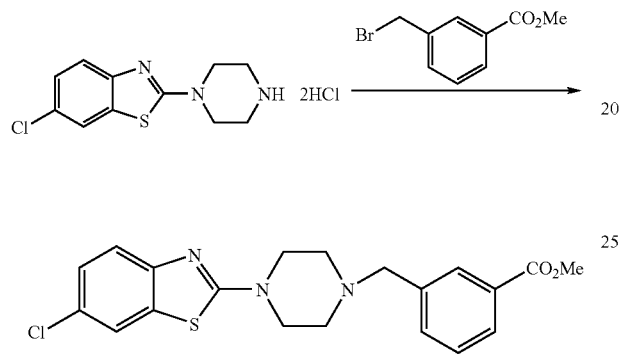

[Formula 258]

A mixture of 4-(6-chlorobenzothiazole-2-yl)piperazine dihydrochloride (3.00 g; 9.18 mmol), 3-(bromomethyl)methyl butanoate (2.31 g; 10.1 mmol), potassium carbonate (3.81 g; 27.6 mmol) and anhydrous N,N-dimethylformamide (30 ml) was stirred at room temperature for 14 hours. Water was added to the reaction solution. The precipitate was collected and washed with diisopropyl ether to give 3-[[4-(6-chlorobenzothiazole-2-yl)piperazine-1-yl]methyl]benzoic acid methyl ester as colorless crystal (3.06 g; 83%).

$^1$H-NMR (CDCl$_3$): δ2.58 (4H, t, J=5 Hz), 3.61 (2H, s), 3.64 (4H, t, J=5 Hz), 3.93 (3H, s), 7.23 (1H, dd, J=8.5, 2 Hz), 7.35-7.45 (1H, m), 7.43 (1H, d, J=8.5 Hz), 7.55 (1H, d, J=2 Hz), 7.55-7.60 (1H, m), 7.96 (1H, d, J=7.5 Hz), 8.01 (1H, s).

Compounds in Example 2 to 127 were obtained by similar methods as Example 1.

Example 2

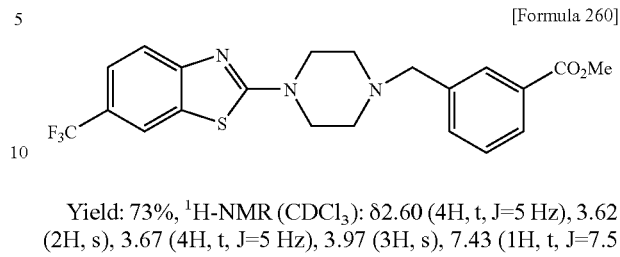

[Formula 259]

Yield: 88%, $^1$H-NMR (CDCl$_3$): δ2.01-2.05 (2H, m), 2.69 (2H, t, J=5.4 Hz), 2.80-2.83 (2H, m), 3.67 (2H, s) 3.72-3.78 (4H, m), 3.92 (3H, s), 7.23 (1H, dd, J=8.7 Hz, 2.1 Hz), 7.37-7.44 (2H, m), 7.53 (1H, s), 7.55 (1H, d, J=2.1 Hz), 7.94 (1H, d, J=7.5 Hz), 7.99 (1H, s).

Example 3

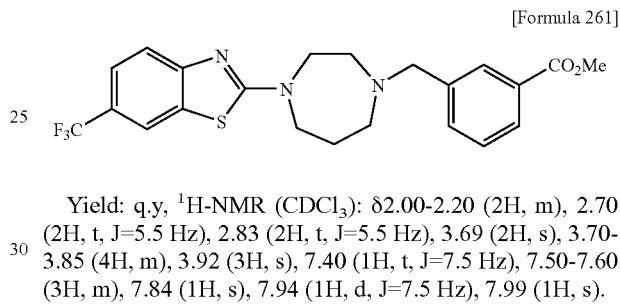

[Formula 260]

Yield: 73%, $^1$H-NMR (CDCl$_3$): δ2.60 (4H, t, J=5 Hz), 3.62 (2H, s), 3.67 (4H, t, J=5 Hz), 3.97 (3H, s), 7.43 (1H, t, J=7.5 Hz), 7.50-7.60 (3H, m), 7.85 (1H, s), 7.97 (1H, d, J=7.5 Hz), 8.02 (1H, s).

Example 4

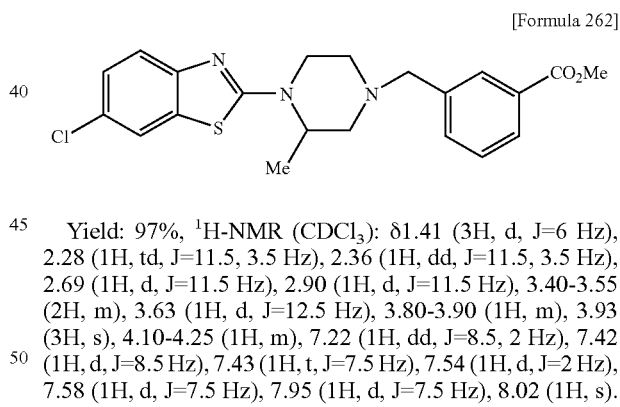

[Formula 261]

Yield: q.y, $^1$H-NMR (CDCl$_3$): δ2.00-2.20 (2H, m), 2.70 (2H, t, J=5.5 Hz), 2.83 (2H, t, J=5.5 Hz), 3.69 (2H, s), 3.70-3.85 (4H, m), 3.92 (3H, s), 7.40 (1H, t, J=7.5 Hz), 7.50-7.60 (3H, m), 7.84 (1H, s), 7.94 (1H, d, J=7.5 Hz), 7.99 (1H, s).

Example 5

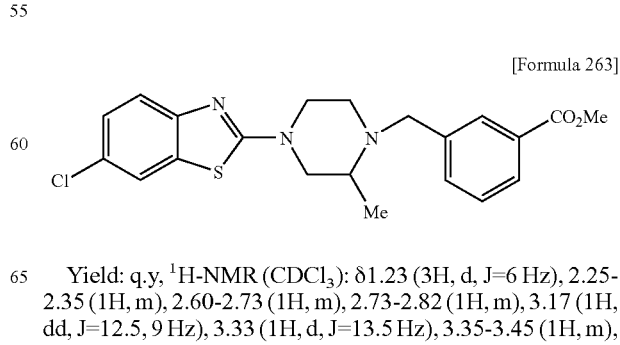

[Formula 262]

Yield: 97%, $^1$H-NMR (CDCl$_3$): δ1.41 (3H, d, J=6 Hz), 2.28 (1H, td, J=11.5, 3.5 Hz), 2.36 (1H, dd, J=11.5, 3.5 Hz), 2.69 (1H, d, J=11.5 Hz), 2.90 (1H, d, J=11.5 Hz), 3.40-3.55 (2H, m), 3.63 (1H, d, J=12.5 Hz), 3.80-3.90 (1H, m), 3.93 (3H, s), 4.10-4.25 (1H, m), 7.22 (1H, dd, J=8.5, 2 Hz), 7.42 (1H, d, J=8.5 Hz), 7.43 (1H, t, J=7.5 Hz), 7.54 (1H, d, J=2 Hz), 7.58 (1H, d, J=7.5 Hz), 7.95 (1H, d, J=7.5 Hz), 8.02 (1H, s).

Example 6

[Formula 263]

Yield: q.y, $^1$H-NMR (CDCl$_3$): δ1.23 (3H, d, J=6 Hz), 2.25-2.35 (1H, m), 2.60-2.73 (1H, m), 2.73-2.82 (1H, m), 3.17 (1H, dd, J=12.5, 9 Hz), 3.33 (1H, d, J=13.5 Hz), 3.35-3.45 (1H, m), 3.65-3.75 (1H, m), 3.85-3.90 (1H, m), 3.93 (3H, s), 4.08 (1H, d, J=13.5 Hz), 7.22 (1H, dd, J=8.5, 2 Hz), 7.41 (1H, t, J=7.5 Hz), 7.43 (1H, d, J=8.5 Hz), 7.54 (1H, d, J=2 Hz), 7.56 (1H, d, J=7.5 Hz), 7.94 (1H, d, J=7.5 Hz), 8.01 (1H, s).

Example 7

[Formula 264]

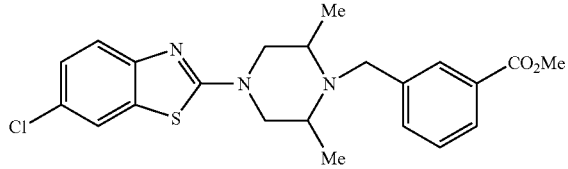

Yield: 83%, $^1$H-NMR (CDCl$_3$): δ1.15 (6H, d, J=6 Hz), 2.75-2.85 (2H, m), 3.06 (2H, dd, J=13, 12.5 Hz), 3.80-3.92 (4H, m), 3.92 (3H, s), 7.24 (1H, dd, J=8.5, 2 Hz), 7.37 (1H, d, J=7.5 Hz), 7.43 (1H, d, J=8.5 Hz), 7.55 (1H, d, J=2 Hz), 7.62 (1H, d, J=7.5 Hz), 7.89 (1H, d, J=7.5 Hz), 8.04 (1H, s).

Example 8

[Formula 265]

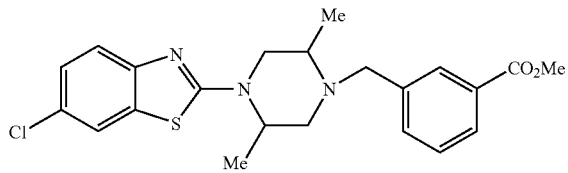

Yield: 79%, $^1$H-NMR (CDCl$_3$): δ1.10 (3H, d, J=6.5 Hz), 1.38 (3H, d, J=6.5 Hz), 2.31 (1H, d, J=12 Hz), 2.91 (1H, dd, J=12.4 Hz), 3.10-3.20 (1H, m), 3.59 (2H, t, J=14 Hz), 3.71 (2H, t, J=14 Hz), 3.93 (3H, s), 4.16-4.28 (1H, m), 7.22 (1H, dd, J=8.5, 2 Hz), 7.42 (1H, d, J=8.5 Hz), 7.43 (1H, d, J=7.5 Hz), 7.53 (1H, d, J=2 Hz), 7.61 (1H, d, J=7.5 Hz), 7.95 (1H, d, J=7.5 Hz), 8.06 (1H, s).

Example 9

[Formula 266]

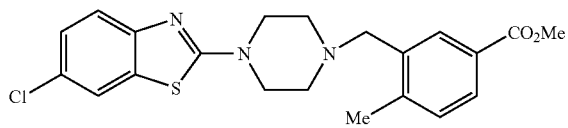

Yield 92%, $^1$H-NMR (CDCl$_3$): δ2.45 (3H, s), 2.58 (4H, t, J=5 Hz), 3.55 (2H, s), 3.61 (4H, t, J=5 Hz), 3.91 (3H, s), 7.23 (1H, dd, J=8.5, 2 Hz), 7.24 (1H, d, J=8 Hz), 7.43 (1H, d, J=8.5 Hz), 7.55 (1H, d, J=2 Hz), 7.87 (1H, dd, J=8, 1.5 Hz), 7.92 (1H, d, J=1.5 Hz).

Example 10

[Formula 267]

Yield 93%, $^1$H-NMR (CDCl$_3$): δ2.66 (4H, t, J=5 Hz), 3.66 (4H, t, J=5 Hz), 3.71 (2H, s), 3.96 (3H, s), 7.24 (1H, dd, J=8.5, 2 Hz), 7.44 (1H, d, J=8.5 Hz), 7.45 (1H, d, J=8 Hz), 7.55 (1H, d, J=2 Hz), 7.88 (1H, dd, J=8.2 Hz), 8.15 (1H, d, J=2 Hz).

Example 11

[Formula 268]

Yield 79%, $^1$H-NMR (CDCl$_3$): δ1.99-2.05 (2H, m), 2.40 (3H, s), 2.69 (2H, t, J=5.1 Hz), 2.79-2.82 (2H, m), 3.61 (2H, s), 3.71-3.75 (4H, m), 3.90 (3H, s), 7.21-7.25 (2H, m), 7.42 (1H, d, J=8.4 Hz), 7.55 (1H, d, J=2.4 Hz), 7.38-7.87 (1H, m), 7.92 (1H, s).

Example 12

[Formula 269]

Yield 79%, $^1$H-NMR (CDCl$_3$): δ2.03-2.10 (2H, m), 2.75 (2H, t, J=5.4 Hz), 2.87-2.90 (2H, m), 3.73-3.80 (6H, m), 3.92 (3H, s), 7.22-7.26 (1H, m), 7.41 (1H, s), 7.44 (1H, s), 7.55 (1H, d, J=2.1 Hz), 7.87 (1H, dd, J=8.4 Hz, 2.1 Hz), 8.15 (1H, d, J=2.1 Hz).

Example 13

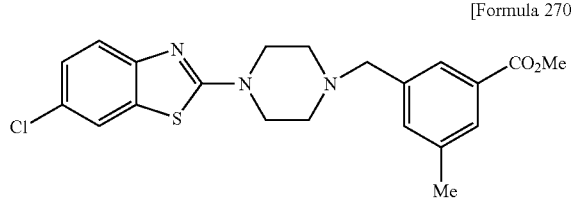
[Formula 270]

Yield 90%, $^1$H-NMR (CDCl$_3$): δ2.38 (3H, s), 2.57 (4H, t, J=5 Hz), 3.51 (2H, s), 3.64 (4H, t, J=5 Hz), 3.92 (3H, s), 7.23 (1H, dd, J=8.5, 2 Hz), 7.37 (1H, s), 7.43 (1H, d, J=8.5 Hz), 7.55 (1H, d, J=2 Hz), 7.78 (1H, s), 7.80 (1H, s).

Example 14

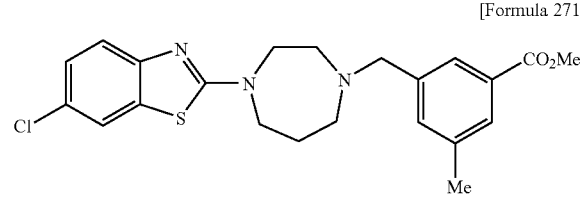
[Formula 271]

Yield 90%, $^1$H-NMR (CDCl$_3$): δ1.59 (3H, s), 2.00-2.06 (2H, m), 2.39 (3H, s), 2.69 (2H, t, J=5.4 Hz), 2.79-2.82 (2H, m), 3.64 (2H, s) 3.74-3.77 (4H, m), 7.23 (1H, dd, J=8.4 Hz, 1.8 Hz), 7.35 (1H, s), 7.42 (1H, d, J=8.4 Hz), 7.55 (1H, d, J=1.8 Hz), 7.75 (1H, s), 7.78 (1H, s).

Example 15

[Formula 272]

$^1$H-NMR (CDCl$_3$): δ2.65 (4H, t, J=5.1 Hz), 3.64-3.67 (4H, m), 3.78 (2H, s), 3.88 (3H, s), 6.93 (1H, d, J=3.3 Hz), 7.24 (1H, dd, J=8.7, 2.1 Hz), 7.44 (1H, d, J=8.7 Hz), 7.56 (1H, d, J=2.1 Hz), 7.67 (1H, d, J=3.3 Hz).

Example 16

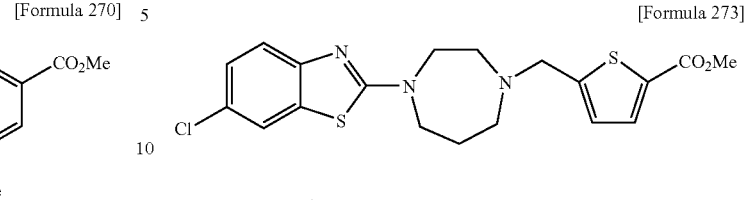
[Formula 273]

Yield 65%, $^1$H-NMR (CDCl$_3$): δ2.01-2.08 (2H, m), 2.71-2.75 (2H, m), 2.85-2.89 (2H, m), 3.72-3.76 (2H, m), 3.79-3.82 (2H, m), 3.86 (2H, s), 3.87 (3H, s), 6.89 (1H, d, J=3.9 Hz), 7.23 (1H, dd, J=8.7 Hz, 2.1 Hz), 7.42 (1H, d, J=8.7 Hz), 7.55 (1H, d, J=2.4 Hz), 7.65 (1H, d, J=3.9 Hz).

Example 17

[Formula 274]

$^1$H-NMR (CDCl3): δ1.37 (3H, t, J=7 Hz), 2.65 (4H, t, J=5 Hz), 3.65 (4H, t, J=5 Hz), 3.69 (2H, s), 4.36 (2H, q, J=7 Hz), 6.37 (1H, d, J=3.5 Hz), 7.13 (1H, d, J=3.5 Hz), 7.24 (1H, dd, J=8.5, 2 Hz), 7.43 (1H, d, J=8.5 Hz), 7.55 (1H, d, J=2 Hz).

Example 18

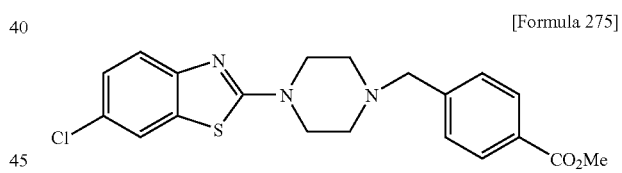
[Formula 275]

$^1$H-NMR (CDCl$_3$): δ2.56-2.60 (4H, m), 3.62-3.66 (6H, m), 3.92 (3H, s), 7.24 (1H, dd, J=8.7, 2.1 Hz), 7.42-7.44 (3H, m), 7.55 (1H, d, J=2.1 Hz), 8.01 (2H, d, J=8.4 Hz).

Example 19

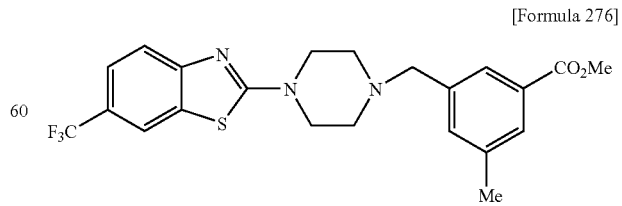
[Formula 276]

Yield 76%, $^1$H-NMR (CDCl$_3$): δ2.41 (3H, s), 2.59 (4H, t, J=5 Hz), 3.58 (2H, s), 3.69 (4H, t, J=5 Hz), 3.96 (3H, s), 7.37

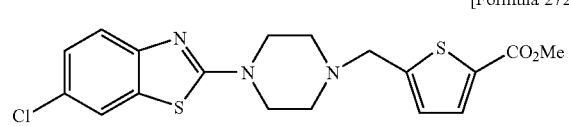

(1H, s), 7.50-7.60 (2H, m), 7.79 (1H, s), 7.80 (1H, s), 7.85 (1H, s).

Example 20

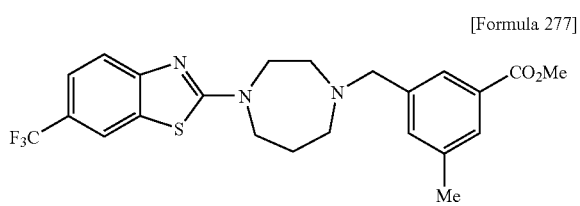

[Formula 277]

Yield 74%, $^1$H-NMR (CDCl$_3$): δ2.00-2.10 (2H, m), 2.38 (3H, s), 2.70 (2H, t, J=5 Hz), 2.82 (2H, t, J=5 Hz), 3.65 (2H, s), 3.70-3.90 (4H, m), 3.91 (3H, s), 7.34 (1H, s), 7.50-7.60 (2H, m), 7.75 (1H, s), 7.79 (1H, s), 7.85 (1H, s).

Example 21

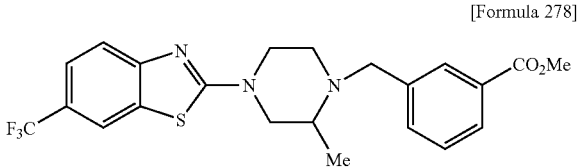

[Formula 278]

Yield 98%, 1H-NMR (CDCl3): δ1.24 (3H, d, J=6.5 Hz), 2.25-2.37 (1H, m), 2.64-2.75 (1H, m), 2.75-2.83 (1H, m), 3.23 (1H, dd, J=13, 9 Hz), 3.29 (1H, d, J=13.5 Hz), 3.40-3.50 (1H, m), 3.70-3.80 (1H, m), 3.87-3.95 (1H, m), 3.93 (3H, s), 4.08 (1H, d, J=13.5 Hz), 7.42 (1H, t, J=7.5 Hz), 7.50-7.60 (3H, m), 7.84 (1H, s), 7.95 (1H, d, J=8 Hz), 8.01 (1H, s).

Example 22

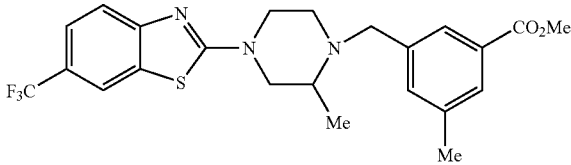

[Formula 279]

Yield 85%, 1H-NMR (CDCl3): δ1.24 (3H, d, J=6.5 Hz), 2.23-2.35 (1H, m), 2.41 (3H, s), 2.60-2.73 (1H, m), 2.80 (1H, dt, J=12, 3.5 Hz), 3.21 (1H, d, J=13 Hz), 3.24 (1H, d, J=13.5 Hz), 3.39-3.50 (1H, m), 3.70-3.80 (1H, m), 3.91 (3H, s), 3.91-3.95 (1H, m), 4.05 (1H, d, J=13.5 Hz), 7.36 (1H, s), 7.51 (1H, d, J=8.5 Hz), 7.55 (1H, d, J=8.5 Hz), 7.77 (1H, s), 7.80 (1H, s), 7.84 (1H, s).

Example 23

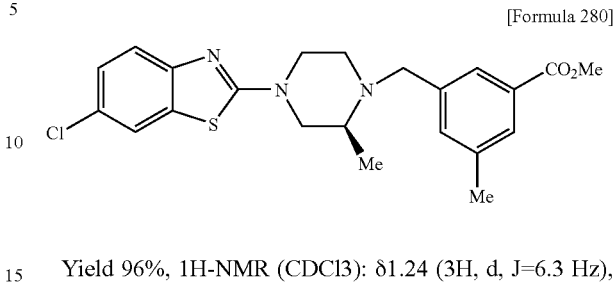

[Formula 280]

Yield 96%, 1H-NMR (CDCl3): δ1.24 (3H, d, J=6.3 Hz), 2.24-2.32 (1H, m), 2.40 (3H, s), 2.63-2.68 (1H, m), 2.78 (1H, dt, J=3.6, 12.0 Hz), 3.17 (1H, dd, J=9.0 Hz), 3.22 (1H, d, J=13.2 Hz), 3.35-3.43 (1H, m), 3.71 (1H, dt, J=3.3, 12.6 Hz), 3.88 (1H, dd, J=3.0, 15.0 Hz), 3.91 (3H, s), 4.05 (1H, d, J=13.2 Hz), 7.23 (1H, dd, J=2.4, 8.4 Hz), 7.36 (1H, s), 7.43 (1H, d, J=8.4 Hz), 7.54 (1H, d, J=2.4 Hz), 7.76 (1H, s), 7.79 (1H, s)

Example 24

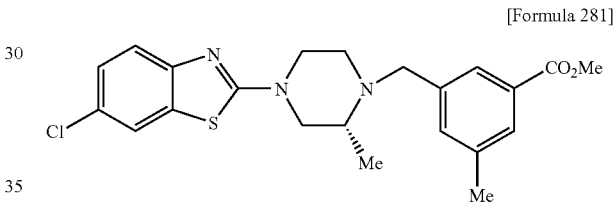

[Formula 281]

Yield 98%, 1H-NMR (CDCl3): δ1.24 (3H, d, J=6.3 Hz), 2.28 (1H, ddd, J=3.3, 8.7, 9.6 Hz), 2.40 (3H, s), 2.62-2.68 (1H, m), 2.78 (1H, dt, J=3.6, 12.0 Hz), 3.17 (1H, dd, J=8.7, 12.6 Hz), 3.22 (1H, d, J=12.9 Hz), 3.39 (1H, m), 3.71 (1H, d, 12.3 Hz), 3.88 (1H, dd, 3.3, 13.2 Hz), 3.92 (3H, s), 4.05 (1H, d, J=13.2 Hz), 7.23 (1H, dd, J=2.1, 8.4 Hz), 7.36 (1H, s), 7.43 (1H, d, J=8.4 Hz), 7.54 (1H, d, J=2.1 Hz), 7.76 (1H, s), 7.79 (1H, s)

Example 25

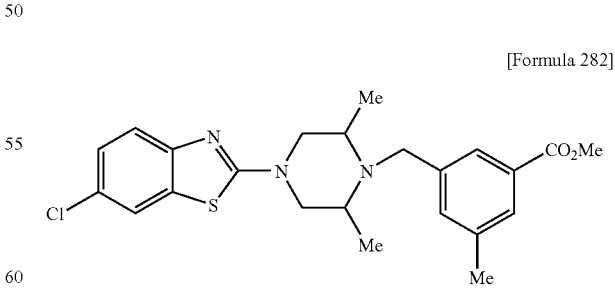

[Formula 282]

Yield 86%, 1H-NMR (CDCl3): δ1.11 (6H, d, J=6 Hz), 2.40 (3H, s), 2.70-2.85 (2H, m), 3.00-3.15 (2H, m), 3.83 (2H, s), 3.83-3.90 (2H, m), 3.91 (3H, s), 7.23 (1H, dd, J=8.5, 2 Hz), 7.40 (1H, s), 7.43 (1H, d, J=8.5 Hz), 7.55 (1H, d, J=2 Hz), 7.72 (1H, s), 7.84 (1H, s).

Example 26

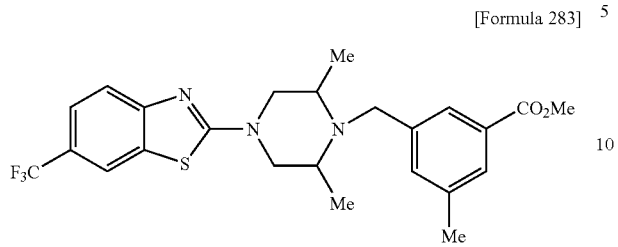
[Formula 283]

Yield 67%, 1H-NMR (CDCl3): δ1.13 (6H, d, J=6.5 Hz), 2.40 (3H, s), 2.75-2.88 (2H, m), 3.05-3.18 (2H, m), 3.84 (2H, s), 3.91 (3H, s), 3.91-3.95 (2H, m), 7.40 (1H, s), 7.52 (1H, d, J=8.5 Hz), 7.57 (1H, d, J=8.5 Hz), 7.72 (1H, s), 7.84 (2H, s).

Example 27

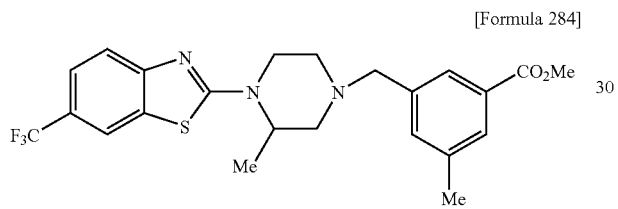
[Formula 284]

Yield 75%, 1H-NMR (CDCl3): δ1.42 (3H, d, J=6.5 Hz), 2.26 (1H, td, J=11.5, 3.5 Hz), 2.36 (1H, dd, J=11.5, 3.5 Hz), 2.41 (3H, s), 2.65-2.75 (1H, m), 2.85-2.95 (1H, m), 3.47 (1H, d, J=13.5 Hz), 3.48-3.55 (1H, m), 3.60 (1H, d, J=13.5 Hz), 3.80-3.90 (1H, m), 3.91 (3H, s), 4.20-4.30 (1H, m), 7.38 (1H, s), 7.51 (1H, dd, J=8.5, 2 Hz), 7.56 (1H, d, J=8.5 Hz), 7.77 (1H, s), 7.83 (1H, d, J=2 Hz), 7.84 (1H, s).

Example 28

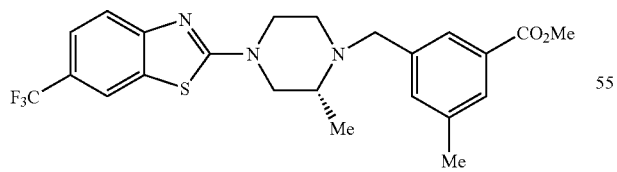
[Formula 285]

Yield 78%, 1H-NMR (CDCl$_3$): δ1.24 (3H, t, J=6.0 Hz), 2.24-2.36 (1H, m), 2.41 (3H, s), 2.61-2.73 (1H, m), 2.75-2.84 (1H, m), 3.21 (1H, d, J=13.0 Hz), 3.24 (1H, d, J=13.5 Hz), 3.38-3.51 (1H, m), 3.71-3.82 (1H, m), 3.88-3.98 (1H, m), 3.92 (3H, s), 4.05 (1H, d, J=13.0 Hz), 7.36 (1H, s), 7.51 (1H, d, J=8.5), 7.56 (1H, d, J=8.5 Hz), 7.77 (1H, s), 7.80 (1H, s), 7.84 (1H, s).

Example 29

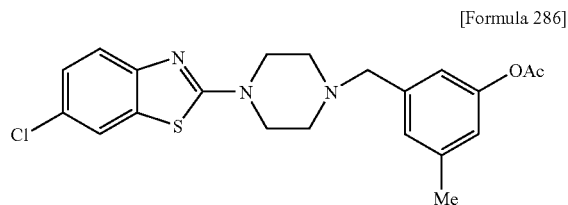
[Formula 286]

Yield 58%, $^1$H-NMR (DMSO-d$_6$): δ2.25 (3H, s), 2.31 (3H, s), 2.51 (4H, t, J=5 Hz), 3.51 (2H, s), 3.57 (4H, t, J=5 Hz), 6.85 (1H, s), 6.89 (1H, s), 7.04 (1H, s), 7.28 (1H, dd, J=8.5, 2.5 Hz), 7.42 (1H, d, J=8.5 Hz), 7.91 (1H, d, J=2.5 Hz).

Example 30

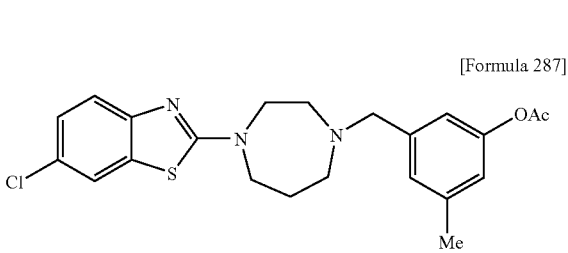
[Formula 287]

Yield 89%, $^1$H-NMR (CDCl$_3$): δ1.99-2.06 (2H, m), 2.29 (3H, s), 2.34 (3H, s), 2.68 (2H, t, J=5.7 Hz), 2.78-2.82 (2H, m), 3.61 (2H, s), 3.72-3.78 (4H, m), 6.79 (1H, s), 6.88 (1H, s), 6.98 (1H, s), 7.22 (1H, dd, J=7.5, 3.3 Hz), 7.42 (1H, d, J=6.3 Hz), 7.54 (1H, d, J=2.1 Hz).

Example 31

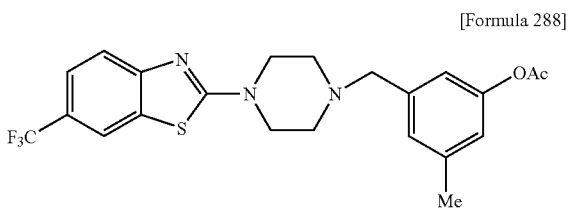
[Formula 288]

Yield 71%, $^1$H-NMR (CDCl$_3$): δ2.30 (3H, s), 2.36 (3H, s), 2.59 (4H, t, J=5 Hz), 3.53 (2H, s), 3.68 (4H, t, J=5 Hz), 6.83 (1H, s), 6.90 (1H, s), 7.02 (1H, s), 7.50-7.60 (2H, m), 7.85 (1H, s).

Example 32

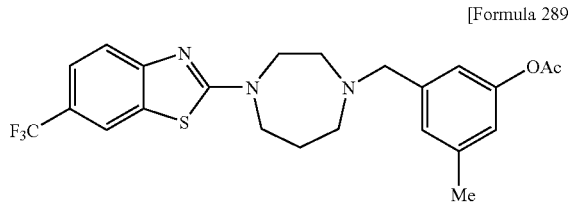
[Formula 289]

Yield 65%, ¹H-NMR (CDCl₃): δ1.95-2.10 (2H, m), 2.28 (3H, s), 2.34 (3H, s), 2.69 (2H, t, J=5 Hz), 2.83 (2H, t, J=5 Hz), 3.61 (2H, s), 3.70-3.85 (4H, m), 6.80 (1H, s), 6.89 (1H, s), 6.99 (1H, s), 7.48-7.60 (2H, m), 7.85 (1H, s).

Example 33

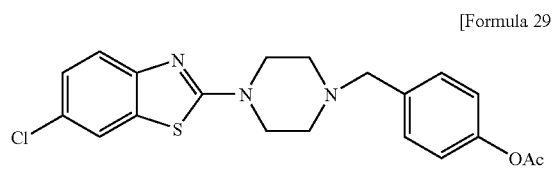
[Formula 290]

Yield 69%, ¹H-NMR (CDCl₃): δ2.31 (3H, s), 2.57 (4H, t, J=5.1 Hz), 3.55 (2H, s), 3.63 (4H, t, J=5.1 Hz), 7.06 (2H, d, J=8.1 Hz), 7.24 (1H, dd, J=8.4, 2.1 Hz), 7.35 (2H, d, J=8.1 Hz), 7.43 (1H, d, J=8.4 Hz), 7.55 (1H, d, J=2.1 Hz).

Example 34

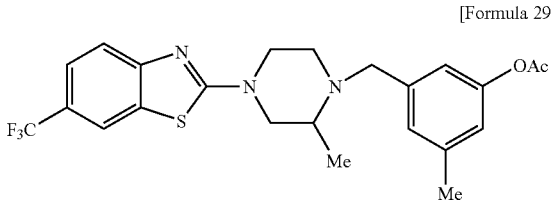
[Formula 291]

Yield 56%, 1H-NMR (CDCl3): δ1.22 (3H, d, J=6 Hz), 2.24-2.35 (1H, m), 2.29 (3H, s), 2.35 (3H, s), 2.62-2.72 (1H, m), 2.83 (1H, dt, J=12, 4 Hz), 3.15-3.25 (2H, m), 3.40-3.50 (1H, m), 3.70-3.80 (1H, m), 3.87-3.95 (1H, m), 4.03 (1H, d, J=13.5 Hz), 6.81 (1H, s), 6.90 (1H, s), 7.01 (1H, s), 7.52 (1H, d, J=8.5 Hz), 7.56 (1H, d, J=8.5 Hz), 7.84 (1H, s).

Example 35

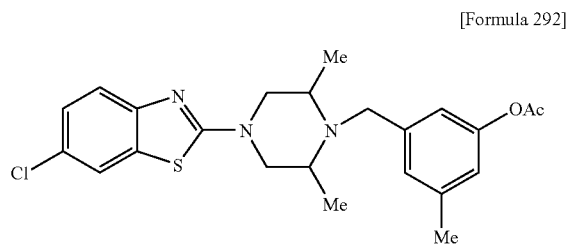
[Formula 292]

Yield 41%, 1H-NMR (CDCl3): δ1.10 (6H, d, J=6 Hz), 2.29 (3H, s), 2.34 (3H, s), 2.70-2.85 (2H, m), 3.00-3.10 (2H, m), 3.79 (2H, s), 3.80-3.90 (2H, m), 6.76 (1H, s), 6.95 (1H, s), 7.02 (1H, s), 7.23 (1H, dd, J=8.5, 2 Hz), 7.43 (1H, d, J=8.5 Hz), 7.55 (1H, d, J=2 Hz).

Example 36

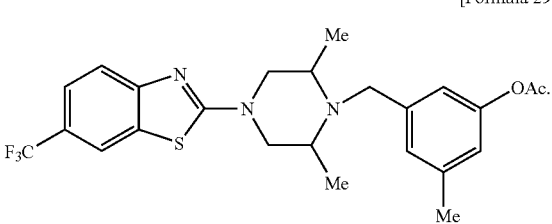
[Formula 293]

Yield 63%, 1H-NMR (CDCl3): δ1.11 (6H, d, J=6 Hz), 2.30 (3H, s), 2.35 (3H, s), 2.70-2.86 (2H, m), 3.00-3.15 (2H, m), 3.80 (2H, s), 3.85-3.95 (2H, m), 6.77 (1H, s), 6.95 (1H, s), 7.02 (1H, s), 7.52 (1H, d, J=8.5 Hz), 7.57 (1H, d, J=8.5 Hz), 7.85 (1H, s).

Example 37

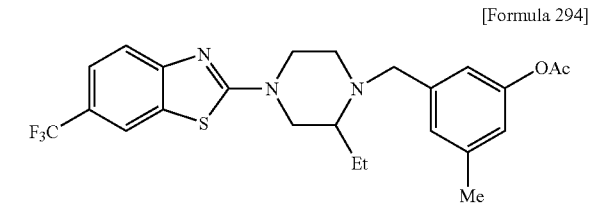
[Formula 294]

Yield 53%, 1H-NMR (CDCl3): δ1.02 (3H, t, J=7.5 Hz), 1.55-1.78 (2H, m), 2.30 (3H, s), 2.30-2.35 (1H, m), 2.36 (3H, s), 2.49-2.60 (1H, m), 2.78-2.90 (1H, m), 3.26 (1H, d, J=13.5 Hz), 3.38-3.46 (1H, m), 3.46-3.58 (1H, m), 3.63-3.72 (1H, m), 3.85 (1H, dd, J=13, 3.5 Hz), 3.98 (1H, d, J=13.5 Hz), 6.81 (1H, s), 6.91 (1H, s), 7.02 (1H, s), 7.51 (1H, dd, J=8.5, 1.5 Hz), 7.56 (1H, d, J=8.5 Hz), 7.84 3 (1H, d, J=1.5 Hz)

Example 38

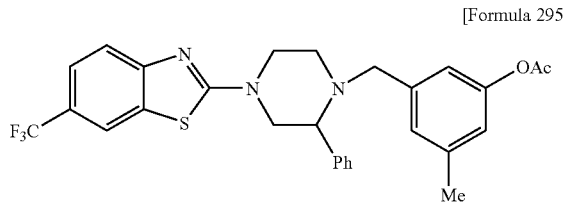

[Formula 295]

Yield 69%, 1H-NMR (CDCl3): δ2.25-2.35 (1H, m), 2.30 (3H, s), 2.34 (3H, s), 2.86 (1H, d, J=13.5 Hz), 3.02 (1H, d, J=11.5 Hz), 3.25-3.50 (3H, m), 3.82 (1H, d, J=13.5 Hz), 4.00-4.10 (2H, m), 6.79 (1H, s), 6.82 (1H, s), 6.93 (1H, s), 7.30-7.45 (3H, m), 7.48-7.55 (4H, m), 7.84 (1H, d, J=0.5 Hz).

Example 39

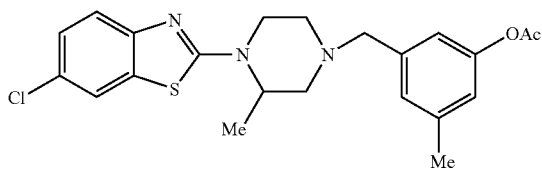

[Formula 296]

Yield 48%, 1H-NMR (CDCl3): δ1.40 (3H, d, J=6.5 Hz), 2.15-2.30 (2H, m), 2.31 (3H, s), 2.36 (3H, s), 2.68-2.75 (1H, m), 2.85-2.95 (1H, m), 3.38-3.60 (3H, m), 3.80-3.90 (1H, m), 4.15-4.25 (1H, m), 6.81 (1H, s), 6.92 (1H, s), 7.02 (1H, s), 7.23 (1H, dd, J=8.5, 2 Hz), 7.42 (1H, d, J=8.5 Hz), 7.54 (1H, d, J=2 Hz).

Example 40

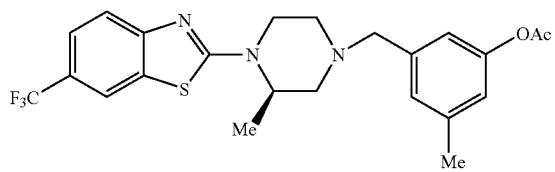

[Formula 297]

Yield 81%, 1H-NMR (CDCl3): δ1.42 (3H, d, J=6.5 Hz), 2.18-2.29 (1H, m), 2.30 (3H, s), 2.30-2.35 (1H, m), 2.36 (3H, s), 2.75 (1H, d, J=11.5 Hz), 2.92 (1H, d, J=11.5 Hz), 3.43 (1H, d, J=13.5 Hz), 3.52 (1H, td, J=12.5, 3.5 Hz), 3.57 (1H, d, J=13.5 Hz), 3.91 (1H, d, J=12.5 Hz), 4.17-4.30 (1H, m), 6.81 (1H, s), 6.92 (1H, s), 7.02 (1H, s), 7.51 (1H, d, J=8.5 Hz), 7.55 (1H, d, J=8.5 Hz), 7.84 (1H, s).

Example 41

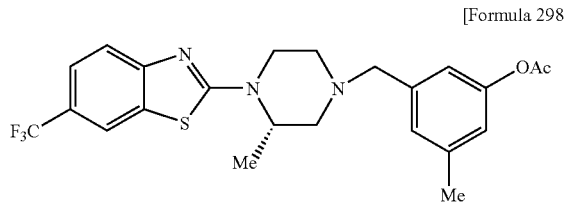

[Formula 298]

Yield 57%, 1H-NMR (CDCl3): δ1.42 (3H, d, J=6.5 Hz), 2.18-2.38 (2H, m), 2.30 (3H, s), 2.36 (3H, s), 2.70-2.80 (1H, m), 2.86-2.97 (1H, m), 3.38-3.61 (3H, m), 3.85-3.97 (1H, m), 4.17-4.30 (1H, m), 6.82 (1H, s), 6.92 (1H, s), 7.03 (1H, s), 7.48-7.59 (2H, m), 7.84 (1H, s).

Example 42

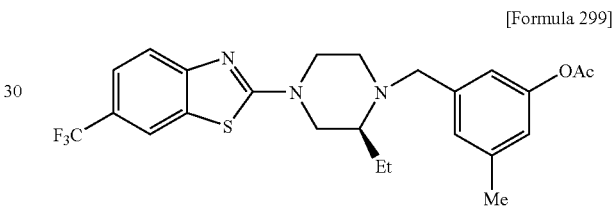

[Formula 299]

Yield 63%, 1H-NMR (CDCl3): δ1.02 (3H, t, J=7.5 Hz), 1.60-1.75 (2H, m), 2.30 (3H, s), 2.30-2.35 (1H, m), 2.36 (3H, s), 2.48-2.58 (1H, m), 2.79-2.90 (1H, m), 3.26 (1H, d, J=13.5 Hz), 3.38-3.58 (2H, m), 3.63-3.73 (1H, m), 3.80-3.90 (1H, m), 3.98 (1H, d, J=13.5 Hz), 6.81 (1H, s), 6.91 (1H, s), 7.02 (1H, s), 7.51 (1H, d, J=8.5 Hz), 7.55 (1H, d, J=8.5 Hz), 7.84 (1H, s).

Example 43

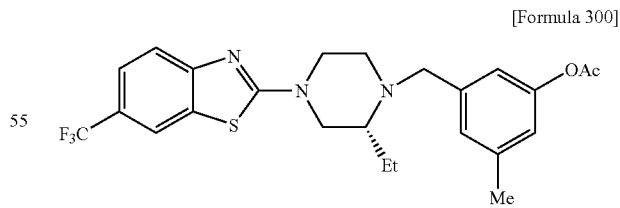

[Formula 300]

Yield 79%, 1H-NMR (CDCl3): δ1.02 (3H, t, J=7.5 Hz), 1.57-1.80 (2H, m), 2.21 (3H, s), 2.21-2.35 (1H, m), 2.36 (3H, s), 2.50-2.60 (1H, m), 2.80-2.90 (1H, m), 3.26 (1H, d, J=13.5 Hz), 3.38-3.60 (2H, m), 3.63-3.74 (1H, m), 3.85 (1H, dd, J=12.5, 3.5 Hz), 3.98 (1H, d, J=13.5 Hz), 6.81 (1H, s), 6.91 (1H, s), 7.02 (1H, s), 7.53 (1H, d, J=8.5 Hz), 7.55 (1H, d, J=8.5 Hz), 7.84 (1H, s).

Example 44

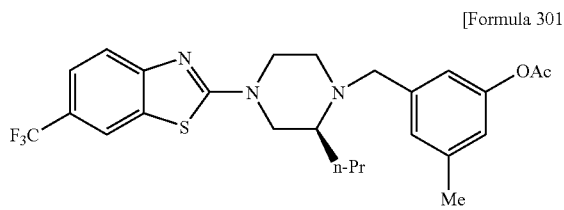

[Formula 301]

Yield 63%, 1H-NMR (CDCl3): δ1.20 (3H, t, J=7.5 Hz), 1.30-1.70 (4H, m), 2.29 (3H, s), 2.29-2.35 (1H, m), 2.36 (3H, s), 2.55-2.65 (1H, m), 2.79-2.89 (1H, m), 3.28 (1H, d, J=13.5 Hz), 3.41 (1H, dd, J=13, 7.5 Hz), 3.50-3.60 (1H, m), 3.60-3.70 (1H, m), 3.84 (1H, dd, J=13, 3 Hz), 3.97 (1H, d, J=13.5 Hz), 6.81 (1H, s), 6.90 (1H, s), 7.02 (1H, s), 7.51 (1H, dd, J=8.5, 1.5 Hz), 7.56 (1H, d, J=8.5 Hz), 7.83 (1H, d, J=1.5 Hz).

Example 45

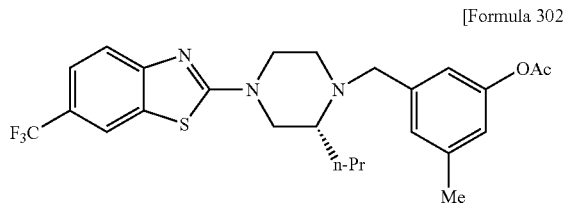

[Formula 302]

Yield 62%, 1H-NMR (CDCl3): δ0.95 (3H, t, J=7.2 Hz), 1.36-1.43 (2H, m), 1.50-1.66 (2H, m), 2.30 (3H, s), 2.35 (3H, s), 2.32-2.39 (1H, m), 2.58-2.63 (1H, m), 2.80-2.87 (1H, m), 3.28 (1H, d, J=13.5 Hz), 3.41 (1H, dd, J=7.5, 12.6 Hz), 3.50-3.59 (1H, m), 3.62-3.68 (1H, m), 3.84 (1H, dd, J=3.0, 12.6 Hz), 3.97 (1H, d, J=13.5 Hz), 6.81 (1H, s), 6.90 (1H, s), 7.01 (1H, s), 7.53-7.55 (2H, m), 7.83 (1H, s)

Example 46

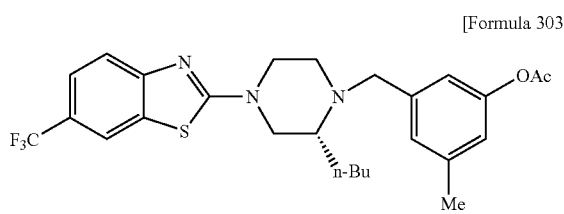

[Formula 303]

Yield 70%, 1H-NMR (CDCl3): δ0.93 (3H, t, J=7.5 Hz), 1.23-1.75 (6H, m), 2.30 (3H, s), 2.30-2.34 (1H, m), 2.35 (3H, s), 2.54-2.64 (1H, m), 2.79-2.89 (1H, m), 3.27 (1H, d, J=13.5 Hz), 3.41 (1H, dd, J=12.5, 7.5 Hz), 3.49-3.60 (1H, m), 3.61-3.71 (1H, m), 3.84 (1H, dd, J=12.5, 2.5 Hz), 3.97 (1H, d, J=13.5 Hz), 6.81 (1H, s), 6.90 (1H, s), 7.02 (1H, s), 7.51 (1H, dd, J=8.5, 1.5 Hz), 7.56 (1H, d, J=8.5 Hz), 7.84 (1H, d, J=1.5 Hz).

Example 47

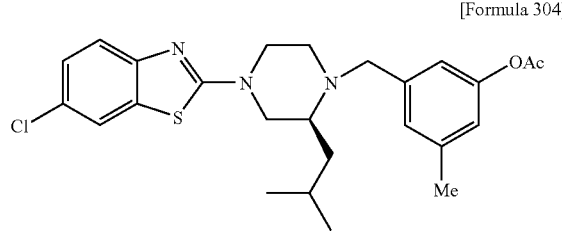

[Formula 304]

Yield 69%, 1H-NMR (CDCl3): δ0.91 (3H, d, J=6.5 Hz), 0.95 (3H, d, J=6.5 Hz), 1.33-1.45 (1H, m), 1.45-1.58 (1H, m), 1.62-1.77 (1H, m), 2.29 (3H, s), 2.35 (3H, s), 2.36-2.45 (1H, m), 2.62-2.73 (1H, m), 2.77-2.88 (1H, m), 3.33 (1H, d, J=13.5 Hz), 3.35 (1H, dd, J=13, 7 Hz), 3.58 (2H, t, J=5.5 Hz), 3.75 (1H, dd, J=13, 3.5 Hz), 3.90 (1H, d, J=13.5 Hz), 6.80 (1H, s), 6.90 (1H, s), 7.02 (1H, s), 7.23 (1H, dd, J=8.5, 2 Hz), 7.42 (1H, d, J=8.5 Hz), 7.54 (1H, d, J=2 Hz).

Example 48

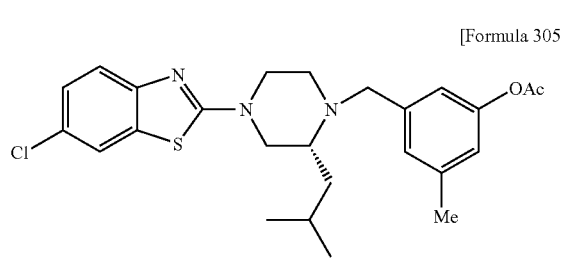

[Formula 305]

Yield 49%, 1H-NMR (CDCl3): δ0.92 (3H, d, J=6.5 Hz), 0.95 (3H, d, J=6.5 Hz), 1.32-1.60 (2H, m), 1.62-1.78 (1H, m), 2.29 (3H, s), 2.31-2.46 (1H, m), 2.35 (3H, s), 2.62-2.72 (1H, m), 2.75-2.88 (1H, m), 3.29-3.42 (2H, m), 3.58 (2H, t, J=5.0 Hz), 3.75 (1H, dd, J=13.0, 3.5 Hz), 3.90 (1H, d, J=13.5 Hz), 6.80 (1H, s), 6.91 (1H, s), 7.02 (1H, s), 7.23 (1H, dd, J=8.5, 2.0 Hz), 7.43 (1H, d, J=8.5 Hz), 7.54 (1H, d, J=2.0 Hz).

Example 49

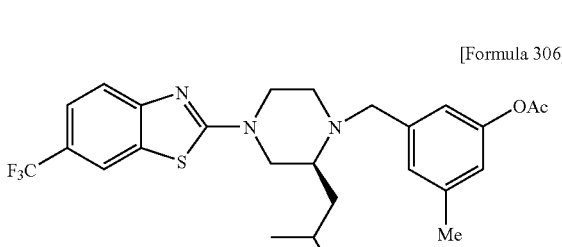

[Formula 306]

Yield 72%, 1H-NMR (CDCl3): δ0.92 (3H, d, J=7.5 Hz), 0.95 (3H, d, J=7.5 Hz), 1.33-1.45 (1H, m), 1.46-1.60 (1H, m), 1.64-1.78 (1H, m), 2.30 (3H, s), 2.35 (3H, s), 2.36-2.46 (1H, m), 2.63-2.75 (1H, m), 2.77-2.88 (1H, m), 3.35 (1H, d, J=13.5 Hz), 3.40 (1H, dd, J=13, 6.5 Hz), 3.55-3.70 (2H, m), 3.79 (1H, dd, J=12, 3 Hz), 3.90 (1H, d, J=13.5 Hz), 6.81 (1H, s), 6.91

(1H, s), 7.02 (1H, s), 7.51 (1H, dd, J=8.5, 1.5 Hz), 7.55 (1H, d, J=8.5 Hz), 7.83 (1H, d, J=1.5 Hz).

Example 50

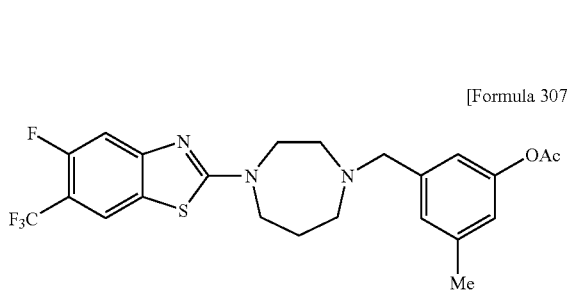

[Formula 307]

Yield 65%, 1H-NMR (CDCl3): δ1.98-2.08 (2H, m), 2.28 (3H, s), 2.34 (3H, s), 2.65-2.74 (2H, m), 2.78-2.85 (2H, m), 3.61 (2H, s), 3.65-3.88 (4H, m), 6.80 (1H, s), 6.88 (1H, s), 6.99 (1H, s), 7.27 (1H, d, J=12.0 Hz), 7.75 (1H, d, J=7.0 Hz).

Example 51

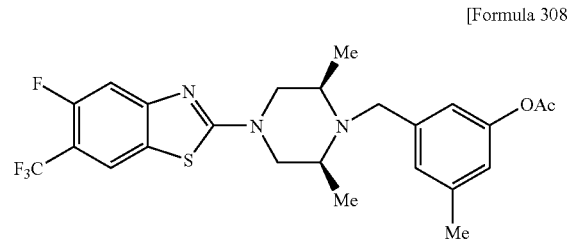

[Formula 308]

Yield 57%, 1H-NMR (CDCl3): δ1.11 (6H, d, J=6.0 Hz), 2.29 (3H, s), 2.34 (3H, s), 2.71-2.86 (2H, m), 3.07 (1H, d, J=13.0 Hz), 3.10 (1H, d, J=13.0 Hz), 3.79 (2H, s), 3.88 (2H, d, J=13.0 Hz), 6.77 (1H, s), 6.96 (1H, s), 7.01 (1H, s), 7.26 (1H, d, J=11.5 Hz), 7.73 (1H, d, J=7.0 Hz).

Example 52

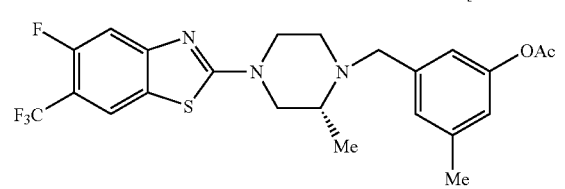

[Formula 309]

Yield 57%, 1H-NMR (CDCl3): δ1.21 (3H, d, J=6 Hz), 2.24-2.29 (1H, m), 2.30 (3H, s), 2.36 (3H, s), 2.60-2.72 (1H, m), 2.83 (1H, dt, J=12, 3.5 Hz), 3.18 (1H, d, J=13.5 Hz), 3.18-3.25 (1H, m), 3.48-3.51 (1H, m), 3.67-3.80 (1H, m), 3.85-3.95 (1H, m), 4.02 (1H, d, J=13.5 Hz), 6.81 (1H, s), 6.90 (1H, s), 7.01 (1H, s), 7.26 (1H, d, J=12 Hz), 7.73 (1H, d, J=7 Hz).

Example 53

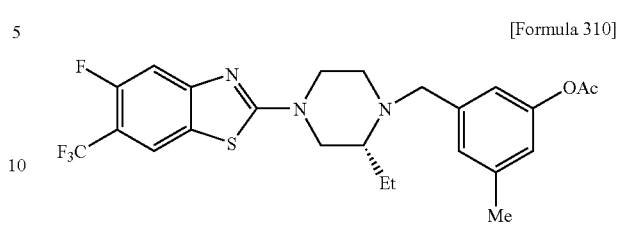

[Formula 310]

Yield 65%, 1H-NMR (CDCl3): δ1.02 (3H, t, J=7.5 Hz), 1.50-1.78 (2H, m), 2.26-2.42 (1H, m), 2.30 (3H, s), 2.36 (3H, s), 2.48-2.59 (1H, m), 2.78-2.89 (1H, m), 3.27 (1H, d, J=13.5 Hz), 3.38-3.58 (2H, m), 3.61-3.72 (1H, m), 3.78-3.89 (1H, m), 3.98 (1H, d, J=13.5 Hz), 6.81 (1H, s), 6.90 (1H, s), 7.01 (1H, s), 7.26 (1H, d, J=12.0 Hz), 7.74 (1H, d, J=7.0 Hz).

Example 54

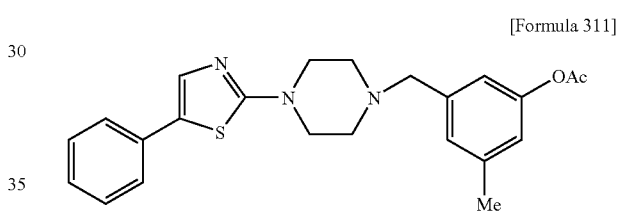

[Formula 311]

Yield 61%, 1H-NMR (CDCl3): δ2.29 (3H, s), 2.36 (3H, s), 2.58 (4H, t, J=5.0 Hz), 3.52 (2H, s), 3.53 (4H, t, J=5.0 Hz), 6.82 (1H, s), 6.90 (1H, s), 7.02 (1H, s), 7.17-7.24 (1H, m), 7.27-7.37 (2H, m), 7.38-7.47 (3H, m).

Example 55

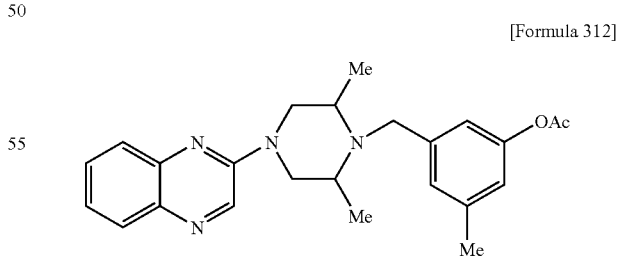

[Formula 312]

Yield 49%, 1H-NMR (CDCl3): δ1.15 (6H, d, J=6.0 Hz), 2.30 (3H, s), 2.35 (3H, s), 2.68-2.83 (2H, m), 2.94 (1H, d, J=13.0 Hz), 2.97 (1H, d, J=13.0 Hz), 3.80 (2H, s), 4.33 (2H, d, J=14.0 Hz), 6.76 (1H, s), 6.97 (1H, s), 7.04 (1H, s), 7.34-7.43 (1H, m), 7.52-7.61 (1H, m), 7.67 (1H, d, J=8.0, 1.5 Hz), 7.87 (1H, dd, J=8.0, 1.5 Hz), 8.56 (1H, s)

Example 56

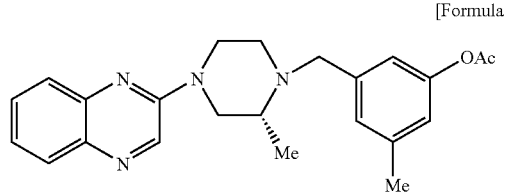

Yield 56%, 1H-NMR (CDCl3): δ1.21 (3H, d, J=6.0 Hz), 1.18-2.30 (1H, m), 2.28 (3H, s), 2.35 (3H, s), 2.52-2.65 (1H, m), 2.78-2.89 (1H, m), 3.05-3.20 (2H, m), 3.27-3.41 (1H, m), 3.97-4.12 (2H, m), 4.15-4.25 (1H, m), 6.80 (1H, s), 6.92 (1H, s), 7.01 (1H, s), 7.32-7.40 (1H, m), 7.50-7.59 (1H, m), 7.67 (1H, dd, J=8.0, 1.5 Hz), 7.87 (1H, dd, J=8.0, 1.5 Hz), 8.53 (1H, s).

Example 57

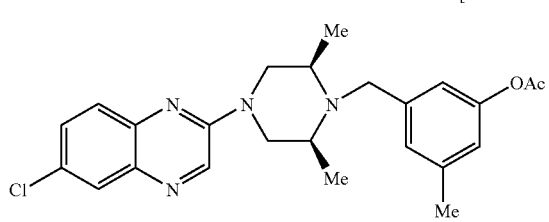

Yield 55%, 1H-NMR (CDCl3): δ1.14 (6H, d, J=6.0 Hz), 2.29 (3H, s), 2.35 (3H, s), 2.68-2.82 (2H, m), 2.94 (1H, d, J=13.0 Hz), 2.98 (1H, d, J=13.0 Hz), 3.80 (2H, s), 4.30 (2H, d, J=13.0 Hz), 6.76 (1H, s), 6.97 (1H, s), 7.03 (1H, s), 7.50 (1H, dd, J=9.0, 2.5 Hz), 7.59 (1H, d, J=9.0 Hz), 7.85 (1H, d, J=2.5 Hz), 8.54 (1H, s).

Example 58

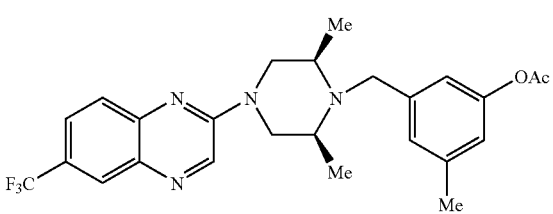

Yield 34%, 1H-NMR (CDCl3): δ1.13 (6H, d, J=6.0 Hz), 2.28 (3H, s), 2.34 (3H, s), 2.65-2.79 (2H, m), 2.95 (1H, d, J=13.0 Hz), 2.98 (1H, d, J=13.0 Hz), 3.78 (2H, s), 4.34 (2H, d, J=13.0 Hz), 6.77 (1H, s), 6.98 (1H, s), 7.02 (1H, s), 7.67-7.73 (2H, m), 8.13 (1H, s), 8.58 (1H, s).

Example 59

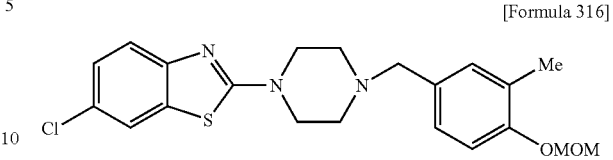

Yield 92%, $^1$H-NMR (CDCl$_3$): δ2.25 (3H, s), 2.56 (4H, t, J=5.1 Hz), 3.48 (2H, s), 3.50 (3H, s), 3.63 (4H, t, J=5.1 Hz), 5.20 (2H, s), 7.00 (1H, d), 7.08 (1H, d, 8.1 Hz), 7.12 (1H, s), 7.23 (1H, dd, J=8.7, 2.1 Hz), 7.43 (1H, d, J=8.7 Hz), 7.53 (1H, d, 2.1 Hz).

Example 60

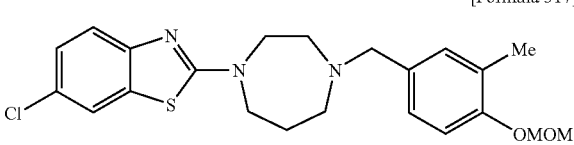

Yield 90%, $^1$H-NMR (CDCl$_3$): δ1.98-2.05 (2H, m), 2.24 (3H, s), 2.68 (2H, t, J=5.4 Hz), 2.79 (2H, t, J=4.8 Hz), 3.49 (3H, s), 3.55 (2H, s), 3.71-3.78 (4H, m), 5.19 (2H, s), 6.98 (1H, s), 7.07 (2H, m), 7.22 (1H, dd, 8.7, 2.1 Hz), 7.42 (1H, d, J=8.7 Hz), 7.54 (1H, d, J=2.1 Hz).

Example 61

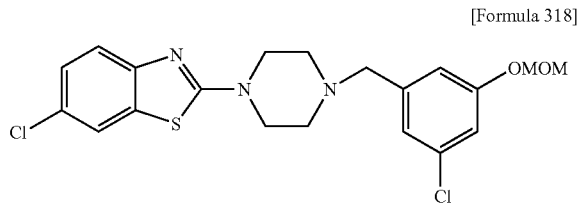

Yield 60%, $^1$H-NMR (CDCl$_3$): δ2.57 (4H, t, J=5.1 Hz), 3.48 (3H, s), 3.50 (2H, s), 3.64 (4H, t, J=5.1 Hz), 5.17 (2H, s), 6.91 (1H, s), 6.97-7.01 (2H, m), 7.24 (1H, dd, 8.7, 2.1 Hz), 7.44 (1H, d, J=8.7 Hz), 7.56 (1H, d, J=2.1 Hz).

Example 62

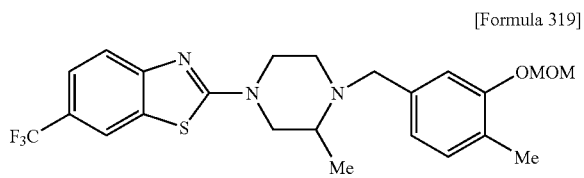
[Formula 319]

Yield 70%, 1H-NMR (CDCl3): δ1.22 (3H, d, J=6.5 Hz), 2.24 (3H, s), 2.24-2.35 (1H, m), 2.60-2.70 (1H, m), 2.78-2.88 (1H, m), 3.19 (1H, dt, J=13, 4.5 Hz), 3.24 (1H, d, J=13 Hz), 3.38-3.50 (1H, m), 3.50 (3H, s), 3.70-3.80 (1H, m), 3.85-3.93 (1H, m), 4.01 (1H, d, J=13 Hz), 5.21 (2H, s), 6.89 (1H, d, J=7.5 Hz), 7.02 (1H, s), 7.10 (1H, d, J=7.5 Hz), 7.50 (1H, d, J=8.5 Hz), 7.53 (1H, d, J=8.5 Hz), 7.83 (1H, s).

Example 63

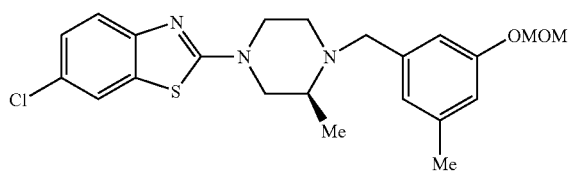
[Formula 320]

Yield 92%, 1H-NMR (CDCl3): δ1.22 (3H, d, J=6.0 Hz), 2.23-2.33 (1H, m), 2.33 (3H, s), 2.60-2.67 (1H, m), 2.83 (1H, dt, J=3.3, 12.0 Hz), 3.16 (2H, dd, J=4.2, 13.2 Hz), 3.44-3.35 (1H, m), 3.49 (3H, s), 3.71 (1H, d, J=12.0 Hz), 3.86 (1H, dd, J=2.1, 12.6 Hz), 3.99 (1H, d, J=13.2 Hz), 5.17 (2H, s), 6.77 (1H, s), 6.80 (1H, s), 6.83 (1H, s), 7.23 (1H, dd, J=2.1, 8.7 Hz), 7.42 (1H, d, J=8.7 Hz), 7.54 (1H, d, J=2.1 Hz)

Example 64

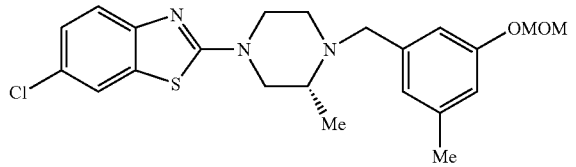
[Formula 321]

Yield 95%, 1H-NMR (CDCl3): δ1.22 (3H, d, J=6.0 Hz), 2.25-2.31 (1H, m), 2.33 (3H, s), 2.60-2.67 (1H, m), 2.83 (1H, dt, J=3.6, 12.0 Hz), 3.16 (2H, dt, J=3.6, 13.5 Hz), 3.44-3.35 (1H, m), 3.49 (3H, s), 3.71 (1H, dt, J=3.0, 12.3 Hz), 3.86 (1H, ddd, J=1.5, 3.6, 12.6 Hz), 3.99 (1H, d, J=13.5 Hz), 5.16 (2H, s), 6.77 (1H, s), 6.80 (1H, s), 6.83 (1H, s), 7.23 (1H, dd, J=2.1, 8.7 Hz), 7.42 (1H, d, J=8.7 Hz), 7.54 (1H, d, J=2.1 Hz),

Example 65

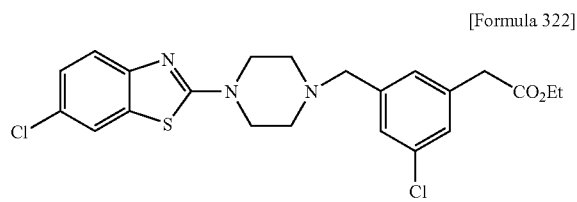
[Formula 322]

Yield 38%, 1H-NMR (CDCl₃): δ1.27 (3H, t, J=7.2 Hz), 2.57 (4H, t, J=4.8 Hz), 3.52 (2H, s), 3.59 (2H, s), 3.64 (4H, t, J=4.8 Hz), 4.17 (2H, q, J=7.2 Hz), 7.14 (1H, s), 7.20 (1H, s), 7.23 (1H, dd, J=7.8, 2.4 Hz), 7.26 (1H, s), 7.43 (1H, d, J=7.8 Hz), 7.56 (1H, d, J=2.4 Hz).

Example 66

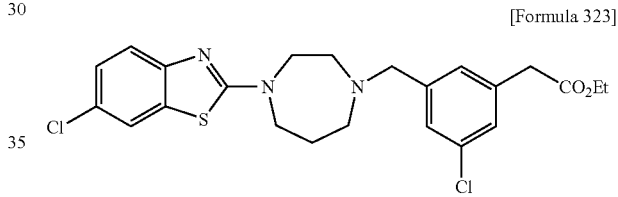
[Formula 323]

Yield 60%, ¹H-NMR (CDCl₃): δ1.26 (3H, t, J=7.2 Hz), 1.98-2.06 (2H, m), 2.68 (2H, t, J=5.4 Hz), 2.80 (2H, t, J=5.4 Hz), 3.56 (2H, s), 3.60 (2H, s), 3.71-3.78 (4H, m), 4.16 (2H, q, J=7.2 Hz), 7.12 (1H, s), 7.18 (1H, s), 7.23 (1H, dd, J=8.4, 2.1 Hz), 7.25 (1H, s), 7.42 (1H, d, J=8.4 Hz), 7.55 (1H, d, J=2.1 Hz)

Example 67

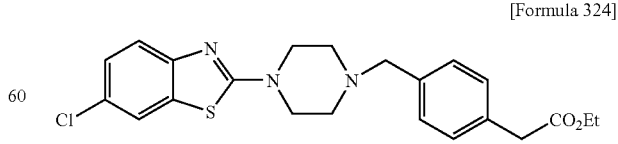
[Formula 324]

Yield 89%, ¹H-NMR (CDCl₃): δ1.26 (3H, t, J=7 Hz), 2.57 (4H, t, J=5 Hz), 3.55 (2H, s), 3.61 2H, s), 3.62 (4H, t, J=5 Hz), 4.15 (2H, q, J=7 Hz), 7.23 (1H, dd, J=8.5, 2 Hz), 7.25-7.35 (4H, m), 7.42 (1H, d, J=8.5 Hz), 7.55 (1H, d, J=2 Hz).

Example 68

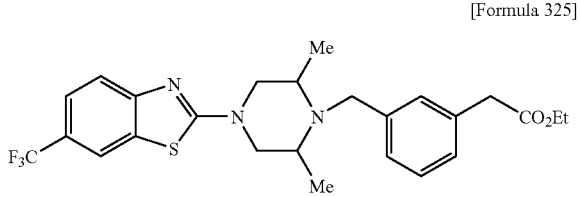
[Formula 325]

Yield 79%, 1H-NMR (CDCl3): δ1.13 (6H, d, J=6 Hz), 1.25 (3H, t, J=7 Hz), 2.73-2.90 (2H, m), 3.05-3.15 (2H, m), 3.61 (2H, s), 3.85 (2H, s), 3.85-3.95 (2H, m), 4.14 (2H, q, J=7 Hz), 7.10-7.35 (4H, m), 7.52 (1H, d, J=8.5 Hz), 7.56 (1H, d, J=8.5 Hz), 7.84 (1H, s).

Example 69

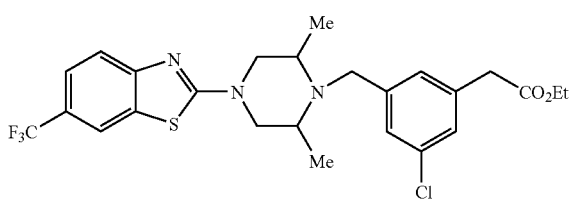
[Formula 326]

Yield 54%, 1H-NMR (CDCl3): δ1.09 (6H, d, J=6.5 Hz), 1.26 (3H, t, J=7 Hz), 2.70-2.95 (2H, m), 3.10 (2H, dd, J=13, 13 Hz), 3.58 (2H, s), 3.78 (2H, s), 3.86-3.96 (2H, m), 4.15 (2H, q, J=7 Hz), 7.14 (1H, s), 7.17 (1H, s), 7.33 (1H, s), 7.53 (1H, d, J=8.5 Hz), 7.57 (1H, d, J=8.5 Hz), 7.85 (1H, s).

Example 70

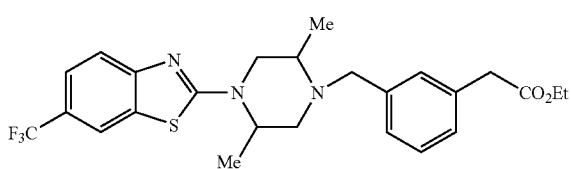
[Formula 327]

Yield 71%, 1H-NMR (CDCl3): δ1.08 (3H, d, J=6.5 Hz), 1.25 (3H, t, J=7 Hz), 1.40 (3H, d, J=6.5 Hz), 2.25-2.35 (1H, m), 2.90 (1H, dd, J=12, 4 Hz), 3.10-3.20 (1H, m), 3.52 (1H, d, J=13.5 Hz), 3.62 (2H, s), 3.63-3.78 (3H, m), 4.16 (2H, q, J=7 Hz), 4.20-4.35 (1H, m), 7.20-7.35 (4H, m), 7.45-7.56 (2H, m), 7.82 (1H, s).

Example 71

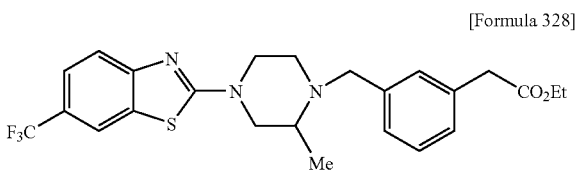
[Formula 328]

Yield 92%, 1H-NMR (CDCl3): δ1.23 (3H, d, J=6 Hz), 1.25 (3H, t, J=7 Hz), 2.23-2.35 (1H, m), 2.60-2.75 (1H, m), 2.83 (1H, dt, J=12, 4 Hz), 3.20 (1H, d, J=12.5 Hz), 3.22 (1H, d, J=13 Hz), 3.38-3.50 (1H, m), 3.62 (2H, s), 3.70-3.80 (1H, m), 3.85-3.95 (1H, m), 4.05 (1H, d, J=13 Hz), 4.16 (2H, q, J=7 Hz), 7.15-7.35 (4H, m), 7.45-7.60 (2H, m), 7.84 (1H, s).

Example 72

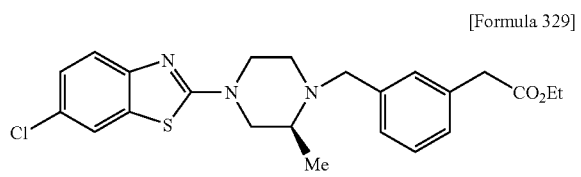
[Formula 329]

Yield 88%, 1H-NMR (CDCl3): δ1.23 (3H, t, J=7.2 Hz), 1.26 (3H, t, J=6.9 Hz), 2.27 (1H, ddd, J=3.3, 8.7, 9.9 Hz), 2.61-2.67 (1H, m), 2.80 (1H, dt, J=3.3, 11.7 Hz), 3.21 (2H, d, J=13.5 Hz), 3.34-3.43 (1H, m), 3.62 (2H, s), 3.71 (1H, d, J=12.6 Hz), 3.87 (1H, dd, J=2.1, 12.6 Hz), 4.05 (1H, d, J=13.5 Hz), 4.16 (2H, q, J=7.2 Hz), 7.18-7.32 (5H, m), 7.42 (1H, d, J=8.7 Hz), 7.54 (1H, d, J=2.4 Hz)

Example 73

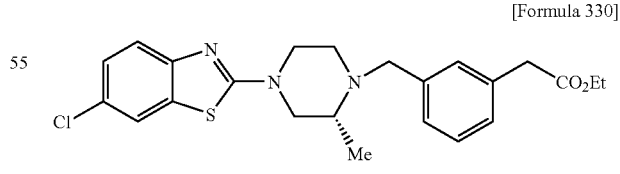
[Formula 330]

Yield 93%, 1H-NMR (CDCl3): δ1.24 (3H, t, J=6.0 Hz), 1.26 (3H, t, J=7.2 Hz), 2.27 (1H, ddd, J=3.3, 8.7, 9.9 Hz), 2.62-2.67 (1H, m), 2.80 (1H, dt, J=3.6, 12.0 Hz), 3.21 (2H, d, J=13.5 Hz), 3.39-3.42 (1H, m), 3.62 (2H, s), 3.71 (1H, dt, J=12.0 Hz), 3.87 (1H, dd, J=2.1, 12.6 Hz), 4.06 (1H, d, J=13.5 Hz), 4.16 (2H, q, J=7.2 Hz), 7.18-7.32 (5H, m), 7.42 (1H, d, J=8.4 Hz), 7.54 (1H, d, J=2.1 Hz)

Example 74

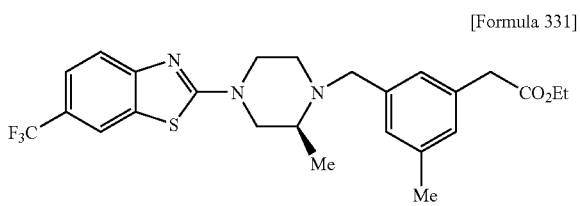

[Formula 331]

Yield 82%, 1H-NMR (CDCl3): δ1.23 (3H, d, J=6 Hz), 1.26 (3H, t, J=7 Hz), 2.20-2.35 (1H, m), 2.34 (3H, s), 2.58-2.71 (1H, m), 2.82 (1H, dt, J=12, 4 Hz), 3.16 (1H, d, J=13.5 Hz), 3.16-3.25 (1H, m), 3.38-3.50 (1H, m), 3.58 (2H, s), 3.70-3.80 (1H, m), 3.86-3.96 (1H, m), 4.03 (1H, d, J=13.5 Hz), 4.15 (2H, q, J=7 Hz), 7.01 (1H, s), 7.05 (2H, s), 7.51 (1H, d, J=8.5 Hz), 7.55 (1H, d, J=8.5 Hz), 7.84 (1H, s).

Example 75

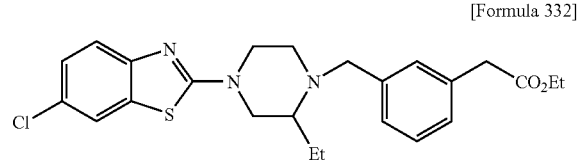

[Formula 332]

Yield 92%, 1H-NMR (CDCl3): δ1.02 (3H, t, J=7.2 Hz), 1.26 (3H, t, J=7.2 Hz), 1.61-1.74 (2H, m), 2.29-2.37 (1H, m), 2.50-2.55 (1H, m), 2.79-2.84 (1H, m), 3.29 (1H, d, J=13.5 Hz), 3.37 (1H, dd, J=8.1, 12.9 Hz), 3.40-3.50 (1H, m), 3.62 (3H, s), 3.80 (1H, dd, J=3.3, 12.9 Hz), 4.01 (1H, d, J=13.5 Hz), 4.16 (2H, t, J=7.2 Hz), 7.18 (5H, m), 7.42 (1H, d, J=8.7 Hz), 7.54 (1H, d, J=2.1 Hz)

Example 76

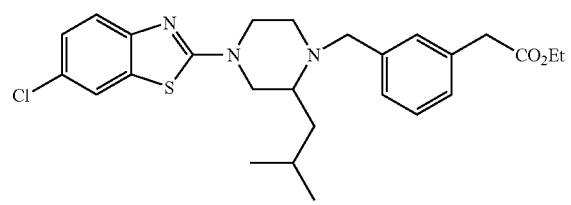

[Formula 333]

Yield 90%, 1H-NMR (CDCl3): δ0.93 (6H, dd, J=6.3, 11.7 Hz), 1.26 (3H, t, J=7.2 Hz), 1.35-1.44 (1H, m), 1.50-1.56 (1H, m), 1.65-1.76 (1H, m), 2.37-2.44 (1H, m), 2.67-2.72 (1H, m), 2.78-2.85 (1H, m), 3.36 (1H, d, J=12.9 Hz), 3.39 (1H, d, J=13.2 Hz), 3.58 (2H, t, J=4.8 Hz), 3.61 (2H, s), 3.75 (1H, dd, J=3.3, 12.9 Hz), 3.93 (1H, d, J=13.2 Hz), 4.16 (2H, q, J=7.2 Hz), 7.17-7.31 (5H, m), 7.42 (1H, d, J=8.7 Hz), 7.54 (1H, d, J=1.8 Hz)

Example 77

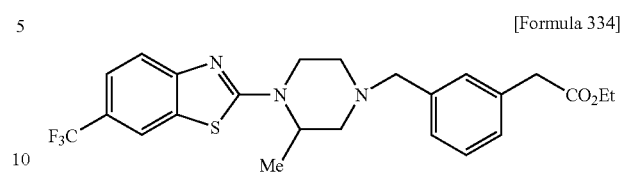

[Formula 334]

Yield 68%, 1H-NMR (CDCl3): δ1.26 (3H, t, J=7 Hz), 1.42 (3H, d, J=6.5 Hz), 2.25 (1H, td, J=11.5, 3.5 Hz), 2.32 (1H, dd, J=11.5, 4 Hz), 2.74 (1H, d, J=11.5 Hz), 2.91 (1H, dt, J=11.5, 2 Hz), 3.46 (1H, d, J=13.5 Hz), 3.52 (1H, td, J=11.5, 4 Hz), 3.59 (1H, d, J=13.5 Hz), 3.62 (2H, s), 3.85-4.00 (1H, m), 4.15 (2H, q, J=7 Hz), 4.20-4.30 (1H, m), 7.15-7.33 (4H, m), 7.51 (1H, d, J=8.5 Hz), 7.55 (1H, d, J=8.5 Hz), 7.84 (1H, s).

Example 78

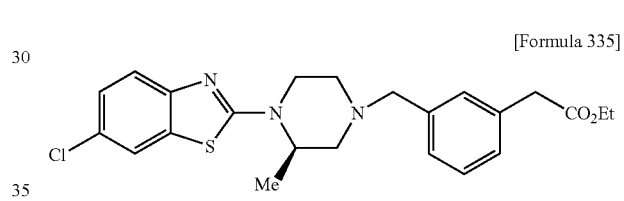

[Formula 335]

Yield 86%, 1H-NMR (CDCl3): δ1.25 (3H, t, J=7 Hz), 1.40 (3H, d, J=6.5 Hz), 2.24 (1H, td, J=11.5, 3.5 Hz), 2.33 (1H, dd, J=11.5, 3.5 Hz), 2.72 (1H, d, J=11 Hz), 2.91 (1H, d, J=11 Hz), 3.43 (1H, d, J=13.5 Hz), 3.49 (1H, td, J=11.5, 3.5 Hz), 3.59 (1H, d, J=13.5 Hz), 3.62 (2H, s), 3.80-3.90 (1H, m), 4.10-4.18 (1H, m), 4.19 (2H, q, J=7 Hz), 7.15-7.35 (5H, m), 7.42 (1H, d, J=7.5 Hz), 7.54 (1H, d, J=2 Hz).

Example 79

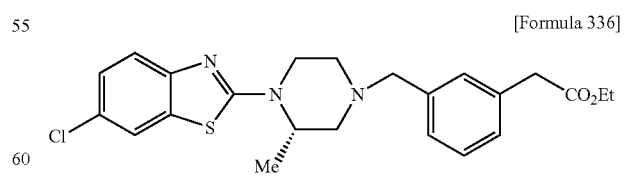

[Formula 336]

Yield 71%, 1H-NMR (CDCl3): δ1.26 (3H, t, J=7.0 Hz), 1.40 (3H, d, J=7.0 Hz), 2.17-2.38 (2H, m), 2.68-2.77 (1H, m), 2.88-2.96 (1H, m), 3.41-3.67 (5H, m), 3.82-3.92 (1H, m), 4.07-4.23 (1H, m), 4.16 (2H, q, J=7.0 Hz), 7.16-7.34 (5H, m), 7.42 (1H, d, J=8.5 Hz), 7.54 (1H, d, J=2.0 Hz).

Example 80

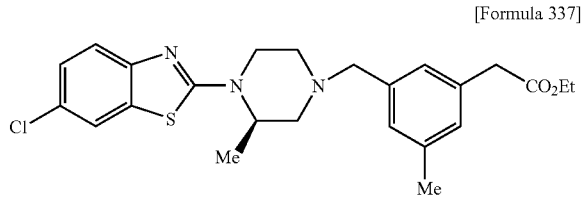

[Formula 337]

Yield 85%, 1H-NMR (CDCl3): δ1.26 (3H, t, J=7 Hz), 1.40 (3H, d, J=6.5 Hz), 2.23 (1H, td, J=11.5, 3.5 Hz), 2.27-2.33 (1H, m), 2.34 (3H, s), 2.72 (1H, d, J=11.5 Hz), 2.90 (1H, d, J=11.5 Hz), 3.41 (1H, d, J=13.5 Hz), 3.45-3.54 (1H, m), 3.55 (1H, d, J=13.5 Hz), 3.58 (2H, s), 3.85 (1H, d, J=12 Hz), 4.10-4.15 (1H, m), 4.16 (2H, q, J=7 Hz), 7.01 (1H, s), 7.07 (1H, s), 7.08 (1H, s), 7.22 (1H, dd, J=8.5, 2 Hz), 7.42 (1H, d, J=8.5 Hz), 7.54 (1H, d, J=2 Hz).

Example 81

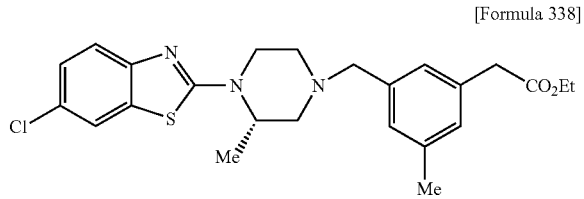

[Formula 338]

Yield 74%, 1H-NMR (CDCl3): δ1.26 (3H, t, J=7.0 Hz), 1.40 (3H, d, J=7.0 Hz), 2.16-2.37 (5H, m), 2.68-2.77 (1H, m), 2.86-2.96 (1H, m), 3.36-3.62 (5H, m), 3.80-3.90 (1H, m), 4.15 (3H, m), 7.01 (1H, s), 7.04-7.10 (2H, m), 7.23 (1H, dd, J=8.5, 2.0 Hz), 7.42 (1H, d, J=8.5 Hz), 7.54 (1H, d, J=2.0 Hz).

Example 82

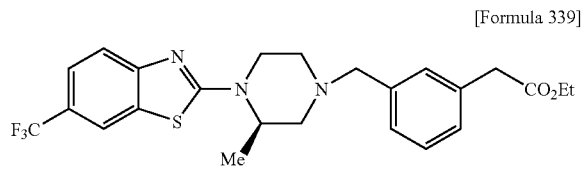

[Formula 339]

Yield 83%, 1H-NMR (CDCl3): δ1.26 (3H, t, J=7 Hz), 1.42 (3H, d, J=6.5 Hz), 2.25 (1H, dt, J=12.5, 3.5 Hz), 2.33 (1H, dd, J=11, 3.5 Hz), 2.73 (1H, d, J=11 Hz), 2.93 (1H, d, J=11 Hz), 3.42-3.60 (3H, m), 3.62 (2H, s), 3.85-3.97 (1H, m), 4.16 (2H, q, J=7 Hz), 4.18-4.28 (1H, m), 7.18-7.35 (4H, m), 7.51 (1H, d, J=8.5 Hz), 7.56 (1H, d, J=8.5 Hz), 7.84 (1H, s).

Example 83

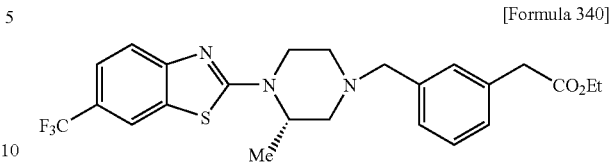

[Formula 340]

Yield 72%, 1H-NMR (CDCl3): δ1.26 (3H, t, J=7.0 Hz), 1.42 (3H, d, J=6.5 Hz), 2.25 (1H, td, J=11.5, 3.5 Hz), 2.34 (1H, dd, J=11.5, 3.5 Hz), 2.74 (1H, d, J=11.5 Hz), 2.93 (1H, d, J=11.5 Hz), 3.42-3.66 (5H, m), 3.91 (1H, d, J=11.5 Hz), 4.08-4.29 (3H, m), 7.16-7.35 (4H, m), 7.47-7.60 (2H, m), 7.84 (1H, s).

Example 84

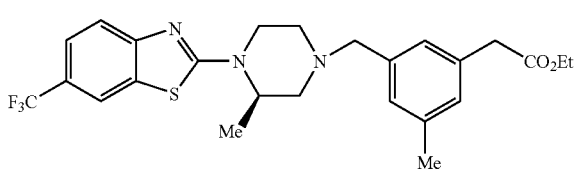

[Formula 341]

Yield 74%, 1H-NMR (CDCl3): δ1.26 (3H, t, J=7 Hz), 1.42 (3H, d, J=6.5 Hz), 2.18-2.34 (2H, m), 2.35 (3H, s), 2.74 (1H, d, J=11 Hz), 2.92 (1H, d, J=11.5 Hz), 3.42 (1H, d, J=13.5 Hz), 3.53 (1H, td, J=11.5, 3.5 Hz), 3.56 (1H, d, J=13.5 Hz), 3.58 (2H, s), 3.91 (1H, d, J=12 Hz), 4.15 (2H, q, J=7 Hz), 4.15-4.30 (1H, m), 7.02 (1H, s), 7.07 (1H, s), 7.09 (1H, s), 7.51 (1H, d, J=8.5 Hz), 7.55 (1H, d, J=8.5 Hz), 7.84 (1H, s).

Example 85

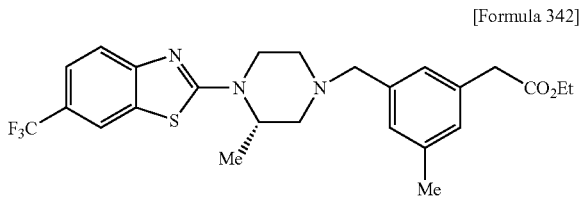

[Formula 342]

Yield 69%, 1H-NMR (CDCl3): δ1.26 (3H, t, J=7.0 Hz), 1.43 (3H, d, J=6.5 Hz), 2.17-2.39 (5H, m), 2.70-2.79 (1H, m), 2.87-2.97 (1H, m), 3.43 (1H, d, J=13.0 Hz), 3.46-3.62 (4H, m), 3.85-3.97 (1H, m), 4.16 (2H, q, J=7.0 Hz), 4.17-4.29 (1H, m), 7.02 (1H, s), 7.05-7.11 (2H, m), 7.47-7.59 (2H, m), 7.84 (1H, s).

Example 86

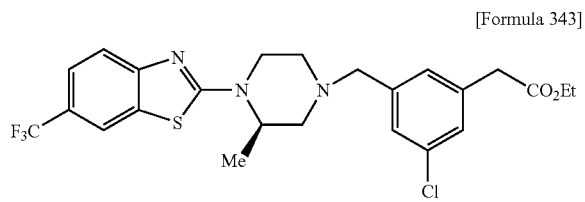

[Formula 343]

Yield 86%, 1H-NMR (CDCl3): δ1.27 (3H, t, J=7 Hz), 1.43 (3H, d, J=6.5 Hz), 2.26 (1H, td, J=12, 3.5 Hz), 2.36 (1H, dd, J=11, 3.5 Hz), 2.72 (1H, d, J=11 Hz), 2.91 (1H, d, J=11 Hz), 3.44 (1H, d, J=13.5 Hz), 3.52 (1H, td, J=12.5, 3.5 Hz), 3.55 (1H, d, J=13.5 Hz), 3.59 (2H, s), 3.86-3.96 (1H, m), 4.16 (2H, q, J=7 Hz), 4.20-4.30 (1H, m), 7.17 (1H, s), 7.20 (1H, s), 7.29 (1H, s), 7.51 (1H, d, J=8.5 Hz), 7.56 (1H, d, J=8.5 Hz), 7.84 (1H, s).

Example 87

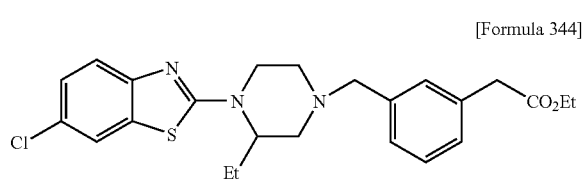

[Formula 344]

Yield 41%, 1H-NMR (CDCl3): δ0.87 (3H, t, J=7.5 Hz), 1.26 (3H, t, J=7.0 Hz), 1.80-2.02 (2H, m), 2.16-2.30 (2H, m), 2.79-2.94 (2H, m), 3.38-3.52 (2H, m), 3.54-3.65 (3H, m), 3.76-3.88 (1H, m), 3.94-4.06 (1H, m), 4.15 (2H, q, J=7.0 Hz), 7.15-7.34 (5H, m), 7.39 (1H, d, J=8.5 Hz), 7.52 (1H, d, J=2.0 Hz).

Example 88

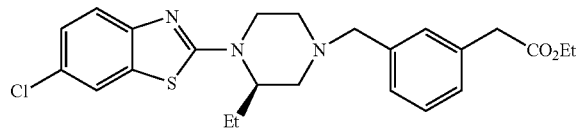

[Formula 345]

Yield 79%, 1H-NMR (CDCl3): δ0.87 (3H, t, J=7.5 Hz), 1.26 (3H, t, J=7 Hz), 1.85-2.00 (2H, m), 2.18-2.29 (2H, m), 2.80-2.84 (2H, m), 3.42 (1H, d, J=13.5 Hz), 3.44 (1H, td, J=12.5, 3.5 Hz), 3.59 (1H, d, J=13.5 Hz), 3.62 (2H, s), 3.70-3.86 (1H, m), 3.95-4.05 (1H, m), 4.15 (2H, q, J=7 Hz), 7.15-7.33 (5H, m), 7.39 (1H, d, J=8.5 Hz), 7.52 (1H, d, J=2 Hz).

Example 89

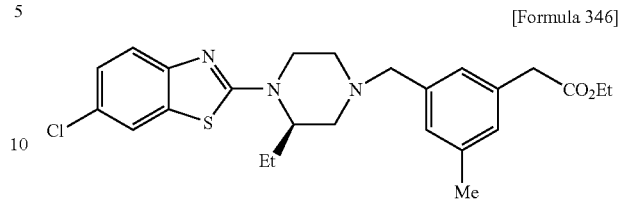

[Formula 346]

Yield 25%, 1H-NMR (CDCl3): δ0.88 (3H, t, J=7.5 Hz), 1.26 (3H, t, J=7 Hz), 1.83-2.03 (2H, m), 2.22 (2H, td, J=12.5, 3.5 Hz), 2.34 (3H, s), 2.80-2.92 (2H, m), 3.38 (1H, d, J=13.5 Hz), 3.45 (1H, td, J=12.5, 3.5 Hz), 3.55 (1H, d, J=13.5 Hz), 3.57 (2H, s), 3.75-3.88 (1H, m), 3.95-4.03 (1H, m), 4.15 (2H, q, J=7 Hz), 7.01 (1H, s), 7.05 (1H, s), 7.06 (1H, s), 7.21 (1H, dd, J=8.5, 2 Hz), 7.39 (1H, d, J=8.5 Hz), 7.52 (1H, d, J=2 Hz).

Example 90

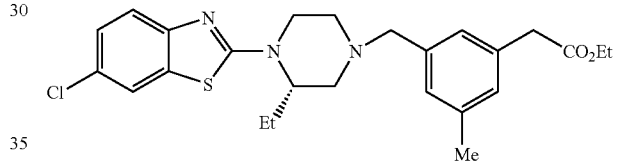

[Formula 347]

Yield 67%, 1H-NMR (CDCl3): δ0.88 (3H, t, J=7.5 Hz), 1.26 (3H, t, J=7.0 Hz), 1.80-2.03 (2H, m), 2.22 (2H, td, J=11.5, 3.5 Hz), 2.34 (3H, s), 2.80-2.93 (2H, m), 3.38 (1H, d, J=13.0 Hz), 3.46 (1H, td, J=12.5, 3.0 Hz), 3.56 (1H, d, J=13.0 Hz), 3.57 (2H, s), 3.76-3.87 (1H, m), 3.94-4.05 (1H, m), 4.15 (2H, q, J=7.0 Hz), 7.01 (1H, s), 7.06 (2H, s), 7.22 (1H, dd, J=8.5, 2.0 Hz), 7.39 (1H, d, J=8.5 Hz), 7.52 (1H, d, J=2.0 Hz).

Example 91

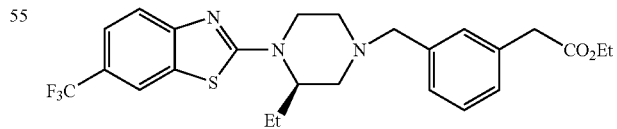

[Formula 348]

Yield 80%, 1H-NMR (CDCl3): δ0.88 (3H, t, J=7.5 Hz), 1.26 (3H, t, J=7 Hz), 1.96 (2H, quant, J=7.5 Hz), 2.19-2.30 (2H, m), 2.82-2.95 (2H, m), 3.44 (1H, d, J=13.5 Hz), 3.49 (1H, td, J=12.5, 3.5 Hz), 3.59 (1H, d, J=13.5 Hz), 3.62 (2H, s), 3.73-3.83 (1H, m), 4.00-4.10 (1H, m), 4.17 (2H, q, J=7 Hz), 7.15-7.33 (4H, m), 7.48-7.55 (2H, m), 7.82 (1H, s).

Example 92

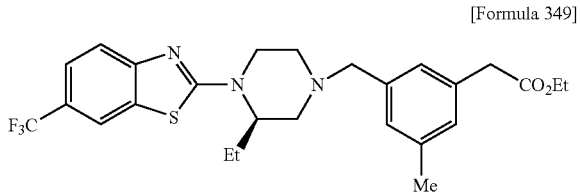

[Formula 349]

Yield 53%, 1H-NMR (CDCl3): δ 0.89 (3H, t, J=7.5 Hz), 1.20 (3H, t, J=7 Hz), 1.87-2.03 (2H, m), 2.24 (2H, td, J=11, 3.5 Hz), 2.34 (2H, s), 2.82-2.95 (2H, m), 3.38 (1H, d, J=13 Hz), 3.49 (1H, td, J=13, 3.5 Hz), 3.56 (1H, d, J=13 Hz), 3.57 (2H, s), 3.80-3.95 (1H, m), 4.00-4.10 (1H, m), 4.16 (2H, q, J=7 Hz), 7.01 (1H, s), 7.05 (1H, s), 7.06 (1H, s), 7.48-7.55 (2H, m), 7.82 (1H, s).

Example 93

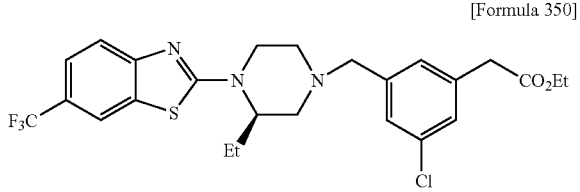

[Formula 350]

Yield 74%, 1H-NMR (CDCl3): δ 0.90 (3H, t, J=7.5 Hz), 1.27 (3H, t, J=7 Hz), 1.94 (2H, quant, J=7.5 Hz), 2.20-2.32 (2H, m), 2.80-2.93 (2H, m), 3.41 (1H, d, J=13.5 Hz), 3.49 (1H, td, J=12.5, 3.5 Hz), 3.55 (1H, d, J=13.5 Hz), 3.59 (2H, s), 3.85-3.95 (1H, m), 4.00-4.10 (1H, m), 4.17 (2H, q, J=7 Hz), 7.14 (1H, s), 7.20 (1H, s), 7.28 (1H, s), 7.45-7.56 (2H, m), 7.82 (1H, s).

Example 94

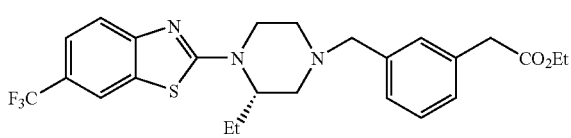

[Formula 351]

Yield 85%, 1H-NMR (CDCl3): δ 0.88 (3H, t, J=7.5 Hz), 1.20 (3H, t, J=7 Hz), 1.94 (2H, quant, J=7.5 Hz), 2.19-2.30 (2H, m), 2.80-2.95 (2H, m), 3.43 (1H, d, J=13.5 Hz), 3.51 (1H, td, J=12.5, 3.5 Hz), 3.59 (1H, d, J=13.5 Hz), 3.62 (2H, s), 3.80-3.95 (1H, m), 4.00-4.10 (1H, m), 4.15 (2H, q, J=7 Hz), 7.15-7.33 (4H, m), 7.50 (1H, d, J=8.5 Hz), 7.52 (1H, d, J=8.5 Hz), 7.82 (1H, s).

Example 95

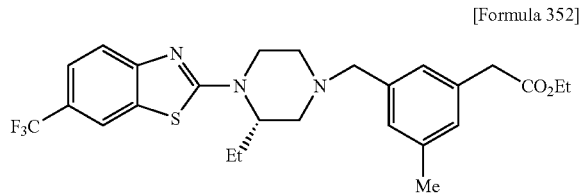

[Formula 352]

Yield 73%, 1H-NMR (CDCl3): δ 0.88 (3H, t, J=7.5 Hz), 1.26 (3H, t, J=7 Hz), 1.95 (2H, quant, J=7.5 Hz), 2.15-2.28 (2H, m), 2.34 (3H, s), 2.82-2.93 (2H, m), 3.39 (1H, d, J=13.5 Hz), 3.48 (1H, td, J=12.5, 3.5 Hz), 3.55 (1H, d, J=13.5 Hz), 3.57 (2H, s), 3.80-3.95 (1H, m), 3.98-4.10 (1H, m), 4.15 (2H, q, J=7 Hz), 7.01 (1H, s), 7.06 (2H, s), 7.52 (2H, s), 7.82 (1H, s).

Example 96

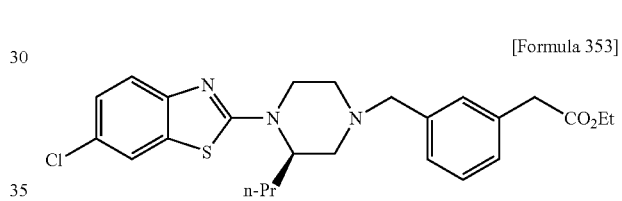

[Formula 353]

Yield 67%, 1H-NMR (CDCl3): δ 0.93 (3H, t, J=7.5 Hz), 1.19-1.35 (2H, m), 1.26 (3H, t, J=7.0 Hz), 1.73-2.00 (2H, m), 2.15-2.30 (2H, m), 2.81 (1H, d, J=11.5 Hz), 2.88 (1H, d, J=11.0 Hz), 3.42 (1H, d, J=13.5 Hz), 3.46 (1H, td, J=12.5, 3.5 Hz), 3.58 (1H, d, J=13.5 Hz), 3.61 (2H, s), 3.84-4.05 (2H, m), 4.16 (2H, q, J=7.0 Hz), 7.14-7.34 (5H, m), 7.39 (1H, d, J=8.5 Hz), 7.52 (1H, d, J=2.0 Hz).

Example 97

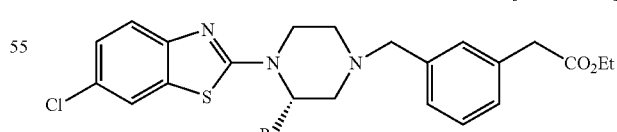

[Formula 354]

Yield 64%, 1H-NMR (CDCl3): δ 0.93 (3H, t, J=7.2 Hz), 1.21-1.31 (5H, m), 1.78-1.96 (2H, m), 2.19-2.28 (2H, m), 2.81 (1H, d, J=11.4 Hz), 2.88 (1H, d, J=11.4 Hz), 3.42 (1H, d, J=13.2 Hz), 3.47 (1H, td, J=3.3, 12.6 Hz), 3.59 (1H, d, J=13.2 Hz), 3.62 (2H, s), 3.90 (1H, s), 4.00 (1H, d, J=12.6 Hz), 4.16 (2H, q, J=7.2 Hz), 7.19-7.33 (5H, m), 7.39 (1H, d, J=8.4 Hz), 7.53 (1H, d, J=2.1 Hz)

Example 98

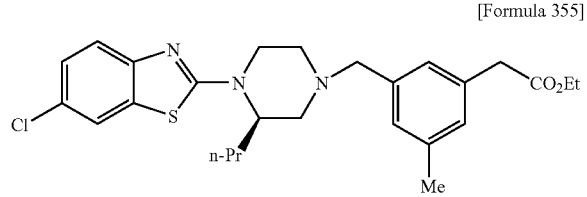

[Formula 355]

Yield 58%, 1H-NMR (CDCl3): δ0.34 (3H, t, J=7.0 Hz), 1.19-1.35 (2H, m), 1.26 (3H, t, J=7.0 Hz), 1.72-2.02 (2H, m), 2.15-2.29 (2H, m), 2.34 (3H, s), 2.81 (1H, d, J=11.5 Hz), 2.89 (1H, d, J=11.5 Hz), 3.37 (1H, d, J=13.5 Hz), 3.47 (1H, td, J=13.5, 3.0 Hz), 3.57 (1H, d, J=13.5 Hz), 3.57 (2H, s), 3.83-3.93 (1H, m), 3.94-4.04 (1H, m), 4.16 (2H, q, J=7.0 Hz), 7.01 (1H, s), 7.05 (2H, s), 7.22 (1H, dd, J=8.5, 2.0 Hz), 7.39 (1H, d, J=8.5 Hz), 7.52 (1H, d, J=2.0 Hz).

Example 99

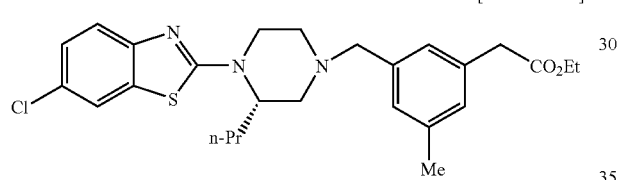

[Formula 356]

Yield 68%, 1H-NMR (CDCl3): δ0.94 (3H, t, J=7.5 Hz), 1.24-1.31 (5H, m), 1.73-1.85 (1H, m), 1.89-2.01 (1H, m), 2.17-2.27 (2H, m), 2.34 (3H, s), 2.81 (1H, d, J=11.4 Hz), 2.88 (1H, d, J=11.1 Hz), 3.37 (1H, d, J=13.5 Hz), 3.47 (1H, dt, J=3.3, 12.6 Hz), 3.57 (1H, d, J=13.5 Hz), 3.57 (2H, s), 3.89 (1H, s), 3.99 (1H, d, J=12.0 Hz), 4.16 (2H, q, J=7.2 Hz), 7.01 (1H, s), 7.06 (2H, s), 7.22 (1H, dd, J=2.1, 8.4 Hz), 7.39 (1H, d, J=8.4 Hz), 7.52 (1H, d, J=2.1 Hz)

Example 100

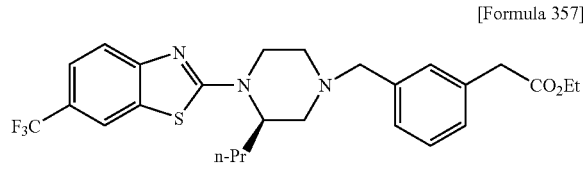

[Formula 357]

Yield 69%, 1H-NMR (CDCl3): δ0.93 (3H, t, J=7.0 Hz), 1.18-1.35 (2H, m), 1.26 (3H, t, J=7.0 Hz), 1.76-1.99 (2H, m), 2.16-2.29 (2H, m), 2.82 (1H, d, J=11.5 Hz), 2.89 (1H, d, J=11.5 Hz), 3.42 (1H, d, J=13.5 Hz), 3.49 (1H, td, J=13.0, 3.5 Hz), 3.59 (1H, d, J=13.5 Hz), 3.62 (2H, s), 3.90-4.09 (2H, m), 4.16 (2H, q, J=7.0 Hz), 7.15-7.34 (4H, m), 7.49 (1H, d, J=8.5 Hz), 7.53 (1H, d, J=8.5 Hz), 7.81 (1H, s).

Example 101

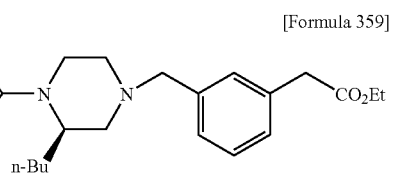

[Formula 358]

Yield 80%, 1H-NMR (CDCl3): δ0.94 (3H, t, J=7.2 Hz), 1.24-1.31 (5H, m), 1.83-1.91 (2H, m), 2.20-2.29 (2H, m), 2.83 (1H, d, J=11.4 Hz), 2.90 (1H, d, J=11.4 Hz), 3.34 (1H, d, J=13.5 Hz), 3.50 (1H, td, J=3.6, 12.6 Hz), 3.60 (1H, d, J=13.5 Hz), 3.62 (2H, s), 3.97 (1H, s), 4.05 (1H, d, J=12.6 Hz), 4.16 (2H, q, J=7.2 Hz), 7.19-7.33 (4H, m), 7.51 (2H, s), 7.82 (1H, s)

Example 102

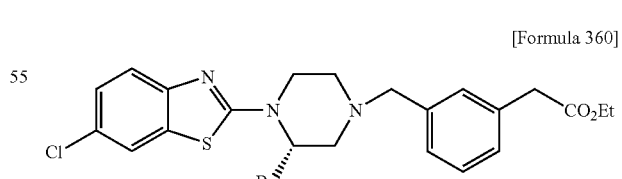

[Formula 359]

Yield 79%, 1H-NMR (CDCl3): δ0.87 (3H, t, J=7 Hz), 1.15-1.40 (7H, m), 1.74-2.00 (2H, m), 2.17-2.29 (2H, m), 2.77-2.94 (2H, m), 3.41 (1H, d, J=13.5 Hz), 3.46 (1H, td, J=13, 3.5 Hz), 3.59 (1H, d, J=13.5 Hz), 3.61 (2H, s), 3.80-3.93 (1H, m), 3.95-4.08 (1H, m), 4.16 (2H, q, J=7 Hz), 7.15-7.32 (5H, m), 7.39 (1H, d, J=9 Hz), 7.52 (1H, d, J=2 Hz).

Example 103

[Formula 360]

Yield 75%, 1H-NMR (CDCl3): δ0.87 (3H, t, J=7 Hz), 1.15-1.40 (7H, m), 1.76-2.01 (2H, m), 2.20-2.30 (2H, m), 2.77-2.93 (2H, m), 3.42 (1H, d, J=13.5 Hz), 3.46 (1H, td, J=13, 3.5 Hz), 3.59 (1H, d, J=13.5 Hz), 3.61 (2H, s), 3.80-3.92 (1H, m), 3.95-4.06 (1H, m), 4.16 (2H, q, J=7 Hz), 7.16-7.33 (5H, m), 7.39 (1H, d, J=9 Hz), 7.52 (1H, d, J=2 Hz).

Example 104

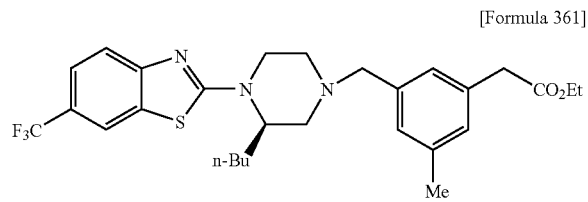
[Formula 361]

Yield 75%, 1H-NMR (CDCl3): δ0.88 (3H, t, J=7 Hz), 1.15-1.40 (7H, m), 1.75-2.03 (2H, m), 2.17-2.30 (2H, m), 2.34 (3H, s), 2.80-2.96 (2H, m), 3.37 (1H, d, J=13.5 Hz), 3.50 (1H, td, J=13, 3.5 Hz), 3.57 (2H, s), 3.58 (1H, d, J=13.5 Hz), 3.85-4.00 (1H, m), 4.00-4.10 (1H, m), 4.15 (2H, q, J=7 Hz), 7.01 (1H, s), 7.05 (1H, s), 7.07 (1H, s), 7.45-7.55 (2H, m), 7.82 (1H, s).

Example 105

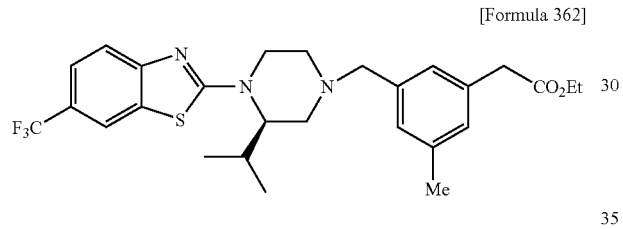
[Formula 362]

Yield 44%, 1H-NMR (CDCl3): δ0.90 (3H, d, J=6.5 Hz), 0.91 (3H, d, J=6.5 Hz), 1.26 (3H, t, J=7.0 Hz), 2.12 (1H, dd, J=11.5, 3.5 Hz), 2.23 (1H, td, J=11.5, 3.5 Hz), 2.34 (3H, s), 2.56-2.72 (1H, m), 2.88 (1H, d, J=11.5 Hz), 2.98 (1H, d, J=11.5 Hz), 3.34 (1H, d, J=13.0 Hz), 3.40-3.65 (2H, m), 3.56 (1H, d, J=13.0 Hz), 3.57 (2H, s), 4.08-4.22 (1H, m), 4.15 (2H, q, J=7.0 Hz), 7.01 (1H, s), 7.05 (2H, s), 7.49 (2H, s), 7.79 (1H, s).

Example 106

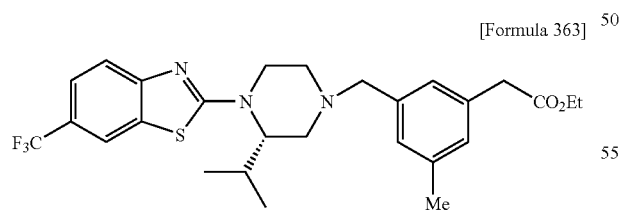
[Formula 363]

Yield 70%, 1H-NMR (CDCl3): δ0.90 (3H, d, J=2.5 Hz), 0.91 (3H, d, J=2.5 Hz), 1.26 (3H, t, J=7 Hz), 2.12 (1H, dd, J=11.5, 3.5 Hz), 2.23 (1H, td, J=11.5, 3.5 Hz), 2.34 (3H, s), 2.55-2.73 (1H, m), 2.88 (1H, d, J=9.5 Hz), 2.98 (1H, d, =9.5 Hz), 3.34 (1H, d, J=13 Hz), 3.40-3.54 (1H, m), 3.56 (1H, d, J=13 Hz), 3.57 (2H, s), 3.57-3.60 (1H, m), 4.11-4.15 (1H, m), 4.16 (2H, q, J=7 Hz), 7.01 (1H, s), 7.04 (1H, s), 7.05 (1H, s), 7.49-7.50 (2H, m), 7.79 (1H, s).

Example 107

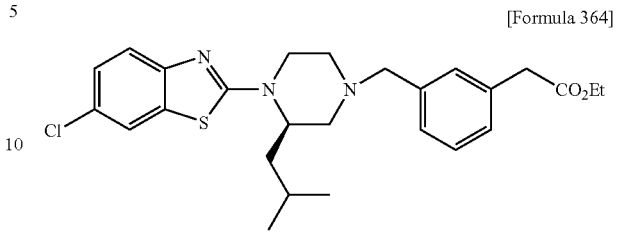
[Formula 364]

Yield 73%, 1H-NMR (CDCl3): δ0.93 (6H, d, J=6.5 Hz), 1.26 (3H, t, J=7.0 Hz), 1.32-1.53 (1H, m), 1.54-1.67 (1H, m), 1.85-1.98 (1H, m), 2.24 (2H, td, J=11.5, 3.5 Hz), 2.79 (1H, d, J=11.5 Hz), 2.89 (1H, d, J=11.5 Hz), 3.40 (1H, d, J=13.5 Hz), 3.47 (1H, td, J=13.0, 3.5 Hz), 3.61 (1H, d, J=13.5 Hz), 3.61 (2H, s), 3.88-4.08 (2H, m), 4.16 (2H, q, J=7.0 Hz), 7.15-7.33 (5H, m), 7.39 (1H, d, J=8.5 Hz), 7.53 (1H, d, J=2.0 Hz).

Example 108

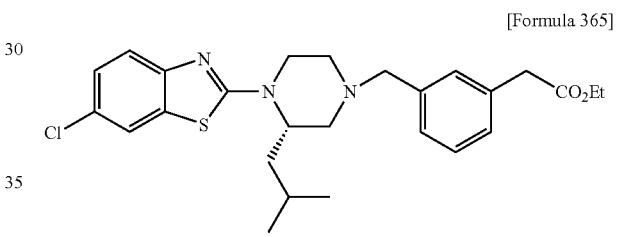
[Formula 365]

Yield 81%, 1H-NMR (CDCl3): δ0.93 (6H, d, J=6.5 Hz), 1.26 (3H, t, J=7 Hz), 1.38-1.47 (1H, m), 1.55-1.67 (1H, m), 1.85-1.96 (1H, m), 2.19-2.30 (2H, m), 2.78 (1H, d, J=11.5 Hz), 2.88 (1H, d, J=11.5 Hz), 3.40 (1H, d, J=13.5 Hz), 3.47 (1H, td, J=13, 3.5 Hz), 3.60 (1H, d, J=13.5 Hz), 3.61 (2H, s), 3.90-4.08 (2H, m), 4.15 (2H, q, J=7 Hz), 7.15-7.35 (5H, m), 7.39 (1H, d, J=8.5 Hz), 7.53 (1H, d, J=2 Hz).

Example 109

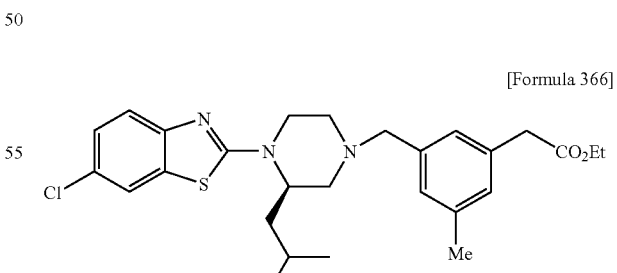
[Formula 366]

Yield 63%, 1H-NMR (CDCl3): δ0.93 (3H, d, J=6.5 Hz), 0.94 (3H, d, J=6.5 Hz), 1.26 (3H, t, J=7.0 Hz), 1.36-1.64 (2H, m), 1.88-2.02 (1H, m), 2.13-2.44 (2H, m), 2.34 (3H, s), 2.79 (1H, d, J=11.0 Hz), 2.89 (1H, d, J=11.0 Hz), 3.35 (1H, d, J=13.5 Hz), 3.41-3.68 (2H, m), 3.57 (2H, s), 3.86-4.09 (2H, m), 4.16 (2H, q, J=7.0 Hz), 7.01 (1H, s), 7.04 (1H, s), 7.06 (1H, s), 7.22 (1H, dd, J=8.5, 2.0 Hz), 7.39 (1H, d, J=8.5 Hz), 7.53 (1H, d, J=2.0 Hz).

J=13.2 Hz), 3.52 (1H, dt, J=3.6, 12.6 Hz), 3.57 (2H, s), 3.60 (1H, d, J=13.2 Hz), 4.04 (2H, br), 4.16 (2H, q, J=7.2 Hz), 7.01 (1H, s), 7.04 (1H, s), 7.06 (1H, s), 7.2 (2H, s), 7.83 (1H, s)

Example 110

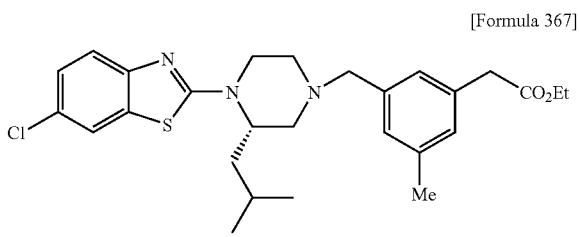

[Formula 367]

Yield 81%, 1H-NMR (CDCl3): δ0.92 (3H, d, J=3 Hz), 0.95 (3H, d, J=3 Hz), 1.26 (3H, t, J=7 Hz), 1.39-1.65 (2H, m), 1.90-2.02 (1H, m), 2.15-2.32 (2H, m), 2.34 (3H, s), 2.78 (1H, d, J=11.5 Hz), 2.89 (1H, d, J=11.5 Hz), 3.35 (1H, d, J=13.5 Hz), 3.48 (1H, td, J=13, 3.5 Hz), 3.57 (2H, s), 3.59 (1H, d, J=13.5 Hz), 3.86-4.08 (2H, m), 4.15 (2H, q, J=7 Hz), 7.01 (1H, s), 7.04 (1H, s), 7.06 (1H, s), 7.21 (1H, dd, J=8.5, 2 Hz), 7.39 (1H, d, J=8.5 Hz), 7.53 (1H, d, J=2 Hz).

Example 111

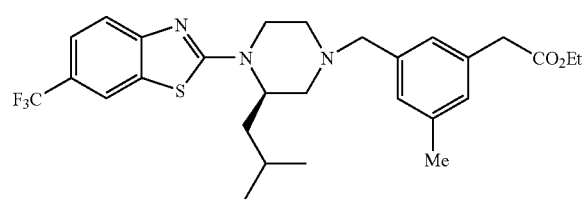

[Formula 368]

Yield 47%, 1H-NMR (CDCl3): δ0.94 (3H, d, J=6.5 Hz), 0.95 (3H, d, J=6.5 Hz), 1.27 (3H, t, J=7.0 Hz), 1.38-1.67 (2H, m), 1.89-2.04 (1H, m), 2.14-2.38 (2H, m), 2.34 (3H, s), 2.80 (1H, d, J=11.5 Hz), 2.90 (1H, d, J=11.5 Hz), 3.35 (1H, d, J=13.5 Hz), 3.44-3.64 (2H, m), 3.57 (2H, s), 3.94-4.21 (2H, m), 4.16 (2H, q, J=7.0 Hz), 7.01 (1H, s), 7.06 (2H, s), 7.49 (1H, d, J=8.5 Hz), 7.53 (1H, d, J=8.5 Hz), 7.82 (1H, s).

Example 112

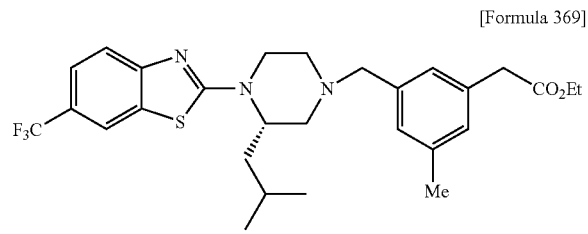

[Formula 369]

Yield 80%, 1H-NMR (CDCl3): δ0.94 (6H, dd, J=3.0, 6.3 Hz), 1.26 (3H, t, J=7.2 Hz), 1.44-1.48 (1H, m), 1.56-1.62 (1H, m), 1.91-2.00 (1H, m), 2.18-2.26 (2H, m), 2.34 (3H, s), 2.80 (1H, d, J=11.4 Hz), 2.91 (1H, d, J=11.4 Hz), 3.36 (1H, d,

Example 113

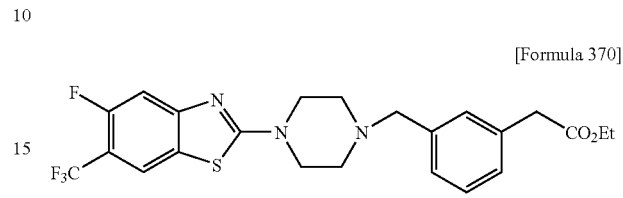

[Formula 370]

Yield 69%, 1H-NMR (CDCl3): δ1.26 (3H, t, J=7.0 Hz), 2.59 (4H, t, J=5.0 Hz), 3.57 (2H, s), 3.62 (2H, s), 3.68 (4H, t, J=5.0 Hz), 4.16 (2H, q, J=7.0 Hz), 7.18-7.34 (5H, m), 7.75 (1H, d, J=7.0 Hz).

Example 114

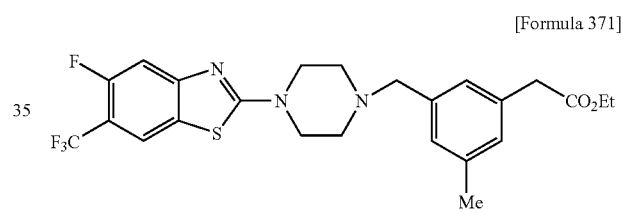

[Formula 371]

Yield 72%, 1H-NMR (CDCl3): δ1.26 (3H, t, J=7.0 Hz), 2.34 (3H, s), 2.58 (4H, t, J=5.0 Hz), 3.52 (2H, s), 3.58 (2H, s), 3.68 (4H, t, J=5.0 Hz), 4.16 (2H, q, J=7.0 Hz), 7.00-7.12 (3H, m), 7.26 (1H, d, J=11.5 Hz), 7.75 (1H, d, J=7.0 Hz).

Example 115

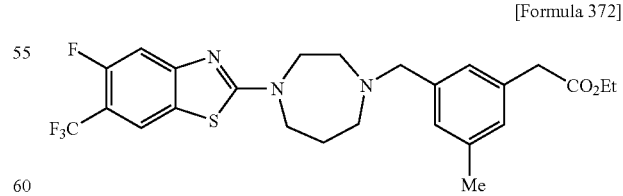

[Formula 372]

Yield 41%, 1H-NMR (CDCl3): δ1.25 (3H, t, J=7.0 Hz), 1.96-2.08 (2H, m), 2.32 (3H, s), 2.69 (2H, t, J=5.0 Hz), 2.75-2.85 (2H, m), 3.56 (2H, s), 3.60 (2H, s), 3.61-3.89 (4H, m), 4.15 (2H, q, J=7.0 Hz), 6.50-7.07 (3H, m), 7.26 (1H, d, J=12.0 Hz), 7.73 (1H, d, J=7.0 Hz).

Example 116

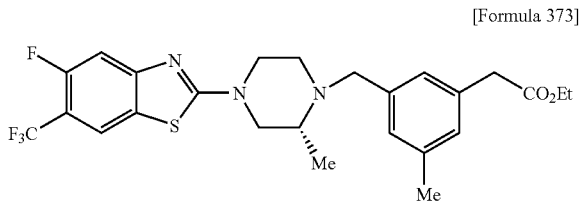

[Formula 373]

Yield 80%, 1H-NMR (CDCl3): δ1.23 (3H, d, J=6 Hz), 1.26 (3H, t, J=7 Hz), 2.23-2.33 (1H, m), 2.34 (3H, s), 2.69-2.70 (1H, m), 2.82 (1H, dt, J=12, 4 Hz), 3.17 (1H, d, J=13 Hz), 3.18-3.26 (1H, m), 3.36-3.48 (1H, m), 3.58 (2H, s), 3.70-3.80 (1H, m), 3.85-3.95 (1H, m), 4.02 (1H, d, J=13 Hz), 4.13 (2H, q, J=7 Hz), 7.01 (1H, s), 7.04 (1H, s), 7.05 (1H, s), 7.26 (1H, d, J=12 Hz), 7.73 (1H, d, J=7 Hz).

Example 117

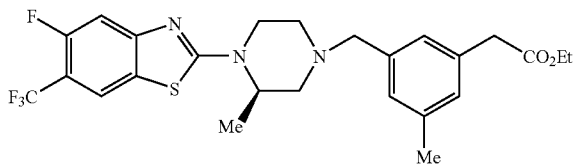

[Formula 374]

Yield 63%, 1H-NMR (CDCl3): δ1.26 (3H, t, J=7.0 Hz), 1.43 (3H, d, J=7.0 Hz), 2.17-2.37 (2H, m), 2.34 (3H, s), 2.71-2.79 (1H, m), 2.87-2.98 (1H, m), 3.43 (1H, d, J=13.0 Hz), 3.46-3.60 (2H, m), 3.58 (2H, s), 3.83-3.94 (1H, m), 4.15-4.28 (1H, m), 4.16 (2H, q, J=7.0 Hz), 7.02 (1H, s), 7.06 (1H, s), 7.08 (1H, s), 7.26 (1H, d, J=11.5 Hz), 7.74 (1H, d, J=7.0 Hz).

Example 118

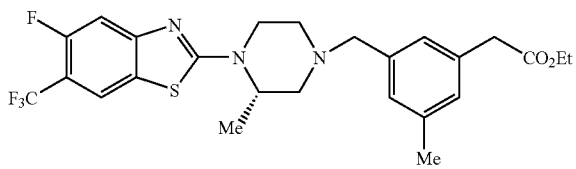

[Formula 375]

Yield 60%, 1H-NMR (CDCl3): δ1.26 (3H, t, J=7.0 Hz), 1.43 (3H, d, J=7.0 Hz), 2.16-2.36 (2H, m), 2.34 (3H, s), 2.70-2.79 (1H, m), 2.87-2.98 (1H, m), 3.43 (1H, d, J=13.0 Hz), 3.45-3.61 (4H, m), 3.84-3.94 (1H, m), 4.14-4.28 (1H, m), 4.16 (2H, q, J=7.0 Hz), 7.01 (1H, s), 7.04-7.12 (2H, m), 7.26 (1H, d, J=11.5 Hz), 7.74 (1H, d, J=7.0 Hz).

Example 119

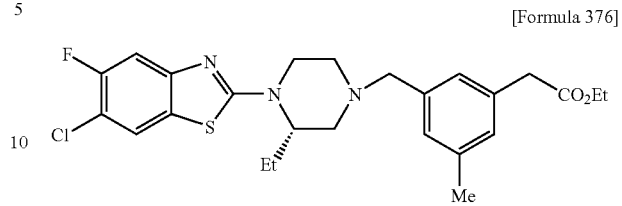

[Formula 376]

Yield 90%, 1H-NMR (CDCl3): δ0.87 (3H, t, J=7.5 Hz), 1.25 (3H, t, J=7.0 Hz), 1.82-2.03 (2H, m), 2.14-2.53 (2H, m), 2.33 (3H, s), 2.78-2.93 (2H, m), 3.37 (1H, d, J=13.5 Hz), 3.45 (1H, td, J=12.5, 3.5 Hz), 3.55 (1H, d, J=13.5 Hz), 3.57 (2H, s), 3.76-3.88 (1H, m), 3.90-4.03 (1H, m), 4.15 (2H, q, J=7.0 Hz), 7.00 (1H, s), 7.03-7.09 (2H, m), 7.24 (1H, d, J=10.5 Hz), 7.49 (1H, d, J=7.0 Hz).

Example 120

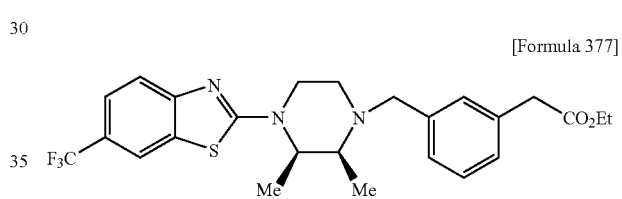

[Formula 377]

Yield 18%, 1H-NMR (CDCl3): δ1.20 (3H, d, J=6.5 Hz), 1.25 (3H, t, J=7.0 Hz), 1.36 (3H, d, J=6.5 Hz), 2.15 (1H, td, J=12.0, 3.5 Hz), 2.60-2.72 (1H, m), 2.74-2.84 (1H, m), 2.98 (1H, d, J=13.5 Hz), 3.40 (1H, td, J=12.5, 3.5 Hz), 3.62 (2H, s), 3.67-3.81 (1H, m), 4.03-4.22 (4H, m), 7.13-7.34 (4H, m), 7.50 (1H, dd, J=8.5, 1.5 Hz), 7.55 (1H, d, J=8.5 Hz), 7.82 (1H, d, J=1.5 Hz).

Example 121

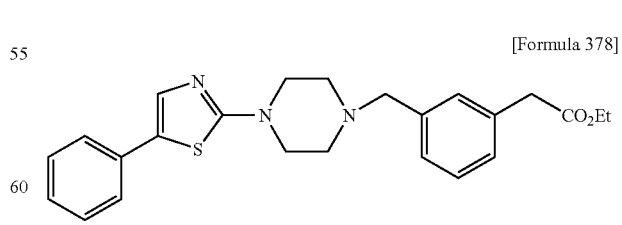

[Formula 378]

Yield 73%, 1H-NMR (CDCl3): δ1.26 (3H, t, J=7.0 Hz), 2.58 (4H, t, J=5.0 Hz), 3.54 (4H, t, J=5.0 Hz), 3.56 (2H, s), 3.62 (2H, s), 4.16 (2H, q, J=7.0 Hz), 7.17-7.24 (2H, m), 7.25-7.37 (5H, m), 7.39-7.45 (2H, m), 7.40 (1H, s).

Example 122

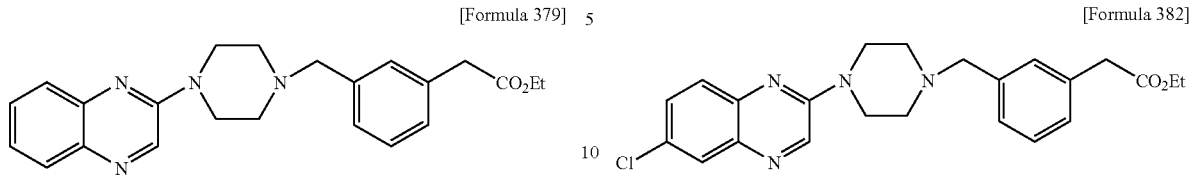

[Formula 379]

Yield 56%, 1H-NMR (CDCl3): δ1.26 (3H, t, J=7.0 Hz), 2.61 (4H, t, J=5.0 Hz), 3.57 (2H, s), 3.63 (2H, s), 3.81 (4H, t, J=5.0), 4.16 (2H, q, J=7.0 Hz), 7.14-7.34 (4H, m), 7.35-7.43 (1H, m), 7.53-7.62 (1H, m), 7.68 (1H, dd, J=8.0, 1.5 Hz), 7.87 (1H, dd, J=8.0, 1.5 Hz), 8.57 (1H, s).

Example 123

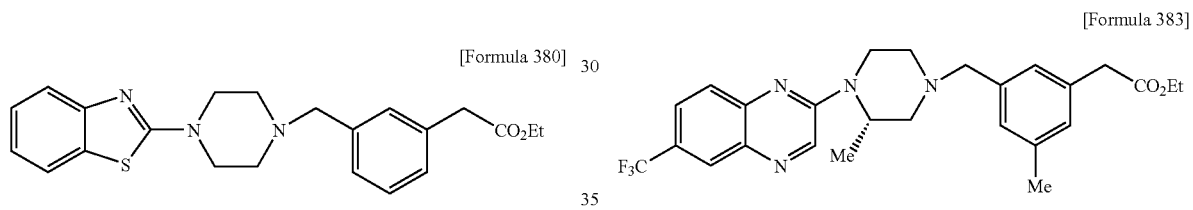

[Formula 380]

Yield 70%, 1H-NMR (CDCl3): δ1.26 (3H, t, J=7.0 Hz), 2.58 (4H, t, J=5.0 Hz), 3.56 (2H, s), 3.62 (2H, s), 3.65 (4H, t, J=5.0 Hz), 4.16 (2H, q, J=7.0 Hz), 7.07 (1H, t, J=7.5 Hz), 7.16-7.34 (5H, m), 7.55 (1H, d, J=8.0 Hz), 7.59 (1H, d, J=8.0 Hz).

Example 124

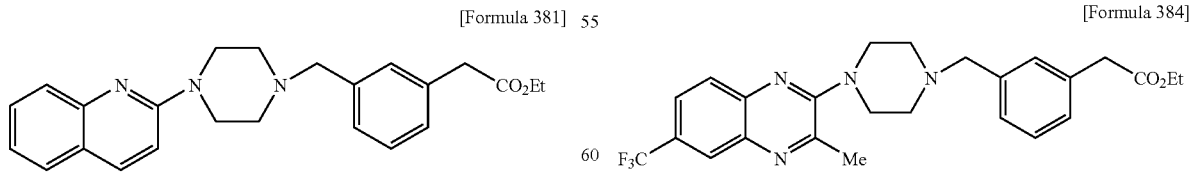

[Formula 381]

Yield 66%, 1H-NMR (CDCl3): δ1.26 (3H, t, J=7.0 Hz), 2.59 (4H, t, J=5.0 Hz), 3.57 (2H, s), 3.63 (2H, s), 3.76 (4H, t, J=5.0 Hz), 4.16 (2H, q, J=7.0 Hz), 6.97 (1H, d, J=9.0 Hz), 7.17-7.38 (5H, m), 7.48-7.64 (2H, m), 7.69 (1H, d, J=8.5 Hz), 7.88 (1H, d, J=9.0 Hz).

Example 125

[Formula 382]

Yield 88%, 1H-NMR (CDCl3): δ1.26 (3H, t, J=7.0 Hz), 2.60 (4H, t, J=5.0 Hz), 3.57 (2H, s), 3.63 (2H, s), 3.80 (4H, t, J=5.0 Hz), 4.16 (2H, q, J=7.0 Hz), 7.16-7.35 (4H, m), 7.50 (1H, dd, J=90, 2.5 Hz), 7.59 (1H, d, J=9.0 Hz), 7.85 (1H, d, J=2.5 Hz), 8.55 (1H, s).

Example 126

[Formula 383]

Yield 80%, 1H-NMR (CDCl3): δ1.26 (3H, t, J=7.0 Hz), 1.39 (3H, d, J=7.0 Hz), 2.20 (1H, t, J=11.5, 3.5 Hz), 2.25-2.37 (4H, m), 2.82 (1H, d, J=11.5 Hz), 3.00 (1H, d, J=11.5 Hz), 3.31-3.46 (2H, m), 3.53-3.63 (3H, m), 4.16 (2H, q, J=7.0 Hz), 4.33-4.43 (1H, m), 4.64-4.77 (1H, m), 7.02 (1H, s), 7.09 (1H, s), 7.11 (1H, s), 7.70 (2H, s), 8.14 (1H, s), 8.58 (1H, s).

Example 127

[Formula 384]

Yield 90%, 1H-NMR (CDCl3): δ1.26 (3H, t, J=7.0 Hz), 2.66 (4H, t, J=5.0 Hz), 2.70 (3H, s), 3.47 (4H, t, J=5.0 Hz), 3.60 (2H, s), 3.63 (2H, s), 4.16 (2H, q, J=7.0 Hz), 7.16-7.34 (4H, m), 7.74 (1H, d, J=8.5 Hz), 7.87 (1H, d, J=8.5 Hz), 8.16 (1H, s).

Example 128

Preparation of 6-chloro-2-[4-(3-methoxymethoxy-4-methylbenzyl)piperazine-1-yl]benzothiazole

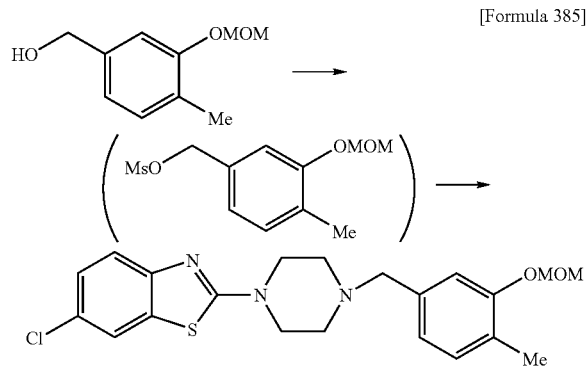

[Formula 385]

To a mixture of [3-(methoxymethoxy)-4-methyl]benzyl alcohol described in Reference Example 68 of WO2004/022551 (1.23 g; 6.75 mmol), triethylamine (0.55 ml; 7.09 mmol) and THF (12 ml) was added dropwise methanesulfonyl chloride (0.55 ml; 7.09 mmol) under ice-cooling. The mixture was stirred for 1 hour, and the reaction solution was concentrated under reduced pressure. To the residue were added 4-(6-chlorobenzothiazole-2-yl)piperazine dihydrochloride (2.10 g; 6.43 mmol), potassium carbonate (2.67 g; 19.3 mmol) and anhydrous N,N-dimethylformamide (20 ml). The mixture was stirred at room temperature for 14 hours. Water was added to the reaction solution, and the precipitate was collected and washed with diisopropyl ether to give 6-chloro-2-[4-(3-methoxymethoxy-4-methylbenzyl)piperazine-1-yl]benzothiazole as colorless crystal (1.70 g; 63%).

$^1$H-NMR (CDCl$_3$): δ2.24 (3H, s), 2.57 (4H, t, J=5 Hz), 3.50 (3H, s), 3.52 (2H, s), 3.63 (4H, t, J=5 Hz), 5.22 (2H, s), 6.89 (1H, d, J=7.5 Hz), 7.03 (1H, s), 7.10 (1H, d, J=7.5 Hz), 7.23 (1H, dd, J=8.5, 2 Hz), 7.45 (1H, d, J=8.5 Hz), 7.59 (1H, d, J=2 Hz).

Example 129

Preparation of 3-[4-[(6-chlorobenzothiazole-2-yl)piperazine-1-yl]methyl]benzyl alcohol

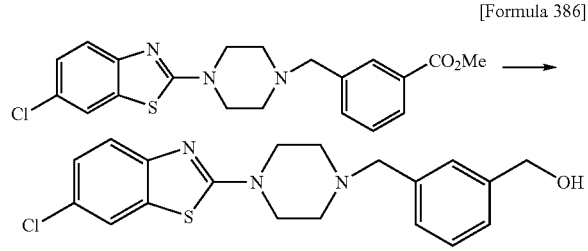

[Formula 386]

To a suspension of lithium aluminium hydride (0.52 g; 13.7 mmol) in anhydrous THF (27 ml) was added dropwise a solution of 3-[[4-(6-chlorobenzothiazole-2-yl)piperazine-1-yl]methyl]methyl butanoate (2.76 g; 6.87 mmol) in anhydrous THF (27 ml) under ice-cooling. After stirring at room temperature for 1 hour, a mixture of water/THF (0.25 ml/5 mL) and 2N-aqueous sodium hydroxide solution (0.5 ml) was sequentially added dropwise thereto under ice-cooling. The mixture was stirred at room temperature for 1 hour. After filtration of aluminium hydroxide, the filtrate was concentrated under reduced pressure. To the residue were added ethyl acetate and brine to separate. The organic layer was dried over anhydrous sodium sulphate. The solvent was evaporated under reduced pressure to give yellow crystal. The crystal was washed with diisopropyl ether to give 3-[4-[(6-chlorobenzothiazole-2-yl)piperazine-1-yl]methyl]benzyl alcohol as pale yellow crystal (2.35 g; 92%).

$^1$H-NMR (CDCl$_3$): 1.83 (1H, t, J=5.5 Hz), 2.57 (4H, t, J=5 Hz), 3.51 (2H, s), 3.63 (4H, t, J=5 Hz), 4.71 (2H, d, J=5.5 Hz), 7.23 (1H, dd, J=8.5, 2 Hz), 7.25-7.38 (4H, m), 7.42 (1H, d, J=8.5 Hz), 7.55 (1H, d. J=2 Hz).

Compounds in Example 130 to 153 were obtained by similar methods as Example 129.

Example 130

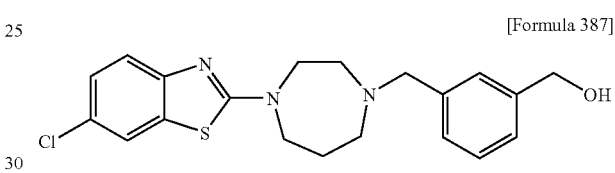

[Formula 387]

Yield: 100%, $^1$H-NMR (CDCl$_3$); δ1.65 (1H, brs), 1.98-2.05 (2H, m), 2.70 (2H, t, J=5.1 Hz), 2.79-2.82 (2H, m), 3.65 (2H, s), 3.71-3.77 (4H, m), 4.69 (2H, s), 7.23 (1H, dd, J=8.7 Hz, 2.4 Hz), 7.26-7.34 (4H, m), 7.43 (1H, d, J=8.4 Hz), 7.55 (1H, d, J=2.1 Hz).

Example 131

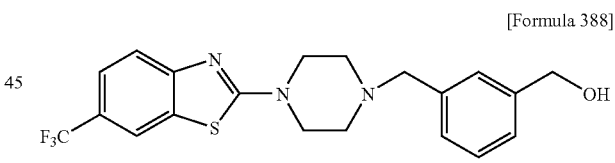

[Formula 388]

Yield: 100%, $^1$H-NMR (CDCl$_3$); δ1.26 (1H, brs), 2.59 (4H, t, J=5 Hz), 3.58 (2H, s), 3.68 (4H, t, J=5 Hz), 4.72 (2H, s), 7.20-7.40 (4H, m), 7.50-7.60 (2H, m), 7.84 (1H, s).

Example 132

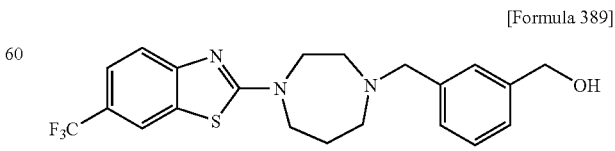

[Formula 389]

Yield: 60%, $^1$H-NMR (DMSO-d$_6$): δ1.88-1.99 (2H, m), 2.58-2.67 (2H, m), 2.74-2.84 (2H, m), 3.62 (2H, s), 3.63-3.85

(4H, m), 4.47 (2H, d, J=5.5 Hz), 5.16 (1H, t, J=5.5 Hz), 7.13-7.20 (2H, m), 7.22-7.30 (2H, m), 7.52-7.57 (2H, m), 8.22 (1H, s).

Example 133

[Formula 390]

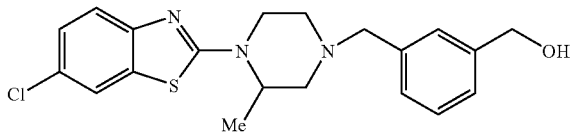

Yield: 96% $^1$H-NMR (CDCl$_3$); δ1.41 (3H, d, J=6.5 Hz), 1.63 (1H, brs), 2.25 (1H, td, J=11.5, 3.5 Hz), 2.33 (1H, dd, J=11.5, 3.5 Hz), 2.72 (1H, d, J=11.5 Hz), 2.86-2.95 (1H, m), 3.47 (1H, td, J=12.5, 3.5 Hz), 3.48 (1H, d, J=13.5 Hz), 3.60 (1H, d, J=13.5 Hz), 3.85 (1H, d, J=12.5 Hz), 4.10-4.25 (1H, m), 4.72 (2H, s), 7.22 (1H, dd, J=8.5, 2 Hz), 7.25-7.40 (4H, m), 7.42 (1H, d, J=8.5 Hz), 7.54 (1H, d, J=2 Hz).

Example 134

[Formula 391]

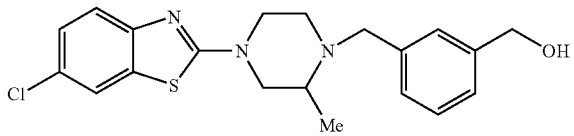

Yield: 98%, $^1$H-NMR (CDCl$_3$); δ1.23 (3H, d, J=6.5 Hz), 1.55-1.70 (1H, m), 2.22-2.32 (1H, m), 2.60-2.70 (1H, m), 2.75-2.85 (1H, m), 3.10-3.20 (1H, m), 3.22 (1H, d, J=13.5 Hz), 3.35-3.45 (1H, m), 3.65-3.75 (1H, m), 3.83-3.90 (1H, m), 4.06 (1H, d, J=13.5 Hz), 4.71 (2H, s), 7.20-7.35 (5H, m), 7.42 (1H, d, J=8.5 Hz), 7.54 (1H, d, J=2 Hz).

Example 135

[Formula 392]

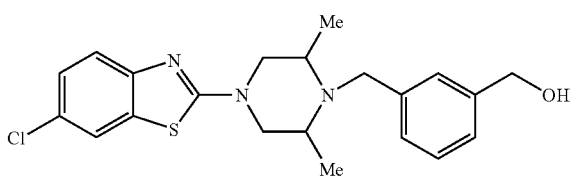

Yield: q.y., $^1$H-NMR (CDCl$_3$); δ1.12 (6H, d, J=6 Hz), 1.64 (1H, brs), 2.75-2.85 (2H, m), 3.05 (2H, dd, J=13, 12.5 Hz), 3.85 (2H, s), 3.80-3.90 (2H, m), 4.70 (2H, s), 7.23 (1H, dd, J=8.5, 2 Hz), 7.25-7.28 (1H, m), 7.30-7.35 (2H, m), 7.38 (1H, s), 7.42 (1H, d, J=8.5 Hz), 7.55 (1H, d, J=2 Hz).

Example 136

[Formula 393]

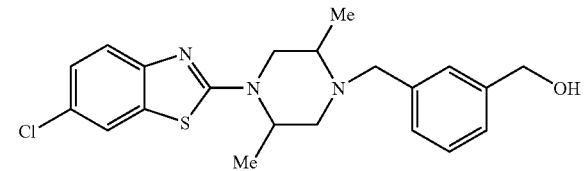

Yield: q.y., $^1$H-NMR (CDCl$_3$); δ1.08 (3H, d, J=6.5 Hz), 1.38 (3H, d, J=6.5 Hz), 1.74 (1H, brs), 2.33 (1H, d, J=11.5 Hz), 2.89 (1H, dd, J=11.5, 4 Hz), 3.06-3.19 (1H, m), 3.53 (1H, d, J=14.5 Hz), 3.60-3.75 (3H, m), 4.15-4.28 (1H, m), 4.70 (2H, s), 7.21 (1H, dd, J=8.5, 2 Hz), 7.25-7.35 (4H, m), 7.40 (1H, d, J=8.5 Hz), 7.53 (1H, d, J=2 Hz).

Example 137

[Formula 394]

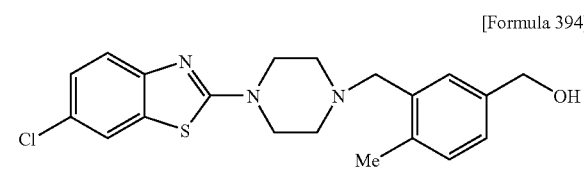

Yield: 60%, $^1$H-NMR (CDCl$_3$); δ1.71 (1H, brs), 2.38 (3H, s), 2.58 (4H, t, J=5 Hz), 3.52 (2H, s), 3.61 (4H, t, J=5 Hz), 4.67 (2H, s), 7.15-7.20 (2H, m), 7.23 (1H, dd, J=8.5, 2 Hz), 7.25-7.28 (1H, m), 7.43 (1H, d, J=8.5 Hz), 7.55 (1H, d, J=2 Hz).

Example 138

[Formula 395]

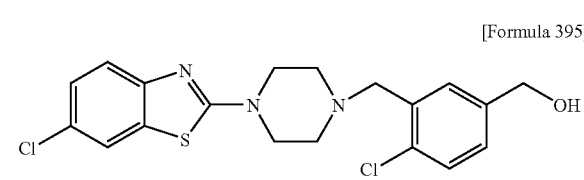

Yield: 39%, $^1$H-NMR (CDCl$_3$); δ1.80 (1H, brs), 2.65 (4H, t, J=5 Hz), 3.65 (4H, t, J=5 Hz), 3.68 (2H, s), 4.70 (2H, s), 7.23 (1H, dd, J=8.2 Hz), 7.24 (1H, dd, 8.5, 2 Hz), 7.36 (1H, d, J=8 Hz), 7.42 (1H, d, J=8.5 Hz), 7.48 (1H, d, J=2 Hz), 7.55 (1H, d, J=2 Hz).

Example 139

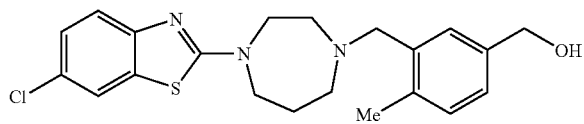

[Formula 396]

Yield: 92%, ¹H-NMR (CDCl₃); δ1.66-1.73, (1H, br-s), 1.97-2.04 (2H, m), 2.33 (3H, s), 2.69 (2H, t, J=5.4 Hz), 2.78-2.81 (2H, m), 3.59 (2H, s), 3.70-3.75 (4H, m), 4.65 (2H, s), 7.16-7.17 (2H, m), 7.23 (1H, dd, J=8.7 Hz, 2.1 Hz), 7.28 (1H, s), 7.43 (1H, d, J=8.7 Hz), 7.55 (1H, d, J=2.4 Hz).

Example 140

[Formula 397]

Yield: 100%, ¹H-NMR (CDCl₃); δ1.70-1.88 (1H, br-s), 1.98-2.07 (2H, m), 2.75 (2H, t, J=5.4 Hz), 2.84-2.89 (2H, m), 3.72-3.84 (6H, m), 4.68 (2H, s), 7.17-7.25 (2H, m), 7.33 (1H, d, J=8.1 Hz), 7.44 (1H, d, J=8.1 Hz), 7.50 (1H, d, J=2.1 Hz), 7.55 (1H, d, J=2.4 Hz).

Example 141

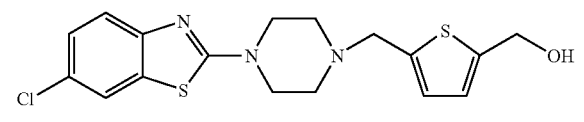

[Formula 398]

Yield: 30%, ¹H-NMR (CDCl₃); δ1.90 (1H, brs), 2.62 (4H, t, J=5 Hz), 3.64 (4H, t, J=5 Hz), 3.74 (2H, s), 4.79 (2H, s), 6.79 (1H, d, J=3.5 Hz), 6.85 (1H, d, J=3.5 Hz), 7.23 (1H, dd, J=8.5, 2 Hz), 7.43 (1H, d, J=8.5 Hz), 7.55 (1H, d, J=2 Hz).

Example 142

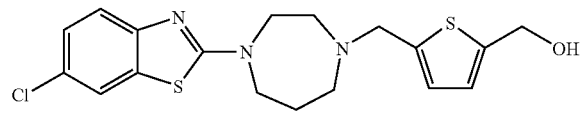

[Formula 399]

Yield: 80%, ¹H-NMR (CDCl₃); δ1.86 (1H, s), 2.00-2.07 (2H, m), 2.71-2.74 (2H, m), 2.84-2.87 (2H, m), 3.73 (2H, t, J=6.0 Hz), 3.77-3.80 (2H, m), 3.82 (2H, s), 4.78 (2H, s), 6.76 (1H, d, J=3.3 Hz), 6.84 (1H, d, J=3.3 Hz), 7.23 (1H, dd, J=8.7, 2.4 Hz), 7.42 (1H, d, J=9.0 Hz), 7.55 (1H, d, J=2.4 Hz).

Example 143

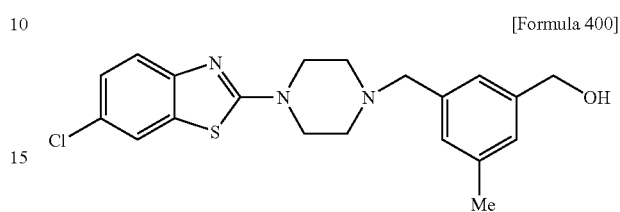

[Formula 400]

Yield: 90%, ¹H-NMR (CDCl₃); δ1.81 (1H, brs), 2.36 (3H, s), 2.57 (4H, t, J=5 Hz), 3.53 (2H, s), 3.63 (4H, t, J=5 Hz), 4.67 (2H, s), 7.08 (1H, s), 7.11 (1H, s), 7.13 (1H, s), 7.23 (1H, dd, J=8.5, 2 Hz), 7.43 (1H, d, J=8.5 Hz), 7.55 (1H, d, J=2 Hz).

Example 144

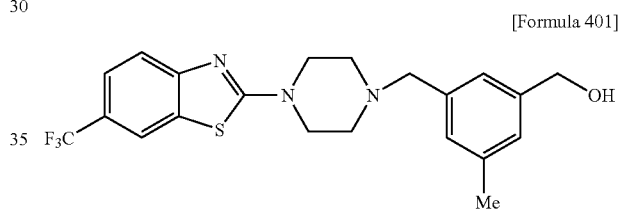

[Formula 401]

Yield: q. y, ¹H-NMR (CDCl₃); δ1.79 (1H, t, J=4.5 Hz), 2.36 (3H, s), 2.59 (4H, t, J=5 Hz), 3.54 (2H, s), 3.68 (4H, t, J=5 Hz), 4.67 (2H, d, J=4.5 Hz), 7.09 (1H, s), 7.11 (1H, s), 7.14 (1H, s), 7.45-7.60 (2H, m), 7.84 (1H, s).

Example 145

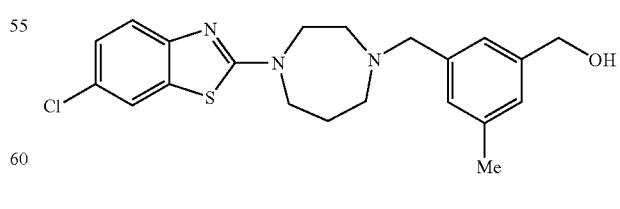

[Formula 402]

Yield: 93%, ¹H-NMR (CDCl₃); δ1.70 (1H, s), 1.99-2.06 (2H, m), 2.35 (3H, s), 2.70 (2H, t, J=5.4 Hz), 2.79-2.82 (2H, m), 3.61 (2H, s), 3.71-3.77 (4H, m), 4.65 (2H, s), 7.07 (1H, s), 7.09 (1H, s), 7.13 (1H, s), 7.23 (1H, dd, J=8.7 Hz, 2.1 Hz), 7.43 (1H, d, J=8.7 Hz), 7.55 (1H, d, J=2.1 Hz).

Example 146

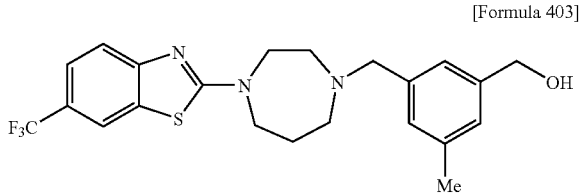
[Formula 403]

Yield: q. y, ¹H-NMR (CDCl₃); δ1.77 (1H, brs), 1.95-2.10 (2H, m), 2.34 (3H, s), 2.68 (2H, t, J=5.5 Hz), 2.82 (2H, t, J=5.5 Hz), 3.61 (2H, s), 3.70-3.85 (4H, m), 4.65 (2H, s), 7.06 (1H, s), 7.08 (1H, s), 7.13 (1H, s), 7.45-7.60 (2H, m), 7.84 (1H, s).

Example 147

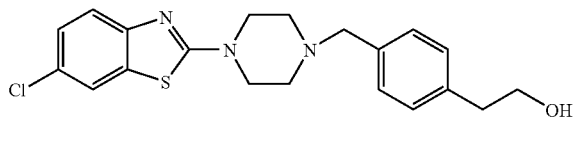
[Formula 404]

Yield: 80%, ¹H-NMR (DMSO-d₆): δ1.59 (1H, brs), 2.57 (4H, t, J=5 Hz), 2.88 (2H, t, J=6.5 Hz), 3.55 (2H, s), 3.63 (4H, t, J=5 Hz), 3.88 (2H, t, J=6.5 Hz), 7.20 (2H, d, J=7.5 Hz), 7.26 (1H, dd, J=8.5, 2 Hz), 7.29 (2H, d, J=7.5 Hz), 7.43 (1H, d, J=8.5 Hz), 7.55 (1H, d, J=2 Hz).

Example 148

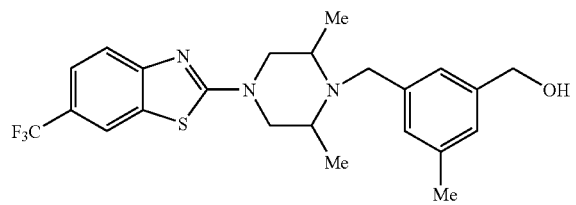
[Formula 405]

Yield: 46%, 1H-NMR (CDCl3): δ1.14 (6H, d, J=6 Hz), 1.68 (1H, brs), 2.30 (3H, s), 2.70-2.87 (2H, m), 3.03-3.15 (2H, m), 3.82 (2H, s), 3.85-3.95 (2H, m), 4.66 (2H, s), 7.05 (1H, s), 7.11 (1H, s), 7.17 (1H, s), 7.51 (1H, d, J=8.5 Hz), 7.55 (1H, d, J=8.5 Hz), 7.84 (1H, s).

Example 149

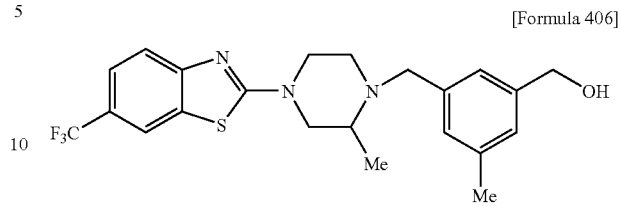
[Formula 406]

Yield: 95%, 1H-NMR (CDCl3): δ1.24 (3H, d, J=6 Hz), 1.69 (1H, brs), 2.20-2.35 (1H, m), 2.36 (3H, s), 2.60-2.72 (1H, m), 2.82 (1H, dt, J=12, 3.5 Hz), 3.15-3.25 (2H, m), 3.35-3.48 (1H, m), 3.70-3.80 (1H, m), 3.85-3.95 (1H, m), 4.04 (1H, d, J=13.5 Hz), 4.67 (2H, s), 7.00-7.15 (3H, m), 7.52 (1H, dd, J=8.5, 1 Hz), 7.56 (1H, d, J=8.5 Hz), 7.83 (1H, d, J=1 Hz).

Example 150

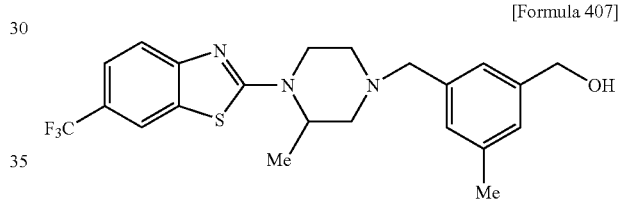
[Formula 407]

Yield: quant. %, 1H-NMR (DMSO-d6): δ1.30 (3H, d, J=7 Hz), 2.05-2.25 (2H, m), 2.27 (3H, s), 2.65-2.75 (1H, m), 2.80-2.95 (1H, m), 3.30-3.85 (3H, m), 4.15-4.30 (1H, m), 4.43 (2H, d, J=5.5 Hz), 4.48 (1H, t, J=5 Hz), 5.21 (1H, t, J=5.5 Hz), 7.00 (2H, s), 7.06 (1H, s), 7.54 (2H, s), 8.19 (1H, s).

Example 151

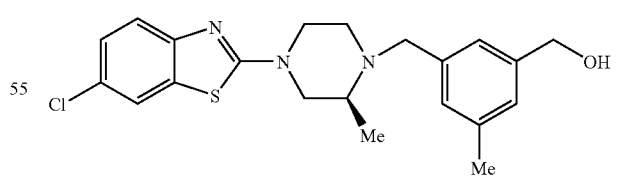
[Formula 408]

Yield: 45%, 1H-NMR (CDCl3): δ1.23 (3H, d, J=6.3 Hz), 2.26 (1H, ddd, J=3.3, 9.5, 12.3 Hz), 2.36 (3H, s), 2.60-2.66 (1H, m), 2.80 (1H, dt, J=3.3, 12.0 Hz), 3.17 (2H, d, J=13.2 Hz), 3.20-3.33 (1H, m), 3.71 (1H, dt, J=2.1, 12.0 Hz), 3.87 (1H, dd, J=2.1, 12.6 Hz), 4.03 (1H, d, J=13.2 Hz), 4.67 (2H, s), 7.09 (2H, s), 7.14 (1H, s), 7.23 (1H, dd, J=2.1, 8.4 Hz), 7.42 (1H, d, J=8.4 Hz), 7.54 (1H, d, J=2.1 Hz)

Example 152

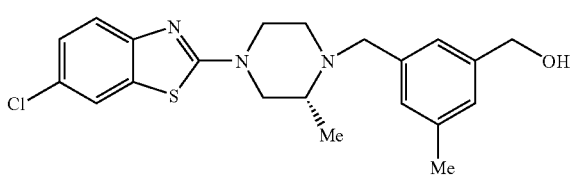

[Formula 409]

Yield: 54%, 1H-NMR (CDCl3): δ1.24 (3H, d, J=6.3 Hz), 2.23-2.31 (1H, m), 2.36 (3H, s), 2.60-2.66 (1H, m), 2.81 (1H, dt, J=3.3, 11.7 Hz), 3.18 (2H, d, J=12.9 Hz), 3.34-3.42 (1H, m), 3.71 (1H, d, J=12.9 Hz), 3.87 (1H, d, J=10.2 Hz), 4.04 (1H, d, J=13.5 Hz), 4.67 (2H, s), 7.09 (2H, s), 7.14 (1H, s), 7.23 (1H, dd, J=2.4, 8.4 Hz), 7.43 (1H, d, J=8.4 Hz), 7.55 (1H, d, J=2.4 Hz)

Example 153

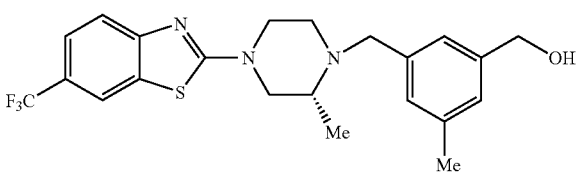

[Formula 410]

Yield: 84%, 1H-NMR (CDCl3): δ1.24 (3H, d, J=6.0 Hz), 1.63-1.73 (1H, m), 2.23-2.34 (1H, m), 2.37 (3H, s), 2.59-2.72 (1H, m), 2.78-2.88 (1H, m), 3.15-3.26 (1H, m), 3.19 (1H, d, J=13.0 Hz), 3.37-3.48 (1H, m), 3.72-3.83 (1H, m), 3.86-3.97 (1H, m), 4.04 (1H, d, J=13.0 Hz), 4.67 (2H, d, J=4.5 Hz), 7.07-7.17 (3H, m), 7.48-7.59 (2H, m), 7.84 (1H, s).

Example 154

Preparation of 6-chloro[4-(3-chloromethylbenzyl)piperazine-1-yl]benzothiazole monohydrochloride

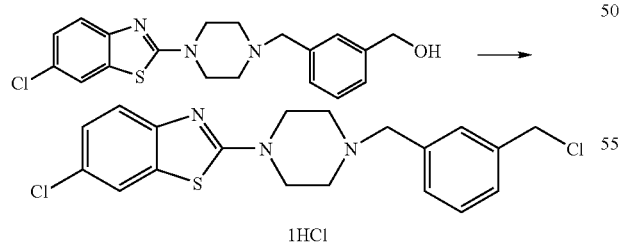

[Formula 411]

To 3-[4-[(6-chlorobenzothiazole-2-yl)piperazine-1-yl]methyl]benzyl alcohol (2.35 g; 6.29 mmol) was added thionyl chloride (12 ml) at room temperature. The mixture was stirred at 60° C. for 1 hour. The reaction solution was concentrated under reduced pressure. To the obtained residue were added ice water and 10% aqueous sodium hydroxide solution to become neutral. The precipitate was collected to give 6-chloro[4-(3-chloromethylbenzyl)piperazine-1-yl]benzothiazole monohydrochloride as colorless crystal (2.50 g; 93%).

$^1$H-NMR (DMSO-d$_6$): δ3.20-3.30 (2H, m), 3.35-3.45 (2H, m), 3.55-3.75 (2H, m), 4.10-4.25 (2H, m), 4.35-4.40 (2H, m), 4.80 (2H, s), 7.34 (1H, dd, J=8.5, 2 Hz), 7.45-7.60 (3H, m), 7.60-7.70 (2H, m), 8.00 (1H, d, J=2 Hz), 11.45 (1H, brs).

Compounds in Examples 155 to 178 were obtained by similar methods as Example 154.

Example 155

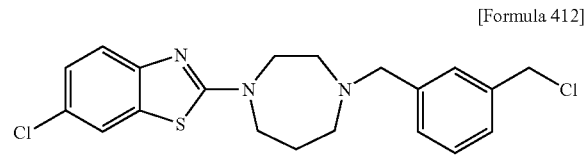

[Formula 412]

Yield: 77%, $^1$H-NMR (CDCl$_3$); δ1.99-2.06 (2H, m), 2.69 (2H, t, J=5.4 Hz), 2.80-2.83 (2H, m), 3.65 (2H, s), 3.72-3.79 (4H, m), 4.58 (2H, s), 7.21-7.31 (4H, m), 7.36 (1H, s), 7.42 (1H, d, J=8.4 Hz), 7.55 (1H, d, J=2.4 Hz).

Example 156

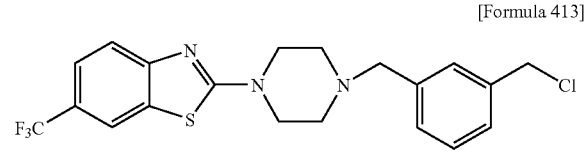

[Formula 413]

Yield: 77%, $^1$H-NMR (CDCl$_3$); δ2.60 (4H, t, J=5 Hz), 3.59 (2H, s), 3.70 (4H, t, J=5 Hz), 4.60 (2H, s), 7.25-7.40 (4H, m), 7.50-7.60 (2H, m), 7.85 (1H, s).

Example 157

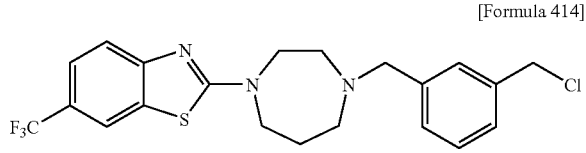

[Formula 414]

Yield: 95%, $^1$H-NMR (CDCl$_3$); δ1.95-2.12 (2H, m), 2.61-2.71 (2H, m), 2.77-2.88 (2H, m), 3.66 (2H, s), 3.68-3.90 (4H, m), 4.58 (2H, s), 7.22-7.40 (4H, m), 7.48-7.60 (2H, m), 7.85 (1H, s).

Example 158

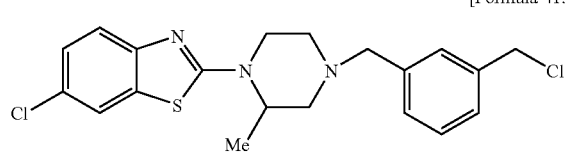

[Formula 415]

Yield: 95%, ¹H-NMR (CDCl₃); δ1.41 (3H, d, J=6.5 Hz), 2.25 (1H, td, J=11, 3 Hz), 2.34 (1H, dd, J=11, 3 Hz), 2.71 (1H, d, J=11 Hz), 2.92 (1H, d, J=11 Hz), 3.47 (1H, d, J=13.5 Hz), 3.49 (1H, td, J=12, 3 Hz), 3.62 (1H, d, J=13.5 Hz), 3.87 (1H, d, J=12 Hz), 4.15-4.25 (1H, m), 4.60 (2H, s), 7.22 (1H, dd, J=8.5, 2 Hz), 7.30-7.38 (3H, m), 7.38-7.42 (1H, m), 7.42 (1H, d, J=8.5 Hz), 7.54 (1H, d, J=2 Hz)

Example 159

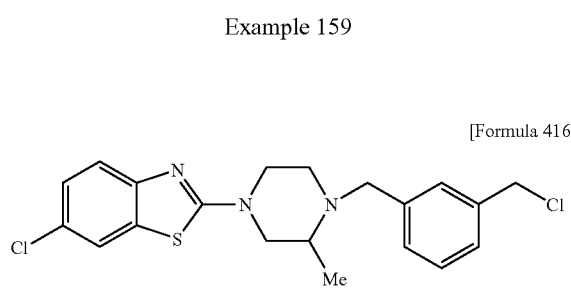

[Formula 416]

Yield: 63%, ¹H-NMR (CDCl₃); δ1.23 (3H, d, J=6 Hz), 2.24-2.34 (1H, m), 2.60-2.73 (1H, m), 2.75-2.85 (1H, m), 3.13-3.23 (1H, m), 3.22 (1H, d, J=13.5 Hz), 3.34-3.44 (1H, m), 3.66-3.76 (1H, m), 3.84-3.92 (1H, m), 4.06 (1H, d, J=13.5 Hz), 4.60 (2H, s), 7.23 (1H, dd, J=8.5, 2 Hz), 7.25-7.40 (4H, m), 7.43 (1H, d, J=8.5 Hz), 7.55 (1H, d, J=2 Hz).

Example 160

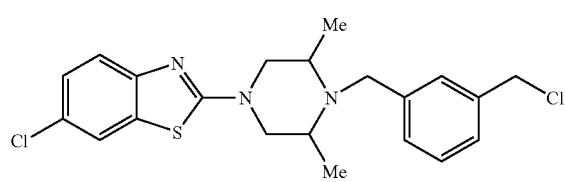

[Formula 417]

Yield: 71%, ¹H-NMR (CDCl₃); δ1.11 (6H, d, J=6 Hz), 2.70-2.85 (2H, m), 3.06 (2H, dd, J=13, 13 Hz), 3.84 (2H, s), 3.85-3.90 (2H, m), 4.60 (2H, s), 7.20-7.45 (6H, m), 7.55 (1H, d, J=2 Hz).

Example 161

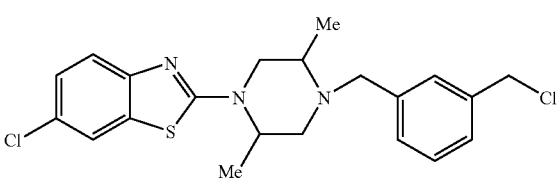

[Formula 418]

Yield: 90%, ¹H-NMR (CDCl₃); δ1.09 (3H, d, J=6.5 Hz), 1.39 (3H, d, J=6.5 Hz), 2.32 (1H, d, J=10.5 Hz), 2.89 (1H, dd, J=12, 4 Hz), 3.08-3.20 (1H, m), 3.52 (1H, d, J=13.5 Hz), 3.64 (1H, d, J=12 Hz), 3.70 (1H, d, J=13.5 Hz), 3.73 (1H, dd, J=12, 4 Hz), 4.15-4.30 (1H, m), 4.60 (2H, s), 7.23 (1H, dd, J=8.5, 2 Hz), 7.25-7.35 (3H, m), 7.41 (1H, d, J=8.5 Hz), 7.44 (1H, s), 7.53 (1H, d, J=2 Hz).

Example 162

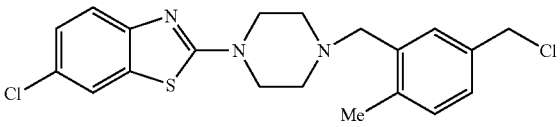

[Formula 419]

Yield: 85%, ¹H-NMR (CDCl₃); δ2.38 (3H, s), 2.58 (4H, t, J=5 Hz), 3.52 (2H, s), 3.63 (4H, t, J=5 Hz), 4.60 (2H, s), 7.15-7.30 (4H, m), 7.44 (1H, d, J=8 Hz), 7.56 (1H, d, J=2 Hz).

Example 163

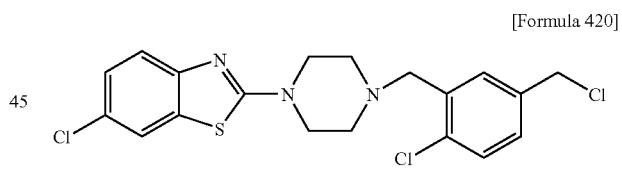

[Formula 420]

Yield: 68%, ¹H-NMR (CDCl₃); δ2.66 (4H, t, J=5 Hz), 3.66 (4H, t, J=5 Hz), 3.68 (2H, s), 4.58 (2H, s), 720-7.25 (2H, m), 7.37 (1H, d, J=8 Hz), 7.44 (1H, d, J=8.5 Hz), 7.55 (1H, d, J=2 Hz), 7.56 (1H, d, J=2 Hz).

Example 164

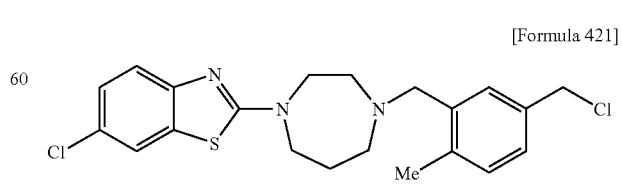

[Formula 421]

Yield: 99%, ¹H-NMR (CDCl₃); δ1.97-2.05 (2H, m), 2.33 (3H, s), 2.67 (2H, t, J=5.4 Hz), 2.79-2.82 (2H, m), 3.58 (2H, s), 3.72-3.77 (4H, m), 4.56 (2H, s), 7.12-7.25 (3H, m), 7.30 (1H, d, J=1.8 Hz), 7.42 (1H, d, J=8.4 Hz), 7.55 (1H, d, J=2.4 Hz).

Example 165

[Formula 422]

Yield: 81%, ¹H-NMR (CDCl₃); δ2.01-2.09 (2H, m), 2.75 (2H, t, J=5.1 Hz), 2.87-2.90 (2H, m), 3.74-3.83 (6H, m), 4.54 (2H, s), 7.20-7.25 (2H, m), 7.33 (1H, d, J=8.4 Hz), 7.43 (1H, d, J=9.0 Hz), 7.52 (1H, d, J=2.1 Hz), 7.55 (1H, d, J=2.1 Hz).

Example 166

[Formula 423]

Yield: 85%, ¹H-NMR (CDCl₃); δ2.36 (3H, s), 2.58 (4H, t, J=5 Hz), 3.53 (2H, s), 3.64 (4H, t, J=5 Hz), 4.56 (2H, s), 7.12 (1H, s), 7.13 (1H, s), 7.17 (1H, s), 7.23 (1H, dd, J=8.5, 2 Hz), 7.43 (1H, d, J=8.5 Hz), 7.55 (1H, d, J=2 Hz).

Example 167

[Formula 424]

Yield: 91%, ¹H-NMR (CDCl₃); δ1.98-2.06 (2H, m), 2.34 (3H, s), 2.69 (2H, t, J=5.4 Hz), 2.78-2.83 (2H, m), 3.61 (2H, s), 3.72-3.78 (4H, m), 4.55 (2H, s), 7.09-7.11 (2H, m), 7.14 (1H, s), 7.23 (1H, dd, J=8.4, 2.1 Hz), 7.43 (1H, d, J=8.7 Hz), 7.55 (1H, d, J=2.1 Hz).

Example 168

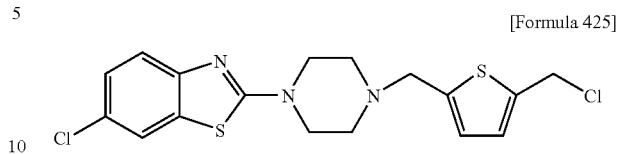

[Formula 425]

Yield: 45%, ¹H-NMR (DMSO-d₆): δ2.55 (4H, t, J=5 Hz), 3.57 (4H, t, J=5 Hz), 3.74 (2H, s), 4.99 (2H, s), 6.86 (1H, d, J=3.5 Hz), 7.04 (1H, d, J=3.5 Hz), 7.28 (1H, dd, J=8.5, 2 Hz), 7.42 (1H, d, J=8.5 Hz), 7.91 (1H, d, J=2 Hz).

Example 169

[Formula 426]

Yield: 45%, ¹H-NMR (CDCl₃); δ2.00-2.07 (2H, m), 2.71-2.74 (2H, m), 2.84-2.87 (2H, m), 3.73 (2H, t, J=6.0 Hz), 3.75-3.81 (2H, m), 3.81 (2H, s), 4.76 (2H, s), 6.73 (1H, d, J=3.3 Hz), 6.91 (1H, d, J=3.3 Hz), 7.23 (1H, dd, J=8.7, 2.4 Hz), 7.42 (1H, d, J=8.4 Hz), 7.55 (1H, d, J=2.1 Hz).

Example 170

[Formula 427]

Yield: 59%, ¹H-NMR (CDCl₃); δ2.37 (3H, s), 2.59 (4H, t, J=5 Hz), 3.54 (2H, s), 3.69 (4H, t, J=5 Hz), 4.57 (2H, s), 7.12 (1H, s), 7.13 (1H, s), 7.17 (1H, s), 7.50-7.60 (2H, m), 7.85 (1H, s).

Example 171

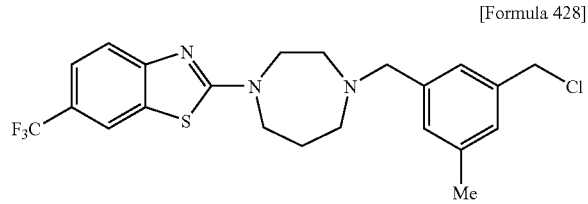
[Formula 428]

Yield: 71%, ¹H-NMR (CDCl₃); δ1.95-2.10 (2H, m), 2.34 (3H, s), 2.70 (2H, t, J=5.5 Hz), 2.82 (2H, t, J=5.5 Hz), 3.61 (2H, s), 3.70-3.90 (4H, m), 4.54 (2H, s), 7.05-7.14 (2H, m), 7.15 (1H, s), 7.48-7.60 (2H, m), 7.85 (1H, s).

Example 172

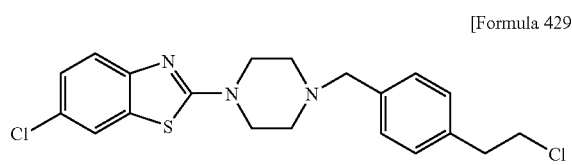
[Formula 429]

Yield: 77%, ¹H-NMR (CDCl₃); δ2.57 (4H, t, J=5 Hz), 3.07 (2H, t, J=7.5 Hz), 3.55 (2H, s), 3.63 (4H, t, J=5 Hz), 3.72 (2H, t, J=7.5 Hz), 7.19 (2H, d, J=8 Hz), 7.23 (1H, dd, J=8.5, 2 Hz), 7.29 (2H, d, J=8 Hz), 7.43 (1H, d, J=8.5 Hz), 7.55 (1H, d, J=2 Hz).

Example 173

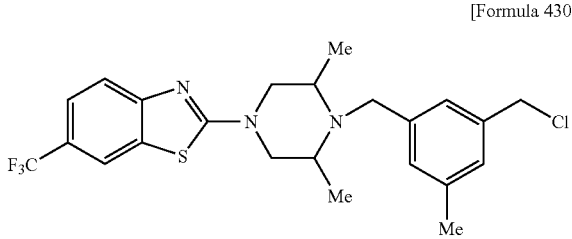
[Formula 430]

Yield: 91%, 1H-NMR (CDCl3): δ1.12 (6H, d, J=6 Hz), 2.35 (3H, s), 2.68-2.86 (2H, m), 3.05-3.15 (2H, m), 3.81 (2H, s), 3.85-3.98 (2H, m), 4.56 (2H, s), 7.07 (1H, s), 7.14 (1H, s), 7.21 (1H, s), 7.52 (1H, d, J=8.5 Hz), 7.57 (1H, d, J=8.5 Hz), 7.84 (1H, s).

Example 174

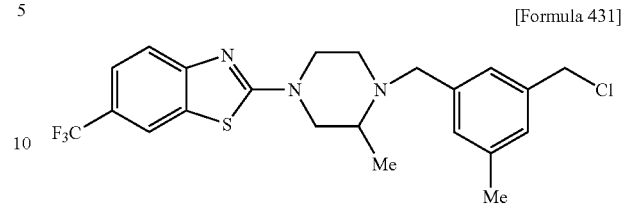
[Formula 431]

Yield: 74%, 1H-NMR (CDCl3): δ1.24 (3H, d, J=6 Hz), 2.23-2.35 (1H, m), 2.36 (3H, s), 2.60-2.70 (1H, m), 2.80 (1H, dt, J=13, 3.5 Hz), 3.17 (1H, d, J=13.5 Hz), 3.18-3.26 (1H, m), 3.38-3.50 (1H, m), 3.72-3.80 (1H, m), 3.87-3.95 (1H, m), 4.03 (1H, d, J=13.5 Hz), 4.56 (2H, s), 7.11 (2H, s), 7.17 (1H, s), 7.53 (1H, d, J=8.5 Hz), 7.56 (1H, d, J=8.5 Hz), 7.84 (1H, s).

Example 175

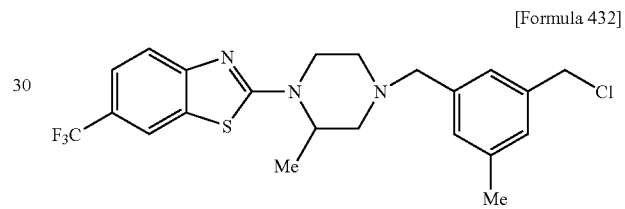
[Formula 432]

Yield: 81%, 1H-NMR (CDCl3): δ1.43 (3H, d, J=6.5 Hz), 2.26 (1H, td, J=11.5, 3.5 Hz), 2.30-2.36 (1H, m), 2.37 (3H, s), 2.73 (1H, d, J=11.5 Hz), 2.93 (1H, d, J=11.5 Hz), 3.43 (1H, d, J=13.5 Hz), 3.54 (1H, td, J=12.5, 3.5 Hz), 3.58 (1H, d, J=13.5 Hz), 3.85-3.98 (1H, m), 4.20-4.30 (1H, m), 4.57 (2H, s), 7.12 (2H, s), 7.21 (1H, s), 7.51 (1H, dd, J=8.5, 1.5 Hz), 7.56 (1H, d, J=8.5 Hz), 7.84 (1H, d, J=1.5 Hz).

Example 176

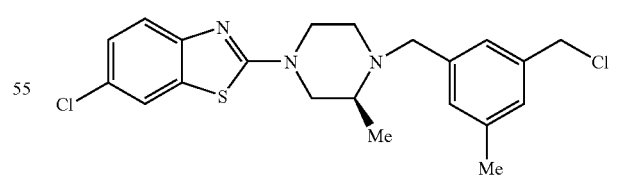
[Formula 433]

Yield: 83%, 1H-NMR (CDCl3): δ1.23 (3H, d, J=6.0 Hz), 2.23-2.31 (1H, m), 2.36 (3H, s), 2.61-2.83 (1H, m), 2.80 (1H, dt, J=3.6, 11.7 Hz), 3.13-3.20 (2H, m), 3.35-3.43 (1H, m), 3.72 (1H, dt, J=2.7 Hz), 3.87 (1H, dd, J=1.8, 12.3 Hz), 4.03 (1H, d, J=13.2 Hz), 4.56 (2H, s), 7.11 (2H, s), 7.16 (1H, s), 7.23 (1H, dd, J=2.1, 8.7 Hz), 7.43 (1H, d, J=8.7 Hz), 7.54 (1H, d, J=2.1 Hz)

Example 177

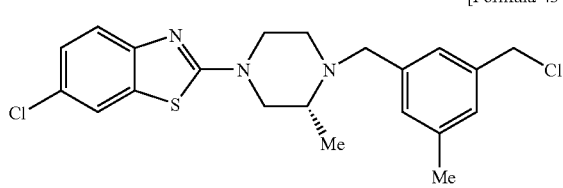

[Formula 434]

Yield: 77%, 1H-NMR (CDCl3): δ1.23 (3H, d, J=6.0 Hz), 2.27 (1H, ddd, J=3.3, 8.7, 9.9 Hz), 2.35 (3H, s), 2.61-2.67 (1H, m), 2.80 (1H, dt, J=3.6, 12.0 Hz), 3.13-3.20 (2H, m), 3.35-3.43 (1H, m), 3.72 (1H, d, J=12.6 Hz), 3.87 (1H, dd, J=1.8, 12.6 Hz), 4.03 (1H, d, J=13.2 Hz), 4.56 (2H, s), 7.11 (2H, s), 7.16 (1H, s), 7.23 (1H, dd, J=1.8, 8.7 Hz), 7.53 (1H, d, J=8.7 Hz), 7.54 (1H, d, J=1.8 Hz)

Example 178

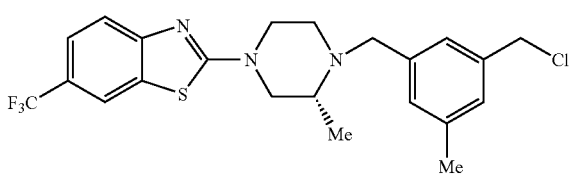

[Formula 435]

Yield: 60%, 1H-NMR (CDCl3): δ1.24 (3H, d, J=6.0 Hz), 2.23-2.34 (1H, m), 2.36 (3H, s), 2.60-2.72 (1H, m), 2.77-2.87 (1H, m), 3.14-3.27 (2H, m), 3.38-3.51 (1H, m), 3.72-3.82 (1H, m), 3.87-3.98 (1H, m), 4.04 (1H, d, J=13.0 Hz), 4.56 (2H, s), 7.12 (2H, s), 7.17 (1H, s), 7.48-7.59 (2H, m), 7.84 (1H, s).

Example 179

Preparation of {3-[[4-(6-chlorobenzothiazole-2-yl)piperazine-1-yl]methyl]phenyl}acetonitrile

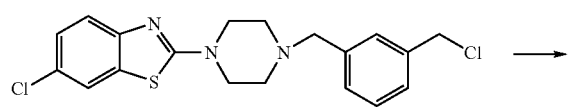

[Formula 436]

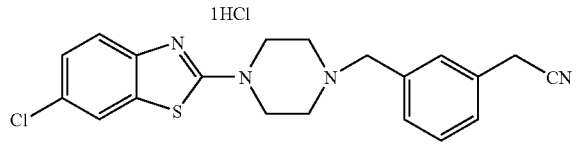

The mixture of 6-chloro[4-(3-chloromethylbenzyl)piperazine-1-yl]benzothiazole monohydrochloride (0.50 g; 1.27 mmol) and sodium cyanide (0.19 g; 3.82 mmol) in anhydrous N,N-dimethylformamide (5 ml) were stirred at 40° C. for 1.5 hours. After cooling, water and ethyl acetate were added to the reaction solution. The organic layer was separated and washed with brine, dried over anhydrous sodium sulphate, and evaporated under reduced pressure and the percipitate was washed with diisopropyl ether to give {3-[[4-(6-chlorobenzothiazole-2-yl)piperazine-1-yl]methyl]phenyl}acetonitrile as pale blackish brown crystal (0.35 g; 72%).

$^1$H-NMR (CDCl$_3$): δ2.58 (4H, t, J=5 Hz), 3.57 (2H, s), 3.67 (4H, t, J=5 Hz), 3.77 (2H, s), 7.24 (1H, dd, J=8.5, 2 Hz), 7.25-7.40 (4H, m), 7.43 (1H, d, J=8.5 Hz), 7.55 (1H, d, J=2 Hz).

Compounds in Examples 180 to 203 were obtained by similar methods as Example 179.

Example 180

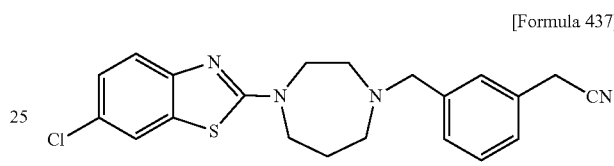

[Formula 437]

Yield: 95%, $^1$H-NMR (CDCl$_3$); δ1.98-2.06 (2H, m), 2.69 (2H, t, J=5.4 Hz), 2.79-2.83 (2H, m), 3.65 (2H, s) 3.72-3.80 (6H, m), 7.21-7.25 (2H, m), 7.29-7.33 (3H, m), 7.43 (1H, d, J=8.7 Hz), 7.55 (1H, d, J=2.4 Hz).

Example 181

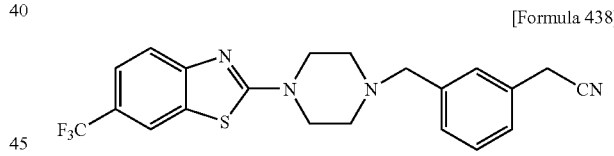

[Formula 438]

Yield: 99%, $^1$H-NMR (CDCl$_3$); δ2.59 (4H, t, J=5 Hz), 3.58 (2H, s), 3.69 (4H, t, J=5 Hz), 3.77 (2H, s), 7.20-7.40 (4H, m), 7.50-7.60 (2H, m), 7.85 (1H, d, J=0.5 Hz).

Example 182

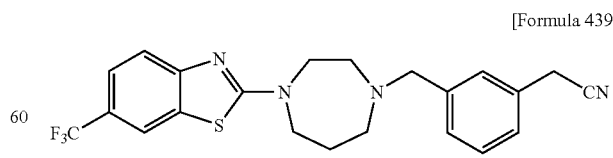

[Formula 439]

Yield: 74%, $^1$H-NMR (CDCl$_3$); δ1.98-2.10 (2H, m), 2.64-2.74 (2H, m), 2.77-2.88 (2H, m), 3.65 (2H, s), 3.68-3.90 (4H, m), 3.74 (2H, s), 7.18-7.38 (4H, m), 7.48-7.59 (2H, m), 7.84 (1H, s).

Example 183

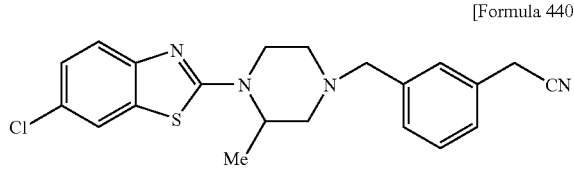

[Formula 440]

Yield: 68%, ¹H-NMR (CDCl₃); δ1.41 (3H, d, J=6.5 Hz), 2.26 (1H, td, J=11, 2.5 Hz), 2.35 (1H, dd, J=11, 4 Hz), 2.71 (1H, d, J=11 Hz), 2.89 (1H, d, J=11 Hz), 3.47 (1H, d, J=13 Hz), 3.50 (1H, td, J=13, 3 Hz), 3.61 (1H, d, J=13 Hz), 3.77 (2H, s), 3.87 (1H, d, J=13 Hz), 4.15-4.25 (1H, m), 7.23 (1H, dd, J=8.5, 2 Hz), 7.25-7.30 (1H, m), 7.30-7.40 (3H, m), 7.42 (1H, d, J=8.5 Hz), 7.55 (1H, d, J=2 Hz).

Example 184

[Formula 441]

Yield: 86%, ¹H-NMR (CDCl₃); δ1.23 (3H, d, J=6.5 Hz), 2.23-2.35 (1H, m), 2.58-2.72 (1H, m), 2.72-2.85 (1H, m), 3.10-3.20 (1H, m), 3.22 (1H, d, J=13.5 Hz), 3.33-3.45 (1H, m), 3.60-3.75 (1H, m), 3.76 (2H, s), 3.83-3.93 (1H, m), 4.06 (1H, d, J=13.5 Hz), 7.23 (1H, dd, J=8.5, 2 Hz), 7.25-7.35 (4H, m), 7.43 (1H, d, J=8.5 Hz), 7.55 (1H, d, J=2 Hz).

Example 185

[Formula 442]

Yield: 59%, ¹H-NMR (CDCl₃); δ1.10 (6H, d, J=6 Hz), 2.70-2.85 (2H, m), 3.05 (2H, dd, J=13, 13 Hz), 3.76 (2H, s), 3.83 (2H, s), 3.88 (2H, dd, J=13, 2 Hz), 7.18 (1H, d, J=7 Hz), 7.25 (1H, dd, J=8.5, 2 Hz), 7.30-7.40 (3H, m), 7.43 (1H, d, J=8.5 Hz), 7.55 (1H, d, J=2 Hz).

Example 186

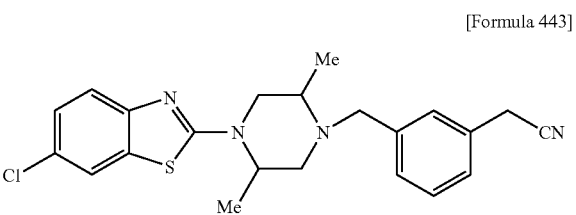

[Formula 443]

Yield: 97%, ¹H-NMR (CDCl₃); δ1.09 (3H, d, J=6.5 Hz), 1.39 (3H, d, J=6.5 Hz), 2.31 (1H, d, J=11.5 Hz), 2.90 (1H, dd, J=11.5, 4 Hz), 3.08-3.20 (1H, m), 3.53 (1H, t, J=14 Hz), 3.64 (1H, d, J=12.5 Hz), 3.70 (1H, d, J=14 Hz), 3.72 (1H, dd, J=12.5, 4 Hz), 3.76 (2H, s), 4.18-4.30 (1H, m), 7.21 (1H, dd, J=8.5, 2 Hz), 7.21-7.25 (1H, m), 7.30-7.40 (3H, m), 7.41 (1H, d, J=8.5 Hz), 7.53 (1H, d, J=2 Hz).

Example 187

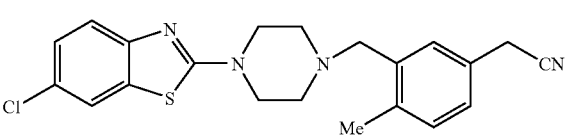

[Formula 444]

Yield: 35%, ¹H-NMR (CDCl₃); δ2.37 (3H, s), 2.58 (4H, t, J=5 Hz), 3.52 (2H, s), 3.63 (4H, t, J=5 Hz), 3.73 (2H, s), 7.10-7.30 (4H, m), 7.43 (1H, d, J=8.5 Hz), 7.55 (1H, d, J=2 Hz).

Example 188

[Formula 445]

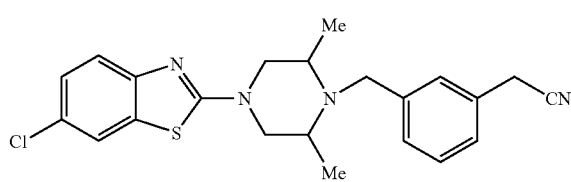

Yield: 69%, ¹H-NMR (CDCl₃); δ2.65 (4H, t, J=5 Hz), 3.66 (4H, t, J=5 Hz), 3.68 (2H, s), 3.76 (2H, s), 7.19 (1H, dd, J=8, 2 Hz), 7.24 (1H, dd, 8.5, 2 Hz), 7.38 (1H, d, J=8 Hz), 7.44 (1H, d, J=8.5 Hz), 7.51 (1H, d, J=2 Hz), 7.56 (1H, d, J=2 Hz).

Example 189

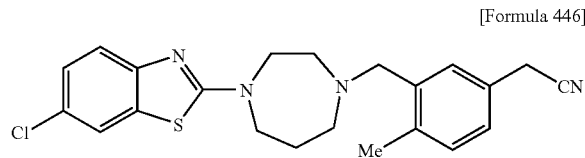

[Formula 446]

Yield: 78%, ¹H-NMR (CDCl₃); δ1.99-2.05 (2H, m), 2.32 (3H, s), 2.67 (2H, t, J=5.4 Hz), 2.79-2.83 (2H, m), 3.58 (2H, s), 3.70 (2H, s), 3.72-3.78 (4H, m), 7.13-7.14 (2H, m), 7.21-7.26 (2H, m), 7.42 (1H, d, J=8.4 Hz), 7.55 (1H, d, J=2.1 Hz).

Example 190

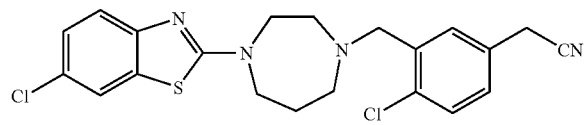

[Formula 447]

Yield: 99%, ¹H-NMR (CDCl₃); δ2.03-2.07 (2H, m), 2.75 (2H, t, J=5.4 Hz), 2.87-2.90 (2H, m), 3.70 (2H, s), 3.75 (2H, s), 3.75 (2H, t, J=6.0 Hz), 3.82 (2H, t, J=5.1 Hz), 7.16 (1H, dd, J=8.1, 2.1 Hz), 7.23 (1H, dd, J=8.4 Hz, 2.1 Hz), 7.35 (1H, d, J=8.4 Hz), 7.42 (1H, d, J=8.4 Hz), 7.49 (1H, d, J=2.4 Hz), 7.56 (1H, d, J=2.1 Hz).

Example 191

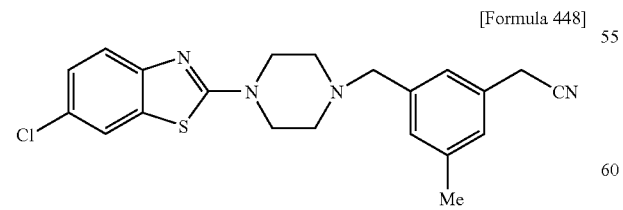

[Formula 448]

Yield: 78%, ¹H-NMR (CDCl₃); δ2.36 (3H, s), 2.57 (4H, t, J=5 Hz), 3.51 (2H, s), 3.64 (4H, t, J=5 Hz), 3.72 (2H, s), 7.06 (1H, s), 7.10 (1H, s), 7.11 (1H, s), 7.23 (1H, dd, J=8.5, 2 Hz), 7.42 (1H, d, J=8.5 Hz), 7.55 (1H, d, J=2 Hz).

Example 192

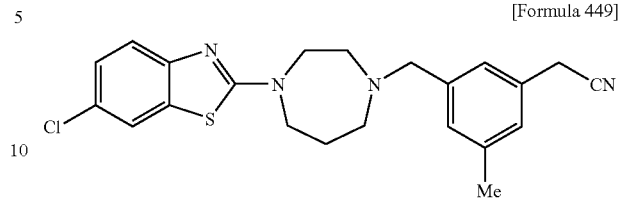

[Formula 449]

Yield: q. y, ¹H-NMR (CDCl₃); δ1.99-2.06 (2H, m), 2.35 (3H, s), 2.67 (2H, t, J=5.4 Hz), 2.78-2.82 (2H, m), 3.60 (2H, s), 3.70-3.78 (6H, m), 7.04 (1H, s), 7.09 (2H, s), 7.23 (1H, dd, J=8.7, 2.1 Hz), 7.43 (1H, d, J=8.7 Hz), 7.55 (1H, d, J=2.1 Hz).

Example 193

[Formula 450]

Yield: 68%, ¹H-NMR (CDCl₃); δ2.50-2.60 (4H, m), 3.50-3.60 (4H, m), 3.72 (2H, s), 4.24 (2H, s), 6.88 (1H, d, J=3 Hz), 6.91 (1H, d, J=3 Hz), 7.28 (1H, dd, J=8.5, 1.5 Hz), 7.42 (1H, d, J=8.5 Hz), 7.91 (1H, d, J=1.5 Hz).

Example 194

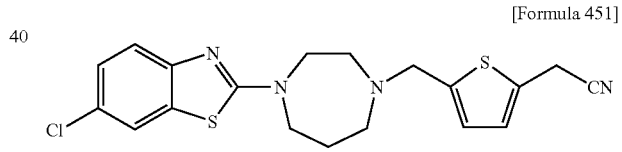

[Formula 451]

Yield: 32%, ¹H-NMR (CDCl₃); δ1.99-2.07 (2H, m), 2.70-2.74 (2H, m), 2.83-2.87 (2H, m), 3.73 (2H, t, J=6.0 Hz), 3.77-3.80 (2H, m), 3.80 (2H, s), 3.86 (2H, s), 6.76 (1H, d, J=3.3 Hz), 6.88 (1H, td, J=3.3, 0.9 Hz), 7.23 (1H, dd, J=8.7, 2.1 Hz), 7.42 (1H, d, J=8.4 Hz), 7.55 (1H, d, J=2.4 Hz).

Example 195

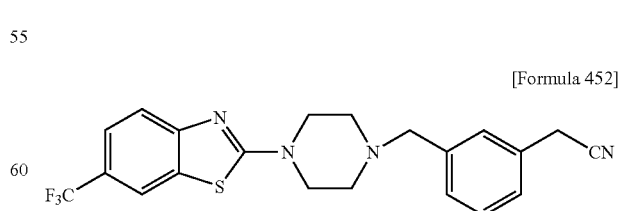

[Formula 452]

Yield: 93%, ¹H-NMR (CDCl₃); δ2.27 (3H, s), 2.58 (4H, t, J=5 Hz), 3.53 (2H, s), 3.69 (4H, t, J=5 Hz), 3.72 (2H, s), 7.07

(1H, s), 7.11 (1H, s), 7.12 (1H, s), 7.52 (1H, d, J=8.5 Hz), 7.57 (1H, d, J=8.5 Hz), 7.85 (1H, s).

Example 196

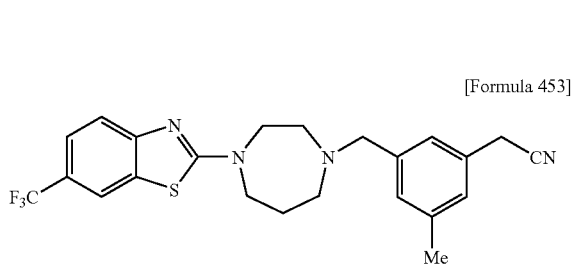

[Formula 453]

Yield: 86%, ¹H-NMR (CDCl₃); δ1.95-2.10 (2H, m), 2.34 (3H, s), 2.69 (2H, t, J=5.5 Hz), 2.82 (2H, t, J=5.5 Hz), 3.61 (2H, s), 3.69 (2H, s), 3.70-3.90 (4H, m), 7.04 (1H, s), 7.08 (1H, s), 7.09 (1H, s), 7.51 (1H, d, J=8.5 Hz), 7.56 (1H, d, J=8.5 Hz), 7.85 (1H, s).

Example 197

[Formula 454]

Yield: 85%, ¹H-NMR (DMSO-d₆): δ2.45-2.55 (4H, m), 2.81 (2H, t, J=5 Hz), 2.87 (2H, t, J=5 Hz), 3.52 (2H, s), 3.56 (4H, t, J=5.5 Hz), 7.20-7.35 (5H, m), 7.42 (1H, d, J=8.5 Hz), 7.91 (1H, d, J=2 Hz).

Example 198

[Formula 455]

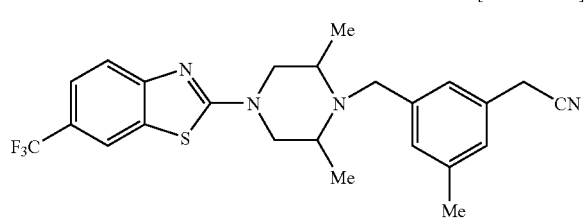

Yield: 84%, 1H-NMR (CDCl3): δ1.12 (6H, d, J=6 Hz), 2.36 (3H, s), 2.75-2.87 (2H, m), 3.10 (1H, d, J=13 Hz), 3.13 (1H, d, J=13 Hz), 3.71 (2H, s), 3.79 (2H, s), 3.92 (2H, dd, J=13, 2 Hz), 7.00 (1H, s), 7.14 (1H, s), 7.16 (1H, s), 7.52 (1H, dd, J=8.5, 1 Hz), 7.57 (1H, d, J=8.5 Hz), 7.84 (1H, d, J=1 Hz).

Example 199

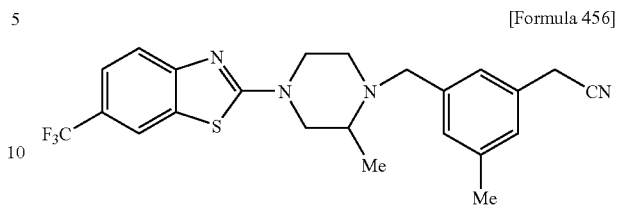

[Formula 456]

Yield: 86%, 1H-NMR (CDCl3): δ1.23 (3H, d, J=6 Hz), 2.20-2.35 (1H, m), 2.36 (3H, s), 2.61-2.73 (1H, m), 2.80 (1H, dt, J=12, 3.5 Hz), 3.15-3.28 (2H, m), 3.40-3.50 (1H, m), 3.71 (2H, s), 3.71-3.81 (1H, m), 3.87-3.97 (1H, m), 4.02 (1H, d, J=13.5 Hz), 7.05 (1H, s), 7.11 (2H, s), 7.50 (1H, d, J=8.5 Hz), 7.56 (1H, d, J=8.5 Hz), 7.84 (1H, s)

Example 200

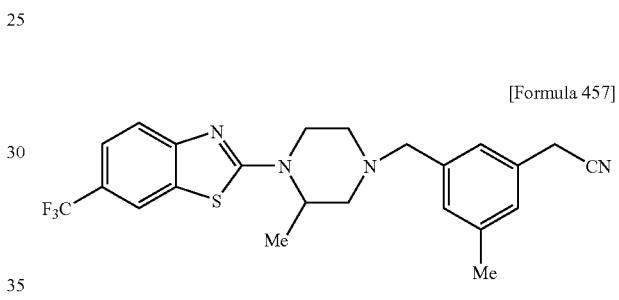

[Formula 457]

Yield: 79%, 1H-NMR (CDCl3): δ1.43 (3H, d, J=6.5 Hz), 2.26 (1H, td, J=11.5, 3.5 Hz), 2.30-2.33 (1H, m), 2.34 (3H, s), 2.72 (1H, d, J=11 Hz), 2.91 (1H, d, J=11.5 Hz), 3.45 (1H, d, J=13.5 Hz), 3.54 (1H, td, J=13, 3.5 Hz), 3.58 (1H, d, J=13.5 Hz), 3.72 (2H, s), 3.92 (1H, d, J=13 Hz), 4.20-4.30 (1H, m), 7.06 (1H, s), 7.13 (1H, s), 7.15 (1H, s), 7.51 (1H, d, J=8.5 Hz), 7.56 (1H, d, J=8.5 Hz), 7.84 (1H, s).

Example 201

[Formula 458]

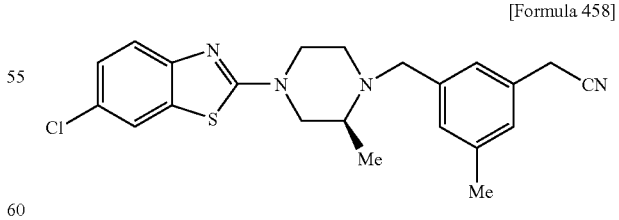

Yield: 90%, 1H-NMR (CDCl3): δ1.22 (3H, d, J=6.3 Hz), 2.23-2.32 (1H, m), 2.36 (3H, s), 2.59-2.69 (1H, m), 2.78 (1H, dt, J=3.6, 8.1 Hz), 3.17 (2H, dt, J=3.6, 13.5 Hz), 3.35-3.44 (1H, m), 3.70-3.75 (1H, m), 3.71 (2H, s), 3.85-3.90 (1H, m), 4.02 (1H, s), 7.05 (1H, s), 7.11 (2H, s), 7.23 (1H, dd, J=2.1, 8.7 Hz), 7.43 (1H, d, J=8.7 Hz), 7.55 (1H, d, J=2.1 Hz)

Example 202

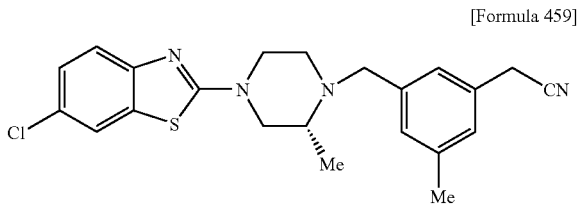

[Formula 459]

Yield: 98%, 1H-NMR (CDCl3): δ1.22 (3H, d, J=6.3 Hz), 2.23-2.32 (1H, m), 2.36 (3H, s), 2.62-2.66 (1H, m), 2.78 (1H, dt, J=3.9, 11.7 Hz), 3.17 (2H, dt, J=3.9, 13.5 Hz), 3.35-3.44 (1H, m), 3.71 (2H, s), 3.70-3.74 (1H, m), 3.87 (1H, dd, J=2.1, 12.6 Hz), 4.02 (1H, d, J=13.5 Hz), 7.05 (1H, s), 7.11 (2H, s), 7.23 (1H, dd, J=2.1, 8.4 Hz), 7.43 (1H, d, J=8.4 Hz), 7.55 (1H, d, J=2.1 Hz)

Example 203

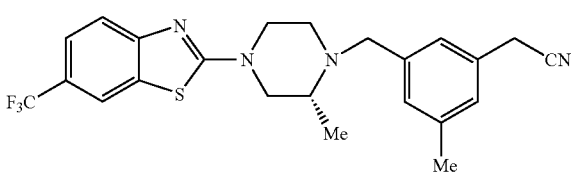

[Formula 460]

Yield: 85%, 1H-NMR (CDCl3): δ1.24 (3H, d, J=6.5 Hz), 2.23-2.34 (1H, m), 2.37 (3H, s), 2.60-2.73 (1H, m), 2.80 (1H, dt, J=12.0, 3.5 Hz), 3.13-3.27 (2H, m), 3.39-3.51 (1H, m), 3.70-3.83 (3H, m), 3.87-3.97 (1H, m), 4.03 (1H, d, J=13.5 Hz), 7.06 (1H, s), 7.11 (2H, s), 7.48-7.59 (2H, m), 7.84 (1H, s).

Example 204

Preparation of 2-{3-[4-(6-chlorobenzothiazole-2-yl)piperazine-1-ylmethyl]benzyl}diethyl malonate

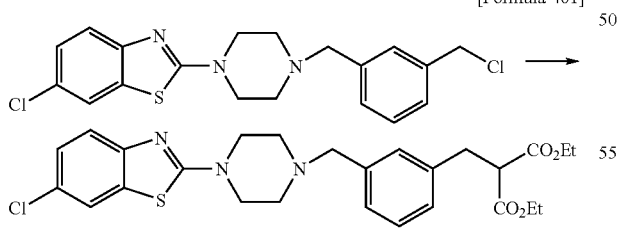

[Formula 461]

To a suspension of sodium hydride (0.15 g; 60%, 3.81 mmol) in anhydrous THF suspension was added dropwise diethyl malonate (0.58 ml; 3.81 mmol) under ice-cooling. The mixture was stirred at room temperature for 30 minutes. To the reaction solution was added 6-chloro[4-(3-chloromethylbenzyl)piperazine-1-yl]benzothiazole monohydrochloride (0.50 g; 1.27 mmol). The mixture was stirred at the same temperature for 14.5 hours and at 50° C. for 38 hours. Water and ethyl acetate were added to the reaction solution and extracted. The organic layer was washed with brine, dried over anhydrous sodium sulphate, and evaporated under reduced pressure. The residue was purified by column chromatograph on silica gel (hexane:ethyl acetate=3:1) to give 2-{3-[4-(6-chlorobenzothiazole-2-yl)piperazine-1-ylmethyl]benzyl}diethyl malonate as colorless oil (0.38 g; 58%).

$^1$H-NMR (DMSO-$d_6$): δ1.10 (6H, t, J=7 Hz), 2.49 (4H, t, J=5 Hz), 3.08 (2H, d, J=8 Hz), 3.50 (2H, s), 3.56 (4H, t, J=5 Hz), 3.81 (1H, t, J=8 Hz), 4.06 (4H, q, J=7 Hz), 7.10-7.20 (3H, m), 7.24 (1H, d, J=7.5 Hz), 7.28 (1H, dd, J=8.5, 2 Hz), 7.42 (1H, d, J=8.5 Hz), 7.91 (1H, d, J=2 Hz).

Compounds in Examples 205 and 206 were obtained by similar methods as Example 204.

Example 205

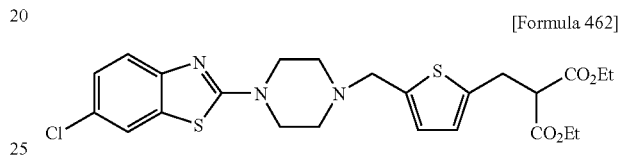

[Formula 462]

Yield: 46%, $^1$H-NMR (CDCl$_3$); δ1.26 (6H, t, J=7 Hz), 2.59 (4H, t, J=5 Hz), 3.38 (2H, d, J=7.5 Hz), 3.60-3.68 (5H, m), 3.69 (2H, s), 4.24 (4H, q, J=7 Hz), 6.68 (1H, d, J=3 Hz), 6.71 (1H, d, J=3 Hz), 7.25 (1H, dd, J=9, 2 Hz), 7.43 (1H, d, J=9 Hz), 7.55 (1H, d, J=2 Hz).

Example 206

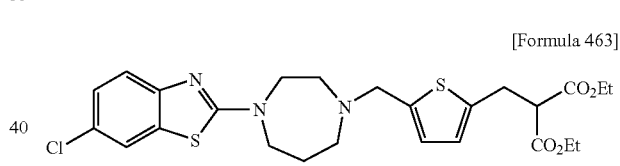

[Formula 463]

Yield: 5%, $^1$H-NMR (CDCl$_3$); δ1.21-1.32 (6H, m), 2.00-2.05 (2H, m), 2.70 (2H, t, J=5.4 Hz), 2.81-2.84 (2H, m), 3.36-3.38 (2H, m), 3.62-3.82 (7H, m), 4.14-4.24 (4H, m), 6.65-6.68 (2H, m), 7.22 (1H, dd, J=9.0, 1.8 Hz), 7.42 (1H, d, J=8.4 Hz), 7.54 (1H, d, J=1.8 Hz).

Reference Example 195

Preparation of 6-chloro-2-[4-(2-hydroxyethyl)piperidine-1-yl]benzothiazole

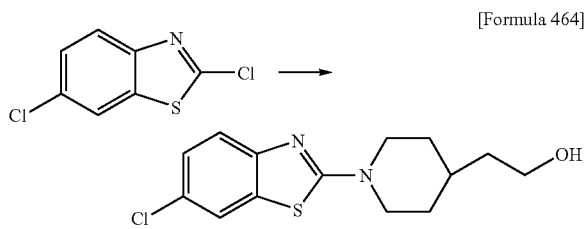

[Formula 464]

A mixture of 2,6-dichlorobenzothiazole (3.00 g; 14.7 mmol), 4-piperidine ethanol (2.09 g; 16.2 mmol), potassium carbonate (2.33 g; 16.2 mmol) and anhydrous N,N-dimethylformamide (15 ml) was stirred at room temperature for 16 hours. Water and ethyl acetate were added to the reaction solution. The organic layer was separated, washed with brine, dried over anhydrous sodium sulphate, and evaporated under reduced pressure. The precipitate was washed with diisopropyl ether to give 6-chloro-2-[4-(2-hydroxyethyl)piperidine-1-yl]benzothiazole as green crystal (2.92 g; 67%).

$^{1}$H-NMR (CDCl$_{3}$): δ1.26-1.44 (3H, m), 1.57 (2H, q, J=6.5 Hz), 1.68-1.91 (3H, m), 3.06-3.19 (2H, m), 3.74 (2H, q, J=6.5 Hz), 4.07-4.17 (2H, m), 7.22 (1H, dd, J=8.5, 2.0 Hz), 7.42 (1H, d, J=8.5 Hz), 7.54 (1H, d, J=2.0 Hz).

Compounds in Reference Examples 196 to 211 were obtained by similar methods as Reference Example 195.

Reference Example 196

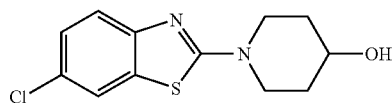

[Formula 465]

Yield: 64%, $^{1}$H-NMR (CDCl$_{3}$); δ1.60-1.75 (3H, m), 1.95-2.18 (2H, m), 3.34-3.48 (2H, m), 3.87-4.10 (3H, m), 7.23 (1H, dd, J=8.5, 2 Hz), 7.43 (1H, d, J=8.5 Hz), 7.53 (1H, d, J=2 Hz).

Reference Example 197

[Formula 466]

Yield: 100%, $^{1}$H-NMR (DMSO-d$_{6}$): δ1.15-1.25 (2H, m), 1.60-1.75 (1H, m), 1.75-1.85 (2H, m), 3.05-3.20 (2H, m), 3.25-3.30 (2H, m), 3.95-4.10 (2H, m), 4.56 (1H, brs), 7.27 (1H, dd, J=8.5, 2 Hz), 7.40 (1H, d, J=8.5 Hz), 7.88 (1H, d, J=2 Hz).

Reference Example 198

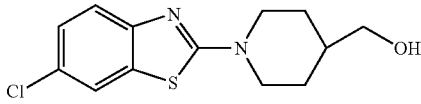

[Formula 467]

Yield: 95%, $^{1}$H-NMR (CDCl$_{3}$); δ1.65 (1H, s), 2.60-2.67 (6H, m), 3.63-3.69 (6H, m), 7.23 (1H, d, J=8.5, 2.0 Hz), 7.44 (1H, d, J=8.5 Hz), 7.57 (1H, d, J=2.0 Hz).

Reference Example 199

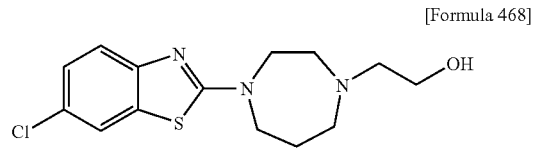

[Formula 468]

Yield: 99%, $^{1}$H-NMR (CDCl$_{3}$); δ2.00-2.07 (2H, m), 2.69 (2H, t, J=5.1 Hz), 2.76 (2H, t, J=5.4 Hz), 2.89-2.93 (2H, m), 2.96 (1H, s), 3.60 (2H, t, J=5.4 Hz), 3.73 (2H, t, J=6.0 Hz), 3.80-3.83 (2H, m), 7.24 (1H, dd, J=7.8, 2.1 Hz), 7.42 (1H, d, J=8.7 Hz), 7.55 (1H, d, J=2.1 Hz).

Reference Example 200

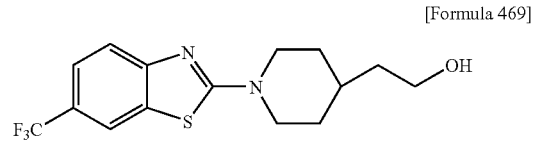

[Formula 469]

Yield: 48%, $^{1}$H-NMR (CDCl$_{3}$); δ1.28-1.46 (2H, m), 1.58 (2H, q, J=6.5 Hz), 1.72-1.94 (3H, m), 3.11-3.24 (2H, m), 3.76 (2H, t, J=6.5 Hz), 4.11-4.22 (2H, m), 7.48-7.57 (2H, m), 7.83 (1H, s).

Reference Example 201

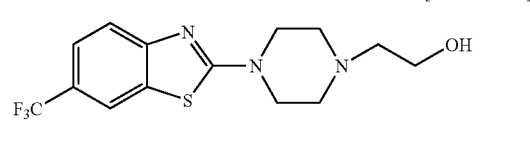

[Formula 470]

Yield: 70%, $^{1}$H-NMR (DMSO-d$_{6}$): δ2.49 (2H, t, J=6 Hz), 2.57 (4H, t, J=5 Hz), 3.55 (2H, t, J=6 Hz), 3.62 (4H, t, J=5 Hz), 4.51 (1H, brs), 7.57 (2H, s), 8.25 (1H, s).

Reference Example 202

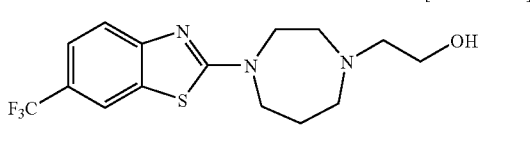

[Formula 471]

Yield: 85%, $^{1}$H-NMR (DMSO-d$_{6}$): δ1.83-1.90 (2H, m), 2.55 (2H, t, J=5.5 Hz), 2.67 (2H, t, J=5 Hz), 2.87 (2H, t, J=5 Hz), 3.47 (2H, q, J=5.5 Hz), 3.60-3.80 (4H, m), 4.39 (1H, t, J=5.5 Hz), 7.55 (1H, s), 7.95 (1H, s), 8.21 (1H, s).

Reference Example 203

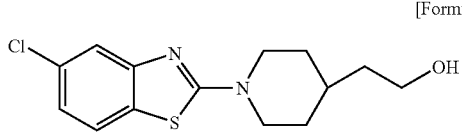
[Formula 472]

Yield: 63%, ¹H-NMR (CDCl$_3$); δ1.23-1.44 (3H, m), 1.53-1.63 (2H, m), 1.68-1.90 (3H, m), 3.08-3.20 (2H, m), 3.75 (2H, q, J=6.0 Hz), 4.08-4.18 (2H, m), 7.02 (1H, dd, J=8.5, 2.0 Hz), 7.46 (1H, d, J=8.5 Hz), 7.49 (1H, d, J=2.0 Hz).

Reference Example 204

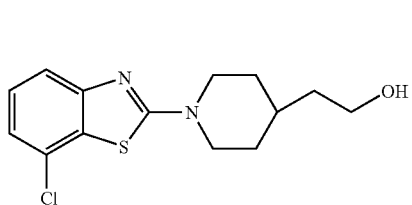
[Formula 473]

Yield: 36%, ¹H-NMR (CDCl$_3$); δ1.25-1.45 (3H, m), 1.57 (2H, q, J=6.5 Hz), 1.70-1.91 (3H, m), 3.08-3.23 (2H, m), 3.75 (2H, t, J=6.5 Hz), 4.08-4.21 (2H, m), 7.04 (1H, dd, J=8.0, 1.0 Hz), 7.21 (1H, t, J=8.0 Hz), 7.39 (1H, dd, J=8.0, 1.0 Hz).

Reference Example 205

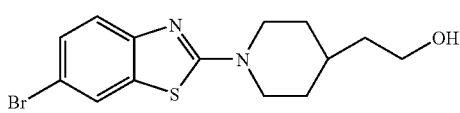
[Formula 474]

Yield: 52%, ¹H-NMR (CDCl$_3$); δ1.26 (1H, t, J=6.5 Hz), 1.27-1.44 (2H, m), 1.57 (2H, q, J=6.5 Hz), 1.68-1.91 (3H, m), 3.06-3.19 (2H, m), 3.75 (2H, q, J=6.5 Hz), 4.05-4.19 (2H, m), 7.35-7.40 (2H, m), 7.68 (1H, s).

Reference Example 206

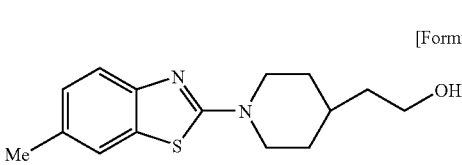
[Formula 475]

Yield: 31%, ¹H-NMR (CDCl$_3$); δ1.22 (1H, t, J=5.0 Hz), 1.27-1.45 (2H, m), 1.57 (2H, q, J=5.0 Hz), 1.65-1.90 (3H, m), 2.38 (3H, s), 3.03-3.19 (2H, m), 3.75 (2H, q, J=5.0 Hz), 4.06-4.17 (2H, m), 7.08 (1H, d, J=8.0 Hz), 7.39 (1H, s), 7.42 (1H, d, J=8.0 Hz).

Reference Example 207

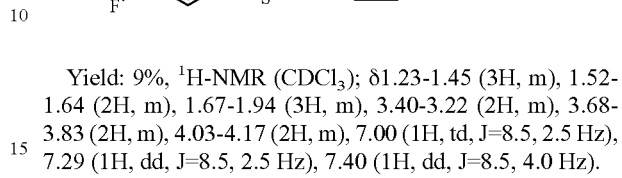
[Formula 476]

Yield: 9%, ¹H-NMR (CDCl$_3$); δ1.23-1.45 (3H, m), 1.52-1.64 (2H, m), 1.67-1.94 (3H, m), 3.40-3.22 (2H, m), 3.68-3.83 (2H, m), 4.03-4.17 (2H, m), 7.00 (1H, td, J=8.5, 2.5 Hz), 7.29 (1H, dd, J=8.5, 2.5 Hz), 7.40 (1H, dd, J=8.5, 4.0 Hz).

Reference Example 208

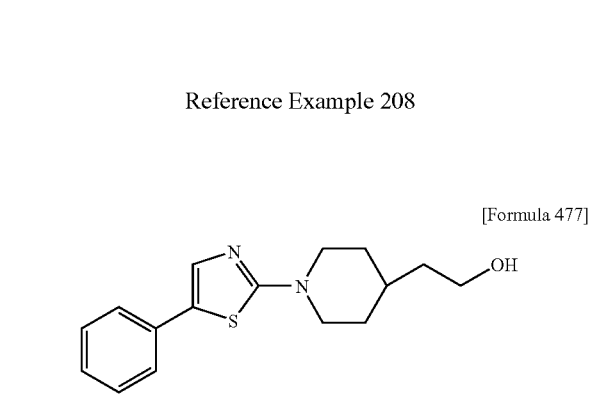
[Formula 477]

Yield: 48%, ¹H-NMR (DMSO-d$_6$): δ1.12-1.29 (2H, m), 1.40 (2H, q, J=6.5 Hz), 1.57-1.81 (3H, m), 2.95-3.10 (2H, m), 3.47 (2H, q, J=6.5 Hz), 3.84-3.97 (2H, m), 4.40 (1H, t, J=6.5 Hz), 7.20 (1H, t, J=7.5 Hz), 7.35 (2H, t, J=7.5 Hz), 7.44 (2H, d, J=7.5 Hz), 7.57 (1H, s).

Reference Example 209

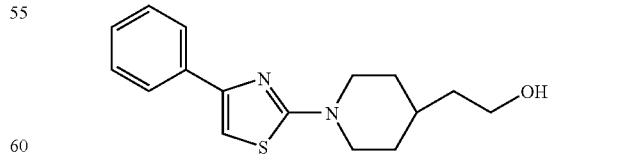
[Formula 478]

Yield: 88%, 1H-NMR (CDCl3): δ1.14-1.32 (2H, m), 1.40 (2H, q, J=6.5 Hz), 1.54-1.83 (3H, m), 2.95-3.08 (2H, m), 3.47 (2H, q, J=6.5 Hz), 3.88-4.00 (2H, m), 4.40 (1H, t, J=6.5 Hz), 7.22 (1H, s), 7.27 (1H, t, J=7.5 Hz), 7.38 (2H, t, J=7.5 Hz), 7.87 (2H, d, J=7.5 Hz).

Reference Example 210

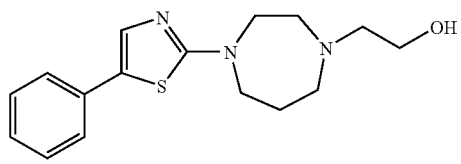

[Formula 479]

Yield: 71%, 1H-NMR (DMSO-d6): δ1.82-1.93 (2H, m), 2.55 (2H, t, J=6.0 Hz), 2.62-2.70 (2H, m), 2.78-2.86 (2H, m), 3.47 (2H, q, J=6.0 Hz), 3.59 (2H, t, J=6.0 Hz), 3.61-3.68 (2H, m), 4.38 (1H, t, J=6.0 Hz), 7.18 (1H, t, J=7.5 Hz), 7.34 (2H, t, J=7.5 Hz), 7.45 (2H, d, J=7.5 Hz), 7.57 (1H, s).

Reference Example 211

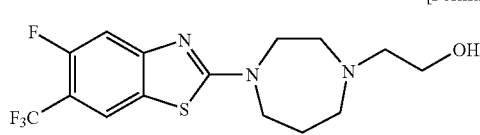

[Formula 480]

Yield: 93%, 1H-NMR (DMSO-d6): δ1.80-2.01 (2H, m), 2.57 (2H, t, J=6.0 Hz), 2.64-2.77 (2H, m), 2.82-2.96 (2H, m), 3.42-3.53 (2H, m), 3.45-3.94 (4H, br), 4.34-4.46 (1H, m), 7.45 (1H, d, J=7.0 Hz), 8.23 (1H, d, J=12.5 Hz).

Reference Example 212

Preparation of 6-chloro-2-[4-(2-chloroethyl)piperidine-1-yl]benzothiazole

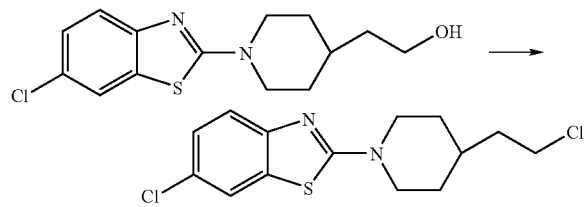

[Formula 481]

To 6-chloro-2-[4-(2-hydroxyethyl)piperidine-1-yl]benzothiazole (1.20 g; 4.03 mmol) was added thionyl chloride (10 ml). The mixture was stirred at 60° C. for 1 hour. The reaction solution was poured into ice water. 5N aqueous sodium hydroxide was added thereto to neutralize and the precipitate was collected. The precipitate was washed with diisopropyl ether to give 6-chloro-2-[4-(2-chloroethyl)piperidine-1-yl]benzothiazole as colorless crystal (0.98 g; 77%).

¹H-NMR (CDCl₃): δ 1.25-1.44 (2H, m), 1.70-1.94 (5H, m), 3.08-3.22 (2H, m), 3.62 (2H, t, J=6.5 Hz), 4.07-4.20 (2H, m), 7.23 (1H, dd, J=8.5, 2.0 Hz), 7.43 (1H, d, J=8.5 Hz), 7.55 (1H, d, J=2.0).

Compounds in Reference Examples 213 to 225 were obtained by similar methods as Reference Example 212.

Reference Example 213

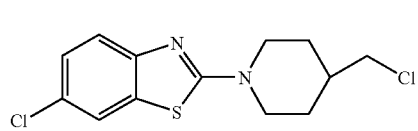

[Formula 482]

Yield: q. y, ¹H-NMR (DMSO-d₆): δ1.20-1.42 (2H, m), 1.80-2.00 (3H, m), 3.10-3.25 (2H, m), 3.60 (2H, d, J=6.5 Hz), 4.00-4.10 (2H, m), 7.28 (1H, dd, J=8.5, 2 Hz), 7.41 (1H, d, J=8.5 Hz), 7.90 (1H, d, J=2 Hz).

Reference Example 214

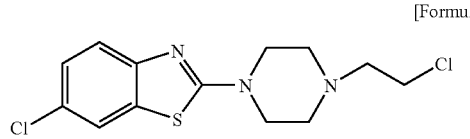

[Formula 483]

Yield: 95%, ¹H-NMR (CDCl₃); δ2.63-2.72 (4H, m), 2.80 (2H, t, J=7.0 Hz), 3.58-3.73 (6H, m), 7.23 (1H, dd, J=8.5, 2.0 Hz), 7.44 (1H, d, J=8.5 Hz), 7.56 (1H, d, J=2.0 Hz).

Reference Example 215

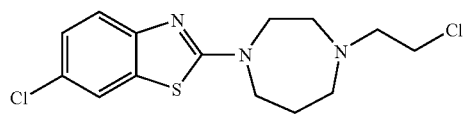

[Formula 484]

Yield: 58%, ¹H-NMR (CDCl₃); δ1.98-2.06 (2H, m), 2.78 (2H, t, J=5.4 Hz), 2.90-2.96 (4H, m), 3.56 (2H, t, J=7.2 Hz), 3.72 (2H, t, J=6.0 Hz), 3.78-3.81 (2H, m), 7.23 (1H, dd, J=8.4, 2.1 Hz), 7.42 (1H, d, J=8.4 Hz), 7.55 (1H, d, J=2.1 Hz).

Reference Example 216

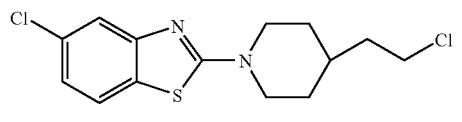

[Formula 485]

Yield: 68%, ¹H-NMR (CDCl₃); δ1.25-1.43 (2H, m), 1.70-1.94 (5H, m), 3.08-3.22 (2H, m), 3.62 (2H, t, J=6.5 Hz), 4.08-4.22 (2H, m), 7.03 (1H, dd, J=8.5, 2.0 Hz), 7.46 (1H, d, J=8.5 Hz), 7.52 (1H, d, J=2.0 Hz).

Reference Example 217

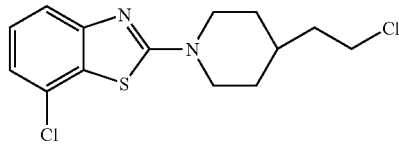

[Formula 486]

Yield: 90%, $^1$H-NMR (CDCl$_3$); δ1.26-1.44 (2H, m), 1.71-1.93 (5H, m), 3.08-3.23 (2H, m), 3.62 (2H, t, J=6.5 Hz), 4.10-4.22 (2H, m), 7.04 (1H, d, J=8.0 Hz), 7.22 (1H, t, J=8.0 Hz), 7.40 (1H, d, J=8.0 Hz).

Reference Example 218

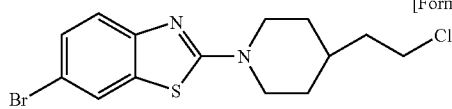

[Formula 487]

Yield: 95%, $^1$H-NMR (CDCl$_3$); δ1.25-1.43 (2H, m), 1.71-1.92 (5H, m), 3.07-3.23 (2H, m), 3.61 (2H, t, J=6.5 Hz), 4.06-4.21 (2H, m), 7.35-7.43 (2H, m), 7.69 (1H, s).

Reference Example 219

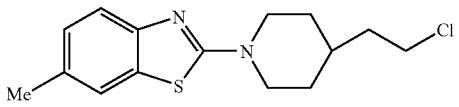

[Formula 488]

Yield: 65%, $^1$H-NMR (CDCl$_3$); δ1.22-1.41 (2H, m), 1.68-1.90 (5H, m), 2.38 (3H, s), 3.02-3.18 (2H, m), 3.59 (2H, t, J=6.5 Hz), 4.05-4.18 (2H, m), 7.06-7.12 (1H, m), 7.36-7.39 (1H, m), 7.43 (1H, d, J=8.0 Hz).

Reference Example 220

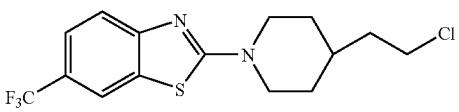

[Formula 489]

Yield: 91%, $^1$H-NMR (CDCl$_3$); δ1.27-1.45 (2H, m), 1.72-1.95 (5H, m), 3.12-3.27 (2H, m), 3.62 (2H, t, J=6.5 Hz), 4.12-4.26 (2H, m), 7.49-7.59 (2H, m), 7.84 (1H, s).

Reference Example 221

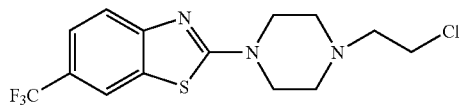

[Formula 490]

Yield: 42%, $^1$H-NMR (CDCl$_3$); δ2.68 (4H, t, J=5 Hz), 2.81 (2H, t, J=7 Hz), 3.63 (2H, t, J=7 Hz), 3.71 (4H, t, J=5 Hz), 7.53 (1H, d, J=8.5 Hz), 7.58 (1H, d, J=8.5 Hz), 7.86 (1H, s).

Reference Example 222

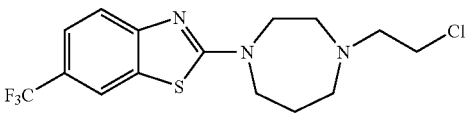

[Formula 491]

Yield: 23%, $^1$H-NMR (CDCl$_3$); δ1.94-2.07 (2H, m), 2.70-2.80 (2H, m), 2.83-2.99 (4H, m), 3.50-3.58 (2H, m), 3.64-3.88 (4H, m), 7.48-7.60 (2H, m), 7.84 (1H, s).

Reference Example 223

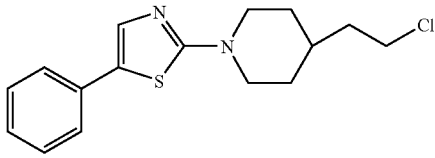

[Formula 492]

Yield: 89%, $^1$H-NMR (CDCl$_3$); δ1.27-1.44 (2H, m), 1.72-1.88 (5H, m), 2.99-3.13 (2H, m), 3.62 (2H, t, J=6.5 Hz), 3.99-4.10 (2H, m), 7.17-7.24 (1H, m), 7.30-7.37 (2H, m), 7.38-7.45 (3H, m).

Reference Example 224

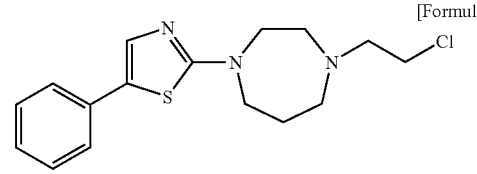

[Formula 493]

Yield: 35%, 1H-NMR (DMSO-d6): δ1.81-1.94 (2H, m), 2.66-2.76 (2H, m), 2.77-2.93 (4H, m), 3.55-3.72 (6H, m), 7.18 (1H, t, J=7.5 Hz), 7.34 (2H, t, J=7.5 Hz), 7.44 (2H, d, J=7.5 Hz), 7.57 (1H, s).

Reference Example 225

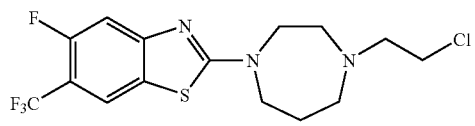

[Formula 494]

Yield: quant. %, 1H-NMR (CDCl3): δ1.95-2.10 (2H, m), 2.73-2.84 (2H, m), 2.85-3.01 (4H, m), 3.56 (2H, t, J=7.0 Hz), 3.66-3.89 (4H, m), 7.27 (1H, d, J=11.5 Hz), 7.75 (1H, d, J=7.0 Hz).

Reference Example 226

Preparation of 2-chloro-1-[4-(6-chlorobenzothiazole-2-yl)piperazine-1-yl]ethane-1-on

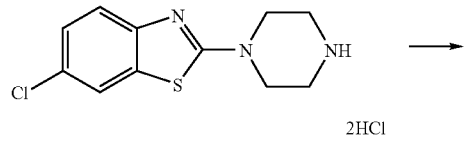

[Formula 495]

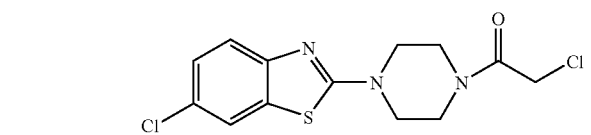

To a mixture of 4-(6-chlorobenzothiazole-2-yl)piperazine dihydrochloride (0.50 g; 1.53 mmol), triethylamine (0.32 ml; 2.25 mmol) and anhydrous THF (10 ml) was added dropwise chloroacetylchloride (0.18 ml; 2.25 mmol) under ice-cooling. The mixture was stirred at room temperature for 24 hours. Water and ethyl acetate were added to the reaction solution and extracted. The organic layer was washed with brine, dried over anhydrous sodium sulphate, and evaporated under reduced pressure. The precipitate was washed with hexane to give 2-chloro-1-[4-(6-chlorobenzothiazole-2-yl)piperazine-1-yl]ethane-1-on as blackish brown crystal (0.15 g; 30%).

$^1$H-NMR (CDCl$_3$): δ3.61-3.81 (8H, m), 4.12 (2H, s), 7.28 (1H, dd, J=8.5, 2.0 Hz), 7.47 (1H, d, J=8.5 Hz), 7.60 (1H, d, J=2.0 Hz).

Reference Example 227

Preparation of [(6-chlorobenzothiazole-2-yl)piperidine-4-yl]methane sulfonate

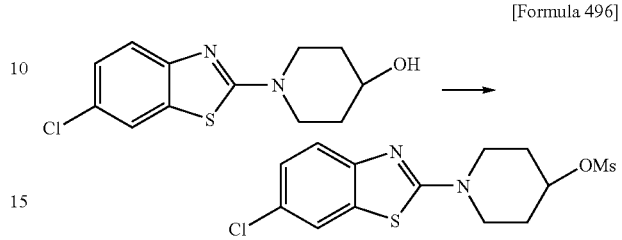

[Formula 496]

To a mixture of 1-(6-chlorobenzothiazole-2-yl)piperidine-4-ol (1.43 g; 5.32 mmol), triethylamine (0.78 ml; 5.59 mmol) and anhydrous THF (30 ml) was added dropwise methanesulfonyl chloride (0.43 ml; 5.59 mmol) under ice-cooling. The mixture was stirred at room temperature for 30 minutes. The reaction solution was condensed under reduced pressure. Water was added to the residue, and the precipitate was collected to give [(6-chlorobenzothiazole-1-yl)piperidine-4-yl]methanesulfonate as pale blackish brown crystal (1.66 g; 90%).

$^1$H-NMR (CDCl$_3$): δ1.97-2.20 (4H, m), 3.08 (3H, s), 3.57-3.68 (2H, m), 3.80-3.91 (2H, m), 4.97-5.08 (1H, m), 7.25 (1H, dd, J=8.5, 2.0 Hz), 7.44 (1H, d, J=8.5 Hz), 7.57 (1H, d, J=2.0 Hz).

Example 207

3-{2-[1-(6-chlorobenzothiazole-2-yl)piperidine-4-yl]ethoxy}ethyl benzoate

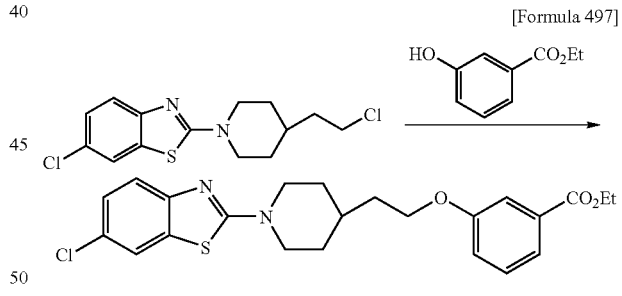

[Formula 497]

A mixture of 6-chloro-2-[4-(2-chloroethyl)piperidine-1-yl]benzothiazole (0.50 g; 1.59 mmol), cesium carbonate (0.78 g; 2.39 mmol), 3-hydroxy ethyl benzoate (0.40 g; 2.39 mmol) and anhydrous N,N-dimethylformamide (5 ml) was stirred at 60° C. for 9 hours. The reaction solution was returned to room temperature. Water and ethyl acetate was added thereto and extracted with ethyl acetate. The organic layer was washed with brine, dried over anhydrous sodium sulphate, and evaporated under reduced pressure. The residue was purified by column chromatograph on silica gel (methylene chloride) to give 3-{2-[1-(6-chlorobenzothiazole-2-yl)piperidine-4-yl]ethoxy}ethyl benzoate as colorless crystal (0.43 g; 62%).

$^1$H-NMR (CDCl$_3$): δ1.30-1.51 (5H, m), 1.74-1.97 (5H, m), 3.09-3.22 (2H, m), 4.04-4.18 (4H, m), 4.38 (2H, q, J=7.0 Hz), 7.09 (1H, dd, J=8.0, 1.5 Hz), 7.23 (1H, dd, J=8.5, 2.0 Hz), 7.35 (1H, t, J=8.0 Hz), 7.42 (1H, d, J=8.5 Hz), 7.52-7.58 (2H, m), 7.65 (1H, dd, J=8.0, 1.5 Hz).

Compounds in Examples 208 to 253 were obtained by similar methods as Example 207.

Example 208

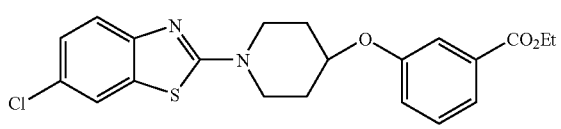

[Formula 498]

Yield: 39%, $^1$H-NMR (CDCl$_3$); δ1.40 (3H, t, J=7.0 Hz), 1.92-2.16 (4H, m), 3.60-3.72 (2H, m), 3.80-3.92 (2H, m), 4.38 (2H, q, J=7.0 Hz), 4.65-4.74 (1H, m), 7.13 (1H, m), 7.24 (1H, dd, J=8.5, 2.0 Hz), 7.37 (1H, t, J=8.0 Hz), 7.44 (1H, d, J=8.5 Hz), 7.56 (1H, d, J=2.0 Hz), 7.58-7.63 (1H, m), 7.67 (1H, m).

Example 209

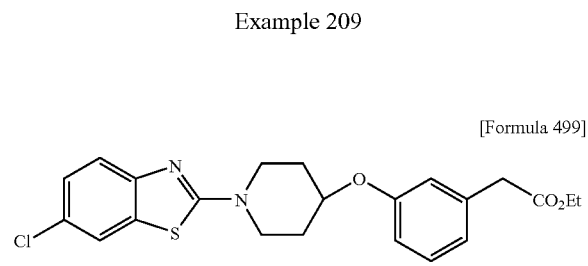

[Formula 499]

Yield: 16%, $^1$H-NMR (CDCl$_3$); δ1.26 (3H, t, J=7.0 Hz), 1.90-2.12 (4H, m), 3.56-3.70 (4H, m), 3.78-3.90 (2H, m), 4.16 (2H, q, J=7.0 Hz), 4.61 (1H, m), 6.80-6.93 (3H, m), 7.20-7.28 (2H, m), 7.43 (1H, d, J=8.5 Hz), 7.55 (1H, d, J=2.0 Hz).

Example 210

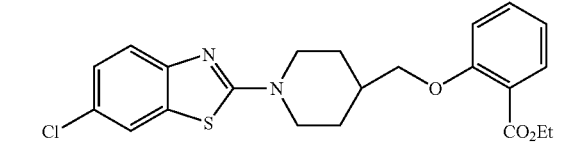

[Formula 500]

Yield: 39%, $^1$H-NMR (CDCl$_3$); δ1.34 (3H, t, J=7 Hz), 1.45-1.65 (2H, m), 1.95-2.10 (2H, m), 2.10-2.25 (1H, m), 3.10-3.30 (2H, m), 3.92 (2H, d, J=6 Hz), 4.15-4.25 (2H, m), 4.32 (2H, q, J=7 Hz), 6.93 (1H, d, J=7.5 Hz), 6.98 (1H, td, J=7.5, 1 Hz), 7.24 (1H, dd, J=8.5, 2 Hz), 7.43 (1H, d, J=8.5 Hz), 7.46 (1H, td, J=7.5, 1 Hz), 7.55 (1H, d, J=2 Hz), 7.80 (1H, dd, J=7.5, 1 Hz).

Example 211

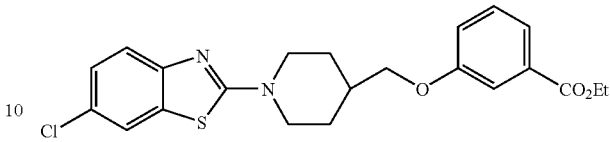

[Formula 501]

Yield: 39%, $^1$H-NMR (CDCl3); δ1.40 (3H, t, J=7 Hz), 1.45-1.60 (2H, m), 1.95-2.05 (2H, m), 2.05-2.20 (1H, m), 3.10-3.25 (2H, m), 3.90 (2H, d, J=6 Hz), 4.15-4.25 (2H, m), 4.37 (2H, q, J=7 Hz), 7.09 (1H, dd, J=8, 1.5 Hz), 7.23 (1H, dd, J=8.5, 2 Hz), 7.34 (1H, t, J=8 Hz), 7.43 (1H, d, J=8.5 Hz), 7.55 (1H, d, J=1.5 Hz), 7.56 (1H, d, J=2 Hz), 7.64 (1H, dd, J=8, 1.5 Hz)

Example 212

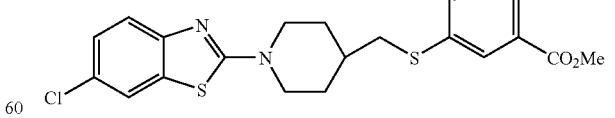

[Formula 502]

Yield: 52%, $^1$H-NMR (CDCl$_3$); δ1.38 (3H, t, J=7 Hz), 1.45-1.60 (2H, m), 1.90-2.05 (2H, m), 2.05-2.20 (1H, m), 3.10-3.25 (2H, m), 3.90 (2H, d, J=6 Hz), 4.10-4.25 (2H, m), 4.35 (2H, q, J=7 Hz), 6.89 (2H, d, J=9 Hz), 7.24 (1H, dd, J=8.5, 2 Hz), 7.43 (1H, d, J=8.5 Hz), 7.55 (1H, d, J=2 Hz), 7.99 (2H, d, J=9 Hz).

Example 213

[Formula 503]

Yield: 63%, $^1$H-NMR (DMSO-d$_6$): δ1.25-1.45 (2H, m), 1.70-1.85 (1H, m), 1.85-2.00 (2H, m), 3.03 (2H, d, J=7 Hz), 3.08-3.24 (2H, m), 3.86 (3H, s), 3.95-4.10 (2H, m), 7.27 (1H, dd, J=8.5, 2 Hz), 7.40 (1H, d, J=8.5 Hz), 7.48 (1H, t, J=8 Hz), 7.64 (1H, d, J=8 Hz), 7.75 (1H, d, J=8 Hz), 7.84 (1H, s), 7.88 (1H, d, J=2 Hz).

Example 214

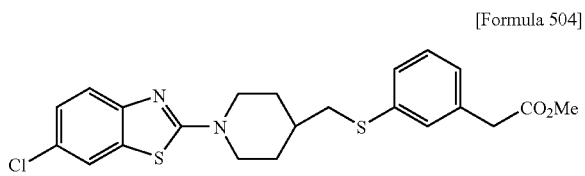

[Formula 504]

Yield: 79%, $^1$H-NMR (CDCl$_3$); δ1.30-1.50 (2H, m), 1.75-2.00 (1H, m), 1.95-2.05 (2H, m), 2.89 (2H, d, J=7 Hz), 3.05-3.18 (2H, m), 3.60 (2H, s), 3.70 (3H, s), 4.05-4.20 (2H, m), 7.20-7.30 (5H, m), 7.42 (1H, d, J=8.5 Hz), 7.54 (1H, d, J=2 Hz).

Example 215

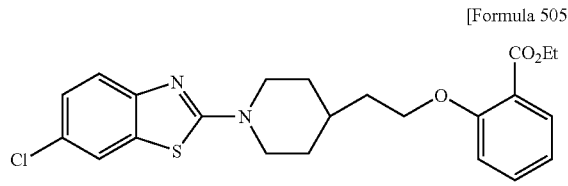

[Formula 505]

Yield: 86%, $^1$H-NMR (CDCl$_3$); δ1.25-1.50 (5H, m), 1.77-2.00 (5H, m), 3.06-3.23 (2H, m), 4.05-4.20 (4H, m), 4.35 (2H, q, J=7.0 Hz), 6.93-7.04 (2H, m), 7.22 (1H, dd, J=8.5, 2.0 Hz), 7.37-7.49 (2H, m), 7.54 (1H, d, J=2.0 Hz), 7.78 (1H, dd, J=8.0, 1.5 Hz).

Example 216

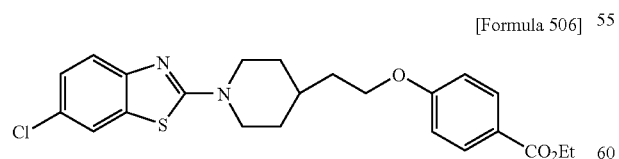

[Formula 506]

Yield: 65%, $^1$H-NMR (CDCl$_3$); δ1.34-1.53 (5H, m), 1.76-1.98 (5H, m), 3.09-3.24 (2H, m), 4.06-4.23 (4H, m), 4.35 (2H, q, J=7.0 Hz), 6.91 (2H, d, J=8.5 Hz), 7.23 (1H, dd, J=8.5, 2.0 Hz), 7.42 (1H, d, J=8.5 Hz), 7.55 (1H, d, J=2.0 Hz), 8.00 (2H, d, J=8.5 Hz).

Example 217

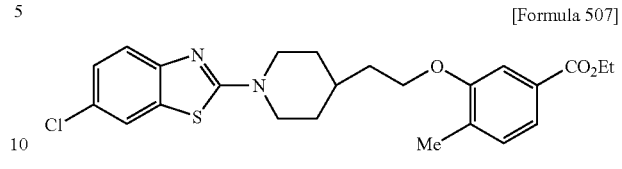

[Formula 507]

Yield: 72%, $^1$H-NMR (CDCl$_3$); δ1.40 (3H, t, J=7.0 Hz), 1.33-1.52 (2H, m), 1.79-1.98 (5H, m), 2.27 (3H, s), 3.08-3.21 (2H, m), 4.07-4.18 (4H, m), 4.37 (2H, q, J=7.0 Hz), 7.19 (1H, dd, J=7.5, 1.5 Hz), 7.23 (1H, dd, J=8.5, 2.0 Hz), 7.42 (1H, d, J=8.5 Hz), 7.47 (1H, d, J=1.5 Hz), 7.55 (1H, d, J=2.0 Hz), 7.57 (1H, dd, J=7.5, 1.5 Hz).

Example 218

[Formula 508]

Yield: 46%, $^1$H-NMR (CDCl$_3$); δ1.24 (3H, t, J=7.0 Hz), 1.23-1.44 (2H, m), 1.67-1.92 (5H, m), 3.02-3.16 (2H, m), 3.57 (2H, s), 3.98 (2H, t, J=6.0 Hz), 4.02-4.15 (2H, m), 4.14 (2H, q, J=7.0 Hz), 6.75-6.90 (3H, m), 7.16-7.26 (2H, m), 7.41 (1H, d, J=8.5 Hz), 7.51 (1H, d, J=2.0 Hz).

Example 219

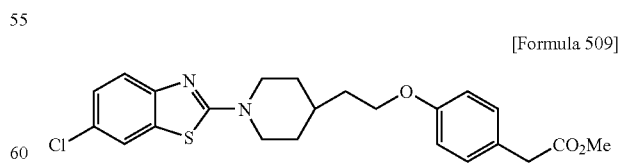

[Formula 509]

Yield: 17%, $^1$H-NMR (CDCl$_3$); δ1.23-1.44 (2H, m), 1.67-1.90 (5H, m), 3.02-3.16 (2H, m), 3.55 (2H, s), 3.67 (3H, s), 3.98 (2H, t, J=6.0 Hz), 4.02-4.14 (2H, m), 6.84 (2H, d, J=8.5 Hz), 7.18 (2H, d, J=8.5 Hz), 7.20 (1H, dd, J=8.5, 2.0 Hz), 7.40 (1H, d, J=8.5 Hz), 7.51 (1H, d, J=2.0).

Example 220

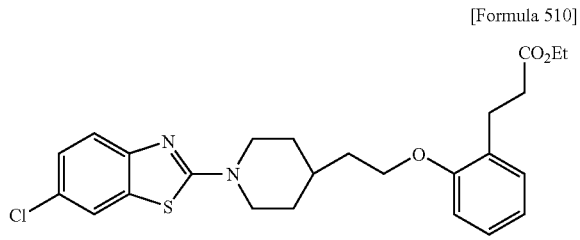

Yield: 58%, $^1$H-NMR (CDCl$_3$); δ1.23 (3H, t, J=7.0 Hz), 1.33-1.50 (2H, m), 1.74-1.96 (5H, m), 2.60 (2H, t, J=8.0 Hz), 2.95 (2H, t, J=8.0 Hz), 3.08-3.22 (2H, m), 4.02-4.19 (6H, m), 6.83 (1H, d, J=7.5 Hz), 6.88 (1H, td, J=7.5, 1.0 Hz), 7.14-7.20 (2H, m), 7.23 (1H, dd, J=8.5, 2.0 Hz), 7.42 (1H, d, J=8.5 Hz), 7.55 (1H, d, J=2.0 Hz).

Example 221

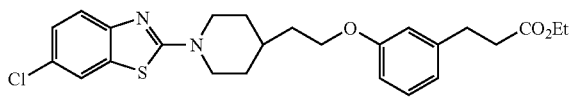

Yield: 71%, $^1$H-NMR (CDCl$_3$); δ1.24 (3H, t, J=7.0 Hz), 1.31-1.49 (2H, m), 1.73-1.95 (5H, m), 2.62 (2H, t, J=8.0 Hz), 2.93 (2H, t, J=8.0 Hz), 3.08-3.21 (2H, m), 4.02 (2H, t, J=6.0 Hz), 4.07-4.20 (2H, m), 4.13 (2H, q, J=7.0 Hz), 6.71-6.84 (3H, m), 7.16-7.25 (2H, m), 7.42 (1H, d, J=8.5 Hz), 7.54 (1H, d, J=2.0 Hz).

Example 222

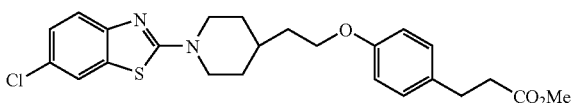

Yield: 58%, $^1$H-NMR (CDCl$_3$); δ1.30-1.47 (2H, m), 1.72-1.95 (5H, m), 2.60 (2H, t, J=8.0 Hz), 2.90 (2H, t, J=8.0 Hz), 3.08-3.20 (2H, m), 3.67 (3H, s), 4.01 (2H, t, J=6.0 Hz), 4.06-4.18 (2H, m), 6.82 (2H, d, J=8.5 Hz), 7.12 (2H, d, J=8.5 Hz), 7.23 (1H, dd, J=8.5, 2.0 Hz), 7.42 (1H, d, J=8.5 Hz), 7.54 (1H, d, J=2.0 Hz).

Example 223

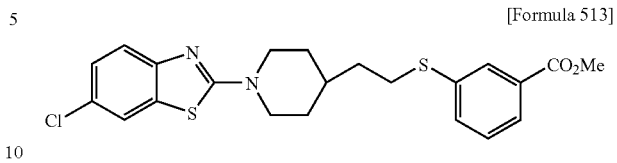

Yield: 58%, $^1$H-NMR (CDCl$_3$); δ1.24-1.43 (2H, m), 1.61-1.92 (5H, m), 2.97-3.20 (4H, m), 3.93 (3H, s), 4.06-4.18 (2H, m), 7.23 (1H, dd, J=8.5, 2.0 Hz), 7.36 (1H, t, J=7.5 Hz), 7.41 (1H, d, J=8.5 Hz), 7.49 (1H, dt, J=7.5, 1.5 Hz), 7.54 (1H, d, J=2.0 Hz), 7.84 (1H, dt, J=7.5, 1.5 Hz), 7.98 (1H, t, J=1.5 Hz).

Example 224

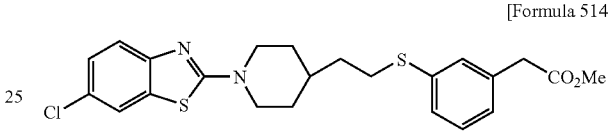

Yield: 45%, $^1$H-NMR (DMSO-d$_6$): δ1.12-1.30 (2H, m), 1.50-1.61 (2H, m), 1.65-1.86 (3H, m), 2.96-3.21 (4H, m), 3.61 (3H, s), 3.67 (2H, s), 3.94-4.07 (2H, m), 7.06 (1H, d, J=7.0 Hz), 7.18-7.32 (4H, m), 7.39 (1H, d, J=8.5 Hz), 7.88 (1H, d, J=2.0 Hz).

Example 225

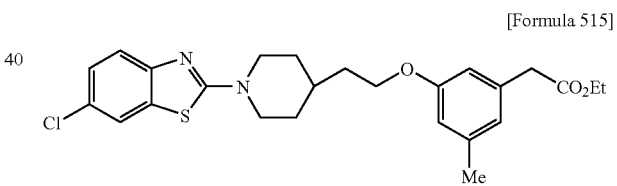

Yield: 50%, $^1$H-NMR (CDCl$_3$): δ1.26 (3H, t, J=7.2 Hz), 1.39-1.46 (2H, m), 1.73-1.80 (1H, m), 1.89 (3H, d, J=12.3 Hz), 2.31 (3H, s), 3.54 (3H, s), 4.01 (2H, t, J=6.0 Hz), 4.05-4.15 (2H, m), 4.15 (2H, q, J=7.2 Hz), 4.10-4.12 (2H, m), 6.58-6.67 (2H, m), 6.69 (1H, m), 7.22 (1H, dd, J=8.7, 2.1 Hz), 7.42 (1H, d, J=8.7 Hz), 7.54 (1H, d, J=2.1 Hz).

Example 226

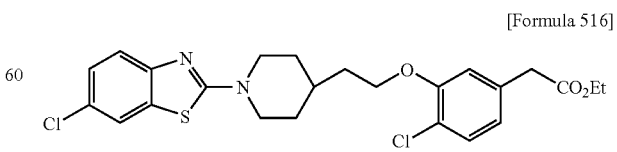

Yield: 53%, $^1$H-NMR (CDCl$_3$); δ1.26 (3H, t, J=7.0 Hz), 1.31-1.51 (2H, m), 1.76-1.98 (5H, m), 3.07-3.23 (2H, m), 3.57 (2H, s), 4.04-4.20 (6H, m), 6.81 (1H, dd, J=7.5, 1.5 Hz), 6.87 (1H, d, J=1.5 Hz), 7.19-7.34 (2H, m), 7.42 (1H, d, J=8.5 Hz), 7.53 (1H, d, J=2.0 Hz).

Example 227

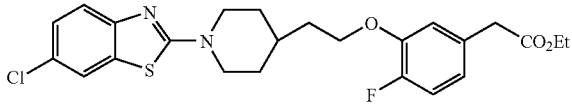

[Formula 517]

Yield: 93%, $^1$H-NMR (CDCl$_3$); δ1.26 (3H, t, J=7 Hz), 1.30-1.50 (1H, m), 1.75-2.00 (4H, m), 3.05-3.23 (2H, m), 3.55 (2H, s), 4.05-4.15 (6H, m), 4.18 (2H, q, J=7 Hz), 6.75-6.85 (1H, m), 6.91 (1H, dd, J=8, 2 Hz), 6.92 (1H, dd, J=11, 2 Hz), 7.22 (1H, dd, J=8.5, 2 Hz), 7.42 (1H, d, J=8.5 Hz), 7.54 (1H, d, J=2 Hz).

Example 228

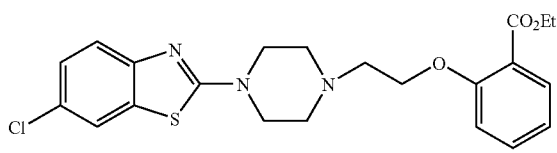

[Formula 518]

Yield: 67%, $^1$H-NMR (CDCl$_3$); δ1.39 (3H, t, J=7.0 Hz), 2.77 (4H, t, J=5.0 Hz), 2.93 (2H, t, J=5.5 Hz), 3.65 (4H, t, J=5.0 Hz), 4.21 (2H, t, J=5.5 Hz), 4.35 (2H, q, J=7.0 Hz), 6.98 (1H, d, J=7.5 Hz), 7.00 (1H, t, J=7.5 Hz), 7.24 (1H, dd, J=8.5, 2.0 Hz), 7.44 (1H, d, J=8.5 Hz), 7.46 (1H, t, J=7.5 Hz), 7.56 (1H, d, J=2.0 Hz), 7.79 (1H, dd, J=7.5, 2.0 Hz).

Example 229

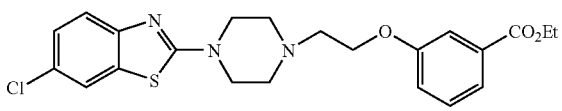

[Formula 519]

Yield: 76%, $^1$H-NMR (CDCl$_3$); δ1.40 (3H, t, J=7.0 Hz), 2.73 (4H, t, J=5.0 Hz), 2.90 (2H, t, J=5.5 Hz), 3.67 (4H, t, J=5.0 Hz), 4.19 (2H, t, J=5.5 Hz), 4.38 (2H, q, J=7.0 Hz), 7.11 (1H, dd, J=8.0, 2.5 Hz), 7.24 (1H, dd, J=8.5, 2.0 Hz), 7.35 (1H, t, J=8.0 Hz), 7.44 (1H, d, J=8.5 Hz), 7.56 (1H, d, J=2.0 Hz), 7.58 (1H, s), 7.66 (1H, dd, J=8.0, 2.5 Hz).

Example 230

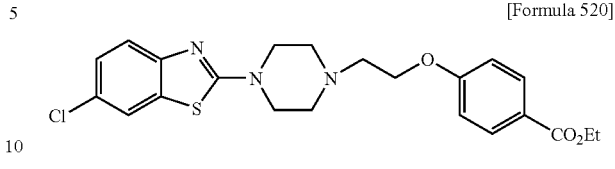

[Formula 520]

Yield: 82%, $^1$H-NMR (CDCl$_3$); δ1.38 (3H, t, J=7.0 Hz), 2.73 (4H, t, J=5.0 Hz), 2.90 (2H, t, J=5.5 Hz), 3.66 (4H, t, J=5.0 Hz), 4.19 (2H, t, J=5.5 Hz), 4.35 (2H, q, J=7.0 Hz), 6.93 (2H, d, J=9.0 Hz), 7.24 (1H, dd, J=8.5, 2.0 Hz), 7.43 (1H, d, J=8.5 Hz), 7.56 (1H, d, J=2.0 Hz), 8.00 (2H, d, J=9.0 Hz).

Example 231

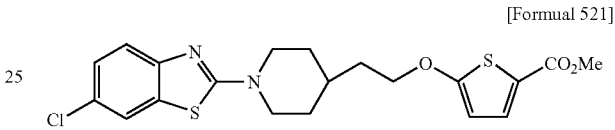

[Formual 521]

Yield: 18%, $^1$H-NMR (CDCl$_3$); δ1.27-1.48 (2H, m), 1.64-1.95 (5H, m), 3.05-3.19 (2H, m), 3.84 (3H, s), 4.06-4.19 (4H, m), 6.22 (1H, d, J=4.0 Hz), 7.22 (1H, dd, J=8.5, 2.0 Hz), 7.42 (1H, d, J=8.5 Hz), 7.51-7.27 (2H, m).

Example 232

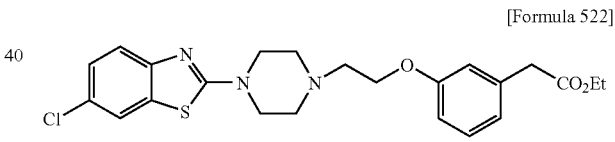

[Formula 522]

Yield: 46%, $^1$H-NMR (CDCl$_3$); δ1.26 (3H, t, J=7.0 Hz), 2.72 (4H, t, J=5.0 Hz), 2.87 (2H, t, J=5.5 Hz), 3.58 (2H, s), 3.66 (4H, t, J=5.0 Hz), 4.14 (2H, t, J=5.5 Hz), 4.15 (2H, q, J=7.0 Hz), 6.79-6.91 (3H, m), 7.23 (1H, d, J=8.0 Hz), 7.24 (1H, dd, J=8.5, 2.0 Hz), 7.44 (1H, d, J=8.5 Hz), 7.56 (1H, d, J=2.0 Hz).

Example 233

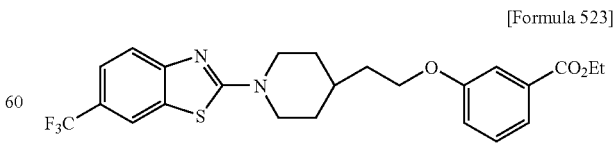

[Formula 523]

Yield: 81%, $^1$H-NMR (CDCl$_3$); δ1.32-1.51 (5H, m), 1.74-1.99 (5H, m), 3.11-3.27 (2H, m), 4.04-4.24 (4H, m), 4.38 (2H, q, J=7.0 Hz), 7.06-7.13 (1H, m), 7.35 (1H, t, J=8.0 Hz), 7.48-7.57 (3H, m), 7.65 (1H, d, J=8.0 Hz), 7.84 (1H, s).

Example 234

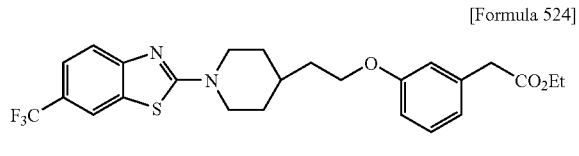

[Formula 524]

Yield: 58%, $^1$H-NMR (CDCl$_3$); δ1.26 (3H, t, J=7.0 Hz), 1.31-1.50 (2H, m), 1.72-1.98 (5H, m), 3.12-3.25 (2H, m), 3.59 (2H, s), 4.04 (2H, t, J=6.0 Hz), 4.10-4.24 (4H, m), 6.77-6.91 (3H, m), 7.23 (1H, t, J=7.5 Hz), 7.48-7.59 (2H, m), 7.84 (1H, s).

Example 235

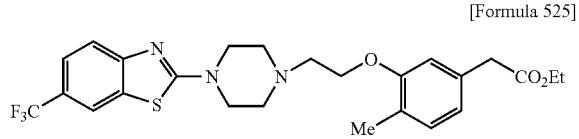

[Formula 525]

Yield: 51%, $^1$H-NMR (DMSO-d$_6$): δ1.26 (3H, t, J=7 Hz), 2.20 (3H, s), 2.77 (4H, t, J=5 Hz), 2.92 (2H, t, J=5.5 Hz), 3.56 (2H, s), 3.70 (4H, t, J=5 Hz), 4.13 (2H, t, J=5.5 Hz), 4.16 (2H, q, J=7 Hz), 6.75-6.80 (2H, m), 7.08 (1H, d, J=7 Hz), 7.52 (1H, dd, J=8.5, 1.5 Hz), 7.55 (1H, d, J=8.5 Hz), 7.85 (1H, d, J=0.5 Hz).

Example 236

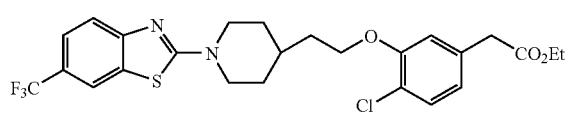

[Formula 526]

Yield: 49%, $^1$H-NMR (CDCl$_3$); δ1.26 (3H, t, J=7.0 Hz), 1.32-1.51 (2H, m), 1.78-2.00 (5H, m), 3.12-3.27 (2H, m), 3.57 (2H, s), 4.05-4.24 (6H, m), 6.81 (1H, dd, J=8.0, 2.0 Hz), 6.87 (1H, d, J=2.0 Hz), 7.30 (1H, d, J=8.0 Hz), 7.47-7.59 (2H, m), 7.83 (1H, s).

Example 237

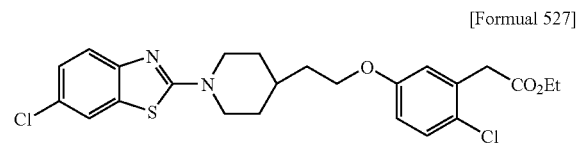

[Formual 527]

Yield: 39%, $^1$H-NMR (CDCl$_3$); δ1.27 (3H, t, J=7.0 Hz), 1.30-1.48 (2H, m), 1.72-1.94 (5H, m), 3.08-3.21 (2H, m), 3.72 (2H, s), 3.97-4.04 (2H, m), 4.07-4.19 (2H, m), 4.19 (2H, q, J=7.0 Hz), 6.76 (1H, dd, J=8.5, 3.0 Hz), 6.84 (1H, d, J=3.0 Hz), 7.23 (1H, dd, J=8.5, 2.0 Hz), 7.27 (1H, d, J=8.5 Hz), 7.42 (1H, d, J=8.5 Hz), 7.54 (1H, d, J=2.0 Hz).

Example 238

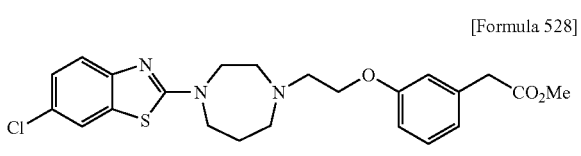

[Formula 528]

Yield: 69%, $^1$H-NMR (CDCl$_3$); δ2.00-2.08 (2H, m), 2.84 (2H, t, J=8.4 Hz), 2.96-3.02 (4H, m), 3.59 (2H, s), 3.69 (3H, s), 3.73 (2H, t, J=6.0 Hz), 3.79-3.84 (2H, m), 4.07 (2H, t, J=5.4 Hz), 6.79-6.88 (3H, m), 7.20-7.27 (2H, m), 7.43 (1H, d, J=8.4 Hz), 7.55 (1H, d, J=2.1 Hz).

Example 239

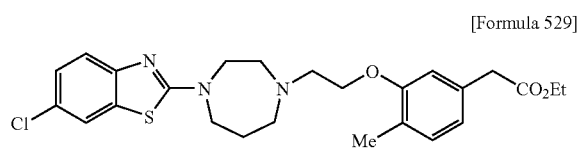

[Formula 529]

Yield: 49%, $^1$H-NMR (CDCl$_3$); δ1.25 (3H, t, J=0.7 Hz), 1.98-2.08 (2H, m), 2.18 (3H, s), 2.82-2.90 (2H, m), 2.98-3.05 (4H, m), 3.55 (2H, s), 3.73 (2H, t, J=5.5 Hz), 3.75-3.85 (2H, m), 4.05-4.10 (2H, m), 4.15 (2H, q, J=7 Hz), 6.74 (1H, s), 6.76 (1H, d, J=7.5 Hz), 7.07 (1H, d, J=7.5 Hz), 7.22 (1H, dd, J=8.5, 2 Hz), 7.43 (1H, d, J=8.5 Hz), 7.54 (1H, d, J=2 Hz).

Example 240

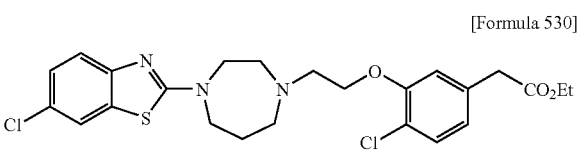

[Formula 530]

Yield: 45%, $^1$H-NMR (CDCl$_3$); δ1.25 (3H, t, J=7 Hz), 1.95-2.10 (2H, m), 2.88 (2H, t, J=5.5 Hz), 3.00-3.10 (4H, m), 3.55 (2H, s), 3.73 (2H, t, J=5.5 Hz), 3.75-3.85 (2H, m), 4.10-4.15 (2H, m), 4.15 (2H, q, J=7 Hz), 6.80 (1H, dd, J=8, 2 Hz), 6.85 (1H, d, J=2 Hz), 7.22 (1H, dd, J=8.5, 2.5 Hz), 7.29 (1H, d, J=8 Hz), 7.42 (1H, d, J=8.5 Hz), 7.54 (1H, d, J=2.5 Hz).

Example 241

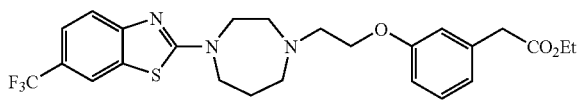

[Formula 531]

Yield: 74%, ¹H-NMR (CDCl₃); δ1.25 (3H, t, J=7.0 Hz), 1.20-2.11 (2H, m), 2.79-2.90 (2H, m), 2.93-3.06 (4H, m), 3.57 (2H, s), 3.69-3.90 (4H, m), 4.04-4.12 (2H, m), 4.15 (2H, q, J=7.0 Hz), 6.76-6.90 (3H, m), 7.22 (1H, t, J=8.0 Hz), 7.48-7.59 (2H, m), 7.84 (1H, s).

Example 242

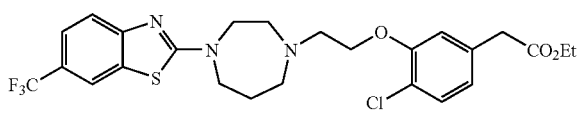

[Formula 532]

Yield: 42%, ¹H-NMR (CDCl₃); δ1.25 (3H, t, J=7.0 Hz), 1.99-2.09 (2H, m), 2.86-2.94 (2H, m), 3.02-3.12 (4H, m), 3.55 (2H, s), 3.69-3.90 (4H, m), 4.10-4.20 (4H, m), 6.81 (1H, dd, J=8.0, 2.0 Hz), 6.87 (1H, d, J=2.0 Hz), 7.29 (1H, d, J=8.0 Hz), 7.48-7.59 (2H, m), 7.84 (1H, s).

Example 243

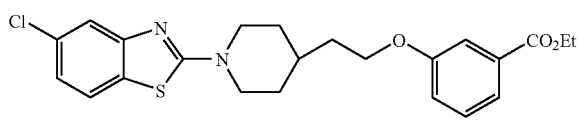

[Formula 533]

Yield: 51%, ¹H-NMR (CDCl₃); δ1.31-1.49 (5H, m), 1.75-1.96 (5H, m), 3.09-3.22 (2H, m), 4.05-4.19 (4H, m), 4.38 (2H, q, J=7.0 Hz), 7.02 (1H, dd, J=8.0, 2.0 Hz), 7.09 (1H, ddd, J=8.0, 2.5, 1.0 Hz), 7.35 (1H, t, J=8.0 Hz), 7.47 (1H, d, J=8.0 Hz), 7.50 (1H, d, J=2.0 Hz), 7.56 (1H, dd, J=2.5, 1.5 Hz), 7.65 (1H, dt, J=8.0, 1.5, 1.0 Hz).

Example 244

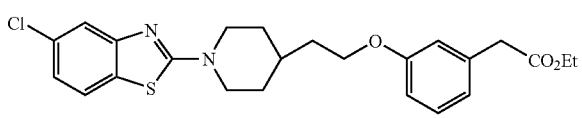

[Formula 534]

Yield: 44%, ¹H-NMR (CDCl₃); δ1.26 (3H, t, J=6.5 Hz), 130-1.48 (2H, m), 1.72-1.95 (5H, m), 3.08-3.21 (2H, m), 3.58 (2H, s), 4.03 (2H, t, J=6.0 Hz), 4.08-4.21 (2H, m), 4.15 (2H, q, J=6.5 Hz), 6.76-6.90 (3H, m), 7.02 (1H, dd, J=8.5, 2.0 Hz), 7.22 (1H, d, J=7.5 Hz), 7.47 (1H, d, J=8.5 Hz), 7.50 (1H, d, J=2.0 Hz).

Example 245

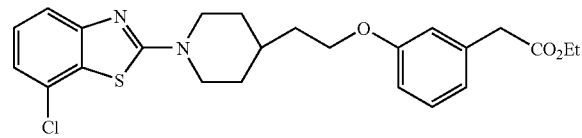

[Formula 535]

Yield: 57%, ¹H-NMR (CDCl₃); δ1.26 (3H, t, J=7.0 Hz), 1.31-1.48 (2H, m), 1.71-1.96 (5H, m), 3.09-3.22 (2H, m), 3.58 (2H, s), 4.03 (2H, t, J=6.0 Hz), 4.09-4.21 (4H, m), 6.77-6.91 (3H, m), 7.03 (1H, dd, J=8.0, 1.0 Hz), 7.17-7.28 (2H, m), 7.40 (1H, dd, J=8.0, 1.0 Hz).

Example 246

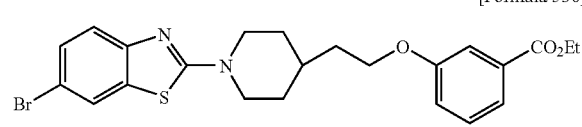

[Formula 536]

Yield: 81%, ¹H-NMR (CDCl₃); δ1.32-1.50 (5H, m), 1.75-1.95 (5H, m), 3.09-3.21 (2H, m), 4.05-4.18 (4H, m), 4.38 (2H, q, J=7.0 Hz), 7.06-7.12 (1H, m), 7.32-7.39 (3H, m), 7.54-7.58 (1H, m), 7.62-7.67 (1H, m), 7.67-7.69 (1H, m).

Example 247

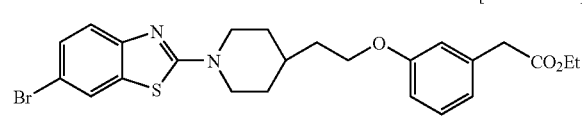

[Formula 537]

Yield: 44%, ¹H-NMR (CDCl₃); δ1.26 (3H, t, J=7.0 Hz), 1.31-1.48 (2H, m), 1.73-1.96 (5H, m), 3.08-3.20 (2H, m), 3.58 (2H, s), 4.00-4.18 (4H, m), 4.16 (2H, q, J=7.0 Hz), 6.78-6.90 (3H, m), 7.20-7.28 (1H, m), 7.36 (2H, m), 7.69 (1H, m).

Example 248

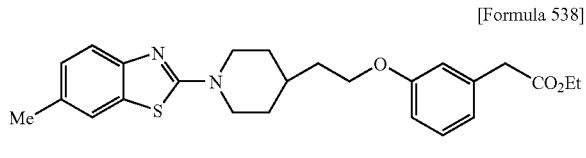

Yield: 48%, ¹H-NMR (CDCl₃); δ1.26 (3H, t, J=7.0 Hz), 1.30-1.49 (2H, m), 1.72-1.95 (5H, m), 2.39 (3H, s), 3.06-3.19 (2H, m), 3.58 (2H, s), 3.98-4.21 (6H, m), 6.77-6.91 (3H, m), 7.06-7.12 (1H, m), 7.23 (1H, t, J=7.5 Hz), 7.37-7.47 (2H, m).

Example 249

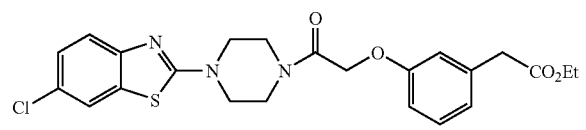

Yield: 54%, ¹H-NMR (CDCl₃); δ1.25 (3H, t, J=7.0 Hz), 3.56-3.82 (10H, m), 4.14 (2H, q, J=7.0 Hz), 4.74 (2H, s), 6.83-6.96 (3H, m), 7.22-7.29 (2H, m), 7.45 (1H, d, J=8.5 Hz), 7.58 (1H, d, J=2.0 Hz).

Example 250

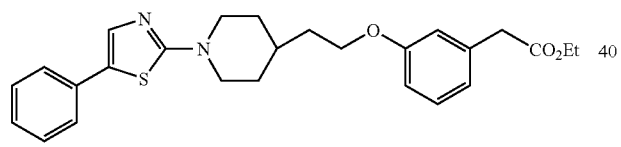

Yield: 49%, ¹H-NMR (CDCl₃); δ1.26 (3H, t, J=7.0 Hz), 1.31-1.50 (2H, m), 1.73-1.93 (5H, m), 2.99-3.12 (2H, m), 3.58 (2H, s), 3.98-4.09 (4H, m), 4.15 (2H, q, J=7.0 Hz), 6.78-6.90 (3H, m), 7.16-7.47 (7H, m).

Example 251

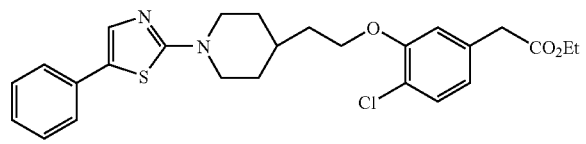

Yield: 54%, ¹H-NMR (CDCl₃); δ1.26 (3H, t, J=7.0 Hz), 1.35-1.52 (2H, m), 1.78-1.97 (5H, m), 3.01-3.14 (2H, m), 3.58 (2H, s), 3.99-4.21 (6H, m), 6.81 (1H, dd, J=8.0, 2.0 Hz), 6.87 (1H, d, J=2.0 Hz), 7.16-7.24 (1H, m), 7.27-7.37 (3H, m), 7.38-7.47 (3H, m).

Example 252

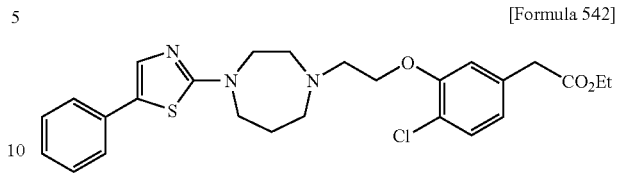

Yield: 58%, 1H-NMR (DMSO-d6): δ1.18 (3H, t, J=7.0 Hz), 1.83-1.95 (2H, m), 2.74-2.84 (2H, m), 2.89-3.01 (4H, m), 3.56-3.72 (6H, m), 4.08 (2H, q, J=7.0 Hz), 4.09-4.17 (2H, m), 6.84 (1H, dd, J=8.0, 1.5 Hz), 7.09 (1H, d, J=1.5 Hz), 7.18 (1H, t, J=7.5 Hz), 7.29-7.38 (3H, m), 7.44 (2H, d, J=7.5 Hz), 7.57 (1H, s).

Example 253

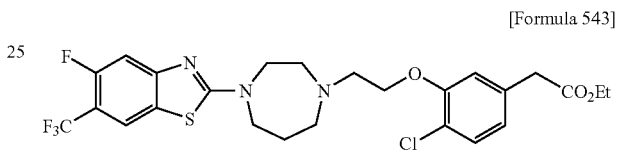

Yield: 31%, 1H-NMR (CDCl3): δ1.24 (3H, t, J=7.0 Hz), 1.95-2.08 (2H, m), 2.88 (2H, t, J=5.5 Hz), 2.98-3.12 (4H, m), 3.55 (2H, s), 3.60-3.90 (4H, m), 4.06-4.19 (4H, m), 6.79 (1H, dd, J=8.0, 1.5 Hz), 6.86 (1H, d, J=1.5 Hz), 7.25 (1H, d, J=12.0 Hz), 7.27 (1H, d, J=8.0 Hz), 7.72 (1H, d, J=7.0 Hz).

Example 254

Preparation of 3-{2-[(6-chlorobenzothiazole-2-yl) piperidine-4-yl]ethoxy}-2-methylphenyl ethyl acetate

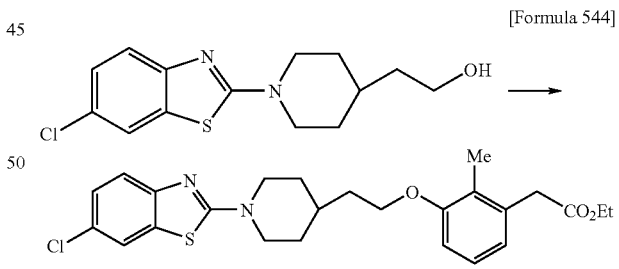

To a mixture of 6-chloro-2-[4-(2-hydroxyethyl)piperidine-1-yl]benzothiazole (0.17 g; 0.562 mmol), [3-hydroxy-2-methyl]phenyl ethyl acetate described in Reference Example 67 of WO2004/0225 (510.11 g; 0.552 mmol), 1,1-azodicarbonyldipiperidine (0.21 g; 0.844 mmol) and anhydrous THF (6 ml) was added dropwise tributyl phosphine (0.21 ml; 0.841 mmol) under argon and ice-cooling. After stirring the reaction solution at the same temperature for 2.5 hours, water and ethyl acetate were added thereto. The organic layer was separated, washed with brine, dried over anhydrous sodium sulphate, and evaporated under reduced pressure. The residue was purified by column chromatograph on silica gel (hexane:

ethyl acetate=10:1→5:1) to give 3-{2-[(6-chlorobenzothiazole-2-yl)piperidine-4-yl]ethoxy}-2-methylphenyl ethyl acetate as colorless oil (0.16 g; 59%).

¹H-NMR (CDCl₃): δ1.26 (3H, t, J=7.2 Hz), 1.38-1.47 (2H, m), 1.78-1.93 (5H, m), 2.18 (3H, s), 3.14 (2H, td, J=12.6, 2.4 Hz), 3.64 (2H, s), 4.02 (2H, t, J=5.7 Hz), 4.10-4.16 (2H, m), 4.15 (2H, t, J=7.2 Hz), 6.80 (2H, q, J=7.8 Hz), 7.11 (1H, t, J=7.8 Hz), 7.23 (1H, dd, J=8.4, 1.8 Hz), 7.42 (1H, d, J=8.4 Hz), 7.54 (1H, d, J=1.8 Hz).

Compounds in Examples 255 and 256 were obtained by similar methods as Example 254.

Example 255

[Formula 545]

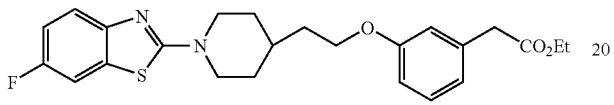

Yield: 39%, ¹H-NMR (CDCl₃); δ1.26 (3H, t, J=7.0 Hz), 1.28-1.50 (2H, m), 1.70-1.98 (5H, m), 3.04-3.21 (2H, m), 3.58 (2H, s), 3.97-4.22 (4H, m), 4.15 (2H, q, J=7.0 Hz), 6.75-6.92 (3H, m), 7.00 (1H, td, J=9.0, 3.0 Hz), 7.23 (1H, t, J=8.0 Hz), 7.29 (1H, dd, J=9.0, 3.0 Hz), 7.44 (1H, dd, J=9.0, 5.0 Hz).

Example 256

[Formula 546]

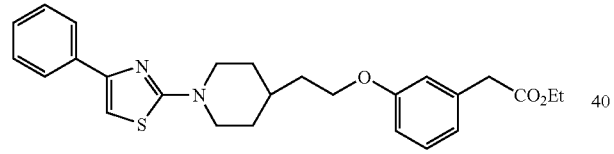

Yield: 22%, 1H-NMR (CDCl3): δ1.24 (3H, t, J=7.0 Hz), 1.26-1.50 (2H, m), 1.68-1.92 (5H, m), 2.94-3.09 (2H, m), 3.58 (2H, m), 3.94-4.13 (4H, m), 4.14 (2H, q, J=7.0 Hz), 6.72 (1H, s), 6.75-6.93 (3H, m), 7.24 (2H, m), 7.35 (2H, t, J=7.0 Hz), 7.83 (2H, d, J=7.0 Hz).

Example 257

Preparation of 3-{2-[(6-phenylbenzothiazole-2-yl)piperidine-4-yl]ethoxy}phenyl ethyl acetate

[Formula 547]

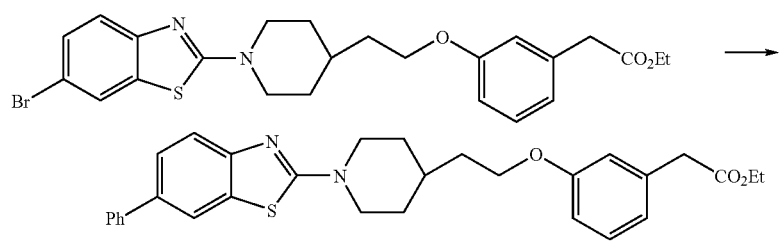

A mixture of 3-{2-[(6-bromobenzothiazole-2-yl)piperidine-4-yl]ethoxy}phenyl ethyl acetate (0.30 g; 0.596 mmol), phenylboronic acid (0.09 g; 0.775 mmol), tetrakis (triphenylphosphine) palladium (0) (0.03 g; 0.03 mmol), cesium carbonate (0.25 g; 0.775 mmol) and dioxane (3 ml) was refluxed under argon for 3 hours. The reaction solution was cooled to room temperature and condensed under reduced pressure. The residue was purified by column chromatograph on silica gel (hexane:ethyl acetate=3:1) to give 3-{2-[(6-phenylbenzothiazole-2-yl)piperidine-4-yl]ethoxy}phenyl ethyl acetate as colorless crystal (0.08 g; 26%).

1H-NMR (CDCl3): δ 1.25 (3H, t, J=7.0 Hz), 1.28-1.48 (2H, m), 1.66-1.96 (5H, m), 3.04-3.21 (2H, m), 3.57 (2H, s), 3.94-4.07 (2H, m), 4.08-4.25 (4H, m), 6.73-6.92 (3H, m), 7.17-7.34 (2H, m), 7.36-7.47 (2H, m), 7.48-7.64 (4H, m), 7.79 (1H, d, J=2.0 Hz).

Example 258

Preparation of 3-{[4-(6-chlorobenzothiazole-2-yl)piperazine-1-yl]methyl}-5-methylphenol

[Formula 548]

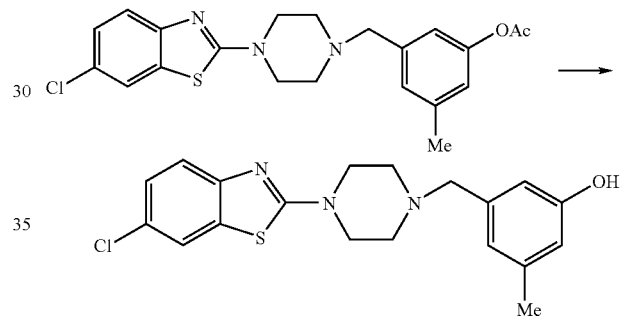

A mixture of acetic acid 3-{[4-(6-chlorobenzothiazole-2-yl)piperazine-1-yl]methyl}-5-methylphenyl ester (1.97 g; 4.88 mmol), 2N-aqueous sodium hydroxide (10 ml) and methanol (20 ml) was stirred at 40° C. for 1 hour. The solvent was evaporated under reduced pressure. To the residue were added water and 2N-aqueous hydrochloric acid to be neutral. Ethyl acetate was added thereto and extracted with ethyl acetate. The organic layer was washed with brine, dried over anhydrous sodium sulphate, and evaporated under reduced pressure. The residue was purified by column chromatograph on silica gel (ethyl acetate) to give 3-{[4-(6-chlorobenzothiazole-2-yl)piperazine-1-yl]methyl}-5-methylphenol as colorless amorphous solid (1.83 g; 100%).

¹H-NMR (CDCl3): δ2.29 (3H, s), 2.57 (4H, t, J=5 Hz), 3.47 (2H, s), 3.67 (4H, t, J=5 Hz), 6.59 (1H, s), 6.67 (2H, s), 7.23 (1H, dd, J=8.5, 2 Hz), 7.45 (1H, d, J=8.5 Hz), 7.55 (1H, d, J=2 Hz).

Compounds in Examples 259 to 286 were obtained by similar methods as Example 258.

Example 259

[Formula 549]

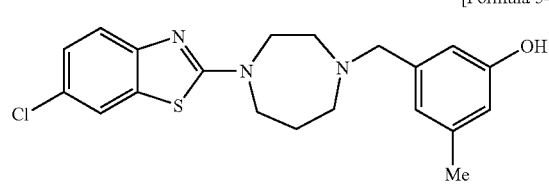

Yield: 85%, ¹H-NMR (CDCl3); δ1.74 (1H, brs), 1.96-2.05 (2H, m), 2.26 (3H, s), 2.67 (2H, t, J=5.1 Hz), 2.75-2.79 (2H, m), 3.52 (2H, s), 3.68-3.74 (4H, m), 6.55 (1H, s), 6.61 (1H, s), 6.65 (1H, s), 7.22 (1H, dd, J=8.7, 2.1 Hz), 7.43 (1H, d, J=8.4 Hz), 7.54 (1H, d, J=2.1 Hz).

Example 260

[Formula 550]

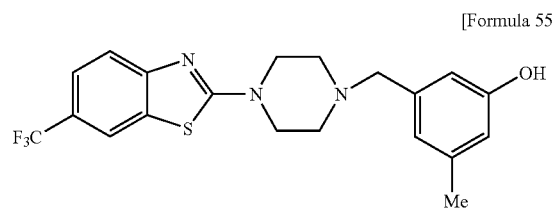

Yield: 100%, ¹H-NMR (CDCl₃); δ2.29 (3H, s), 2.61 (4H, t, J=5 Hz), 3.50 (2H, s), 3.71 (4H, t, J=5 Hz), 6.60 (1H, s), 6.69 (2H, s), 7.52 (1H, d, J=7.5 Hz), 7.58 (1H, d, J=7.5 Hz), 7.85 (1H, s).

Example 261

[Formula 551]

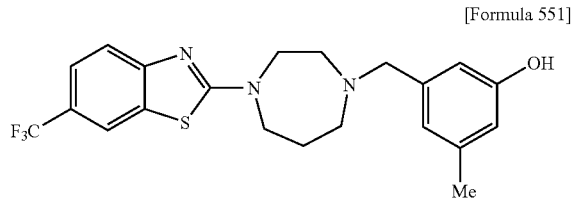

Yield: 71%, ¹H-NMR (CDCl₃); δ2.00-2.10 (2H, m), 2.28 (3H, s), 2.65-2.75 (2H, m), 2.80-2.90 (2H, m), 3.57 (2H, s), 3.70-3.90 (4H, m), 6.56 (1H, s), 6.65-6.70 (2H, m), 7.45-7.60 (2H, m), 7.85 (1H, s).

Example 262

[Formula 552]

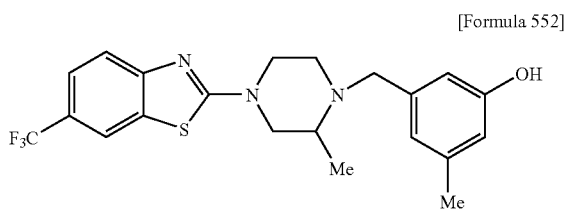

Yield: 99%, 1H-NMR (CDCl3): δ1.22 (3H, d, J=6 Hz), 1.64 (1H, brs), 2.25-2.29 (1H, m), 2.30 (3H, s), 2.60-2.70 (1H, m), 2.80-2.83 (1H, m), 3.13 (1H, d, J=13.5 Hz), 3.17-3.25 (1H, m), 3.40-3.50 (1H, m), 3.73-3.83 (1H, m), 3.85-3.95 (1H, m), 3.98 (1H, d, J=13.5 Hz), 6.57 (1H, s), 6.66 (1H, s), 6.69 (1H, s), 7.52 (1H, d, J=8.5 Hz), 7.57 (1H, d, J=8.5 Hz), 7.84 (1H, s).

Example 263

[Formula 553]

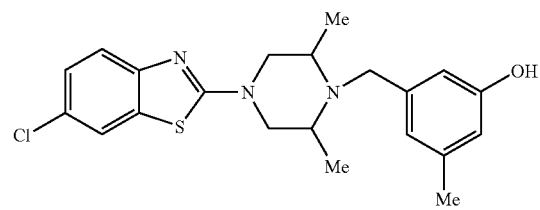

Yield: quant. %, 1H-NMR (CDCl3): δ1.11 (6H, d, J=6 Hz), 2.28 (3H, s), 2.70-2.85 (2H, m), 2.95-3.10 (2H, m), 3.70-3.90 (4H, m), 6.53 (1H, s), 6.68 (1H, s), 6.72 (1H, s), 7.23 (1H, dd, J=8.5, 2 Hz), 7.43 (1H, d, J=8.5 Hz), 7.55 (1H, d, J=2 Hz).

Example 264

[Formula 554]

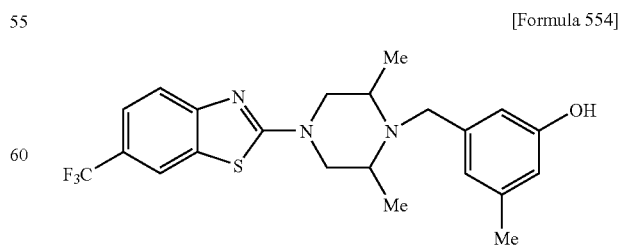

Yield: quant. %, 1H-NMR (CDCl3): δ1.10 (6H, d, J=6 Hz), 2.28 (3H, s), 2.70-2.85 (2H, m), 3.00-3.15 (2H, m), 3.75 (2H, s), 3.82-3.94 (2H, m), 5.53 (1H, brs), 6.52 (1H, s), 6.69 (1H, s), 6.72 (1H, s), 7.51 (1H, d, J=8.5 Hz), 7.56 (1H, d, J=8.5 Hz), 7.84 (1H, s).

Example 265

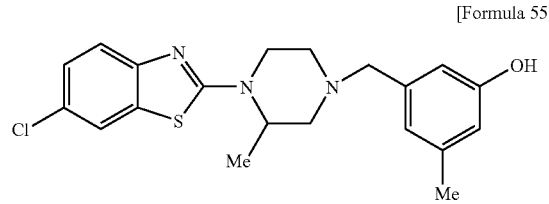

[Formula 555]

Yield: quant. %, 1H-NMR (CDCl3): δ1.42 (3H, d, J=7 Hz), 2.20-2.28 (1H, m), 2.28 (3H, s), 2.30-2.45 (1H, m), 2.70-2.85 (1H, m), 2.90-3.00 (1H, m), 3.43 (1H, d, J=13.5 Hz), 3.45-3.55 (1H, m), 3.58 (1H, d, J=13.5 Hz), 3.80-3.90 (1H, m), 4.15-4.25 (1H, m), 6.60 (1H, s), 6.66 (1H, s), 6.77 (1H, s), 7.22 (1H, dd, J=8.5, 2 Hz), 7.43 (1H, d, J=8.5 Hz), 7.54 (1H, d, J=2 Hz).

Example 266

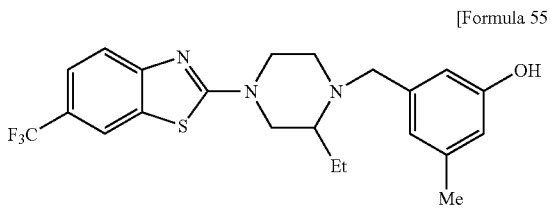

[Formula 556]

Yield: quant. %, 1H-NMR (CDCl3): δ1.01 (3H, t, J=7.5 Hz), 1.55-1.78 (2H, m), 2.29 (3H, s), 2.30-2.40 (1H, m), 2.48-2.56 (1H, m), 2.79-2.83 (1H, m), 3.18 (1H, d, J=13.5 Hz), 3.37-3.56 (2H, m), 3.65-3.77 (1H, m), 3.82 (1H, dd, J=13, 3 Hz), 3.93 (1H, d, J=13.5 Hz), 6.57 (1H, s), 6.67 (1H, s), 6.70 (1H, s), 7.52 (1H, dd, J=8.5, 1.5 Hz), 7.57 (1H, d, J=8.5 Hz), 7.84 (1H, d, J=1.5 Hz).

Example 267

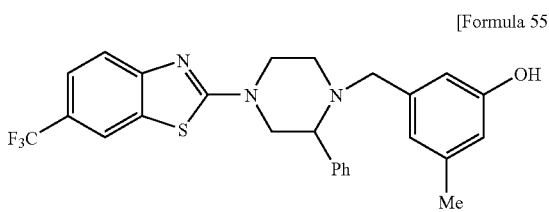

[Formula 557]

Yield 99%, 1H-NMR (CDCl3): δ2.27 (3H, s), 2.27-2.35 (1H, m), 2.77 (1H, d, J=13.5 Hz), 3.02 (1H, d, J=11.5 Hz), 3.28-3.50 (3H, m), 3.75 (1H, d, J=13.5 Hz), 3.98 (1H, d, J=11

Hz), 4.10-4.18 (1H, m), 5.61 (1H, brs), 6.54 (1H, s), 6.61 (1H, s), 6.64 (1H, s), 7.30-7.43 (3H, m), 7.45-7.60 (4H, m), 7.86 (1H, s).

Example 268

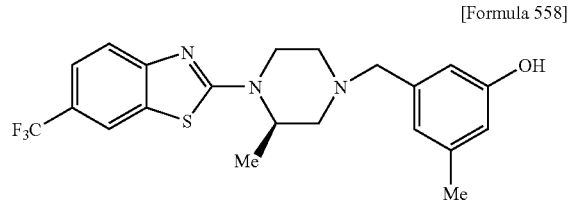

[Formula 558]

Yield: 96%, 1H-NMR (CDCl3): δ1.42 (3H, d, J=6.5 Hz), 2.18 (1H, td, J=12, 3.5 Hz), 2.29 (3H, s), 2.29-2.40 (1H, m), 2.74 (1H, d, J=11.5 Hz), 2.89 (1H, d, J=11.5 Hz), 3.39 (1H, d, J=13 Hz), 3.47 (1H, d, J=13 Hz), 3.55 (1H, td, J=12.5, 3.5 Hz), 3.90 (1H, d, J=13 Hz), 4.16-4.29 (1H, m), 6.58 (1H, s), 6.69 (1H, s), 6.70 (1H, s), 7.51 (1H, dd, J=8.5, 1.5 Hz), 7.57 (1H, d, J=8.5 Hz), 7.84 (1H, d, J=1.5 Hz).

Example 269

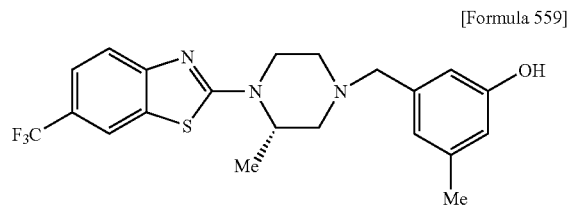

[Formula 559]

Yield: quant. %, 1H-NMR (CDCl3): δ1.43 (3H, d, J=6.5 Hz), 2.14-2.41 (5H, m), 2.71-2.80 (1H, m), 2.86-2.92 (1H, m), 3.35-3.59 (3H, m), 3.85-3.97 (1H, m), 4.17-4.29 (1H, m), 6.58 (1H, s), 6.69 (1H, s), 6.72 (1H, s), 7.48-7.60 (2H, m), 7.84 (1H, s).

Example 270

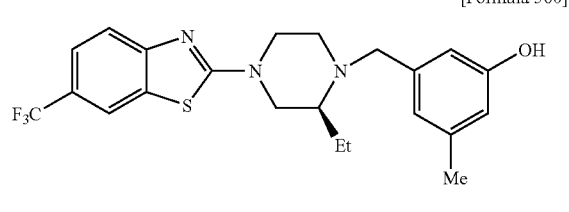

[Formula 560]

Yield: 96%, 1H-NMR (CDCl3): δ1.00 (3H, t, J=7.5 Hz), 1.55-1.75 (2H, m), 2.29 (3H, s), 2.29-2.38 (1H, m), 2.47-2.57 (1H, m), 2.78-2.88 (1H, m), 3.17 (1H, d, J=13.5 Hz), 3.37-3.55 (2H, m), 3.65-3.85 (2H, m), 3.93 (1H, d, J=13.5 Hz), 6.57 (1H, s), 6.67 (1H, s), 6.69 (1H, s), 7.52 (1H, d, J=8.5 Hz), 7.57 (1H, d, J=8.5 Hz), 7.84 (1H, s).

Example 271

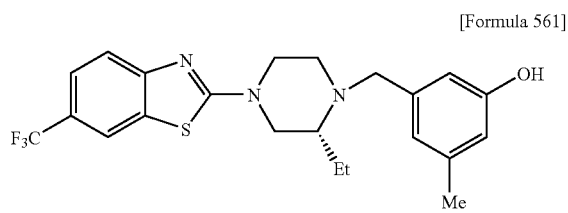

[Formula 561]

Yield: 92%, 1H-NMR (CDCl$_3$): δ1.01 (3H, t, J=7.5 Hz), 1.57-1.79 (2H, m), 2.29 (3H, s), 2.29-2.40 (1H, m), 2.46-2.58 (1H, m), 2.77-2.89 (1H, m), 3.18 (1H, d, J=13 Hz), 3.32-3.58 (2H, m), 3.65-3.87 (2H, m), 3.93 (1H, d, J=13 Hz), 6.57 (1H, s), 6.67 (1H, s), 6.69 (1H, s), 7.52 (1H, d, J=8.5 Hz), 7.57 (1H, d, J=8.5 Hz), 7.84 (1H, s).

Example 272

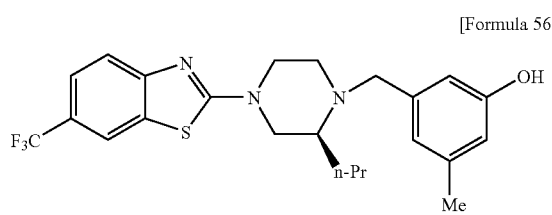

[Formula 562]

Yield: 95%, 1H-NMR (CDCl3): δ0.93 (3H, t, J=7.5 Hz), 1.30-1.70 (4H, m), 2.29 (3H, s), 2.29-2.39 (1H, m), 2.55-2.65 (1H, m), 2.79-2.88 (1H, m), 3.19 (1H, d, J=13.5 Hz), 3.41 (1H, dd, J=12.5, 8 Hz), 3.48-3.58 (1H, m), 3.65-3.75 (1H, m), 3.82 (1H, dd, J=12.5, 2.5 Hz), 3.92 (1H, d, J=13.5 Hz), 6.57 (1H, s), 6.68 (1H, s), 6.70 (1H, s), 7.51 (1H, dd, J=8.5, 1.5 Hz), 7.55 (1H, d, J=8.5 Hz), 7.84 (1H, d, J=1.5 Hz).

Example 273

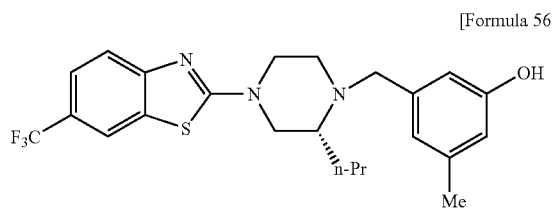

[Formula 563]

Yield: 98%, 1H-NMR (CDCl3): δ0.93 (3H, t, J=7.5 Hz), 1.30-1.41 (1H, m), 1.48-1.63 (3H, m), 2.29 (3H, s), 2.29-2.36 (1H, m), 2.56-2.62 (1H, m), 2.79-2.86 (1H, m), 3.19 (1H, d, J=13.5 Hz), 3.41 (1H, dd, J=7.8, 12.9 Hz), 3.50-3.57 (1H, m), 3.69-3.81 (2H, m), 3.92 (1H, d, J=13.5 Hz), 6.67 (1H, s), 6.68 (2H, s), 7.50-7.59 (2H, m), 7.84 (1H, s)

Example 274

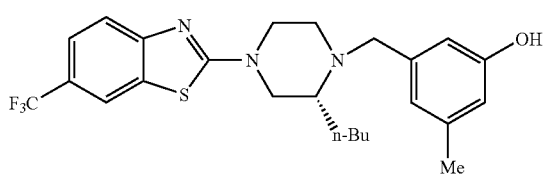

[Formula 564]

Yield: 98%, 1H-NMR (CDCl3): δ0.91 (3H, t, J=7 Hz), 1.26-1.75 (6H, m), 2.30 (3H, s), 2.30-2.40 (1H, m), 2.52-2.63 (1H, m), 2.77-2.87 (1H, m), 3.19 (1H, d, J=13.5 Hz), 3.35-3.45 (1H, m), 3.47-3.57 (1H, m), 3.65-3.75 (1H, m), 3.81 (1H, dd, J=12.5, 2.5 Hz), 3.92 (1H, d, J=13.5 Hz), 5.49 (1H, brs), 6.57 (1H, s), 6.67 (1H, s), 6.69 (1H, s), 7.52 (1H, dd, J=8.5, 1.5 Hz), 7.57 (1H, d, J=8.5 Hz), 7.84 (1H, d, J=1.5 Hz)

Example 275

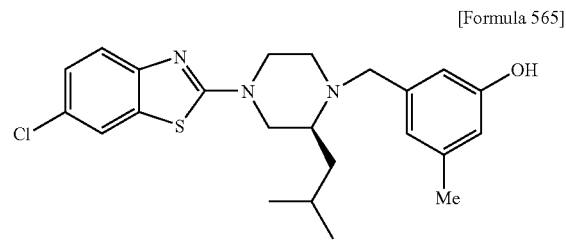

[Formula 565]

Yield: 96%, 1H-NMR (CDCl3): δ0.91 (3H, d, J=6.5 Hz), 0.95 (3H, d, J=6.5 Hz), 1.32-1.46 (1H, m), 1.47-1.59 (1H, m), 1.62-1.78 (1H, m), 2.29 (3H, s), 2.33-2.45 (1H, m), 2.62-2.74 (1H, m), 2.75-2.87 (1H, m), 3.27 (1H, d, J=13.5 Hz), 3.36 (1H, dd, J=12.5, 7.5 Hz), 3.55-3.65 (2H, m), 3.70-3.79 (1H, m), 3.86 (1H, d, J=13.5 Hz), 6.56 (1H, s), 6.69 (2H, s), 7.22 (1H, dd, J=8.5, 2 Hz), 7.43 (1H, d, J=8.5 Hz), 7.54 (1H, d, J=2 Hz).

Example 276

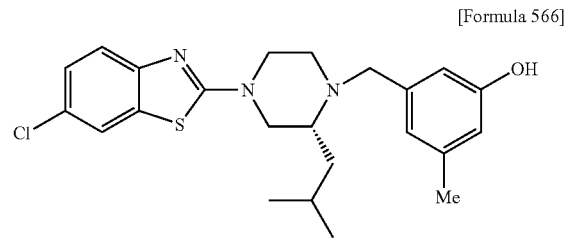

[Formula 566]

Yield: quant. %, 1H-NMR (CDCl3): δ0.91 (3H, d, J=6.5 Hz), 0.95 (3H, d, J=6.5 Hz), 1.30-1.59 (2H, m), 1.62-1.79 (1H, m), 2.18 (1H, s), 2.29 (3H, s), 2.30-2.45 (1H, m), 2.60-2.72 (1H, m), 2.75-2.88 (1H, m), 3.27 (1H, d, J=13.5 Hz), 3.29-3.42 (1H, m), 3.53-3.65 (2H, m), 3.74 (1H, dd, J=12.5, 3.5 Hz), 3.86 (1H, d, J=13.5 Hz), 6.56 (1H, s), 6.67 (1H, s), 6.70 (1H, s), 7.23 (1H, dd, J=8.5, 2.0 Hz), 7.43 (1H, d, J=8.5 Hz), 7.54 (1H, d, J=2.0 Hz).

s), 6.72 (1H, s), 7.24 (1H, d, J=11.5 Hz), 7.72 (1H, d, J=7.0 Hz), 7.85 (1H, s).

Example 277

[Formula 567]

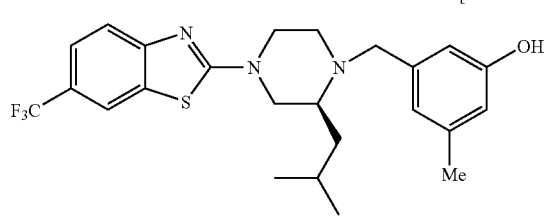

Yield: 98%, 1H-NMR (CDCl3): δ0.91 (3H, d, J=6.5 Hz), 0.95 (3H, d, J=6.5 Hz), 1.37-1.45 (1H, m), 1.46-1.60 (1H, m), 1.64-1.77 (1H, m), 2.29 (3H, s), 2.36-2.47 (1H, m), 2.64-2.75 (1H, m), 2.78-2.90 (1H, m), 3.29 (1H, d, J=13.5 Hz), 3.42 (1H, dd, J=12.5, 7.5 Hz), 3.65 (2H, t, J=5 Hz), 3.78 (1H, dd, J=13, 3 Hz), 3.86 (1H, d, J=13.5 Hz), 6.57 (1H, s), 6.70 (2H, s), 7.51 (1H, dd, J=8.5, 1.5 Hz), 7.57 (1H, d, J=8.5 Hz), 7.84 (1H, d, J=1.5 Hz).

Example 278

[Formula 568]

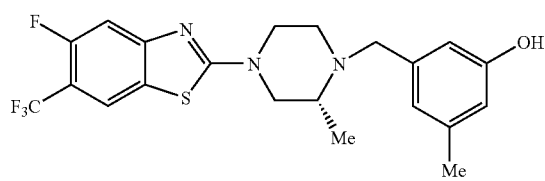

Yield: 99%, 1H-NMR (CDCl3): δ1.21 (3H, d, J=6 Hz), 2.22-2.28 (1H, m), 2.29 (3H, s), 2.59-2.70 (1H, m), 2.83 (1H, dt, J=12, 3.5 Hz), 3.13 (1H, d, J=13.5 Hz), 3.21 (1H, dd, J=11, 8.5 Hz), 3.39-3.50 (1H, m), 3.72-3.83 (1H, m), 3.84-3.93 (1H, m), 3.97 (1H, d, J=13.5 Hz), 6.56 (1H, s), 6.65 (1H, s), 6.70 (1H, s), 7.26 (1H, d, J=11.5 Hz), 7.73 (1H, d, J=7 Hz).

Example 279

[Formula 569]

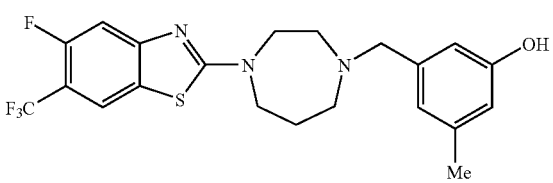

Yield: quant. %, 1H-NMR (CDCl3): δ2.00-2.14 (2H, m), 2.22 (3H, s), 2.68-2.93 (4H, m), 3.53-3.95 (6H, m), 6.60 (2H, Example 280

[Formula 570]

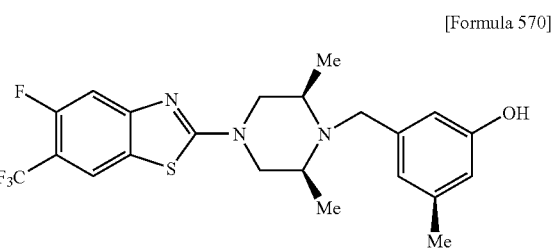

Yield: 89%, 1H-NMR (CDCl3): δ1.13 (6H, d, J=6.0 Hz), 2.29 (3H, s), 2.72-2.88 (2H, m), 3.01-3.19 (2H, m), 3.77 (2H, s), 3.89 (2H, d, J=12.0 Hz), 6.52 (1H, s), 6.70 (1H, s), 6.72 (1H, s), 7.27 (1H, d, J=11.5 Hz), 7.75 (1H, d, J=6.5 Hz).

Example 281

[Formula 571]

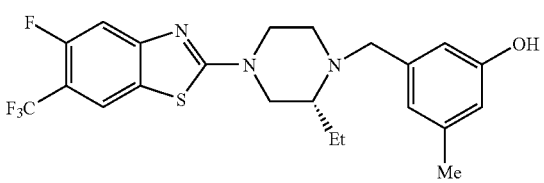

Yield: 95%, 1H-NMR (CDCl3): δ1.01 (3H, t, J=7.5 Hz), 1.48-1.80 (2H, m), 2.25-2.40 (1H, m), 2.30 (3H, s), 2.46-2.58 (1H, m), 2.78-2.89 (1H, m), 3.19 (1H, d, J=13.5 Hz), 3.32-3.57 (2H, m), 3.64-3.75 (1H, m), 3.76-3.87 (1H, m), 3.93 (1H, d, J=13.5 Hz), 6.57 (1H, s), 6.67 (1H, s), 6.70 (1H, s), 7.27 (1H, d, J=11.5 Hz), 7.74 (1H, d, J=7.0 Hz).

Example 282

[Formula 572]

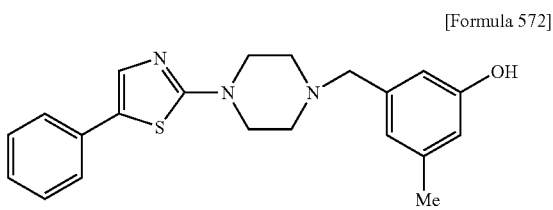

Yield: quant %, 1H-NMR (CDCl3): δ2.23 (3H, s), 2.62-2.80 (4H, m), 3.52-3.73 (6H, m), 6.63 (1H, s), 6.65 (1H, s), 6.78 (1H, s), 7.20 (1H, t, J=7.5 Hz), 7.31 (2H, t, J=7.5 Hz), 7.35-7.44 (3H, m), 8.70 (1H, brs).

Example 283

[Formula 573]

Yield: 93%, 1H-NMR (CDCl3): δ1.13 (6H, d, J=6.0 Hz), 2.29 (3H, s), 2.65-2.80 (2H, m), 2.90 (2H, t, J=11.5 Hz), 3.76 (2H, s), 4.29 (2H, d, J=13.0 Hz), 6.54 (1H, s), 6.70 (1H, s), 6.75 (1H, s), 7.34-7.43 (1H, m), 7.53-7.62 (1H, m), 7.69 (1H, d, J=8.0 Hz), 7.88 (1H, d, J=8.0 Hz), 8.55 (1H, s).

Example 284

[Formula 574]

Yield: 93%, 1H-NMR (CDCl3): δ1.25 (3H, d, J=5.5 Hz), 2.21-2.34 (1H, m), 2.29 (3H, s), 2.54-2.70 (1H, m), 2.83-2.94 (1H, m), 3.07-3.22 (1H, m), 3.14 (1H, d, J=13.5 Hz), 3.30-3.45 (1H, m), 4.02 (1H, d, J=13.5 Hz), 4.06-4.17 (1H, m), 4.18-4.28 (1H, m), 6.58 (1H, s), 6.66-6.74 (2H, m), 7.34-7.43 (1H, m), 7.53-7.61 (1H, m), 7.68 (1H, dd, J=8.5, 1.0 Hz), 7.88 (1H, dd, J=8.5, 1.0 Hz), 8.55 (1H, s).

Example 285

[Formula 575]

Yield: 88%, 1H-NMR (CDCl3): δ1.16 (6H, d, J=6.0 Hz), 2.29 (3H, s), 2.65-2.83 (2H, m) 2.94 (2H, t, J=11.5 Hz), 3.77 (2H, s), 4.30 (2H, d, J=14.0 Hz), 6.52 (1H, s), 6.72 (1H, s), 6.75 (1H, s), 7.50 (1H, dd, J=9.0, 2.5 Hz), 7.60 (1H, d, J=9.0 Hz), 7.85 (1H, d, J=2.5 Hz), 8.54 (1H, s).

Example 286

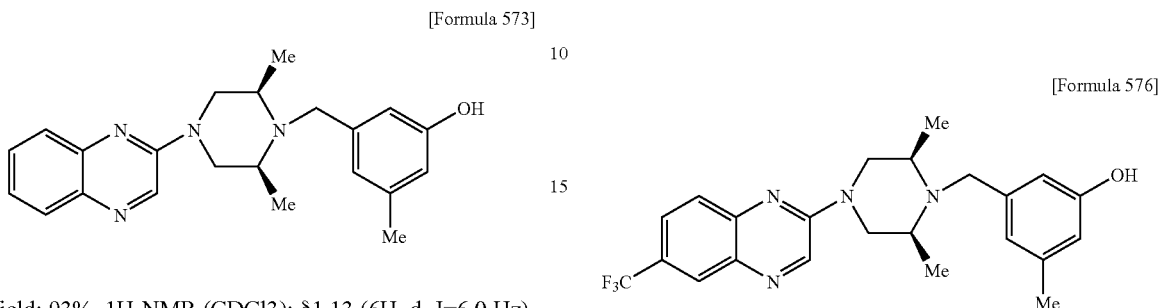

[Formula 576]

Yield: 97%, 1H-NMR (CDCl3): δ1.17 (6H, d, J=6.0 Hz), 2.28 (3H, s), 2.66-2.83 (2H, m), 2.90-3.06 (2H, m), 3.79 (2H, s), 4.34 (2H, d, J=13.0 Hz), 6.55 (1H, s), 6.69 (1H, s), 6.75 (1H, s), 7.72 (2H, s), 8.14 (1H, s), 8.59 (1H, s).

Example 287

Preparation of 5-{[4-(6-chlorobenzothiazole-2-yl)piperazine-1-yl]methyl}-2-methylphenol

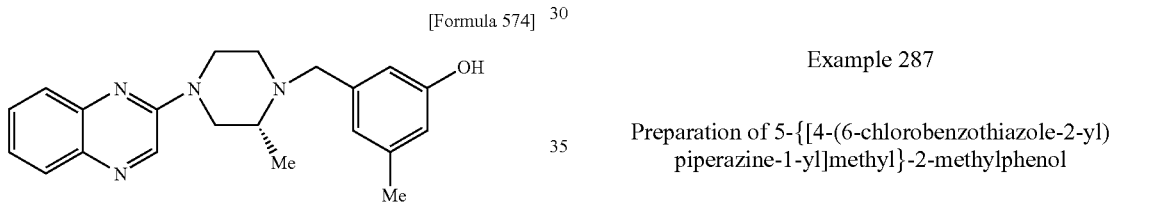

[Formula 577]

A mixture of 6-chloro-2-[4-(2-methoxymethoxy-3-methylbenzyl)piperazine-1-yl]benzothiazole (1.70 g; 4.067 mmol) and 4N hydrochloric acid/dioxane solution (8.5 ml) was stirred at 60° C. for 2 hours. After cooling, the reaction solution was condensed under reduced pressure. To the residue was added saturated aqueous sodium hydrogencarbonate to be alkaline and extracted with ethyl acetate. The organic layer was washed with brine, dried over anhydrous sodium sulphate, and evaporated under reduced pressure. The precipitate was washed with diisopropyl ether to give 5-{[4-(6-chlorobenzothiazole-2-yl)piperazine-1-yl]methyl}-2-methylphenol as colorless crystal (1.33 g; 87%).

$^1$H-NMR (CDCl$_3$): δ2.24 (3H, s), 2.55 (4H, t, J=5 Hz), 3.46 (2H, s), 3.63 (4H, t, J=5 Hz), 5.95 (1H, brs), 6.76 (1H, d, J=7.5 Hz), 6.81 (1H, s), 7.07 (1H, d, J=7.5 Hz), 7.23 (1H, dd, J=8, 2 Hz), 7.45 (1H, d, J=8 Hz), 7.55 (1H, d, J=2 Hz).

Compounds in Examples 288 to 292 were obtained by similar methods as Example 287.

Example 288

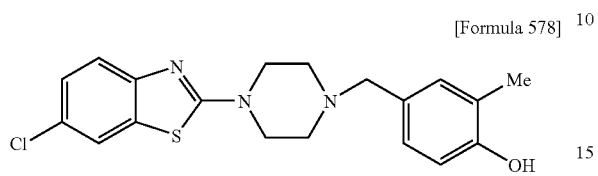
[Formula 578]

Yield: 100%, ¹H-NMR (DMSO-$d_6$): δ2.12 (3H, s), 3.08-3.18 (2H, m), 3.39 (2H, d, J=12.0 Hz), 3.65 (2H, t, J=12.0 Hz), 4.13-4.21 (4H, m), 6.85 (1H, d, J=8.4 Hz), 7.22 (1H, d, J=8.4 Hz), 7.28 (1H, s), 7.28 (1H, m), 7.49 (1H, d, J=8.7 Hz), 7.99 (1H, d, J=2.1 Hz).

Example 289

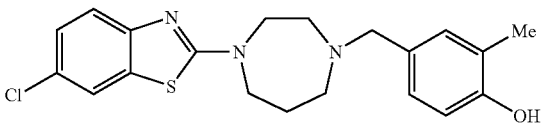
[Formula 579]

Yield: 80%, ¹H-NMR (DMSO-$d_6$): δ2.12 (3H, s), 2.16-2.26 (2H, m), 3.03-3.15 (2H, m), 3.49-3.76 (4H, m), 4.02 (4H, s) 6.83 (1H, d, J=8.1 Hz), 7.19 (1H, d, J=8.1 Hz), 7.25 (1H, s), 7.31 (1H, dd, J=2.4, 8.7 Hz), 7.45 (1H, d, J=9.7 Hz), 7.95 (1H, d, J=2.4 Hz).

Example 290

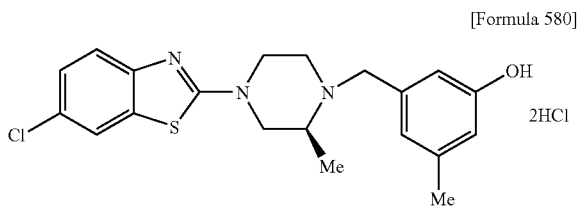
[Formula 580]

Yield: 77%, ¹H-NMR (DMSO-$d_6$): δ1.59 (3H, d, J=6.3 Hz), 2.24 (3H, s), 3.12 (2H, br), 3.54 (1H, br), 3.65 (2H, br), 3.89-3.96 (1H, m), 4.09 (1H, d, J=14.1 Hz), 4.21 (1H, d, J=12.9 Hz), 4.63 (1H, d, J=11.2 Hz), 6.68 (1H, s), 6.81 (1H, s), 6.88 (1H, s), 7.34 (1H, dd, J=2.1, 8.7 Hz), 7.50 (1H, d, J=8.7 Hz), 8.00 (1H, d, J=2.1 Hz), 11.6 (1H, s)

Example 291

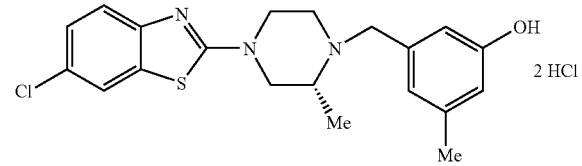
[Formula 581]

Yield: 84%, 1H-NMR (DMSO-d6): δ1.58 (3H, d, J=6.0 Hz), 2.24 (3H, s), 3.16 (2H, br), 3.53 (1H, br), 3.64 (1H, br), 3.89-3.96 (2H, m), 4.08 (1H, d, J=12.9 Hz), 4.21 (1H, d, J=12.9 Hz), 4.63 (1H, d, J=12.0 Hz), 6.68 (1H, s), 6.81 (1H, s), 6.87 (1H, s), 7.34 (1H, dd, J=2.1, 8.7 Hz), 7.50 (1H, d, J=8.7 Hz), 8.00 (1H, d, J=2.1 Hz), 11.6 (1H, br)

Example 292

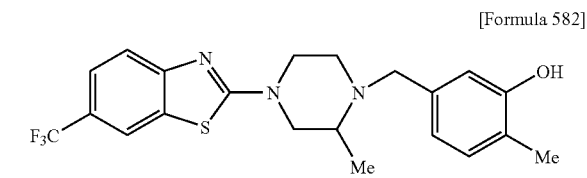
[Formula 582]

Yield: 84%, 1H-NMR (CDCl3): δ1.21 (3H, d, J=6 Hz), 2.24 (3H, s), 2.25-2.33 (1H, m), 2.59-2.70 (1H, m), 2.81 (1H, dt, J=12, 3 Hz), 3.14 (1H, d, J=13.5 Hz), 3.15-3.25 (1H, m), 3.39-3.50 (1H, m), 3.73-3.83 (1H, m), 3.84-3.94 (1H, m), 3.98 (1H, d, J=13.5 Hz), 5.18 (1H, brs), 6.79 (1H, d, J=7.5 Hz), 6.80 (1H, s), 7.07 (1H, d, J=7.5 Hz), 7.51 (1H, d, J=8.5 Hz), 7.57 (1H, d, J=8.5 Hz), 7.84 (1H, s).

Example 293

Preparation of {3-[[4-(6-chlorobenzothiazole-2-yl)piperazine-1-yl]methyl]-5-methyl}phenoxyethyl acetate

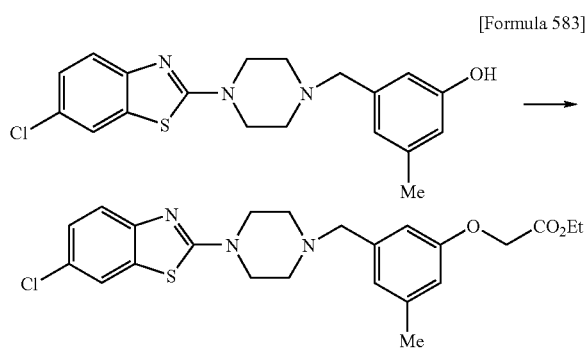
[Formula 583]

A mixture of 3-{[4-(6-chlorobenzothiazole-2-yl)piperazine-1-yl]methyl}-5-methylphenol (0.50 g; 1.34 mmol), bromoethyl acetate (0.22 ml; 2.01 mmol) and cesium carbonate (0.65 g; 2.01 mmol) in anhydrous N,N-dimethylformamide (5 ml) was stirred at 50° C. for 17 hours. Water and ethyl acetate were added to the reaction solution and extracted. The organic layer was washed with brine, dried over anhydrous sodium sulphate, and evaporated under reduced pressure. The residue was purified by column chromatograph on silica gel (hexane:ethyl acetate=2:1) to give {3-[[4-(6-chlorobenzothiazole-2-yl)piperazine-1-yl]methyl]-5-methyl}+phenoxyethyl acetate as pale yellow oil (0.48 g; 78%).

$^1$H-NMR (CDCl$_3$): δ1.28 (3H, t, J=7 Hz), 2.32 (3H, s), 2.56 (4H, t, J=5 Hz), 3.49 (2H, s), 3.63 (4H, t, J=5 Hz), 4.27 (2H, q, J=7 Hz), 4.61 (2H, s), 6.64 (1H, s), 6.74 (1H, s), 6.78 (1H, s), 7.23 (1H, dd, J=8.5, 2 Hz), 7.43 (1H, d, J=8.5 Hz), 7.55 (1H, d, J=2 Hz).

Compounds in Examples 294 to 329 were obtained by similar methods as Example 293.

Example 294

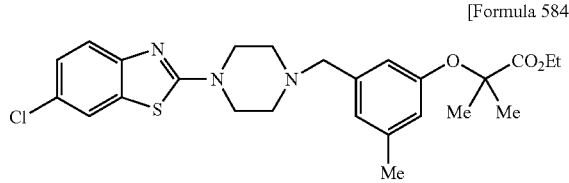

[Formula 584]

Yield: 84%, $^1$H-NMR (CDCl$_3$); δ1.27 (3H, t, J=7 Hz), 1.59 (6H, s), 2.29 (3H, s), 2.55 (4H, t, J=5 Hz), 3.46 (2H, s), 3.62 (4H, t, J=5 Hz), 4.26 (2H, q, J=7 Hz), 6.55 (1H, s), 6.60 (1H, s), 6.77 (1H, s), 7.23 (1H, dd, J=8.5, 2 Hz), 7.42 (1H, d, J=8.5 Hz), 7.55 (1H, d, J=2 Hz).

Example 295

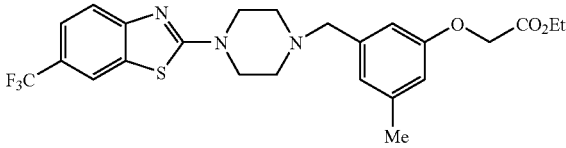

[Formula 585]

Yield: 78%, $^1$H-NMR (CDCl$_3$); δ1.31 (3H, t, J=7 Hz), 2.32 (3H, s), 2.58 (4H, t, J=5 Hz), 3.50 (2H, s), 3.68 (4H, t, J=5 Hz), 4.28 (2H, q, J=7 Hz), 4.62 (2H, s), 6.65 (1H, s), 6.74 (1H, s), 6.78 (1H, s), 7.50-7.60 (2H, m), 7.85 (1H, s).

Example 296

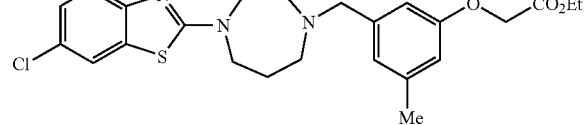

[Formula 586]

Yield: 93%, $^1$H-NMR (CDCl$_3$); δ1.30 (3H, t, J=6.9 Hz), 1.98-2.05 (2H, m), 2.30 (3H, s), 2.67 (2H, t, J=5.1 Hz), 2.77-2.81 (2H, m), 3.57 (2H, s), 3.71-3.75 (4H, m), 4.27 (2H, q, J=7.2 Hz), 4.60 (2H, s), 6.63 (1H, s), 6.73 (1H, s), 6.76 (1H, s), 7.23 (1H, dd, J=8.7, 2.4 Hz), 7.42 (1H, d, J=8.4 Hz), 7.55 (1H, d, J=2.1 Hz).

Example 297

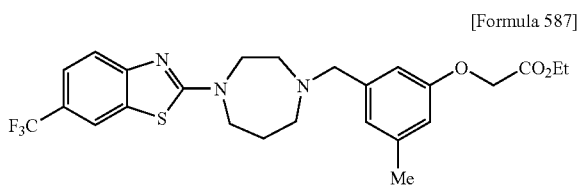

[Formula 587]

Yield: 66%, $^1$H-NMR (CDCl$_3$); δ1.29 (3H, t, J=7 Hz), 1.98-2.06 (2H, m), 2.30 (3H, s), 2.68 (2H, t, J=5.5 Hz), 2.81 (2H, t, J=5.5 Hz), 3.57 (2H, s), 3.70-3.85 (4H, m), 4.27 (2H, q, J=7 Hz), 4.60 (2H, s), 6.63 (1H, s), 6.73 (1H, s), 6.76 (1H, s), 7.48-7.58 (2H, m), 7.84 (1H, s).

Example 298

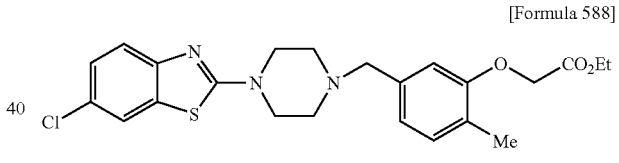

[Formula 588]

Yield: 68%, $^1$H-NMR (CDCl$_3$); δ1.29 (3H, t, J=7 Hz), 2.28 (3H, s), 2.55 (4H, t, J=5 Hz), 3.50 (2H, s), 3.62 (4H, t, J=5 Hz), 4.26 (2H, q, J=7 Hz), 4.65 (2H, s), 6.74 (1H, s), 6.84 (1H, d, J=7.5 Hz), 7.10 (1H, d, J=7.5 Hz), 7.23 (1H, dd, J=8.5, 2 Hz), 7.43 (1H, d, J=8.5 Hz), 7.55 (1H, d, J=2 Hz).

Example 299

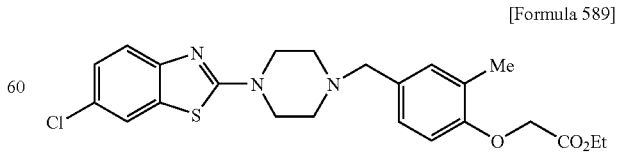

[Formula 589]

Yield: 84%, $^1$H-NMR (CDCl$_3$); δ1.30 (3H, t, J=7.2 Hz), 2.30 (3H, s), 2.55 (4H, t, J=5.1 Hz), 3.46 (2H, s), 3.62 (4H, t, J=5.1 Hz), 4.27 (2H, q, J=7.2 Hz), 4.64 (2H, s), 6.66 (1H, dd, J=8.1 Hz), 7.07 (1H, d, J=8.1 Hz), 7.13 (1H, s), 7.23 (1H, dd, J=8.4, 2.1 Hz), 7.43 (1H, dd, J=8.1 Hz), 7.55 (1H, d, J=2.1 Hz)

(1H, s), 6.78 (1H, s), 6.83 (1H, s), 7.23 (1H, dd, J=8.5, 2 Hz), 7.43 (1H, d, J=8.5 Hz), 7.55 (1H, d, J=2 Hz).

Example 300

[Formula 590]

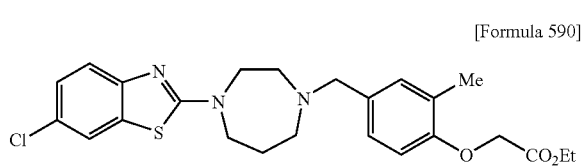

Yield: 90%, $^1$H-NMR (CDCl$_3$); δ1.30 (3H, t, J=7.2 Hz), 1.98-2.05 (2H, m), 2.28 (3H, s), 2.67 (2H, t, J=5.1 Hz), 2.78 (2H, t, J=5.1 Hz), 3.54 (2H, s), 3.71-3.78 (4H, m), 4.27 (2H, q, J=7.2 Hz), 4.63 (2H, s), 6.64 (1H, d, J=8.1 Hz), 7.05 (1H, d, J=8.1 Hz), 7.11 (1H, s), 7.22 (1H, dd, J=8.7, 2.1 Hz), 7.42 (1H, d, J=8.7 Hz), 7.54 (1H, d, J=2.1 Hz).

Example 301

[Formula 591]

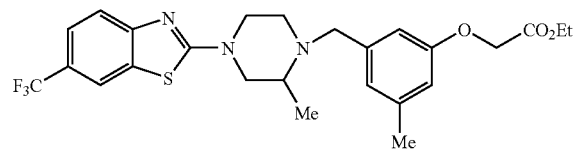

Yield: 92%, 1H-NMR (CDCl3): δ1.21 (3H, d, J=6 Hz), 1.31 (3H, t, J=7 Hz), 2.20-2.32 (1H, m), 2.33 (3H, s), 2.60-2.70 (1H, m), 2.77-2.85 (1H, m), 3.05-3.25 (2H, m), 3.35-3.50 (1H, m), 3.70-3.80 (1H, m), 3.85-3.95 (1H, m), 3.98 (1H, d, J=13.5 Hz), 4.28 (2H, q, J=7 Hz), 4.61 (2H, s), 6.63 (1H, s), 6.75 (1H, s), 6.78 (1H, s), 7.53 (1H, d, J=8.5 Hz), 7.56 (1H, d, J=8.5 Hz), 7.84 (1H, s).

Example 302

[Formula 592]

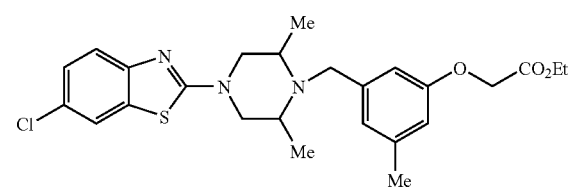

Yield: 74%, 1H-NMR (CDCl3): δ1.10 (6H, d, J=6 Hz), 1.30 (3H, t, J=7 Hz), 2.31 (3H, s), 2.70-2.85 (2H, m), 3.01 (1H, d, J=10.5 Hz), 3.05 (1H d, J=10.5 Hz), 3.76 (2H, s), 3.80-3.90 (2H, m), 4.27 (2H, q, J=7 Hz), 4.60 (2H, s), 6.57

Example 303

[Formula 593]

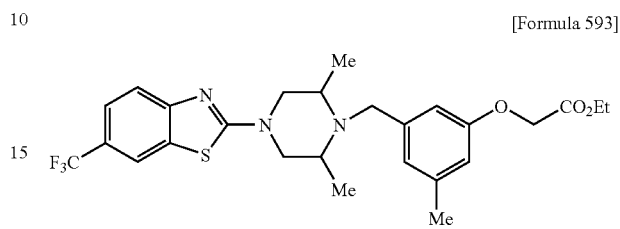

Yield: 93%, 1H-NMR (CDCl3): δ1.12 (6H, d, J=6 Hz), 1.30 (3H, t, J=7 Hz), 2.31 (3H, s), 2.70-2.90 (2H, m), 3.00-3.15 (2H, m), 3.77 (2H, s), 3.85-3.95 (2H, m), 4.27 (2H, q, J=7 Hz), 4.60 (2H, s), 6.57 (1H, s), 6.78 (1H, s), 6.84 (1H, s), 7.52 (1H, d, J=8.5 Hz), 7.56 (1H, d, J=8.5 Hz), 7.84 (1H, s).

Example 304

[Formula 594]

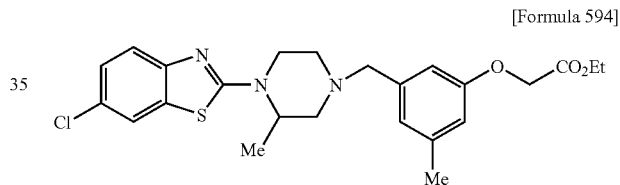

Yield: 95%, 1H-NMR (CDCl3): δ1.30 (3H, t, J=7 Hz), 1.41 (3H, d, J=7 Hz), 2.21 (1H, td, J=12, 3.5 Hz), 2.25-2.35 (1H, m), 2.32 (3H, s), 2.73 (1H, d, J=11 Hz), 2.90 (1H, d, J=11 Hz), 3.38 (1H, d, J=13.5 Hz), 3.48 (1H, td, J=12, 3.5 Hz), 3.52 (1H, d, J=13.5 Hz), 3.85 (1H, d, J=12 Hz), 4.15-4.25 (1H, m), 4.27 (2H, q, J=7 Hz), 4.61 (2H, s), 6.64 (1H, s), 6.76 (1H, s), 6.78 (1H, s), 7.22 (1H, dd, J=8, 2 Hz), 7.42 (1H, d, J=8 Hz), 7.54 (1H, d, J=2 Hz).

Example 305

[Formula 595]

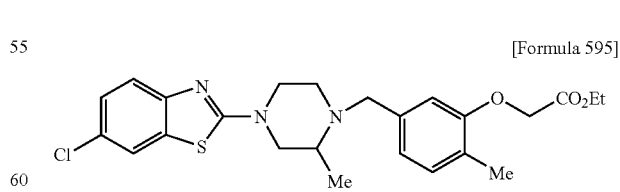

Yield: 43%, 1H-NMR (CDCl3): δ1.21 (3H, d, J=6 Hz), 1.30 (3H, t, J=7 Hz), 2.20-2.27 (1H, m), 2.28 (3H, s), 2.60-2.70 (1H, m), 2.75-2.85 (1H, m), 3.10-3.25 (2H, m), 3.35-3.50 (1H, m), 3.68-3.78 (1H, m), 3.85-3.95 (1H, m), 4.01 (1H, d, J=13 Hz), 4.27 (2H, q, J=7 Hz), 4.65 (2H, s), 6.74 (1H, s), 6.85 (1H, d, J=7.5 Hz), 7.11 (1H, d, J=7.5 Hz), 7.53 (1H, d, J=8.5 Hz), 7.56 (1H, d, J=8.5 Hz), 7.84 (1H, s).

Example 306

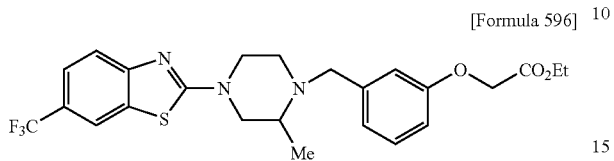

[Formula 596]

Yield: 79%, 1H-NMR (CDCl3): δ1.22 (3H, d, J=6.5 Hz), 1.31 (3H, t, J=7 Hz), 2.23-2.35 (1H, m), 2.60-2.73 (1H, m), 2.75-2.90 (1H, m), 3.15-3.25 (2H, m), 3.40-3.50 (1H, m), 3.70-3.82 (1H, m), 3.85-3.95 (1H, m), 4.03 (1H, d, J=13.5 Hz), 4.28 (2H, q, J=7 Hz), 4.63 (2H, s), 6.80 (1H, dd, J=8, 1.5 Hz), 6.93-7.02 (2H, m), 7.25 (1H, t, J=8 Hz), 7.53 (1H, d, J=8.5 Hz), 7.56 (1H, d, J=8.5 Hz), 7.84 (1H, s).

Example 307

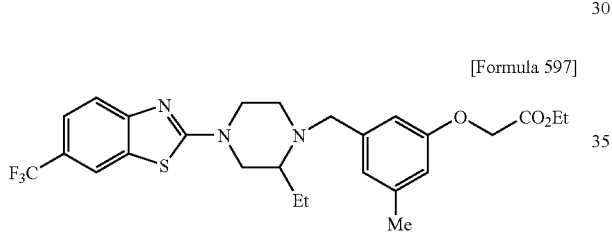

[Formula 597]

Yield: 81%, 1H-NMR (CDCl3): δ1.02 (3H, t, J=7.5 Hz), 1.31 (3H, t, J=7 Hz), 1.58-1.79 (2H, m), 2.31 (3H, s), 2.31-2.38 (1H, m), 2.47-2.58 (1H, m), 2.78-2.88 (1H, m), 3.23 (1H, d, J=13.5 Hz), 3.36-3.58 (2H, m), 3.64-3.75 (1H, m), 3.84 (1H, d, J=11 Hz), 3.95 (1H, d, J=13.5 Hz), 4.28 (2H, q, J=7 Hz), 4.62 (2H, s), 6.63 (1H, s), 6.77 (1H, s), 6.78 (1H, s), 7.51 (1H, d, J=8.5 Hz), 7.56 (1H, d, J=8.5 Hz), 7.84 (1H, s)

Example 308

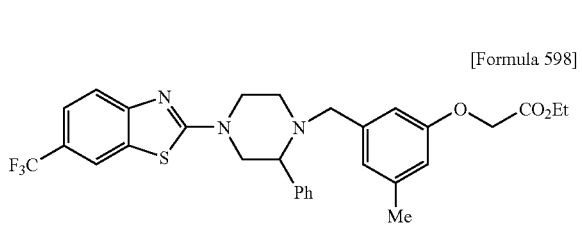

[Formula 598]

Yield: 91%, 1H-NMR (CDCl3): δ1.31 (3H, t, J=7 Hz), 2.25-2.35 (4H, m), 2.82 (1H, d, J=13.5 Hz), 3.01 (1H, d, J=11.5 Hz), 3.25-3.50 (3H, m), 3.79 (1H, d, J=13.5 Hz), 4.00-4.10 (2H, m), 4.28 (2H, q, J=7 Hz), 4.60 (2H, s), 6.59 (1H, s), 6.70 (1H, s), 6.72 (1H, s), 7.30-7.45 (3H, m), 7.50-7.58 (4H, m), 7.84 (1H, s).

Example 309

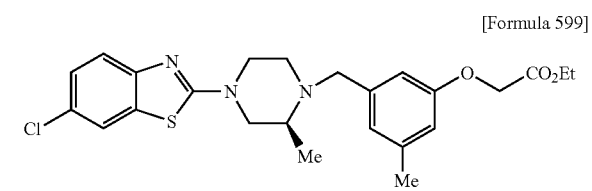

[Formula 599]

Yield: 90%, 1H-NMR (CDCl3): δ1.21 (3H, d, J=6.3 Hz), 1.31 (3H, t, J=7.2 Hz), 2.22-2.31 (1H, m), 2.32 (3H, s), 2.58-2.68 (1H, m), 2.83 (1H, dt, J=3.3, 12.3 Hz), 3.12-3.19 (2H, m), 3.34-3.43 (1H, m), 3.71 (1H, d, J=12.3 Hz), 3.86 (1H, d, J=10.5 Hz), 3.99 (1H, d, J=13.5 Hz), 4.28 (2H, q, J=7.2 Hz), 4.61 (2H, s), 6.63 (1H, s), 6.75 (1H, s), 6.78 (1H, s), 7.23 (1H, d, J=2.4, 8.7 Hz), 7.43 (1H, d, J=8.7 Hz), 7.55 (1H, d, J=2.4 Hz)

Example 310


[Formula 600]

Yield: 70%, 1H-NMR (CDCl3): δ1.21 (3H, d, J=6.3 Hz), 1.30 (3H, t, J=7.2 Hz), 2.23-2.32 (1H, m), 2.32 (3H, s), 2.58-2.67 (1H, m), 2.80 (1H, d, J=3.3, 12.3 Hz), 3.12-3.19 (2H, m), 3.35-3.42 (1H, m), 3.71 (1H, dt, J=12.0 Hz), 3.86 (1H, dt, J=12.0 Hz), 3.99 (1H, d, J=13.2 Hz), 4.28 (2H, q, J=7.2 Hz), 4.61 (2H, s), 6.63 (1H, s), 6.75 (1H, s), 6.78 (1H, s), 7.23 (1H, dd, J=2.1, 8.7 Hz), 7.43 (1H, d, J=8.7 Hz), 7.54 (1H, d, J=2.1 Hz)

Example 311

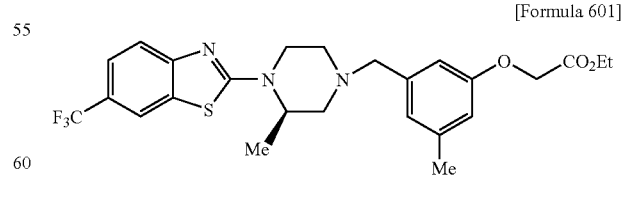

[Formula 601]

Yield: 89%, 1H-NMR (CDCl3): δ1.30 (3H, t, J=7 Hz), 1.43 (3H, d, J=6.5 Hz), 2.23 (1H, td, J=12, 3.5 Hz), 2.31 (3H, s), 2.31-2.40 (1H, m), 2.73 (1H, d, J=11 Hz), 2.91 (1H, d, J=11 Hz), 3.40 (1H, d, J=13 Hz), 3.46-3.51 (1H, m), 3.53 (1H, d, J=13 Hz), 3.85-3.95 (1H, m), 4.20-4.27 (1H, m), 4.28 (2H, q, J=7 Hz), 4.62 (2H, s), 6.65 (1H, s), 6.77 (1H, s), 6.79 (1H, s), 7.52 (1H, d, J=8.5 Hz), 7.56 (1H, d, J=8.5 Hz), 7.84 (1H, s).

Example 312

[Formula 602]

Yield: 84%, 1H-NMR (CDCl3): δ1.31 (3H, t, J=7.0 Hz), 1.43 (3H, d, J=6.5 Hz), 2.16-2.28 (1H, m), 2.30-2.39 (1H, m), 2.33 (3H, s), 2.70-2.78 (1H, m), 2.87-2.96 (1H, m), 3.40 (1H, d, J=13.5 Hz), 3.45-3.58 (2H, m), 3.86-3.97 (1H, m), 4.18-4.30 (1H, m), 4.28 (2H, q, J=7.0 Hz), 4.62 (2H, s), 6.65 (1H, s), 6.75-6.82 (2H, m), 7.48-7.60 (2H, m), 7.84 (1H, s).

Example 313

[Formula 603]

Yield: 86%, 1H-NMR (CDCl3): δ1.02 (3H, t, J=7.5 Hz), 1.31 (3H, t, J=7 Hz), 1.57-1.78 (2H, m), 2.30-2.33 (1H, m), 2.34 (3H, s), 2.48-2.60 (1H, m), 2.78-2.90 (1H, m), 3.17 (1H, d, J=13.5 Hz), 3.37-3.58 (2H, m), 3.62-3.73 (1H, m), 3.79-3.88 (1H, m), 3.95 (1H, d, J=13.5 Hz), 4.28 (2H, q, J=7 Hz), 4.61 (2H, s), 6.63 (1H, s), 6.76 (1H, s), 6.78 (1H, s), 7.51 (1H, d, J=8.5 Hz), 7.55 (1H, d, J=8.5 Hz), 7.83 (1H, s).

Example 314

[Formula 604]

Yield: 85%, 1H-NMR (CDCl3): δ1.02 (3H, t, J=7.5 Hz), 1.29 (3H, t, J=7 Hz), 1.58-1.78 (2H, m), 2.04 (3H, s), 2.05-2.15 (1H, m), 2.48-2.58 (1H, m), 2.79-2.89 (1H, m), 3.23 (1H, d, J=13.5 Hz), 3.42 (1H, dd, J=12.5, 8 Hz), 3.47-3.56 (1H, m), 3.63-3.72 (1H, m), 3.80-3.90 (1H, m), 3.95 (1H, d, J=13.5

Hz), 4.27 (2H, q, J=7 Hz), 4.61 (2H, s), 6.63 (1H, s), 6.78 (1H, s), 7.52 (1H, d, J=8.5 Hz), 7.56 (1H, d, J=8.5 Hz), 7.83 (1H, s).

Example 315

[Formula 605]

Yield: 60%, 1H-NMR (CDCl3): δ0.95 (3H, t, J=7.0 Hz), 1.22-1.68 (4H, m), 1.31 (3H, t, J=7.0 Hz), 2.27-2.40 (1H, m), 2.32 (3H, s), 2.54-2.65 (1H, m), 2.76-2.89 (1H, m), 3.25 (1H, d, J=13.5 Hz), 3.41 (1H, dd, J=13.0, 7.5 Hz), 3.48-3.59 (1H, m), 3.60-3.71 (1H, m), 3.83 (1H, dd, J=12.5, 3.5 Hz), 3.93 (1H, d, J=13.5 Hz), 4.28 (2H, q, J=7.0 Hz), 4.61 (2H, s), 6.63 (1H, s), 6.76 (1H, s), 6.78 (1H, s), 7.52 (1H, d, J=8.5 Hz), 7.56 (1H, d, J=8.5 Hz), 7.83 (1H, s).

Example 316

[Formula 606]

Yield: 90%, 1H-NMR (CDCl3): δ0.95 (3H, t, J=7.2 Hz), 1.31 (3H, t, J=7.2 Hz), 1.33-1.62 (4H, m), 2.32 (3H, s), 2.32-2.38 (1H, m), 2.57-2.62 (1H, m), 2.79-2.86 (1H, m), 3.24 (1H, d, J=13.5 Hz), 3.41 (1H, dd, J=7.8, 12.6 Hz), 3.38-3.44 (1H, m), 3.64-3.69 (1H, m), 3.83 (1H, dd, J=3.0, 12.6 Hz), 3.93 (1H, d, J=13.5 Hz), 4.28 (2H, q, J=7.2 Hz), 4.61 (2H, s), 6.63 (1H, s), 6.77 (2H, d, J=6.3 Hz), 7.53-7.55 (2H, m), 7.83 (1H, s)

Example 317

[Formula 607]

Yield: 64%, 1H-NMR (CDCl3): δ0.93 (3H, t, J=7.0 Hz), 1.22-1.75 (6H, m), 1.31 (3H, t, J=7.0 Hz), 2.27-2.39 (1H, m), 2.32 (3H, s), 2.51-2.64 (1H, m), 2.76-2.88 (1H, m), 3.24 (1H, d, J=13.0 Hz), 3.41 (1H, dd, J=13.0, 7.5 Hz), 3.47-3.59 (1H, m), 3.61-3.72 (1H, m), 3.84 (1H, dd, J=13.0, 3.0 Hz), 3.94 (1H, d, J=13.0 Hz), 4.28 (2H, q, J=7.0 Hz), 4.61 (2H, s), 6.63

(1H, s), 6.76 (1H, s), 6.78 (1H, s), 7.51 (1H, d, J=8.5 Hz), 7.56 (1H, d, J=8.5 Hz), 7.84 (1H, s).

Example 318

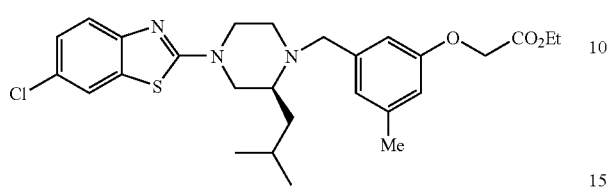

[Formula 608]

Yield: 83%, 1H-NMR (CDCl3): δ0.91 (3H, d, J=6.5 Hz), 0.95 (3H, d, J=6.5 Hz), 1.30 (3H, t, J=7 Hz), 1.35-1.45 (1H, m), 1.46-1.58 (1H, m), 1.65-1.80 (1H, m), 2.32 (3H, s), 2.33-2.44 (1H, m), 2.62-2.73 (1H, m), 2.75-2.86 (1H, m), 3.30 (1H, d, J=13.5 Hz), 3.35 (1H, dd, J=13, 6.5 Hz), 3.58 (2H, t, J=5 Hz), 3.75 (1H, dd, J=13, 6.5 Hz), 3.87 (1H, d, J=13.5 Hz), 4.28 (2H, q, J=7 Hz), 4.61 (2H, s), 6.62 (1H, s), 6.76 (1H, s), 6.78 (1H, s), 7.23 (1H, dd, J=8.5, 2 Hz), 7.42 (1H, d, J=8.5 Hz), 7.54 (1H, d, J=2 Hz).

Example 319

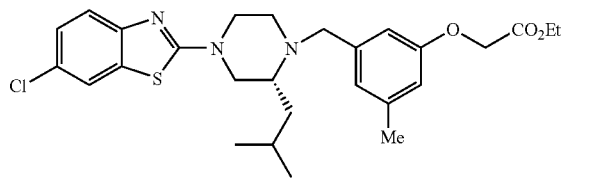

[Formula 609]

Yield: 68%, 1H-NMR (CDCl3): δ0.92 (3H, d, J=6.5 Hz), 0.95 (3H, d, J=7.0 Hz), 1.20-1.44 (1H, m), 1.30 (3H, t, J=6.5 Hz), 1.45-1.80 (2H, m), 2.27-2.47 (1H, m), 2.32 (3H, s), 2.61-2.72 (1H, m), 2.75-2.88 (1H, m), 3.25-3.41 (2H, m), 3.58 (2H, t, J=5.0 Hz), 3.75 (1H, dd, J=12.5, 3.5 Hz), 3.87 (1H, d, J=13.5 Hz), 4.28 (2H, q, J=7.0 Hz), 4.61 (2H, s), 6.62 (1H, s), 6.76 (1H, s), 6.78 (1H, s), 7.23 (1H, dd, J=8.0, 2.0 Hz), 7.42 (1H, d, J=8.0 Hz), 7.54 (1H, d, J=2.0 Hz).

Example 320

[Formula 610]

Yield: 85%, 1H-NMR (CDCl3): δ0.92 (3H, d, J=6.5 Hz), 0.95 (3H, d, J=6.5 Hz), 1.31 (3H, t, J=7 Hz), 1.34-1.45 (1H, m), 1.45-1.55 (1H, m), 1.65-1.80 (1H, m), 2.32 (3H, s), 2.35-2.46 (1H, m), 2.64-2.75 (1H, m), 2.78-2.88 (1H, m), 3.32 (1H, d, J=13.5 Hz), 3.42 (1H, dd, J=13, 6.5 Hz), 3.60-3.67 (2H, m), 3.79 (1H, dd, J=13, 3.5 Hz), 3.87 (1H, d, J=13.5 Hz), 4.28 (2H, q, J=7 Hz), 4.61 (2H, s), 6.63 (1H, s), 6.77 (1H, s), 6.79 (1H, s), 7.51 (1H, d, J=8.5 Hz), 7.56 (1H, d, J=8.5 Hz), 7.83 (1H, s).

Example 321

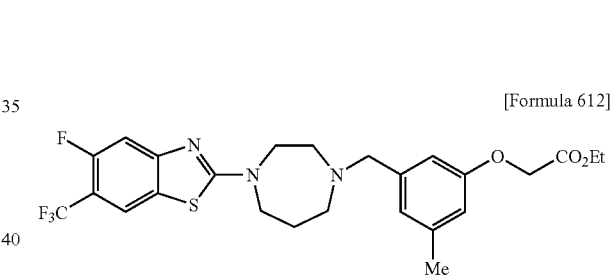

[Formula 611]

Yield: 98%, 1H-NMR (CDCl3): δ1.21 (3H, d, J=6 Hz), 1.31 (3H, t, J=7 Hz), 2.20-2.32 (1H, m), 2.32 (3H, s), 2.59-2.70 (1H, m), 2.75-2.88 (1H, m), 3.16 (1H, d, J=13.5 Hz), 3.17-3.25 (1H, m), 3.48-3.50 (1H, m), 3.69-3.80 (1H, m), 3.85-3.95 (1H, m), 3.98 (1H, d, J=13.5 Hz), 4.28 (2H, q, J=7 Hz), 4.62 (2H, s), 6.63 (1H, s), 6.75 (1H, s), 6.78 (1H, s), 7.26 (1H, d, J=12 Hz), 7.74 (1H, d, J=7 Hz).

Example 322

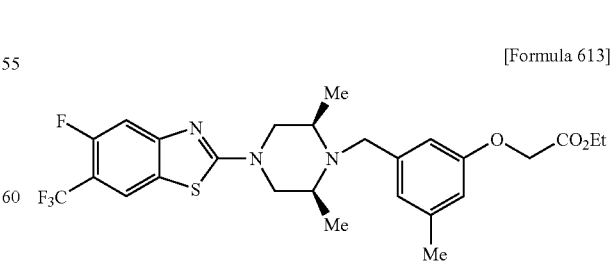

[Formula 612]

Yield: 69%, 1H-NMR (CDCl3): δ1.30 (3H, t, J=7.0 Hz), 1.96-2.08 (2H, m), 2.30 (3H, s), 2.63-2.71 (2H, m), 2.74-2.84 (2H, m), 3.57 (2H, s), 3.60-3.89 (4H, m), 4.27 (2H, q, J=7.0 Hz), 4.60 (2H, s), 6.62 (1H, s), 6.73 (1H, s), 6.75 (1H, s), 7.27 (1H, d, J=7.0 Hz), 7.75 (1H, d, J=11.5 Hz).

Example 323

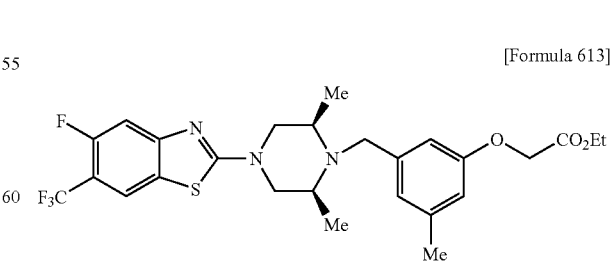

[Formula 613]

Yield: 75%, 1H-NMR (CDCl3): δ1.12 (6H, d, J=6.0 Hz), 1.30 (3H, t, J=7.0 Hz), 2.32 (3H, s), 2.72-2.86 (2H, m), 3.07 (1H, d, J=13.0 Hz), 3.11 (1H, d, J=13.0 Hz), 3.77 (2H, s), 3.89

(2H, d, J=11.0 Hz), 4.28 (2H, q, J=7.0 Hz), 4.60 (2H, s), 6.57 (1H, s), 6.78 (1H, s), 6.84 (1H, s), 7.27 (1H, d, J=11.5 Hz), 7.75 (1H, d, J=6.0 Hz).

(1H, s), 6.80 (1H, s), 6.86 (1H, s), 7.34-7.43 (1H, m), 7.52-7.62 (1H, m), 7.67 (1H, dd, J=8.5, 1.5 Hz), 7.87 (1H, dd, J=8.5, 1.5 Hz), 8.56 (1H, s).

Example 324

[Formula 614]

Yield: 79%, 1H-NMR (CDCl3): δ1.01 (3H, t, J=7.5 Hz), 1.31 (3H, t, J=7.0 Hz), 1.50-1.80 (2H, m), 2.26-2.39 (1H, m), 2.32 (3H, s), 2.47-2.58 (1H, m), 2.77-2.88 (1H, m), 3.24 (1H, d, J=13.5 Hz), 3.36-3.57 (2H, m), 3.61-3.73 (1H, m), 3.77-3.88 (1H, m), 3.94 (1H, d, J=13.5 Hz), 4.28 (2H, q, J=7.0 Hz), 4.61 (2H, s), 6.62 (1H, s), 6.73-6.82 (2H, m), 7.26 (1H, d, J=11.5 Hz), 7.74 (1H, d, J=7.0 Hz)

Example 327

[Formula 617]

Yield: 79%, 1H-NMR (CDCl3): δ1.25 (3H, d, J=6.0 Hz), 1.31 (3H, t, J=7.0 Hz), 2.20-2.32 (1H, m), 2.33 (3H, s), 2.55-2.68 (1H, m), 2.85 (1H, dt, J=12.0, 3.5 Hz), 3.14 (1H, d, J=13.0 Hz), 3.16 (1H, d, J=13.5 Hz), 3.30-3.43 (1H, m), 4.02 (1H, d, J=13.0 Hz), 4.04-4.15 (1H, m), 4.17-4.26 (1H, m), 4.28 (2H, q, J=7.0 Hz), 4.62 (2H, s), 6.63 (1H, s), 6.77 (1H, s), 6.80 (1H, s), 7.34-7.42 (1H, m), 7.52-7.61 (1H, m), 7.67 (1H, dd, J=8.5, 1.5 Hz), 7.87 (1H, dd, J=8.5, 1.5 Hz), 8.55 (1H, s).

Example 325

[Formula 615]

Yield: 71%, 1H-NMR (CDCl$_3$): δ1.29 (3H, t, J=7.0 Hz), 2.31 (3H, s), 2.54 (4H, t, J=5.0 Hz), 3.47 (2H, s), 3.52 (4H, t, J=5.0 Hz), 4.26 (2H, q, J=7.0 Hz), 4.60 (2H, s), 6.64 (1H, s), 6.74 (1H, s), 6.78 (1H, s), 7.18 (1H, tt, J=7.5, 1.5 Hz), 7.26-7.35 (2H, m), 7.37-7.44 (3H, m).

Example 328

[Formula 618]

Yield: 74%, 1H-NMR (CDCl3): δ1.15 (6H, d, J=6.0 Hz), 1.30 (3H, t, J=7.0 Hz), 2.32 (3H, s), 2.67-2.81 (2H, m), 2.93 (1H, d, J=13.0 Hz), 2.97 (1H, d, J=13.0 Hz), 3.78 (2H, s), 4.24-4.35 (2H, m), 4.27 (2H, q, J=7.0 Hz), 4.61 (2H, s), 6.66 (1H, s), 6.79 (1H, s), 6.86 (1H, s), 7.50 (1H, dd, J=9.5, 2.0 Hz), 7.59 (1H, d, J=9.5 Hz), 7.85 (1H, d, J=2.0 Hz), 8.54 (1H, s).

Example 326

[Formula 616]

Yield: 74%, 1H-NMR (CDCl3): δ1.15 (6H, d, J=7.0 Hz), 1.30 (3H, t, J=7.0 Hz), 2.32 (3H, s), 2.68-2.83 (2H, m), 2.93 (1H, d, J=13.0 Hz), 2.96 (1H, d, J=13.0 Hz), 3.78 (2H, s), 4.26-4.38 (2H, m), 4.27 (2H, q, J=7.0 Hz), 4.61 (2H, s), 6.57

Example 329

[Formula 619]

Yield: 51%, 1H-NMR (CDCl3): δ1.15 (6H, d, J=6.0 Hz), 1.29 (3H, t, J=7.0 Hz), 2.31 (3H, s), 2.65-2.79 (2H, m), 2.95 (1H, d, J=13.0 Hz), 2.99 (1H, d, J=13.0 Hz), 3.76 (2H, s), 4.26

(2H, q, J=7.0 Hz), 4.35 (2H, d, J=12.0 Hz), 4.62 (2H, s), 6.58 (1H, s), 6.79 (1H, s), 6.86 (1H, s), 7.69 (1H, s), 7.70 (1H, s), 8.13 (1H, s), 8.59 (1H, s).

Example 330

Preparation of 4-{[4-(6-chlorobenzothiazole-2-yl)piperazine-1-yl]methyl}phenoxyethyl acetate

[Formula 620]

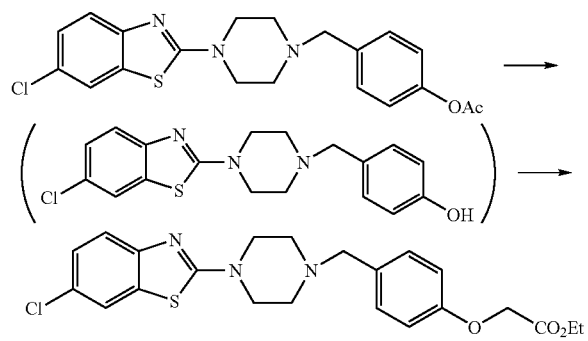

A mixture of acetic acid 4-{[4-(6-chlorobenzothiazole-2-yl)piperazine-1-yl]methyl}phenyl ester (0.33 g; 0.834 mmol), lithium hydroxide (0.04 g; 0.831 mmol) and THF (8 ml) was stirred at room temperature for 5 hours. The solvent was evaporated under reduced pressure. To the residue were added bromoethyl acetate (0.14 ml; 1.26 mmol), cesium carbonate (0.41 g; 1.26 mmol) and anhydrous N,N-dimethylformamide (4 ml). The mixture was stirred at room temperature for 17 hours. Water and ethyl acetate were added to the reaction solution and extracted with ethyl acetate. The organic layer was washed with brine, dried over anhydrous sodium sulphate, and evaporated under reduced pressure. The residue was purified by column chromatograph on silica gel (hexane:ethyl acetate=2:1) to give 4-{[4-(6-chlorobenzothiazole-2-yl)piperazine-1-yl]methyl}phenoxyethyl acetate as colorless oil (0.35 g; 93%).

$^1$H-NMR (CDCl$_3$): δ1.31 (3H, t, J=7.2 Hz), 2.55 (4H, t, J=5.1 Hz), 3.50 (2H, s), 3.62 (4H, t, J=5.1 Hz), 4.28 (2H, q, J=7.2 Hz), 4.66 (2H, s), 6.88 (1H, d, J=8.1 Hz), 7.22-7.26 (4H, m), 7.43 (1H, d, J=8.1 Hz), 7.55 (1H, d, J=2.1 Hz).

Example 331

Preparation of 3-chloro-5-{[4-(6-chlorobenzothiazole-2-yl)piperazine-1-yl]methyl}phenoxyethyl acetate

[Formula 621]

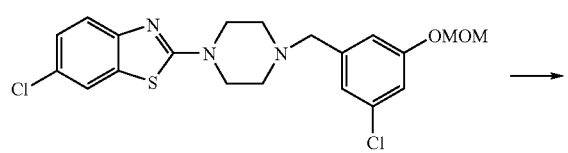

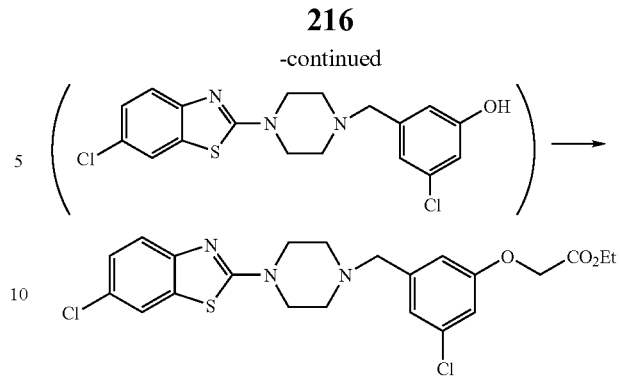

A mixture of 3-chloro-5-[4-(2-methoxymethoxy-3-methylbenzyl)piperazine-1-yl]benzothiazole (0.15 g; 0.346 mmol) and 4N hydrochloric acid/dioxane solution (8.5 ml) was stirred at 60° C. for 2 hours. After cooling, the reaction solution was condensed under reduced pressure. To the residue were added bromoethyl acetate (0.05 ml; 0.451 mmol), cesium carbonate (0.50 g; 1.56 mmol) and anhydrous N,N-dimethylformamide (3 ml). The mixture was stirred at room temperature for 17 hours. Water and ethyl acetate were added to the reaction solution and extracted with etyl acetate. The organic layer was washed with brine, dried over anhydrous sodium sulphate, and evaporated under reduced pressure. The residue was purified by column chromatograph on silica gel (hexane:ethyl acetate=2:1) to give 3-chloro-5-{[4-(6-chlorobenzothiazole-2-yl)piperazine-1-yl]methyl}phenoxyethyl acetate as colorless oil (0.13 g; 77%).

$^1$H-NMR (CDCl$_3$): δ1.31 (3H, t, J=6.9 Hz), 2.56 (4H, t, J=5.1 Hz), 3.49 (2H, s), 3.63 (4H, t, J=5.1 Hz), 4.28 (2H, q, J=6.9 Hz), 4.61 (2H, s), 6.87 (1H, t, J=1.5 Hz), 6.84 (1H, s), 6.99 (1H, t, J=1.5 Hz), 7.24 (1H, dd, J=2.1, 8.7 Hz), 7.44 (1H, d, J=8.7 Hz), 7.55 (1H, dd, J=2.1 Hz)

Example 332

The following compound was obtained by a similar method as Example 129 with a compound in Example 217 as a raw material.

[Formula 622]

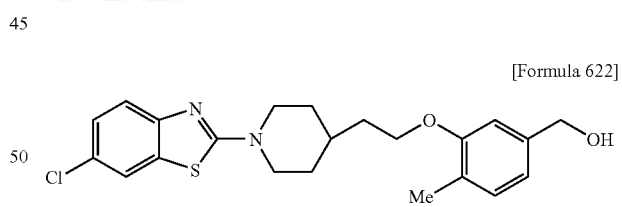

Yield: 84%, $^1$H-NMR (CDCl$_3$); δ1.31-1.50 (2H, m), 1.65 (1H, s), 1.74-1.96 (5H, m), 2.21 (3H, s), 3.07-3.20 (2H, m), 4.02-4.18 (4H, m), 4.65 (2H, d, J=5.5 Hz), 6.83 (1H, d, J=7.5 Hz), 6.86 (1H, s), 7.12 (1H, d, J=7.5 Hz), 7.22 (1H, dd, J=8.5, 2.0 Hz), 7.42 (1H, d, J=8.5 Hz), 7.54 (1H, d, J=2.0 Hz).

Example 333

The following compound was obtained by a similar method as Example 154 with a compound in Example 332 as a raw material.

[Formula 623]

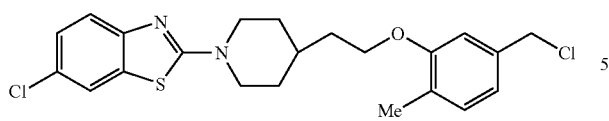

Yield: 79%, ¹H-NMR (CDCl₃); δ1.33-1.52 (2H, m), 1.78-1.98 (5H, m), 2.21 (3H, s), 3.08-3.21 (2H, m), 4.03-4.17 (4H, m), 4.50 (2H, s), 6.82-6.90 (2H, m), 7.11 (1H, d, J=7.5 Hz), 7.22 (1H, dd, J=8.5, 2.0 Hz), 7.42 (1H, d, J=8.5 Hz), 7.55 (1H, d, J=2.0 Hz).

Example 334

The following compound was obtained by a similar method as Example 179 with a compound in Example 333 as a raw material.

[Formula 624]

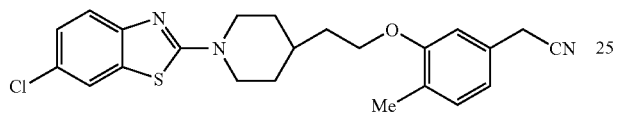

Yield: 96%, ¹H-NMR (CDCl₃); δ1.34-1.52 (2H, m), 1.77-1.97 (5H, m), 2.21 (3H, s), 3.08-3.22 (2H, m), 3.72 (2H, s), 4.01-4.19 (4H, m), 6.75-6.81 (2H, m), 7.13 (1H, d, J=7.5 Hz), 7.23 (1H, dd, J=8.5, 2.0 Hz), 7.42 (1H, d, J=8.5 Hz), 7.55 (1H, d, J=2.0 Hz).

Example 335

Preparation of 3-{2-[1-(6-chlorobenzothiazole-2-yl)piperidine-4-yl]ethoxy}benzoic acid

[Formula 625]

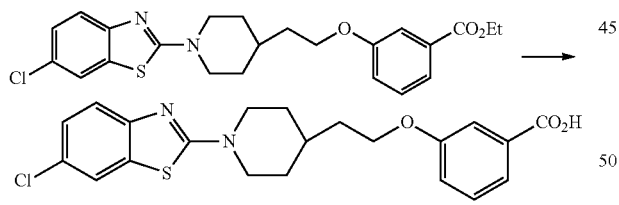

A mixture of Ethyl 3-{2-[1-(6-chlorobenzothiazole-2-yl)piperidine-4-yl]ethoxy}benzoate (0.30 g; 6.671 mmol), 2N-aqueous sodium hydroxide (1.5 ml) and methanol (3 ml) was stirred at 60° C. for 1 hour. The reaction solution was condensed under reduced pressure. To the residue were added water and 2N aqueous hydrochloric acid to be neutral. The precipitate was collected and washed with water and diisopropyl ether to give 3-{2-[1-(6-chlorobenzothiazole-2-yl)piperidine-4-yl]ethoxy}benzoic acid as colorless crystal (0.26 g; 93%).

¹H-NMR (DMSO-d₆): δ1.20-1.39 (2H, m), 1.66-1.93 (5H, m), 3.10-3.26 (2H, m), 3.94-4.16 (4H, m), 7.20 (1H, dd, J=8.5, 2.5 Hz), 7.27 (1H, d, J=8.5, 2.0 Hz), 7.36-7.47 (3H, m), 7.52 (1H, d, J=7.5 Hz), 7.89 (1H, d, J=2.0 Hz).

Compounds in Examples 336 to 489 were obtained by similar methods as Example 335.

Example 336

[Formula 626]

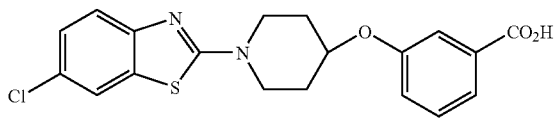

Yield: 18%, ¹H-NMR (DMSO-d₆): δ1.68-1.84 (2H, m), 2.00-2.15 (2H, m), 3.50-3.64 (2H, m), 3.78-3.92 (2H, m), 4.68-4.81 (1H, m), 7.12-7.18 (1H, m), 7.26-7.39 (2H, m), 7.43 (1H, d, J=8.5 Hz), 7.48-7.55 (2H, m), 7.91 (1H, d, J=2.0 Hz).

Example 337

[Formula 627]

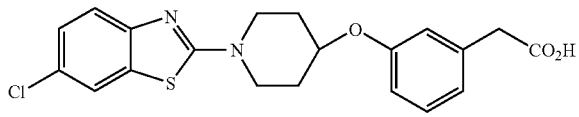

Yield: 27%, ¹H-NMR (DMSO-d₆): δ1.66-1.83 (2H, m), 2.00-2.15 (2H, m), 3.48-3.64 (4H, m), 3.78-3.93 (2H, m), 4.62-4.75 (1H, m), 6.80-6.98 (3H, m), 7.19-7.28 (1H, m), 7.29 (1H, dd, J=8.5, 2.5 Hz), 7.44 (1H, d, J=8.5 Hz), 7.90 (1H, d, J=2.5 Hz), 12.29 (1H, s).

Example 338

[Formula 628]

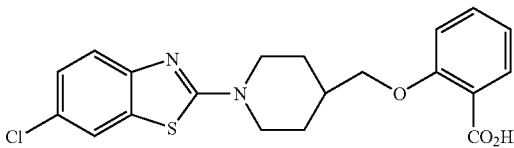

Yield: 84%, ¹H-NMR (DMSO-d₆): δ1.35-1.55 (2H, m), 1.85-2.00 (2H, m), 2.00-2.20 (1H, m), 3.10-3.30 (2H, m), 3.94 (2H, d, J=6 Hz), 4.00-4.15 (2H, m), 6.98 (1H, t, J=7.5 Hz), 7.10 (1H, d, J=7.5 Hz), 7.27 (1H, dd, J=8.5, 2 Hz), 7.41 (1H, d, J=8.5 Hz), 7.47 (1H, t, J=7.5 Hz), 7.61 (1H, d, J=7.5 Hz), 7.89 (1H, d, J=2 Hz), 12.50 (1H, brs).

Example 339

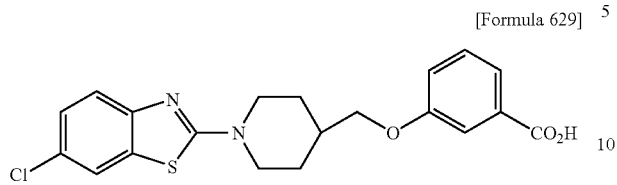

[Formula 629]

Yield: 84%, ¹H-NMR (DMSO-d₆): δ1.30-1.50 (2H, m), 1.80-1.95 (2H, m), 2.00-2.15 (1H, m), 3.15-3.30 (2H, m), 3.93 (2H, d, J=6 Hz), 4.00-4.15 (2H, m), 7.20 (1H, dd, J=8, 2.5 Hz), 7.27 (1H, dd, J=8.5, 2 Hz), 7.35-7.45 (3H, m), 7.52 (1H, d, J=8 Hz), 7.88 (1H, d, J=2 Hz), 13.0 (1H, brs).

Example 340

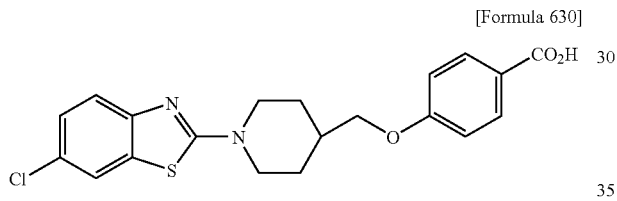

[Formula 630]

Yield: 59%, ¹H-NMR (DMSO-d₆): δ1.30-1.50 (2H, m), 1.85-1.95 (2H, m), 2.00-2.20 (1H, m), 3.00-3.20 (2H, m), 3.96 (2H, d, J=6.5 Hz), 4.04-4.14 (2H, m), 7.00 (2H, d, J=8 Hz), 7.28 (1H, dd, J=8.5, 1.5 Hz), 7.41 (1H, d, J=8.5 Hz), 7.87 (2H, d, J=8 Hz), 7.89 (1H, d, J=1.5 Hz).

Example 341

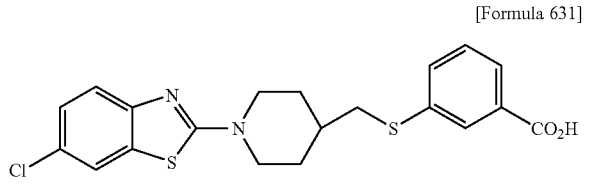

[Formula 631]

Yield: 88%, ¹H-NMR (DMSO-d₆): δ1.20-1.45 (2H, m), 1.70-1.90 (1H, m), 1.90-2.05 (2H, m), 3.02 (2H, d, J=7 Hz), 3.10-3.25 (2H, m), 3.95-4.10 (2H, m), 7.70 (1H, dd, J=8.5, 2 Hz), 7.40 (1H, d, J=8.5 Hz), 7.44 (1H, t, J=7.5 Hz), 7.59 (1H, d, J=7.5 Hz), 7.73 (1H, d, J=7.5 Hz), 7.83 (1H, s), 7.88 (1H, d, J=2 Hz), 13.40 (1H, brs).

Example 342

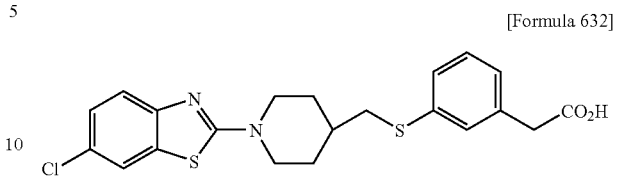

[Formula 632]

Yield: 32%, ¹H-NMR (CDCl₃); δ1.30-1.48 (2H, m), 1.70-1.90 (1H, m), 1.85-2.05 (2H, m), 2.88 (2H, d, J=7 Hz), 3.02-3.15 (2H, m), 3.63 (2H, s), 4.05-4.18 (2H, m), 7.05-7.15 (1H, m), 7.24 (1H, dd, J=8.5, 2 Hz), 7.25-7.30 (3H, m), 7.42 (1H, d, J=8.5 Hz), 7.53 (1H, d, J=2 Hz).

Example 343

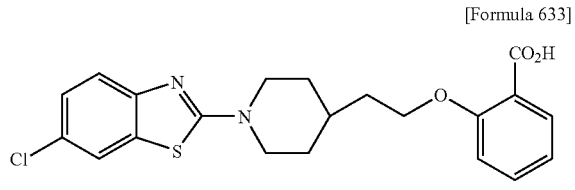

[Formula 633]

Yield: 88%, ¹H-NMR (DMSO-d₆): δ1.20-1.38 (2H, m), 1.71 (2H, q, J=6.0 Hz), 1.78-1.94 (3H, m), 3.09-3.23 (2H, m), 3.95-4.07 (2H, m), 4.10 (2H, t, J=6.0 Hz), 6.99 (1H, td, J=7.5, 1.5 Hz), 7.14 (1H, d, J=7.5 Hz), 7.27 (1H, dd, J=8.5, 2.0 Hz), 7.40 (1H, d, J=8.5 Hz), 7.48 (1H, td, J=1.5, 7.5 Hz), 7.60 (1H, dd, J=7.5, 1.5 Hz), 7.88 (1H, d, J=2.0 Hz), 12.55 (1H, br).

Example 344

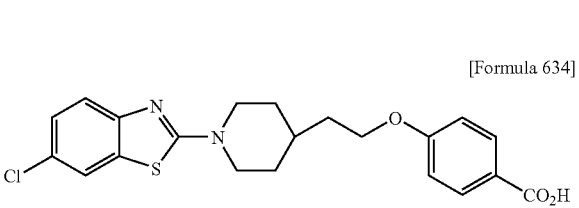

[Formula 634]

Yield: 82%, ¹H-NMR (DMSO-d₆): δ1.20-1.39 (2H, m), 1.68-1.92 (5H, m), 3.10-3.26 (2H, m), 3.08-4.08 (2H, m), 4.12 (2H, t, J=6.0 Hz), 7.03 (2H, d, J=9.0 Hz), 7.27 (1H, dd, J=8.5, 2.0 Hz), 7.40 (1H, d, J=8.5 Hz), 7.88 (1H, d, J=2.0 Hz), 7.88 (2H, d, J=9.0 Hz), 12.62 (1H, br).

Example 345

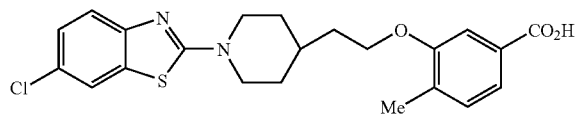
[Formula 635]

Yield: 75%, ¹H-NMR (DMSO-d₆): δ1.22-1.40 (2H, m), 1.70-1.92 (5H, m), 2.21 (3H, s), 3.12-3.24 (2H, m), 3.96-4.08 (2H, m), 4.09 (2H, t, J=6.0 Hz), 7.25 (1H, d, J=8.0 Hz), 7.27 (1H, dd, J=8.5, 2.0 Hz), 7.40 (1H, d, J=8.5 Hz), 7.43 (2H, m), 7.88 (1H, d, J=2.0 Hz).

Example 346

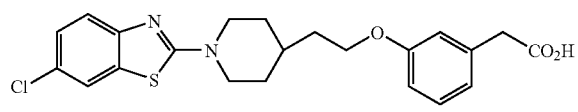
[Formula 636]

Yield: 78%, ¹H-NMR (DMSO-d₆): δ1.18-1.38 (2H, m), 1.64-1.91 (5H, m), 3.11-3.24 (2H, m), 3.52 (2H, s), 3.96-4.07 (4H, m), 6.78-6.87 (3H, m), 7.21 (1H, t, J=7.5 Hz), 7.27 (1H, dd, J=8.5, 2.0 Hz), 7.40 (1H, d, J=8.5 Hz), 7.88 (1H, d, J=2.0 Hz), 12.31 (1H, brs).

Example 347

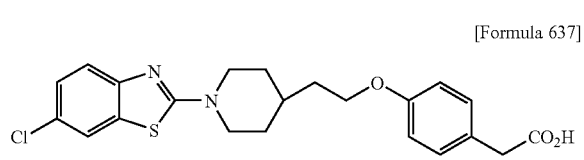
[Formula 637]

Yield: 84%, ¹H-NMR (DMSO-d₆): δ1.19-1.39 (2H, m), 1.64-1.92 (5H, m), 3.09-3.28 (2H, m), 3.47 (2H, s), 3.95-4.10 (4H, m), 6.80 (2H, d, J=8.5 Hz), 7.15 (2H, d, J=8.5 Hz), 7.27 (1H, dd, J=8.5, 2.0 Hz), 7.40 (1H, d, J=8.5 Hz), 7.88 (1H, d, J=2.0 Hz).

Example 348

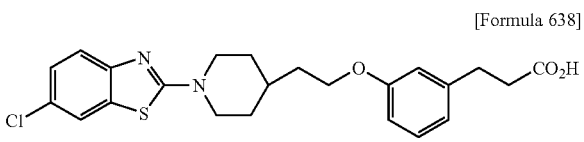
[Formula 638]

Yield: 35%, ¹H-NMR (CDCl₃); δ1.18-1.37 (2H, m), 1.68-1.91 (5H, m), 2.77 (2H, t, J=7.5 Hz), 3.09-3.43 (4H, m), 3.94-4.06 (4H, m), 6.71-6.83 (3H, m), 7.16 (1H, t, J=8.0 Hz), 7.27 (1H, dd, J=8.5, 2.0 Hz), 7.40 (1H, d, J=8.5 Hz), 7.88 (1H, d, J=2.0 Hz).

Example 349

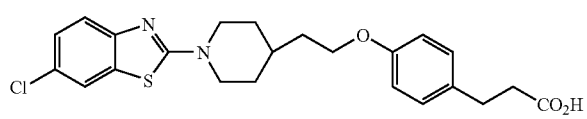
[Formula 639]

Yield: 27%, ¹H-NMR (DMSO-d₆): δ1.18-1.42 (2H, m), 1.68-1.94 (5H, m), 2.47 (2H, t, J=7.5 Hz), 2.80 (2H, t, J=7.5 Hz), 3.10-3.23 (2H, m), 3.96-4.10 (4H, m), 6.84 (1H, t, J=7.5 Hz), 6.96 (1H, d, J=7.5 Hz), 7.12-7.21 (2H, m), 7.27 (1H, dd, J=8.5, 2.0 Hz), 7.40 (1H, d, J=8.5 Hz), 7.88 (1H, d, J=2.0 Hz), 12.09 (1H, s).

Example 350

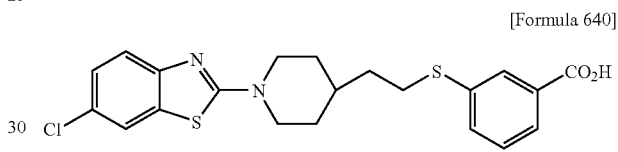
[Formula 640]

Yield: 27%, ¹H-NMR (DMSO-d₆): δ1.14-1.31 (2H, m), 1.50-1.61 (2H, m), 1.64-1.86 (3H, m), 2.96-3.22 (4H, m), 3.93-4.03 (2H, m), 7.23-7.36 (3H, m), 7.39 (1H, d, J=8.5 Hz), 7.67 (1H, d, J=7.0 Hz), 7.81 (1H, s), 7.88 (1H, d, J=2.0 Hz).

Example 351

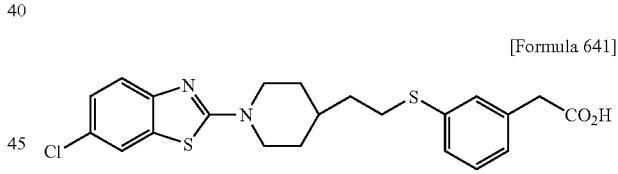
[Formula 641]

Yield: 72%, ¹H-NMR (DMSO-d₆): δ1.12-1.32 (2H, m), 1.50-1.63 (2H, m), 1.64-1.87 (3H, m), 2.95-3.06 (2H, m), 3.07-3.22 (2H, m), 3.55 (2H, s), 3.92-4.08 (2H, m), 4.05 (1H, d, J=2.0 Hz), 7.17-7.31 (4H, m), 7.39 (1H, d, J=8.5 Hz), 7.87 (1H, d, J=7.5 Hz), 12.36 (1H, brs).

Example 352

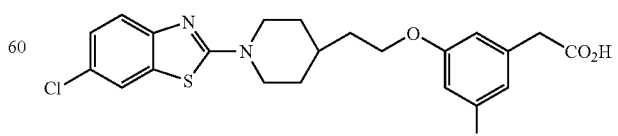
[Formula 642]

Yield: 65%, ¹H-NMR (CDCl₃); δ1.33 (2H, m), 1.73-1.90 (5H, m), 2.31 (3H, s), 3.14 (2H, t, J=12.6 Hz), 3.58 (2H, s), 4.01 (2H, t, J=5.7 Hz), 4.11 (2H, d, J=14.1 Hz), 6.65 (2H, s), 6.70 (1H, s), 7.23 (1H, dd, J=8.4, 2.1 Hz), 7.43 (1H, d, J=8.4 Hz), 7.54 (1H, d, J=2.1 Hz)

Example 353

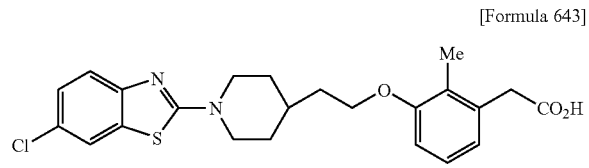
[Formula 643]

Yield: 90%, $^1$H-NMR (DMSO-d$_6$): δ1.23-1.36 (2H, m), 1.72-1.87 (5H, m), 2.07 (3H, s), 3.15-3.23 (2H, m), 3.56 (2H, s), 4.01 (4H, t, J=5.7 Hz), 6.77 (1H, d, J=8.1 Hz), 6.87 (1H, d, J=8.1 Hz), 7.07 (1H, t, J=8.1 Hz), 7.28 (1H, dd, J=8.7, 2.1 Hz), 7.40 (1H, d, J=8.7 Hz), 7.89 (1H, d, J=2.1 Hz).

Example 354

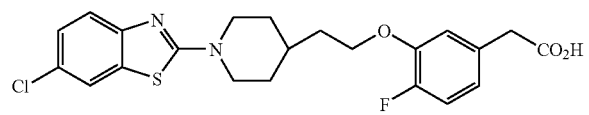
[Formula 644]

Yield: 65%, $^1$H-NMR (DMSO-d$_6$): δ1.20-1.35 (1H, m), 1.65-1.90 (6H, m), 3.10-3.25 (2H, m), 3.54 (2H, s), 3.95-4.15 (4H, m), 6.75-6.85 (1H, m), 7.10 (1H, dd, J=8, 3.5 Hz), 7.14 (1H, d, J=8 Hz), 7.24 (1H, dd, J=8.5, 2 Hz), 7.40 (1H, d, J=8.5 Hz), 7.88 (1H, d, J=2 Hz), 12.34 (1H, brs).

Example 355

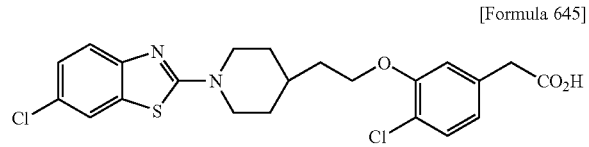
[Formula 645]

Yield: 36%, $^1$H-NMR (DMSO-d$_6$): δ1.20-1.39 (2H, m), 1.66-1.93 (5H, m), 3.08-3.23 (2H, m), 3.40 (2H, s), 3.94-4.13 (4H, m), 6.76-6.84 (1H, m), 7.06 (1H, s), 7.23-7.32 (2H, m), 7.36-7.43 (1H, m), 7.87 (1H, d, J=2.0 Hz).

Example 356

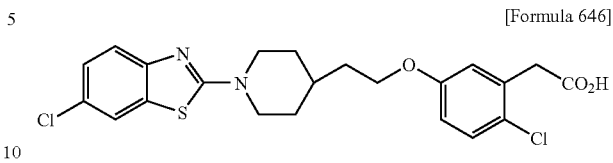
[Formula 646]

Yield: 59%, $^1$H-NMR (DMSO-d$_6$): δ1.17-1.37 (2H, m), 1.62-1.91 (5H, m), 3.09-3.25 (2H, m), 3.34 (2H, s), 3.92-4.07 (4H, m), 6.75 (1H, dd, J=8.5, 3.0 Hz), 6.92 (1H, d, J=3.0 Hz), 7.21 (1H, d, J=8.5 Hz), 7.27 (1H, dd, J=8.5, 2.0 Hz), 7.40 (1H, d, J=8.5 Hz), 7.88 (1H, d, J=2.0 Hz).

Example 357

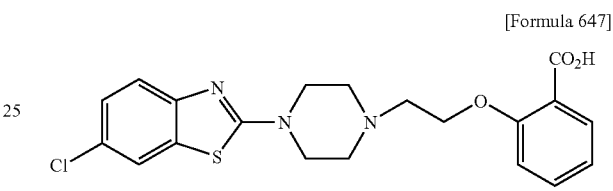
[Formula 647]

Yield: 63%, $^1$H-NMR (DMSO-d$_6$): δ2.69 (4H, t, J=4.5 Hz), 2.80 (2H, t, J=5.5 Hz), 3.56 (4H, t, J=4.5 Hz), 4.22 (2H, t, J=5.5 Hz), 7.01 (1H, t, J=7.5 Hz), 7.16 (1H, d, J=7.5 Hz), 7.29 (1H, dd, J=8.5, 2.0 Hz), 7.43 (1H, d, J=8.5 Hz), 7.48 (1H, t, J=7.5 Hz), 7.61 (1H, d, J=7.5 Hz), 7.91 (1H, d, J=2.0 Hz).

Example 358

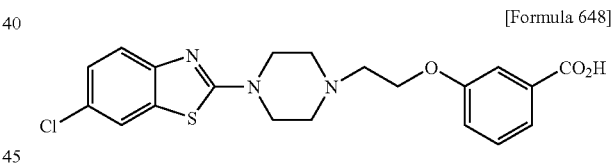
[Formula 648]

Yield: 31%, $^1$H-NMR (DMSO-d$_6$): δ2.65 (4H, t, J=5.0 Hz), 2.80 (2H, t, J=5.5 Hz), 3.57 (4H, t, J=5.0 Hz), 4.15 (2H, t, J=5.5 Hz), 7.10 (1H, d, J=8.0 Hz), 7.27-7.36 (2H, m), 7.41-7.52 (3H, m), 7.91 (1H, d, J=2.2 Hz).

Example 359

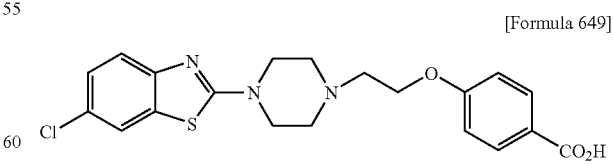
[Formula 649]

Yield: 50%, $^1$H-NMR (DMSO-d$_6$): δ2.64 (4H, t, J=5.0 Hz), 2.80 (2H, t, J=5.5 Hz), 3.57 (4H, t, J=5.0 Hz), 4.20 (2H, t, J=5.5 Hz), 7.03 (2H, d, J=9 Hz), 7.29 (1H, dd, J=8.5, 2.0 Hz), 7.42 (1H, d, J=8.5 Hz), 7.87 (2H, d, J=9.0 Hz), 7.91 (1H, d, J=2.0 Hz).

Example 360

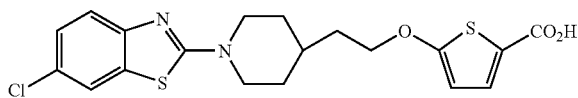
[Formula 650]

Yield: 29%, ¹H-NMR (DMSO-d₆): δ1.18-1.36 (2H, m), 1.68-1.88 (5H, m), 3.00-3.25 (2H, m), 3.94-4.07 (2H, m), 4.20 (2H, t, J=6.0 Hz), 6.41 (1H, d, J=4.0 Hz), 7.27 (1H, dd, J=8.5, 2.0 Hz), 7.40 (1H, d, J=8.5 Hz), 7.44 (1H, d, J=4.0 Hz), 7.88 (1H, d, J=2.0 Hz).

Example 361

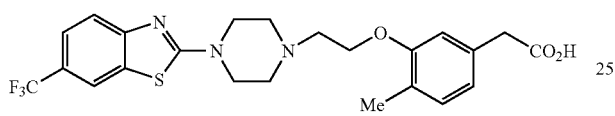
[Formula 651]

Yield: 64%, ¹H-NMR (DMSO-d₆): δ2.13 (3H, s), 2.68 (4H, t, J=5 Hz), 2.82 (2H, t, J=5.5 Hz), 3.47 (2H, s), 3.63 (4H, t, J=5 Hz), 4.10 (2H, t, J=5.5 Hz), 6.72 (1H, d, J=8 Hz), 6.86 (1H, s), 7.05 (1H, d, J=7.5 Hz), 7.57 (2H, s), 8.25 (1H, s), 12.50 (1H, brs).

Example 362

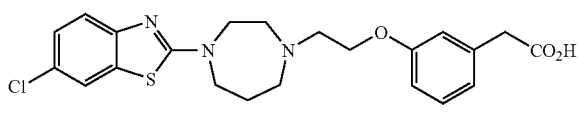
[Formula 652]

Yield: 25%, ¹H-NMR (DMSO-d₆): δ1.88-1.94 (2H, m), 2.73-2.75 (2H, m), 2.87 (2H, t, J=5.1 Hz), 2.92-2.95 (2H, m), 3.25 (2H, s), 3.67-3.72 (4H, m), 4.01 (2H, t, J=5.7 Hz), 6.68-6.82 (3H, m), 7.10 (1H, t, J=7.5 Hz), 7.26 (1H, dd, J=8.7, 2.1 Hz), 7.40 (1H, d, J=8.7 Hz), 7.88 (1H, d, J=2.1 Hz).

Example 363

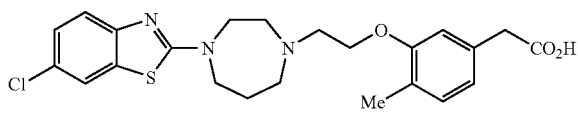
[Formula 653]

Yield: 68%, ¹H-NMR (DMSO-d₆): δ1.85-1.95 (2H, m), 2.09 (3H, s), 2.75-2.82 (2H, m), 2.92 (2H, t, J=5.5 Hz), 2.95-3.02 (2H, m), 3.49 (2H, s), 3.60-3.75 (4H, m), 4.03 (2H, t, J=5.5 Hz), 6.71 (1H, d, J=7.5 Hz), 6.83 (1H, s), 7.03 (1H, d, J=7.5 Hz), 7.26 (1H, dd, J=8.5, 2 Hz), 7.39 (1H, d, J=8.5 Hz), 7.87 (1H, d, J=2 Hz), 12.37 (1H, brs).

Example 364

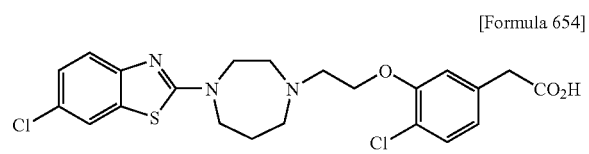
[Formula 654]

Yield: 67%, ¹H-NMR (DMSO-d₆): δ1.85-1.95 (2H, m), 2.75-2.85 (2H, m), 2.93 (2H, t, J=5.5 Hz), 2.95-3.05 (2H, m), 3.55 (2H, s), 3.60-3.80 (4H, m), 4.12 (2H, t, J=5.5 Hz), 6.83 (1H, dd, J=8, 1.5 Hz), 7.07 (1H, d, J=1.5 Hz), 7.25 (1H, dd, J=8.5, 2 Hz), 7.33 (1H, d, J=8 Hz), 7.39 (1H, d, J=8.5 Hz), 7.87 (1H, d, J=2 Hz), 12.37 (1H, brs).

Example 365

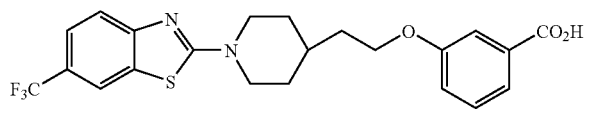
[Formula 655]

Yield: 45%, ¹H-NMR (DMSO-d₆): δ1.20-1.39 (2H, m), 1.65-1.94 (5H, m), 3.17-3.32 (2H, m), 3.99-4.12 (4H, m), 6.92-6.99 (1H, m), 7.23 (1H, t, J=7.5 Hz), 7.40-7.48 (2H, m), 7.51-7.59 (2H, m), 8.21 (1H, s).

Example 366

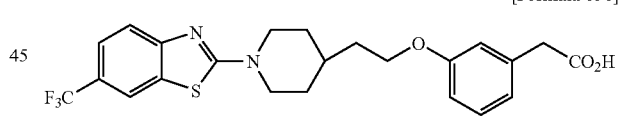
[Formula 656]

Yield: 48%, ¹H-NMR (DMSO-d₆): δ1.18-1.38 (2H, m), 1.63-1.94 (5H, m), 3.13-3.30 (2H, m), 3.32 (2H, s), 3.93-4.13 (4H, m), 6.70-6.85 (3H, m), 7.13 (1H, t, J=8.0 Hz), 7.49-7.60 (2H, m), 8.21 (1H, s).

Example 367

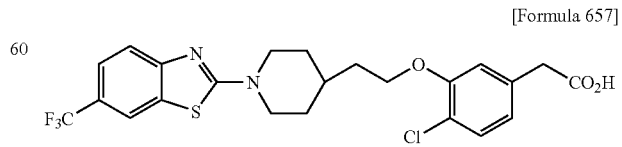
[Formula 657]

Yield: 82%, ¹H-NMR (DMSO-d₆): δ1.17-1.42 (2H, m), 1.68-1.96 (5H, m), 3.13-3.30 (2H, m), 3.43 (2H, s), 3.95-4.19

(4H, m), 6.81 (1H, d, J=7.5 Hz), 7.07 (1H, s), 7.28 (1H, d, J=7.5 Hz), 7.49-7.61 (2H, m), 8.21 (1H, s).

Example 368

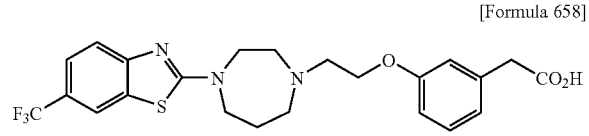

[Formula 658]

Yield: 77%, ¹H-NMR (DMSO-$d_6$): δ1.85-2.00 (2H, m), 2.68-2.81 (2H, m), 2.82-3.03 (4H, m), 3.51 (2H, s), 3.60-3.89 (4H, m), 3.97-4.09 (2H, m), 6.75-6.90 (3H, m), 7.19 (1H, t, J=8.0 Hz), 7.50-7.60 (2H, m), 8.22 (1H, s), 12.26 (1H, br).

Example 369

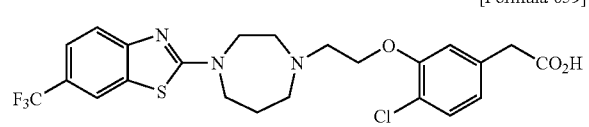

[Formula 659]

Yield: 78%, ¹H-NMR (DMSO-$d_6$): δ1.84-1.98 (2H, m), 2.74-2.85 (2H, m), 2.86-3.07 (4H, m), 3.56 (2H, s), 3.60-3.85 (4H, m), 4.06-4.18 (2H, m), 6.83 (1H, dd, J=8.0, 2.0 Hz), 7.07 (1H, d, J=2.0 Hz), 7.33 (1H, d, J=8.0 Hz), 7.51-7.57 (2H, m), 8.22 (1H, s), 12.35 (1H, br).

Example 370

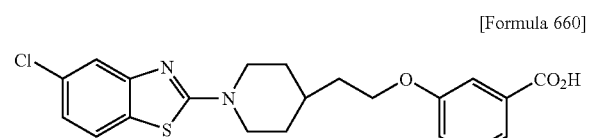

[Formula 660]

Yield: 68%, ¹H-NMR (CDCl$_3$); δ1.19-1.39 (2H, m), 1.64-1.92 (5H, m), 3.12-3.27 (2H, m), 3.96-4.08 (4H, m), 6.80-6.87 (1H, m), 7.06 (1H, dd, J=8.0, 2.0 Hz), 7.15 (1H, t, J=8.0 Hz), 7.38-7.47 (3H, m), 7.76 (1H, d, J=8.0 Hz).

Example 371

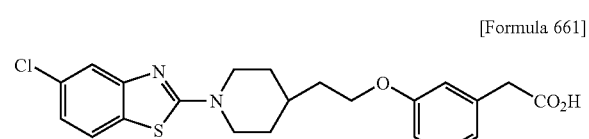

[Formula 661]

Yield: 87%, ¹H-NMR (DMSO-$d_6$): δ1.19-1.40 (2H, m), 1.63-1.92 (5H, m), 3.10-3.27 (2H, m), 3.51 (2H, s), 3.94-4.10

(4H, m), 6.77-6.86 (3H, m), 7.07 (1H, dd, J=8.5, 2.0 Hz), 7.20 (1H, t, J=7.5 Hz), 7.44 (1H, d, J=2.0 Hz), 7.76 (1H, d, J=8.5 Hz), 12.33 (1H, br).

Example 372

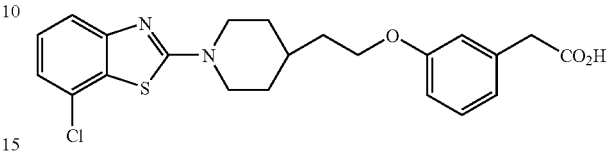

[Formula 662]

Yield: 36%, ¹H-NMR (DMSO-$d_6$): δ1.20-1.39 (2H, m), 1.63-1.93 (5H, m), 3.12-3.28 (2H, m), 3.53 (2H, s), 3.95-4.12 (4H, m), 6.78-6.88 (3H, m), 7.13 (1H, dd, J=8.0, 1.0 Hz), 7.20 (1H, t, J=7.5 Hz), 7.31 (1H, d, J=8.0 Hz), 7.39 (1H, dd, J=8.0, 1.0 Hz), 12.31 (1H, s).

Example 373

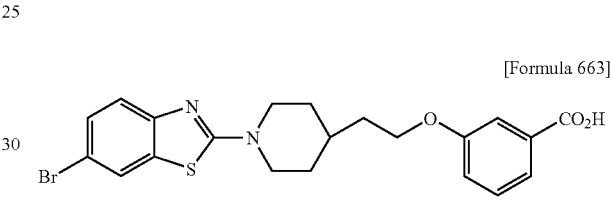

[Formula 663]

Yield: 89%, ¹H-NMR (DMSO-$d_6$): δ1.19-1.39 (2H, m), 1.65-1.93 (5H, m), 3.10-3.25 (2H, m), 3.96-4.09 (4H, m), 6.87-6.94 (1H, m), 7.20 (1H, t, J=8.0 Hz), 7.31-7.48 (4H, m), 8.00 (1H, d, J=2.0 Hz).

Example 374

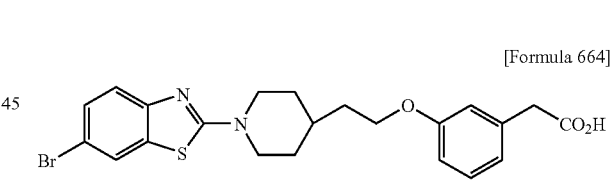

[Formula 664]

Yield: 58%, ¹H-NMR (DMSO-$d_6$): δ1.18-1.37 (2H, m), 1.63-1.91 (5H, m), 3.10-3.26 (4H, m), 3.92-4.07 (4H, m), 6.63-6.84 (3H, m), 7.08 (1H, t, J=8.0 Hz), 7.31-7.42 (2H, m), 7.99 (1H, d, J=2.0 Hz).

Example 375

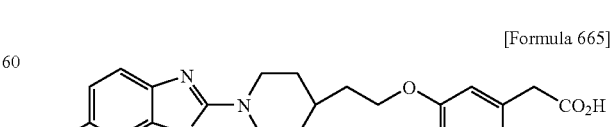

[Formula 665]

Yield: 46%, ¹H-NMR (DMSO-$d_6$): δ1.18-1.36 (2H, m), 1.61-1.90 (5H, m), 2.32 (3H, s), 3.04-3.19 (2H, m), 3.39 (2H, s), 3.91-4.07 (4H, m), 6.72-6.86 (3H, m), 7.06 (1H, d, J=8.5 Hz), 7.16 (1H, t, J=8.0 Hz), 7.31 (1H, d, J=8.5 Hz), 7.53 (1H, s).

Example 376

[Formula 666]

Yield: 83%, $^1$H-NMR (DMSO-$d_6$): δ1.18-1.39 (2H, m), 1.63-1.92 (5H, m), 3.07-3.24 (2H, m), 3.52 (2H, s), 3.93-4.09 (4H, m), 6.77-6.78 (3H, m), 7.10 (1H, td, J=9.0, 2.5 Hz), 7.21 (1H, t, J=8.0 Hz), 7.41 (1H, dd, J=9.0, 4.5 Hz), 7.69 (1H, dd, J=9.0, 2.5 Hz), 12.34 (1H, br).

Example 377

[Formula 667]

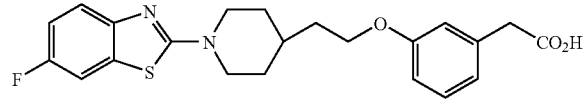

Yield: 51%, $^1$H-NMR (DMSO-$d_6$): δ1.18-1.35 (2H, m), 1.63-1.93 (5H, m), 3.09-3.26 (2H, m), 3.52 (2H, s), 3.95-4.13 (4H, m), 6.77-6.90 (3H, m), 7.20 (1H, t, J=8.0 Hz), 7.31 (1H, t, J=8.0 Hz), 7.43 (2H, t, J=8.0 Hz), 7.48 (1H, d, J=8.5 Hz), 7.57 (1H, d, J=8.5 Hz), 7.66 (2H, d, J=8.0 Hz), 8.07 (1H, s), 12.31 (1H, br).

Example 378

[Formula 668]

Yield: 77%, $^1$H-NMR (DMSO-$d_6$): δ1.19-1.40 (2H, m), 1.64-1.91 (5H, m), 2.98-3.14 (2H, m), 3.53 (2H, s), 3.86-4.10 (4H, m), 6.78-6.90 (3H, m), 7.16-7.26 (2H, m), 7.31-7.34 (2H, m), 7.44-7.50 (2H, m), 7.58 (1H, s), 12.30 (1H, s).

Example 379

[Formula 669]

Yield: 76%, $^1$H-NMR (DMSO-$d_6$): δ1.22-1.41 (2H, m), 1.68-1.90 (5H, m), 2.97-3.13 (2H, m), 3.56 (2H, s), 3.86-3.99 (2H, m), 4.06-4.16 (2H, m), 6.84 (1H, dd, J=8.0, 1.5 Hz), 7.09 (1H, d, J=1.5 Hz), 7.20 (1H, t, J=7.5 Hz), 7.31-7.41 (3H, m), 7.43-7.51 (2H, m), 7.58 (1H, s).

Example 380

[Formula 670]

Yield: 69%, 1H-NMR (DMSO-d6): δ1.83-1.95 (2H, m), 2.73-2.83 (2H, m), 2.87-3.00 (4H, m), 3.52-3.71 (6H, m), 4.12 (2H, m), 6.83 (1H, d, J=7.0 Hz), 7.08 (1H, s), 7.18 (1H, t, J=7.5 Hz), 7.28-7.38 (3H, m), 7.40-7.47 (2H, m), 7.56 (1H, s).

Example 381

[Formula 671]

Yield: 79%, $^1$H-NMR (DMSO-d6): δ1.20-1.41 (2H, m), 1.65-1.93 (5H, m), 3.05 (2H, m), 3.53 (2H, s), 3.90-4.10 (4H, m), 6.76-6.87 (3H, m), 7.16-7.32 (3H, m), 7.38 (2H, t, J=7.5 Hz), 7.85 (2H, d, J=7.5 Hz), 12.29 (1H, s).

Example 382

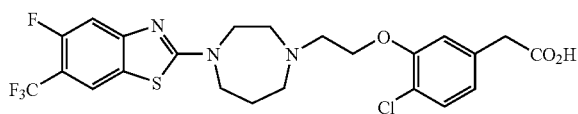

Yield: 54%, 1H-NMR (CDCl3): 1.88-2.03 (2H, m), 2.73-3.04 (6H, m), 3.30 (2H, s), 3.47-3.84 (4H, m), 3.86-4.02 (2H, m), 6.59 (1H, d, J=8.0 Hz), 6.68 (1H, s), 7.07 (1H, d, J=8.0 Hz), 7.20 (1H, d, J=11.5 Hz), 7.68 (1H, d, J=7.0 Hz).

Example 383

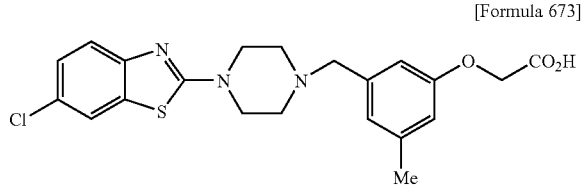

Yield 12%, $^1$H-NMR (DMSO-$d_6$): δ2.25 (3H, s), 2.45-2.55 (4H, m), 3.44 (2H, s), 3.50-3.60 (4H, m), 4.47 (2H, s), 6.59 (1H, s), 6.65 (1H, s), 7.00 (1H, s), 7.28 (1H, dd, J=8.5, 2 Hz), 7.42 (1H, d, J=8.5 Hz), 7.90 (1H, d, J=2 Hz).

Example 384

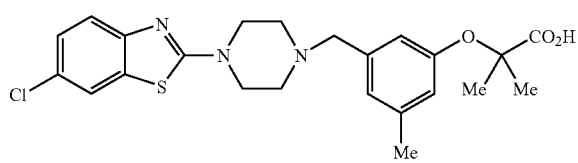

Yield 68%, $^1$H-NMR (CDCl$_3$); δ1.60 (6H, s), 2.23 (3H, s), 2.65 (4H, t, J=5 Hz), 3.57 (2H, s), 3.62 (4H, t, J=5 Hz), 6.19 (1H, brs), 6.70-6.88 (3H, m), 7.24 (1H, dd, J=8.5, 2 Hz), 7.42 (1H, d, J=8.5 Hz), 7.54 (1H, d, J=2 Hz).

Example 385

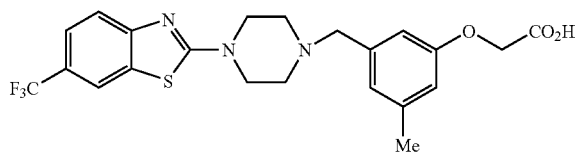

Yield 64%, $^1$H-NMR (DMSO-$d_6$): δ2.24 (3H, s), 2.51 (4H, t, J=5.5 Hz), 3.43 (2H, s), 3.62 (4H, t, J=5.5 Hz), 4.10 (2H, s), 6.53 (1H, s), 6.61 (1H, s), 6.64 (1H, s), 7.57 (2H, s), 8.24 (1H, s).

Example 386

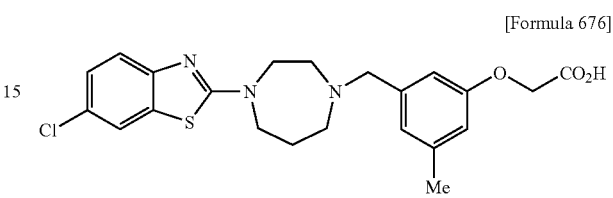

Yield 96%, $^1$H-NMR (DMSO-$d_6$): δ1.89-1.97 (2H, m), 2.23 (3H, s), 2.60 (2H, t, J=4.2 Hz), 2.74-2.77 (2H, m), 3.55 (2H, s), 3.68-3.70 (4H, m), 4.56 (2H, s), 6.58 (1H, s), 6.65 (1H, s), 6.70 (1H, s), 7.26 (1H, dd, J=9.0, 2.1 Hz), 7.39 (1H, d, J=8.7 Hz), 7.86 (1H, d, J=2.4 Hz).

Example 387


Yield 98%, $^1$H-NMR (DMSO-$d_6$): δ1.85-2.00 (2H, m), 2.20 (3H, s), 2.55-2.65 (2H, m), 2.70-2.83 (2H, m), 3.52 (2H, s), 3.55-3.85 (4H, m), 4.14 (2H, s), 6.52 (1H, s), 6.58-6.65 (2H, m), 7.55 (2H, s), 8.22 (1H, s).

Example 388

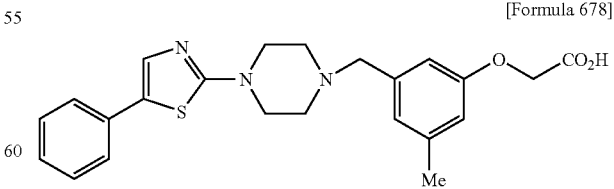

Yield 59%, 1H-NMR (CD3OD): δ2.29 (3H, s), 2.60 (4H, t, J=5.0 Hz), 3.46-3.57 (6H, m), 4.36 (2H, s), 6.69 (1H, s), 6.75 (2H, s), 7.21 (1H, t, J=7.5 Hz), 7.33 (2H, t, J=7.5 Hz), 7.41 (1H, s), 7.45 (2H, d, J=7.5 Hz).

Example 389

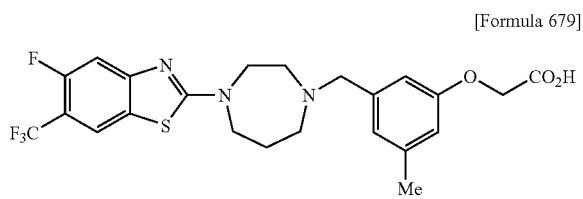

Yield 67%, 1H-NMR (CD3OD): δ1.98-2.12 (2H, m), 2.27 (3H, s), 2.70-2.81 (2H, m), 2.84-2.94 (2H, m), 3.65 (2H, s), 3.67-3.93 (4H, m), 4.39 (2H, s), 6.67 (1H, s), 6.73 (1H, s), 6.74 (1H, s), 7.27 (1H, d, J=12.0 Hz), 7.96 (1H, d, J=7.0 Hz).

Example 390

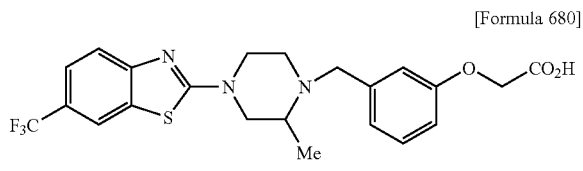

Yield 97%, 1H-NMR (DMSO-d6): δ1.15 (3H, d, J=6 Hz), 2.18-2.33 (1H, m), 2.58-2.70 (1H, m), 2.70-2.83 (1H, m), 3.15-3.30 (2H, m), 3.35-3.50 (1H, m), 3.65-3.80 (1H, m), 3.83 (1H, d, J=11 Hz), 3.93 (1H, d, J=14 Hz), 4.65 (2H, s), 6.78 (1H, d, J=8 Hz), 6.90-6.95 (2H, m), 7.24 (1H, t, J=8 Hz), 7.56 (2H, s), 8.24 (1H, s), 13.0 (1H, brs).

Example 391

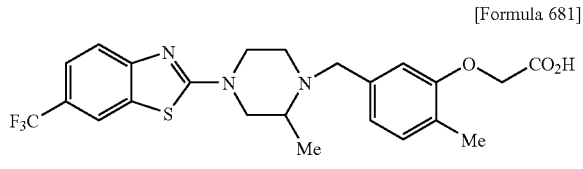

Yield 86%, 1H-NMR (DMSO-d6): δ1.13 (3H, d, J=6 Hz), 2.17 (3H, s), 2.20-2.30 (1H, m), 2.55-2.65 (1H, m), 2.68-2.80 (1H, m), 3.15-3.50 (3H, m), 3.65-3.75 (1H, m), 3.82 (1H, d, J=9 Hz), 3.88 (1H, d, J=13.5 Hz), 4.68 (2H, s), 6.80 (1H, s), 6.83 (1H, d, J=7.5 Hz), 7.09 (1H, d, J=7.5 Hz), 7.56 (2H, s), 8.23 (1H, s), 12.30 (1H, brs).

Example 392

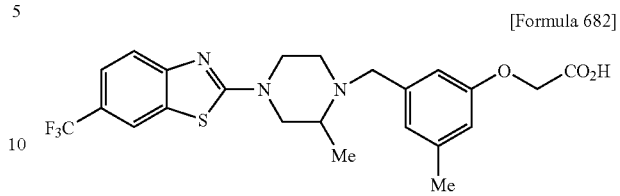

Yield 86%, 1H-NMR (DMSO-d6): δ1.14 (3H, d, J=6 Hz), 2.20-2.25 (1H, m), 2.26 (3H, s), 2.55-2.65 (1H, m), 2.70-2.80 (1H, m), 3.10-3.50 (3H, m), 3.70-3.82 (3H, m), 4.63 (2H, s), 6.61 (1H, s), 6.70 (1H, s), 6.75 (1H, s), 7.55-7.59 (2H, m), 8.24 (1H, s), 12.9 (1H, brs).

Example 393

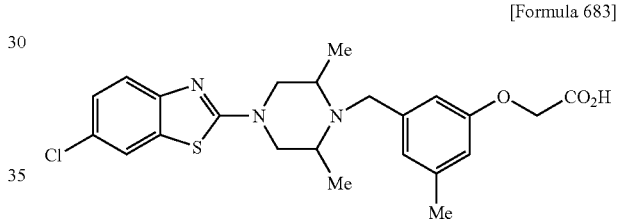

Yield 73%, 1H-NMR (DMSO-d6): δ1.03 (6H, d, J=6 Hz), 2.25 (3H, s), 2.60-2.80 (2H, m), 2.95-3.10 (2H, m), 3.71 (2H, s), 3.80-3.85 (2H, m), 4.61 (2H, s), 6.55 (1H, s), 6.76 (2H, s), 7.28 (1H, dd, J=8.5, 2 Hz), 7.42 (1H, d, J=8.5 Hz), 7.90 (1H, d, J=2 Hz), 12.95 (1H, s).

Example 394

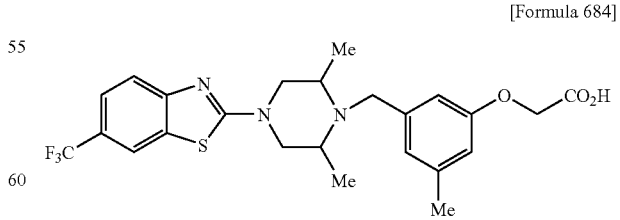

Yield 82%, 1H-NMR (DMSO-d6): δ1.04 (6H, d, J=6 Hz), 2.25 (3H, s), 2.70-2.80 (2H, m), 2.95-3.15 (2H, m), 3.71 (2H, s), 3.80-3.95 (2H, m), 4.61 (2H, s), 6.55 (1H, s), 6.76 (2H, s), 7.57 (2H, s), 8.24 (1H, s), 12.94 (1H, brs).

Example 395

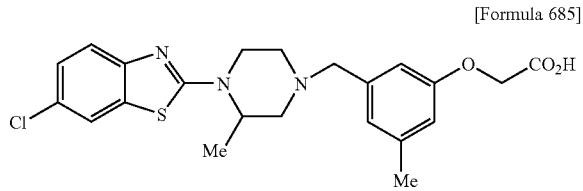

[Formula 685]

Yield 72%, 1H-NMR (DMSO-d6): δ1.31 (3H, d, J=6.5 Hz), 2.02-2.24 (2H, m), 2.25 (3H, s), 2.70 (1H, d, J=11 Hz), 2.88 (1H, d, J=12 Hz), 3.20-3.35 (1H, m), 3.37 (1H, d, J=13.5 Hz), 3.51 (1H, d, J=13.5 Hz), 3.77 (1H, d, J=13 Hz), 4.10-4.25 (1H, m), 4.60 (2H, s), 6.61 (1H, s), 6.70 (1H, s), 6.73 (1H, s), 7.26 (1H, dd, J=8.5, 2 Hz), 7.40 (1H, d, J=8.5 Hz), 7.88 (1H, d, J=2 Hz), 13.00 (1H, brs).

Example 396

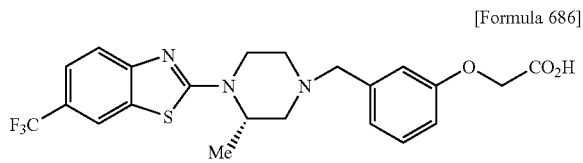

[Formula 686]

Yield 76%, 1H-NMR (DMSO-d6): δ1.34 (3H, d, J=6.5 Hz), 2.06-2.30 (5H, m), 2.73 (1H, d, J=10.5 Hz), 2.90 (1H, d, J=10.5 Hz), 3.30-3.56 (3H, m), 3.84 (1H, d, J=11.5 Hz), 4.19-4.32 (1H, m), 4.38 (2H, s), 6.58 (1H, s), 6.67 (1H, s), 6.70 (1H, s), 7.56 (2H, s), 8.24 (1H, s).

Example 397

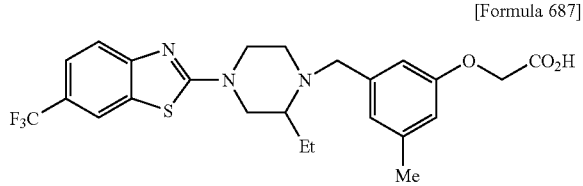

[Formula 687]

Yield 82%, 1H-NMR (CDCl3): δ0.97 (3H, t, J=7.5 Hz), 1.62-1.85 (2H, m), 2.28 (3H, s), 2.80-3.00 (3H, m), 3.55 (1H, d, J=13 Hz), 3.65-3.77 (1H, m), 3.77-3.90 (3H, m), 4.23 (1H, d, J=13 Hz), 4.65 (2H, s), 6.63 (1H, s), 6.80 (1H, s), 7.01 (1H, s), 7.53 (1H, d, J=8.5 Hz), 7.56 (1H, d, J=8.5 Hz), 7.84 (1H, s).

Example 398

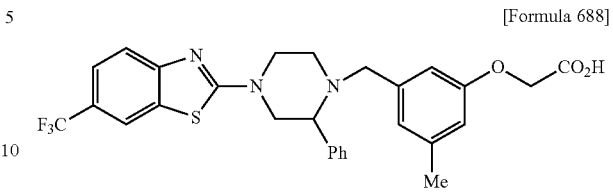

[Formula 688]

Yield 92%, 1H-NMR (CDCl3): δ2.27 (3H, s), 2.27-2.40 (1H, m), 2.90 (1H, d, J=13.5 Hz), 3.06 (1H, d, J=11.5 Hz), 3.32-3.55 (3H, m), 3.80 (1H, d, J=13.5 Hz), 3.95-4.10 (2H, m), 5.30 (2H, s), 6.63 (1H, s), 6.66 (1H, s), 6.72 (1H, s), 7.30-7.45 (3H, m), 7.45-7.60 (4H, m), 7.82 (1H, s).

Example 399

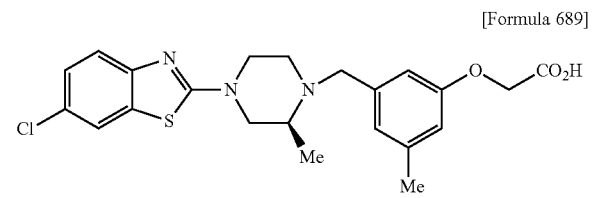

[Formula 689]

Yield 81%, 1H-NMR (CDCl3): δ1.32 (3H, d, J=6.6 Hz), 2.26 (3H, s), 2.76 (1H, s), 2.93-3.02 (2H, m), 3.37 (1H, d, J=12.9 Hz), 3.49-3.56 (1H, m), 3.70 (2H s), 3.87 (1H, d, J=10.8 Hz), 4.25 (1H, d, J=12.9 Hz), 4.63 (2H, s), 6.62 (1H, s), 6.77 (1H, s), 6.99 (1H, s), 7.24 (1H, dd, J=2.1, 8.7 Hz), 7.42 (1H, d, J=8.7 Hz), 7.54 (1H, d, J=2.1 Hz)

Example 400

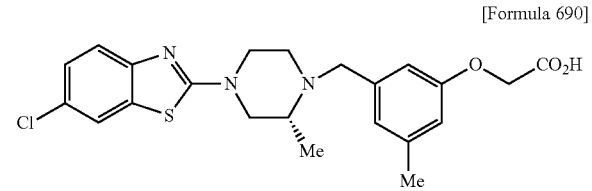

[Formula 690]

Yield 80%, 1H-NMR (CDCl3): δ1.33 (3H, d, J=6.0 Hz), 2.27 (3H, s), 2.76 (1H, br), 2.93-3.02 (2H, m), 3.38 (1H, d, J=12.6 Hz), 3.49-3.56 (1H, m), 3.71 (2H, s), 3.87 (1H, d, J=11.1 Hz), 4.25 (1H, d, J=12.6 Hz), 4.63 (2H, s), 6.62 (1H, s), 6.77 (1H, s), 6.99 (1H, s), 7.24 (1H, dd, J=1.8, 8.7 Hz), 7.42 (1H, d, J=8.7 Hz), 7.54 (1H, d, J=1.8 Hz)

Example 401

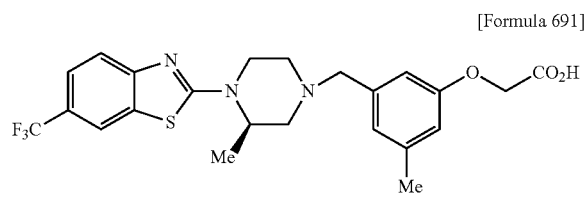

[Formula 691]

Yield 88%, 1H-NMR (CDCl3): δ1.41 (3H, d, J=6.5 Hz), 2.29 (3H, s), 2.35 (1H, td, J=12, 3.5 Hz), 2.48 (1H, dd, J=12, 4 Hz), 2.91 (1H, d, J=12 Hz), 3.26 (1H, d, J=11.5 Hz), 3.52 (1H, d, J=13 Hz), 3.54-3.65 (1H, m), 3.80 (1H, d, J=13 Hz), 3.89 (1H, d, J=13 Hz), 4.25-4.36 (1H, m), 4.62 (2H, s), 6.69 (1H, s), 6.75 (1H, s), 6.86 (1H, s), 7.52 (1H, d, J=8.5 Hz), 7.56 (1H, d, J=8.5 Hz), 7.83 (1H, s).

Example 402

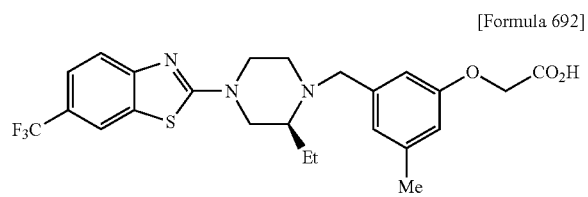

[Formula 692]

Yield 94%, 1H-NMR (CDCl3): δ0.96 (3H, t, J=7 Hz), 1.60-1.86 (2H, m), 2.29 (3H, s), 2.75-2.86 (1H, m), 2.87-3.00 (1H, m), 3.00-3.10 (1H, m), 3.51 (1H, d, J=13 Hz), 3.65-3.80 (1H, m), 3.80-3.93 (3H, m), 4.28 (1H, d, J=13 Hz), 4.63 (1H, d, J=16.5 Hz), 4.71 (1H, d, J=16.5 Hz) 6.63 (1H, s), 6.81 (1H, s), 7.02 (1H, s), 7.53 (1H, d, J=8.5 Hz), 7.57 (1H, d, J=8.5 Hz), 7.84 (1H, s).

Example 403

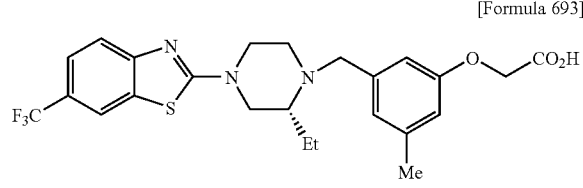

[Formula 693]

Yield 86%, 1H-NMR (CDCl3): δ0.96 (3H, t, J=7.5 Hz), 1.62-1.86 (2H, m), 2.28 (3H, s), 2.76-2.88 (1H, m), 2.89-3.00 (1H, m), 3.01-3.13 (1H, m), 3.52 (1H, d, J=13 Hz), 3.65-3.93 (4H, m), 4.30 (1H, d, J=13 Hz), 4.63 (1H, d, J=16.5 Hz), 4.72 (1H, d, J=16.5 Hz), 6.63 (1H, s), 6.82 (1H, s), 7.03 (1H, s), 7.49-7.60 (2H, m), 7.84 (1H, s).

Example 404

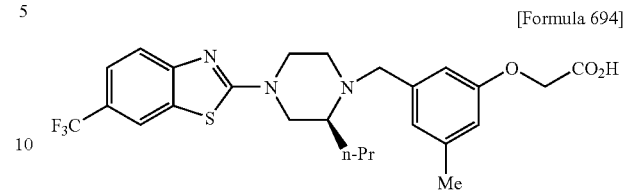

[Formula 694]

Yield 68%, 1H-NMR (DMSO-d6): δ0.89 (3H, t, J=7.0 Hz), 1.22-1.69 (4H, m), 2.22-2.37 (1H, m), 2.24 (3H, s), 2.49-2.62 (1H, m), 2.68-2.82 (1H, m), 3.28 (1H, d, J=13.5 Hz), 3.38-3.68 (3H, m), 3.69-3.80 (1H, m), 3.83 (1H, d, J=13.5 Hz), 4.28 (2H, s), 6.53 (1H, s), 6.64 (1H, s), 6.67 (1H, s), 7.53 (1H, d, J=8.5 Hz), 7.57 (1H, d, J=8.5 Hz), 8.22 (1H, s).

Example 405

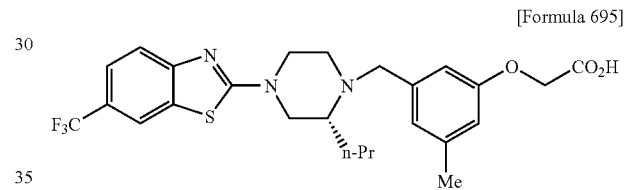

[Formula 695]

Yield 87%, 1H-NMR (CDCl3): δ0.90 (3H, t, J=7.2 Hz), 1.19-1.28 (1H, m), 1.45-1.52 (1H, m), 1.65 (2H, br), 2.78 (3H, s), 2.93 (2H, br), 3.05 (1H, br), 3.52 (1H, d, J=12.6 Hz), 3.67-3.74 (1H, m), 3.81-3.91 (3H, m), 4.30 (1H, d), 4.66 (2H, q, J=11.1 Hz), 6.62 (1H, s), 6.81 (1H, s), 7.03 (1H, s), 7.52-7.61 (2H, m), 7.84 (1H, s)

Example 406

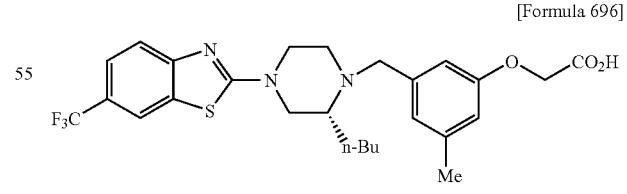

[Formula 696]

Yield 82%, 1H-NMR (DMSO-d6): δ0.88 (3H, t, J=6.5 Hz), 1.18-1.70 (6H, m), 2.23 (3H, s), 2.24-2.37 (1H, m), 2.48-2.60 (1H, m), 2.67-2.80 (1H, m), 3.27 (1H, d, J=13.5 Hz), 3.36-3.82 (4H, m), 3.83 (1H, d, J=13.5 Hz), 4.31 (2H, s), 6.54 (1H, s), 6.65 (1H, s), 6.67 (1H, s), 7.53 (1H, d, J=9.0 Hz), 7.56 (1H, d, J=9.0 Hz), 8.22 (1H, s).

Example 407

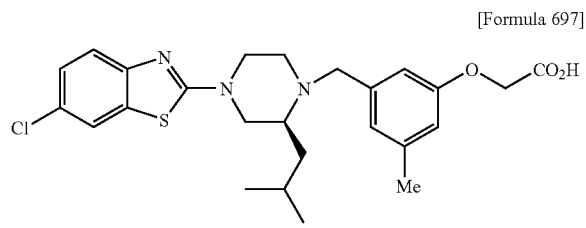

[Formula 697]

Yield 70%, 1H-NMR (DMSO-d6): δ0.88 (6H, t, J=6.5 Hz), 1.21-1.35 (1H, m), 1.45-1.58 (1H, m), 1.58-1.73 (1H, m), 2.23 (3H, s), 2.32-2.43 (1H, m), 2.59-2.80 (2H, m), 3.35 (1H, d, J=13.5 Hz), 3.37-3.45 (1H, m), 3.45-3.60 (2H, m), 3.60-3.71 (1H, m), 3.77 (1H, d, J=13.5 Hz), 4.19 (2H, s), 6.51 (1H, s), 6.63 (1H, s), 6.66 (1H, s), 7.27 (1H, dd, J=8.5, 2 Hz), 7.40 (1H, d, J=8.5 Hz), 7.88 (1H, d, J=2 Hz).

Example 408

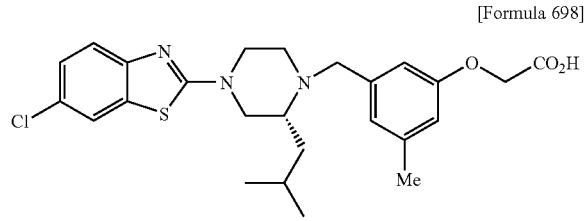

[Formula 698]

Yield 77%, 1H-NMR (DMSO-d6): δ0.87 (3H, d, J=6.5 Hz), 0.89 (3H, d, J=6.5 Hz), 1.21-1.36 (1H, m), 1.43-1.57 (1H, m), 1.58-1.73 (1H, m), 2.23 (3H, s), 2.30-2.43 (1H, m), 2.60-2.79 (2H, m), 3.34 (1H, d, J=13.5 Hz), 3.35-3.72 (4H, m), 3.77 (1H, d, J=13.5 Hz), 4.25 (2H, s), 6.53 (1H, s), 6.64 (1H, s), 6.70 (1H, s), 7.27 (1H, dd, J=8.5, 2.0 Hz), 7.40 (1H, d, J=8.5 Hz), 7.88 (1H, d, J=2.0 Hz).

Example 409

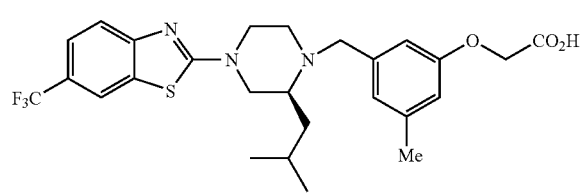

[Formula 699]

Yield 76%, 1H-NMR (CDCl3): δ0.77 (3H, d, J=6.5 Hz), 0.92 (3H, d, J=6.5 Hz), 1.40-1.75 (3H, m), 2.25 (3H, s), 2.80-3.05 (3H, m), 3.46 (1H, d, J=13 Hz), 3.60-3.95 (4H, m), 4.22 (1H, d, J=13 Hz), 4.56 (1H, d, J=16 Hz), 4.65 (1H, d, J=16 Hz), 6.63 (1H, s), 6.77 (1H, s), 7.01 (1H, s), 7.52 (1H, d, J=8.5 Hz), 7.59 (1H, d, J=8.5 Hz), 7.83 (1H, s).

Example 410

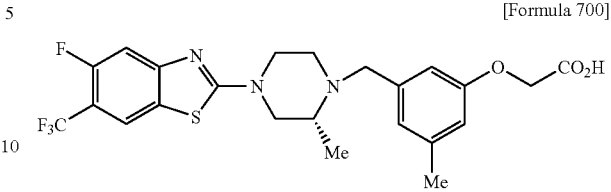

[Formula 700]

Yield 79%, 1H-NMR (CDCl3): δ1.33 (3H, d, J=6.5 Hz), 2.28 (3H, s), 2.70-2.83 (1H, m), 2.92-3.08 (2H, m), 3.38 (1H, d, J=13 Hz), 3.54-3.65 (1H, m), 3.70-3.82 (2H, m), 3.87-3.97 (1H, m), 4.25 (1H, d, J=13 Hz), 4.60 (1H, d, J=16.5 Hz), 4.67 (1H, d, J=16.5 Hz), 6.64 (1H, s), 6.78 (1H, s), 6.99 (1H, s), 7.26 (1H, d, J=11.5 Hz), 7.74 (1H, d, J=7 Hz).

Example 411

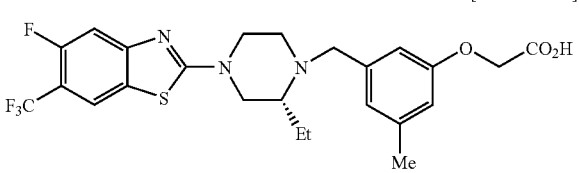

[Formula 701]

Yield 93%, 1H-NMR (CDCl3): δ0.92 (3H, t, J=7.0 Hz), 1.42-1.74 (2H, m), 2.13 (3H, s), 2.27-2.57 (2H, m), 2.62-2.82 (1H, m), 3.08-3.24 (1H, m), 3.35-3.77 (4H, m), 3.80-3.97 (1H, m), 4.37 (2H, s), 6.58 (1H, s), 6.63 (1H, s), 6.74 (1H, s), 7.20 (1H, d, J=11.5 Hz), 7.66 (1H, d, J=7.0 Hz).

Example 412

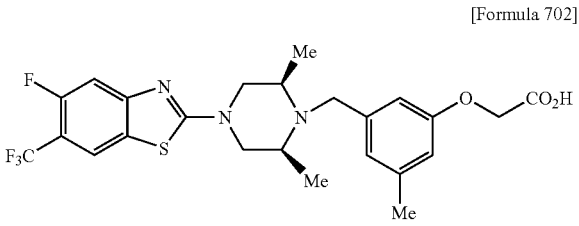

[Formula 702]

Yield 80%, 1H-NMR (CDCl3): δ1.18 (6H, d, J=6.0 Hz), 2.25 (3H, s), 2.78-2.94 (2H, m), 3.13-3.29 (2H, m), 3.78-3.94 (4H, m), 4.54 (2H, s), 6.61 (1H, s), 6.74 (1H, s), 6.80 (1H, s), 7.24 (1H, d, J=11.5 Hz), 7.72 (1H, d, J=7.0 Hz).

Example 413

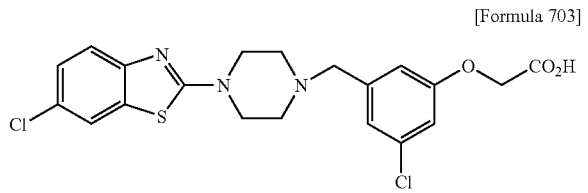

[Formula 703]

Yield 82%, ¹H-NMR (DMSO-d₆): δ3.52 (2H, s), 3.57 (8H, s), 4.65 (2H, s), 6.87 (2H, s), 6.98 (1H, s), 7.29 (1H, d, J=8.7, 2.4 Hz), 7.42 (1H, dd, J=8.7 Hz), 7.91 (1H, d, J=2.4 Hz)

Example 414

[Formula 704]

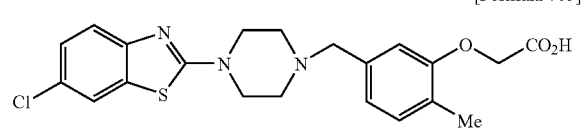

Yield 83%, ¹H-NMR (DMSO-d₆): δ2.40-2.55 (4H, m), 3.46 (2H, s), 3.53-3.56 (4H, m), 4.55 (2H, s), 6.85 (2H, d, J=8.4 Hz), 7.22 (2H, d, J=8.4 Hz), 7.28 (1H, dd, J=8.4, 2.4 Hz), 7.42 (1H, d, J=8.4 Hz), 7.90 (1H, d, J=2.4 Hz).

Example 415

[Formula 705]

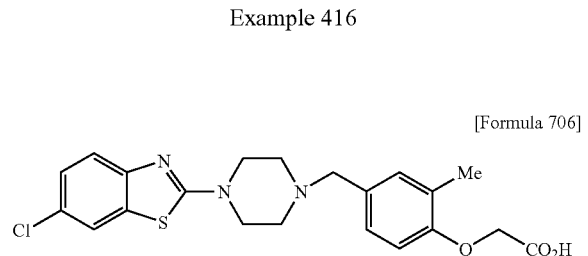

Yield 51%, ¹H-NMR (DMSO-d₆): δ2.16 (3H, s), 2.40-2.55 (4H, m), 3.47 (2H, s), 3.50-3.60 (4H, m), 4.67 (2H, s), 6.75-6.85 (2H, m), 7.08 (1H, d, J=7.5 Hz), 7.27 (1H, dd, J=8.5, 1 Hz), 7.41 (1H, d, J=8 Hz), 7.88 (1H, d, J=2 Hz), 12.9 (1H, brs).

Example 416

[Formula 706]

Yield 92%, ¹H-NMR (DMSO-d₆): δ2.19 (3H, s), 2.50-2.55 (4H, m), 3.52 (4H, s), 3.55-3.58 (4H, m), 6.76 (1H, d, J=8.4 Hz), 7.07 (1H, d, J=8.4 Hz), 7.11 (1H, s), 7.28 (1H, dd, 8.7, 1.5 Hz), 7.42 (1H, d, J=8.7 Hz), 7.90 (1H, d, J=1.5 Hz).

Example 417

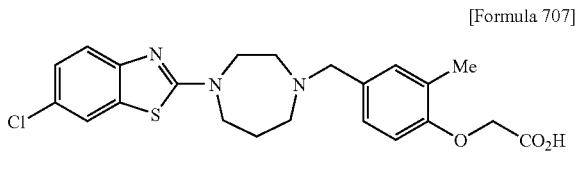

[Formula 707]

Yield 91%, ¹H-NMR (DMSO-d₆): δ1.90 (2H, m), 2.14 (3H, s), 2.58 (2H, m), 2.73 (2H, m), 3.50 (2H, s), 3.65-3.70 (4H, m), 4.49 (2H, s), 6.68 (1H, d, J=8.4 Hz), 7.01 (1H, d, J=8.4 Hz), 705 (1H, s), 7.26 (1H, dd, J=8.7, 2.1 Hz), 7.40 (1H, d, J=8.7 Hz), 7.88 (1H, d, J=2.1 Hz).

Example 418

[Formula 708]

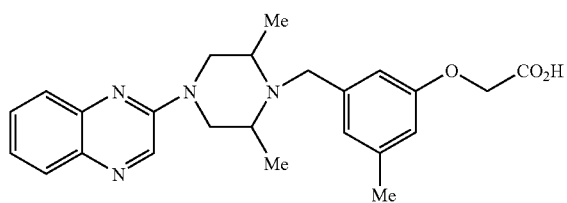

Yield 28%, 1H-NMR (CDCl3): δ1.33 (6H, d, J=6.0 Hz), 2.27 (3H, s), 2.87-3.04 (2H, m), 3.12-3.29 (2H, m), 4.02 (2H, s), 4.30 (2H, d, J=13.0 Hz), 4.59 (2H, s), 6.70 (2H, s), 6.83 (1H, s), 7.35-7.44 (1H, m), 7.52-7.61 (1H, m), 7.65 (1H, d, J=7.0 Hz), 7.86 (1H, d, J=7.0 Hz), 8.51 (1H, s).

Example 419

[Formula 709]

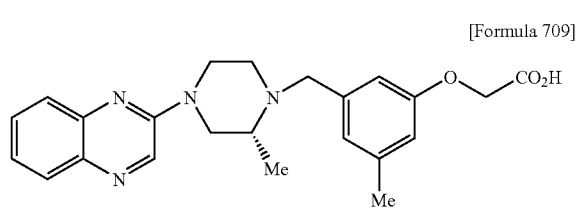

Yield 37%, 1H-NMR (CDCl3): δ1.37 (3H, d, J=6.5 Hz), 2.26 (3H, s), 2.84-3.23 (3H, m), 3.45 (1H, d, J=13.0 Hz), 3.71-4.14 (4H, m), 4.34 (1H, d, J=13.0 Hz), 4.62 (1H, d, J=16.0 Hz), 4.69 (1H, d, J=16.0 Hz), 6.60 (1H, s), 6.81 (1H, s), 7.12 (1H, s), 7.37-7.47 (1H, m), 7.53-7.63 (1H, m), 7.67 (1H, d, J=8.0 Hz), 7.89 (1H, d, J=8.0 Hz), 8.52 (1H, s).

Example 420

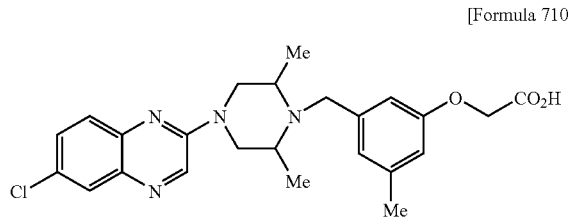

[Formula 710]

Yield 55%, 1H-NMR (CDCl3): δ1.24 (6H, d, J=6.0 Hz), 2.20 (3H, s), 2.77-2.92 (2H, m), 3.03-3.18 (2H, m), 3.89 (2H, s), 4.23 (2H, d, J=11.5 Hz), 4.48 (2H, s), 6.61 (1H, s), 6.69 (1H, s), 6.78 (1H, s), 7.46 (1H, dd, J=9.0, 2.0 Hz), 7.54 (1H, d, J=9.0 Hz), 7.81 (1H, d, J=2.0 Hz), 8.47 (1H, s).

Example 421

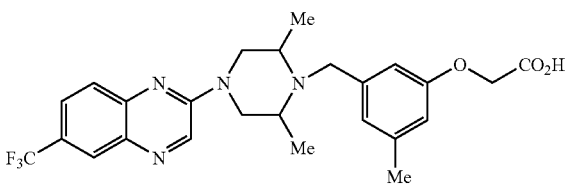

[Formula 711]

Yield 60%, 1H-NMR (CDCl3): δ1.32 (6H, d, J=6.0 Hz), 2.27 (3H, s), 2.85-3.00 (2H, m), 3.16-3.30 (2H, m), 3.98 (2H, s), 4.29-4.41 (2H, m), 4.60 (2H, s), 6.67 (1H, s), 6.73 (1H, s), 6.83 (1H, s), 7.65-7.75 (2H, m), 8.12 (1H, s), 8.57 (1H, s).

Example 422

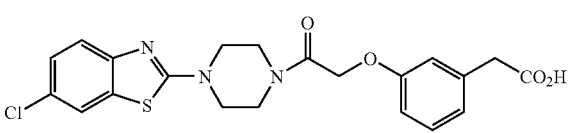

[Formula 712]

Yield 46%, $^1$H-NMR (DMSO-$d_6$): δ3.53 (2H, s), 3.54-3.74 (8H, m), 4.87 (2H, s), 6.79-6.90 (3H, m), 7.22 (1H, t, J=7.5 Hz), 7.32 (1H, dd, J=8.5, 2.0 Hz), 7.46 (1H, d, J=8.5 Hz), 7.94 (1H, d, J=2.0 Hz), 12.31 (1H, br).

Example 423

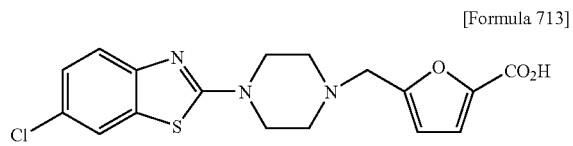

[Formula 713]

Yield 21%, $^1$H-NMR (DMSO-$d_6$): δ2.45-2.55 (4H, m), 3.33 (2H, s), 3.55-3.60 (4H, m), 6.50-6.60 (1H, m), 7.15-7.20 (1H, m), 7.29 (1H, dd, J=8.5, 2 Hz), 7.43 (1H, d, J=8.5 Hz), 7.92 (1H, d, J=2.5 Hz).

Example 424

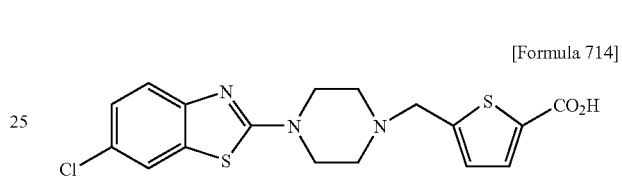

[Formula 714]

Yield 76%, $^1$H-NMR (DMSO-$d_6$): δ2.58 (4H, s), 3.35 (2H, s), 3.59 (2H, s), 3.81 (2H, s), 7.06 (1H, d, J=3.6 Hz), 7.29 (1H, dd, J=8.7, 2.1 Hz), 7.43 (1H, d, J=8.4 Hz), 7.60 (1H, d, J=3.3 Hz), 7.91 (1H, d, J=2.1 Hz), 12.99 (1H, brs).

Example 425

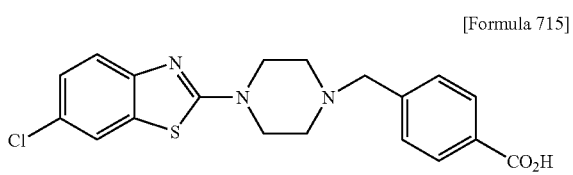

[Formula 715]

Yield 76%, $^1$H-NMR (DMSO-$d_6$): δ1.25 (2H, m), 3.30 (2H, m), 3.62 (2H, m), 4.20 (2H, m), 4.45 (2H, brs), 7.33 (1H, dd, J=8.4, 1.8 Hz), 7.49 (1H, d, J=8.7 Hz), 7.69-7.71 (2H, m), 7.98 (1H, d, J=1.8 Hz), 8.02 (2H, d, J=8.1 Hz).

Example 426

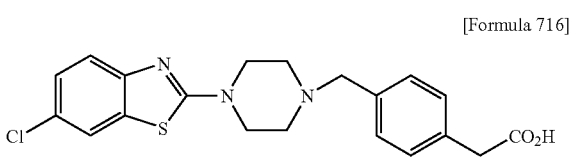

[Formula 716]

Yield 81%, $^1$H-NMR (DMSO-$d_6$): δ2.45-2.50 (4H, m), 3.45-3.60 (8H, m), 7.15-7.35 (5H, m), 7.42 (1H, d, J=8.5 Hz), 7.91 (1H, d, J=2 Hz), 12.31 (1H, brs).

Example 427

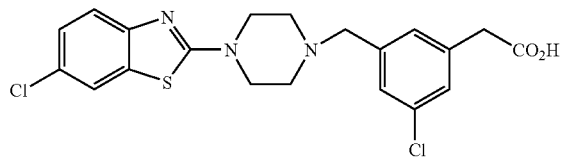

[Formula 717]

Yield 94%, ¹H-NMR (DMS-d₆): δ2.50-2.55 (4H, m), 3.52 (4H, s), 3.57 (4H, s), 7.17 (1H, s), 7.24 (2H, s), 7.29 (1H, dd, J=2.1, 8.4 Hz), 7.42 (1H, d, J=8.4 Hz), 7.91 (1H, d, J=2.1 Hz)

Example 428

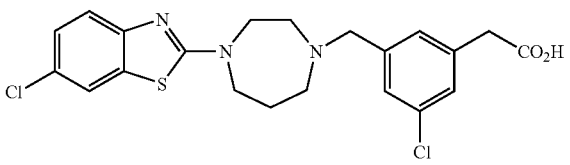

[Formula 718]

Yield 86%, ¹H-NMR (DMS-d₆): δ1.92 (2H, s), 2.61 (2H, s), 2.77 (2H, s), 3.53 (2H, s), 3.61 (2H, s), 3.60-3.65 (4H, m), 7.15 (1H, s), 7.21 (1H, s), 7.22 (1H, s), 7.26 (1H, dd, J=8.4, 2.1 Hz), 7.40 (1H, d, J=8.4 Hz), 7.88 (1H, d, J=2.1 Hz).

Example 429

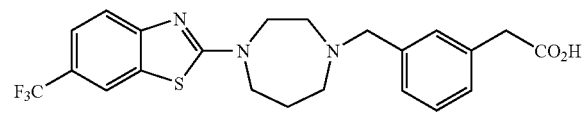

[Formula 719]

Yield 18%, 1H-NMR (DMSO-d6): δ1.85-2.00 (2H, m), 2.57-2.68 (2H, m), 2.74-2.85 (2H, m), 3.52 (2H, s), 3.61 (2H, s), 3.62-3.85 (4H, m), 7.09-7.31 (4H, m), 7.52-7.58 (2H, m), 8.22 (1H, s).

Example 430

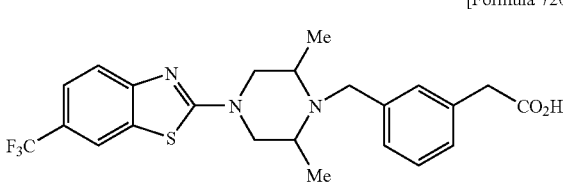

[Formula 720]

Yield 95%, 1H-NMR (DMSO-d6): δ1.05 (6H, d, J=6.5 Hz), 2.65-2.80 (2H, m), 3.04-3.15 (2H, m), 3.55 (2H, s), 3.79 (2H, s), 3.83-3.95 (2H, m), 7.05-7.15 (1H, m), 7.20-7.30 (3H, m), 7.57 (2H, s), 8.24 (1H, s), 12.27 (1H, brs).

Example 431

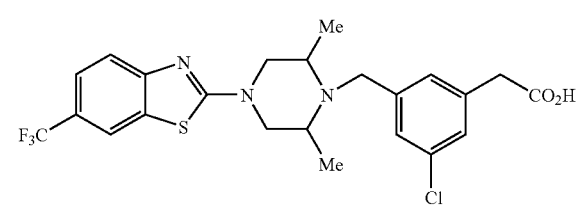

[Formula 721]

Yield 61%, 1H-NMR (CDCl3): δ1.08 (6H, d, J=6.5 Hz), 2.74-2.86 (2H, m), 3.08 (1H, d, J=13 Hz), 3.12 (1H, d, J=13 Hz), 3.62 (2H, s), 3.78 (2H, s), 3.86-3.95 (2H, m), 7.16-7.18 (2H, m), 7.34 (1H, s), 7.52 (1H, d, J=8.5 Hz), 7.57 (1H, d, J=8.5 Hz), 7.84 (1H, s).

Example 432

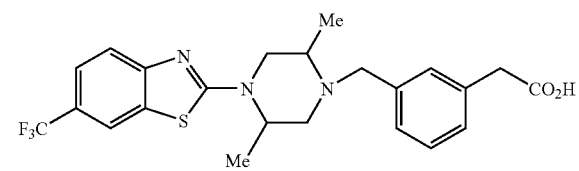

[Formula 722]

Yield 87%, 1H-NMR (DMSO-d6): δ1.01 (3H, d, J=6.5 Hz), 1.33 (3H, d, J=6.5 Hz), 2.25-2.35 (1H, m), 2.75-2.85 (1H, m), 3.08-3.20 (1H, m), 3.49 (1H, d, J=14 Hz), 3.56 (2H, s), 3.63-3.75 (3H, m), 4.23-4.35 (1H, m), 7.10-7.20 (1H, m), 7.20-7.35 (3H, m), 7.50-7.60 (2H, m), 8.21 (1H, s), 12.23 (1H, brs).

Example 433

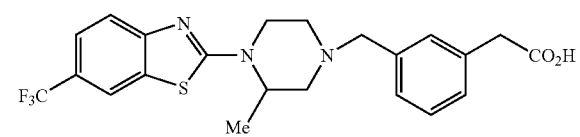

[Formula 723]

Yield 87%, 1H-NMR (DMSO-d6): δ1.33 (3H, d, J=6.5 Hz), 2.10-2.30 (2H, m), 2.72 (1H, d, J=11.5 Hz), 2.94 (1H, d, J=12 Hz), 3.35-3.50 (2H, m), 3.57 (2H, s), 3.60 (1H, d, J=13.5 Hz), 3.75-3.90 (1H, m), 4.20-4.30 (1H, m), 7.15-7.32 (4H, m), 7.56 (2H, s), 8.22 (1H, s), 12.28 (1H, brs).

Example 434

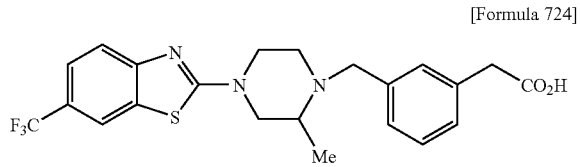
[Formula 724]

Yield 82%, 1H-NMR (DMSO-d6): δ1.16 (3H, d, J=6 Hz), 2.15-2.35 (1H, m), 2.55-2.68 (1H, m), 2.70-2.80 (1H, m), 3.15-3.30 (2H, m), 3.35-3.50 (1H, m), 3.56 (2H, s), 3.70-3.80 (1H, m), 3.80-3.90 (1H, m), 3.97 (1H, d, J=13.5 Hz), 7.10-7.35 (4H, m), 7.56 (2H, s), 8.23 (1H, s), 12.29 (1H, brs).

Example 435

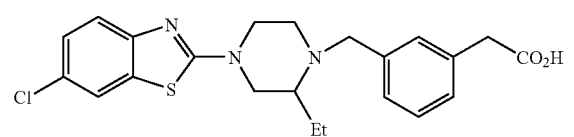
[Formula 725]

Yield 98%, 1H-NMR (CDCl3): δ1.00 (3H, t, J=7.5 Hz), 1.59-1.69 (1H, m), 1.73-1.80 (1H, m), 2.37-2.45 (1H, m), 2.54-2.59 (1H, m), 2.80-2.86 (1H, m), 3.34-3.54 (3H, m), 3.59-3.63 (1H, m), 3.63 (2H, s), 3.79 (1H, dd, J=2.7, 13.2 Hz), 4.04 (1H, d, J=13.2 Hz), 7.20-7.29 (5H, m), 7.42 (1H, d, J=8.7 Hz), 7.53 (1H, d, J=2.1 Hz)

Example 436

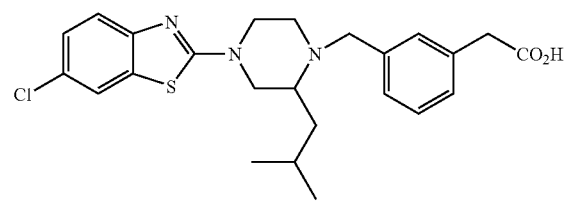
[Formula 726]

Yield 96%, 1H-NMR (CDCl3): δ0.92 (6H, dd, J=6.3, 16.2 Hz), 1.38-1.47 (1H, m), 1.51-1.59 (1H, m), 1.64-1.75 (1H, m), 2.43-2.51 (1H, m), 2.71-2.76 (1H, m), 2.79-2.87 (1H, m), 3.40 (2H, dt, J=3.0, 13.2 Hz), 3.57-3.64 (2H, m), 3.63 (2H, s), 3.76 (1H, dd, J=3.0, 12.9 Hz), 3.99 (1H, d, J=13.2 Hz), 7.21-7.31 (5H, m), 7.43 (1H, d, J=8.4 Hz), 7.53 (1H, d, J=2.4 Hz)

Example 437

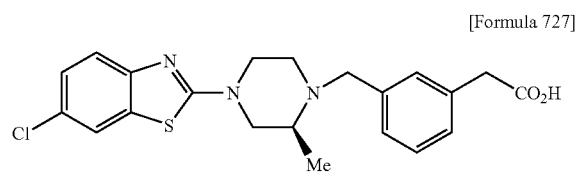
[Formula 727]

Yield 89%, 1H-NMR (CDCl3): δ1.25 (3H, d, J=6.0 Hz), 2.30-2.38 (1H, m), 2.68-2.74 (1H, m), 2.83 (1H, dt, J=3.9, 12.0 Hz), 3.18-3.28 (2H, m), 3.39-3.49 (1H, m), 3.63 (2H, s), 3.63-3.70 (1H, m), 3.86 (1H, dd, J=2.4, 12.0 Hz), 4.10 (1H, d, J=13.2 Hz), 7.19-7.30 (5H, m), 7.43 (1H, d, J=8.4 Hz), 7.53 (1H, d, J=2.4 Hz)

Example 438

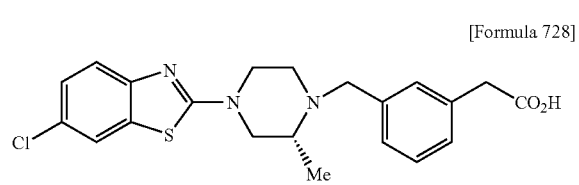
[Formula 728]

Yield 91%, 1H-NMR (CDCl3): δ1.30 (3H, d, J=6.0 Hz), 2.40 (1H, t, J=9.6 Hz), 2.78 (1H, br), 2.88 (1H, br), 3.33 (2H, d, J=12.6 Hz), 3.48-3.54 (1H, m), 3.64 (2H, s), 3.72 (1H, d, J=13.2 Hz), 3.89 (1H, d, J=10.2 Hz), 4.16 (1H, d, J=13.2 Hz), 7.22-7.33 (5H, m), 7.43 (1H, d, J=8.7 Hz), 7.54 (1H, d, J=2.1 Hz)

Example 439

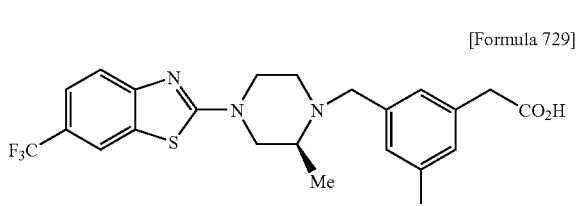
[Formula 729]

Yield 96%, 1H-NMR (CDCl3): δ1.26 (3H, d, J=6 Hz), 2.25-2.40 (4H, m), 2.65-2.75 (1H, m), 2.80-2.90 (1H, m), 3.20 (1H, d, J=13 Hz), 3.25-3.30 (1H, m), 3.45-3.53 (1H, m), 3.61 (2H, s), 3.68-3.80 (1H, m), 3.84-3.95 (1H, m), 4.07 (1H, d, J=13 Hz), 7.03 (2H, s), 7.10 (1H, s), 7.51 (1H, d, J=8.5 Hz), 7.53 (1H, d, J=8.5 Hz), 7.83 (1H, s)

Example 440

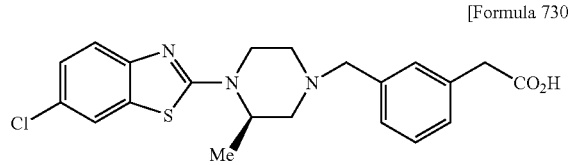

[Formula 730]

Yield 67%, 1H-NMR (DMSO-d6): δ1.31 (3H, d, J=6.5 Hz), 2.03-2.25 (2H, m), 2.70 (1H, d, J=11.5 Hz), 2.91 (1H, d, J=12 Hz), 3.35-3.43 (2H, m), 3.56 (2H, s), 3.56-3.65 (1H, m), 3.79 (1H, d, J=11 Hz), 4.15-4.25 (1H, m), 7.15 (1H, d, J=7 Hz), 7.20-7.33 (4H, m), 7.41 (1H, d, J=8.5 Hz), 7.89 (1H, d, J=1.5 Hz), 12.30 (1H, brs).

Example 441

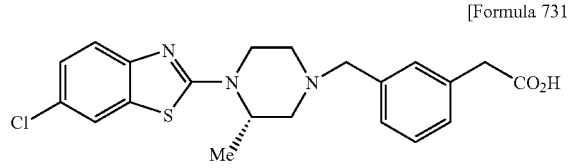

[Formula 731]

Yield 86%, 1H-NMR (CDCl3): δ1.37 (3H, d, J=7.0 Hz), 2.23 (1H, td, J=11.0, 3.5 Hz), 2.31 (1H, dd, J=11.0, 3.5 Hz), 2.71 (1H, d, J=11.0 Hz), 2.91 (1H, d, J=11.0 Hz), 3.44 (1H, d, J=13.5 Hz), 3.47 (1H, td, J=12.5, 3.5 Hz), 3.60 (1H, d, J=11.0 Hz), 3.64 (2H, s), 3.83 (1H, d, J=12.5 Hz), 4.09-4.21 (1H, m), 7.14-7.33 (5H, m), 7.42 (1H, d, J=8.5 Hz), 7.53 (1H, d, J=2.0 Hz).

Example 442

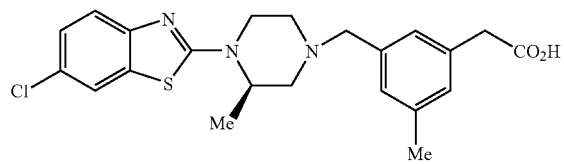

[Formula 732]

Yield 94%, 1H-NMR (CDCl3): δ1.37 (3H, d, J=6.5 Hz), 2.23 (1H, td, J=11.5, 3.5 Hz), 2.25-2.30 (1H, m), 2.32 (3H, s), 2.71 (1H, d, J=11.5 Hz), 2.91 (1H, d, J=11 Hz), 3.39 (1H, d, J=13.5 Hz), 3.45-3.54 (1H, m), 3.55 (1H, d, J=13.5 Hz), 3.60 (2H, s), 3.83 (1H, d, J=11.5 Hz), 4.10-4.20 (1H, m), 7.01 (1H, s), 7.06 (1H, s), 7.09 (1H, s), 7.23 (1H, dd, J=8.5, 2 Hz), 7.42 (1H, d, J=8.5 Hz), 7.54 (1H, d, J=2 Hz).

Example 443

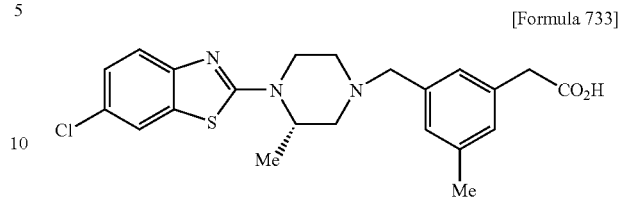

[Formula 733]

Yield 82%, 1H-NMR (CDCl3): δ1.37 (3H, d, J=6.5 Hz), 2.13-2.36 (5H, m), 2.70 (1H, d, J=11.5 Hz), 2.89 (1H, d, J=11.5 Hz), 3.32-3.62 (5H, m), 3.76-3.87 (1H, m), 4.07-4.22 (1H, m), 6.99 (1H, s), 7.05 (1H, s), 7.07 (1H, s), 7.22 (1H, dd, J=8.5, 2.0 Hz), 7.42 (1H, d, J=8.5 Hz), 7.53 (1H, d, J=2.0 Hz).

Example 444

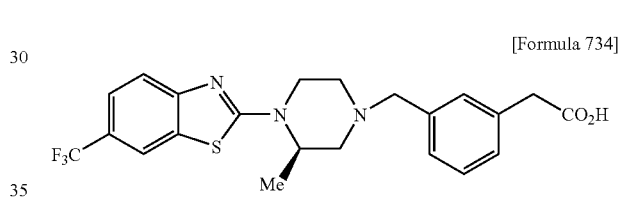

[Formula 734]

Yield 87%, 1H-NMR (DMSO-d6): δ1.33 (3H, d, J=6.5 Hz), 2.10-2.30 (2H, m), 2.72 (1H, d, J=11.5 Hz), 2.93 (1H, d, J=11.5 Hz), 3.30-3.50 (2H, m), 3.56 (2H, s), 3.59 (1H, d, J=13.5 Hz), 3.86 (1H, d, J=12.5 Hz), 4.20-4.30 (1H, m), 7.10-7.35 (4H, m), 7.56 (2H, s), 8.24 (1H, s), 12.43 (1H, brs).

Example 445

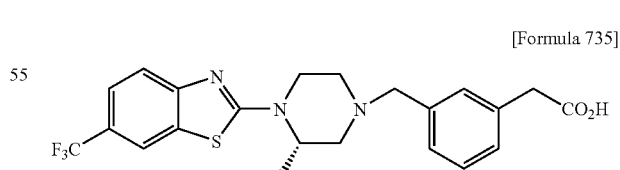

[Formula 735]

Yield 96%, 1H-NMR (CDCl3): δ1.34 (3H, d, J=6.5 Hz), 2.14 (1H, td, J=11.5, 3.5 Hz), 2.25 (1H, dd, J=11.5, 3.5 Hz), 2.66 (1H, d, J=11.5 Hz), 2.83 (1H, d, J=11.5 Hz), 3.37 (1H, d, J=13.5 Hz), 3.38-3.55 (4H, m), 3.82 (1H, d, J=11.5 Hz), 4.08-4.22 (1H, m), 7.10 (1H, s), 7.14-7.23 (3H, m), 7.45-7.56 (2H, m), 7.81 (1H, s).

Example 446

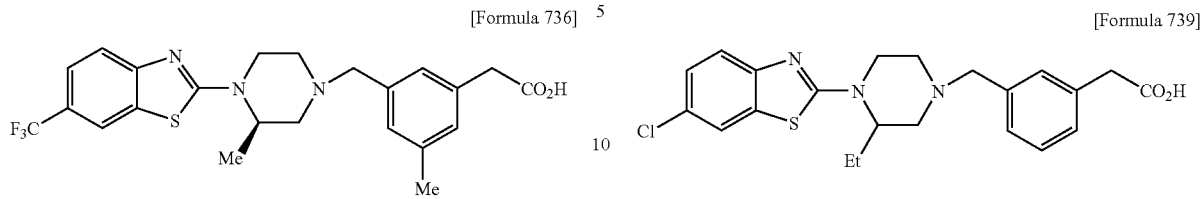

[Formula 736]

Yield 98%, 1H-NMR (CDCl3): δ1.39 (3H, d, J=6.5 Hz), 2.23 (1H, td, J=12, 3.5 Hz), 2.25-2.31 (1H, m), 2.32 (3H, s), 2.73 (1H, d, J=11.5 Hz), 2.92 (1H, d, J=12 Hz), 3.41 (1H, d, J=13 Hz), 3.45-3.55 (1H, m), 3.56 (1H, d, J=13 Hz), 3.59 (2H, s), 3.88 (1H, d, J=12 Hz), 4.17-4.28 (1H, m), 7.01 (1H, s), 7.06 (1H, s), 7.09 (1H, s), 7.51 (1H, d, J=8.5 Hz), 7.55 (1H, d, J=8.5 Hz), 7.83 (1H, s).

Example 447

[Formula 737]

Yield 72%, 1H-NMR (CDCl3): δ1.39 (3H, d, J=6.5 Hz), 2.13-2.34 (5H, m), 2.71 (1H, d, J=11.5 Hz), 2.90 (1H, d, J=11.5 Hz), 3.39 (1H, d, J=13.0 Hz), 3.43-3.60 (4H, m), 3.87 (1H, d, J=12.5 Hz), 4.13-4.26 (1H, m), 6.99 (1H, s), 7.05 (2H, s), 7.46-7.58 (2H, m), 7.83 (1H, s).

Example 448

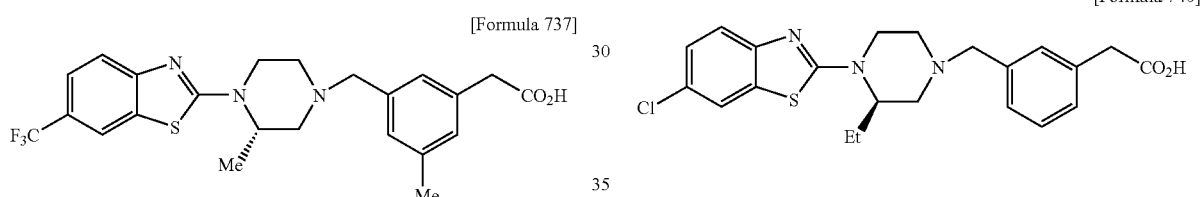

[Formula 738]

Yield 90%, 1H-NMR (CDCl3): δ1.40 (3H, d, J=6.5 Hz), 2.26 (1H, td, J=12, 3.5 Hz), 2.35 (1H, dd, J=11.5, 3.5 Hz), 2.72 (1H, d, J=11.5 Hz), 2.91 (1H, d, J=12 Hz), 3.43 (1H, d, J=13.5 Hz), 3.52 (1H, td, J=12.5, 3.5 Hz), 3.57 (1H, d, J=13.5 Hz), 3.64 (2H, s), 3.85-3.95 (1H, m), 4.19-4.30 (1H, m), 7.18 (1H, s), 7.21 (1H, s), 7.29 (1H, s), 7.51 (1H, d, J=8.5 Hz), 7.57 (1H, d, J=8.5 Hz), 7.84 (1H, s).

Example 449

[Formula 739]

Yield 68%, 1H-NMR (CDCl3): δ0.85 (3H, t, J=7.5 Hz), 1.82-1.99 (2H, m), 2.17-2.29 (2H, m), 2.78-2.92 (2H, m), 3.37-3.51 (1H, m), 3.42 (1H, d, J=13.0 Hz), 3.59 (1H, d, J=13.0 Hz), 3.65 (2H, s), 3.76-3.87 (1H, m), 3.93-4.04 (1H, m), 7.16-7.34 (5H, m), 7.39 (1H, d, J=8.5 Hz), 7.52 (1H, d, J=2.0 Hz).

Example 450

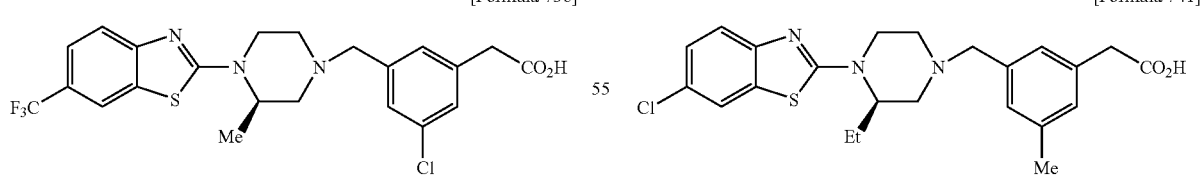

[Formula 740]

Yield 95%, 1H-NMR (DMSO-d6): δ0.79 (3H, t, J=7.5 Hz), 1.72-1.95 (2H, m), 2.07-2.20 (2H, m), 2.81 (1H, d, J=11 Hz), 2.89 (1H, d, J=11 Hz), 3.25-3.39 (2H, m), 3.40 (1H, d, J=13.5 Hz), 3.55 (2H, s), 3.59 (1H, d, J=13.5 Hz), 3.80-3.95 (1H, m), 7.13-7.34 (5H, m), 7.38 (1H, d, J=8.5 Hz), 7.87 (1H, d, J=2 Hz), 12.45 (1H, brs).

Example 451

[Formula 741]

Yield 96%, 1H-NMR (CDCl3): δ0.86 (3H, t, J=7.5 Hz), 1.80-2.00 (2H, m), 2.16-2.29 (2H, m), 2.33 (3H, s), 2.79-2.94 (2H, m), 3.38 (1H, d, J=13.5 Hz), 3.50 (1H, td, J=12.5, 3.5 Hz), 3.57 (1H, d, J=13.5 Hz), 3.61 (2H, s), 3.75-3.87 (1H, m), 3.93-4.03 (1H, m), 7.02 (1H, s), 7.06 (1H, s), 7.08 (1H, s), 7.21 (1H, dd, J=8.5, 2 Hz), 7.39 (1H, d, J=8.5 Hz), 7.52 (1H, d, J=2 Hz).

Example 452

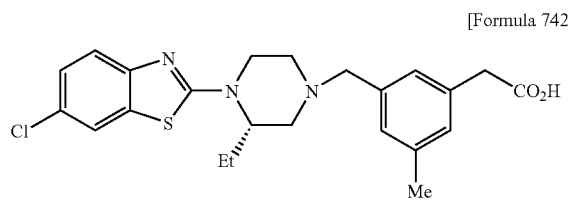
[Formula 742]

Yield 77%, 1H-NMR (DMSO-d6): δ0.80 (3H, t, J=7.5 Hz), 1.67-1.97 (2H, m), 2.03-2.19 (2H, m), 2.28 (3H, s), 2.81 (1H, d, J=11.5 Hz), 2.89 (1H, d, J=11.0 Hz), 3.27-3.44 (2H, m), 3.48 (2H, s), 3.55 (1H, d, J=13.5 Hz), 3.81-3.95 (2H, m), 6.96 (1H, s), 7.02 (2H, s), 7.26 (1H, dd, J=8.5, 2.0 Hz), 7.38 (1H, d, J=8.5 Hz), 7.87 (1H, d, J=2.0 Hz).

Example 453

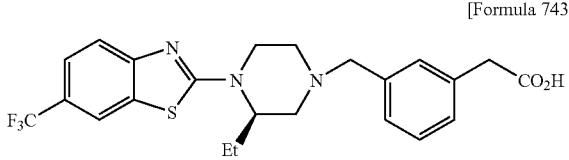
[Formula 743]

Yield 96%, 1H-NMR (DMSO-d6): δ0.80 (3H, t, J=7.5 Hz), 1.76-1.96 (2H, m), 2.09-2.20 (2H, m), 2.82 (1H, d, J=11.5 Hz), 2.89 (1H, d, J=11.5 Hz), 3.30-3.42 (2H, m), 3.43 (1H, d, J=13.5 Hz), 3.56 (2H, s), 3.60 (1H, d, J=13.5 Hz), 3.88-4.00 (1H, m), 7.12-7.32 (4H, m), 7.51 (1H, d, J=8.5 Hz), 7.56 (1H, d, J=8.5 Hz), 8.21 (1H, s), 12.3 (1H, brs).

Example 454

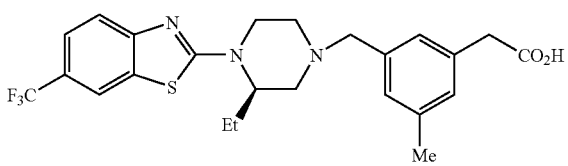
[Formula 744]

Yield 89%, 1H-NMR (CDCl3): δ0.87 (3H, t, J=7.5 Hz), 1.85-2.00 (2H, m), 2.23 (2H, td, J=12.5, 3.5 Hz), 2.34 (3H, s), 2.81-2.96 (2H, m), 3.38 (1H, d, J=13.5 Hz), 3.49 (1H, td, J=12.5, 3.5 Hz), 3.58 (1H, d, J=13.5 Hz), 3.62 (2H, s), 3.80-3.95 (1H, m), 3.97-4.10 (1H, m), 7.02 (1H, s), 7.06 (1H, s), 7.08 (1H, s), 7.46-7.50 (2H, m), 7.81 (1H, s).

Example 455

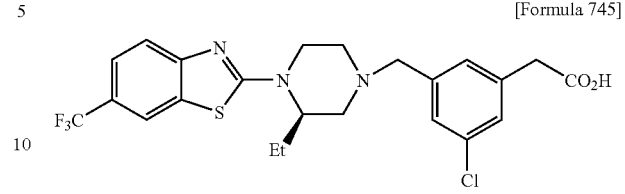
[Formula 745]

Yield 89%, 1H-NMR (CDCl3): δ0.88 (3H, t, J=7.5 Hz), 1.93 (2H, quant, J=7.5 Hz), 2.19-2.32 (2H, m), 2.78-2.93 (2H, m), 3.40 (1H, d, J=13.5 Hz), 3.49 (1H, td, J=12.5, 3.5 Hz), 3.57 (1H, d, J=13.5 Hz), 3.64 (2H, s), 3.84-3.95 (1H, m), 3.96-4.10 (1H, m), 7.16 (1H, s), 7.22 (1H, s), 7.28 (1H, s), 7.45-7.57 (2H, m), 7.82 (1H, s).

Example 456

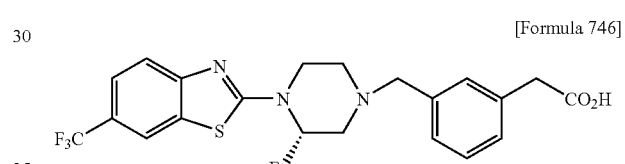
[Formula 746]

Yield 93%, 1H-NMR (CDCl3): δ0.86 (3H, t, J=7.5 Hz), 1.92 (2H, quant, J=7.5 Hz), 2.15-2.31 (2H, m), 2.80-2.96 (2H, m), 3.42 (1H, d, J=13 Hz), 3.48 (1H, td, J=12.5, 3 Hz), 3.61 (1H, d, J=13 Hz), 3.66 (2H, s), 3.80-3.95 (1H, m), 3.96-4.10 (1H, m), 7.15-7.33 (4H, m), 7.49 (1H, d, J=8.5 Hz), 7.50 (1H, d, J=8.5 Hz) 7.81 (1H, s).

Example 457

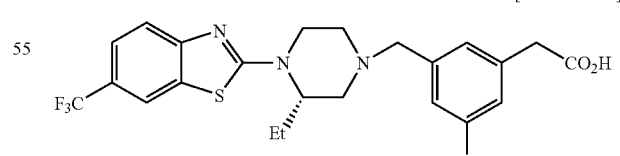
[Formula 747]

Yield 96%, 1H-NMR (CDCl3): δ0.87 (3H, t, J=7.5 Hz), 1.85-2.00 (2H, m), 2.15-2.28 (2H, m), 2.34 (3H, s), 2.80-2.95 (2H, m), 3.39 (1H, d, J=13 Hz), 3.51 (1H, td, J=13, 3.5 Hz), 3.58 (1H, d, J=13 Hz), 3.62 (2H, s), 3.80-3.95 (1H, m), 3.96-4.10 (1H, m), 7.02 (1H, s), 7.06 (1H, s), 7.08 (1H, s), 7.50 (1H, d, J=8.5 Hz), 7.53 (1H, d, J=8.5 Hz) 7.81 (1H, s).

Example 458

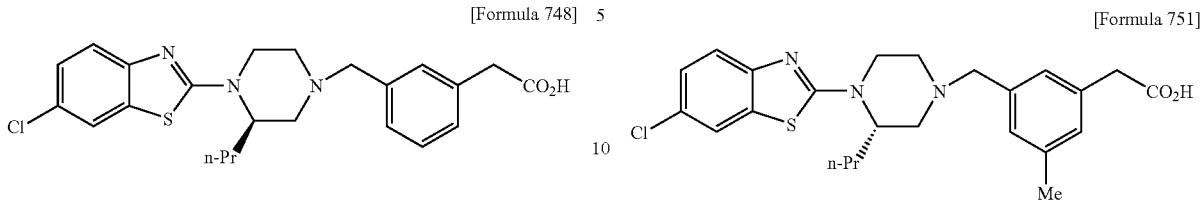

[Formula 748]

Yield 98%, 1H-NMR (CDCl3): δ0.87 (3H, t, J=7.5 Hz), 1.11-1.28 (2H, m), 1.68-1.88 (2H, m), 2.20-2.18 (2H, m), 2.64-2.79 (2H, m), 3.23-3.48 (5H, m), 3.74-3.96 (2H, m), 6.98-7.23 (5H, m), 7.35 (1H, d, J=8.5 Hz), 7.49 (1H, d, J=2.0 Hz).

Example 459

[Formula 749]

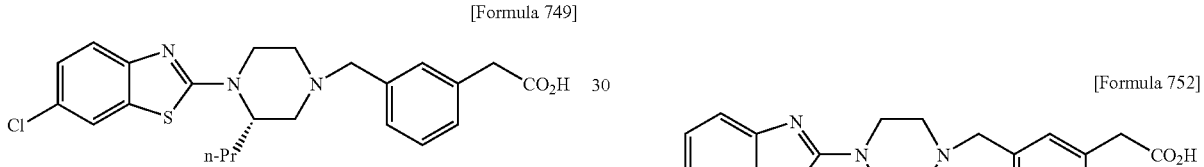

Yield 98%, 1H-NMR (CDCl3): δ0.91 (3H, t, J=7.2 Hz), 1.19-1.29 (2H, m), 1.77-1.94 (2H, m), 2.18-2.28 (2H, m), 2.81 (1H, d, J=11.1 Hz), 2.89 (1H, d, J=11.1 Hz), 3.40-3.47 (2H, m), 3.61 (1H, d, J=13.2 Hz), 3.66 (2H, s), 3.90 (1H, s), 3.99 (1H, d, J=12.0 Hz), 7.20-7.31 (5H, m), 7.39 (1H, d, J=8.7 Hz), 7.52 (1H, d, J=2.1 Hz)

Example 460

[Formula 750]

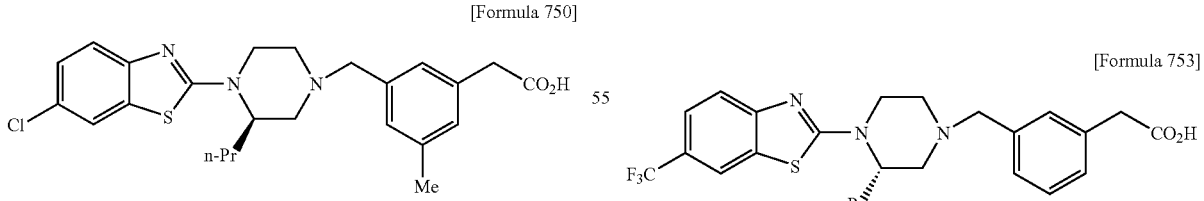

Yield 69%, 1H-NMR (CDCl3): δ0.92 (3H, t, J=7.0 Hz), 1.16-1.34 (2H, m), 1.68-2.00 (2H, m), 2.12-2.27 (2H, m), 2.32 (3H, s), 2.79 (1H, d, J=11.5 Hz), 2.86 (1H, d, J=11.5 Hz), 3.35 (1H, d, J=13.5 Hz), 3.39-3.62 (2H, m), 3.58 (2H, s), 3.82-4.03 (2H, m), 6.99 (1H, s), 7.03 (1H, s), 7.06 (1H, s), 7.21 (1H, dd, J=8.5, 2.0 Hz), 7.39 (1H, d, J=8.5 Hz), 7.52 (1H, d, J=2.0 Hz).

Example 461

[Formula 751]

Yield 91%, 1H-NMR (CDCl3): δ0.92 (3H, t, J=7.2 Hz), 1.20-1.30 (2H, m), 1.75-1.84 (1H, m), 1.87-1.97 (1H, m), 2.18-2.28 (2H, m), 2.34 (3H, s), 2.86 (2H, dd, J=11.1 Hz), 3.37 (1H, d, J=13.2 Hz), 3.48 (1H, dt, J=3.3, 12.6 Hz), 3.61 (1H, d, J=12.1 Hz), 3.62 (2H, s), 3.90 (1H, s), 3.99 (1H, d, J=11.1 Hz), 7.02 (1H, s), 7.07 (2H, s), 7.22 (1H, dd, J=2.1, 8.7 Hz), 7.40 (1H, d, J=8.7 Hz), 7.52 (1H, d, J=2.1 Hz)

Example 462

[Formula 752]

Yield 70%, 1H-NMR (CDCl3): δ0.92 (3H, t, J=7.0 Hz), 1.18-1.35 (2H, m), 1.75-1.98 (2H, m), 2.15-2.29 (2H, m), 2.81 (1H, d, J=11.5 Hz), 2.88 (1H, d, J=11.5 Hz), 3.41 (1H, d, J=13.0 Hz), 3.48 (1H, td, J=12.5, 3.0 Hz), 3.58 (1H, d, J=13.0 Hz), 3.62 (2H, s), 3.89-4.09 (2H, m), 7.14-7.32 (4H, m), 7.49 (1H, d, J=8.5 Hz), 7.53 (1H, d, J=8.5 Hz), 7.81 (1H, s).

Example 463

[Formula 753]

Yield 81%, 1H-NMR (CDCl3): δ0.92 (3H, t, J=7.2 Hz), 1.21-1.31 (2H, m), 1.80-1.94 (2H, m), 2.20-2.29 (2H, m), 2.82 (1H, d, J=11.4 Hz), 2.91 (1H, d, J=11.1 Hz), 3.43 (1H, d, J=13.2 Hz), 3.50 (1H, dt, J=3.0, 12.6 Hz), 3.61 (1H, d, J=13.2 Hz), 3.67 (2H, s), 3.99 (1H, d, J=14.1 Hz), 4.06 (1H, s), 7.20-7.34 (4H, m), 7.52 (2H, s), 7.82 (1H, s)

Example 464

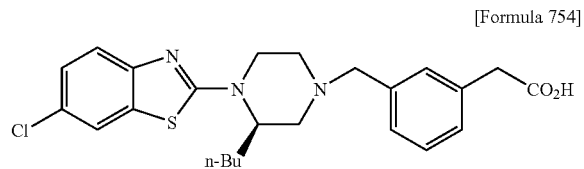
[Formula 754]

Yield 81%, 1H-NMR (CDCl3): δ 0.86 (3H, t, J=7.5 Hz), 1.14-1.38 (4H, m), 1.74-1.99 (2H, m), 2.16-2.30 (2H, m), 2.81 (1H, d, J=11.5 Hz), 2.89 (1H, d, J=11.5 Hz), 3.42 (1H, d, J=13 Hz), 3.46 (1H, td, J=13.5, 3.5 Hz), 3.60 (1H, d, J=13 Hz), 3.66 (2H, s), 3.80-3.93 (1H, m), 3.95-4.06 (1H, m), 7.15-7.35 (5H, m), 7.40 (1H, d, J=8.5 Hz), 7.52 (1H, d, J=2.5 Hz).

Example 465

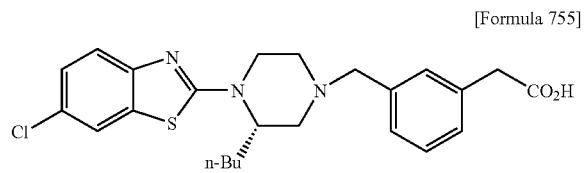
[Formula 755]

Yield 91%, 1H-NMR (CDCl3): δ 0.86 (3H, t, J=7.5 Hz), 1.13-1.40 (4H, m), 1.74-2.00 (2H, m), 2.16-2.30 (2H, m), 2.82 (1H, d, J=12 Hz), 2.88 (1H, d, J=11.5 Hz), 3.41 (1H, d, J=13.5 Hz), 3.41-3.51 (1H, m), 3.60 (1H, d, J=13.5 Hz), 3.66 (2H, s), 3.80-3.92 (1H, m), 3.94-4.05 (1H, m), 7.16-7.34 (5H, m), 7.39 (1H, d, J=8.5 Hz), 7.52 (1H, d, J=2 Hz).

Example 466

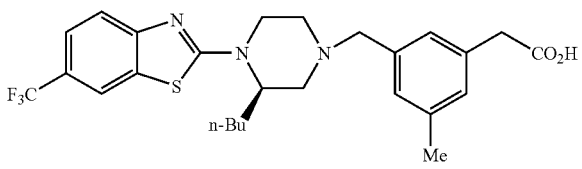
[Formula 756]

Yield 81%, 1H-NMR (CDCl3): δ 0.87 (3H, t, J=7.5 Hz), 1.17-1.39 (4H, m), 1.75-2.03 (2H, m), 2.17-2.30 (2H, m), 2.34 (3H, s), 2.83 (1H, d, J=11.5 Hz), 2.91 (1H, d, J=10.5 Hz), 3.38 (1H, d, J=13.5 Hz), 3.44-3.55 (1H, m), 3.58 (1H, d, J=13.5 Hz), 3.62 (2H, s), 3.85-3.97 (1H, m), 4.00-4.10 (1H, m), 7.02 (1H, s), 7.06 (1H, s), 7.07 (1H, s), 7.51 (2H, s), 7.82 (1H, s).

Example 467

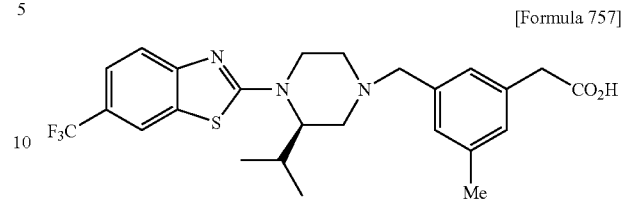
[Formula 757]

Yield 53%, 1H-NMR (DMSO-d6): δ 0.87 (3H, d, J=6.5 Hz), 0.89 (3H, d, J=6.5 Hz), 2.02-2.25 (2H, m), 2.29 (3H, s), 2.45-3.05 (4H, m), 3.10 (1H, d, J=13.0 Hz), 3.35-3.58 (2H, m), 3.53 (2H, s), 4.01-4.22 (1H, m), 6.96 (1H, s), 7.00 (1H, s), 7.03 (1H, s), 7.49 (2H, s), 7.78 (1H, s).

Example 468

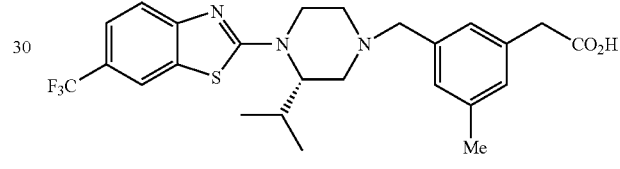
[Formula 758]

Yield 70%, 1H-NMR (DMSO-d6): δ 0.85 (6H, t, J=7.5 Hz), 2.00 (1H, d, J=11.5 Hz), 2.14 (1H, t, J=11.5 Hz), 2.28 (3H, s), 2.50-2.57 (1H, m), 2.93 (2H, t, J=11.5 Hz), 3.32 (1H, d, J=13.5 Hz), 3.32-3.48 (1H, m), 3.49 (2H, s), 3.57 (1H, d, J=13.5 Hz), 3.58-3.65 (1H, m), 3.95-4.10 (1H, m), 6.97 (1H, s), 7.02 (2H, s), 7.49 (1H, d, J=8.5 Hz), 7.55 (1H, d, J=8.5 Hz), 8.18 (1H, s), 12.4 (1H, brs).

Example 469

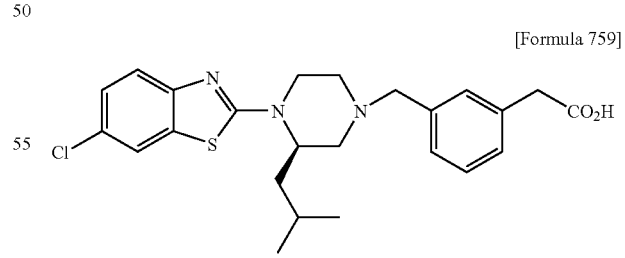
[Formula 759]

Yield 67%, 1H-NMR (DMSO-d6): δ 0.88 (3H, d, J=6.5 Hz), 0.90 (3H, d, J=6.5 Hz), 1.32-1.58 (2H, m), 1.80-1.96 (1H, m), 2.05-2.23 (2H, m), 2.75 (1H, d, J=10.5 Hz), 2.89 (1H, d, J=11.5 Hz), 3.30-3.53 (2H, m), 3.48 (2H, s), 3.59 (1H, d, J=13.5 Hz), 3.80-4.08 (2H, m), 7.10-7.30 (5H, m), 7.38 (1H, d, J=8.5 Hz), 7.87 (1H, d, J=2.0 Hz).

Example 470

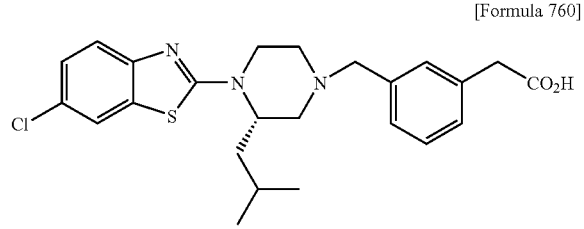
[Formula 760]

Yield 88%, 1H-NMR (CDCl3): δ0.90 (6H, dd, J=6, 2 Hz), 1.30-1.59 (2H, m), 1.80-1.95 (1H, m), 2.08-2.24 (2H, m), 2.75 (1H, d, J=11.5 Hz), 2.91 (1H, d, J=11.5 Hz), 3.20-3.37 (1H, m), 3.38 (1H, d, J=13.5 Hz), 3.55 (2H, s), 3.62 (1H, d, J=13.5 Hz), 3.80-3.96 (1H, m), 3.97-4.10 (1H, m), 7.10-7.32 (5H, m), 7.38 (1H, d, J=8.5 Hz), 7.89 (1H, d, J=2 Hz), 12.43 (1H, brs).

Example 471

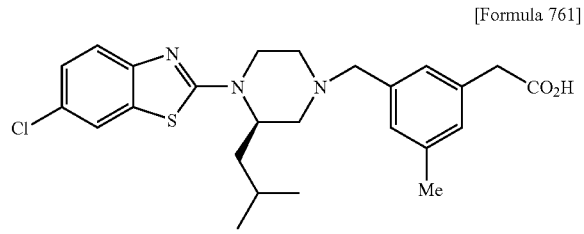
[Formula 761]

Yield 62%, 1H-NMR (CDCl3): δ0.91 (3H, d, J=6.5 Hz), 0.93 (3H, d, J=6.5 Hz), 1.34-1.64 (2H, m), 1.85-2.00 (1H, m), 2.11-2.38 (2H, m), 2.31 (3H, s), 2.77 (1H, d, J=11.0 Hz), 2.86 (1H, d, J=10.5 Hz), 3.32 (1H, d, J=13.0 Hz), 3.38-3.64 (2H, m), 3.56 (2H, s), 3.83-4.07 (2H, m), 6.98 (1H, s), 7.01 (1H, s), 7.05 (1H, s), 7.21 (1H, dd, J=8.5, 2.0 Hz), 7.39 (1H, d, J=8.5 Hz), 7.52 (1H, d, J=2.0 Hz).

Example 472

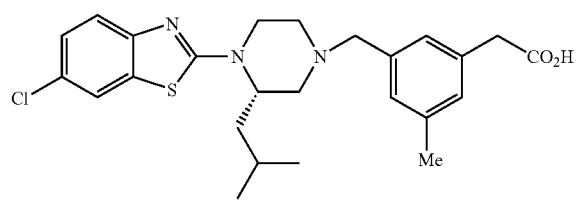
[Formula 762]

Yield 92%, 1H-NMR (CDCl3): δ0.90 (6H, t, J=6 Hz), 1.42-1.53 (2H, m), 1.93-2.01 (1H, m), 2.02-2.12 (2H, m), 2.29 (3H, s), 2.75 (1H, d, J=11.5 Hz), 2.91 (1H, d, J=11.5 Hz), 3.31 (1H, d, J=13.5 Hz), 3.32-3.50 (1H, m), 3.51 (2H, s), 3.61 (1H, d, J=13.5 Hz), 3.87-4.04 (2H, m), 6.97 (1H, s), 7.02 (1H, s), 7.04 (1H, s), 7.27 (1H, dd, J=8.5, 2 Hz), 7.38 (1H, d, J=8.5 Hz), 7.89 (1H, d, J=2 Hz), 12.28 (1H, brs).

Example 473

[Formula 763]

Yield 99%, 1H-NMR (CDCl3): δ0.90 (3H, d, J=6.0 Hz), 0.92 (3H, d, J=6.0 Hz), 1.34-1.64 (2H, m), 1.84-1.98 (1H, m), 2.07-2.30 (2H, m), 2.26 (3H, s), 2.74 (1H, d, J=11.0 Hz), 2.82 (1H, d, J=10.5 Hz), 3.28 (1H, d, J=13.5 Hz), 3.35-3.54 (4H, m), 3.87-4.07 (2H, m), 6.91 (1H, s), 6.93 (1H, s), 7.02 (1H, s), 7.50 (2H, s), 7.81 (1H, s).

Example 474

[Formula 764]

Yield 98%, 1H-NMR (CDCl3): δ0.93 (6H, dd, J=3.6, 6.3 Hz), 1.42-1.50 (1H, m), 1.55-1.64 (1H, m), 1.90-1.99 (1H, m), 2.23 (2H, td, J=3.6, 11.4 Hz), 2.34 (3H, s), 2.81 (1H, d, J=11.4 Hz), 2.92 (1H, d, J=10.2 Hz), 3.37 (1H, d, J=13.2 Hz), 3.52 (1H, td, J=3.3, 12.9 Hz), 3.62 (1H, d, J=13.2 Hz), 3.62 (2H, s), 4.04 (2H, br), 7.02 (1H, s), 7.07 (2H, s), 7.52 (2H, s), 7.82 (1H, s)

Example 475

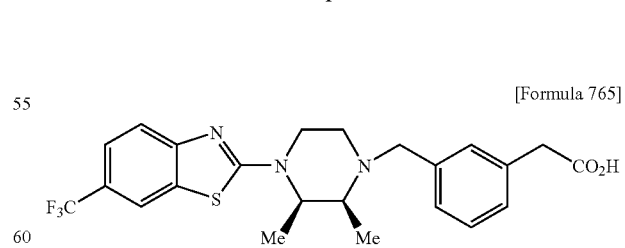
[Formula 765]

Yield 62%, 1H-NMR (CDCl3): δ1.23 (3H, d, J=6.5 Hz), 1.38 (3H, d, J=6.5 Hz), 2.11-2.26 (1H, m), 2.65-2.89 (2H, m), 2.98-3.15 (1H, m), 3.35-3.52 (1H, m), 3.67 (2H, s), 3.68-3.82 (1H, m), 4.03-4.22 (2H, m), 7.17-7.36 (4H, m), 7.48-7.60 (2H, m), 7.83 (1H, s).

Example 476

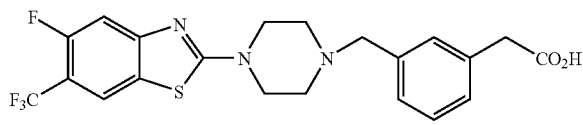

[Formula 766]

Yield 80%, 1H-NMR (DMSO-d6): δ2.43-2.58 (4H, m), 3.54 (2H, s), 3.57 (2H, s), 3.58-3.70 (4H, m), 7.13-7.34 (4H, m), 7.47 (1H, d, J=12.5 Hz), 8.27 (1H, d, J=7.5 Hz), 12.28 (1H, s).

Example 477

[Formula 767]

Yield 92%, 1H-NMR (CDCl3): δ2.28 (3H, s), 2.50-2.62 (4H, m), 3.47 (2H, s), 3.52 (2H, s), 3.58-3.68 (4H, m), 6.97 (2H, s), 7.04 (1H, s), 7.25 (1H, d, J=11.5 Hz), 7.73 (1H, d, J=7.0 Hz).

Example 478

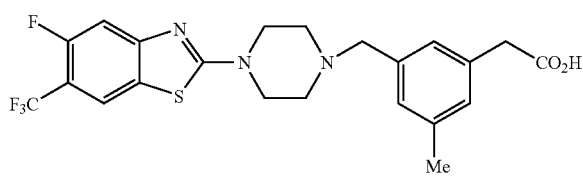

[Formula 768]

Yield 59%, 1H-NMR (CD3OD): δ2.06-2.18 (2H, m), 2.31 (3H, s), 2.87-2.97 (2H, m), 2.99-3.08 (2H, m), 3.52 (2H, s), 3.70-3.98 (4H, m), 3.82 (2H, s), 7.07 (2H, s), 7.11 (1H, s), 7.29 (1H, d, J=12.0 Hz), 7.98 (1H, d, J=7.0 Hz).

Example 479

[Formula 769]

Yield 85%, 1H-NMR (DMSO-d6): δ1.15 (3H, d, J=6 Hz), 2.16-2.27 (1H, m), 2.28 (3H, s), 2.55-2.68 (1H, m), 2.69-2.80 (1H, m), 3.17 (1H, d, J=13.5 Hz), 3.18-3.26 (1H, m), 3.35-3.48 (1H, m), 3.49 (2H, s), 3.65-3.79 (1H, m), 3.80-3.90 (1H, m), 3.92 (1H, d, J=13.5 Hz), 6.96 (1H, s), 7.00 (1H, s), 7.01 (1H, s), 7.45 (1H, d, J=12 Hz), 8.25 (1H, d, J=8 Hz), 12.40 (1H, brs).

Example 480

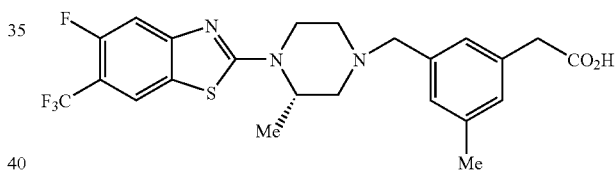

[Formula 770]

Yield 67%, 1H-NMR (CDCl3): δ1.39 (3H, d, J=7.0 Hz), 2.14-2.35 (2H, m), 2.32 (3H, s), 2.72 (1H, d, J=11.0 Hz), 2.91 (1H, d, J=11.0 Hz), 3.40 (1H, d, J=14.0 Hz), 3.43-3.62 (2H, m), 3.58 (2H, s), 3.86 (1H, d, J=12.5 Hz), 4.12-4.28 (1H, m), 6.99 (1H, s), 7.02-7.10 (2H, m), 7.25 (1H, d, J=11.5 Hz), 7.73 (1H, d, J=7.0 Hz).

Example 481

[Formula 771]

Yield 78%, 1H-NMR (CDCl3): δ1.38 (3H, d, J=7.0 Hz), 2.12-2.35 (2H, m), 2.30 (3H, s), 2.70 (1H, d, J=11.5 Hz), 2.88 (1H, d, J=11.5 Hz), 3.32-3.60 (5H, m), 3.84 (1H, d, J=11.5 Hz), 4.10-4.25 (1H, m), 6.97 (1H, s), 7.04 (2H, s), 7.24 (1H, d, J=12.0 Hz), 7.73 (1H, d, J=7.0 Hz).

Example 482

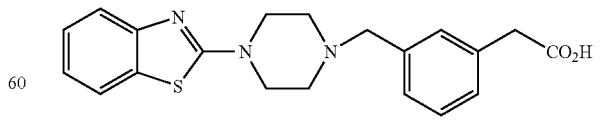

[Formula 772]

Yield 82%, 1H-NMR (DMSO-d6): δ2.45-2.60 (4H, m), 3.48-3.63 (8H, m), 7.06 (1H, td, J=7.5, 1.0 Hz), 7.13-7.33 (5H, m), 7.45 (1H, d, J=7.5 Hz), 7.76 (1H, d, J=7.5 Hz), 12.32 (1H, brs).

Example 483

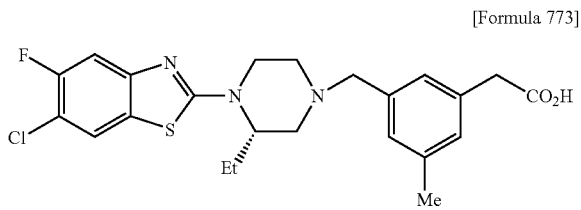

[Formula 773]

Yield 60%, 1H-NMR (CDCl3): δ0.85 (3H, t, J=7.5 Hz), 1.80-2.00 (2H, m), 2.12-2.26 (2H, m), 2.31 (3H, s), 2.77-2.91 (2H, m), 3.36 (1H, d, J=13.5 Hz), 3.36-3.62 (2H, m), 3.57 (2H, s), 3.75-3.87 (1H, m), 3.88-4.02 (1H, m), 6.98 (1H, s), 7.04 (2H, s), 7.24 (1H, d, J=10.5 Hz), 7.51 (1H, d, J=7.0 Hz).

Example 484

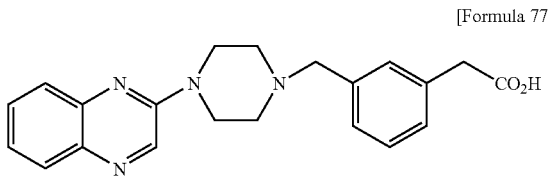

[Formula 774]

Yield 67%, 1H-NMR (CDCl3): δ2.75 (4H, t, J=5.0 Hz), 3.68 (4H, s), 3.85 (4H, t, J=5.0 Hz), 7.13-7.21 (1H, m), 7.22-7.34 (2H, m), 7.37-7.46 (2H, m), 7.54-7.64 (1H, m), 7.69 (1H, dd, J=8.0, 51.0 Hz), 7.89 (1H, dd, J=8.0, 1.0 Hz), 8.56 (1H, s).

Example 485

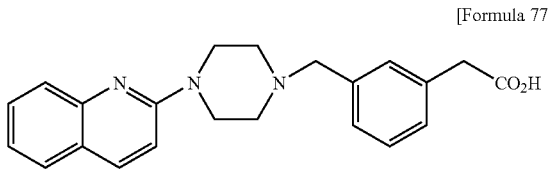

[Formula 775]

Yield 57%, 1H-NMR (CDCl3): δ2.82 (4H, t, J=4.5 Hz), 3.66 (2H, s), 3.74 (2H, s), 3.83 (4H, t, J=4.5 Hz), 6.93 (1H, d, J=9.0 Hz), 7.07-7.15 (1H, m), 7.20-7.31 (3H, m), 7.47 (1H, s), 7.54 (1H, td, J=8.0, 1.5 Hz), 7.60 (1H, d, J=8.0), 7.70 (1H, d, J=8.0 Hz), 7.89 (1H, d, J=9.0 Hz).

Example 486

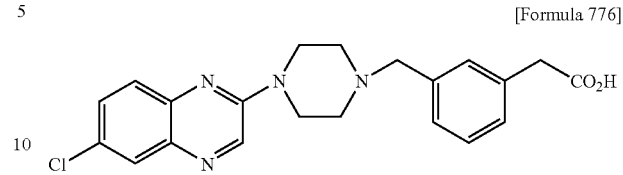

[Formula 776]

Yield 42%, 1H-NMR (CDCl3): δ2.65-2.77 (4H, m), 3.64 (4H, s), 3.76-3.88 (4H, m), 7.13-7.32 (3H, m), 7.38 (1H, s), 7.50 (1H, dd, J=9.0, 2.0 Hz), 7.59 (1H, d, J=9.0 Hz), 7.86 (1H, d, J=2.0 Hz), 8.53 (1H, s).

Example 487

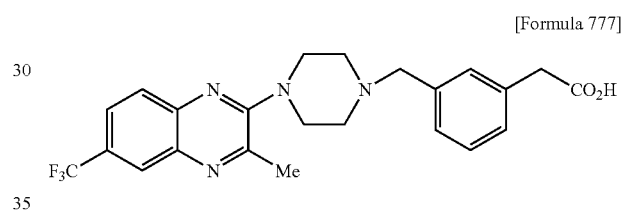

[Formula 777]

Yield 81%, 1H-NMR (CDCl3): δ2.60-2.74 (4H, m), 2.63 (3H, s), 3.35-3.49 (4H, m), 3.52 (2H, s), 3.54 (2H, s), 7.05-7.23 (3H, m), 7.29 (1H, s), 7.69 (1H, d, J=9.0 Hz), 7.80 (1H, d, J=9.0 Hz), 8.14 (1H, s).

Example 488

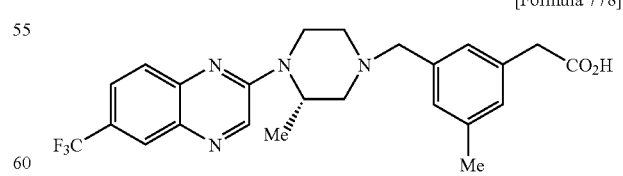

[Formula 778]

Yield 79%, 1H-NMR (CDCl3): δ1.35 (3H, d, J=6.5 Hz), 2.12-2.35 (5H, m), 2.79 (1H, d, J=11.5 Hz), 2.99 (1H, d, J=11.5 Hz), 3.27-3.43 (2H, m), 3.50-3.62 (3H, m), 4.35 (1H, d, J=12.5 Hz), 4.59-4.72 (1H, m), 6.98 (1H, s), 7.05 (1H, s), 7.08 (1H, s), 7.70 (2H, s), 8.13 (1H, s), 8.56 (1H, s).

Example 489

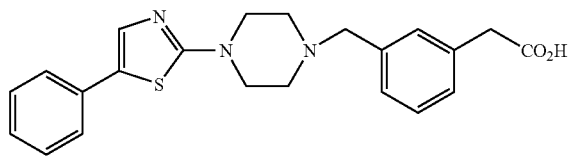

[Formula 779]

Yield 76%, 1H-NMR (CD3OD): δ2.69-2.78 (4H, m), 3.52-3.60 (4H, m), 3.61 (2H, s), 3.71 (2H, s), 7.18-7.39 (7H, m), 7.42-7.50 (3H, m).

Example 490

3-[[4-(6-chlorobenzothiazole-2-yl)piperazine-1-yl]methyl]phenyl acetic acid

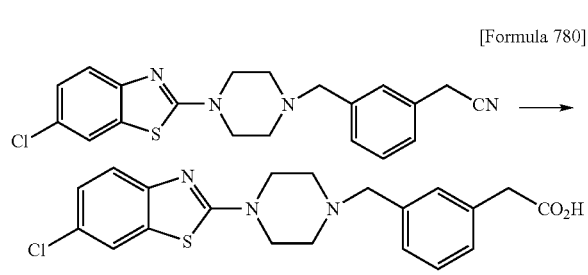

[Formula 780]

A mixture of {3-[[4-(6-chlorobenzothiazole-2-yl)piperazine-1-yl]methyl]phenyl}acetonitrile (0.35 g; 0.914 mmol), concentrated sulfuric acid (2 ml) and water (2 ml) was stirred at 80° C. for 2 hours. After air cooling, 5N-aqueous sodium hydroxide was added thereto to be alkaline. Ethyl acetate was added thereto and back-extracted. The water layer became neutral with 2N-aqueous hydrochloric acid and extracted with ethyl acetate. The organic layer was washed with brine, dried over anhydrous sodium sulphate, and evaporated under reduced pressure to give 3-[[4-(6-chlorobenzothiazole-2-yl)piperazine-1-yl]methyl]phenyl acetic acid as colorless amorphous solid (0.08 g; 22%).

$^1$H-NMR (DMSO-$d_6$): δ2.45-2.50 (4H, m), 3.53 (2H, s), 3.53-3.65 (6H, m), 7.10-7.35 (5H, m), 7.42 (1H, d, J=8.5 Hz), 7.91 (1H, d, J=2 Hz), 12.28 (1H, brs).

Compounds in Examples 491 to 512 were obtained by similar methods as Example 490.

Example 491

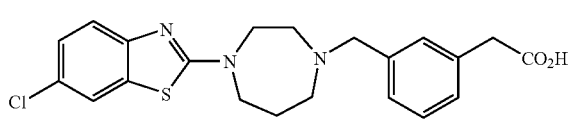

[Formula 781]

Yield: 43%, $^1$H-NMR (DMSO-$d_6$): δ1.90-1.96 (2H, m), 2.61 (2H, t, J=4.8 Hz), 2.77-2.80 (2H, m), 3.57-3.62 (4H, m), 3.62-3.71 (4H, m), 7.12-7.16 (2H, m), 7.21-7.28 (3H, m), 7.40 (1H, d, J=8.5 Hz), 7.88 (1H, d, J=2.4 Hz).

Example 492

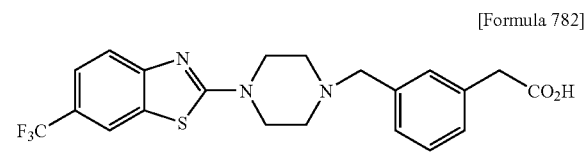

[Formula 782]

Yield: 78%, $^1$H-NMR (DMSO-$d_6$): δ2.52 (4H, t, J=5 Hz), 3.54 (2H, s), 3.57 (2H, s), 3.63 (4H, t, J=5 Hz), 7.10-7.35 (4H, m), 7.57 (2H, s), 8.24 (1H, s), 12.31 (1H, s).

Example 493

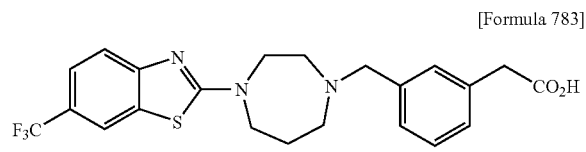

[Formula 783]

Yield: 18%, $^1$H-NMR (DMSO-$d_6$): δ1.85-2.00 (2H, m), 2.57-2.68 (2H, m), 2.74-2.85 (2H, m), 3.52 (2H, s), 3.61 (2H, s), 3.62-3.85 (4H, m), 7.09-7.31 (4H, m), 7.52-7.58 (2H, m), 8.22 (2H, s).

Example 494

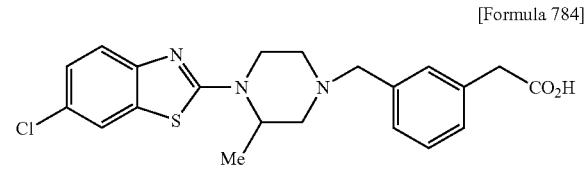

[Formula 784]

Yield: 79%, $^1$H-NMR (DMSO-$d_6$): δ1.31 (3H, d, J=6.5 Hz), 2.15 (1H, td, J=12, 3.5 Hz), 2.22 (1H, dd, J=11.5, 3.5 Hz), 2.70 (1H, d, J=11.5 Hz), 2.91 (1H, d, J=12 Hz), 3.41 (1H, td, J=12, 3.5 Hz), 3.44 (1H, d, J=13.5 Hz), 3.56 (2H, s), 3.59 (1H, d, J=13.5 Hz), 3.80 (1H, d, J=12 Hz), 4.10-4.30 (1H, m), 7.10-7.35 (5H, m), 7.41 (1H, d, J=8.5 Hz), 7.90 (1H, d, J=2 Hz), 12.40 (1H, brs).

Example 495

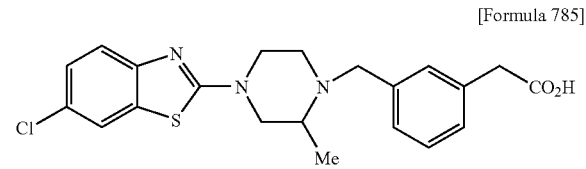

[Formula 785]

Yield: 69%, $^1$H-NMR (DMSO-$d_6$): δ1.05-1.25 (3H, m), 2.15-2.30 (1H, s), 2.50-2.65 (1H, m), 2.65-2.80 (1H, m), 3.05-3.40 (3H, m), 3.57 (2H, s), 3.60-3.70 (1H, m), 3.70-3.85 (1H, m), 3.90-4.00 (1H, m), 7.05-7.35 (5H, m), 7.41 (1H, d, J=8.5 Hz), 7.90 (1H, s), 12.29 (1H, s).

Example 496

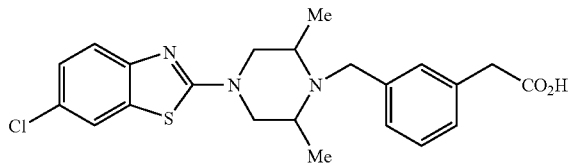

[Formula 786]

Yield: 92%, $^1$H-NMR (DMSO-$d_6$): δ1.04 (6H, d, J=6 Hz), 2.60-2.80 (2H, m), 2.95-3.10 (2H, m), 3.53 (2H, s), 3.77 (2H, s), 3.77-3.87 (2H, m), 7.00-7.10 (1H, m), 7.20-7.30 (4H, m), 7.42 (1H, d, J=8.5 Hz), 7.90 (1H, d, J=2 Hz), 12.5 (1H, brs).

Example 497

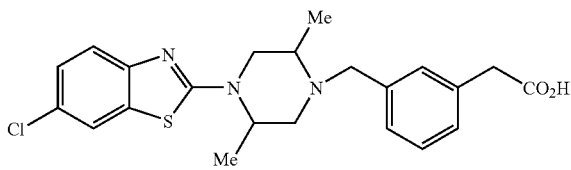

[Formula 787]

Yield: 76%, $^1$H-NMR (DMSO-$d_6$): δ1.00 (3H, d, J=6 Hz), 1.30 (3H, d, J=6 Hz), 2.30 (1H, d, J=9.5 Hz), 2.70-2.85 (1H, m), 3.05-3.15 (1H, m), 3.40-3.45 (1H, m), 3.49 (2H, s), 3.62 (2H, s), 3.63-3.70 (1H, m), 4.10-4.30 (1H, m), 7.05-7.10 (1H, m), 7.20-7.35 (4H, m), 7.38 (1H, d, J=9 Hz), 7.87 (1H, d, J=2 Hz).

Example 498

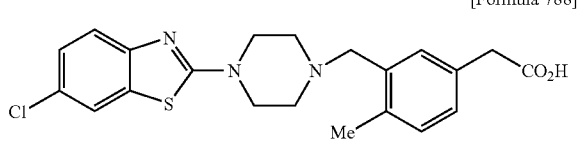

[Formula 788]

Yield: 42%, $^1$H-NMR (DMSO-$d_6$): 2.31 (3H, s), 2.50 (4H, t, J=5 Hz), 3.47 (2H, s), 3.52 (2H, s), 3.55 (4H, t, J=5 Hz), 7.00-7.18 (3H, m), 7.28 (1H, dd, J=8.5, 2 Hz), 7.42 (1H, d, J=8.5 Hz), 7.91 (1H, d, J=2 Hz), 12.25 (1H, brs).

Example 499

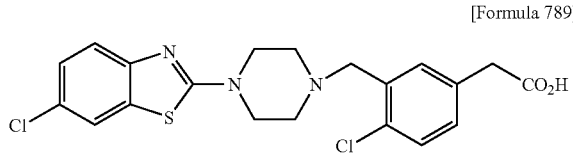

[Formula 789]

Yield: 39%, $^1$H-NMR (DMSO-$d_6$): δ2.58 (4H, t, J=5 Hz), 3.58 (4H, t, J=5 Hz), 3.61 (2H, s), 3.62 (2H, s), 7.19 (1H, dd, J=8, 2 Hz), 7.29 (1H, dd, J=8.5, 1.5 Hz), 7.39 (1H, d, J=8.5 Hz), 7.42 (1H, d, J=8 Hz), 7.43 (1H, d, J=1.5 Hz), 7.91 (1H, d, J=2 Hz), 12.41 (1H, brs).

Example 500

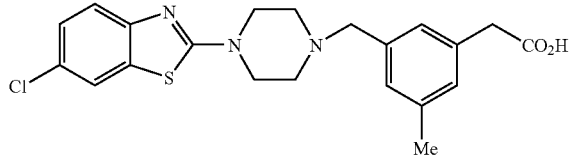

[Formula 790]

Yield: 68%, $^1$H-NMR (CDCl$_3$); δ2.32 (3H, s), 2.67 (4H, t, J=5 Hz), 3.59 (2H, s), 3.61 (2H, s), 3.67 (4H, t, J=5 Hz), 6.99 (1H, s), 7.04 (1H, s), 7.14 (1H, s), 7.24 (1H, dd, J=8.5, 2 Hz), 7.43 (1H, d, J=8.5 Hz), 7.55 (1H, d, J=2 Hz).

Example 501

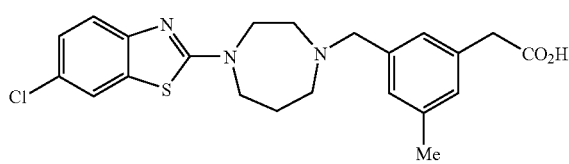

[Formula 791]

Yield: 73%, $^1$H-NMR (DMSO-$d_6$): δ1.88-1.94 (2H, m), 2.25 (3H, s), 2.60 (2H, t, J=4.5 Hz), 2.74-2.78 (2H, m), 3.48 (2H, s), 3.56 (2H, s), 3.66-3.73 (4H, m), 6.94-6.98 (3H, m), 7.26 (1H, dd, J=8.7, 2.1 Hz), 7.40 (1H, d, J=8.4 Hz), 7.88 (1H, d, J=2.1 Hz).

Example 502

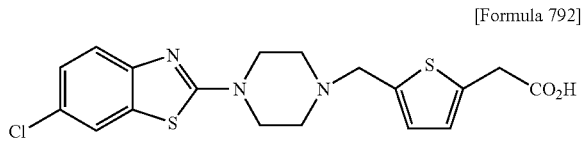
[Formula 792]

Yield: 67%, ¹H-NMR (CDCl₃); δ2.71 (4H, t, J=5 Hz), 3.67 (4H, t, J=5 Hz), 3.78 (2H, s), 3.81 (2H, s), 6.78 (2H, s), 7.24 (1H, dd, J=8.5, 2 Hz), 7.43 (1H, d, J=8.5 Hz), 7.56 (1H, d, J=2 Hz).

Example 503

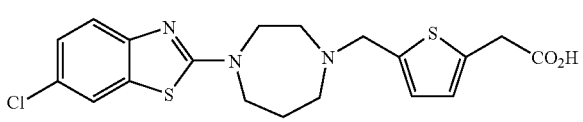
[Formula 793]

Yield: 46%, ¹H-NMR (CDCl₃); δ2.16-2.20 (2H, m), 2.91-2.95 (2H, m), 3.03-3.06 (2H, m), 3.68 (2H, t, J=6.0 Hz), 3.79 (2H, s), 3.90-3.91 (2H, m), 3.97 (2H, s), 6.75 (1H, d, J=3.6 Hz), 6.77 (1H, d, J=3.3 Hz), 7.24 (1H, dd, J=9.0, 2.4 Hz), 7.43 (1H, d, J=9.0 Hz), 7.55 (1H, d, J=2.1 Hz).

Example 504

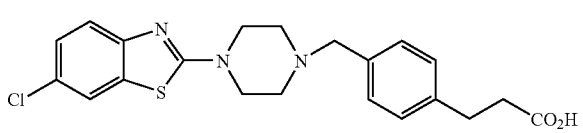
[Formula 794]

Yield: 2%, ¹H-NMR (DMSO-d₆): δ2.40-2.50 (4H, m), 2.53 (2H, t, J=7.5 Hz), 2.81 (2H, t, J=7.5 Hz), 3.50 (2H, s), 3.55 (4H, t, J=5 Hz), 7.19 (2H, d, J=8 Hz), 7.23 (2H, d, J=8 Hz), 7.29 (1H, dd, J=8.5, 2 Hz), 7.41 (1H, d, J=8.5 Hz), 7.90 (1H, d, J=2 Hz), 12.05 (1H, brs).

Example 505

[Formula 795]

Yield: 70%, ¹H-NMR (DMSO-d₆): δ2.28 (3H, s), 2.45-2.55 (4H, m), 3.49 (2H, s), 3.51 (2H, s), 3.60-3.65 (4H, m), 6.97 (1H, s), 7.02 (2H, s), 7.57 (2H, s), 8.25 (1H, s), 12.4 (1H, brs).

Example 506

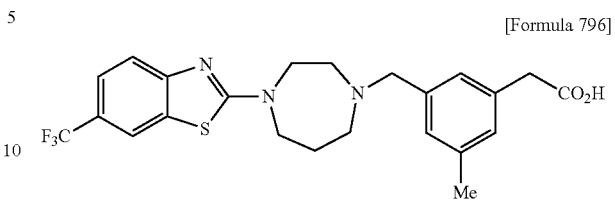
[Formula 796]

Yield: 55%, ¹H-NMR (DMSO-d₆): δ1.85-2.00 (2H, m), 2.25 (3H, s), 2.55-2.70 (2H, m), 2.70-2.85 (2H, m), 3.49 (2H, s), 3.57 (2H, s), 3.60-3.85 (4H, m), 6.94 (1H, s), 6.99 (2H, s), 7.55 (2H, s), 8.22 (1H, s), 12.4 (1H, brs).

Example 507

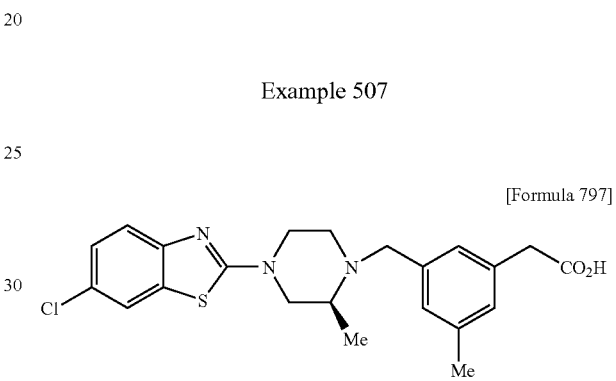
[Formula 797]

Yield 99%, 1H-NMR (CDCl3): δ1.24 (3H, d, J=6.0 Hz), 2.26-2.33 (1H, m), 2.33 (3H, s), 2.64-2.71 (1H, m), 2.82 (1H, dt, J=3.6, 12.0 Hz), 3.19 (2H, d, J=12.9 Hz), 3.38-3.45 (1H, m), 3.61 (2H, s), 3.70 (1H, dt, J=3.6, 12.9 Hz), 3.86 (1H, dd, J=2.1, 11.7 Hz), 4.05 (1H, d, J=12.9 Hz), 7.03 (2H, d, J=4.5 Hz), 7.09 (1H, s), 7.23 (1H, dd, J=2.1, 8.7 Hz), 7.43 (1H, d, J=8.7 Hz), 7.54 (1H, d, J=2.1 Hz)

Example 508

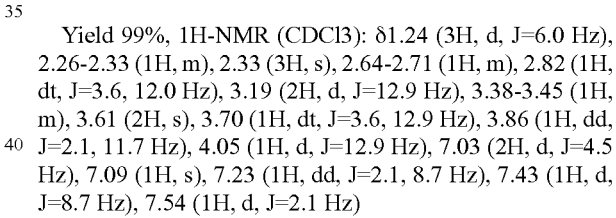
[Formula 798]

Yield 93%, 1H-NMR (CDCl3): δ1.24 (3H, d, J=6.3 Hz), 2.27-2.37 (1H, m), 2.33 (3H, s), 2.56-2.71 (1H, m), 2.83 (1H, dt, J=3.3, 12.0 Hz), 3.19 (2H, d, J=13.2 Hz), 3.38-3.47 (1H, m), 3.60 (2H, s), 3.70 (1H, dt, J=4.8, 12.6 Hz), 3.86 (1H, dd, J=2.7, 12.6 Hz), 4.06 (1H, d, J=13.2 Hz), 7.03 (2H, s), 7.09 (1H, s), 7.23 (1H, dd, J=2.1, 8.7 Hz), 7.43 (1H, d, J=8.7 Hz), 7.54 (1H, d, J=2.1 Hz)

Example 509

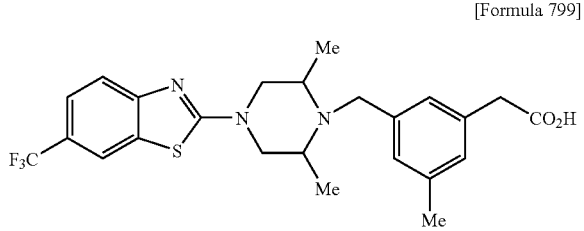
[Formula 799]

Yield 95%, 1H-NMR (DMSO-d6): δ1.04 (6H, d, J=6 Hz), 2.26 (3H, s), 2.60-2.80 (2H, m), 3.07 (1H, d, J=13 Hz), 3.09 (1H, d, J=13 Hz), 3.48 (2H, s), 3.73 (2H, s), 3.80-3.90 (2H, m), 6.88 (1H, s), 7.05 (2H, s), 7.55 (2H, s), 8.22 (1H, s), 12.21 (1H, brs).

Example 510

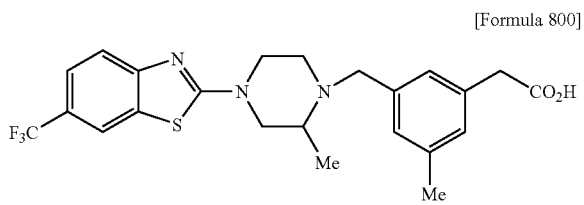
[Formula 800]

Yield 82%, 1H-NMR (DMSO-d6): δ1.15 (3H, d, J=6.5 Hz), 2.18-2.25 (1H, m), 2.28 (3H, s), 2.55-2.68 (1H, m), 2.68-2.80 (1H, m), 3.15-3.48 (3H, m), 3.50 (2H, s), 3.70-3.76 (1H, m), 3.80-3.90 (1H, m), 3.93 (1H, d, J=13.5 Hz), 6.96 (1H, s), 7.02 (2H, s), 7.56 (2H, s), 8.23 (1H, s), 12.43 (1H, brs).

Example 511

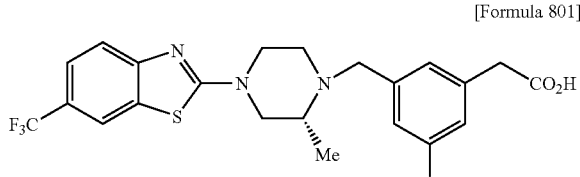
[Formula 801]

Yield 64%, 1H-NMR (CDCl3): δ1.23 (3H, d, J=6.5 Hz), 2.22-2.40 (4H, m), 2.60-2.74 (1H, m), 2.76-2.89 (1H, m), 3.10-3.31 (2H, m), 3.38-3.52 (1H, m), 3.59 (2H, s), 3.67-3.80 (1H, m), 3.84-3.96 (1H, m), 4.04 (1H, d, J=13.0 Hz), 6.97-7.12 (3H, m), 7.47-7.60 (2H, m), 7.83 (1H, s).

Example 512

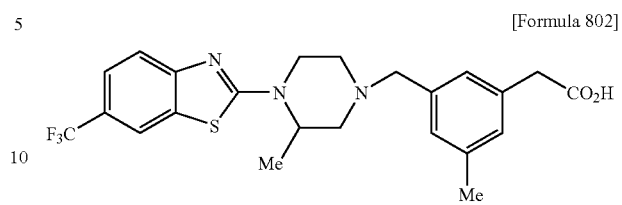
[Formula 802]

Yield 93%, 1H-NMR (DMSO-d6): δ1.33 (3H, d, J=6.5 Hz), 2.05-2.28 (2H, m), 2.29 (3H, s), 2.72 (1H, d, J=11 Hz), 2.93 (1H, d, J=11 Hz), 3.25-3.50 (2H, m), 3.51 (2H, s), 3.51-3.60 (1H, m), 3.86 (1H, d, J=11 Hz), 4.20-4.35 (1H, m), 6.97 (1H, s), 7.05 (2H, s), 7.56 (2H, s), 8.24 (1H, s), 12.43 (1H, brs).

Example 513

Preparation of 3-{3-[4-(6-chlorobenzothiazole-2-yl)piperazine-1-yl]methyl}phenylpropionic acid

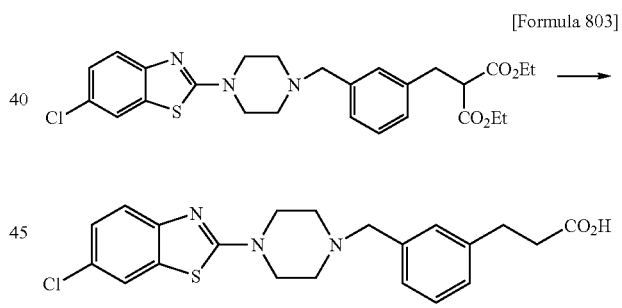
[Formula 803]

To 2-{3-[4-(6-chlorobenzothiazole-2-yl)piperazine-1-yl-methyl]benzyl}diethyl malonate (0.38 g; 0.736 mmol) was added 6N-aqueous hydrochloric acid. The mixture was refluxed for 2 hours. After cooling, saturated aqueous sodium hydrogencarbonate was added thereto to become neutral. Ethyl acetate was added thereto and extracted with ethyl acetate. The organic layer was washed with brine, dried over anhydrous sodium sulphate, and evaporated under reduced pressure. The residue was washed with diisopropyl ether to give 3-{3-[4-(6-chlorobenzothiazole-2-yl)piperazine-1-yl]methyl}phenylpropionic acid as colorless crystal (0.08 g; 22%).

1H-NMR (DMSO-d6): δ2.50-2.52 (4H, m), 2.53 (2H, t, J=7.5 Hz), 2.82 (2H, t, J=7.5 Hz), 3.51 (2H, s), 3.57 (4H, t, J=5 Hz), 7.10-7.20 (3H, m), 7.24 (1H, d, J=7.5 Hz), 7.28 (1H, dd, J=8.5, 2 Hz), 7.42 (1H, d, J=8.5 Hz), 7.91 (1H, d, J=2 Hz), 12.15 (1H, brs).

A compound in Example 514 was obtained by a similar method as Example 513.

Example 514

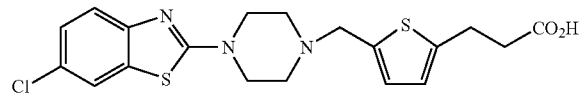

[Formula 804]

Yield: 55%, ¹H-NMR (CDCl₃): δ2.63 (4H, t, J=5 Hz), 2.72 (2H, t, J=7.5 Hz), 3.13 (2H, t, J=7.5 Hz), 3.64 (4H, t, J=5 Hz), 3.72 (2H, s), 6.68 (1H, d, J=3.5 Hz), 6.73 (1H, d, J=3.5 Hz), 7.24 (1H, dd, J=8.5, 2 Hz), 7.43 (1H, d, J=8.5 Hz), 7.55 (1H, d, J=2 Hz).

Example 515

Preparation of 3-{3-[4-(6-chlorobenzothiazole-2-yl)piperazine-1-yl]methyl}phenoxyacetic acid The following compound was obtained by a similar method as Reference Example 155.

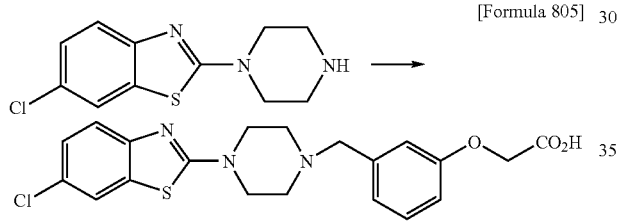

[Formula 805]

Yield: 55%, ¹H-NMR (DMSO-d₆): δ2.50-2.55 (4H, m), 3.51 (2H, s), 3.55-3.65 (4H, m), 4.61 (2H, s), 6.75-7.00 (3H, m), 7.20-7.35 (2H, m), 7.42 (1H, d, J=8 Hz), 7.90 (1H, d, J=2 Hz).

Example 516

Preparation of 3-{2-[1-(6-chlorobenzothiazole-2-yl)piperidine-4-yl]ethoxy}-4-methylphenyl acetic acid

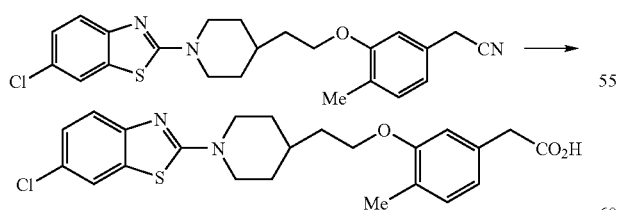

[Formula 806]

A mixture of [3-{2-[1-(6-chlorobenzothiazole-2-yl)piperidine-4-yl]ethoxy}-4-methylphenyl]acetonitrile (1.14 g; 2.68 mmol), sodium hydroxide (0.54 g; 13.5 mmol), water (1.6 ml) and ethanol (21 ml) was stirred at 80° C. for 6 hours. The reaction solution was concentrated under reduced pressure and became pH=7 with 2N-aqueous hydrochloric acid. The precipitate was collected to give 3-{2-[1-(6-chlorobenzothiazole-2-yl)piperidine-4-yl]ethoxy}-4-methylphenyl acetic acid as colorless crystal (0.63 g; 53%).

¹H-NMR (DMSO-d₆): δ1.20-1.38 (2H, m), 1.67-1.91 (5H, m), 2.09 (3H, s), 3.10-3.25 (4H, m), 3.93-4.06 (4H, m), 6.54 (1H, d, J=7.5 Hz), 6.82 (1H, s), 6.92 (1H, d, J=7.5 Hz), 7.27 (1H, dd, J=8.5, 2.0 Hz), 7.40 (1H, d, J=8.5 Hz), 7.88 (1H, d, J=2.0 Hz).

The present invention includes the following compounds synthesized by similar methods.

Example 517

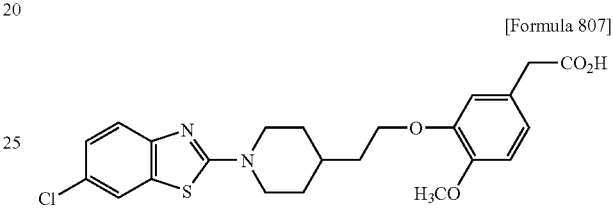

[Formula 807]

m/z=461 (M+H)+

Example 518

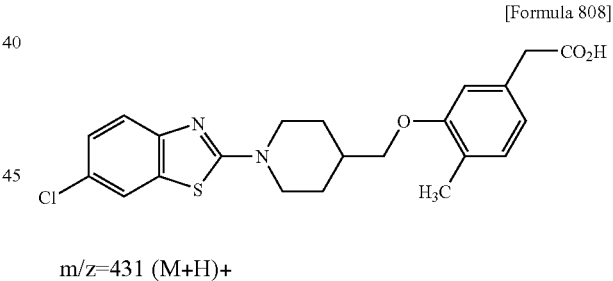

[Formula 808]

m/z=431 (M+H)+

Example 519

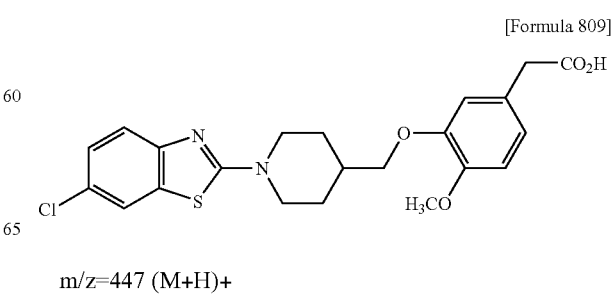

[Formula 809]

m/z=447 (M+H)+

Example 520
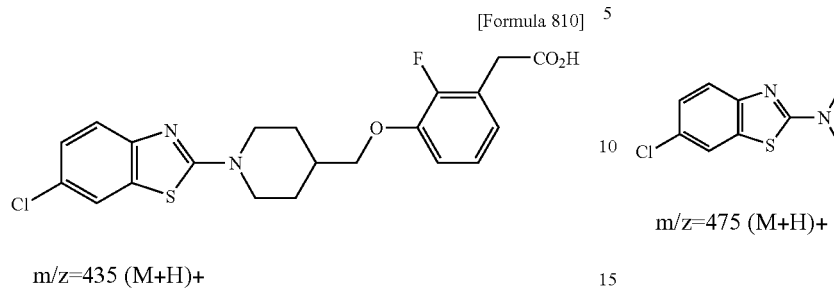
[Formula 810]
m/z=435 (M+H)+
Example 521
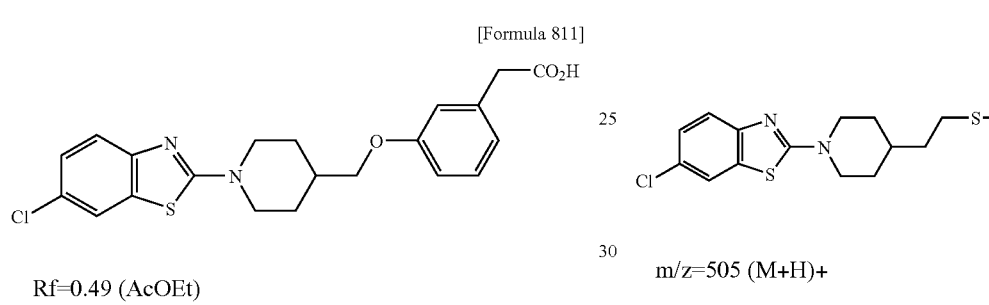
[Formula 811]
Rf=0.49 (AcOEt)
Example 522
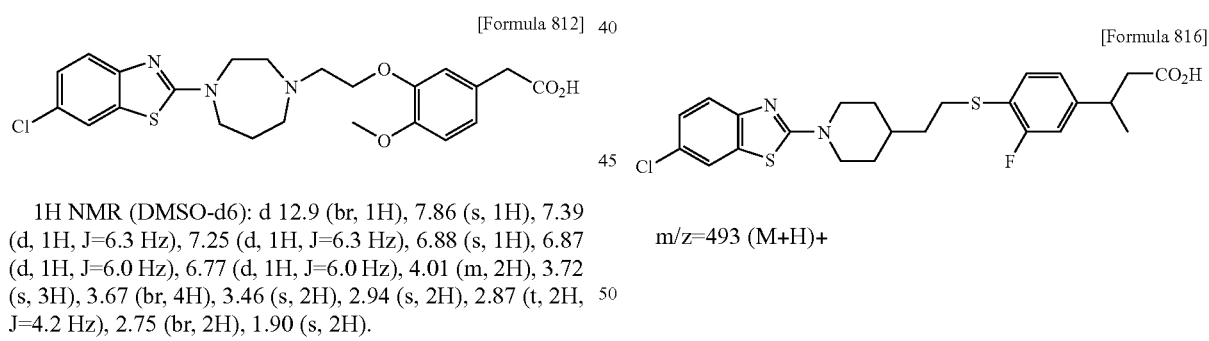
[Formula 812]
1H NMR (DMSO-d6): d 12.9 (br, 1H), 7.86 (s, 1H), 7.39 (d, 1H, J=6.3 Hz), 7.25 (d, 1H, J=6.3 Hz), 6.88 (s, 1H), 6.87 (d, 1H, J=6.0 Hz), 6.77 (d, 1H, J=6.0 Hz), 4.01 (m, 2H), 3.72 (s, 3H), 3.67 (br, 4H), 3.46 (s, 2H), 2.94 (s, 2H), 2.87 (t, 2H, J=4.2 Hz), 2.75 (br, 2H), 1.90 (s, 2H).
Example 523
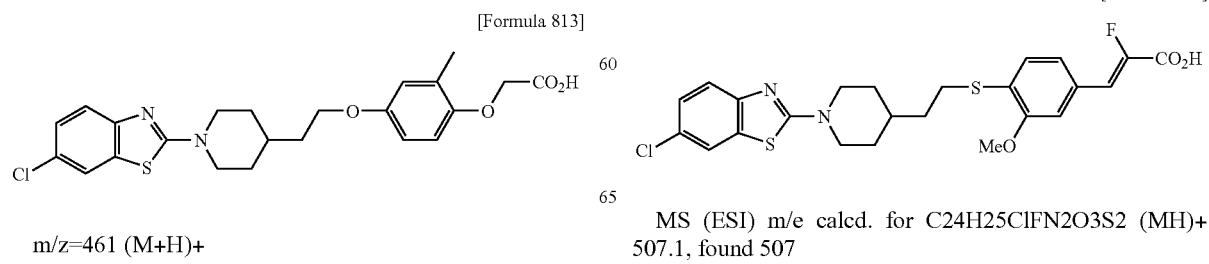
[Formula 813]
m/z=461 (M+H)+
Example 524
[Formula 814]
m/z=475 (M+H)+
Example 525
[Formula 815]
m/z=505 (M+H)+
Example 526
[Formula 816]
m/z=493 (M+H)+
Example 527
[Formula 817]
MS (ESI) m/e calcd. for C24H25ClFN2O3S2 (MH)+ 507.1, found 507

Example 528

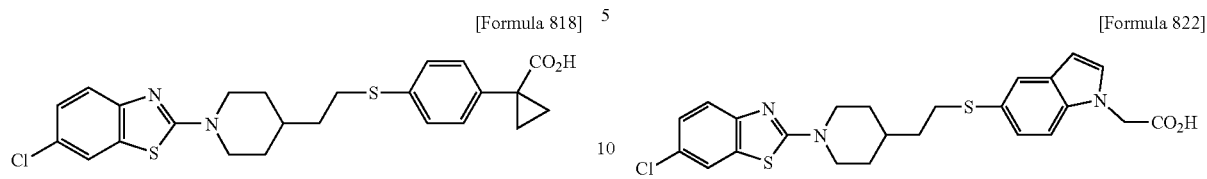

[Formula 818]

MS (ESI) m/e calcd. for C24H26ClN2O2S2 (MH)+ 473.1, found 473

Example 529

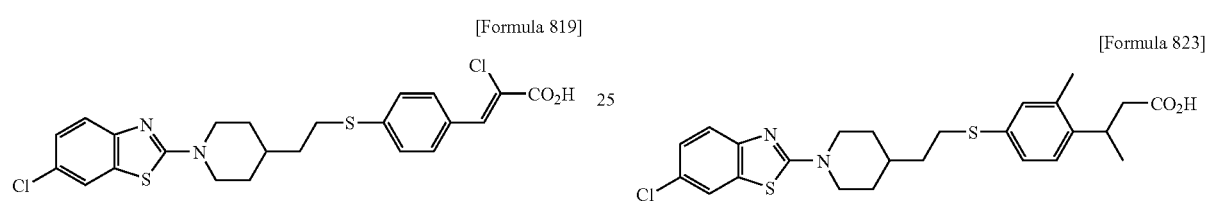

[Formula 819]

MS (ESI) m/e calcd. for C23H23Cl2N2O2S2 (MH)+ 493.1, found 493

Example 530

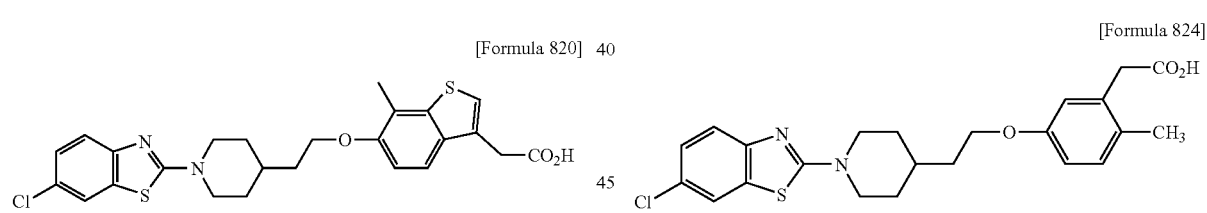

[Formula 820]

MS (ESI) m/e calcd. for $C_{25}H_{26}ClN_2O_3S_2$ (MH$^+$) 501.1, found 501.4

Example 531

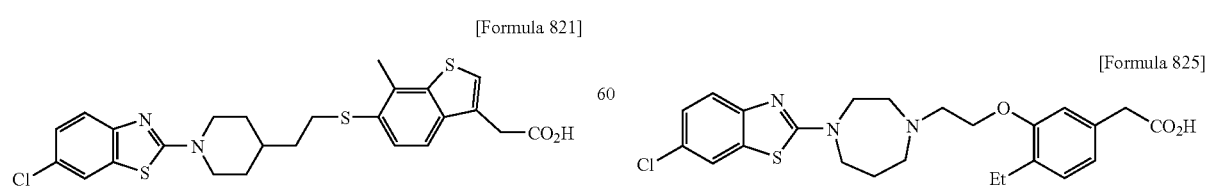

[Formula 821]

MS (ESI) m/e calcd. for $C_{25}H_{26}ClN_2O_2S_3$ (MH$^+$) 517.1, found 517.4

Example 532

[Formula 822]

MS (ESI) m/e calcd. for $C_{24}H_{25}ClN_3O_2S_2$ (MH$^+$) 486.1, found 486.4

Example 533

[Formula 823]

m/z=489 (M+H)+

Example 534

[Formula 824]

m/z=445 (M+H)+

Example 535

[Formula 825]

MS (ESI) m/e calcd. for $C_{24}H_{29}ClN_3O_3S$(MH$^+$) 474.2, found 474.4

Example 536
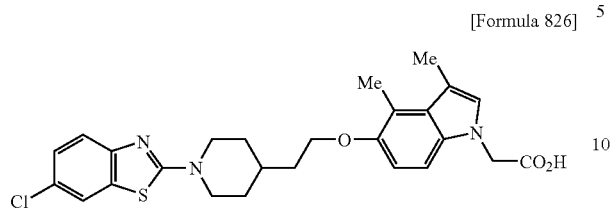
[Formula 826]
MS (ESI) m/e calcd. for C26H29ClN3O3S(MH)+ 498.2, found 498
Example 537
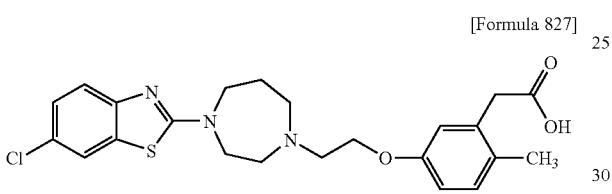
[Formula 827]
m/z=460 (M+H)+
Example 538
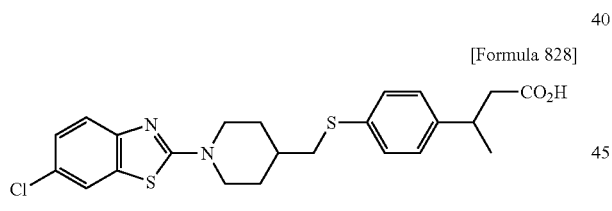
[Formula 828]
m/z=461 (M+H)+
Example 539
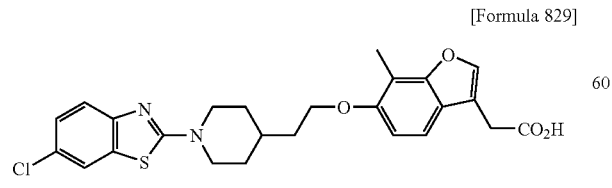
[Formula 829]
MS (ESI) m/e calcd. for $C_{25}H_{26}ClN_2O_4S(MH^+)$ 485.1, found 485.2
Example 540
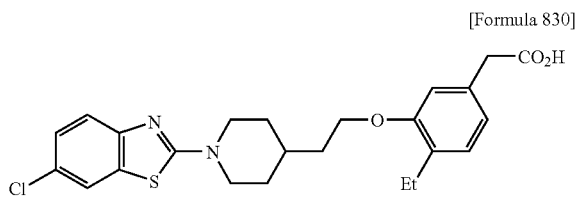
[Formula 830]
MS (ESI) m/e calcd. for $C_{24}H_{28}ClN_2O_3S(MH^+)$ 459.2, found 459.4
Example 541
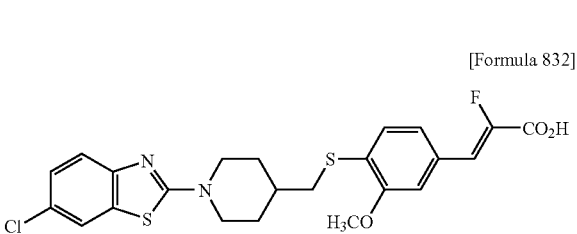
[Formula 831]
m/z=479 (M+H)+
Example 542
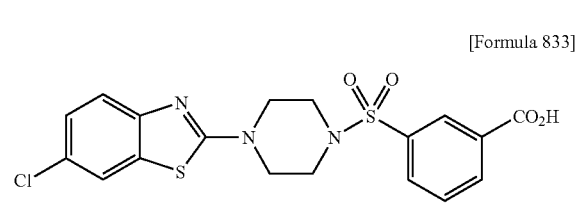
[Formula 832]
m/z=493 (M+H)+
Example 543
[Formula 833]
MS (ESI) m/z 438 [M+H]+

Example 544
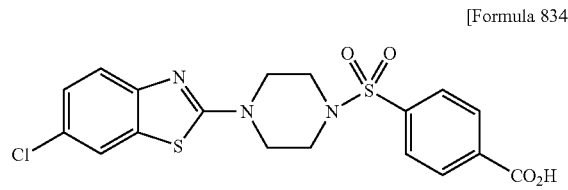
MS (ESI) m/z 438 [M+H]+
Example 545
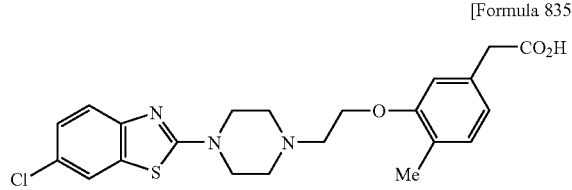
m/z=446 (M+H)+
Example 546
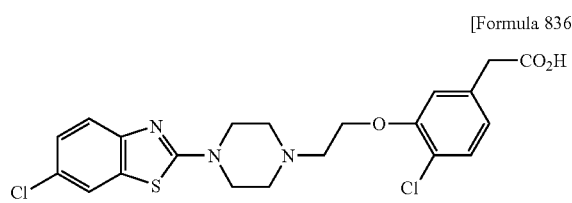
m/z=466 (M+H)+
Example 547
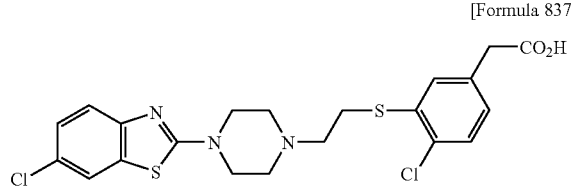
m/z=482 (M+H)+
Example 548
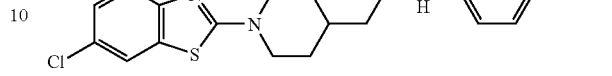
m/z=430 (M+H)+
Example 549
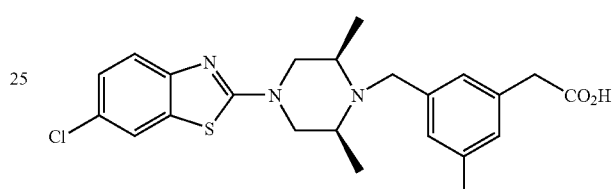
m/z=444 (M+H)+
Example 550
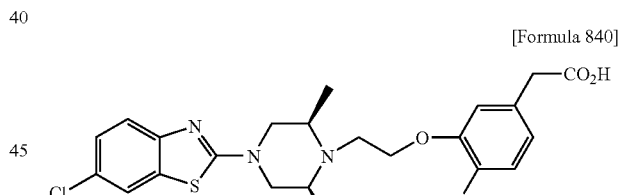
m/z=494 (M+H)+
Example 551
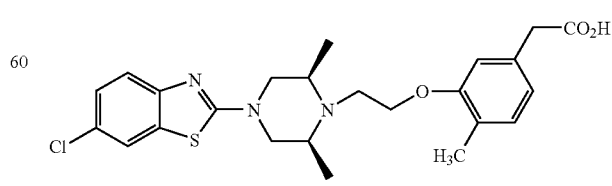
m/z=474 (M+H)+

Example 552

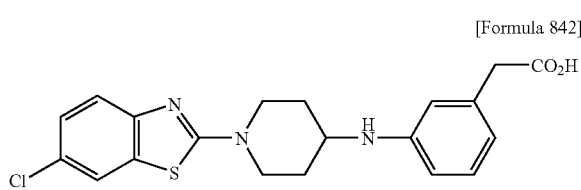

m/z=402 (M+H)+

Example 553

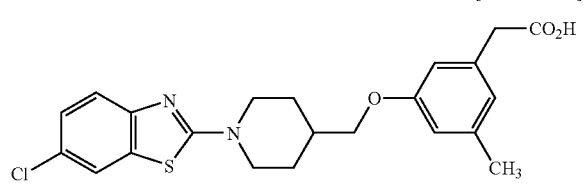

m/z=431 (M+H)+

Example 554

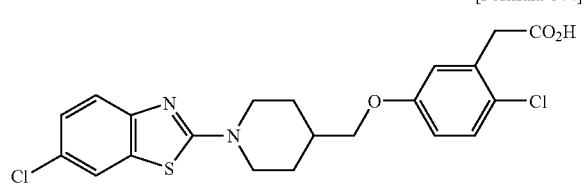

m/z=451 (M+H)+

Example 555

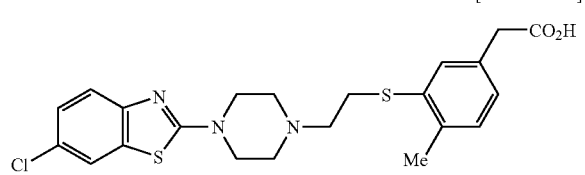

m/z=462 (M+H)+

Example 556

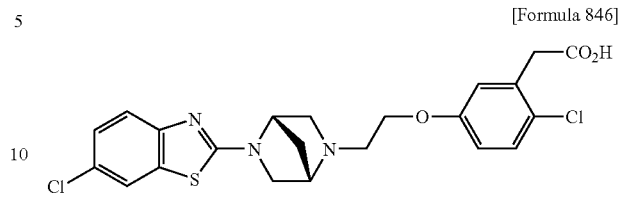

m/z=478 (M+H)+

Example 557

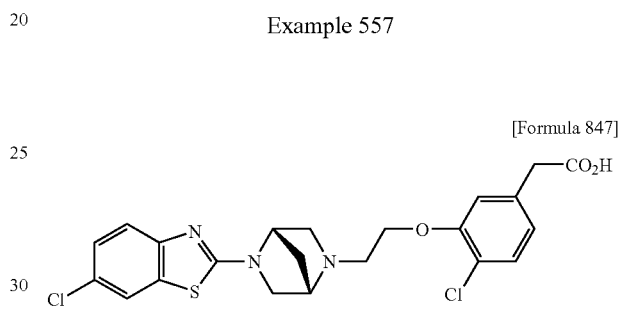

m/z=478 (M+H)+

Reference Example 228

Preparation of
1-(5-bromothiazole-2-yl)-3,5-dimethyl piperazine

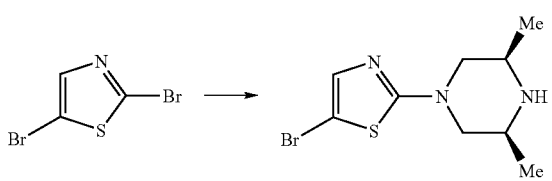

A mixture of 2,5-dibromothiazole (29.5 g), 2,6-dimethyl piperazine (13.8 g), potassium carbonate (20.1 g) and dimethylformamide (150 mL) was stirred at 60° C. for 6 hours. To the reaction solution was added water and extracted with ethyl acetate. The organic layer was washed with water and brine, and dried over sodium sulphate. The solvent was evaporated under reduced pressure to give the title compound (21.5 g). Yield: 64%.

$^1$H-NMR (CDCl$_3$) δ: 1.14 (6H, d, J=6.3 Hz), 2.05 (1H, br), 2.59-2.63 (2H, m), 2.98-3.02 (2H, m), 3.70-3.74 (2H, m), 7.06 (1H, s).

Reference Example 229

Preparation of [4-(5-bromothiazole-2-yl)-2,6-dimethyl piperazine-1-yl]acetic acid methyl ester

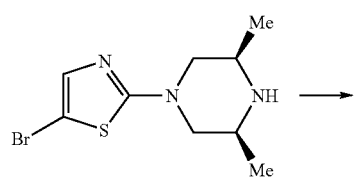
[Formula 849]

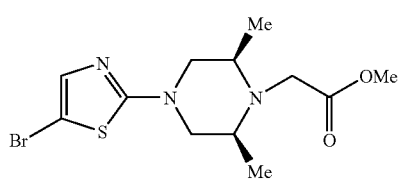

A mixture of 1-(5-bromothiazole-2-yl)-3,5-dimethyl piperazine (21.5 g), bromo acetic acid methyl ester (8.8 mL), potassium carbonate (12.9 g) and dimethylformamide (150 mL) was stirred at 60° C. for 2.5 hours. To the reaction solution was added water and extracted with ethyl acetate. The organic layer was washed with water and brine, and dried over magnesium sulphate. The solvent was evaporated under reduced pressure. The residue was purified by column chromatograph on silica gel to give the title compound (20.1 g). Yield: 74%.

$^1$H-NMR (CDCl3) δ: 1.17 (6H, d, J=6.0 Hz), 2.80-2.84 (2H, m), 3.13-3.16 (2H, m), 3.65 (2H, s), 3.65-3.68 (2H, m), 3.73 (3H, s), 7.08 (1H, s).

Reference Example 230

Preparation of 2-[4-(5-bromothiazole-2-yl)-2,6-dimethyl piperazine-1-yl]ethanol

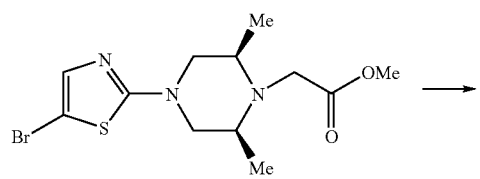
[Formula 850]

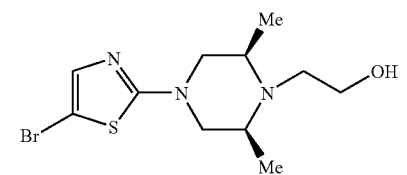

To a solution of [4-(5-bromothiazole-2-yl)-2,6-dimethyl piperazine-1-yl]acetic acid methyl ester (20.1 g) in tetrahydrofuran (300 mL) was added dropwise diisobutyl aluminium hydride (1M toluene solution, 200 mL) at -78° C. The mixture was stirred at -78° C. for 3.5 hours. To the reaction solution were added aqueous ammonium chloride solution (150 mL) and diethyl ether (45 mL). The insoluble material was filtrated. The filtrate was extracted diethyl ether. The organic layer was washed with water and brine, and dried over magnesium sulphate. The solvent was evaporated under reduced pressure. The residue was purified by column chromatograph on silica gel to give the title compound (13.2 g). Yield: 71%.

$^1$H-NMR (CDCl$_3$) δ: 1.17 (6H, d, J=5.8 Hz), 2.44 (1H, br), 2.84 (6H, dd, J=16.9, 11.1 Hz), 3.60-3.64 (4H, m), 7.06 (1H, s).

Reference Example 231

Preparation of [3-[2-[4-(5-bromothiazole-2-yl)-2,6-dimethyl piperazine-1-yl]ethoxy]-4-methylphenyl] acetic acid methyl ester

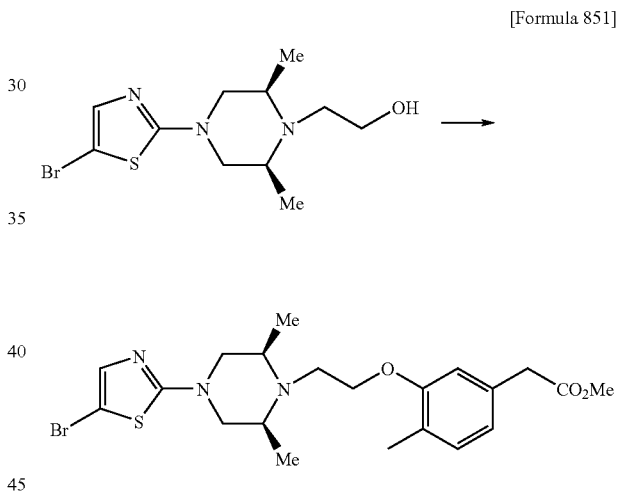
[Formula 851]

To a mixture of 2-[4-(5-bromothiazole-2-yl)-2,6-dimethyl piperazine-1-yl]ethanol (9.87 g), triethylamine (8.6 mL) and methylene chloride (100 mL) was added dropwise methanesulfonyl chloride (2.9 mL) at 0° C. After stirring at 0° C. for 0.5 hour, to the reaction solution was added water and extracted with chloroform. The organic layer was washed with water and brine, and dried over magnesium sulphate. The solvent was evaporated under reduced pressure. The obtained residue was dissolved in acetonitrile (100 mL). (3-hydroxy-4-methylphenyl)acetic acid methyl ester (5.0 g) and cesium carbonate (12.0 g) were added thereto and stirred at 60° C. for 1 hour. The reaction solution was diluted with ethyl acetate and the insoluble material was filtrated. The filtrate was evaporated under reduced pressure. The residue was purified by column chromatograph on silica gel to give the title compound (8.49 g). Yield: 57%.

$^1$H-NMR (CDCl$_3$) δ: 1.27 (6H, d, J=6.6 Hz), 2.20 (3H, s), 2.87-2.91 (4H, m), 3.25-3.27 (2H, m), 3.60 (2H, s), 3.68 (2H, brm), 3.71 (3H, s), 4.03-4.05 (2H, m), 6.75 (1H, d, J=1.4 Hz), 6.79 (1H, dd, J=7.7, 1.4 Hz), 7.07 (1H, s), 7.10 (1H, d, J=7.7 Hz).

Reference Example 232

Preparation of [3-[2-[4-(5-bromothiazole-2-yl)-2,6-dimethyl piperazine-1-yl]ethoxy]-4-methylphenyl] acetic acid

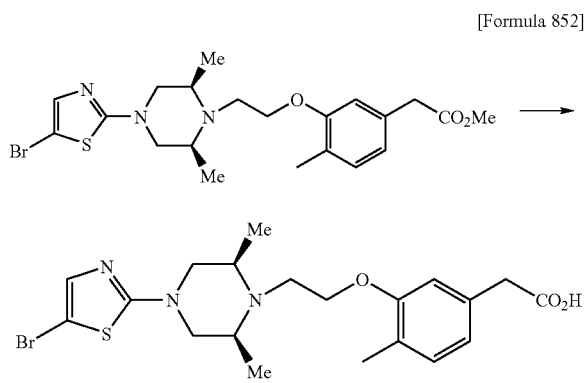

[Formula 852]

A mixture of [3-[2-[4-(5-bromothiazole-2-yl)-2,6-dimethyl piperazine-1-yl]ethoxy]-4-methylphenyl]acetic acid methyl ester (8.49 g), 2N aqueous sodium hydroxide solution (22 mL), methanol (50 mL) and tetrahydrofuran (50 mL) was stirred at room temperature for 1.5 hours. To the reaction solution were added water and brine. The mixture was washed with ethyl acetate. The water layer was neutralized with 2N hydrochloric acid and extracted with chloroform. The organic layer was washed with water and brine, and dried over magnesium sulphate. The solvent was evaporated under reduced pressure and the residue was washed with diisopropyl ether to give the title compound (5.81 g).

Yield: 71%.

$^1$H-NMR (DMSO-$d_6$) δ: 1.16 (6H, d, J=5.5 Hz), 2.13 (3H, s), 2.71-2.83 (4H, m), 3.12-3.14 (2H, m), 3.52 (2H, s), 3.65-3.68 (2H, m), 3.99-4.01 (2H, m), 6.74 (1H, d, J=7.4 Hz), 6.87 (1H, s), 7.07 (1H, d, J=7.4 Hz), 8.34 (1H, s).

Example 558

Preparation of [3-[2-[4-[5-(2,5-difluorophenyl)thiazole-2-yl]-2,6-dimethyl piperazine-1-yl]ethoxy]-4-methylphenyl]acetic acid

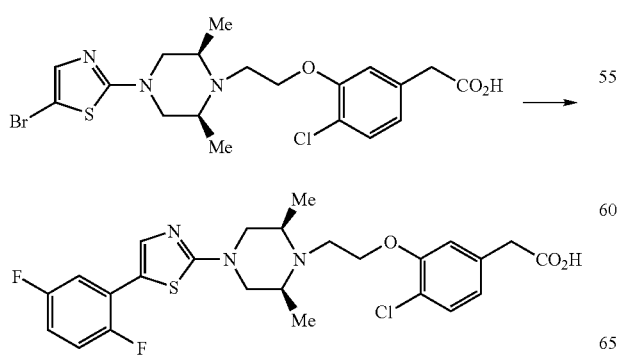

[Formula 853]

A mixture of [3-[2-[4-(5-bromothiazole-2-yl)-2,6-dimethyl piperazine-1-yl]ethoxy]-4-methylphenyl]acetic acid (400 mg), 2,5-difluorophenyl boronic acid (270 mg), tetrakis (triphenylphosphine) palladium (100 mg), 1M sodium carbonate (4.3 mL) and dimethylformamide (8 mL) was reacted with a microwave reaction device at 180° C. for 5 minutes. To the reaction solution was added water and extracted with chloroform. The organic layer was washed with water and brine, and dried over magnesium sulphate. The solvent was evaporated under reduced pressure. The residue was purified by column chromatograph on silica gel to give the title compound (369 mg). Yield: 87%.

MS (ESI) m/z 502 [M+H]

The following compounds were obtained by similar methods as above.

Example 559

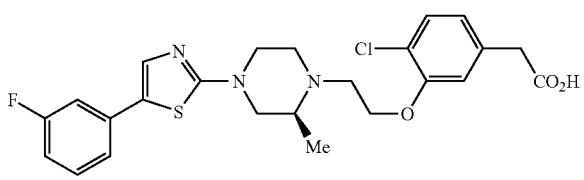

[Formula 854]

MS (ESI) m/z 508 [M+]

Example 560

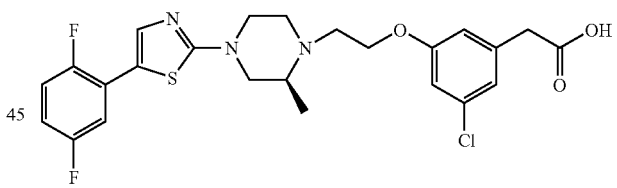

[Formula 855]

MS (ESI) m/z 508 [M+]

Example 561

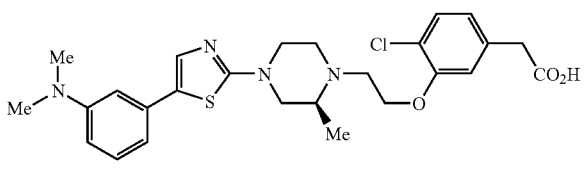

[Formula 856]

MS (ESI) m/z 515, 517 [M+H]+

Example 562
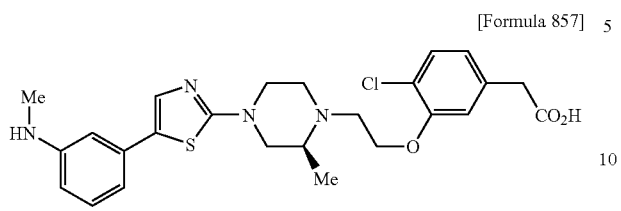
[Formula 857]
MS (ESI) m/z 501, 503 [M+H]+
Example 563
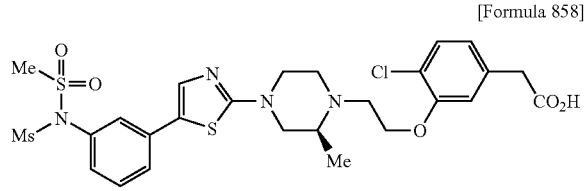
[Formula 858]
MS (ESI) m/z 579, 581 [+H]+
Example 564
[Formula 859]
MS (ESI) m/z 529, 531 [M+H]+
Example 565
[Formula 860]
1H-NMR (DMSO-d6) δ: 1.11 (6H, d, J=5.1 Hz), 2.60-2.70 (2H, m), 3.00-3.05 (2H, m), 3.55 (2H, s), 3.96-4.05 (2H, m), 4.32-4.45 (2H, m), 6.80-6.96 (3H, m), 8.44 (2H, s).
Example 566
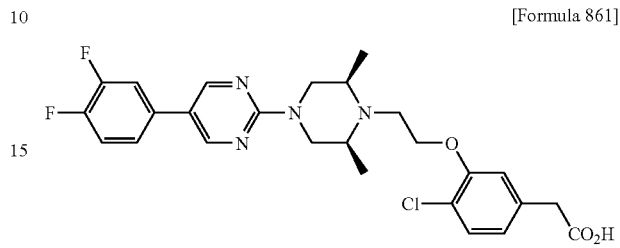
[Formula 861]
1H-NMR (DMSO-d6) δ: 1.17 (6H, d, J=4.9 Hz), 2.64-2.74 (4H, m), 3.09-3.18 (2H, m), 3.55 (2H, s), 4.03-4.10 (2H, m), 4.48-4.60 (2H, m), 6.83 (1H, dd, J=8.0, 0.8 Hz), 7.09 (1H, d, J=1.1 Hz), 7.33 (1H, d, J=8.0 Hz), 7.47-7.83 (3H, m), 8.71 (2H, s).
Example 567
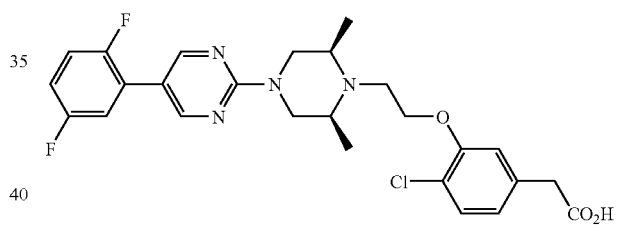
[Formula 862]
1H-NMR (DMSO-d6) δ: 1.17 (6H, d, J=4.4 Hz), 2.64-2.76 (4H, m), 3.10-3.18 (2H, m), 3.56 (2H, s), 4.04-4.11 (2H, m), 4.49-4.60 (2H, m), 6.83 (1H, d, J=8.0 Hz), 7.07-7.59 (5H, m), 8.59 (2H, s).
Example 568
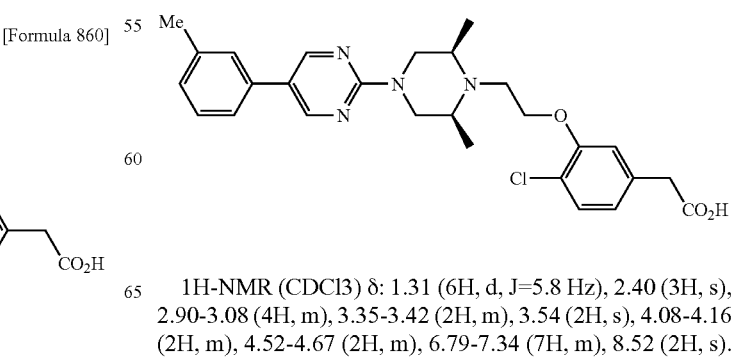
[Formula 863]
1H-NMR (CDCl3) δ: 1.31 (6H, d, J=5.8 Hz), 2.40 (3H, s), 2.90-3.08 (4H, m), 3.35-3.42 (2H, m), 3.54 (2H, s), 4.08-4.16 (2H, m), 4.52-4.67 (2H, m), 6.79-7.34 (7H, m), 8.52 (2H, s).

Example 569

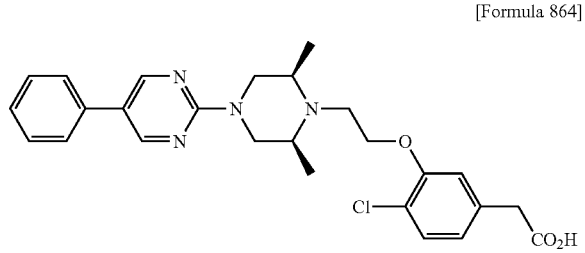

[Formula 864]

1H-NMR (Acetone) δ: 8.62 (2.0H, s), 7.61-7.59 (2.0H, m), 7.45 (2.0H, dd, J=7.55, 7.55 Hz), 7.37-7.28 (2.0H, m), 7.14 (1.0H, d, J=1.89 Hz), 6.89 (1.0H, dd, J=8.10, 1.89 Hz), 4.64 (2.0H, d, J=11.81 Hz), 4.16 (2.0H, dd, J=6.11, 6.11 Hz), 3.59 (2.0H, s), 3.24 (2.0H, dd, J=6.11, 6.11 Hz), 2.93-2.64 (4.0H, m), 1.25 (6.0H, d, J=6.04 Hz).

Example 570

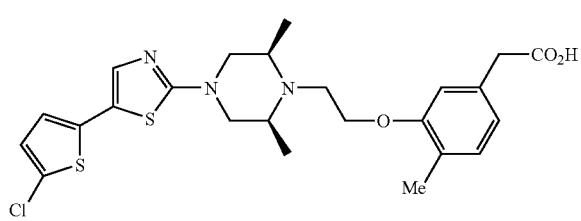

[Formula 865]

MS (ESI) m/z 508 [M+H]+

Example 571

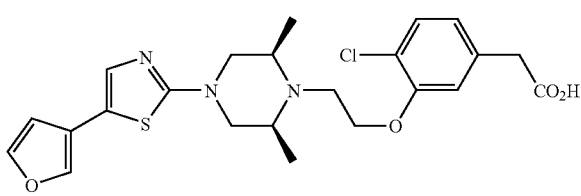

[Formula 866]

1H-NMR (DMSO-d6)) d: 7.81 (1H, s), 7.67 (1H, s), 7.32-7.29 (2H, m), 7.07 (1H, s), 6.81 (1H, d, J=8.8 Hz), 6.75 (1H, s), 4.06-4.03 (2H, m), 3.67 (2H, d, J=10.8 Hz), 3.52 (2H, s), 3.12-3.09 (2H, m), 2.82-2.69 (4H, m), 1.13 (6H, d, J=5.7 Hz).

Example 572

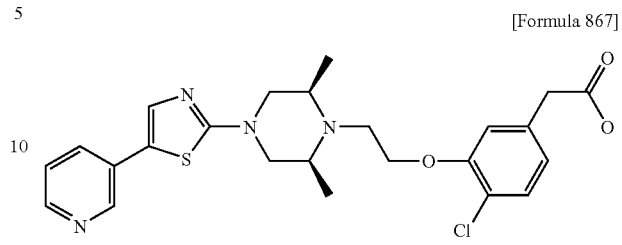

[Formula 867]

MS (ESI) m/z 525 [M+H]+

Example 573

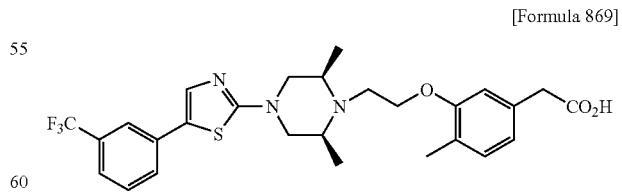

[Formula 868]

1H-NMR (DMSO-d6) δ: 7.79 (1.0H, s), 7.70-7.64 (4.0H, m), 7.03 (1.0H, d, J=7.56 Hz), 6.85 (1.0H, s), 6.71 (1.0H, d, J=7.56 Hz), 3.99 (2.0H, dd, J=5.49, 5.49 Hz), 3.79 (2.0H, d, J=9.06 Hz), 3.47 (2.0H, s), 3.15-3.11 (2.0H, m), 2.89-2.78 (4.0H, m), 2.11 (3.0H, s), 1.17 (6.0H, d, J=5.22 Hz).

Example 574

[Formula 869]

1H-NMR (DMSO-d6) δ: 7.83-7.70 (3.0H, m), 7.63-7.50 (2.0H, m), 7.03 (1.0H, d, J=7.69 Hz), 6.85 (1.0H, s), 6.70 (1.0H, d, J=7.69 Hz), 4.02-3.96 (2.0H, m), 3.79 (2.0H, d, J=9.06 Hz), 3.47 (2.0H, s), 3.17-3.10 (2.0H, m), 2.91-2.76 (4.0H, m), 2.12 (3.0H, s), 1.26-1.11 (6.0H, d, J=6.0 Hz).

Example 575

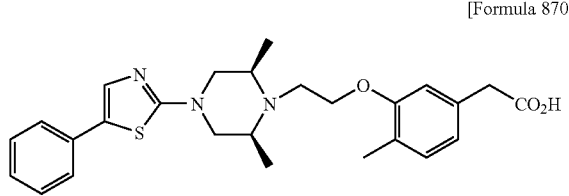

[Formula 870]

1H-NMR (DMSO-d6) δ: 7.58 (1.0H, s), 7.46 (2.0H, d, J=7.42 Hz), 7.35 (2.0H, dd, J=7.42, 7.42 Hz), 7.21 (1.0H, dd, J=7.42, 7.42 Hz), 7.03 (1.0H, d, J=7.80 Hz), 6.85 (1.0H, s), 6.70 (1.0H, d, J=7.80 Hz), 4.01-3.97 (2.0H, m), 3.76 (2.0H, d, J=10.99 Hz), 3.45 (2.0H, s), 3.14-3.11 (2.0H, m), 2.89-2.74 (4.0H, m), 2.11 (3.0H, s), 1.17 (6.0H, d, J=5.49 Hz).

Example 576

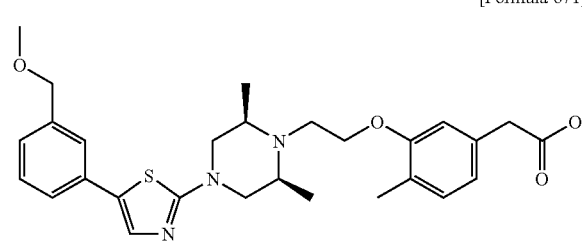

[Formula 871]

1H-NMR (CDCl3) δ 1.17 (6H, m), 2.12 (3H, s), 2.82 (4H, m), 2.13 (2H, br), 3.30 (3H, d, J=2.1 Hz), 3.49 (2H, s), 3.77 (2H, d, J=10.2 Hz), 3.99 (2H, br), 4.41 (2H, s), 6.71 (1H, brd), 6.85 (1H, brd), 7.04 (1H, brd), 7.15 (1H, brd), 7.30-7.41 (3H, m), 7.60 (1H, d, 1.8 Hz)

Example 577

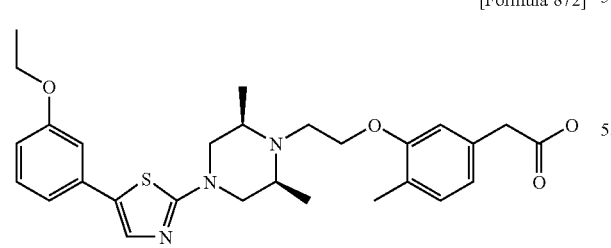

[Formula 872]

1H-NMR (DMSO-d6) δ 1.16 (6H, d, J=6.0 Hz), 1.33 (3H, t, J=6.9 Hz), 2.12 (3H, s), 2.74-2.90 (4H, m), 3.13 (2H, t, J=5.1 Hz), 3.49 (2H, s), 3.76 (2H, d, J=10.5 Hz), 3.97-4.08 (4H, m), 6.72 (1H, d, J=7.8 Hz), 6.78 (1H, dd, J=8.4 Hz, 2.4 Hz), 6.85 (1H, s), 6.98-7.06 (3H, m), 7.24 (1H, t, J=8.1 Hz), 7.61 (1H, s)

Example 578

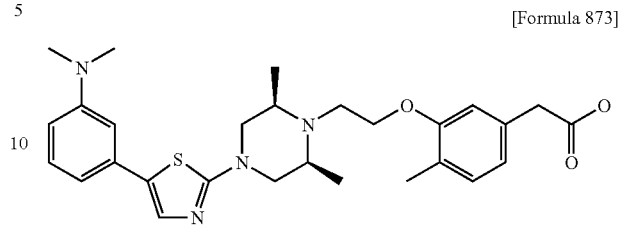

[Formula 873]

1H-NMR (DMSO-d6) δ 1.16 (6H, d, J=5.7 Hz), 2.12 (3H, s), 2.72-2.91 (4H, m), 2.91 (6H, s), 3.12 (2H, brs), 3.49 (2H, s), 3.76 (2H, d, J=10.5 Hz), 3.99 (2H, brs), 6.57-6.61 (1H, m), 6.70-6.77 (3H, m), 6.85 (1H, s), 7.05 (1H, d, J=7.5 Hz), 7.15 (1H, t, J=7.8 Hz), 7.54 (1H, s)

Example 579

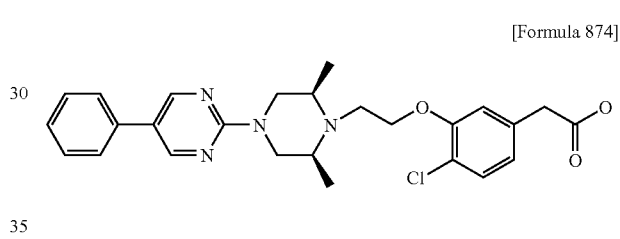

[Formula 874]

1H-NMR (Acetone) δ: 8.62 (2.0H, s), 7.61-7.59 (2.0H, m), 7.45 (2.0H, dd, J=7.55, 7.55 Hz), 7.37-7.28 (2.0H, m), 7.14 (1.0H, d, J=1.89 Hz), 6.89 (1.0H, dd, J=8.10, 1.89 Hz), 4.64 (2.0H, d, J=11.81 Hz), 4.16 (2.0H, dd, J=6.11, 6.11 Hz), 3.59 (2.0H, s), 3.24 (2.0H, dd, J=6.11, 6.11 Hz), 2.93-2.64 (4.0H, m), 1.25 (6.0H, d, J=6.04 Hz).

Example 580

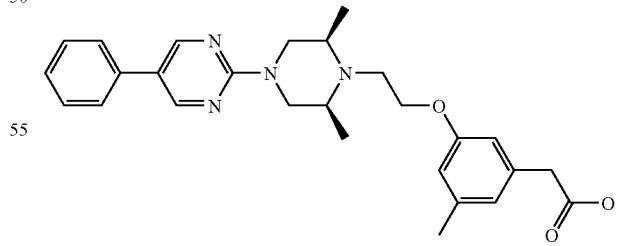

[Formula 875]

1H-NMR (DMSO-$d_6$) δ: 8.69 (2.0H, s), 7.63 (2.0H, d, J=7.42 Hz), 7.45 (2.0H, dd, J=7.42, 7.42 Hz), 7.35 (1.0H, d, J=7.42 Hz), 6.62 (3.0H, s), 4.53 (2.0H, d, J=8.79 Hz), 3.96 (2.0H, dd, J=6.48, 6.48 Hz), 3.45 (2.0H, s), 3.03 (2.0H, dd, J=6.48, 6.48 Hz), 2.67 (4.0H, d, J=7.97 Hz), 2.23 (3.0H, s), 1.14 (6.0H, d, J=4.94 Hz).

Example 581

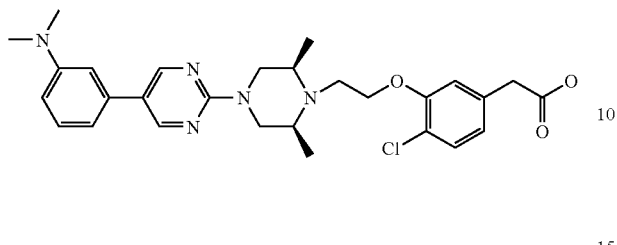

[Formula 876]

1H-NMR (DMSO-d6) δ: 8.65 (2.0H, s), 7.32 (1.0H, d, J=8.23 Hz), 7.23 (1.0H, dd, J=8.10, 8.10 Hz), 7.09 (1.0H, d, J=1.65 Hz), 6.87-6.81 (3.0H, m), 6.72-6.67 (1.0H, m), 4.52 (2.0H, d, J=9.61 Hz), 4.07 (2.0H, dd, J=5.40, 5.40 Hz), 3.55 (2.0H, s), 3.13 (2.0H, dd, J=5.40, 5.40 Hz), 2.93 (6.0H, s), 2.73-2.62 (4.0H, m), 1.18 (6.0H, d, J=6.04 Hz).

Reference Example 233

Preparation of 3,5-dimethyl carbonyl piperazine-1-carboxylic acid t-butyl ester

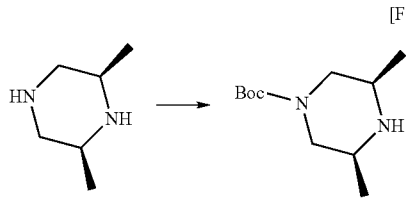

[Formula 877]

To a mixture of 2,6-dimethyl piperazine (10.0 g) in methylene chloride (200 mL) was added di-t-butyldicarbonate (19.1 g) under ice-cooling. After stirring at room temperature for 17 hours, to the reaction solution was added water and extracted with methylene chloride. The organic layer was washed with brine, and dried over magnesium sulphate. The solvent was evaporated under reduced pressure to give the title compound (18.7 g). Yield: 100%.

1H-NMR (CDCl3) δ 1.15 (6H, d, J=6.3), 1.32 (2H, m), 1.49 (9H, s), 2.43 (1H, m), 2.85 (2H, m), 3.99 (1H, m).

Reference Example 234

Preparation of 4-methoxycarbonyl methyl-3,5-dimethyl piperazine-1-carboxylic acid t-butyl ester

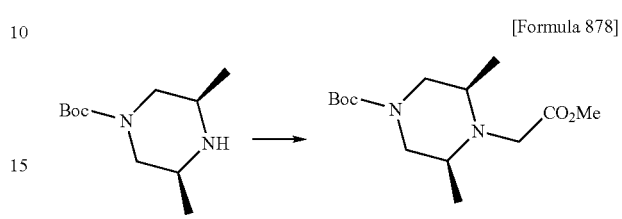

[Formula 878]

A mixture of 3,5-dimethyl carbonyl piperazine-1-carboxylic acid t-butyl ester (18.7 g), potassium carbonate (14.5 g), bromo acetic acid methyl ester (14.7 g), DMF (90 mL) was stirred at 60° C. for 3 hours. To the reaction solution was added water and extracted with ethyl acetate. The organic layer was washed with water and brine, and dried over magnesium sulphate. The solvent was evaporated under reduced pressure to give the title compound. This compound was provided to the next reaction without further purification.

Reference Example 235

Preparation of 4-(2-hydroxyethyl)-3,5-dimethyl piperazine-1-carboxylic acid t-butyl ester

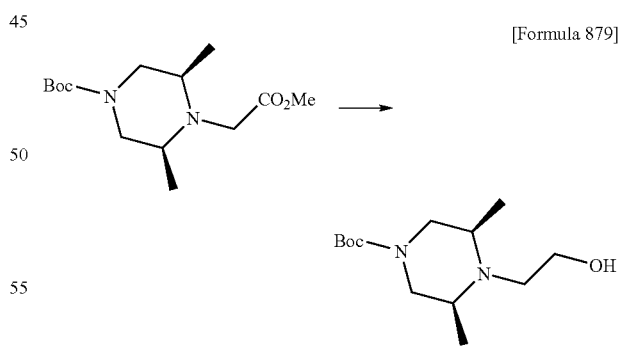

[Formula 879]

3,5-Dimethyl carbonyl piperazine-1-carboxylic acid t-butyl ester derived from the above reaction was dissolved in THF (300 mL) and lithium aluminium hydride (3.31 g) was added thereto under ice-cooling. After stirring at 0° C. for 1 hour, water and 2N aqueous sodium hydroxide solution was sequentially added. After filtration of the insoluble material, the filtrate was concentrated under reduced pressure to give the title compound (20.3 g). Yield: 90%.

Reference Example 236

Preparation of 4-[2-(5-carbonylmethyl-2-chlorophenoxy)ethyl]-3,5-dimethyl piperazine-1-1-carboxylic acid t-butyl ester

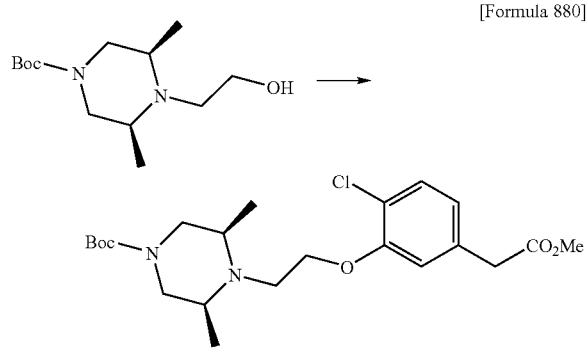

[Formula 880]

A mixture of 4-(2-hydroxyethyl)-3,5-dimethyl piperazine-1-carboxylic acid t-butyl ester (3.0 g), triethylamine (1.76 g), mesyl chloride (1.60 g) and methylene chloride (60 mL) was stirred at under ice-cooling for 1.5 hours. To the reaction solution was added water and extracted with ethyl acetate. The organic layer was washed with water and brine, and dried over magnesium sulphate. The solvent was evaporated under reduced pressure. The obtained residue was dissolved in acetonitrile (60 mL), and (4-chloro-3-hydroxyphenyl)acetic acid methyl ester (2.33 g) and cesium carbonate (4.54 g) were added thereto. The mixture was stirred at 60° C. for 5 hours. After filtration of the insoluble material, the filtrate was concentrated and the obtained residue was purified by column chromatograph on silica gel to give the title compound (3.58 g). Yield: 70%.

1H-NMR (DMSO-$d_6$) δ: 1.09 (6H, d, J=6.0), 1.40 (9H, s), 2.40-2.50 (2H, m), 2.52-2.61 (2H, m), 3.08-3.12 (2H, m), 3.64 (3H, s), 3.71 (2H, 2), 3.77 (2H, m), 4.02-4.09 (2H, m), 6.87 (1H, d, J=8.0), 7.13 (1H, s), 7.37 (1H, d, J=8.0)

Reference Example 237

Preparation of [4-chloro-3-[2-(2,6-dimethylpiperazine-1-yl)ethoxy]phenyl]acetic acid methyl ester

[Formula 881]

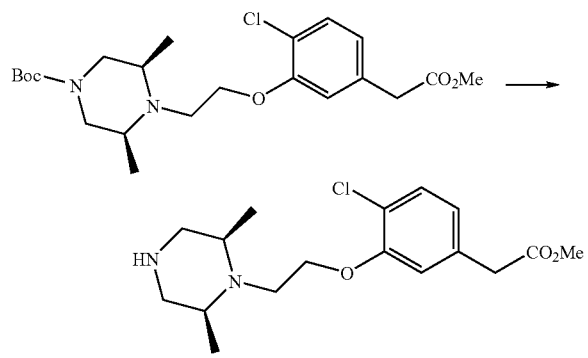

A solution of 4-[2-(5-carbonyl methyl-2-chlorophenoxy)ethyl]-3,5-dimethyl piperazine-1-1-carboxylic acid t-butyl ester (400 mg) in 4N hydrochloric acid-dioxane (4 mL) was stirred at room temperature for 2 hours. To the reaction solution were added water and ethyl acetate. The mixture was neutralized with sodium carbonate. The mixture was extracted with ethyl acetate and the organic layer was washed with brine. The solvent was evaporated under reduced pressure to give the title compound (291 mg). Yield: 94%.

1H-NMR (DMSO-d6) δ: 1.02 (3H, d, J=6.3), 2.22-2.29 (2H, m), 2.50-2.54 (2H, m), 2.72-2.76 (2H, m), 3.03-3.07 (2H, m), 4.03-4.07 (2H, m), 6.87 (1H, d, J=8.2), 7.13 (1H, s), 7.37 (1H, d, J=8.2)

Example 582

Preparation of [4-chloro-3-[2-(2,6-dimethyl-4-phenyl carbamoyl piperazine-1-yl)ethoxy]phenyl]acetic acid methyl ester

[Formula 882]

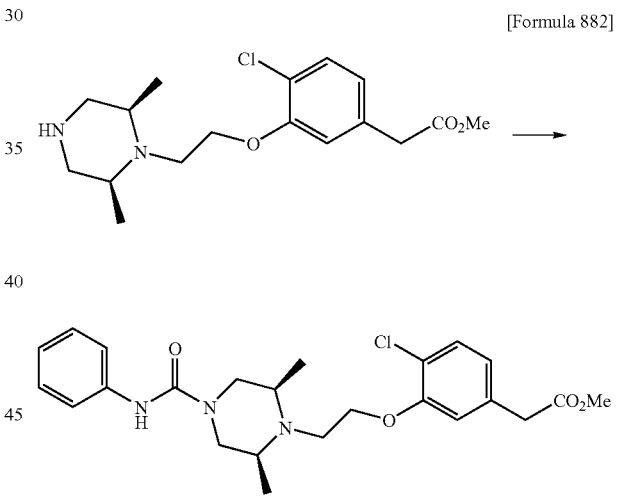

A mixture of [4-chloro-3-[2-(2,6-dimethyl piperazine-1-yl)ethoxy]phenyl]acetic acid methyl ester (50 mg), phenylisocyanate (19 mg), potassium carbonate (41 mg) and methylene chloride (2 mL) was stirred at room temperature for 3 hours. After filtration of the insoluble material, the filtrate was concentrated under reduced pressure. The residue was purified by column chromatograph on silica gel to give the title compound (52 m). Yield: 77%.

1H-NMR (DMSO-d6) δ: 1.15 (6H, d, J=5.8), 2.11 (2H, brm), 2.57 (2H, brm), 2.67 (2H, brm), 3.13 (2H, brm), 3.64 (3H, s), 3.71 (2H, s), 4.04-4.09 (2H, m), 6.86-6.97 (2H, m), 7.14 (1H, s), 7.22-7.25 (2H, m), 7.36-7.47 (3H, m), 8.48 (1H, s).

Example 583

Preparation of [4-chloro-3-[2-(2,6-dimethyl-4-phenyl carbamoyl piperazine-1-yl)ethoxy]phenyl]acetic acid

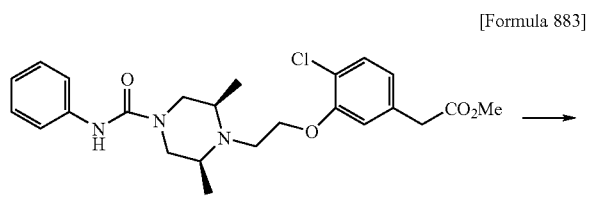

A mixture of [4-chloro-3-[2-(2,6-dimethyl-4-phenyl carbamoyl piperazine-1-yl)ethoxy]phenyl]acetic acid methyl ester (50 mg), 2N sodium hydroxide (0.1 mL) and tetrahydrofuran (1 mL) was stirred at room temperature for 4 hours. After neutralizing with 2N hydrochloric acid, the mixture was extracted with ethyl acetate. The organic layer was washed with brine, and dried over magnesium sulphate. The solvent was evaporated under reduced pressure. The residue was purified by column chromatograph on silica gel to give the title compound (18 mg). Yield: 37%.

1H-NMR (DMSO-d6) δ: 1.12 (6H, d, J=5.8 Hz), 2.42-2.70 (4H, m), 3.06-3.16 (2H, m), 3.56 (2H, s), 3.93-4.11 (4H, m), 6.81-7.47 (6H, m), 8.46 (1H, s).

The following compound was obtained by a similar method as above.

Example 584

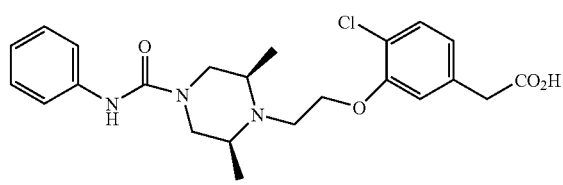

1H-NMR (DMSO-d6) δ: 1.10-1.29 (2H, m), 1.70-1.83 (4H, m), 2.73-2.87 (2H, m), 3.59 (2H, s), 4.07-4.20 (4H, m), 6.83-7.51 (6H, m), 8.46 (1H, s).

Reference Example 238

Preparation of 2-(2,6-dimethyl piperazine-1-yl)-6-trifluoromethyl benzothiazole

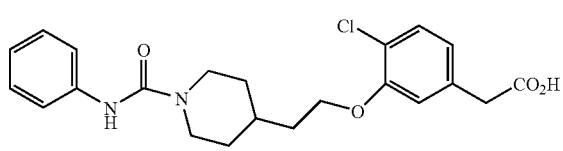

To a solution of cis-2,6-dimethyl piperazine (247 mg) in tetrahydrofuran (5 mL) was added n-BuLi (2.67 M hexane solution, 1.62 mL) at −78° C. The mixture was stirred at room temperature for 30 minutes, and trimethyl silyl chloride (0.27 mL) was added thereto. After stirring for 40 minutes, a solution of 2-chloro-6-trifluoromethyl benzothiazole (500 mg) in tetrahydrofuran (2 mL) was added thereto and the mixture was stirred for 2 hours. To the reaction solution was added water and extracted with ethyl acetate. The organic layer was washed with water and dried over sodium carbonate. The residue was purified by column chromatograph on silica gel to give the title compound (367 mg). Yield: 54%.

1H-NMR (CDCl3) δ: 1.47 (6H, d, J=6.87 Hz), 2.13 (2H, s), 2.91-3.10 (4H, m), 4.14-4.23 (2H, m), 7.51-7.59 (2H, m), 7.85 (1H, s).

Reference Example 239

Preparation of 2-[3,5-dimethyl-4-(6-trifluoromethyl-benzothiazole-2-yl)piperazine-1-yl]ethanol A mixture of 2-(2,6-dimethyl piperazine-1-yl)-6-trifluoromethyl benzothiazole (360 mg), (2-bromoethoxy)-t-butyldimethyl silane (257 uL), potassium carbonate (157 mg) and dimethylformamide (2 mL) was stirred at 60° C. for 20 hours. To the reaction solution was added water and extracted with ethyl acetate. The organic layer was washed with water and dried over sodium carbonate. After evaporating the solvent, the residue was purified by column chromatograph on silica gel to give the title compound (265 mg). Yield: 65%.

1H-NMR (CDCl3) δ: 1.53 (6H, d, J=6.59 Hz), 2.54-2.57 (2H, br m), 2.67-2.70 (2H, br m), 2.80-2.90 (2H, br m), 3.74-3.77 (2H, br m), 4.29-4.32 (2H, br m), 7.52-7.61 (2H, m), 7.87 (1H, s).

Example 585

Preparation of [4-chloro-3-[2-[3,5-dimethyl-4-(6-trifluoromethyl benzothiazole-2-yl)piperazine-1-yl]ethoxy]phenyl]acetic acid methyl ester

[Formula 887]

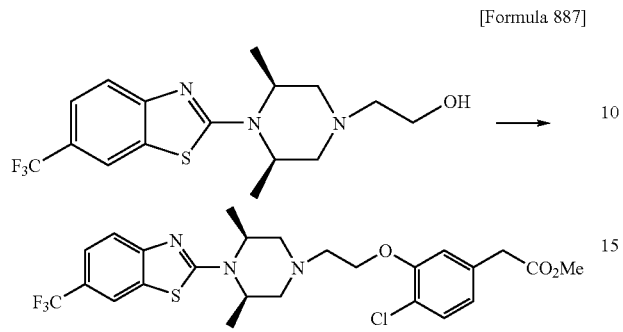

To a solution of 2-[3,5-dimethyl-4-(6-trifluoromethylbenzothiazole-2-yl)piperazine-1-yl]ethanol (138 mg) in methylene chloride (3 mL) were added methanesulfonyl chloride (45 µL) and triethylamine (107 µL). The mixture was stirred at room temperature for 1 hour. To the reaction solution was added water and extracted with chloroform. The organic layer was washed with water and brine, and dried over sodium sulphate. The solvent was evaporated under reduced pressure. To the obtained residue were added dimethylformamide (2 mL), cesium carbonate (248 mg) and (4-chloro-3-hydroxyphenyl)acetic acid methyl ester (92 mg). The mixture was stirred at 60° C. for 2 hours. To the reaction solution was added 2N hydrochloric acid to neutralize and extracted with ethyl acetate. The organic layer was washed with water and dried over magnesium sulphate. The residue was purified by column chromatograph on silica gel to give the title compound (178 mg). Yield: 89%.

Example 586

Preparation of [4-chloro-3-[2-[3,5-dimethyl-4-(6-trifluoromethyl benzothiazole-2-yl)piperazine-1-yl]ethoxy]phenyl]acetic acid

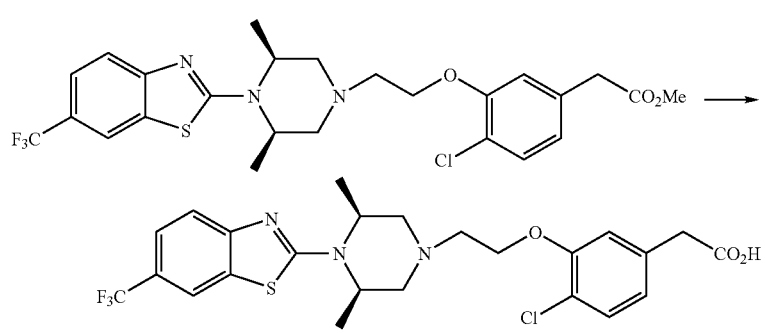

[Formula 888]

A mixture of [4-chloro-3-[2-[3,5-dimethyl-4-(6-trifluoromethyl benzothiazole-2-yl)piperazine-1-yl]ethoxy]phenyl]acetic acid methyl ester (178 mg), 2N aqueous sodium hydroxide (0.66 mL), tetrahydrofuran (2 mL) and methanol (2 mL) was stirred at room temperature for 2 hours. The mixture was neutralized with 2N hydrochloric acid and extracted with ethyl acetate. The organic layer was washed with water and dried over sodium sulphate. The solvent was evaporated under reduced pressure and the residue was purified by column chromatograph on silica gel to give the title compound (83 mg). Yield: 48%.

MS (ESI) m/z 528 [M+H]+

The following compound was obtained by a similar method as above.

Example 587

[Formula 889]

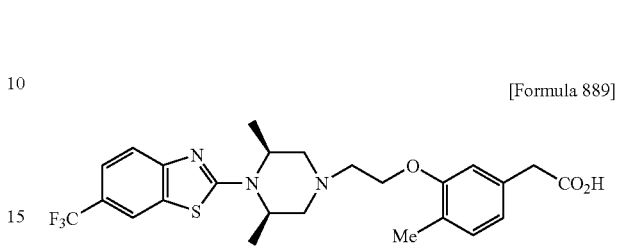

MS (ESI) m/z 508 [M+H]+

Example 588

Preparation of [3-[3,5-dimethyl-4-(6-trifluoromethyl benzothiazole-2-yl)piperazine-1-ylmethyl]phenyl]acetic acid methyl ester

[Formula 890]

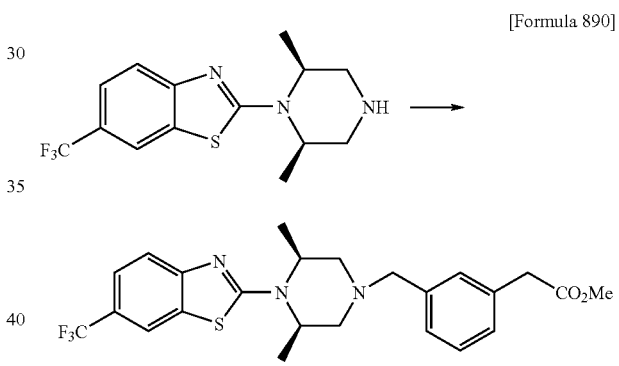

[Formula 888]

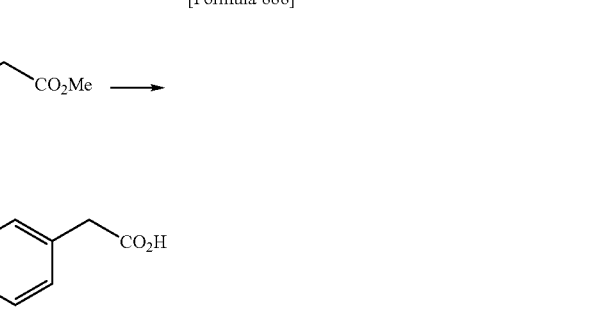

A mixture of 2-(2,6-dimethyl piperazine-1-yl)-6-trifluoromethyl benzothiazole (163 mg), (3-bromomethylphenyl) acetic acid methyl ester (126 mg), potassium carbonate (75 mg) and dimethylformamide (4 mL) was stirred at room temperature for 18 hours. To the reaction solution was added water and extracted with ethyl acetate. The organic layer was washed with water and dried over sodium sulphate. The solvent was evaporated under reduced pressure and the residue was purified by column chromatograph on silica gel to give the title compound (171 mg). Yield: 65%.

Example 589

Preparation of [3-[3,5-dimethyl-4-(6-trifluoromethyl benzothiazole-2-yl)piperazine-1-ylmethyl]phenyl]acetic acid

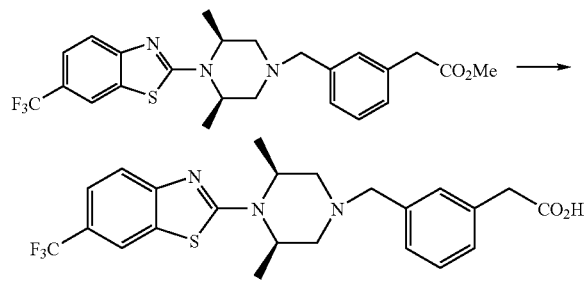
[Formula 891]

A mixture of [3-[3,5-dimethyl-4-(6-trifluoromethyl benzothiazole-2-yl)piperazine-1-ylmethyl]phenyl]acetic acid methyl ester (171 mg), 2N sodium hydroxide (1 mL) and methanol (2 mL) was stirred at room temperature for 1 hour. The mixture was neutralized with 2N hydrochloric acid and extracted with ethyl acetate. The solvent was evaporated under reduced pressure and the residue was purified by column chromatograph on silica gel to give the title compound (82 mg). Yield: 52%.

MS (ESI) m/z 464 [M+H]+

The following compounds were obtained by similar methods as above.

Example 590

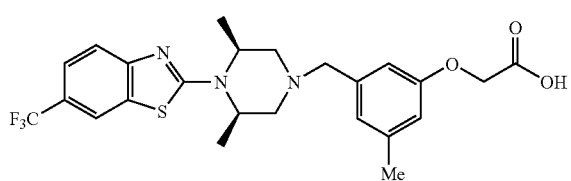
[Formula 892]

MS (ESI) m/z 494 [M+H]+

Example 591

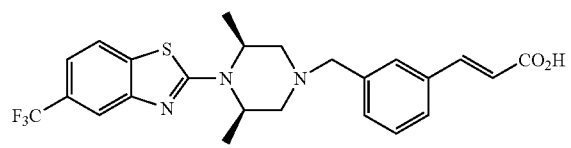
[Formula 893]

MS (ESI) m/z 475 [M+H]+

Example 592

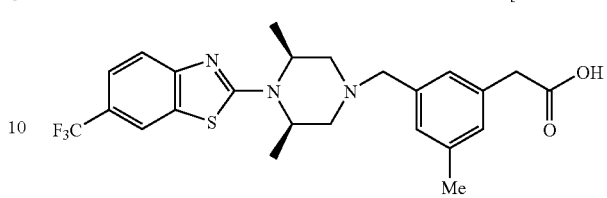
[Formula 894]

MS (ESI) m/z 478 [M+H]+

Reference Example 240

Preparation of 4-methoxycarboxylmethylene piperidine-1-carboxylic acid t-butyl ester

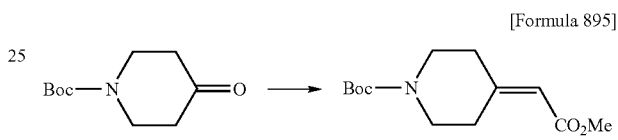
[Formula 895]

To a suspension of sodium hydride (4.02 g) in tetrahydrofuran (300 mL) was added phosphonoacetic acid trimethyl at 0° C. After stirring at 0° C. for 1 hours, a solution of 1-Boc-4-piperidone (20 g) in tetrahydrofuran (150 mL) was added thereto. After stirring at 50° C. for 1.5 hours, to the reaction solution was added water and extracted with ethyl acetate. The organic layer was washed with water and brine, and dried over sodium sulphate. The solvent was evaporated under reduced pressure and the residue was purified by column chromatograph on silica gel to give the title compound (27.0 g). Yield: 100%.

$^1$H-NMR (CDCl$_3$) δ: 1.47 (9H, s), 2.27-2.29 (2H, m), 2.93-2.94 (2H, m), 3.47-3.51 (4H, m), 3.70 (3H, s), 5.72 (1H, s).

Reference Example 241

Preparation of [1-(6-chlorobenzothiazole-2-yl)piperidine-4-ylidene]acetic acid methyl ester

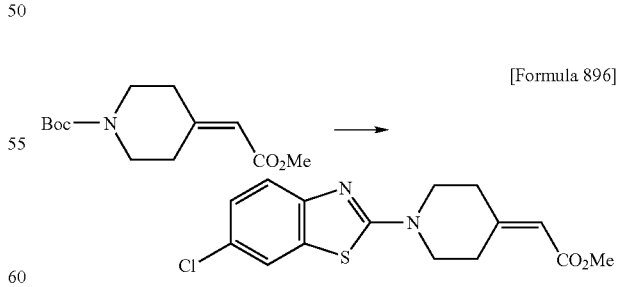
[Formula 896]

A solution of 4-carboxylmethylene piperidine-1-carboxylic acid t-butyl ester (8.00 g) in 4N hydrochloric acid/dioxane (80 mL) was stirred at room temperature for 1 hour. The solvent was evaporated under reduced pressure and the residue was dissolved in dimethylformamide (60 mL). Potassium carbonate (8.65 g) and 2,6-dichlorobenzothiazole (6.39 g)

were added thereto at 0° C. After stirring at 50° C. for 1 hour and at 60° C. for 3 hours, water was added thereto and extracted with ethyl acetate. The organic layer was washed with water and brine, and dried over sodium sulphate. The solvent was evaporated under reduced pressure and the residue was purified by column chromatograph on silica gel to give the title compound (9.48 g). Yield: 94%.

$^1$H-NMR (CDCl$_3$) δ: 2.47-2.49 (2H, m), 3.14-3.19 (2H, m), 3.72 (3H, s), 3.70-3.77 (4H, m), 5.81 (1H, s), 7.25 (1H, dd, J=8.5, 2.2 Hz), 7.46 (1H, d, J=8.8 Hz), 7.57 (1H, d, J=2.2 Hz).

Reference Example 242

Preparation of [1-(6-chlorobenzothiazole-2-yl)-4-ethyl piperidine-4-yl]acetic acid methyl ester

[Formula 897]

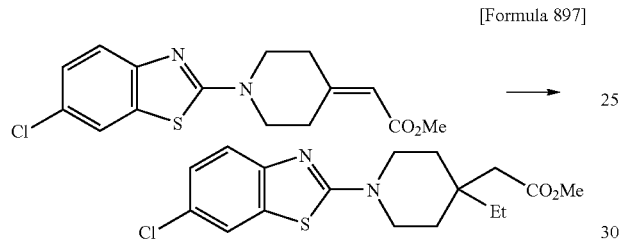

Copper iodide (1.77 g) was suspended in tetrahydrofuran (18 mL), and ethyl magnesium bromide (1.0 M tetrahydrofuran solution, 18.6 mL) was added thereto at −30° C. After stirring at −25° C. for 0.5 hour, the reaction solution was cooled to −78° C. To the mixture was added dropwise a solution of [1-(6-chlorobenzothiazole-2-yl)piperidine-4-ylidene]acetic acid methyl ester (1.00 g) in tetrahydrofuran (10 mL), and then added trimethylsilyl trifluoromethansulfonate (1.12 mL). After stirring at −78° C. for 2 hours, aqueous sodium hydrogencarbonate solution was added thereto. After filtration of the insoluble material, the filtrate was extracted with ethyl acetate. The organic layer was washed with water and brine, and dried over magnesium sulphate. The solvent was evaporated under reduced pressure and the residue was purified by column chromatograph on silica gel to give the title compound (979 mg). Yield: 90%.

$^1$H-NMR (CDCl$_3$) δ: 0.93 (3H, t, J=7.6 Hz), 1.67-1.75 (6H, m), 2.42 (2H, s), 3.57-3.68 (4H, m), 3.70 (3H, s), 7.26 (1H, dd, J=8.5, 2.2 Hz), 7.47 (1H, d, J=8.5 Hz), 7.58 (1H, d, J=2.2 Hz).

Reference Example 243

Preparation of 2-[1-(6-chlorobenzothiazole-2-yl)-4-ethyl piperidine-4-yl]ethanol

[Formula 898]

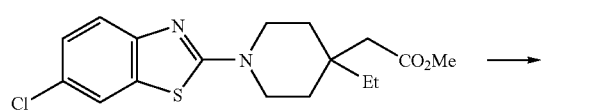

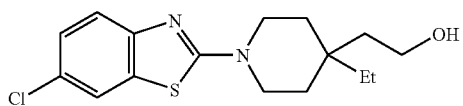

Lithium aluminium hydride (202 mg) was suspended in tetrahydrofuran (10 mL). A solution of [1-(6-chlorobenzothiazole-2-yl)-4-ethyl piperidine-4-yl]acetic acid methyl ester (940 mg) in tetrahydrofuran (10 mL) was added thereto at 0° C. After stirring at 0° C. for 1 hour, to the reaction solution were sequentially added water (0.2 mL), 10% sodium hydroxide (0.2 mL) and water (0.6 mL). The insoluble material was filtrated and the filtrate was extracted with ethyl acetate. The organic layer was washed with water and brine, and dried over sodium sulphate. The solvent was evaporated under reduced pressure and the residue was purified by column chromatograph on silica gel to give the title compound (790 mg). Yield: 91%.

$^1$H-NMR (CDCl$_3$) δ: 0.87 (3H, t, J=7.5 Hz), 1.44 (2H, q, J=7.5 Hz), 1.58-1.60 (4H, m), 1.68 (2H, t, J=7.5 Hz), 1.81 (1H, br), 3.60-3.62 (4H, m), 3.71-3.74 (2H, m), 7.23 (1H, dd, J=8.8, 2.2 Hz), 7.44 (1H, d, J=8.8 Hz), 7.55 (1H, d, J=2.2 Hz).

Reference Example 244

Preparation of 6-chloro-2-[4-(2-chloroethyl)-4-ethyl piperidine-1-yl]benzothiazole

[Formula 899]

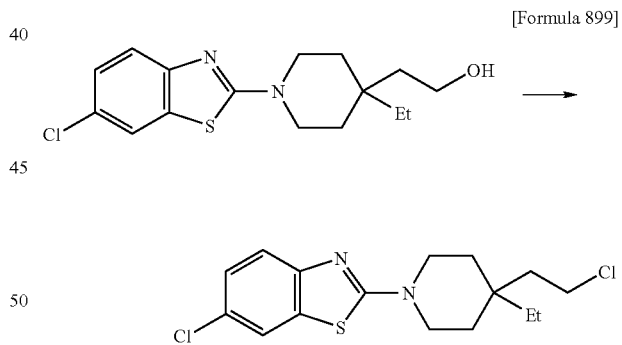

A mixture of 2-[1-(6-chlorobenzothiazole-2-yl)-4-ethyl piperidine-4-yl]ethanol (764 mg) and thionyl chloride (4 mL) were stirred at 60° C. for 1.5 hours. To the reaction solution was added ice and extracted with ethyl acetate. The organic layer was washed with sodium hydrogencarbonate and brine and dried over sodium sulphate. The solvent was evaporated under reduced pressure and the residue was purified by column chromatograph on silica gel to give the title compound (739 mg). Yield: 92%.

$^1$H-NMR (CDCl$_3$) δ: 0.91 (3H, t, J=7.6 Hz), 1.47 (2H, q, J=7.6 Hz), 1.60-1.63 (4H, m), 1.92-1.94 (2H, m), 3.53-3.56 (2H, m), 3.62-3.65 (4H, m), 7.26 (1H, dd, J=8.5, 2.2 Hz), 7.47 (1H, d, J=8.5 Hz), 7.58 (1H, d, J=2.2 Hz).

Example 593

Preparation of [4-Chloro-3-[2-[1-(6-chlorobenzothiazole-2-yl)-4-ethyl piperidine-4-yl]ethoxy]phenyl] acetic acid methyl ester

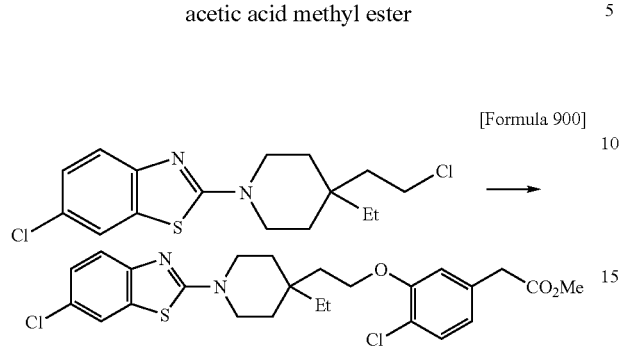

[Formula 900]

A mixture of 6-chloro-2-[4-(2-chloroethyl)-4-ethyl piperidine-1-yl]benzothiazole (150 mg), (4-chloro-3-hydroxyphenyl)acetic acid methyl ester (176 mg), cesium carbonate (285 mg) and dimethylformamide (2 mL) was stirred at 75° C. for 24 hours. To the reaction solution was added water and extracted with ethyl acetate. The organic layer was washed with brine, and dried over sodium sulphate. The solvent was evaporated under reduced pressure and the residue was purified by column chromatograph on silica gel to give the title compound (174 mg). Yield: 79%.

$^1$H-NMR (CDCl$_3$) δ: 0.94 (3H, t, J=7.6 Hz), 1.52-1.78 (8H, m), 3.59 (2H, s), 3.60-3.63 (2H, m), 3.68-3.70 (2H, m), 3.72 (3H, s), 4.09-4.18 (2H, m), 6.80-6.88 (2H, m), 6.98-6.98 (1H, m), 7.27-7.32 (1H, m), 7.48 (1H, d, J=8.5 Hz), 7.57 (1H, d, J=1.9 Hz).

Example 594

Preparation of [4-Chloro-3-[2-[1-(6-chlorobenzothiazole-2-yl)-4-ethyl piperidine-4-yl]ethoxy]phenyl] acetic acid

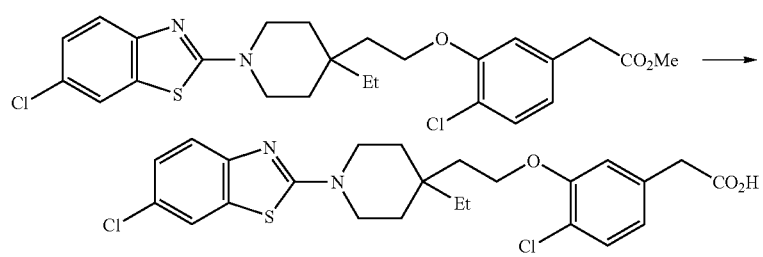

[Formula 901]

A mixture of [4-Chloro-3-[2-[1-(6-chlorobenzothiazole-2-yl)-4-ethyl piperidine-4-yl]ethoxy]phenyl]acetic acid methyl ester (152 mg), 2N aqueous sodium hydroxide (0.45 mL), tetrahydrofuran (1 mL) and methanol (1 mL) was stirred at room temperature for 2 hours. The reaction solution was neutralized with 2N hydrochloric acid and extracted with ethyl acetate. The organic layer was washed with water and brine, and dried over sodium sulphate. The solvent was evaporated under reduced pressure and the residue was purified by column chromatograph on silica gel to give the title compound (53 mg). Yield: 36%.

MS (ESI) m/z 493 [M+H]+

The following compounds were obtained by similar methods as above.

Example 595

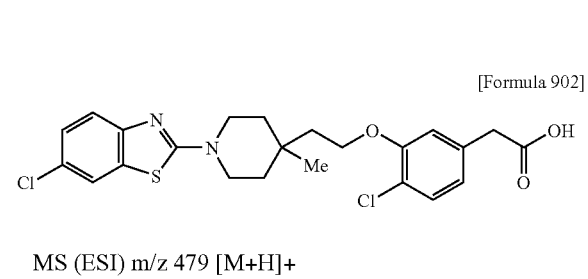

[Formula 902]

MS (ESI) m/z 479 [M+H]+

Example 596

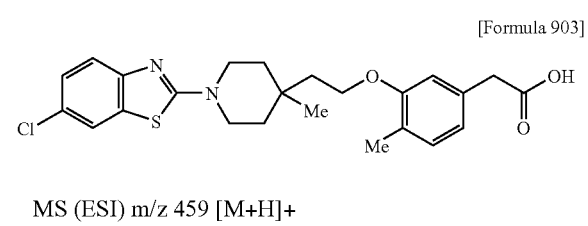

[Formula 903]

MS (ESI) m/z 459 [M+H]+

Example 597

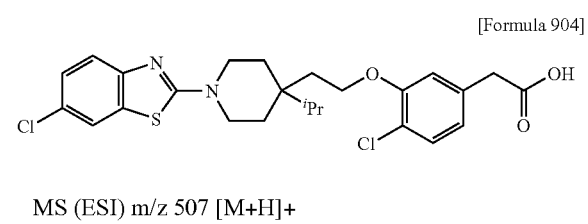

[Formula 904]

MS (ESI) m/z 507 [M+H]+

Example 598

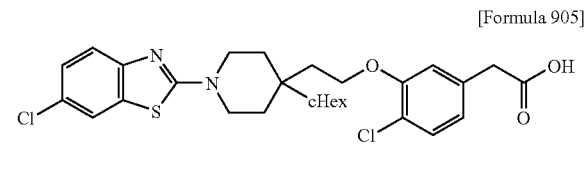

[Formula 905]

MS (ESI) m/z 547 [M+H]+

Example 599

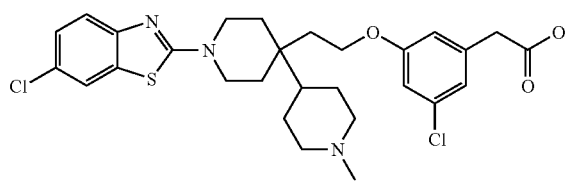

MS (ESI) m/z 564 [M+H]+

Example 600

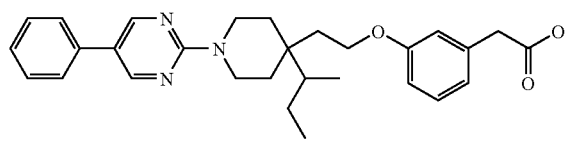

1H-NMR (Acetone-d₆) δ: 8.65 (1H, s), 7.60-7.63 (2H, m), 7.48 (2H, t, J=7.55 Hz), 7.36 (1H, t, J=7.55 Hz), 7.20-7.25 (1H, m), 6.97 (1H, s), 6.84-6.87 (2H, m), 4.19-4.27 (2H, m), 4.14 (2H, t, J=7.42 Hz), 3.65-3.72 (2H, m), 3.62 (2H, s), 2.05-2.10 (2H, m), 1.57-1.79 (7H, m), 0.96-1.00 (6H, m).

Example 601

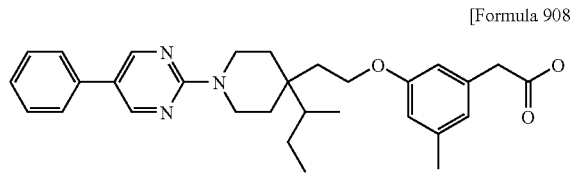

1H-NMR (Acetone-d6) δ: 8.65 (1H, s), 7.62-7.65 (2H, m), 7.48 (2H, t, J=7.55 Hz), 7.36 (1H, t, J=7.55 Hz), 6.76 (1H, s), 6.72 (2H, s), 4.19-4.27 (2H, m), 4.14 (2H, t, J=7.42 Hz), 3.65-3.72 (2H, m), 3.62 (2H, s), 2.25 (3H, s), 2.05-2.10 (2H, m), 1.57-1.79 (7H, m), 0.96-1.00 (6H, m).

Example 602

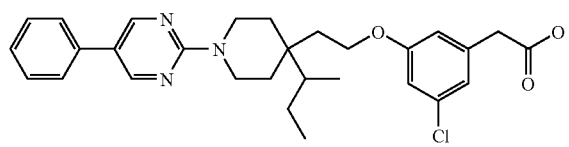

1H-NMR (Acetone) δ: 8.65 (1H, s), 7.62-7.65 (2H, m), 7.48 (2H, t, J=7.55 Hz), 7.36 (1H, t, J=7.55 Hz), 6.76 (1H, s), 6.72 (2H, s), 4.19-4.27 (2H, m), 4.14 (2H, t, J=7.42 Hz), 3.65-3.72 (2H, m), 3.62 (2H, s), 2.05-2.10 (2H, m), 1.57-1.79 (7H, m), 0.96-1.00 (6H, m).

Example 603

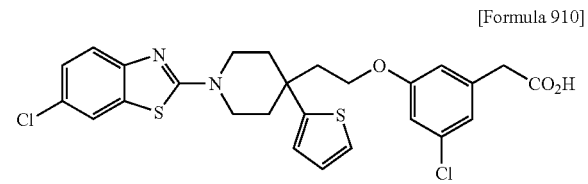

MS (ESI) m/z 547 [M+H]+

Example 604

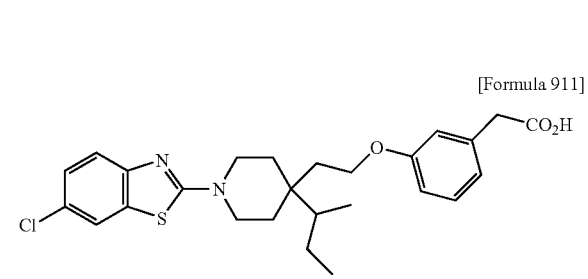

1H-NMR (CDCl3) δ: 0.87-1.98 (15H, m), 3.44-3.78 (6H, m), 4.03 (3H, t, J=7.1 Hz), 6.78-7.45 (7H, m), 7.54 (1H, d, J=1.9 Hz).

Example 605

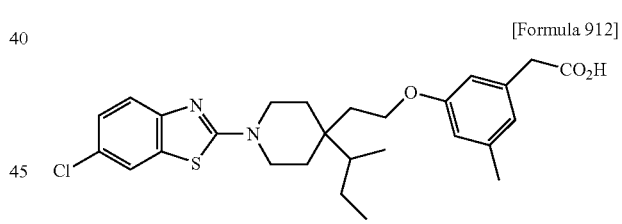

1H-NMR (CDCl3) δ: 0.83-1.99 (15H, m), 2.30 (3H, s), 3.47-3.79 (6H, m), 4.02 (2H, t, J=7.1 Hz), 6.62 (2H, s), 6.69 (1H, s), 7.22-7.26 (1H, m), 7.46 (1H, d, J=9.1 Hz), 7.54 (1H, d, J=2.2 Hz).

Example 606

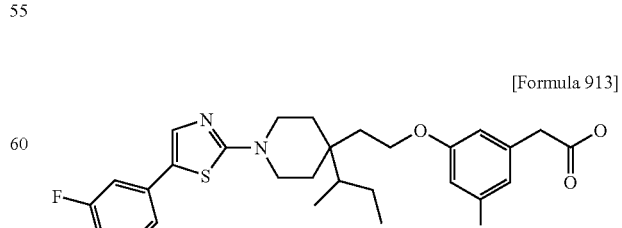

1H-NMR (CDCl3) δ: 7.42 (1.0H, s), 7.29-7.24 (1.0H, m), 7.17 (1.0H, ddd, J=7.97, 1.30, 1.30 Hz), 7.10 (1.0H, ddd, J=9.89, 2.13, 2.13 Hz), 6.93-6.85 (2.0H, m), 6.80 (1.0H, dd, J=1.92, 1.92 Hz), 6.72 (1.0H, dd, J=1.79, 1.79 Hz), 4.03 (2.0H, dd, J=7.14, 7.14 Hz), 3.67-3.57 (4.0H, m), 3.47-3.39 (2.0H, m), 1.93 (2.0H, dd, J=7.14, 7.14 Hz), 1.82-1.77 (2.0H, m), 1.67-1.54 (4.0H, m), 1.50-1.42 (1.0H, m), 0.98-0.90 (6.0H, m).

Example 607

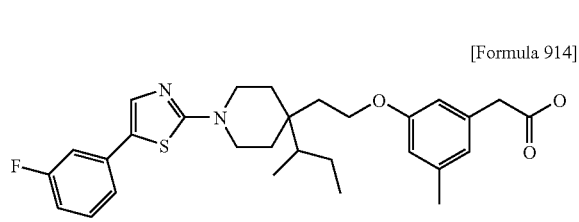

[Formula 914]

1H-NMR (CDCl3) δ: 7.42 (1.0H, s), 7.30 (1.0H, dd, J=5.63, 2.06 Hz), 7.17 (1.0H, d, J=8.79 Hz), 7.12-7.07 (1.0H, m), 6.92-6.85 (1.0H, m), 6.69 (1.0H, s), 6.63 (2.0H, d, J=4.67 Hz), 4.04 (2.0H, dd, J=7.00, 7.00 Hz), 3.68-3.57 (4.0H, m), 3.47-3.39 (2.0H, m), 2.31 (3.0H, s), 1.95-1.54 (8.0H, m), 1.49-1.42 (1.0H, m), 0.97-0.90 (6.0H, m).

Example 608

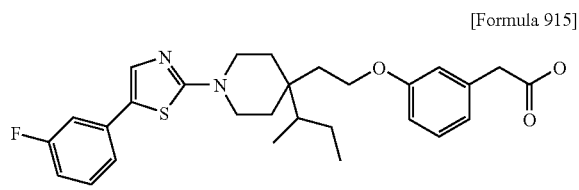

[Formula 915]

1H-NMR (Acetone) δ: 7.60 (1.0H, d, J=1.65 Hz), 7.42-7.33 (1.0H, m), 7.30-7.18 (3.0H, m), 6.99-6.92 (2.0H, m), 6.89-6.83 (2.0H, m), 4.15-4.09 (2.0H, m), 3.72-3.47 (6.0H, m), 1.85-1.56 (6.0H, m), 1.31-1.27 (3.0H, m), 0.99-0.92 (6.0H, m).

Example 609

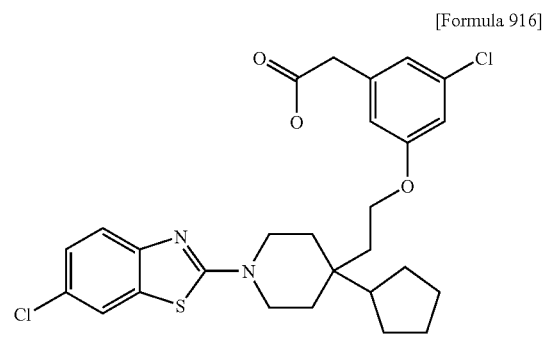

[Formula 916]

1H-NMR (DMSO-d6) δ 1.25 (2H, br), 1.46-1.64 (10H, m), 1.94 (2H, t, J=6.9 Hz), 2.12 (1H, m), 3.43-3.52 (2H, m), 3.56 (2H, s), 3.70-3.80 (2H, br), 4.02 (3H, 2H, J=6.9 Hz), 6.83 (1H, s), 6.90 (1H, s), 6.96 (1H, s), 7.25-7.29 (1H, m), 7.40 (1H, d, J=8.7 Hz), 7.89 (1H, d, J=2.4 Hz)

Reference Example 245

Preparation of 1-(6-chlorobenzothiazole-2-yl)pyrrolidine-3-ylamine

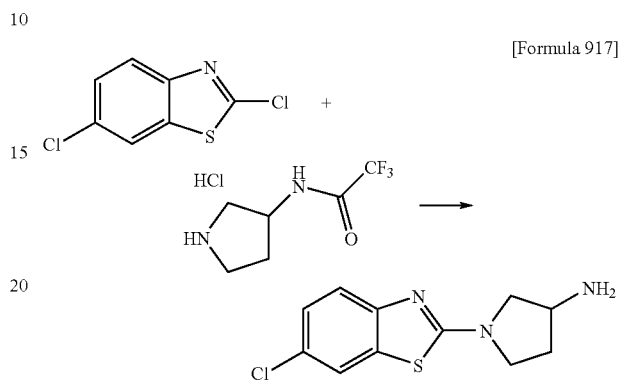

[Formula 917]

A mixture of 2,6-dichlorobenzothiazole (2.00 g), 2-(trifluoroacetamide)pyrrolidine hydrochloride (2.14 g), potassium carbonate (4.06 g) and dimethylformamide (15 mL) was stirred at 60° C. for 2 hours. To the reaction solution was added water and extracted with ethyl acetate. The organic layer was washed with water and brine, and dried over magnesium sulphate. The solvent was evaporated under reduced pressure and the residue was washed with n-hexane. The obtained purified product was dissolved in tetrahydrofuran (20 mL) and methanol (10 mL). 2N sodium hydroxide was added thereto and the mixture was stirred for 2.5 hours. The solvent was evaporated under reduced pressure. Water was added thereto and extracted with ethyl acetate. The organic layer was washed with water and brine, and dried over sodium sulphate. The solvent was evaporated under reduced pressure to give the title compound (2.49 g). Yield: 100%.

1H-NMR (DMSO-d$_6$) δ: 1.72-1.80 (2H, m), 3.45-3.63 (5H, m), 7.26 (1H, dd, H=2.0, 8.0), 7.41 (1H, d, J=8.5), 7.88 (1H, d, J=2.0)

Reference Example 246

Preparation of N-[1(6-chlorobenzothiazole-2-yl)pyrrolidine-3-yl]-2-nitro benzenesulfonamide

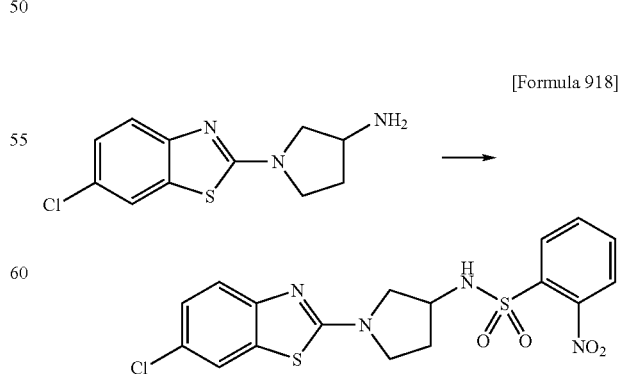

[Formula 918]

A mixture of 1-(6-chlorobenzothiazole-2-yl)pyrrolidine-3-ylamine (2.49 g), 2-nitrobenzenesulphonyl chloride (2.40 g), triethylamine (3.02 mL) and dimethylformamide (15 mL) was stirred at 60° C. for 3 hours. To the reaction solution was added water and extracted with ethyl acetate. The organic layer was washed with water and brine, and dried over sodium sulphate. The solvent was evaporated under reduced pressure and the residue was purified by column chromatograph on silica gel to give the title compound (2.01 g). Yield: 47

$^1$H-NMR (DMSO-$d_6$) δ: 1.99-2.03 (1H, m), 2.19-2.23 (1H, m), 3.55-3.63 (4H, m), 4.07-4.09 (1H, m), 7.30 (1H, dd, J=8.5, 2.2 Hz), 7.45 (1H, d, J=8.8 Hz), 7.90-7.94 (3H, m), 8.01-8.10 (2H, m).

Reference Example 247

Preparation of [3-[[[1-(6-chlorobenzothiazole-2-yl)pyrrolidine-3-yl]-(2-nitrobenzensulphonyl)amino]methyl]phenyl]acetic acid methyl ester

[Formula 919]

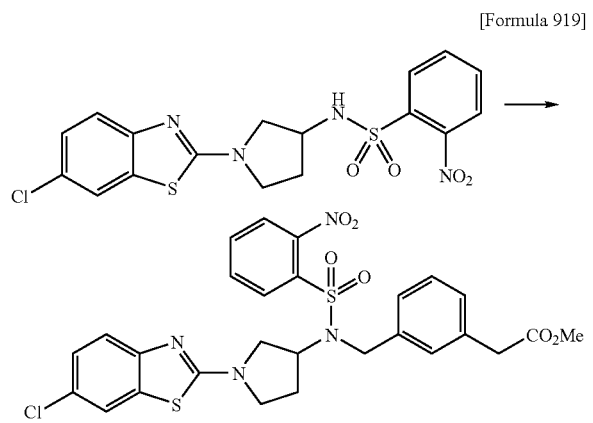

N-[1(6-chlorobenzothiazole-2-yl)pyrrolidine-3-yl]-2-nitrobenzenesulfonamide (500 mg) was dissolved in dimethylformamide (5 mL). Sodium hydride (60%, oil, 50 mg) was added thereto and the mixture was stirred at room temperature for 1 hour. (3-bromomethylphenyl)acetic acid methyl ester (305 mg) was added thereto and the mixture was stirred for 16 hours. To the reaction solution was added water and extracted with ethyl acetate. The organic layer was washed with water and brine, and dried over magnesium sulphate. The solvent was evaporated under reduced pressure and the residue was purified by column chromatograph on silica gel to give the title compound (412 mg). Yield: 60%.

$^1$H-NMR (CDCl$_3$) δ: 2.11-2.19 (1H, m), 2.34-2.37 (1H, m), 3.53-3.59 (6H, m), 3.69 (3H, s), 3.78-3.81 (1H, m), 4.53-4.63 (2H, m), 7.07-7.19 (4H, m), 7.25-7.32 (1H, m), 7.50-7.58 (3H, m), 7.65-7.67 (2H, m), 7.85 (1H, d, J=7.7 Hz).

Example 610

Preparation of [3-[[1-(6-chlorobenzothiazole-2-yl)pyrrolidine-3-ylamino]methyl]phenyl]acetic acid methyl ester

[Formula 920]

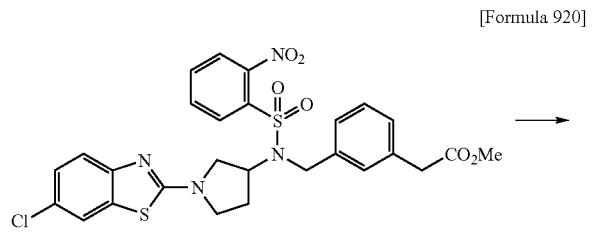

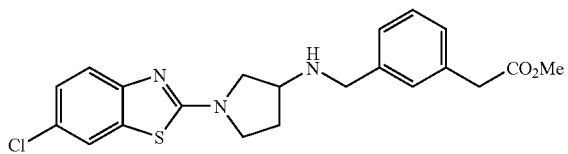

A mixture of [3-[[[1-(6-chlorobenzothiazole-2-yl)pyrrolidine-3-yl]-(2-nitrobenzensulphonyl)amino]methyl]phenyl]acetic acid methyl ester (412 mg), mercaptoacetic acid (95 mL), 1,8-diazabicyclo[5,4,0]-7-undecene (4 mL) and dimethylformamide (4 mL) was stirred at room temperature for 1 hour. To the reaction solution was added water and extracted with ethyl acetate. The organic layer was washed with water and brine, and dried over sodium sulphate. The solvent was evaporated under reduced pressure and the residue was purified by column chromatograph on silica gel to give the title compound (204 mg). Yield: 71%.

$^1$H-NMR (CDCl$_3$) δ: 2.11-2.14 (1H, m), 2.27-2.32 (1H, m), 3.49-3.59 (2H, m), 3.63 (2H, s), 3.70 (3H, s), 3.74-3.82 (2H, m), 3.89 (2H, s), 7.23 (2H, dd, J=8.5, 2.2 Hz), 7.31-7.33 (3H, m), 7.45 (1H, d, J=8.5 Hz), 7.46 (1H, s), 7.54 (1H, d, J=2.2 Hz), 8.02 (1H, brs).

Example 611

Preparation of [3-[[butyl[1-(6-chlorobenzothiazole-2-yl)pyrrolidine-3-yl]amino]methyl]phenyl]acetic acid methyl ester

[Formula 921]

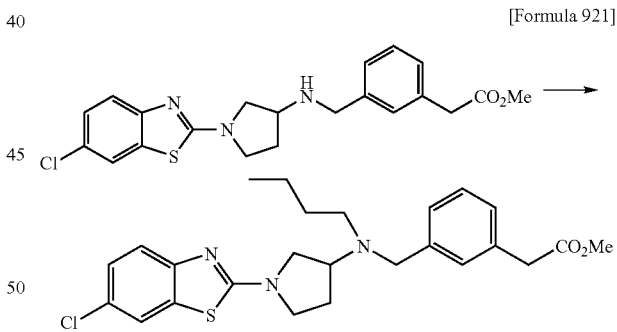

A mixture of [3-[[1-(6-chlorobenzothiazole-2-yl)pyrrolidine-3-ylamino]methyl]phenyl]acetic acid methyl ester (68 mg), 1-iodobutane (37 µL), potassium carbonate (45 mg) and dimethylformamide (1 mL) was stirred at 80° C. for 3.5 hours. To the reaction solution was added water and extracted with ethyl acetate. The organic layer was washed with water and brine, and dried over sodium sulphate. The residue was purified by column chromatograph on silica gel to give the title compound (28 mg). Yield: 36%.

$^1$H-NMR (CDCl$_3$) δ: 0.90 (3H, t, J=7.3 Hz), 1.24-1.36 (2H, m), 1.47-1.50 (2H, m), 2.54-2.56 (2H, m), 3.51-3.71 (14H, m), 7.21-7.29 (5H, m), 7.50 (1H, d, J=8.8 Hz), 7.58 (1H, d, J=2.2 Hz).

Example 612

Preparation of [3-[[butyl[1-(6-chlorobenzothiazole-2-yl)pyrrolidine-3-yl]amino]methyl]phenyl]acetic acid

[Formula 922]

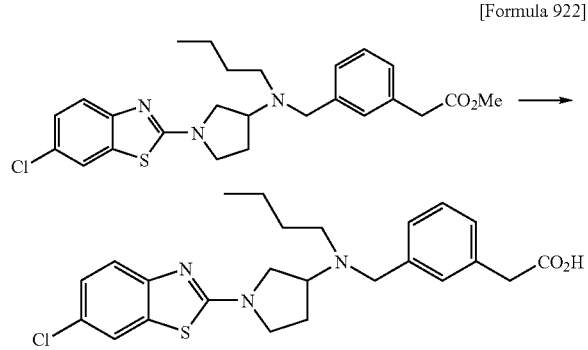

A mixture of [3-[[butyl[1-(6-chlorobenzothiazole-2-yl)pyrrolidine-3-yl]amino]methyl]phenyl]acetic acid methyl ester (28 mg), 2N sodium hydroxide (0.15 mL), tetrahydrofuran (1 mL) and methanol (0.5 mL) was stirred at room temperature for 1 hour. The mixture was neutralized with 2N hydrochloric acid and concentrated under reduced pressure. The solution was extracted with ethyl acetate. The organic layer was washed with water and brine, and dried over sodium sulphate to give the title compound (19 mg). Yield: 68%.

MS (ESI) m/z 458 [M+H]+

The following compounds were obtained by similar methods as above.

Example 613

[Formula 923]

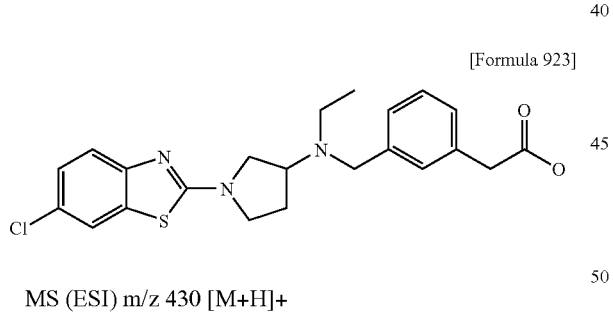

MS (ESI) m/z 430 [M+H]+

Example 614

[Formula 924]

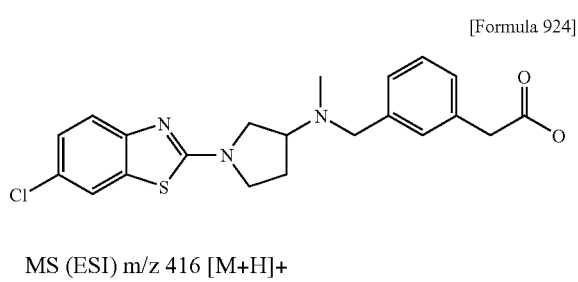

MS (ESI) m/z 416 [M+H]+

Example 615

[Formula 925]

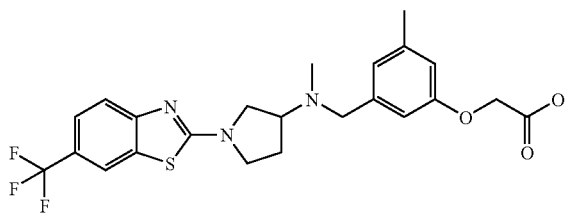

MS (ESI) m/z 480 [M+H]+

Example 616

[Formula 926]

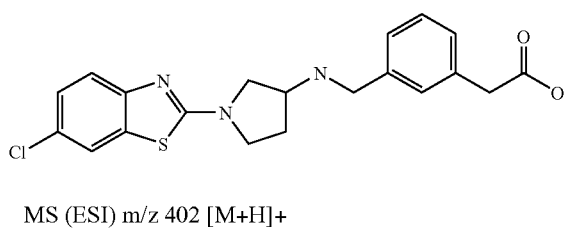

MS (ESI) m/z 402 [M+H]+

Reference Example 248

Preparation of [1-(6-chlorobenzothiazole-2-yl)piperidine-4-yl]carbamic acid tert-butyl ester

[Formula 927]

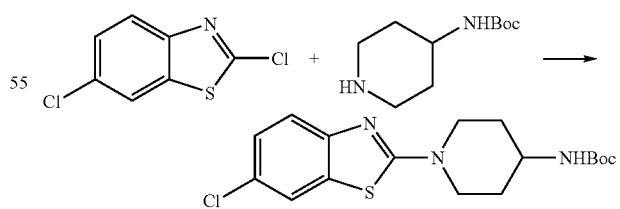

A mixture of 4-Boc-amino piperidine (3.23 g), 2,6-dichlorobenzothiazole (3.29 g), potassium carbonate (6.68 g) and dimethylformamide (20 mL) was stirred at 60° C. for 16 hours. Water was added to the reaction solution. The precipitate was collected and the obtained title compound was provided to the next reaction without purification.

Reference Example 249

Synthesis of 1-(6-chlorobenzothiazole-2-yl)piperidine-4-ylamine

[Formula 928]

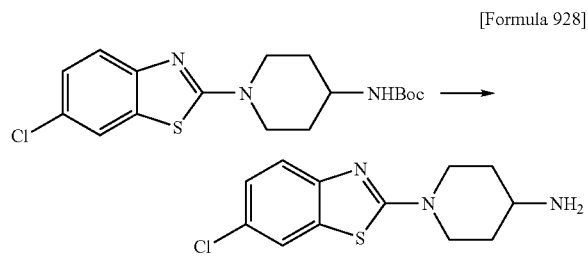

[1-(6-chlorobenzothiazole-2-yl)piperidine-4-yl]carbamic acid tert-butyl ester obtained from the above reaction was dissolved in chloroform. 4N solution of hydrochloric acid/dioxane was added thereto and the mixture was stirred at room temperature for 16 hours. The solvent was concentrated under reduced pressure. Water was added thereto and washed with ethyl acetate. The water layer was neutralized with 2N sodium hydroxide and extracted with ethyl acetate. The organic layer was washed with magnesium sulphate and the solvent was evaporated under reduced pressure to give the title compound (3.31 g). Yield: 77%.

$^1$H-NMR (DMSO-$d_6$) δ: 1.24-1.33 (4H, m), 3.20-3.30 (3H, m), 3.90-3.95 (2H, m), 7.27 (1H, dd, J=8.5, 2.2 Hz), 7.40 (1H, d, J=8.8 Hz), 7.88 (1H, d, J=2.2 Hz).

Example 617

Preparation of [3-[[1-(6-chlorobenzothiazole-2-yl)piperidine-4-ylamino]methyl]phenyl]acetic acid methyl ester

[Formula 929]

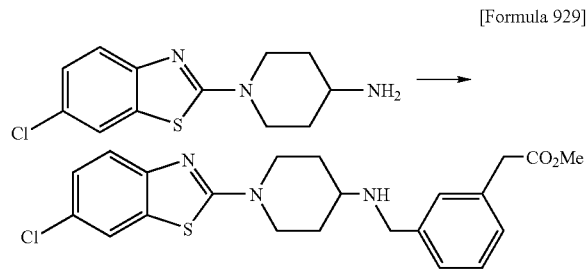

A mixture of 1-(6-chlorobenzothiazole-2-yl)piperidine-4-ylamine (500 mg), (3-bromomethylphenyl)acetic acid methyl ester (454 mg), potassium carbonate (284 mg) and dimethylformamide (6 mL) was stirred at room temperature for 1 hour. To the reaction solution was added water and extracted with ethyl acetate. The organic layer was washed with water and brine, and dried over sodium sulphate. The solvent was evaporated under reduced pressure and the residue was purified by column chromatograph on silica gel to give the title compound (434 mg). Yield: 55%.

Example 618

Preparation of [3-[[[1-(6-chlorobenzothiazole-2-yl)piperidine-4-yl]ethylamino]methyl]phenyl]acetic acid methyl ester

[Formula 930]

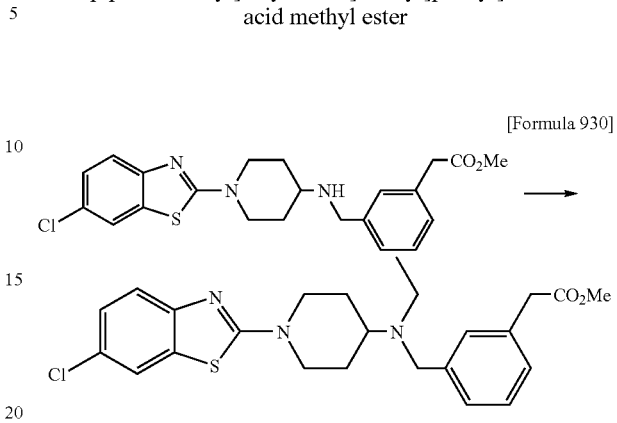

A mixture of [3-[[1-(6-chlorobenzothiazole-2-yl)piperidine-4-ylamino]methyl]phenyl]acetic acid methyl ester (110 mg), methyl iodide (800 mg), potassium carbonate (71 mg) and dimethylformamide (2 mL) was stirred at 80° C. for 5 hours. To the reaction solution was added water and extracted with ethyl acetate. The organic layer was washed with water and brine, and dried over sodium sulphate. The solvent was evaporated under reduced pressure and the residue was purified by column chromatograph on silica gel to give the title compound (65 mg). Yield: 56%.

$^1$H-NMR (CDCl$_3$) δ: 1.03-1.07 (3H, br m), 1.63-1.66 (2H, br m), 1.89-1.92 (2H, br m), 2.58-2.62 (1H, br m), 2.91 (2H, s), 2.98 (2H, s), 3.09-3.13 (2H, m), 3.64-3.67 (2H, br m), 3.71 (3H, s), 4.20-4.23 (2H, br m), 7.25-7.28 (5H, m), 7.44 (1H, d, J=8.5 Hz), 7.57 (1H, d, J=10.0 Hz).

Example 619

Preparation of [3-[[[1-(6-chlorobenzothiazole-2-yl)piperidine-4-yl]ethylamino]methyl]phenyl]acetic acid

[Formula 931]

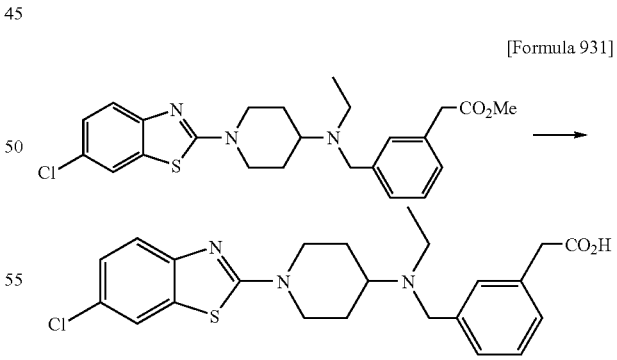

A mixture of [3-[[[1-(6-chlorobenzothiazole-2-yl)piperidine-4-yl]ethylamino]methyl]phenyl]acetic acid methyl ester (65 mg), 2N sodium hydroxide (0.36 mL), tetrahydrofuran (1 mL) and methanol (1 mL) was stirred at room temperature for 1 hour. The solution was neutralized with 2N hydrochloric acid and extracted with ethyl acetate. The organic layer was washed with water and brine, and dried over sodium sulphate. The solvent was evaporated under reduced pressure and the obtained residue was washed with the mixed solvent of ethyl acetate and n-hexane to give the title compound (19 mg). Yield: 30%.

MS (ESI) m/z 444 [M+H]+

The following compounds were obtained by similar methods as above.

Example 620

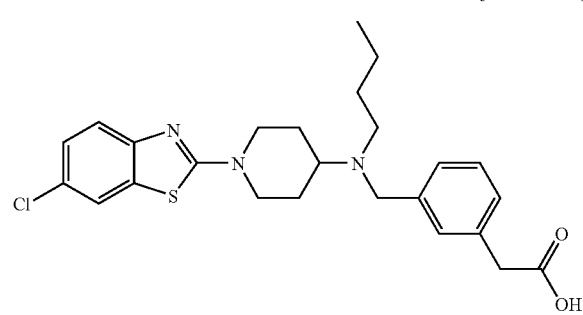
[Formula 932]

MS (ESI) m/z 472 [M+H]+

Example 621

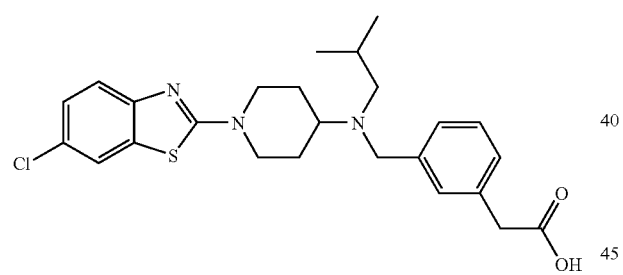
[Formula 933]

MS (ESI) m/z 472 [M+H]+

Example 622

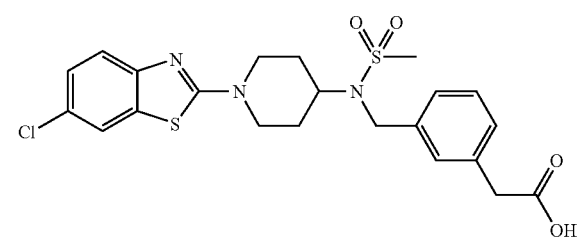
[Formula 934]

MS (ESI) m/z 494 [M+H]+

Reference Example 250

Preparation of [1-(6-chlorobenzothiazole-2-yl)piperidine-4-yl]isopropylamine

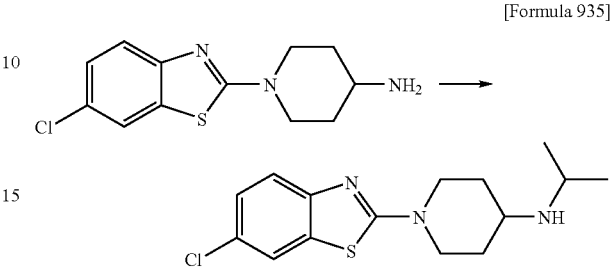
[Formula 935]

A mixture of 1-(6-chlorobenzothiazole-2-yl)piperidine-4-ylamine (335 mg), acetone (92 ul), acetic acid (0.1 mL) and methanol (3 mL) was stirred at room temperature for 5 minutes. To the reaction solution was added triacetoxy sodium boron hydride (332 mg). The mixture was stirred at room temperature for 16 hours. The reaction solution was concentrated under reduced pressure. Aqueous sodium hydrogencarbonate was added thereto and extracted with ethyl acetate. The organic layer was washed with water and brine, and dried over sodium sulphate. The solvent was evaporated under reduced pressure and the residue was purified by column chromatograph on silica gel to give the title compound (160 mg). Yield: 41%.

$^1$H-NMR (CDCl$_3$) δ: 1.11 (6H, d, J=6.3 Hz), 1.48-1.51 (2H, m), 2.01-2.05 (2H, m), 2.84-2.91 (1H, m), 3.00-3.08 (1H, m), 3.14-3.24 (2H, m), 4.08-4.16 (2H, m), 7.23 (1H, dd, J=8.5, 2.2 Hz), 7.42 (1H, d, J=8.5 Hz), 7.55 (1H, d, J=2.2 Hz).

Example 623

Preparation of [3-[[[1-(6-chlorobenzothiazole-2-yl)piperidine-4-yl]isopropylamino]methyl]phenyl]acetic acid methyl ester

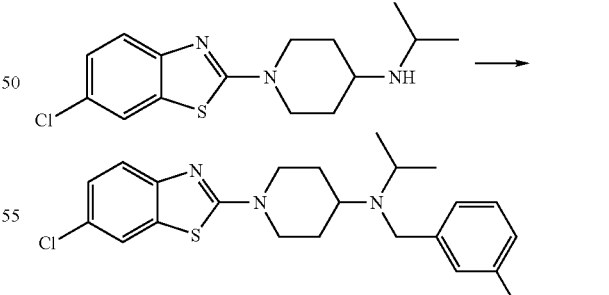
[Formula 936]

A mixture of [1-(6-chlorobenzothiazole-2-yl)piperidine-4-yl]isopropylamine (159 mg), (3-bromomethylphenyl)acetic acid methyl ester (138 mg), potassium carbonate (107 mg) and dimethylformamide (2 mL) was stirred at 80° C. for 8 hours. To the reaction solution was added water and extracted with ethyl acetate. The organic layer was washed with water and brine, and dried over magnesium sulphate. The solvent was evaporated under reduced pressure and the residue was purified by column chromatograph on silica gel to give the title compound (90 mg). Yield: 37%.

Example 624

Preparation of [3-[[[1-(6-chlorobenzothiazole-2-yl)piperidine-4-yl]isopropylamino]methyl]phenyl]acetic acid

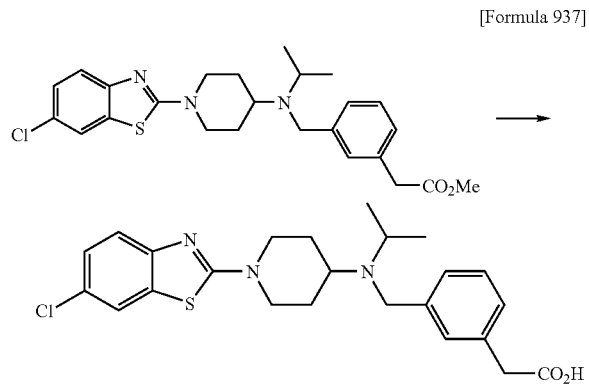

[Formula 937]

A mixture of [3-[[[1-(6-chlorobenzothiazole-2-yl)piperidine-4-yl]isopropylamino]methyl]phenyl]acetic acid methyl ester (90 mg), 2N sodium hydroxide (0.5 mL), tetrahydrofuran (2 mL) and methanol (1 mL) was stirred at room temperature for 1 hour. After neutralizing with 2N hydrochloric acid, the reaction solution was concentrated under reduced pressure and extracted with ethyl acetate. The organic layer was washed with water and brine, and dried over magnesium sulphate. The solvent was evaporated under reduced pressure and the residue was purified by column chromatograph on silica gel to give the title compound (28 mg).
Yield: 32%.
MS (ESI) m/z 458 [M+H]+

Example 625

Preparation of [3-[2-[1-(6-chlorobenzothiazole-2-yl)pyrrolidine-3-ylamino]ethoxy]phenyl]acetic acid methyl ester

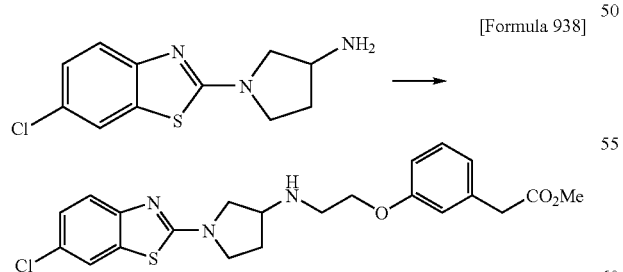

[Formula 938]

A mixture of 1-(6-chlorobenzothiazole-2-yl)pyrrolidine-3-ylamine (190 mg), [3-(2-bromoethoxy)phenyl]acetic acid methyl ester (205 mg) and potassium carbonate (114 mg) was stirred at 80° C. for 2 hours. To the reaction solution, was added water and extracted with ethyl acetate. The organic layer was washed with water and brine, and dried over sodium sulphate. The solvent was evaporated under reduced pressure and the residue was purified by column chromatograph on silica gel to give the title compound (174 mg). Yield: 52%.
$^1$H-NMR (CDCl$_3$) δ: 2.01-2.06 (1H, m), 2.31-2.36 (1H, m), 3.09 (2H, t, J=4.9 Hz), 3.48-3.50 (1H, m), 3.62 (2H, s), 3.64-3.80 (4H, m), 3.72 (3H, s), 4.12 (2H, t, J=4.9 Hz), 6.83-6.91 (3H, m), 7.24-7.28 (3H, m), 7.50 (1H, d, J=8.5 Hz), 7.59 (1H, d, J=1.9 Hz).

Example 626

Preparation of [3-[2-[[1-(6-chlorobenzothiazole-2-yl)pyrrolidine-3-yl]ethylamino]ethoxy]phenyl]acetic acid methyl ester

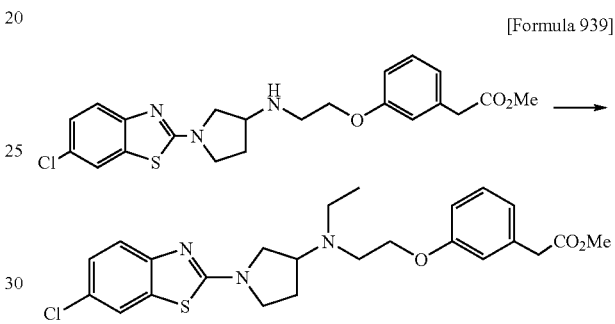

[Formula 939]

A mixture of [3-[2-[1-(6-chlorobenzothiazole-2-yl)pyrrolidine-3-ylamino]ethoxy]phenyl]acetic acid methyl ester (174 mg), ethyl iodide (68 uL), potassium carbonate (81 mg) and dimethylformamide (2 mL) was stirred at 80° C. for 6.5 hours. To the reaction solution was added water and extracted with ethyl acetate. The organic layer was washed with water and brine, and dried over sodium sulphate. The solvent was evaporated under reduced pressure and the residue was purified by column chromatograph on silica gel to give the title compound (101 mg). Yield: 55%.
$^1$H-NMR (CDCl$_3$) δ: 1.14 (3H, t, J=6.7 Hz), 2.08-2.11 (1H, m), 2.29-2.32 (1H, m), 2.79-2.81 (2H, m), 2.98-3.03 (2H, m), 3.46-3.86 (5H, m), 3.62 (2H, s), 3.71 (3H, s), 4.05-4.08 (2H, m), 6.82-6.90 (3H, m), 7.23-7.29 (2H, m), 7.50 (1H, d, J=8.8 Hz), 7.59 (1H, d, J=1.9 Hz).

Example 627

Preparation of [3-[2-[[1-(6-chlorobenzothiazole-2-yl)pyrrolidine-3-yl]ethylamino]ethoxy]phenyl]acetic acid

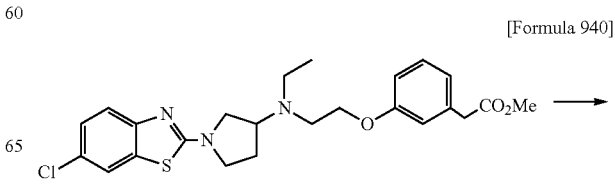

[Formula 940]

-continued

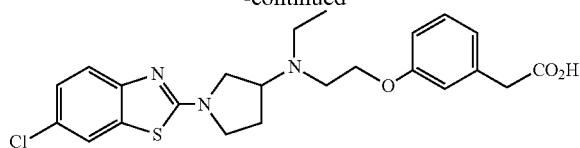

A mixture of [3-[2-[[1-(6-chlorobenzothiazole-2-yl)pyrrolidine-3-yl]ethylamino]ethoxy]phenyl]acetic acid methyl ester (101 mg), 2N aqueous sodium hydroxide (0.535 mL), tetrahydrofuran (1 mL) and methanol (0.5 mL) was stirred at room temperature for 1 hour. The reaction solution was concentrated under reduced pressure and extracted with ethyl acetate. The organic layer was washed with water and brine, and dried over sodium sulphate. The solvent was evaporated under reduced pressure and the residue was washed with ethyl acetate/n-hexane to give the title compound (13 mg). Yield: 14%.

MS (ESI) m/z 459 [M+H]+

The following compounds were obtained by similar methods as above.

Example 628

[Formula 941]

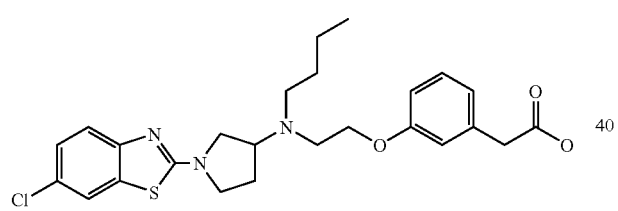

MS (ESI) m/z 487 [M+H]+

Example 629

[Formula 942]

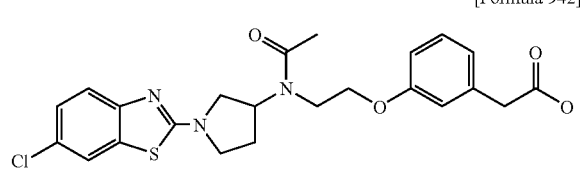

MS (ESI) m/z 473 [M+H]+

Example 630

[Formula 943]

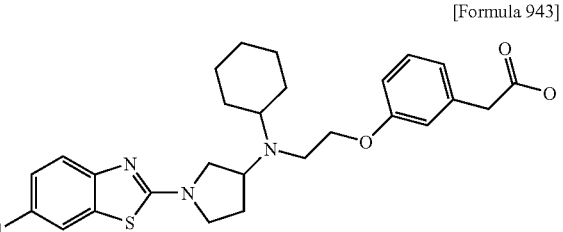

MS (ESI) m/z 516 [M+H]+

Example 631

[Formula 944]

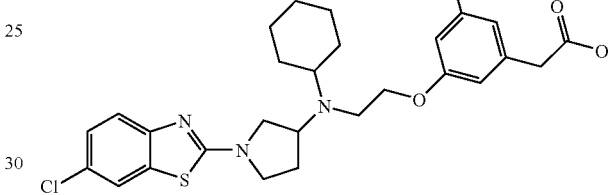

MS (ESI) m/z 548 [M+H]+

Example 632

[Formula 945]

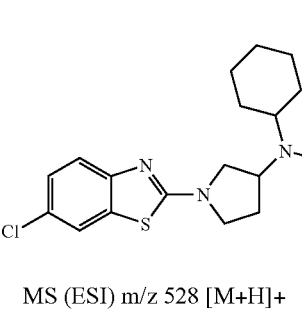

MS (ESI) m/z 528 [M+H]+

Example 633

[Formula 946]

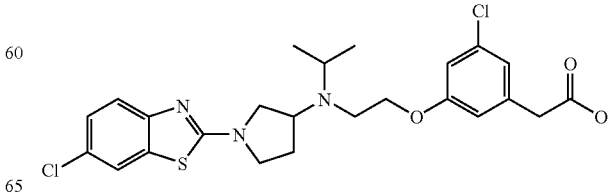

MS (ESI) m/z 508 [M+H]+

Reference Example 251

Preparation of (1-benzyl-4-pyrrolidine-1-ylpiperidine-4-yl)acetic acid methyl ester

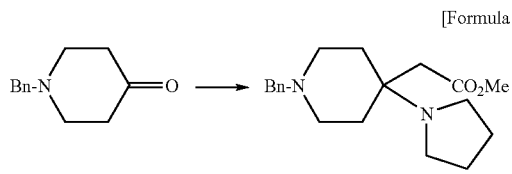

[Formula 947]

A mixture of 1-benzyl-4-piperidone (3 mL), pyrrolidine (6.95 mL) and toluene (30 mL) was refluxed for 1 hour. The solvent was evaporated under reduced pressure. To the residue was added acetic acid (0.96 mL). The mixture was stirred at room temperature for 5 minutes. To the reaction solution were added zinc (1.37 g) and bromo acetic acid methyl ester (2.17 mL). The mixture was stirred at room temperature for 2 hours. To the reaction solution was added aqueous sodium carbonate solution (20 mL) and extracted with ethyl acetate. The organic layer was washed with water and brine, and dried over sodium sulphate. The solvent was evaporated under reduced pressure and the residue was purified by column chromatograph on silica gel to give the title compound (2.77 g). Yield: 52%.

$^1$H-NMR (CDCl3) δ: 1.71-1.73 (4H, m), 1.81-1.84 (4H, m), 2.45-2.56 (10H, m), 3.55-3.58 (2H, m), 3.69 (3H, s), 7.26-7.36 (5H, m).

Reference Example 252

Preparation of 2-(1-benzyl-4-pyrrolidine-1-ylpiperidine-4-yl)ethanol

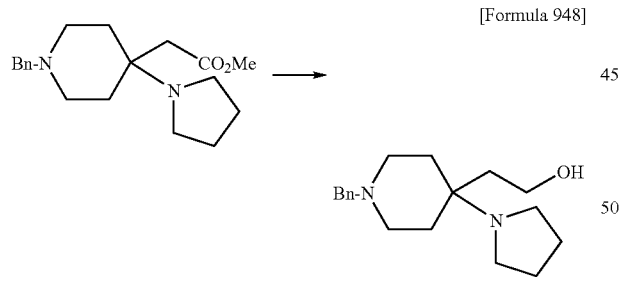

[Formula 948]

Lithium aluminium hydride (324 mg) was suspended in tetrahydrofuran (25 mL). A solution of (1-benzyl-4-pyrrolidine-1-ylpiperidine-4-yl)acetic acid methyl ester (2.70 g) in tetrahydrofuran (25 mL) was added thereto at 0° C. After stirring at 0° C. for 1 hour, to the reaction solution were sequentially added with water (0.35 mL), 10% aqueous sodium hydroxide (0.35 mL) and water (1.05 mL). The insoluble material was filtrated and the filtrate was extracted with ethyl acetate. The organic layer was washed with water and brine, and dried over sodium sulphate. The solvent was evaporated under reduced pressure to give the title compound. The obtained objective substance was provided to the next reaction without further purification.

$^1$H-NMR (CDCl$_3$) δ: 1.74-1.76 (6H, m), 1.89-1.94 (4H, m), 2.06-2.17 (2H, m), 2.80-2.83 (6H, m), 3.54 (3H, s), 3.85-3.87 (2H, m), 7.33 (5H, t, J=3.6 Hz).

Reference Example 253

Preparation of 2-[1-(6-chlorobenzothiazole-2-yl)-4-pyrrolidine-1-ylpiperidine-4-yl]ethanol

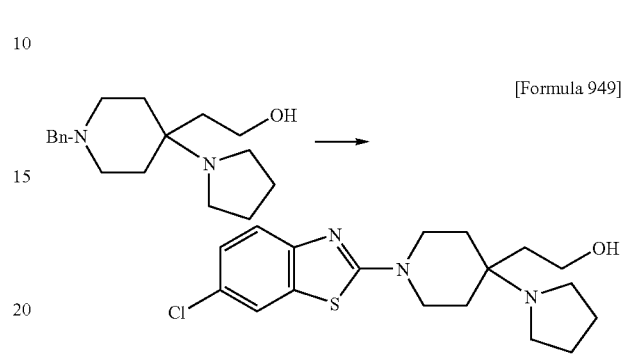

[Formula 949]

2-(1-Benzyl-4-pyrrolidine-1-ylpiperidine-4-yl) ethanol obtained above was dissolved in methanol (60 mL). Pd/C (600 mg) was added thereto and the mixture was stirred under a hydrogen atmosphere for 19 hours. The insoluble material was filtrated and the filtrate was concentrated under reduced pressure. To the obtained residue were added dimethylformamide (30 mL), potassium carbonate (1.24 g) and 2,6-dichlorobenzothiazole (1.83 g). The mixture was stirred at 60° C. for 21 hours. To the reaction solution was added water and extracted with ethyl acetate. The organic layer was washed with water and brine, and dried over sodium sulphate. The solvent was evaporated under reduced pressure and the residue was purified by column chromatograph on silica gel to give the title compound (2.58 g).

Yield: 83%.

$^1$H-NMR (CDCl$_3$) δ: 1.83-1.86 (4H, m), 2.00-2.01 (6H, m), 2.91-2.98 (4H, m), 3.29-3.38 (2H, m), 3.92-4.05 (4H, m), 7.26 (1H, d, J=2.2 Hz), 7.45 (1H, t, J=7.8 Hz), 7.59 (1H, d, J=2.2 Hz).

Example 634

Preparation of [3-chloro-5-[2-[1-(6-chlorobenzothiazole-2-yl)-4-pyrrolidine-1-ylpiperidine-4-yl]ethanol]phenyl]acetic acid methyl ester

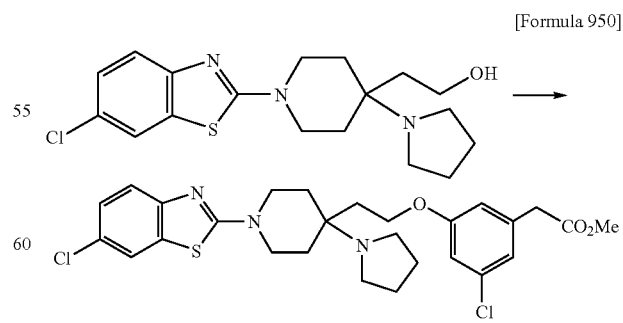

[Formula 950]

A mixture of 2-[1-(6-chlorobenzothiazole-2-yl)-4-pyrrolidine-1-ylpiperidine-4-yl]ethanol (1.60 g), tri-n-butylphosphine (1.15 mL), 1,1'-(azodicarbonyl)dipiperidine (1.16 g)

and tetrahydrofuran (25 mL) was stirred at room temperature for 1 hour. The insoluble material was filtrated. To the filtrate was added aqueous sodium hydrogencarbonate solution and extracted with ethyl acetate. The organic layer was washed with water and brine, and dried over sodium sulphate. The solvent was evaporated under reduced pressure and the residue was purified by column chromatograph on silica gel to give the title compound (874 mg).

Yield: 36%.

$^1$H-NMR (CDCl$_3$) δ: 1.77-1.81 (6H, m), 1.94-2.03 (4H, m), 2.69-2.72 (4H, m), 3.53-3.77 (4H, m), 3.56 (2H, s), 3.72 (3H, s), 4.01 (2H, m), 6.75-6.84 (3H, m), 7.25 (1H, dd, J=8.7, 2.1 Hz), 7.44 (1H, d, J=8.8 Hz), 7.57 (1H, d, J=2.2 Hz).

Example 635

Preparation of [3-chloro-5-[2-[1-(6-chlorobenzothiazole-2-yl)-4-pyrrolidine-1-ylpiperidine-4-yl]ethanol]phenyl]acetic acid

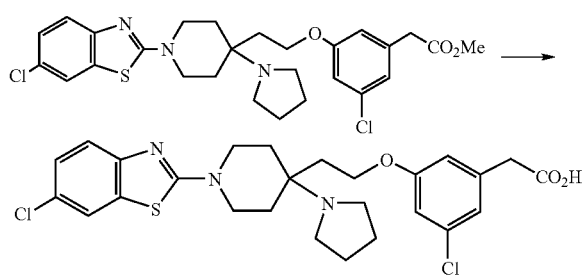

[Formula 951]

A mixture of [3-chloro-5-[2-[1-(6-chlorobenzothiazole-2-yl)-4-pyrrolidine-1-ylpiperidine-4-yl]ethanol]phenyl]acetic acid methyl ester (851 mg), 2N sodium hydroxide (2.33 mL), tetrahydrofuran (5 mL) and methanol (5 mL) was stirred at room temperature for 0.5 hour. The mixture was neutralized with 2N hydrochloric acid and extracted with ethyl acetate. The organic layer was washed with water and brine, and dried over magnesium sulphate. The solvent was evaporated under reduced pressure and the residue was washed with hexane to give the title compound (725 mg). Yield: 88%.

MS (ESI) m/z 534 [M+H]$^+$

The following compounds were obtained by similar methods as above.

Example 636

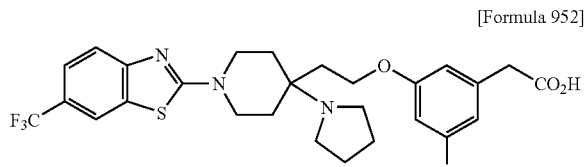

[Formula 952]

MS (ESI) m/z 568 [M+H]$^+$

Example 637

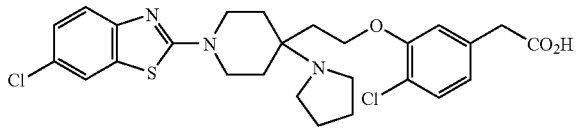

[Formula 953]

MS (ESI) m/z 534 [M+H]$^+$

Example 638

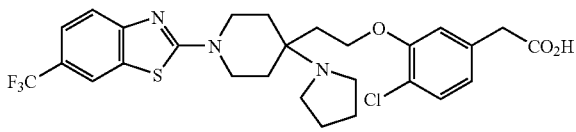

[Formula 954]

MS (ESI) m/z 568 [M+H]$^+$

Example 639

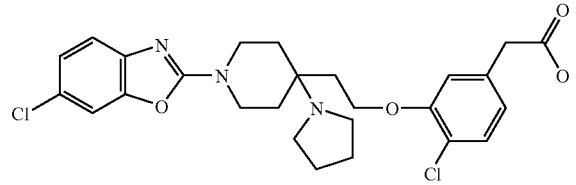

[Formula 955]

MS (ESI) m/z 520 [M+H]$^+$

Example 640

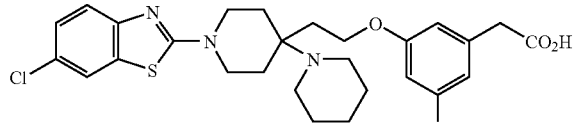

[Formula 956]

MS (ESI) m/z 548 [M+H]$^+$

Example 641
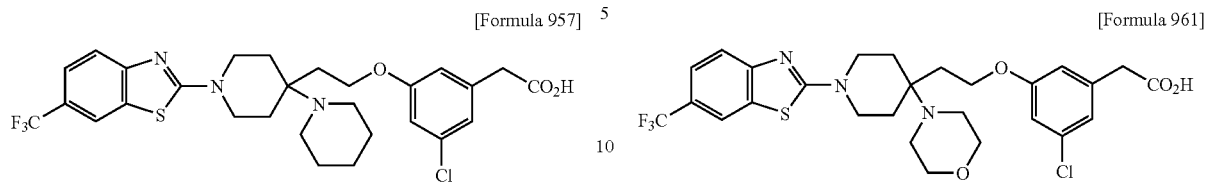
MS (ESI) m/z 582 [M+H]+
Example 642
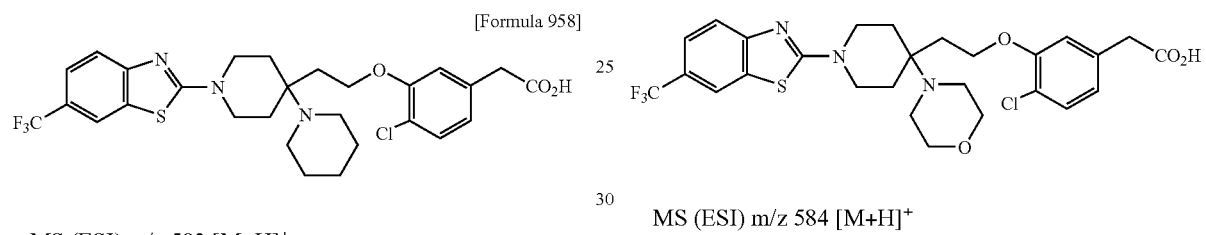
MS (ESI) m/z 582 [M+H]+
Example 643
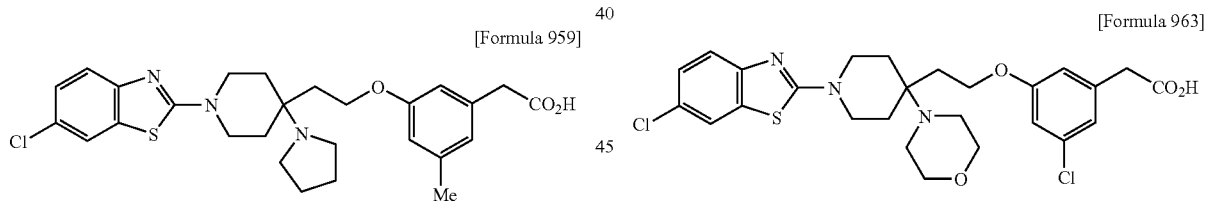
MS (ESI) m/z 514 [M+H]+
Example 644
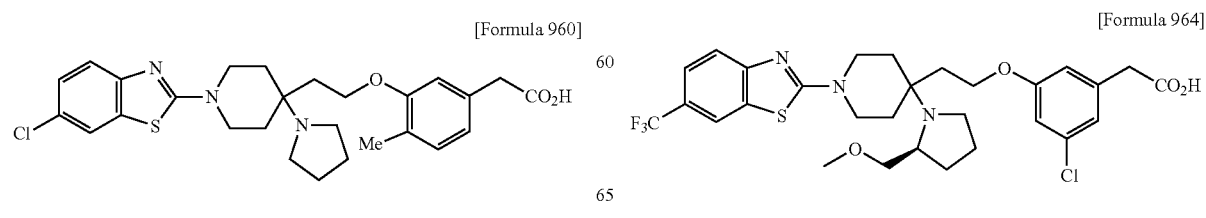
MS (ESI) m/z 514 [M+H]+
Example 645
MS (ESI) m/z 584 [M+H]+
Example 646
MS (ESI) m/z 584 [M+H]+
Example 647
MS (ESI) m/z 550 [M+H]+
Example 648
MS (ESI) m/z 612 [M+H]+

Example 649
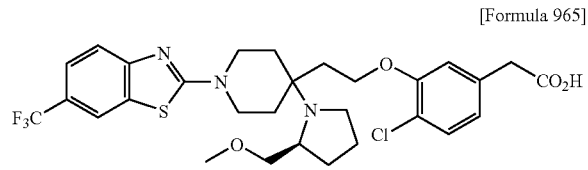
MS (ESI) m/z 612 [M+H]+
Example 650
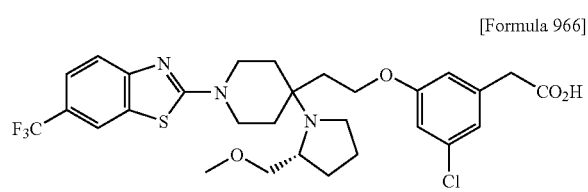
MS (ESI) m/z 612 [M+H]+
Example 651
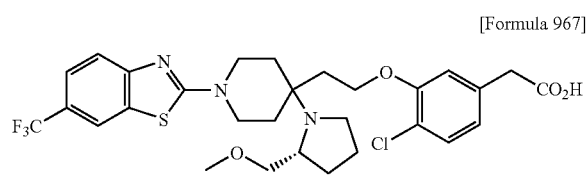
MS (ESI) m/z 612 [M+H]+
Example 652
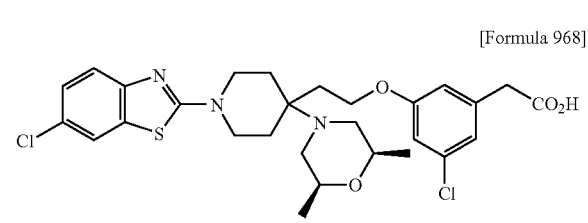
MS (ESI) m/z 578 [M+H]+
Example 653
[Formula 969]
MS (ESI) m/z 578 [M+H]+
Example 654
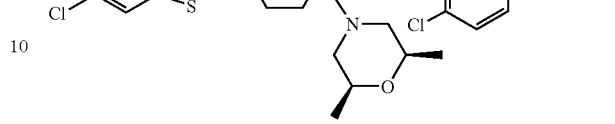
¹H-NMR (CDCl₃) δ: 1.08 (6H, t, J=7.1 Hz), 1.65-1.77 (2H, m), 1.92-2.05 (4H, m), 2.65 (4H, q, J=7.1 Hz), 3.54-3.77 (6H, m), 4.01 (2H, t, J=6.6 Hz), 6.70 (1H, s), 6.78 (1H, s), 6.87 (1H, s), 7.22 (1H, dd, J=8.5, 2.2 Hz), 7.43 (1H, d, J=8.5 Hz), 7.54 (1H, d, J=2.2 Hz).
Example 655
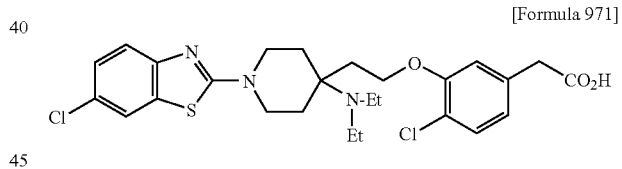
1H-NMR (CDCl3) δ: 1.07 (6H, t, J=7.0 Hz), 1.70-2.10 (6H, m), 2.66 (4H, q, J=7.0 Hz), 3.56-3.79 (6H, m), 4.05-4.13 (2H, m), 6.76-6.85 (2H, m), 7.19-7.30 (2H, m), 7.42 (1H, d, J=8.5 Hz), 7.53 (1H, d, J=1.6 Hz).
Example 656
[Formula 972]
1H-NMR (CDCl3) δ: 1.08 (3H, t, J=6.9 Hz), 1.64-2.03 (6H, m), 2.26 (3H, s), 2.53 (2H, q, J=6.9 Hz), 3.52-3.68 (6H, m), 3.96-4.03 (2H, m), 6.68-6.88 (3H, m), 7.22 (1H, dd, J=8.5, 2.2 Hz), 7.43 (1H, d, J=8.8 Hz), 7.54 (1H, d, J=2.2 Hz).

Example 657

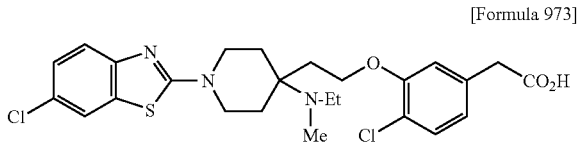
[Formula 973]

1H-NMR (CDCl3) δ: 1.05 (3H, t, J=7.1 Hz), 1.64-2.03 (6H, m), 2.23 (3H, s), 2.44-2.56 (2H, m), 3.45-3.68 (6H, m), 3.98-4.08 (2H, m), 6.68-6.85 (2H, m), 7.18-7.25 (2H, m), 7.41 (1H, d, J=8.8 Hz), 7.52 (1H, d, J=1.4 Hz).

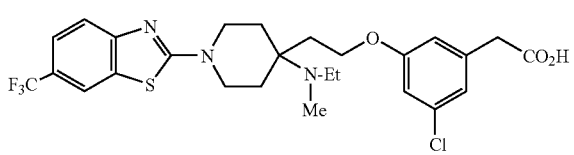
[Formula 974]

1H-NMR (CDCl3) δ: 1.08 (3H, t, J=7.1 Hz), 1.64-2.06 (6H, m), 2.26 (3H, s), 2.52 (2H, q, J=7.1 Hz), 3.56 (2H, s), 3.60-3.80 (4H, m), 4.00 (2H, t, J=6.7 Hz), 6.68-6.89 (3H, m), 7.49-7.58 (2H, m), 7.83 (1H, s).

Example 659

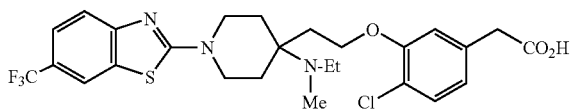
[Formula 975]

1H-NMR (CDCl3) δ: 1.07 (3H, t, J=6.9 Hz), 1.70-2.07 (6H, m), 2.25 (3H, s), 2.52 (2H, q, J=6.9 Hz), 3.53 (2H, s), 3.59-3.76 (5H, m), 4.03-4.10 (2H, m), 6.74-6.84 (2H, m), 7.23-7.28 (1H, m), 7.47-7.57 (2H, m), 7.82 (1H, s).

Example 660

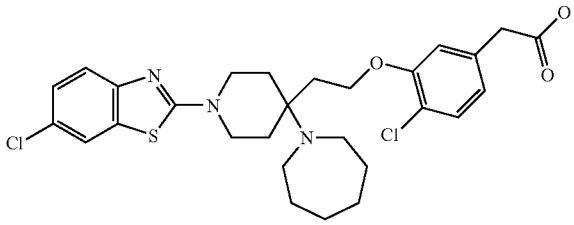
[Formula 976]

1H-NMR (CDCl3) δ: 7.54 (1.0H, d, J=1.92 Hz), 7.42 (1.0H, d, J=8.79 Hz), 7.31-7.29 (1.0H, m), 7.24-7.21 (1.0H, m), 6.85-6.79 (2.0H, m), 4.09 (2.0H, dd, J=7.14, 7.14 Hz), 3.78-3.58 (6.0H, m), 2.79-2.73 (4.0H, br m), 2.10-1.52 (14.0H, m).

Example 661

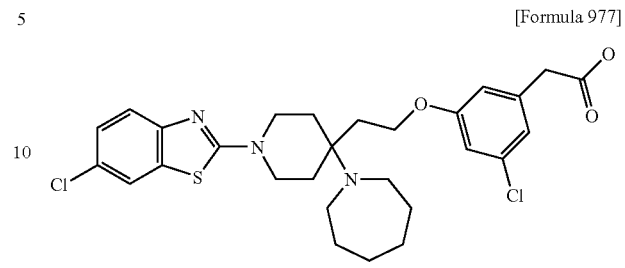
[Formula 977]

1H-NMR (CDCl3) δ: 7.54 (1.0H, d, J=2.20 Hz), 7.43 (1.0H, d, J=8.24 Hz), 7.25-7.20 (1.0H, m), 6.87 (1.0H, s), 6.78 (1.0H, s), 6.70 (1.0H, s), 3.99 (2.0H, dd, J=7.00, 7.00 Hz), 3.77-3.56 (6.0H, m), 2.76-2.72 (4.0H, m), 2.13-1.91 (10.0H, m), 1.73-1.56 (4.0H, m).

Example 662

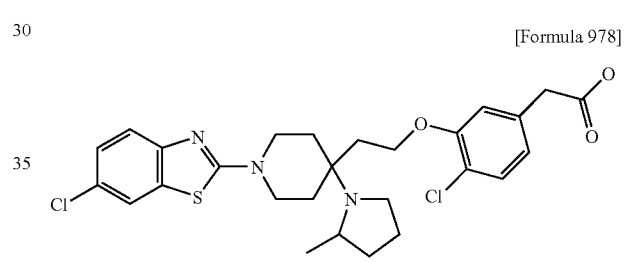
[Formula 978]

1H-NMR (CDCl3) δ: 7.53 (1.0H, d, J=1.92 Hz), 7.41 (1.0H, d, J=8.79 Hz), 7.26-7.20 (2.0H, m), 6.86 (1.0H, s), 6.76 (1.0H, d, J=8.52 Hz), 4.17-4.10 (2.0H, m), 3.92-3.84 (1.0H, m), 3.81-3.40 (4.0H, m), 3.33-3.24 (2.0H, m), 2.97-2.89 (1.0H, m), 2.76-2.66 (1.0H, m), 2.19-1.61 (8.0H, m), 1.54-1.42 (2.0H, m), 1.04 (3.0H, d, J=6.30 Hz).

Example 663

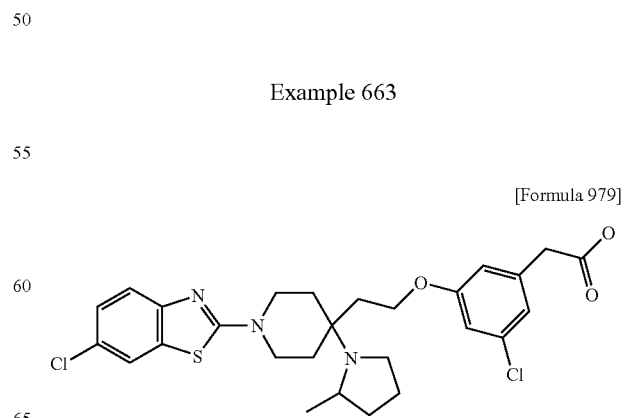
[Formula 979]

MS (ESI) m/z 548 [M+H]+

Example 664

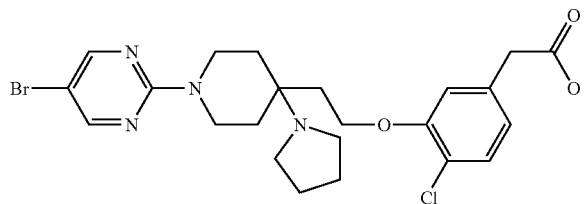

[Formula 980]

MS (ESI) m/z 525 [M+H]+

Example 665

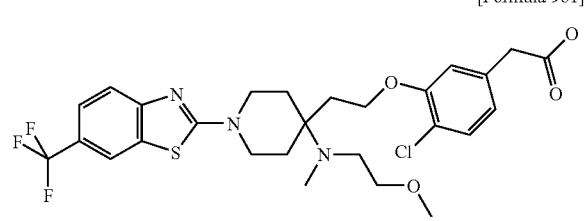

[Formula 981]

1H-NMR (CDCl3) δ: 7.83 (1.0H, d, J=1.24 Hz), 7.55 (1.0H, d, J=8.51 Hz), 7.50 (1.0H, dd, J=8.78, 1.24 Hz), 7.30 (1.0H, d, J=8.10 Hz), 6.85 (1.0H, d, J=1.78 Hz), 6.80 (1.0H, dd, J=8.10, 1.78 Hz), 4.15-4.10 (2.0H, m), 3.79-3.61 (6.0H, m), 3.47 (2.0H, t, J=6.45 Hz), 3.36 (3.0H, s), 2.71 (4.0H, t, J=6.45 Hz), 2.07-1.98 (4.0H, m), 1.82-1.71 (2.0H, m).

Example 666

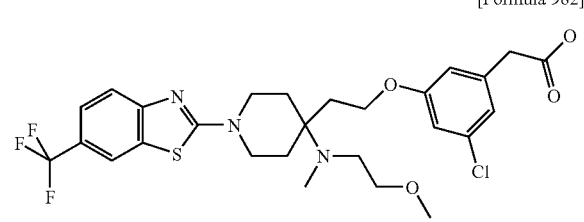

[Formula 982]

1H-NMR (CDCl3) δ: 7.83 (1.0H, d, J=0.89 Hz), 7.56 (1.0H, d, J=8.85 Hz), 7.51 (1.0H, dd, J=8.85, 0.89 Hz), 6.88-6.87 (1.0H, m), 6.79 (1.0H, dd, J=1.92, 0.96 Hz), 6.71-6.69 (1.0H, m), 4.02 (2.0H, t, J=6.31 Hz), 3.79-3.63 (4.0H, m), 3.57 (2.0H, s), 3.46 (2.0H, t, J=6.24 Hz), 3.35 (3.0H, s), 2.68 (3.0H, t, J=6.24 Hz), 2.31 (3.0H, s), 2.07-1.91 (4.0H, m), 1.77-1.64 (2.0H, m).

Reference Example 254

Preparation of 2-(4-pyrrolidine-1-ylpiperidine-4-yl)ethanol

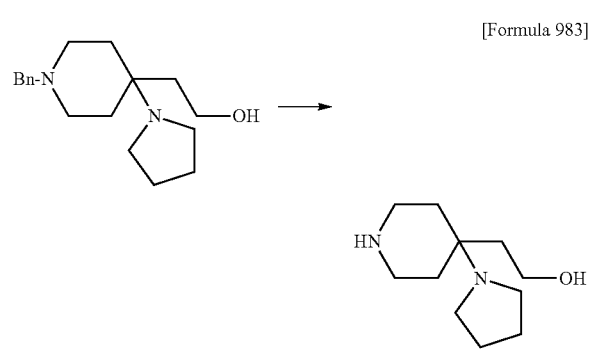

[Formula 983]

A mixture of 2-(1-benzyl-4-pyrrolidine-1-ylpiperidine-4-yl)ethanol (9.28 g), 10% Pd/C (1.86 g) and methanol (100 mL) was stirred under hydrogen (4 atm) for 3 days. The insoluble material was filtrated and the filtrate was concentrated to give the title compound (6.30 g).

Yield: 99%.

$^{1}$H-NMR (DMSO-d$_6$) δ: 1.76-1.79 (6H, m), 1.88-1.91 (4H, m), 2.77-2.80 (4H, m), 3.02-3.05 (2H, br m), 3.15-3.18 (2H, br m), 3.53-3.55 (2H, br m).

Reference Example 255

Preparation of 2-[1-(5-bromothiazole-2-yl)-4-pyrrolidine-1-ylpiperidine-4-yl]ethanol

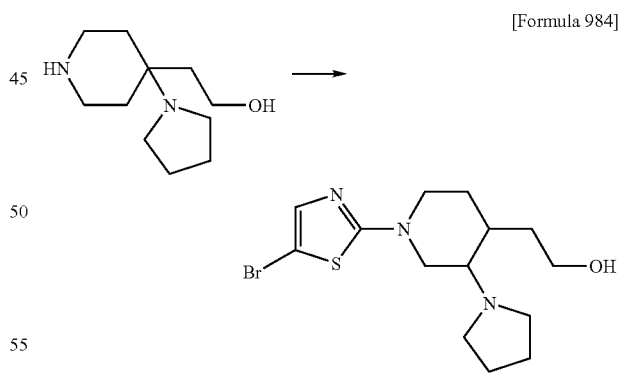

[Formula 984]

A mixture of 2-(4-pyrrolidine-1-ylpiperidine-4-yl)ethanol (4.11 g), 2,5-dibromothiazole (5.03 g), potassium carbonate (3.43 g) and dimethylformamide (75 mL) was stirred at 60° C. for 16 hours. To the reaction solution was added water and extracted with ethyl acetate. The organic layer was washed with water and brine, and washed with magnesium sulphate. The solvent was evaporated under reduced pressure and the residue was purified by column chromatograph on silica gel to give the title compound (3.88 g). Yield: 52%.

Example 667

Preparation of [3-[2-[1-(5-bromothiazole-2-yl)-4-pyrrolidine-1-ylpiperidine-4-yl]ethoxy]-5-chlorophenyl]acetic acid methyl ester

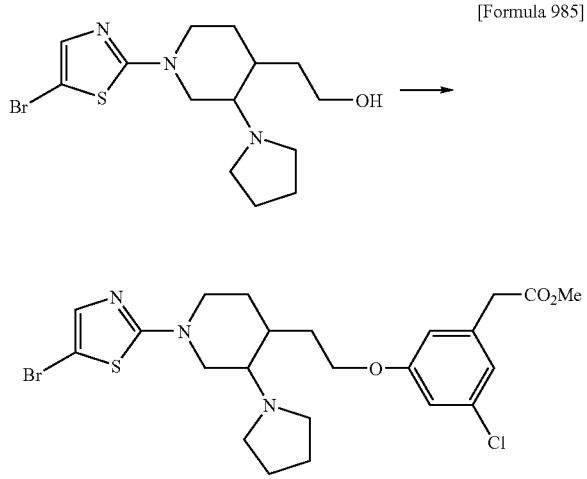

[Formula 985]

A mixture of 2-[1-(5-bromothiazole-2-yl)-4-pyrrolidine-1-ylpiperidine-4-yl]ethanol (1.30 g), (3-chloro-5-hydroxyphenyl)acetic acid (796 mg), tri-n-butylphosphine (0.99 mL), 1,1'-(azodicarbonyl)dipiperidine (1.00 g) and tetrahydrofuran (20 mL) was stirred at room temperature for 4 hours. To the reaction solution was added water and extracted with ethyl acetate. The organic layer was washed with water and brine, and dried over magnesium sulphate. The solvent was evaporated under reduced pressure and the residue was purified by column chromatograph on silica gel to give the title compound (1.45 g). Yield: 74%.

$^1$H-NMR (CDCl$_3$) δ: 1.71-1.85 (8H, m), 2.09-2.10 (2H, m), 2.69-2.71 (4H, br m), 3.48-3.53 (4H, m), 3.61 (2H, s), 3.71 (3H, s), 4.12-4.16 (2H, m), 6.83 (2H, dd, J=8.0, 2.2 Hz), 7.07 (1H, d, J=2.2 Hz), 7.31 (1H, d, J=8.0 Hz).

Example 668

Preparation of [3-[2-[1-(5-bromothiazole-2-yl)-4-pyrrolidine-1-ylpiperidine-4-yl]ethoxy]-5-chlorophenyl]acetic acid

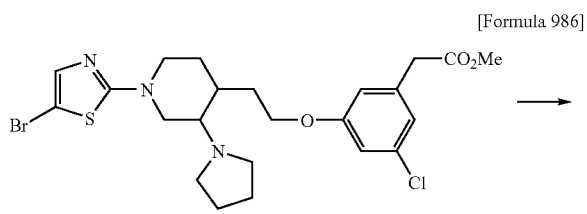

[Formula 986]

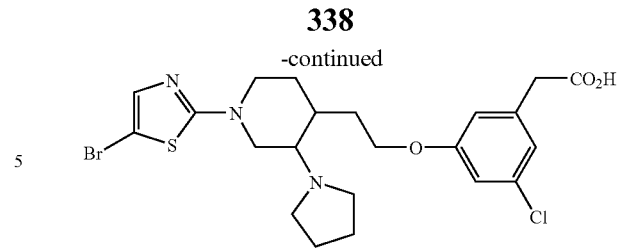

A mixture of [3-[2-[1-(5-bromothiazole-2-yl)-4-pyrrolidine-1-ylpiperidine-4-yl]ethoxy]-5-chlorophenyl]acetic acid methyl ester (1.45 g), 2N sodium hydroxide (3.3 mL), tetrahydrofuran (15 mL) and methanol (15 mL) was stirred at room temperature for 3 hours. To the reaction solution was added water and washed with chloroform. The water layer was neutralized with 2N hydrochloric acid and extracted with chloroform. The organic layer was washed with water and brine, and dried over magnesium sulphate. The solvent was evaporated under reduced pressure and the residue was purified by column chromatograph on silica gel to give the title compound (916 mg). Yield: 65%.

$^1$H-NMR (DMSO-d$_6$) δ: 1.75-1.89 (10H, m), 2.64-2.67 (4H, m), 3.33-3.36 (2H, m), 3.34 (2H, s) 3.51-3.55 (2H, m), 4.11-4.14 (2H, m), 6.85 (1H, dd, J=7.8, 2.1 Hz), 7.10 (1H, d, J=2.1 Hz), 7.19 (1H, s), 7.34 (1H, d, J=7.8 Hz).

Example 669

Preparation of [3-chloro-5-[2-[1-[5-(3-fluorophenyl)thiazole-2-yl]-4-pyrrolidine-1-ylpiperidine-4-yl]ethoxy]phenyl]acetic acid

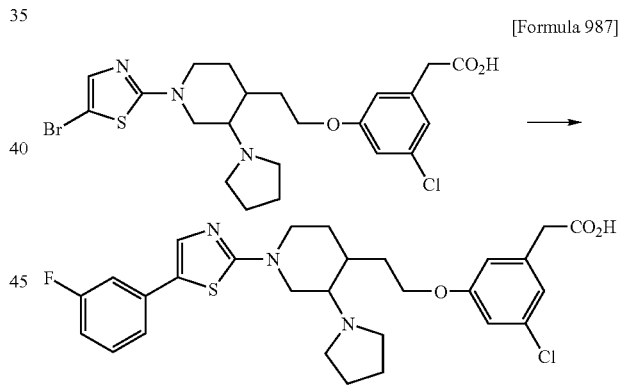

[Formula 987]

A mixture of [3-[2-[1-(5-bromothiazole-2-yl)-4-pyrrolidine-1-ylpiperidine-4-yl]ethoxy]-5-chlorophenyl]acetic acid (60 mg), 3-fluorophenyl boronic acid (32 mg), tetrakis (triphenylphosphine) palladium (13 mg), 1M sodium carbonate (0.55 mL) and dimethylformamide (1 mL) was reacted with a microwave reaction device at 180° C. for 5 minutes. The insoluble material was filtrated. To the filtrate was added formic acid. The solvent was evaporated under reduced pressure and the residue was purified by high performance liquid chromatography to give the title compound (14.4 mg). Yield: 24%.

1H-NMR (DMSO-d$_6$)) δ: 8.18 (1H, s), 7.69 (1H, s), 7.39-7.26 (3H, m), 7.01 (1H, m), 6.90 (1H, d, J=10.8 Hz), 6.82 (1H, s), 4.53 (2H, m), 3.58-3.54 (4H, m), 2.64 (2H, s), 1.94-1.69 (8H, m)

The following compounds were obtained by similar methods as above.

Example 670
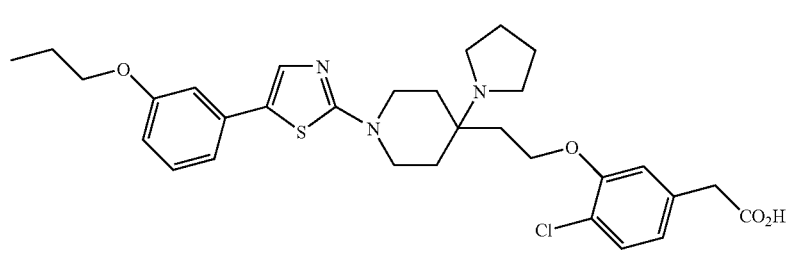
MS (ESI) m/z 584[M+]
Example 671
[Formula 989]
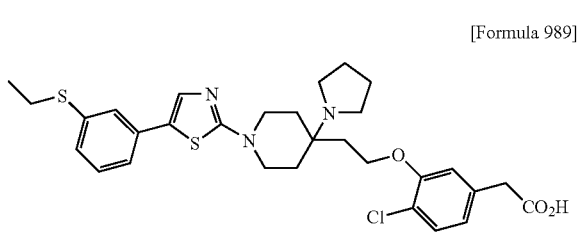
MS (ESI) m/z 586 [M+]
Example 672
[Formula 990]
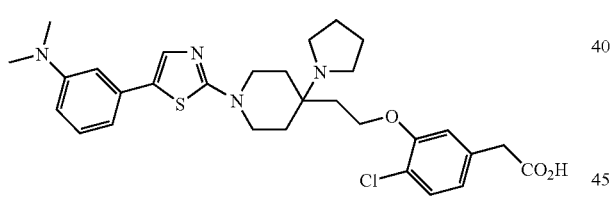
MS (ESI) m/z 569[M+]
Example 673
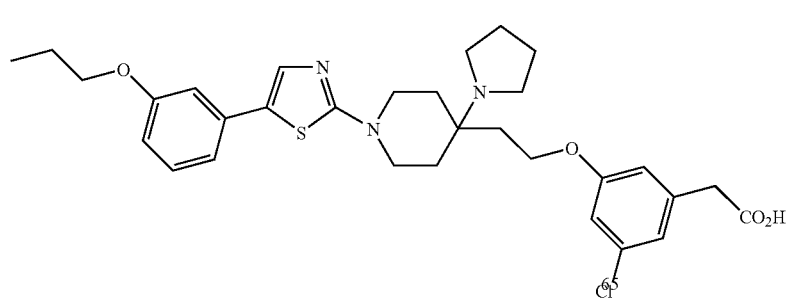
MS (ESI) m/z 584 [M+]
[Formula 988]
Example 674
[Formula 992]
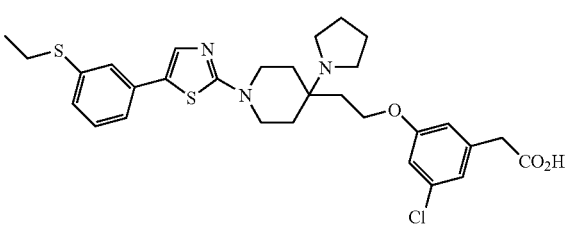
MS (ESI) m/z 586 [M+]
Example 675
[Formula 993]
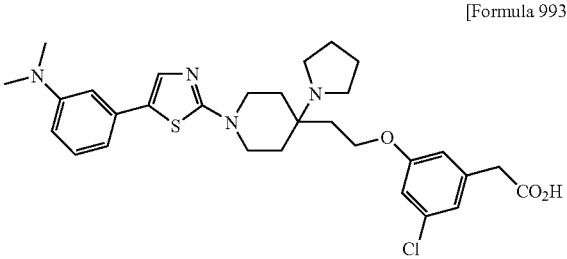
MS (ESI) m/z 569 [M+]
[Formula 991]

Example 676
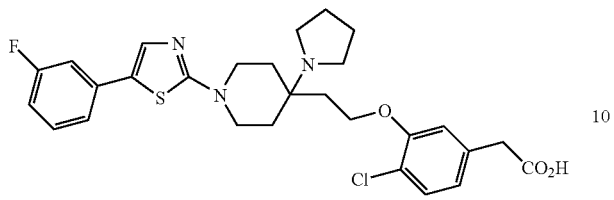
MS (ESI) m/z 546 [M+H]+
Example 677
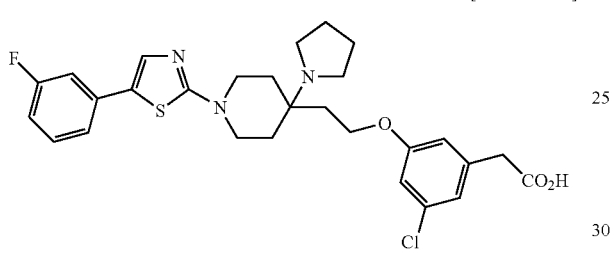
¹H-NMR (DMSO-d6)) d: 8.18 (1H, s), 7.69 (1H, s), 7.39-7.26 (3H, m), 7.01 (1H, m), 6.90 (1H, d, J=10.8 Hz), 6.82 (1H, s), 4.53 (2H, m), 3.58-3.54 (4H, m), 2.64 (2H, s), 1.94-1.69 (8H, m).
Example 678
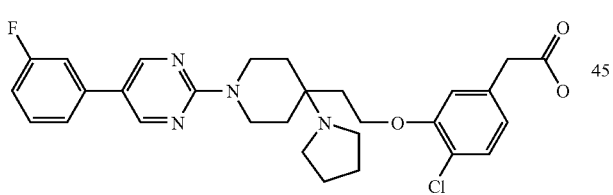
MS (ESI) m/z 540 [M+H]+
Reference Example 256
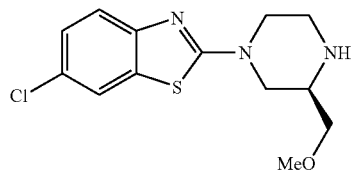
1H-NMR (CDCl3) δ 2.93-3.18 (4H, m), 3.29 (1H, td, J=12.0, 3.2 Hz), 3.35-3.42 (1H, m), 3.39 (3H, s), 3.48 (1H, dd, J=9.2, 3.6 Hz), 3.91 (1H, d, J=12.0 Hz), 3.99 (1H, d, J=12.0 Hz), 7.24 (1H, dd, J=8.8, 2.4 Hz), 7.44 (1H, d, J=8.8 Hz), 7.56 (1H, d, J=2.4 Hz).
Reference Example 257
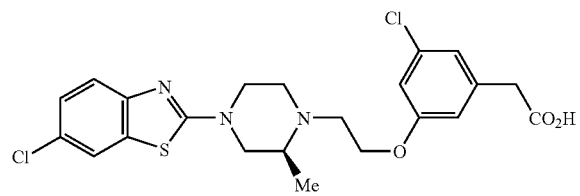
1H-NMR (CDCl3) δ 1.22 (3H, t, J=7.2 Hz), 2.92-3.02 (2H, m), 3.04-3.11 (1H, m), 3.12-3.17 (1H, m), 3.26 (1H, td, J=12.0, 3.2 Hz), 3.39 (1H, dd, J=9.2, 7.2 Hz), 3.48-3.59 (3H, m), 3.91 (1H, brd, J=12.0 Hz), 3.98 (1H, brd, J=12.0 Hz), 7.24 (1H, dd, J=8.8, 2.0 Hz), 7.44 (1H, d, J=8.8 Hz), 7.56 (1H, d, J=2.0 Hz).
Example 679
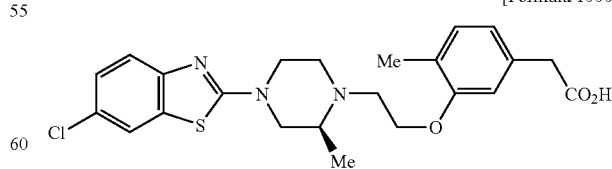
TLC Rf 0.13 (MeOH—CHCl3, 1:10)
Example 680
mp 109-112

Example 681
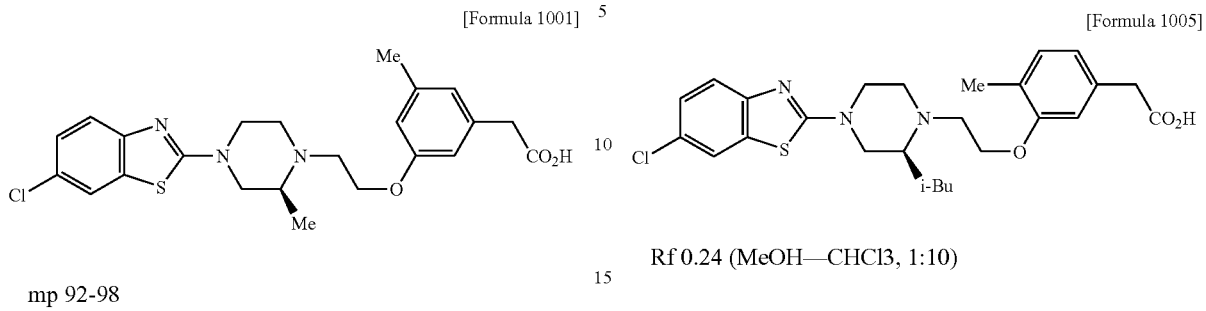
mp 92-98
Example 682
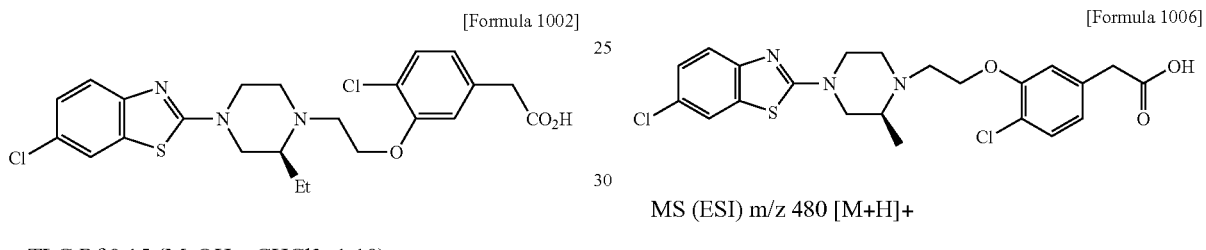
TLC Rf 0.15 (MeOH—CHCl3, 1:10)
Example 683
[Formula 1003]
TLC Rf 0.23 (MeOH—CHCl3, 1:10)
Example 684
[Formula 1004]
Rf 0.12 (MeOH—CHCl3, 1:10)
Example 685
Rf 0.24 (MeOH—CHCl3, 1:10)
Example 686
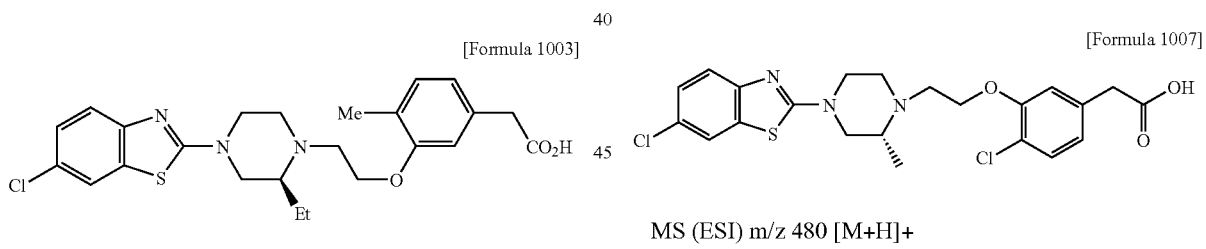
MS (ESI) m/z 480 [M+H]+
Example 687
[Formula 1007]
MS (ESI) m/z 480 [M+H]+
Example 688
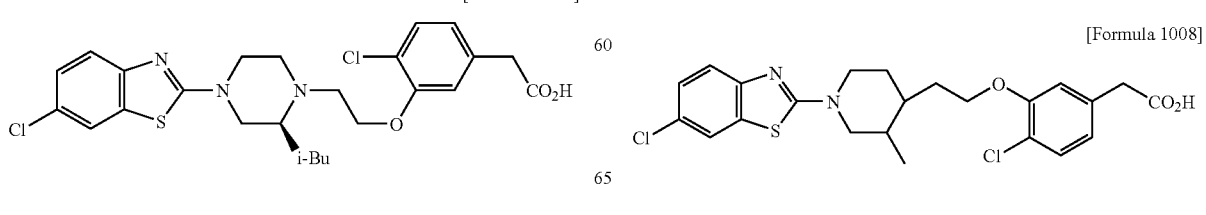
MS (ESI) m/z 479 [M+H]+

Example 689
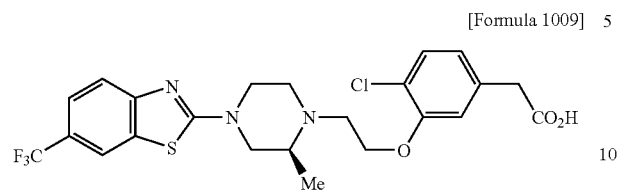
MS (ESI) m/z 514, 516 [M+H]+
Example 690
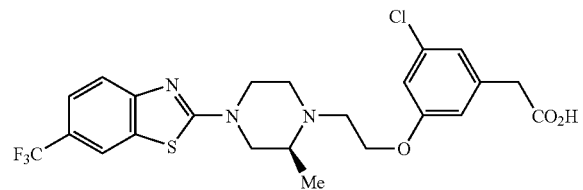
MS (ESI) m/z 514, 516 [M+H]+
Example 691
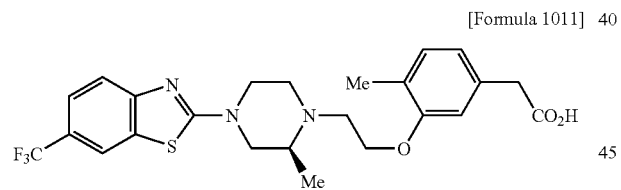
MS (ESI) m/z 494 [M+H]+
Example 692
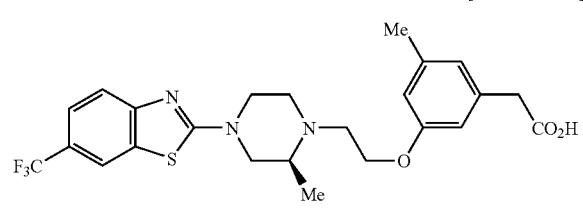
MS (ESI) m/z 494 [M+H]+
Example 693
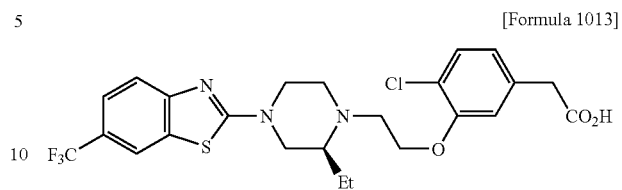
MS (ESI) m/z 528, 530 [M+H]+
Example 694
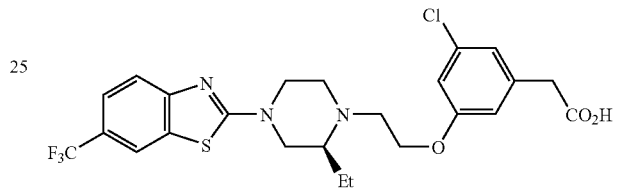
MS (ESI) m/z 528, 530 [M+H]+
Example 695
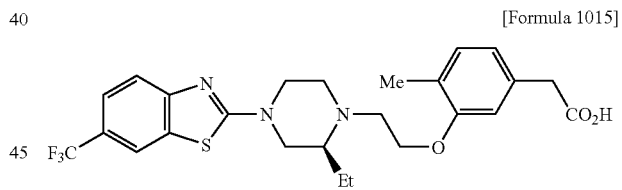
MS (ESI) m/z 508 [M+H]+
Example 696
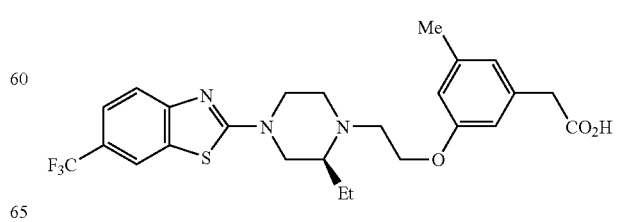
MS (ESI) m/z 508 [M+H]+

Example 697
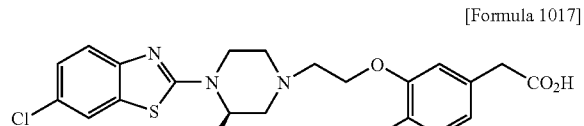
MS (ESI) m/z 480 [M+H]+
Example 698
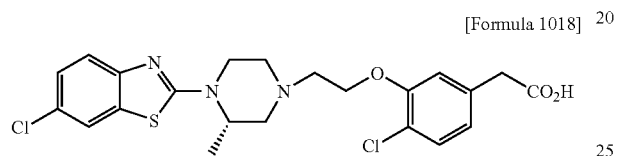
1H-NMR (300 MHz, CDCl3): 1.46 (3H, d, J=6.9 Hz), 2.53-2.60 (1H, m), 2.73-2.77 (1H, m), 3.06 (2H, s), 3.16-3.20 (1H, m), 3.27-3.31 (1H, m), 3.55-3.60 (1H, m), 3.60 (2H, s), 3.89-3.94 (1H, m), 4.29 (3H, m), 6.84 (1H, d, J=8.1 Hz), 6.87 (1H, s), 7.25 (1H, dd, J=8.7 Hz, 2.1 Hz), 7.31 (1H, d, J=8.1 Hz), 7.44 (1H, d, J=8.7 Hz), 7.56 (1H, d, J=2.1 Hz)
Example 699
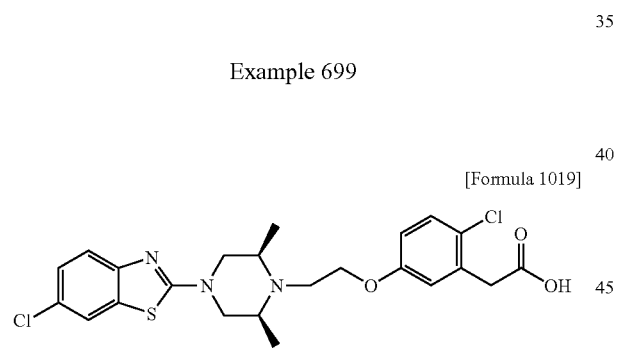
MS (ESI) m/z 494 [M+H]+
Example 700
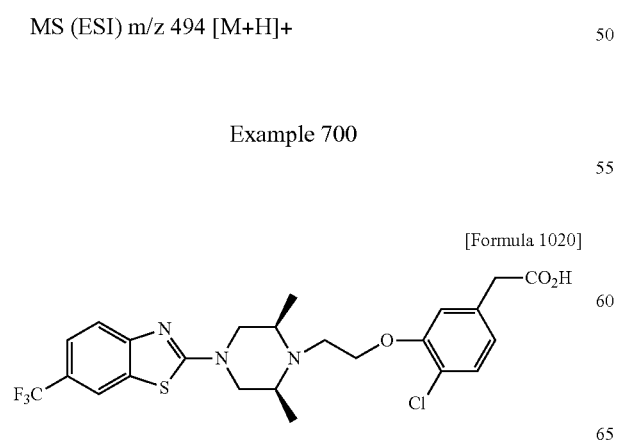
MS (ESI) m/z 528 [M+H]+
Example 701
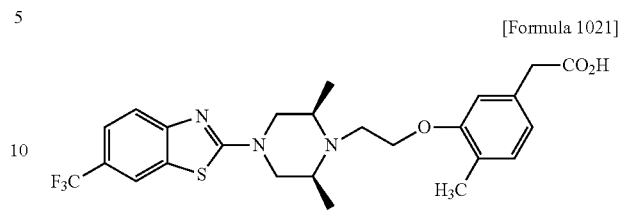
MS (ESI) m/z 508 [M+H]+
Example 702
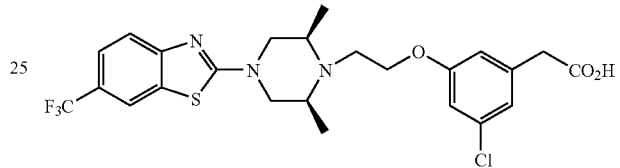
MS (ESI) m/z 528 [M+H]+
Example 703
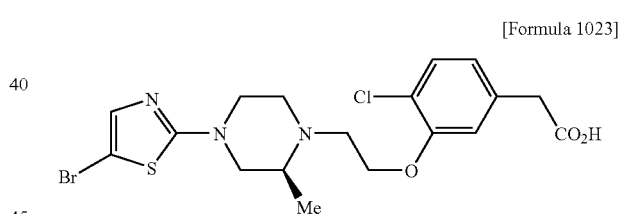
MS (ESI) m/z 474, 476, 478 [M+H]+
Example 704
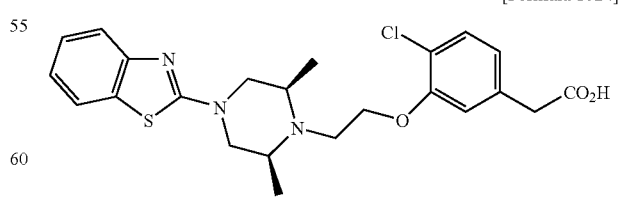
1H-NMR (DMSO-d6) δ: 1.18 (6H, d, J=4.7 Hz), 2.80-2.95 (4H, m), 3.10-3.19 (2H, m), 3.55 (2H, s), 3.85 (2H, d, J=9.9 Hz), 4.03-4.11 (2H, m), 6.83 (1H, d, J=8.2 Hz), 7.02-7.11 (2H, m), 7.22-7.48 (3H, m), 7.75 (1H, d, J=8.0 Hz).

Example 705

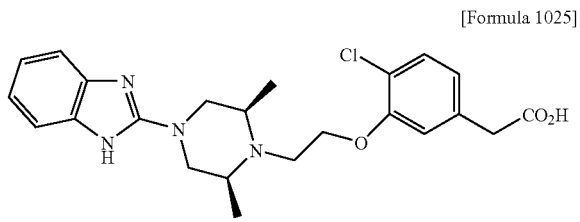

[Formula 1025]

1H-NMR (DMSO-d6) δ: 1.16 (6H, d, J=5.8 Hz), 2.61-2.85 (5H, m), 3.07-3.16 (3H, m), 3.55 (2H, s), 3.89-4.11 (5H, m), 6.79-7.36 (8H, m).

Example 706

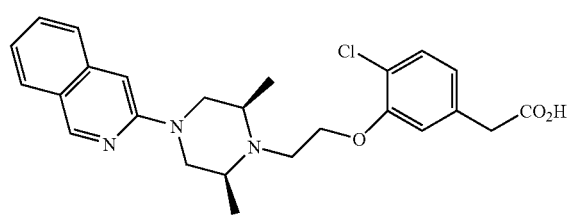

[Formula 1026]

1H-NMR (DMSO-d6) δ: 1.22 (6H, d, J=6.0 Hz), 2.58-2.84 (4H, m), 3.09-3.19 (2H, m), 3.52 (2H, s), 4.06-4.14 (2H, m), 4.34-4.46 (2H, m), 6.84 (1H, d, J=8.2 Hz), 7.09-7.74 (7H, m), 8.03 (1H, d, J=9.1 Hz).

Example 707

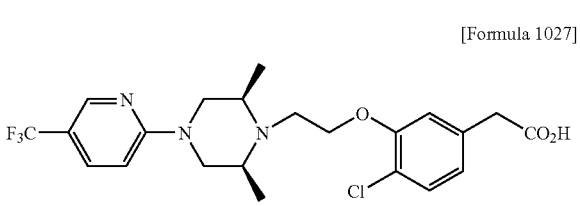

[Formula 1027]

1H-NMR (Acetone) δ: 8.38-8.35 (1.0H, m), 7.71 (1.0H, dd, J=9.34, 2.20 Hz), 7.31 (1.0H, dd, J=7.97, 1.65 Hz), 7.13 (1.0H, d, J=1.92 Hz), 6.97-6.87 (2.0H, m), 4.33 (2.0H, d, J=12.64 Hz), 4.17 (2.0H, dd, J=5.91, 5.91 Hz), 3.61 (2.0H, s), 3.25-3.23 (2.0H, m), 2.83-2.67 (4.0H, m), 1.24 (6.0H, d, J=6.00 Hz).

Example 708

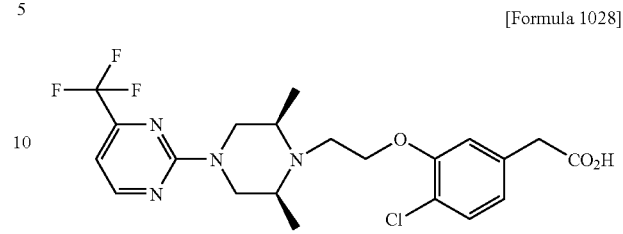

[Formula 1028]

1H-NMR (DMSO-d6) δ: 8.66 (1.0H, d, J=4.94 Hz), 7.31 (1.0H, d, J=8.10 Hz), 7.08 (1.0H, s), 6.99 (1.0H, d, J=4.94 Hz), 6.82 (1.0H, d, J=8.10 Hz), 4.45 (2.0H, d, J=8.24 Hz), 4.08-3.99 (3.0H, m), 3.53 (2.0H, s), 3.13 (2.0H, dd, J=5.63, 5.63 Hz), 2.76-2.65 (4.0H, m), 1.16 (6.0H, d, J=6.32 Hz).

Example 709

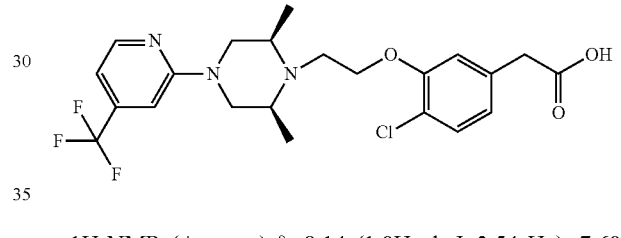

[Formula 1029]

1H-NMR (Acetone) δ: 8.14 (1.0H, d, J=2.54 Hz), 7.60 (1.0H, dd, J=9.13, 2.54 Hz), 7.40 (1.0H, s), 7.34 (1.0H, d, J=7.69 Hz), 7.25 (1.0H, dd, J=7.69, 7.69 Hz), 7.15 (1.0H, d, J=7.69 Hz), 6.81 (1.0H, d, J=9.13 Hz), 4.13 (2.0H, d, J=11.54 Hz), 3.81 (2.0H, s), 3.62 (2.0H, s), 2.76-2.62 (4.0H, m), 1.07 (6.0H, d, J=5.77 Hz).

Example 710

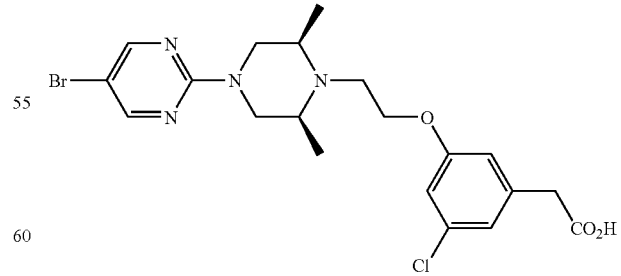

[Formula 1030]

1H-NMR (DMSO-d6) δ: 1.14 (6H, d, J=5.1 Hz), 2.60-2.76 (2H, m), 3.00-3.10 (2H, m), 3.55 (2H, s), 3.97-4.06 (2H, m), 4.46-4.60 (2H, m), 6.80-6.96 (3H, m), 7.30-7.67 (3H, m), 8.69 (2H, s).

Example 711

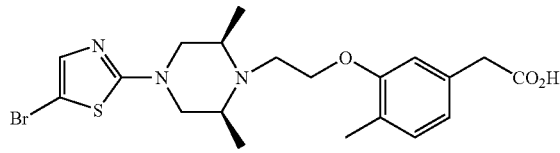
[Formula 1031]

1H-NMR (DMSO-d6) δ: 7.18-7.18 (1.0H, m), 7.04 (1.0H, d, J=7.28 Hz), 6.84 (1.0H, s), 6.71 (1.0H, d, J=7.28 Hz), 3.98 (2.0H, dd, J=5.10, 5.10 Hz), 3.64 (2.0H, d, J=10.99 Hz), 3.48 (2.0H, s), 3.10 (2.0H, dd, J=5.10, 5.10 Hz), 2.84-2.69 (4.0H, m), 2.11 (3.0H, s), 1.14 (6.0H, d, J=5.77 Hz).

Example 712

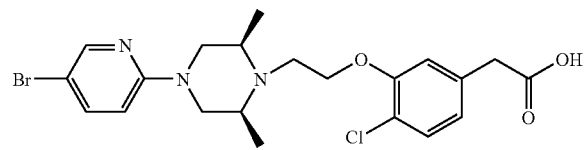
[Formula 1032]

1H-NMR (Acetone) δ: 8.12 (1.0H, d, J=2.68 Hz), 7.59 (1.0H, dd, J=9.13, 2.68 Hz), 7.32 (1.0H, d, J=8.11 Hz), 7.13 (1.0H, d, J=1.92 Hz), 6.90 (1.0H, dd, J=8.11, 1.92 Hz), 6.80 (1.0H, d, J=9.13 Hz), 4.18-4.13 (4.0H, m), 3.63 (2.0H, s), 3.22 (2.0H, dd, J=6.04, 6.04 Hz), 2.85-2.78 (2.0H, m), 2.62-2.53 (2.0H, m), 1.23 (6.0H, d, J=6.04 Hz).

Example 713

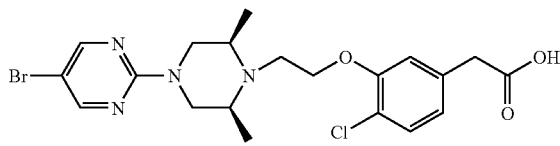
[Formula 1033]

1H-NMR (Acetone) δ: 8.34 (2.0H, s), 7.30 (1.0H, d, J=8.04 Hz), 7.13 (1.0H, d, J=1.65 Hz), 6.90 (1.0H, dd, J=8.04, 1.65 Hz), 4.49 (2.0H, d, J=12.36 Hz), 4.15 (2.0H, dd, J=5.91, 5.91 Hz), 3.60 (2.0H, s), 3.23 (2.0H, dd, J=6.04, 6.04 Hz), 2.82-2.60 (4.0H, m), 1.22 (6.0H, d, J=6.04 Hz).

Example 714

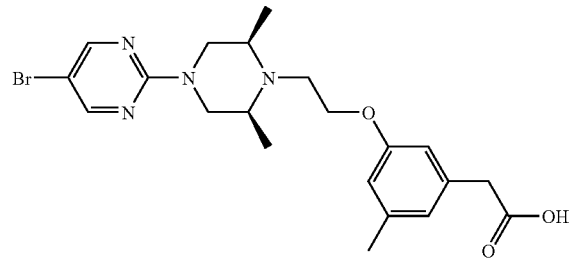
[Formula 1034]

1H-NMR (DMSO-d6) δ: 8.44 (2.0H, s), 6.61 (3.0H, s), 4.43-4.33 (2.0H, m), 3.95 (2.0H, dd, J=6.59, 6.59 Hz), 3.43 (2.0H, s), 3.03 (2.0H, dd, J=6.00, 6.00 Hz), 2.63 (4.0H, d, J=6.90 Hz), 2.23 (3.0H, s), 1.12 (6.0H, d, J=5.22 Hz).

Example 715

[Formula 1035]

1H-NMR (DMSO-d6) δ: 1.23-1.41 (2H, m), 1.70-1.92 (5H, m), 3.09-3.23 (2H, m), 3.57 (2H, s), 3.98-4.15 (4H, m), 6.81-7.46 (6H, m), 7.74 (1H, d, J=8.0 Hz).

Example 716

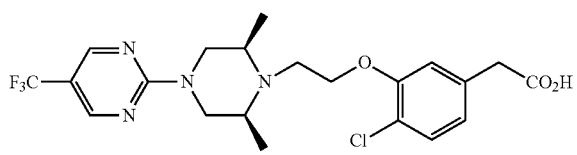
[Formula 1036]

1H-NMR (Acetone) δ: 8.37 (1.0H, s), 7.71 (1.0H, dd, J=9.06, 2.47 Hz), 7.33 (1.0H, d, J=7.97 Hz), 7.12 (1.0H, d, J=1.65 Hz), 6.93-6.89 (2.0H, m), 4.55-4.50 (2.0H, m), 4.19 (2.0H, dd, J=6.32, 6.32 Hz), 3.62 (2.0H, s), 2.96-2.92 (3.0H, m), 1.96-1.79 (4.0H, m), 1.37-1.24 (2.0H, m).

Example 717

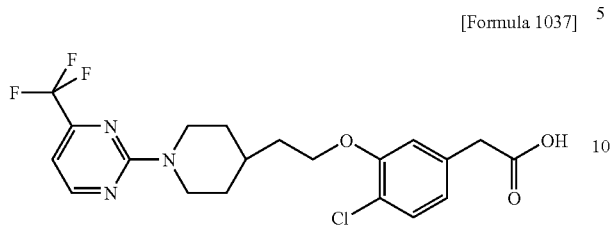

[Formula 1037]

1H-NMR (DMSO-d6) δ: 8.65 (1.0H, d, J=4.67 Hz), 7.33 (1.0H, d, J=8.11 Hz), 7.08 (1.0H, s), 6.95 (1.0H, d, J=4.67 Hz), 6.83 (1.0H, d, J=8.11 Hz), 4.64 (2.0H, d, J=12.42 Hz), 4.10 (2.0H, dd, J=6.59, 6.59 Hz), 3.55 (2.0H, s), 3.40-3.25 (1.0H, m), 2.96 (2.0H, dd, J=12.42, 12.42 Hz), 1.91-1.72 (4.0H, m), 1.24-1.15 (2.0H, m).

Example 718

[Formula 1038]

1H-NMR (DMSO-d6) δ: 1.13-1.36 (2H, m), 1.67-1.87 (5H, m), 2.86-3.00 (2H, m), 3.56 (2H, s), 4.05-4.16 (5H, m), 6.80-7.36 (7H, m).

Example 719

[Formula 1039]

1H-NMR (300 MHz, CDCl3): 1.40 (6H, m), 3.27-3.44 (6H, m), 3.93-3.98 (2H, m), 4.14 (2H, m), 4.53 (2H, s), 6.47-6.55 (3H, m), 7.13-7.26 (2H, m), 7.43 (1H, d, J=8.1 Hz), 7.55 (1H, s).

Example 720

[Formula 1040]

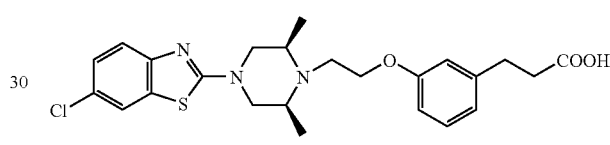

1H-NMR (300 MHz, CDCl3): 1.98-2.17 (5H, m), 3.21-3.29 (2H, m), 3.84 (2H, d, J=6.0 Hz), 4.23 (2H, m), 4.65 (2H, s), 6.49-6.56 (3H, m), 7.20 (1H, t, J=8.1 Hz), 7.26-7.29 (2H, m), 7.55 (1H, d, J=2.1 Hz)

Example 721

[Formula 1041]

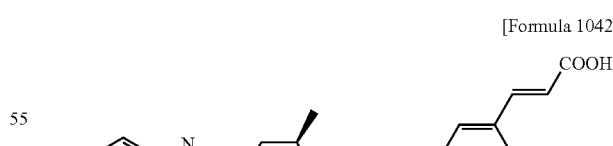

1H-NMR (300 MHz, CDCl3): 1.28 (6H, m), 2.64 (2H, t, J=7.5 Hz), 2.91 (2H, t, J=7.5 Hz), 2.99 (4H, m), 3.24 (2H, m), 3.87-3.91 (2H, m), 4.05 (2H, m), 6.70-6.73 (2H, m), 6.80 (1H, d, J=7.5 Hz), 7.19 (1H, t, J=7.5 Hz), 7.22-7.25 (1H, m), 7.43 (1H, d, J=8.4 Hz), 7.54 (1H, d, J=2.1 Hz).

Example 722

[Formula 1042]

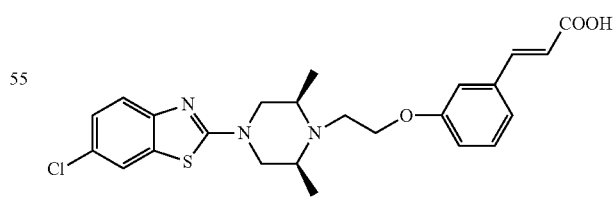

1H-NMR (300 MHz, CDCl3): 1.27 (6H, m), 2.99 (4H, m), 3.23 (2H, m), 3.89-3.93 (2H, m), 4.09 (2H, m), 6.43 (1H, d, J=15.9 Hz), 6.92 (1H, dd, J=8.1 Hz, 2.1 Hz), 7.04 (1H, s), 7.14 (1H, d, J=8.1 Hz), 7.24 (1H, dd, J=8.7 Hz, 2.1 Hz), 7.31 (1H, t, J=8.1 Hz), 7.44 (1H, d, J=8.7 Hz), 7.56 (1H, d, J=2.1 Hz), 7.71 (1H, d, J=15.9 Hz).

Example 723
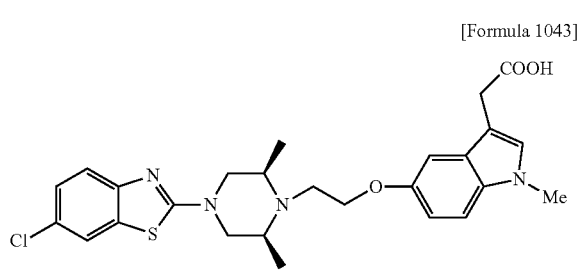
[Formula 1043]
1H-NMR (300 MHz, CDCl3): 1.35 (6H, m), 2.53 (4H, m), 3.15 (2H, m), 3.71 (3H, s), 3.90-3.94 (2H, m), 4.14 (2H, m), 6.81 (1H, dd, J=8.7 Hz, 2.1 Hz), 7.01-7.02 (2H, m), 7.14 (1H, d, J=8.7 Hz), 7.24 (1H, dd, J=8.7 Hz), 7.44 (1H, d, J=8.7 Hz), 7.54 (1H, d, J=2.1 Hz).
Example 724
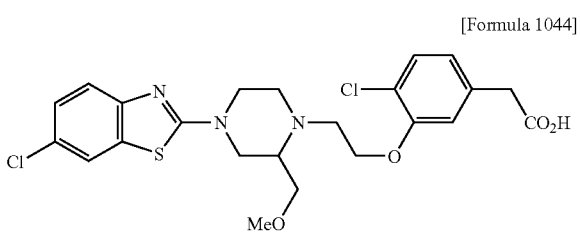
[Formula 1044]
TLC Rf 0.13 (MeOH—CHCl3, 1:10)
Example 725
[Formula 1045]
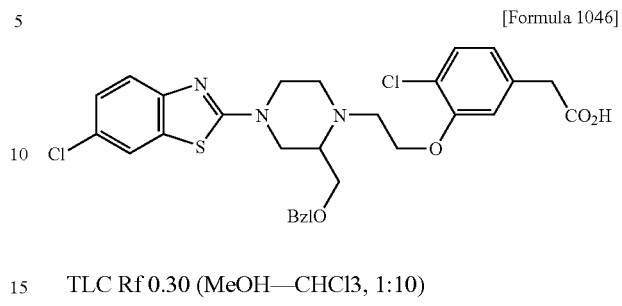
TLC Rf 0.20 (MeOH—CHCl3, 1:10)
Example 726
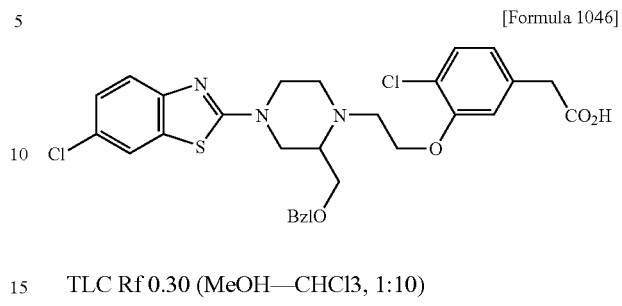
[Formula 1046]
TLC Rf 0.30 (MeOH—CHCl3, 1:10)
Example 727
[Formula 1047]
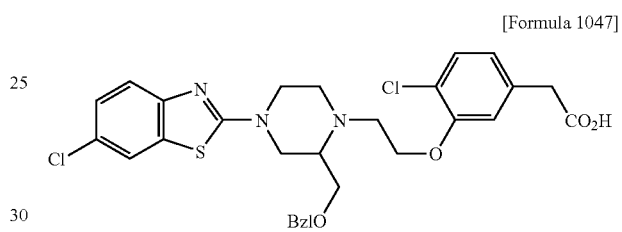
TLC Rf 0.31 (MeOH—CHCl3, 1:10)
Example 728
[Formula 1048]
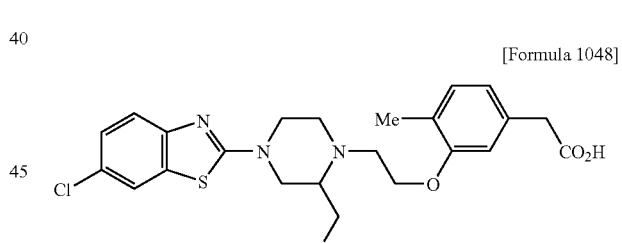
TLC Rf 0.23 (MeOH—CHCl3, 1:5)
Example 729
[Formula 1049]
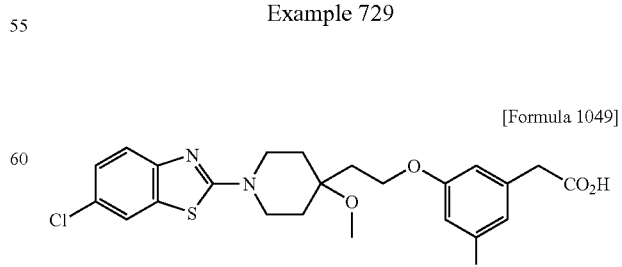
MS (ESI) m/z 495 [M+H]+

Example 730
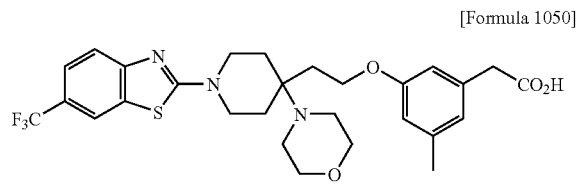
MS (ESI) m/z 564 [M+H]+
Example 731
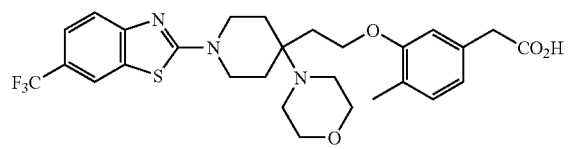
MS (ESI) m/z 564 [M+H]+
Example 732
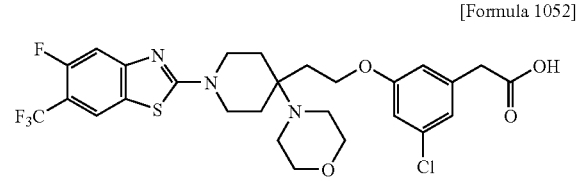
MS (ESI) m/z 602 [M+H]+
Example 733
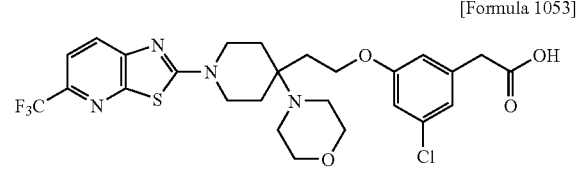
MS (ESI) m/z 585 [M+H]+
Example 734
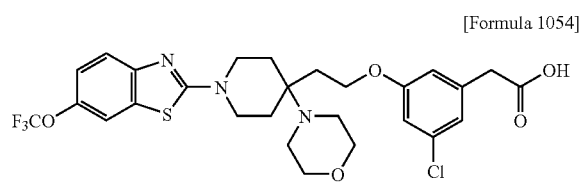
MS (ESI) m/z 600 [M+H]+
Example 735
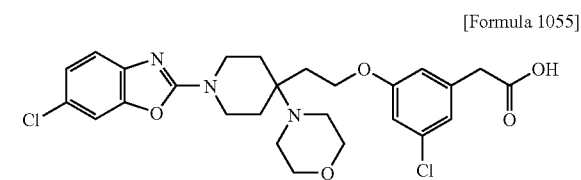
MS (ESI) m/z 534 [M+H]+
Example 736
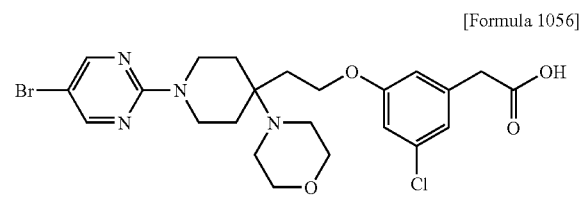
MS (ESI) m/z 539 [M+H]+
Example 737
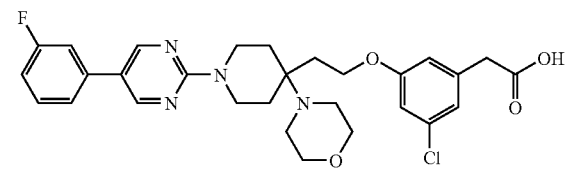
MS (ESI) m/z 555 [M+H]+

Example 738
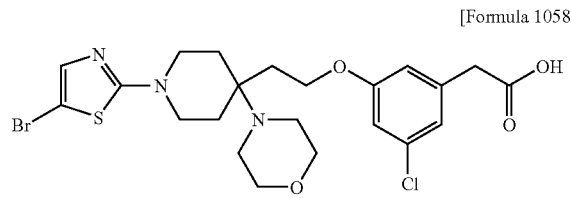
[Formula 1058]
MS (ESI) m/z 544 [M+H]+
Example 739
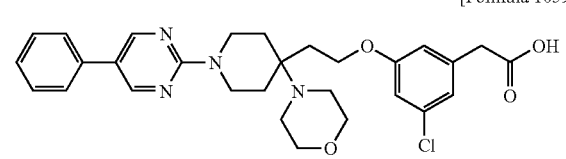
[Formula 1059]
MS (ESI) m/z 537 [M+H]+
Example 740
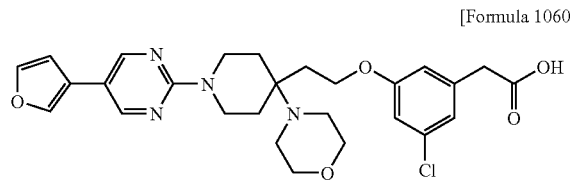
[Formula 1060]
MS (ESI) m/z 527 [M+H]+
Example 741
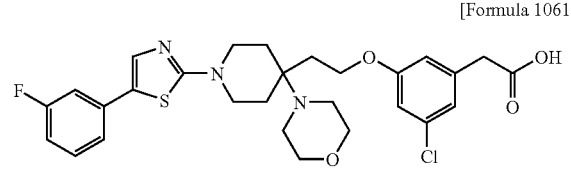
[Formula 1061]
MS (ESI) m/z 560 [M+H]+
Example 742
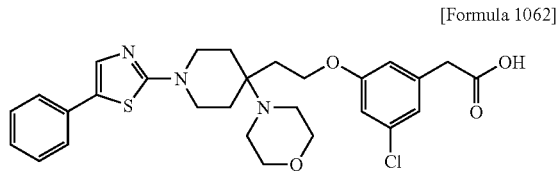
[Formula 1062]
MS (ESI) m/z 542 [M+H]+
Example 743
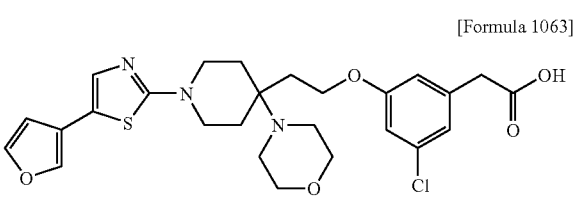
[Formula 1063]
MS (ESI) m/z 532 [M+H]+
Example 744
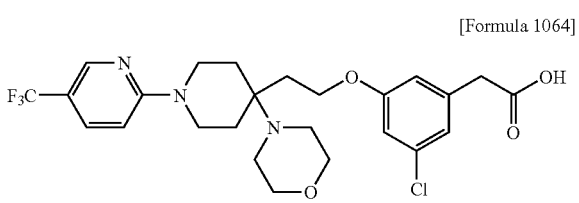
[Formula 1064]
MS (ESI) m/z 528 [M+H]+
Example 745
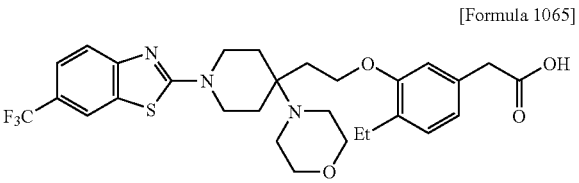
[Formula 1065]
MS (ESI) m/z 578 [M+H]+

Example 746
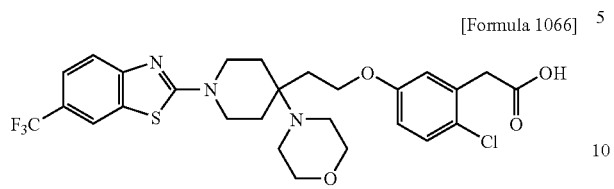
[Formula 1066]
MS (ESI) m/z 584 [M+H]+
Example 747
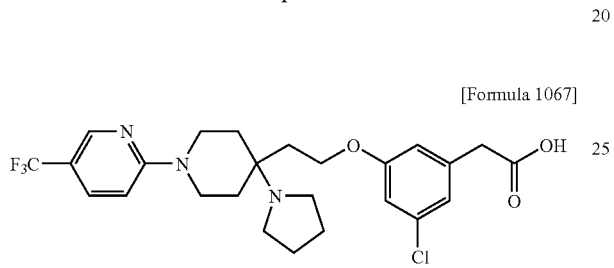
[Formula 1067]
MS (ESI) m/z 512 [M+H]+
Example 748
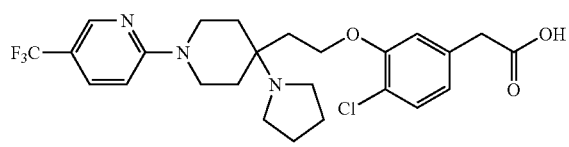
[Formula 1068]
MS (ESI) m/z 512 [M+H]+
Example 749
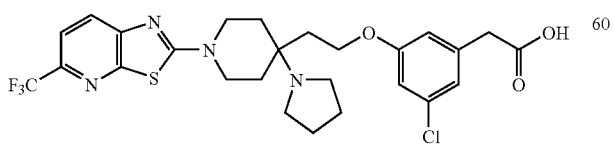
[Formula 1069]
MS (ESI) m/z 569 [M+H]+
Example 750
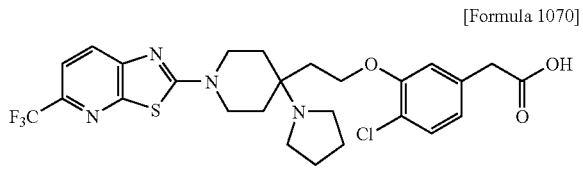
[Formula 1070]
MS (ESI) m/z 569 [M+H]+
Example 751
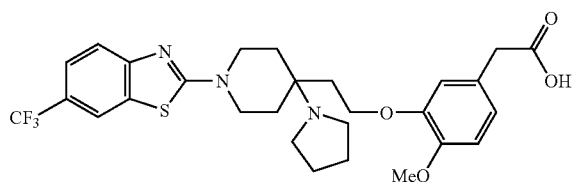
[Formula 1071]
TLC: (SiO2) CHCl3-MeOH (10:1) Rf=0.1
Example 752
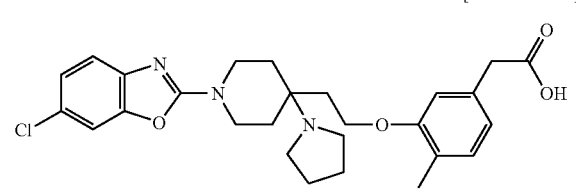
[Formula 1072]
1H-NMR (DMSO-d6) δ: 7.56 (1.0H, d, J=1.92 Hz), 7.26 (1.0H, d, J=8.51 Hz), 7.19 (1.0H, dd, J=8.51, 4.25 Hz), 7.04 (1.0H, d, J=7.41 Hz), 6.86 (1.0H, s), 6.71 (1.0H, d, J=7.41 Hz), 4.06-4.03 (2.0H, m), 3.84-3.80 (2.0H, m), 3.65-3.48 (2.0H, m), 2.68 (4.0H, br s), 2.10 (2.0H, s), 2.03-1.67 (6.0H, m), 1.06 (3.0H, d, J=6.04 Hz).
Example 753
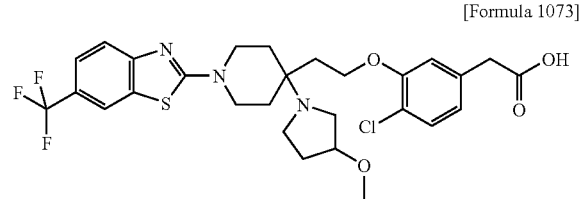
[Formula 1073]
1H-NMR (CDCl3) δ: 7.84-7.82 (1.0H, m), 7.64-7.49 (2.0H, m), 6.93-6.76 (3.0H, m), 4.22-4.11 (1.0H, m), 3.99-3.37 (9.0H, m), 3.31 (3.0H, s), 3.09-2.95 (1.0H, m), 2.89-2.64 (3.0H, m), 2.31-1.12 (8.0H, m).

Example 754

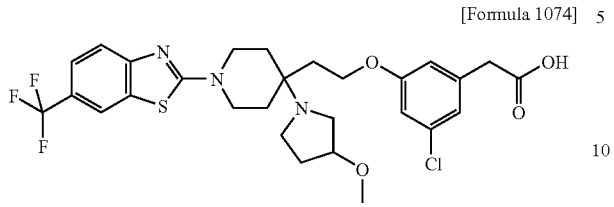

[Formula 1074]

1H-NMR (CDCl3) δ: 7.86-7.82 (1.0H, m), 7.59-7.48 (2.0H, m), 6.89-6.85 (1.0H, m), 6.80-6.77 (1.0H, m), 6.73-6.69 (1.0H, m), 4.05 (2.0H, dd, J=6.59, 6.59 Hz), 3.95-3.87 (1.0H, m), 3.79-3.60 (4.0H, m), 3.56 (2.0H, s), 3.31 (3.0H, s), 3.01 (1.0H, dd, J=7.68, 5.49 Hz), 2.83-2.69 (3.0H, m), 2.07-1.68 (8.0H, m).

Example 755

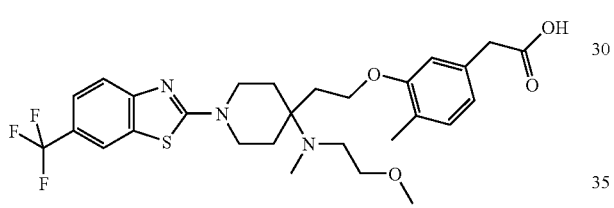

[Formula 1075]

1H-NMR (CDCl3) δ: 7.83 (1.0H, s), 7.58-7.48 (2.0H, m), 7.07 (1.0H, d, J=7.41 Hz), 6.79-6.70 (2.0H, m), 4.04 (2.0H, dd, J=6.59, 6.59 Hz), 3.83-3.56 (6.0H, m), 3.47 (2.0H, dd, J=6.59, 6.59 Hz), 3.36 (3.0H, s), 2.70 (2.0H, dd, J=6.59, 6.59 Hz), 2.33 (3.0H, s), 2.17 (3.0H, s), 2.06-1.95 (4.0H, m), 1.84-1.70 (2.0H, m).

Example 756

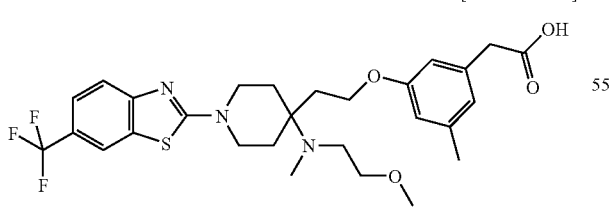

[Formula 1076]

1H-NMR (CDCl3) δ: 7.83 (1.0H, br s), 7.57-7.48 (2.0H, m), 6.68 (1.0H, s), 6.62-6.58 (2.0H, m), 4.00 (2.0H, dd, J=6.59, 6.59 Hz), 3.82-3.61 (4.0H, m), 3.55 (2.0H, s), 3.47 (2.0H, dd, J=6.31, 6.31 Hz), 3.35 (3.0H, s), 2.68 (2.0H, dd, J=6.31, 6.31 Hz), 2.31 (3.0H, s), 2.29 (3.0H, s), 2.04-1.91 (4.0H, m), 1.80-1.66 (2.0H, m).

Example 757

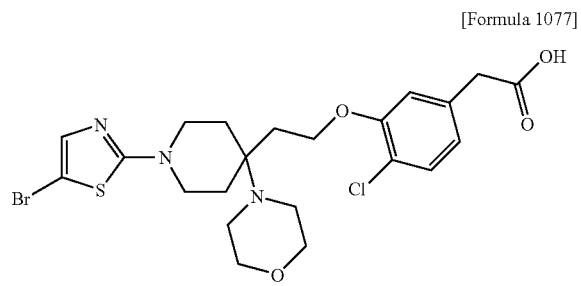

[Formula 1077]

1H-NMR (CDCl3) δ: 7.31 (1.0H, d, J=8.23 Hz), 7.08 (1.0H, s), 6.93-6.87 (1.0H, m), 6.83 (1.0H, dd, J=8.23, 1.65 Hz), 4.30-4.07 (2.0H, m), 3.89-3.66 (4.0H, m), 3.65-3.55 (4.0H, m), 3.53-3.34 (4.0H, m), 2.87-2.52 (4.0H, m), 2.32-1.62 (6.0H, m).

Example 758

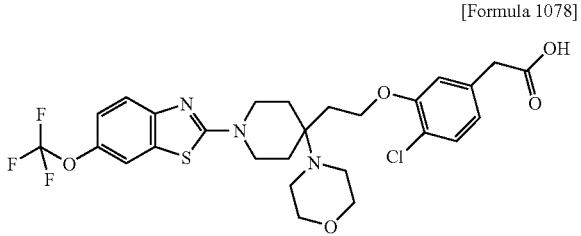

[Formula 1078]

1H-NMR (CDCl3) δ: 7.55-7.44 (2.0H, m), 7.31 (1.0H, d, J=8.23 Hz), 7.19-7.13 (1.0H, m), 6.93-6.80 (2.0H, m), 4.32-4.08 (2.0H, m), 3.91-3.57 (10.0H, m), 2.91-2.51 (4.0H, m), 2.33-1.61 (6.0H, m).

Example 759

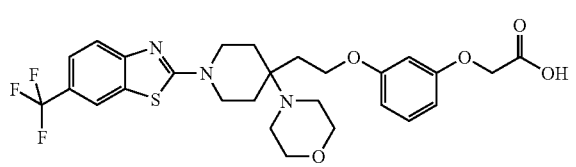

[Formula 1079]

1H-NMR (DMSO-d6) δ: 8.22 (1.0H, s), 7.59-7.52 (2.0H, m), 7.13 (1.0H, dd, J=8.51, 8.51 Hz), 6.54-6.49 (1.0H, m), 6.46-6.41 (3.0H, m), 4.57-4.47 (2.0H, m), 4.00 (2.0H, dd, J=7.14, 7.14 Hz), 3.82-3.67 (2.0H, m), 3.63-3.44 (6.0H, m), 2.60-2.53 (4.0H, m), 2.01 (2.0H, d, J=12.90 Hz), 1.90 (2.0H, dd, J=7.14, 7.14 Hz), 1.77-1.63 (2.0H, m).

Example 760

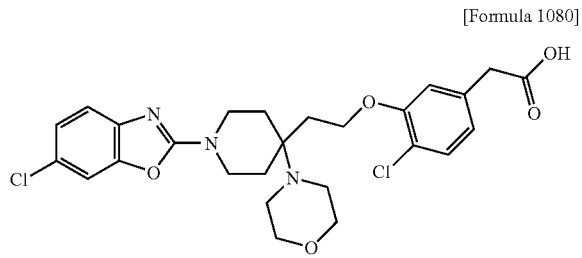

[Formula 1080]

1H-NMR (DMSO-d6) δ: 7.55 (1.0H, d, J=2.20 Hz), 7.30 (1.0H, d, J=8.23 Hz), 7.24 (1.0H, d, J=8.23 Hz), 7.20-7.14 (1.0H, m), 7.07 (1.0H, s), 6.82 (1.0H, d, J=9.61 Hz), 4.12-4.00 (2.0H, m), 3.83-3.71 (2.0H, m), 3.63-3.51 (8.0H, m), 2.58-2.53 (4.0H, m), 2.03-1.89 (4.0H, m), 1.77-1.65 (2.0H, m).

Example 761

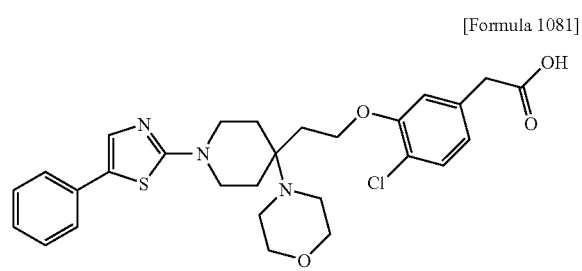

[Formula 1081]

1H-NMR (DMSO-d6) δ: 12.36 (1.0H, br s), 7.59 (1.0H, s), 7.46 (2.0H, d, J=7.41 Hz), 7.38-7.31 (3.0H, m), 7.20 (1.0H, dd, J=7.41, 7.41 Hz), 7.10 (1.0H, d, J=1.65 Hz), 6.83 (1.0H, dd, J=7.41, 1.65 Hz), 4.11 (2.0H, dd, J=6.59, 6.59 Hz), 3.63-3.53 (8.0H, m), 3.47-3.39 (2.0H, m), 2.60-2.53 (4.0H, m), 2.05-1.90 (4.0H, m), 1.80-1.66 (2.0H, m).

Example 762

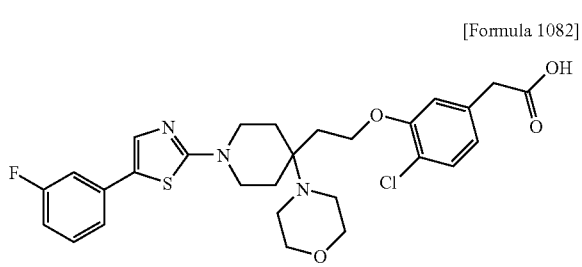

[Formula 1082]

1H-NMR (DMSO-d6) δ: 7.70 (1.0H, s), 7.42-7.30 (3.0H, m), 7.25 (1.0H, d, J=8.23 Hz), 7.10 (1.0H, d, J=1.92 Hz), 7.06-6.97 (1.0H, m), 6.83 (1.0H, dd, J=8.23, 1.92 Hz), 4.11 (2.0H, dd, J=6.59, 6.59 Hz), 3.63-3.54 (8.0H, m), 3.47-3.40 (2.0H, m), 2.60-2.53 (4.0H, m), 2.06-1.90 (4.0H, m), 1.80-1.66 (2.0H, m).

Example 763

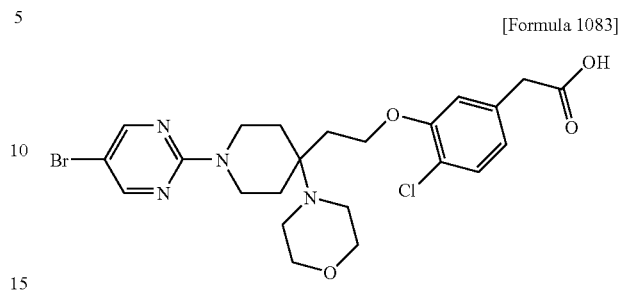

[Formula 1083]

1H-NMR (CDCl3) δ: 8.29 (2.0H, s), 7.31 (1.0H, d, J=8.23 Hz), 6.91 (1.0H, s), 6.85-6.82 (1.0H, m), 4.31-4.16 (2.0H, m), 4.00-3.70 (6.0H, m), 3.69-3.60 (4.0H, m), 2.98-2.69 (4.0H, m), 2.29-1.60 (6.0H, m).

Example 764

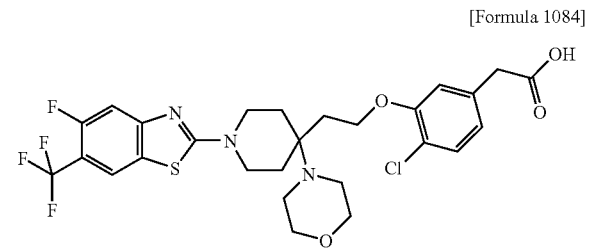

[Formula 1084]

1H-NMR (DMSO-d6) δ: 8.23 (1.0H, d, J=7.41 Hz), 7.44 (1.0H, d, J=12.35 Hz), 7.31 (1.0H, d, J=8.23 Hz), 7.08 (1.0H, d, J=2.20 Hz), 6.82 (1.0H, dd, J=8.23, 2.20 Hz), 4.10 (2.0H, dd, J=7.14, 7.14 Hz), 3.65-3.50 (6.0H, m), 3.49-3.12 (4.0H, m), 2.60-2.53 (4.0H, m), 2.10-1.89 (4.0H, m), 1.82-1.68 (2.0H, m).

Example 765

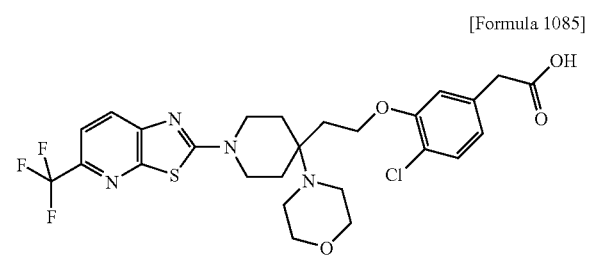

[Formula 1085]

1H-NMR (DMSO-d6) δ: 7.86 (1.0H, d, J=8.51 Hz), 7.76 (1.0H, d, J=8.51 Hz), 7.31 (1.0H, d, J=7.96 Hz), 7.08 (1.0H, d, J=1.92 Hz), 6.83 (1.0H, dd, J=7.96, 1.92 Hz), 4.10 (2.0H, dd, J=6.86, 6.86 Hz), 3.67-3.52 (6.0H, m), 3.44-3.22 (4.0H, m), 2.62-2.54 (4.0H, m), 2.10-1.92 (4.0H, m), 1.83-1.68 (2.0H, m).

Example 766

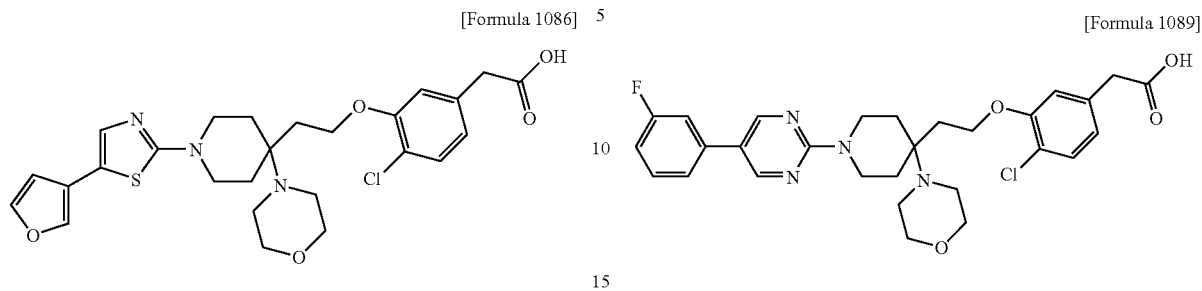
[Formula 1086]

1H-NMR (DMSO-d6) δ: 7.83 (1.0H, s), 7.71-7.67 (1.0H, m), 7.33-7.31 (2.0H, m), 7.09 (1.0H, s), 6.83 (1.0H, d, J=7.96 Hz), 6.78 (1.0H, s), 4.10 (2.0H, dd, J=6.86, 6.86 Hz), 3.63-3.46 (6.0H, m), 3.45-3.24 (4.0H, m), 2.61-2.52 (4.0H, m), 2.03-1.89 (4.0H, m), 1.78-1.65 (2.0H, m), 1.04 (2.7H, d, J=6.04 Hz).

Example 767

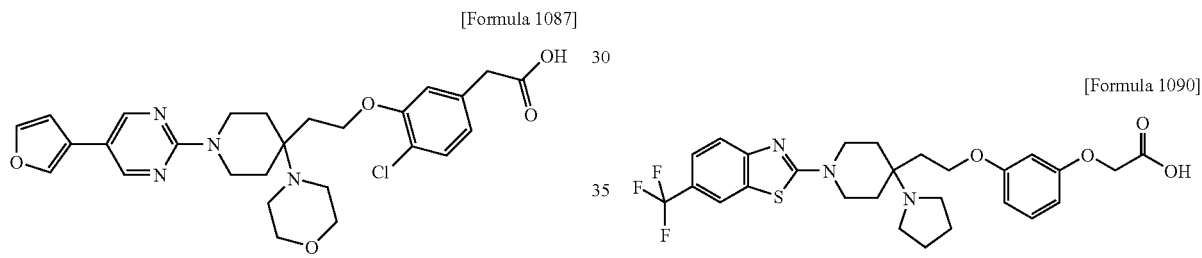
[Formula 1087]

1H-NMR (DMSO-d6) δ: 12.37 (1.0H, br s), 8.61 (2.0H, s), 8.10 (1.0H, s), 7.75-7.72 (1.0H, m), 7.32 (1.0H, d, J=8.23 Hz), 7.08 (1.0H, s), 6.93 (1.0H, s), 6.82 (1.0H, d, J=8.23 Hz), 4.16-3.96 (4.0H, m), 3.64-3.47 (8.0H, m), 2.62-2.53 (4.0H, m), 2.00-1.86 (4.0H, m), 1.67-1.52 (2.0H, m).

Example 768

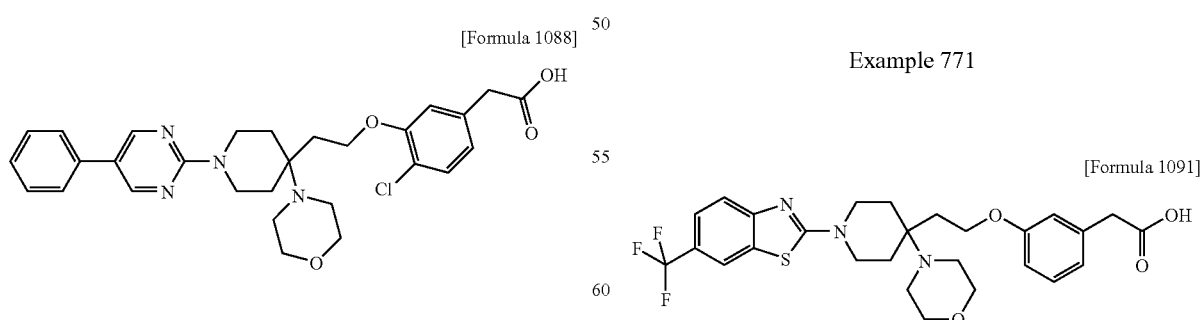
[Formula 1088]

1H-NMR (DMSO-d6) δ: 12.40 (1.0H, br s), 8.69 (2.0H, s), 7.63 (2.0H, d, J=7.72 Hz), 7.43 (2.0H, dd, J=7.72, 7.72 Hz), 7.34-7.31 (2.0H, m), 7.08 (1.0H, d, J=1.85 Hz), 6.82 (1.0H, dd, J=8.23, 1.85 Hz), 4.20-4.06 (4.0H, m), 3.63-3.52 (8.0H, m), 2.62-2.54 (4.0H, m), 2.02-1.87 (4.0H, m), 1.68-1.54 (2.0H, m).

Example 769

[Formula 1089]

1H-NMR (DMSO-d6) δ: 8.73 (2.0H, s), 7.57-7.42 (3.0H, m), 7.31 (1.0H, d, J=8.23 Hz), 7.19-7.07 (2.0H, m), 6.82 (1.0H, d, J=8.23 Hz), 4.20-4.06 (4.0H, m), 3.63-3.51 (8.0H, m), 2.63-2.55 (4.0H, m), 2.01-1.87 (4.0H, m), 1.67-1.54 (2.0H, m).

Example 770

[Formula 1090]

1H-NMR (DMSO-d6) δ: 8.21 (1.0H, s), 7.58-7.51 (2.0H, m), 7.12 (1.0H, dd, J=8.56, 8.56 Hz), 6.54-6.40 (2.0H, m), 4.56-4.41 (1.0H, m), 4.08-3.97 (3.0H, m), 3.84-3.69 (2.0H, m), 3.59-3.46 (2.0H, m), 2.71-2.60 (4.0H, m), 2.00-1.81 (4.0H, m), 1.79-1.65 (6.0H, m).

Example 771

[Formula 1091]

1H-NMR (CDCl3) δ: 7.85 (1.0H, s), 7.62-7.49 (2.0H, m), 7.31-7.20 (1.0H, m), 6.94-6.76 (3.0H, m), 4.14-3.95 (2.0H, m), 3.84-3.58 (8.0H, m), 2.72-2.55 (4.0H, m), 2.12-1.90 (4.0H, m), 1.88-1.69 (2.0H, m).

Reference Example 258

Preparation of piperidine-4-carbonitrile trifluoroacetate

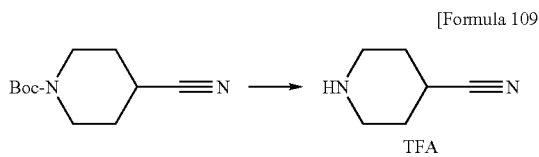

[Formula 1092]

4-Cyanopiperidine-1-carboxylic acid t-butyl ester (5.35 g) was added to trifluoroacetic acid (20 mL) and the mixture was stirred at room temperature for 10 minutes. Trifluoroacetic acid was evaporated under reduced pressure to give the title compound as colorless crystal (5.62 g). Yield: 99%.

$^1$H-NMR (DMSO-$d_6$) δ: 1.83-1.96 (2H, m), 2.08-2.14 (2H, m), 3.00-3.08 (2H, m), 3.14-3.26 (2H, m), 3.41 (1H, br s).

Reference Example 259

Preparation of 1-(6-trifluoromethylbenzothiazole-2-yl)piperidine-4-carbonitrile

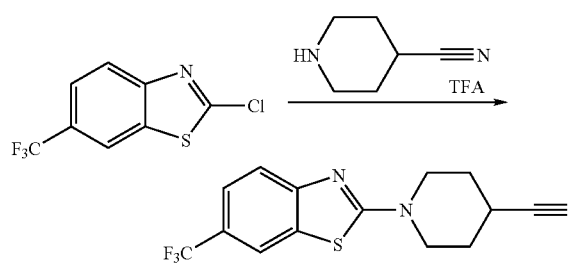

[Formula 1093]

2-Chloro-6-trifluorobenzothiazole (5.84 g), piperidine-4-carbonitrile trifluoroacetate (5.62 g), potassium carbonate (10.39 g) and dimethyl sulfoxide (50 mL) were stirred at 60° C. for 6 hours. To the reaction solution was added water and extracted with ethyl acetate. The organic layer was washed with water and brine, and dried over magnesium sulphate. The solvent was evaporated under reduced pressure and the residue was washed with isopropylether to give the title compound as colorless crystal (6.84 g). Yield: 89%.

$^1$H-NMR (CDCl$_3$) δ: 1.99-2.17 (4H, m), 2.97-3.05 (1H, m), 3.68-3.76 (2H, m), 3.87-3.95 (2H, m), 7.55-7.63 (2H, m), 7.89-7.90 (1H, m).

Reference Example 260

Preparation of 4-[2-(t-butyldimethylsilyloxy)ethyl]-1-(6-trifluoromethyl benzothiazole-2-yl)piperidine-4-carbonitrile

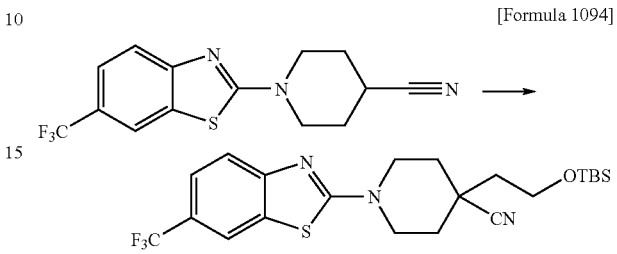

[Formula 1094]

To a solution of 1-(6-trifluoromethyl benzothiazole-2-yl) piperidine-4-carbonitrile (1.00 g) in tetrahydrofuran (10 mL) was added lithium bis(trimethylsilyl)amide (3.21 mL) at −15° C. To the reaction solution was added (2-bromoethoxy)-t-butyldimethyl silane (689 μL). The mixture was stirred at 0° C. for 3 hours. To the reaction solution was added brine and extracted with ethyl acetate. The organic layer was washed with water and brine, and dried over magnesium sulphate. The solvent was evaporated under reduced pressure and the obtained residue was purified by column chromatograph on silica gel to give the title compound (1.23 g). Yield: 82%.

$^1$H-NMR (CDCl$_3$) δ: 0.10 (6H, s), 0.93 (9H, s), 1.71-1.81 (2H, m), 1.88 (2H, t, J=6.0 Hz), 2.17-2.21 (2H, m), 3.49-3.59 (2H, m), 3.94 (2H, t, J=6.0 Hz), 4.11-4.23 (2H, m), 7.55-7.62 (2H, m), 7.89-7.89 (1H, m).

Reference Example 261

Preparation of 4-(2-hydroxyethyl)-1-(6-trifluoromethyl benzothiazole-2-yl)piperidine-4-carbonitrile

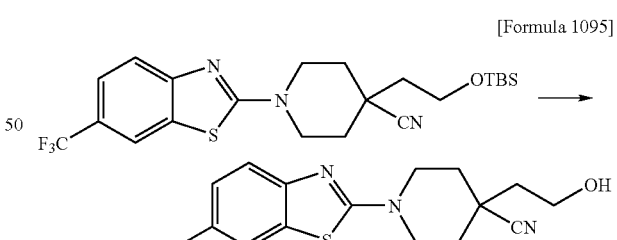

[Formula 1095]

To 4-[2-(t-butyldimethyl silyloxy)ethyl]-1-(6-trifluoromethyl benzothiazole-2-yl)piperidine-4-carbonitrile (510 mg) was added tetramethylammonium fluoride (1 M tetrahydrofuran solution, 1.63 mL). The mixture was stirred at 0° C. for 0.5 hour. To the reaction solution was added aqueous citric acid solution and extracted with ethyl acetate. The organic layer was washed with water and brine, and dried over sodium sulphate. The solvent was evaporated under reduced pressure and the residue was purified by column chromatograph on silica gel to give the title compound (366 mg). Yield: 95%.

$^1$H-NMR (Acetone) δ: 1.82-1.99 (4H, m), 2.20-2.25 (2H, m), 3.44-3.54 (2H, m), 3.89 (2H, t, J=5.9 Hz), 4.25-4.29 (2H, m), 7.62-7.63 (2H, m), 8.13-8.16 (1H, br m).

Example 772

Preparation of [3-chloro-5-[2-[4-cyano-1-(6-trifluoromethyl benzothiazole-2-yl)piperidine-4-yl]ethoxy]phenyl]acetic acid

[Formula 1096]

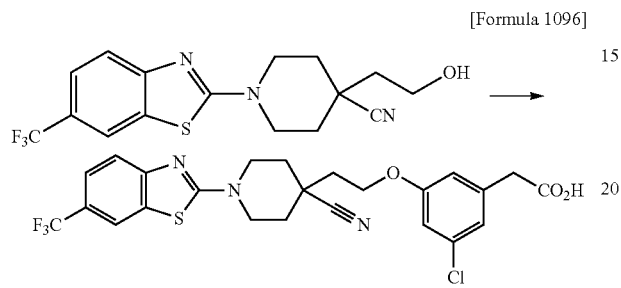

The above compound was synthesized from 4-(2-hydroxyethyl)-1-(6-trifluoromethyl benzothiazole-2-yl)piperidine-4-carbonitrile according to the methods of Example 585 and 586.

MS (ESI) m/z 524 [M+H]+

The following compound was obtained by a similar method as above.

Example 773

[Formula 1097]

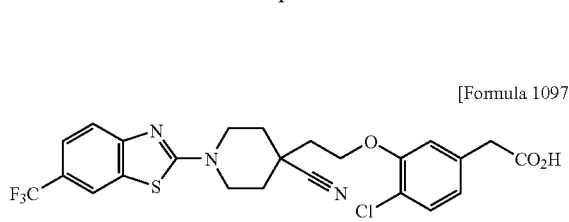

MS (ESI) m/z 524 [M+H]+

Reference Example 262

Preparation of 4-[2-(t-butyldimethyl silanyloxy)ethyl]-1-(6-trifluoromethyl benzothiazole-2-yl)piperidine-4-carboxaldehyde

[Formula 1098]

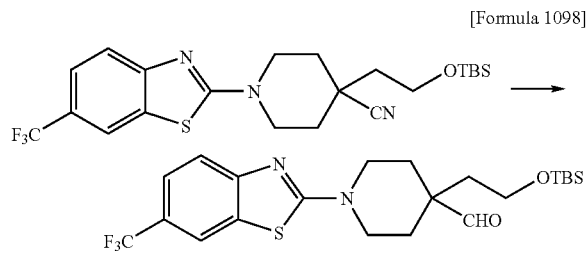

To a solution of 4-[2-(t-butyldimethyl silyloxy)ethyl]-1-(6-trifluoromethyl benzothiazole-2-yl)piperidine-4-carbonitrile (600 mg) in 1,2-dimethoxyethane (12 mL) was added diisobutylaluminum hydride (1.0 M toluene solution, 6.39 mL) at 0° C. The mixture was stirred for 4 hours. To the reaction solution was added aqueous citric acid solution and extracted with ethyl acetate. The organic layer was sequentially washed with aqueous citric acid solution, water and brine, and dried over magnesium sulphate. The solvent was evaporated under reduced pressure and the residue was purified by column chromatograph on silica gel to give the title compound (526 mg). Yield: 87%.

$^1$H-NMR (CDCl$_3$) δ: 0.05 (6H, s), 0.90 (9H, s), 1.64-1.74 (2H, m), 1.85 (2H, t, J=5.8 Hz), 2.13-2.19 (2H, m), 3.40-3.50 (2H, m), 3.68 (2H, t, J=5.8 Hz), 3.93-4.00 (2H, m), 7.52-7.59 (2H, m), 7.85-7.88 (1H, br m), 9.57-9.60 (1H, br m).

Reference Example 263

Preparation of N-[4-(2-hydroxyethyl)-1-(6-trifluoromethyl benzothiazole-2-yl)piperidine-4-yl]formimido ethyl ester

[Formula 1099]

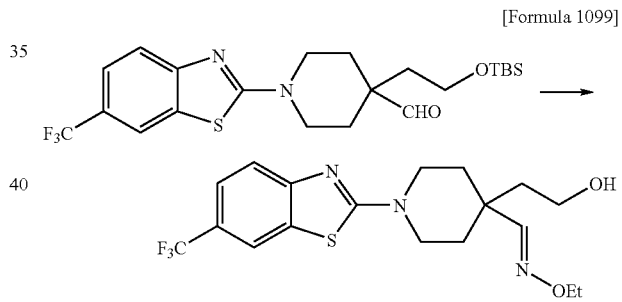

To a solution of 4-[2-(t-butyldimethyl silanyloxy)ethyl]-1-(6-trifluoromethyl benzothiazole-2-yl)piperidine-4-carboxaldehyde (500 mg) in tetrahydrofuran (20 mL) was added ethoxy aminehydrochloride (124 mg). The mixture was stirred at 60° C. for 4 hours. The solvent was evaporated under reduced pressure. To the residue was added tetrabuthyl ammonium fluoride (1M tetrahydrofuran solution, 1.59 mL). The mixture was stirred at 0° C. for 0.5 hour, at room temperature for 1 hour and at 40° C. for 2 hours. To the reaction solution was added aqueous citric acid solution and extracted with ethyl acetate. The organic layer was washed with brine, and dried over magnesium sulphate. The solvent was evaporated under reduced pressure and the residue was purified by column chromatograph on silica gel to give the title compound (394 mg). Yield: 93%.

$^1$H-NMR (CDCl$_3$) δ: 1.28 (3H, t, J=7.0 Hz), 1.68-1.77 (2H, m), 1.80 (2H, t, J=6.7 Hz), 2.03-2.10 (2H, m), 3.47-3.56 (2H, m), 3.74-3.80 (2H, m), 3.92-3.99 (2H, m), 4.13 (2H, q, J=7.0 Hz), 7.33-7.36 (1H, br m), 7.52-7.59 (2H, m), 7.84-7.88 (1H, br m).

Example 774

Preparation of [3-chloro-5-[2-[4-ethoxy methylene-amino-1-(6-trifluoromethyl benzothiazole-2-yl)piperidine-4-yl]ethoxy]phenyl]acetic acid

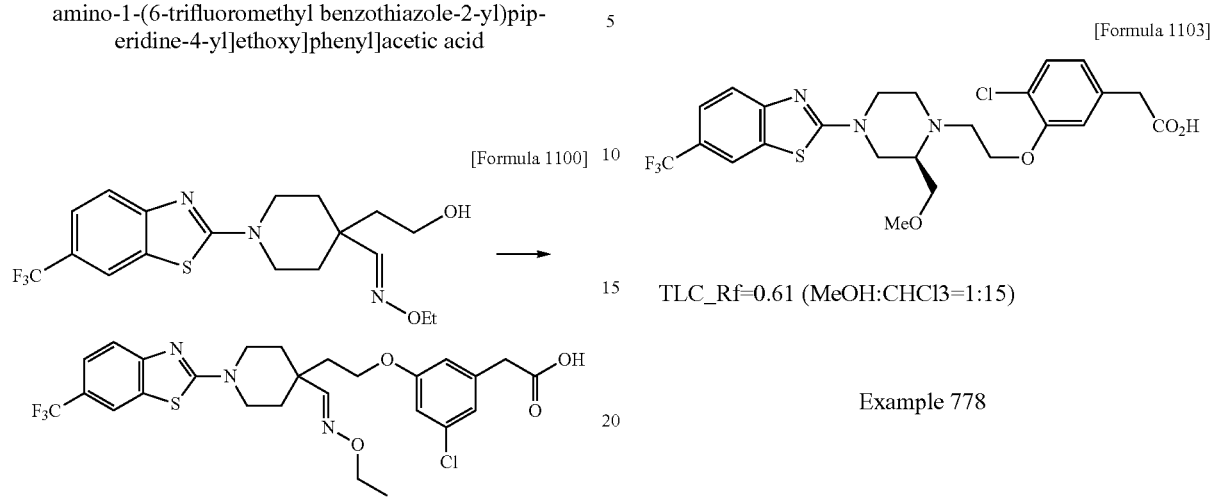

[Formula 1100]

The above compound was synthesized from N-[4-(2-hydroxyethyl)-1-(6-trifluoromethylbenzothiazole-2-yl)piperidine-4-yl]formimido ethyl ester according to the methods of Example 585 and 586.

MS (ESI) m/z 570 [M+H]+

The following compounds were obtained by similar methods as above.

Example 775

[Formula 1101]

MS (ESI) m/z 570 [M+H]+

Example 776

[Formula 1102]

MS (FABMS) m/z 582 [M+H]+

Example 777

[Formula 1103]

TLC_Rf=0.61 (MeOH:CHCl3=1:15)

Example 778

[Formula 1104]

TLC_Rf=0.63 (MeOH:CHCl3=1:15)

Example 779

[Formula 1105]

MS (ESI) m/z 547 [M+H]+

Example 780

[Formula 1106]

MS (ESI) m/z 521 [M+H]+

Example 781
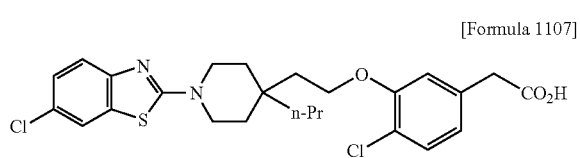
MS (ESI) m/z 507 [M+H]+
Example 782
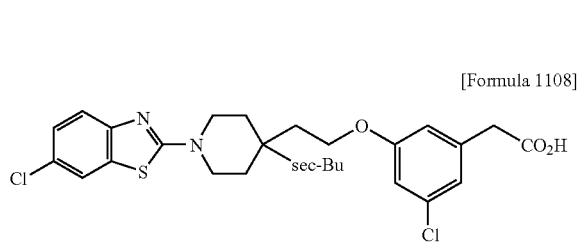
MS (ESI) m/z 521 [M+H]+
Example 783
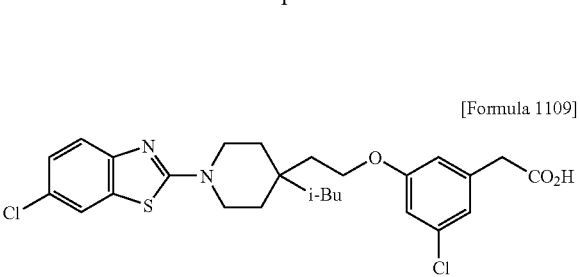
MS (ESI) m/z 521 [M+H]+
Example 784
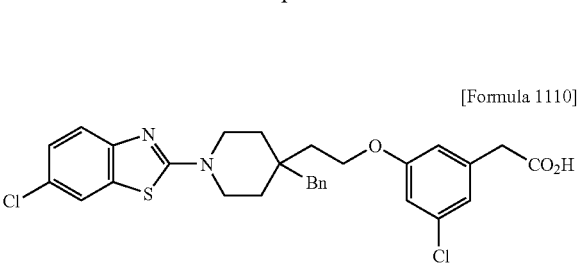
MS (ESI) m/z 555 [M+H]+
Example 785
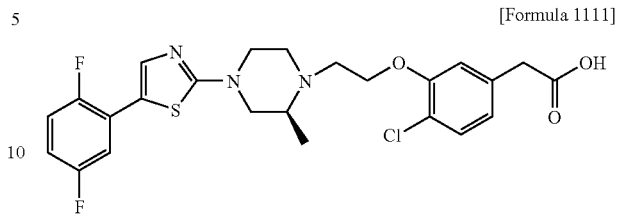
MS (ESI) m/z 508 [M+H]+
Example 786
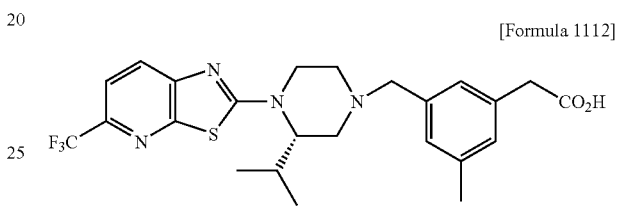
MS (ESI) m/z 493 [M+H]+
Example 787
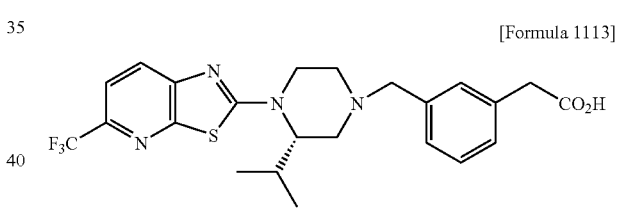
MS (ESI) m/z 479 [M+H]+
Example 788
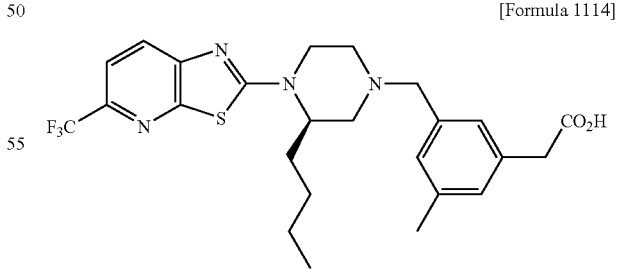
1H-NMR (DMSO-d6) δ: 7.88 (1.0H, d, J=8.51 Hz), 7.78 (1.0H, d, J=8.51 Hz), 7.05 (2.0H, d, J=5.21 Hz), 7.00 (1.0H, s), 4.22-3.91 (1.0H, m), 3.65-3.36 (4.0H, m), 2.97 (1.0H, d, J=11.53 Hz), 2.83 (1.0H, d, J=11.53 Hz), 2.31 (3.0H, s), 2.21-2.16 (3.0H, m), 2.02-1.93 (1.0H, m), 1.83-1.78 (1.0H, m), 1.38-1.16 (4.0H, m), 0.86 (3.0H, t, J=7.27 Hz).

Example 789

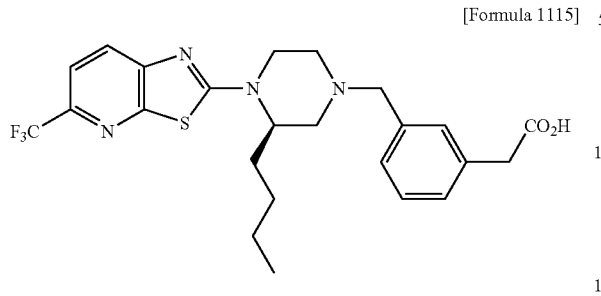

[Formula 1115]

1H-NMR (DMSO-d6) δ: 7.88 (1.0H, d, J=8.23 Hz), 7.78 (1.0H, d, J=8.23 Hz), 7.34-7.18 (4.0H, m), 4.06 (1.0H, br s), 3.61-3.41 (5.0H, m), 2.96 (1.0H, d, J=11.80 Hz), 2.84 (1.0H, d, J=11.80 Hz), 2.19-2.17 (2.0H, m), 1.92-1.84 (2.0H, m), 1.32-1.21 (4.0H, m), 0.86 (3.0H, t, J=7.27 Hz).

Example 790

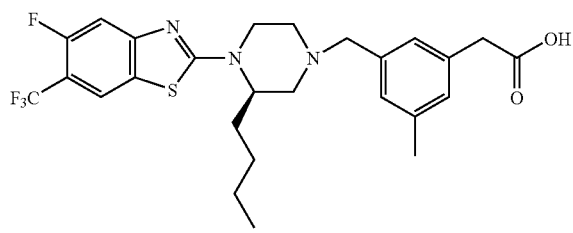

[Formula 1116]

1H-NMR (DMSO-d6) δ: 12.32 (1.0H, br s), 8.26 (1.0H, d, J=7.41 Hz), 7.46 (1.0H, d, J=12.08 Hz), 7.05 (2.0H, d, J=5.76 Hz), 7.00 (1.0H, s), 4.07-4.04 (1.0H, m), 3.58-3.40 (5.0H, m), 2.95 (1.0H, d, J=12.08 Hz), 2.82 (1.0H, d, J=12.08 Hz), 2.31 (3.0H, s), 2.22-2.11 (2.0H, m), 2.02-1.92 (1.0H, m), 1.78-1.74 (1.0H, m), 1.30-1.22 (4.0H, m), 0.86 (3.0H, t, J=7.27 Hz).

Example 791

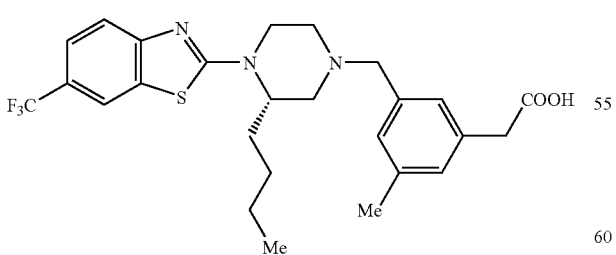

[Formula 1117]

$^1$H-NMR (300 MHz, DMSO-$d_6$): δ 0.83 (3H, t, J=7.2 Hz), 1.13-1.20 (2H, m), 1.27-1.34 (2H, m), 1.71-1.94 (2H, m), 2.09-2.19 (2H, m), 2.28 (3H, s), 2.78-2.94 (2H, m), 3.32-3.61 (5H, m), 3.99 (2H, m), 6.97-7.02 (3H, m), 7.50-7.57 (2H, m), 8.22 (1H, s)

Example 792

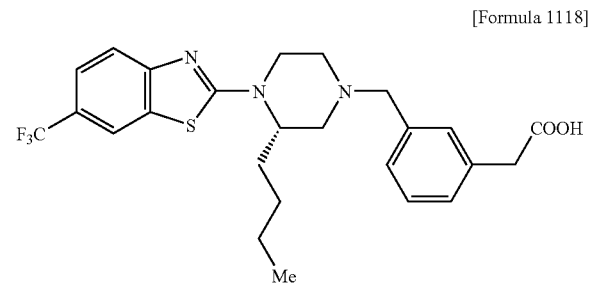

[Formula 1118]

$^1$H-NMR (300 MHz, DMSO-$d_6$): δ 0.83 (3H, t, J=7.2 Hz), 1.13-1.20 (2H, m), 1.27-1.36 (2H, m), 1.72-1.94 (2H, m), 2.12-2.15 (2H, m), 2.78-2.92 (2H, m), 3.37-3.61 (5H, m), 3.99 (2H, m), 7.16-7.29 (4H, m), 7.50-7.57 (2H, m), 8.21 (1H, s)

Example 793

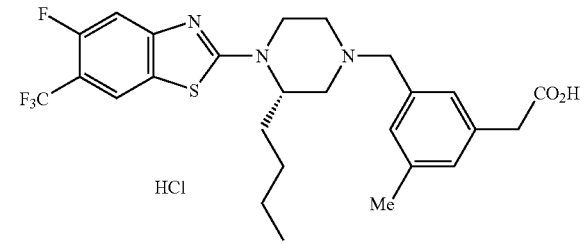

[Formula 1119]

$^1$H-NMR (300 MHz, DMSO-$d_6$): δ 0.81 (3H, t, J=7.2 Hz), 1.07-1.17 (2H, m), 1.25-1.32 (2H, m), 1.68-1.77 (2H, m), 2.09-2.18 (2H, m), 2.26 (3H, s), 2.75-2.93 (2H, m), 3.26-3.42 (3H, m), 3.48 (2H, s), 3.57 (1H, d, J=13.5 Hz), 3.97 (1H, m), 6.95-7.02 (3H, m), 7.41 (1H, d, J=12.3 Hz), 8.22 (1H, d, J=6.6 Hz), 12.24 (1H, br)

Example 794

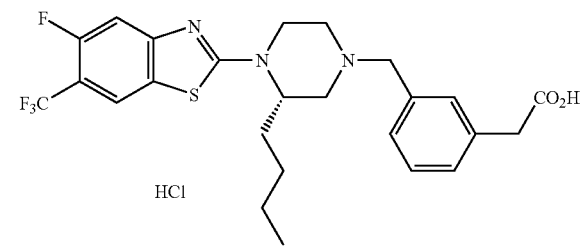

[Formula 1120]

$^1$H-NMR (300 MHz, DMSO-$d_6$): δ 0.81 (3H, t, J=7.2 Hz), 1.13-1.31 (4H, m), 1.75-1.95 (2H, m), 2.10-2.13 (2H, m), 2.76-2.90 (1H, m), 3.21-4.37 (8H, m), 7.15-7.59 (5H, m), 8.21-8.30 (1H, m), 12.34 (1H, br)

Example 795

[Formula 1121]

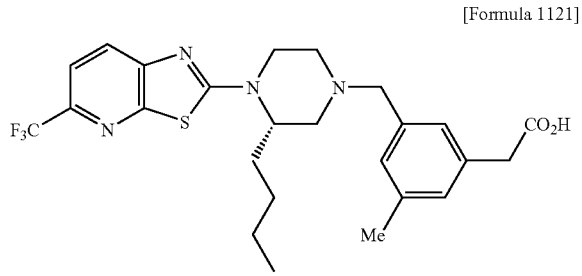

$^1$H-NMR (300 MHz, CDCl$_3$): δ 0.88 (3H, t, J=7.2 Hz), 1.21-1.39 (4H, m), 1.94 (2H, m), 2.27 (2H, m), 2.36 (3H, s), 2.91 (2H, m), 3.45 (3H, m), 3.64 (2H, s). 4.11 (2H, m), 7.06-7.11 (3H, m), 7.58 (1H, d, J=8.4 Hz), 7.71 (1H, d, J=8.4 Hz)

Example 796

[Formula 1122]

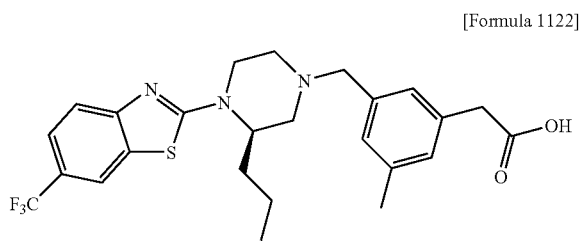

1H-NMR (DMSO-d6) δ: 8.24 (1H, s), 7.58-7.55 (2H, m), 7.06 (2H, s), 7.00 (1H, s), 4.09-3.95 (2H, m), 3.64-3.32 (2H, m), 3.53 (2H, s), 2.94 (1H, d, J=11.2 Hz), 2.82 (1H, d, J=11.4 Hz), 2.31 (3H, s), 2.19-2.14 (2H, m), 1.98-1.89 (1H, m), 1.80-1.71 (1H, m), 1.27-1.19 (2H, m), 0.92 (3H, t, J=7.3 Hz).

Example 797

[Formula 1123]

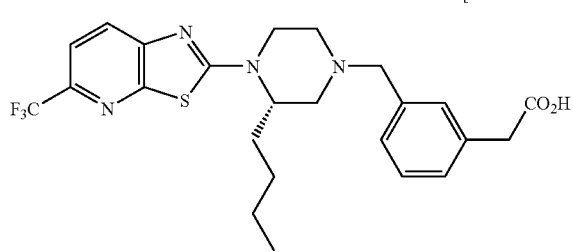

$^1$H-NMR (300 MHz, CDCl$_3$): δ 0.87 (3H, t, J=7.2 Hz), 1.20-1.38 (4H, m), 1.92 (2H, m), 2.27 (2H, m), 2.89 (2H, m), 3.50 (3H, m), 3.67 (2H, s). 4.11 (2H, m), 7.31 (4H, m), 7.57 (1H, d, J=8.4 Hz), 7.70 (1H, d, J=8.4 Hz)

Example 798

[Formula 1124]

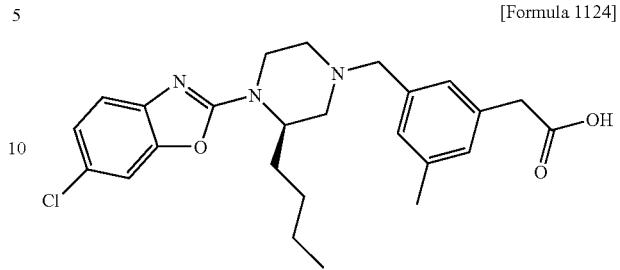

1H-NMR (DMSO-d6) δ: 7.55 (1H, d, J=2.0 Hz), 7.26-7.17 (2H, m), 7.04 (1H, s), 7.02 (1H, s), 6.97 (1H, s), 4.13 (1H, s), 3.95 (1H, d, J=12.3 Hz), 3.50 (2H, s), 3.48 (2H, dd, J=58.3, 14.7 Hz), 2.90 (1H, d, J=12.1 Hz), 2.76 (1H, d, J=12.1 Hz), 2.28 (3H, s), 2.15-2.09 (2H, m), 1.92-1.83 (1H, m), 1.79-1.70 (1H, m), 1.31-1.26 (2H, m), 1.16-1.10 (2H, m), 0.83 (3H, t, J=7.3 Hz).

Example 799

[Formula 1125]

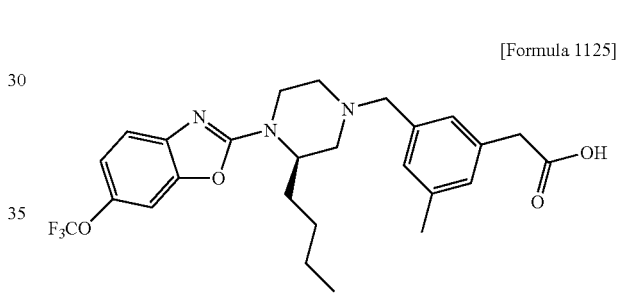

1H-NMR (DMSO-d6) δ: 7.88 (1H, s), 7.45 (1H, d, J=8.8 Hz), 7.24 (1H, d, J=9.1 Hz), 7.03 (1H, s), 7.01 (1H, s), 6.97 (1H, s), 3.99-3.90 (2H, m), 3.50 (2H, s), 3.49 (2H, dd, J=58.4, 12.7 Hz), 2.91 (1H, d, J=11.5 Hz), 2.79 (1H, d, J=11.5 Hz), 2.28 (3H, s), 2.15-2.09 (2H, m), 1.97-1.91 (1H, m), 1.73-1.67 (1H, m), 1.32-1.26 (2H, m), 1.19-1.13 (2H, m), 0.84 (3H, t, J=7.1 Hz).

Example 800

[Formula 1126]

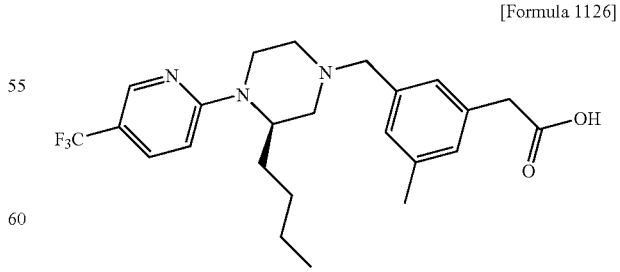

1H-NMR (DMSO-d6) δ: 8.40 (1H, s), 7.77 (1H, dd, J=9.3, 2.6 Hz), 7.05 (2H, d, J=6.2 Hz), 6.99 (1H, s), 6.88 (1H, d, J=9.1 Hz), 4.41 (1H, s), 4.25 (1H, d, J=10.0 Hz), 3.63-3.29 (2H, m), 3.51 (2H, s), 3.14 (1H, t, J=11.3 Hz), 2.93 (1H, d,

J=10.2 Hz), 2.81 (1H, d, J=11.8 Hz), 2.30 (3H, s), 2.11-1.88 (3H, m), 1.53-1.48 (1H, m), 1.32-1.23 (2H, m), 1.16-1.06 (2H, m), 0.84 (3H, t, J=7.3 Hz).

Example 801

[Formula 1127]

1H-NMR (DMSO-d6) δ: 8.37 (1H, s), 7.74 (1H, dd, J=9.1, 2.5 Hz), 7.03 (2H, d, J=6.6 Hz), 6.97 (1H, s), 6.85 (1H, d, J=9.3 Hz), 4.38 (1H, s), 4.22 (1H, d, J=11.6 Hz), 3.50 (2H, s), 3.44 (2H, dd, J=87.8, 13.2 Hz), 3.12 (1H, t, J=11.3 Hz), 2.91 (1H, d, J=11.0 Hz), 2.79 (1H, d, J=11.3 Hz), 2.28 (3H, s), 1.51-1.45 (1H, m), 1.28-1.21 (2H, m), 1.13-1.06 (2H, m), 0.81 (3H, t, J=7.3 Hz).

Example 802

[Formula 1128]

1H-NMR (DMSO-d6) δ: 7.87 (1H, d, J=8.6 Hz), 7.78 (1H, d, J=8.6 Hz), 7.05 (2H, s), 7.00 (1H, s), 4.13-4.02 (2H, m), 3.63-3.34 (2H, m), 3.51 (2H, s), 2.96 (1H, d, J=11.4 Hz), 2.83 (1H, d, J=11.9 Hz), 2.31 (3H, s), 2.21-2.15 (2H, m), 1.95-1.87 (1H, m), 1.84-1.76 (1H, m), 1.27-1.18 (2H, m), 0.92 (3H, t, J=7.3 Hz).

Example 803

[Formula 1129]

1H-NMR (CDCl3) δ: 7.71 (1.0H, d, J=8.23 Hz), 7.58 (1.0H, d, J=8.23 Hz), 7.17-7.00 (3.0H, m), 4.22-4.01 (2.0H, m), 3.67-3.29 (5.0H, m), 3.07-2.72 (2.0H, m), 2.38-2.19 (5.0H, m), 2.03-1.90 (1.0H, m), 1.75-1.56 (2.0H, m), 1.55-1.40 (1.0H, m), 1.02-0.88 (6.0H, m).

Example 804

[Formula 1130]

1H-NMR (CDCl3) δ: 7.70 (1.0H, d, J=8.51 Hz), 7.57 (1.0H, d, J=8.51 Hz), 7.37-7.20 (4.0H, m), 4.22-4.03 (2.0H, m), 3.74-3.38 (5.0H, m), 3.13-2.74 (2.0H, m), 2.43-2.18 (2.0H, m), 2.00-1.85 (1.0H, m), 1.80-1.58 (1.0H, m), 1.50-1.41 (1.0H, m), 0.98-0.89 (6.0H, m).

Example 805

[Formula 1131]

1H-NMR (DMSO-d6) δ: 8.25 (1.0H, d, J=7.41 Hz), 7.42 (1.0H, d, J=12.90 Hz), 7.05-6.95 (3.0H, m), 4.17-3.88 (2.0H, m), 3.59 (2.0H, d, J=14.00 Hz), 3.49 (2.0H, s), 3.45-3.19 (2.0H, m), 2.93 (1.0H, d, J=11.53 Hz), 2.76 (1.0H, d, J=11.53 Hz), 2.28 (3.0H, s), 2.23-2.07 (2.0H, m), 1.98-1.87 (1.0H, m), 1.59-1.34 (1.6H, m), 0.93-0.87 (6.0H, m).

Example 806

[Formula 1132]

1H-NMR (DMSO-d6) δ: 8.24 (1.0H, d, J=7.41 Hz), 7.42 (1.0H, d, J=12.62 Hz), 7.32-7.13 (4.0H, m), 4.24-3.82 (2.0H, m), 3.63 (1.0H, d, J=13.72 Hz), 3.56 (2.0H, s), 3.53-3.36 (3.0H, m), 2.93 (1.0H, d, J=11.53 Hz), 2.77 (1.0H, d, J=11.53

Example 807

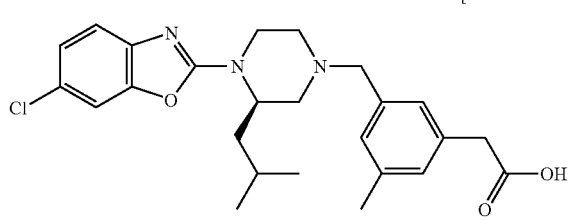
[Formula 1133]

1H-NMR (CDCl3) δ: 7.29-7.19 (3.0H, m), 7.17-7.02 (3.0H, m), 4.43-4.25 (1.0H, m), 4.16-4.01 (1.0H, m), 3.67-3.35 (4.0H, m), 3.11-2.69 (2.0H, m), 2.41-2.16 (5.0H, m), 1.85-1.70 (2.0H, m), 1.53-1.39 (1.0H, m), 0.98-0.86 (6.0H, m).

Example 808

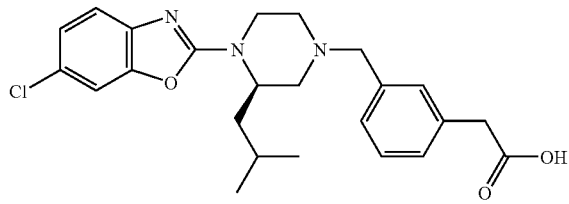
[Formula 1134]

1H-NMR (CDCl3) δ: 7.40-7.19 (6.0H, m), 7.14 (1.0H, dd, J=8.51, 1.92 Hz), 4.49-4.24 (1.0H, m), 4.22-4.01 (1.0H, m), 3.71-3.39 (4.0H, m), 2.99-2.71 (2.0H, m), 2.53-1.69 (4.0H, m), 1.55-1.39 (1.0H, m), 0.96-0.89 (6.0H, m).

Example 809

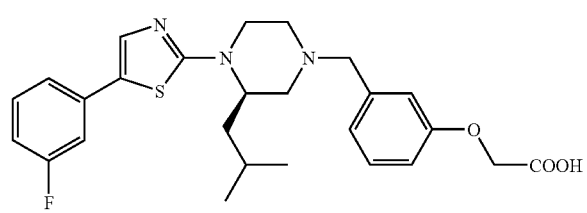
[Formula 1135]

TLC_Rf=0.55 (MeOH:CHCl3=1:10)

Hz), 2.23-2.11 (2.0H, m), 1.95-1.80 (1.0H, m), 1.64-1.50 (1.0H, m), 1.48-1.32 (1.0H, m), 0.94-0.86 (6.0H, m).

Reference Example 264

(S)-4-(6-trifluoromethyl benzothiazole-2-yl)piperazine-1,3-dicarboxylic acid-1-t-butyl ester-3-methyl ester

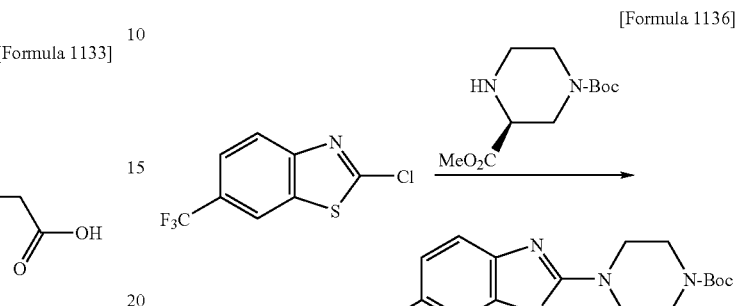
[Formula 1136]

2-Chloro-6-trifluoromethyl benzothiazole (2.79 g), (S)-4-N-Boc-piperazine carboxylic acid methyl ester (3.10 g), potassium carbonate (1.95 g) and dimethylformamide (20 mL) were stirred at 55° C. for 16 hours and at 90° C. for 7 hours. To the reaction solution was added water and extracted with ethyl acetate. The organic layer was washed with brine, and dried over magnesium sulphate. The solvent was evaporated under reduced pressure and the residue was purified by column chromatograph on silica gel to give the title compound (1.40 g).

Yield: 27%.

1H-NMR (CDCl3) δ: 1.47 (9H, s), 2.97-3.18 (1H, m), 3.20-3.38 (1H, m), 3.58-3.81 (2H, m), 3.76 (3H, s), 4.09-4.37 (1H, m), 4.61-4.77 (1H, m), 5.06 (1H, brs), 7.55 (1H, d, J=8.4, 1.2 Hz), 7.61 (1H, d, J=8.4 Hz), 7.90 (1H, d, J=1.2 Hz).

Reference Example 265

Preparation of (S)-3-hydroxymethyl-4-(6-trifluoromethyl benzothiazole-2-yl)piperazine-1-carboxylic acid t-butyl ester

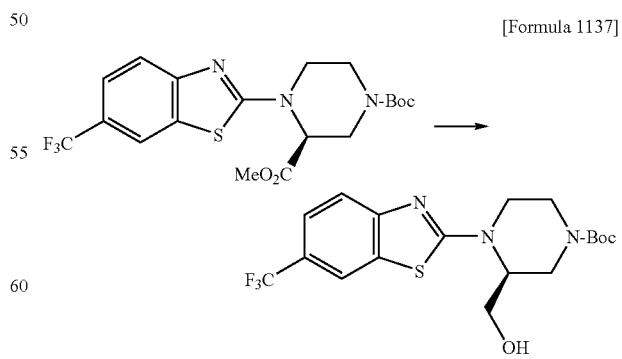
[Formula 1137]

To a solution of (S)-4-(6-trifluoromethyl benzothiazole-2-yl)piperazine-1,3-dicarboxylic acid-1-t-butyl ester-3-methyl ester (1.18 g) in tetrahydrofuran (10 mL) was added lithium borohydride (65.7 mg). The mixture was stirred for 20 hours. To the reaction solution was added aqueous ammonium chloride solution and extracted with ethyl acetate. The organic layer was washed with brine, and dried over magnesium sulphate. The solvent was evaporated under reduced pressure and the residue was purified by column chromatograph on silica gel to give the title compound (840 mg). Yield: 76%.

1H-NMR (CDCl3) δ: 1.50 (9H, s), 3.03-3.30 (2H, m), 3.35-3.55 (1H, m), 3.68-4.00 (3H, m), 4.00-4.43 (3H, m), 7.51-7.59 (2H, m), 7.87 (1H, d, J=0.8 Hz).

Reference Example 266

Preparation of (S)-3-methoxymethyl-4-(6-trifluoromethyl benzothiazole-2-yl)piperazine-1-carboxylic acid t-butyl ester

[Formula 1138]

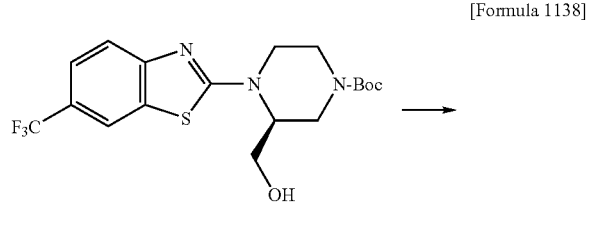

To a solution of (S)-3-hydroxymethyl-4-(6-trifluoromethyl benzothiazole-2-yl) piperazine-1-carboxylic acid t-butyl ester (209 mg) in dimethylformamide (2 mL) were sequentially added methyl iodide (0.5 mL) and sodium hydride (62.4 mg). The mixture was stirred at room temperature for 24 hours. To the reaction solution was added ice water and extracted with ethyl acetate. The organic layer was washed with brine, and dried over magnesium sulphate. The solvent was evaporated under reduced pressure and the residue was purified by column chromatograph on silica gel to give the title compound (167 mg).

Yield: 77%.

1H-NMR (CDCl3) δ: 1.50 (9H, s), 2.96-3.19 (2H, m), 3.34-3.45 (1H, m), 3.38 (3H, s), 3.57 (2H, d, J=6.9 Hz), 3.94-4.06 (1H, m), 4.20-4.33 (3H, m), 7.53 (1H, dd, J=8.7, 1.5 Hz), 7.58 (1H, d, J=8.7 Hz), 7.86 (1H, d, J=1.5 Hz).

Reference Example 267

Preparation of 2-((S)-2-methoxymethylpiperazine-1-yl)-6-trifluoromethyl benzothiazole

[Formula 1139]

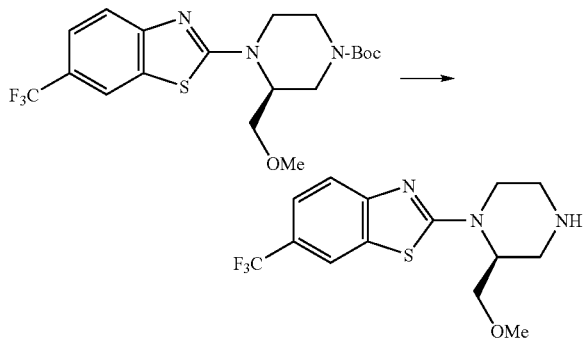

To a solution of (S)-3-methoxymethyl-4-(6-trifluoromethyl benzothiazole-2-yl)piperazine-1-carboxylic acid t-butyl ester (167 mg) in methylene chloride (1.5 mL) was added trifluoroacetic acid (0.3 mL). The mixture was stirred at room temperature for 20 hours. The reaction solution was concentrated under reduced pressure. Saturated aqueous sodium hydrogencarbonate solution was added thereto and extracted with ethyl acetate. The organic layer was washed with brine, and dried over magnesium sulphate. The solvent was evaporated under reduced pressure to give the title compound (123 mg). Yield: 96%.

1H-NMR (CDCl3) δ: 2.84-2.96 (3H, m), 3.01 (1H, dd, J=12.0, 3.9 Hz), 3.06-3.16 (1H, m), 3.26 (1H, d, J=12.9 Hz), 3.39 (1H, s), 3.46 (1H, dd, J=12.0, 3.3 Hz), 3.66 (1H, dd, J=12.4, 5.1 Hz), 3.91 (1H, dd, J=12.4, 7.2 Hz), 3.90-3.96 (1H, m), 4.12-4.21 (1H, m), 7.52 (1H, dd, J=8.4, 2.1 Hz), 7.56 (1H, d, J=8.4 Hz), 7.85 (1H, d, J=2.1 Hz).

Reference Example 268

Preparation of [3-[(S)-3-methoxymethyl-4-(6-trifluoromethyl benzothiazole-2-yl)piperazine-1-ylmethyl] phenyl]ethyl acetate ester

[Formula 1140]

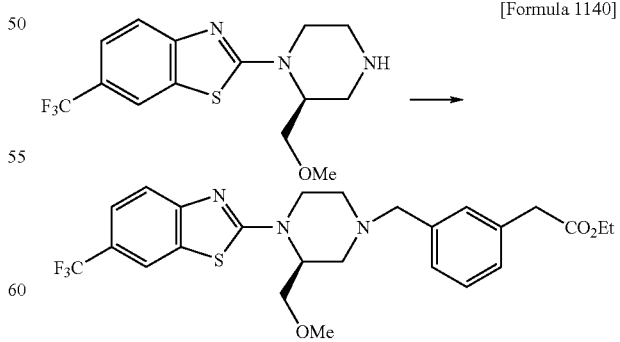

A mixture of 2-((S)-2-methoxymethylpiperazine-1-yl)-6-trifluoromethyl benzothiazole (123 mg), (3-bromomethylphenyl)ethyl acetate ester (104 mg), potassium carbonate (259 mg) and dimethylformamide (1.5 mL) was stirred at room temperature for 2 hours. To the reaction solution was added water and extracted with ethyl acetate. The organic layer was washed with brine, and dried over magnesium sulphate. The solvent was evaporated under reduced pressure and the residue was purified by column chromatograph on silica gel to give the title compound (169 mg). Yield: 90%.

1H-NMR (CDCl3) δ: 1.26 (3H, t, J=7.2 Hz), 2.20-2.32 (2H, m), 2.90 (1H, brd, J=10.8 Hz), 3.04 (1H, d, J=11.7 Hz), 3.36 (3H, s), 3.39-3.64 (3H, m), 3.62 (2H, s), 3.70 (1H, dd, J=9.0, 6.0 Hz), 3.83 (1H, t, J=9.0 Hz), 4.03 (1H, brd, J=12.6 Hz), 4.16 (2H, q, J=7.2 Hz), 4.13-4.24 (1H, m), 7.18-7.33 (4H, m), 7.51 (1H, dd, J=8.4, 1.8 Hz), 7.56 (1H, d, J=8.4 Hz), 7.83 (1H, d, J=1.8 Hz).

Example 810

Preparation of [3-[(S)-3-methoxymethyl-4-(6-trifluoromethyl benzothiazole-2-yl)piperazine-1-ylmethyl]phenyl]acetic acid

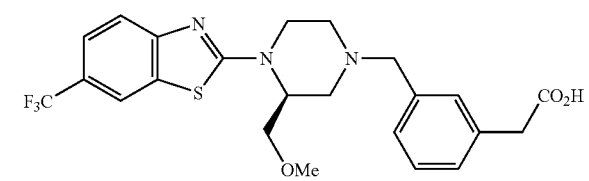

[Formula 1141]

A mixture of [3-[(S)-3-methoxymethyl-4-(6-trifluoromethyl benzothiazole-2-yl)piperazine-1-ylmethyl]phenyl] ethyl acetate ester (167 mg), 2N aqueous sodium hydroxide solution (0.8 mL), tetrahydrofuran (1.2 mL) and methanol (1.2 mL) was stirred at room temperature for 16 hours. The reaction solution was concentrated under reduced pressure. To the residue was added 2N hydrochloric acid and extracted with ethyl acetate. The organic layer was washed with brine, and dried over magnesium sulphate. The solvent was evaporated under reduced pressure to give the title compound (153 mg). Yield: 97%.

TLC_Rf=0.40 (MeOH:CHCl3=1:10)

The following compounds were obtained by similar methods as above.

Example 811

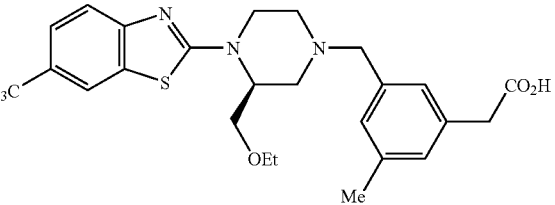

[Formula 1142]

TLC_Rf=0.33 (MeOH:CHCl3=1:10)

Example 812

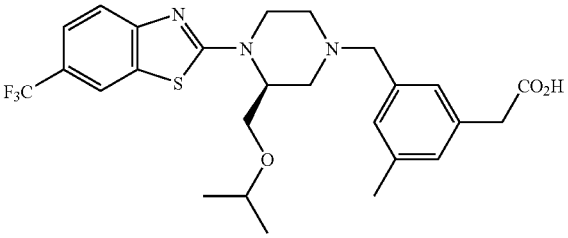

[Formula 1143]

TLC_Rf=0.52 (MeOH:CHCl3=1:15)

Example 813

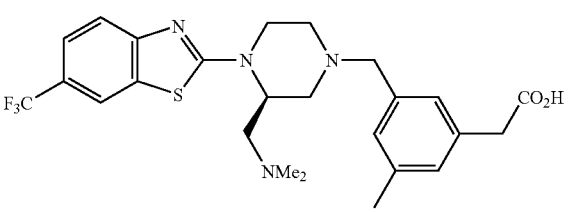

[Formula 1144]

TLC_Rf=0.088 (MeOH:CHCl3=1:5)

Example 814
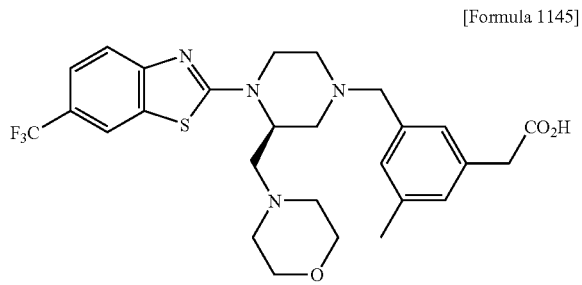
TLC_Rf=0.17 (MeOH:CHCl3=1:15)
Example 815
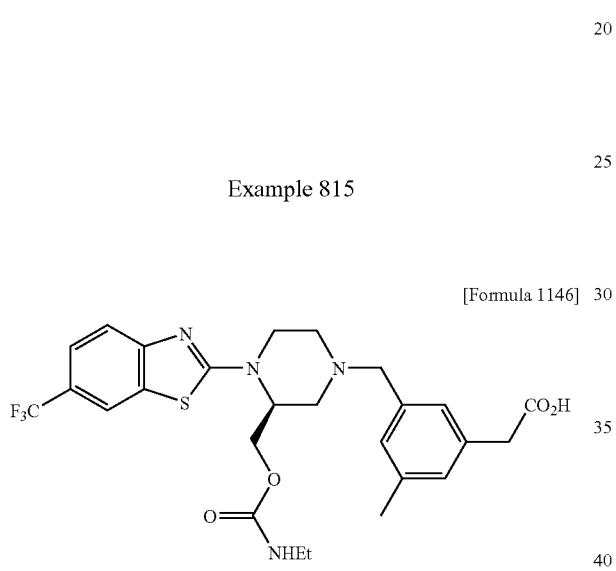
TLC_Rf=0.29 (MeOH:CHCl3=1:15)
Example 816
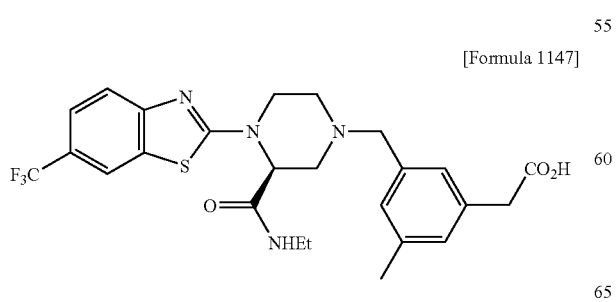
TLC_Rf=0.23 (MeOH:CHCl3=1:15)
Example 817
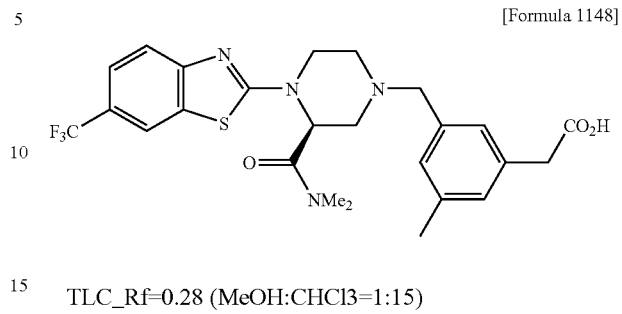
TLC_Rf=0.28 (MeOH:CHCl3=1:15)
Example 818
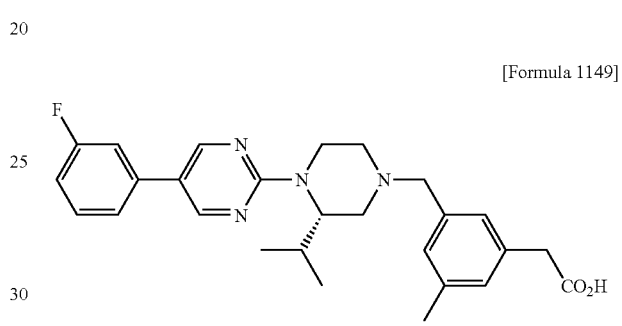
MS (ESI); m/z 463 [M+H]+
Example 819
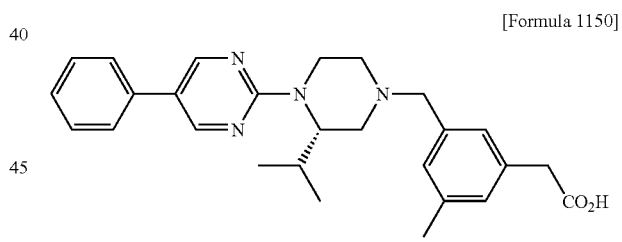
MS (ESI); m/z 445 [M+H]+
Example 820
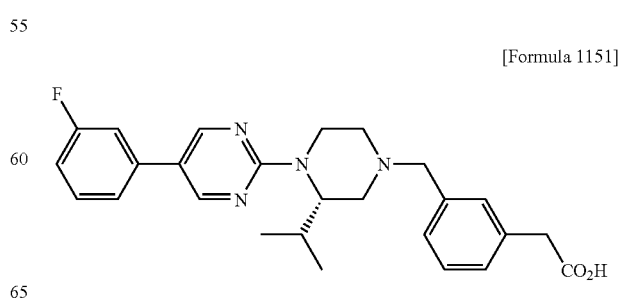
MS (ESI); m/z 449 [M+H]+

391
Example 821
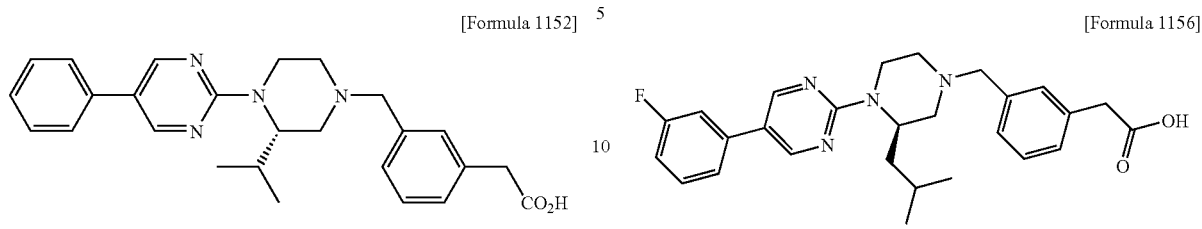
[Formula 1152]
MS (ESI); m/z 431 [M+H]+
Example 822
[Formula 1153]
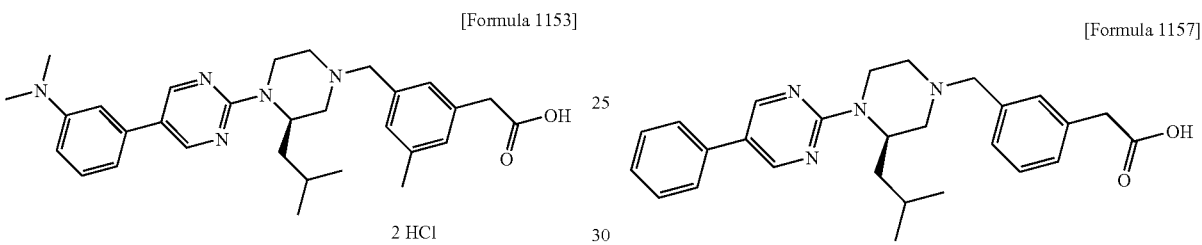
2 HCl
TLC: (SiO2) AcOEt-Hexane (3:1) Rf=0.21
Example 823
[Formula 1154]
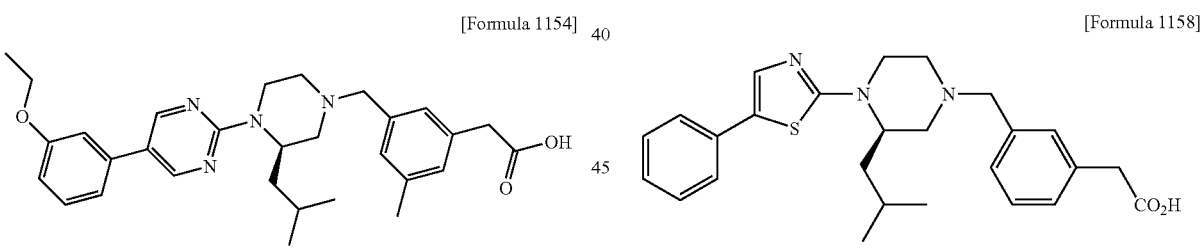
TLC: (SiO2) AcOEt Rf=0.46
Example 824
[Formula 1155]
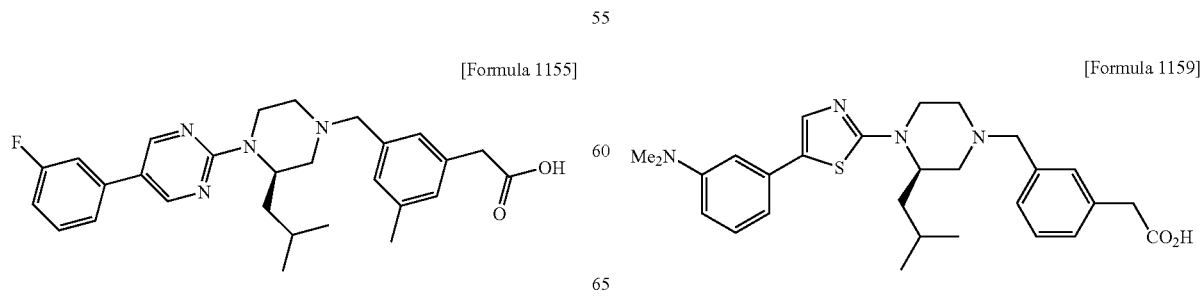
TLC: (SiO2) AcOEt Rf=0.45
392
Example 825
[Formula 1156]
TLC: (SiO2) AcOEt Rf=0.67
Example 826
[Formula 1157]
TLC: (SiO2) AcOEt Rf=0.60
Example 827
[Formula 1158]
TLC: (SiO2) AcOEt-Hexane (1:1) Rf=0.18
Example 828
[Formula 1159]
TLC: (SiO2) AcOEt-Hexane (1:1) Rf=0.25

393
Example 829
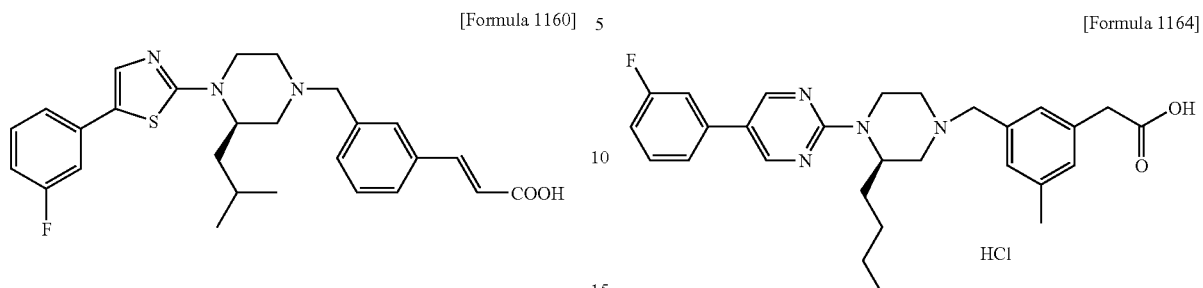
TLC: (SiO2) AcOEt-Hexane (1:1) Rf=0.34
Example 830
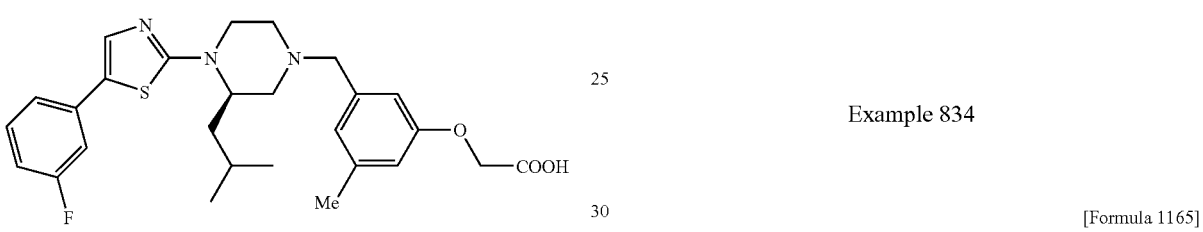
TLC: (SiO2) AcOEt Rf=0.29
Example 831
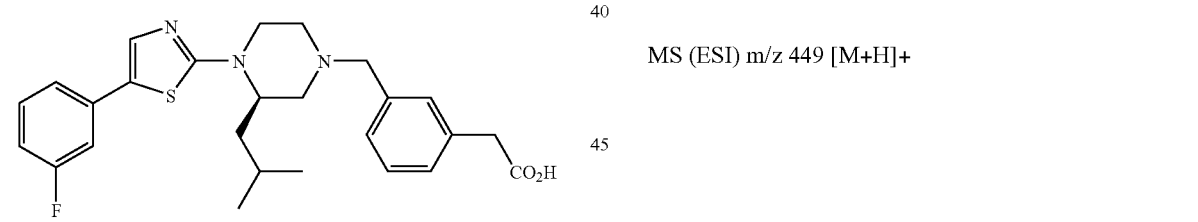
TLC: (SiO2) AcOEt Rf=0.25
Example 832
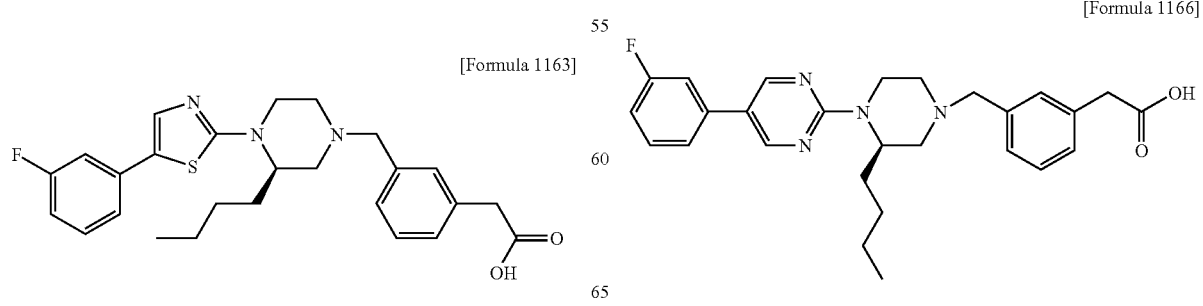
MS (ESI) m/z 468 [M+H]+
394
Example 833
[Formula 1164]
MS (ESI) m/z 477 [M+H]+
Example 834
[Formula 1165]
MS (ESI) m/z 449 [M+H]+
Example 835
[Formula 1166]
MS (ESI) m/z 463 [M+H]+

Example 836
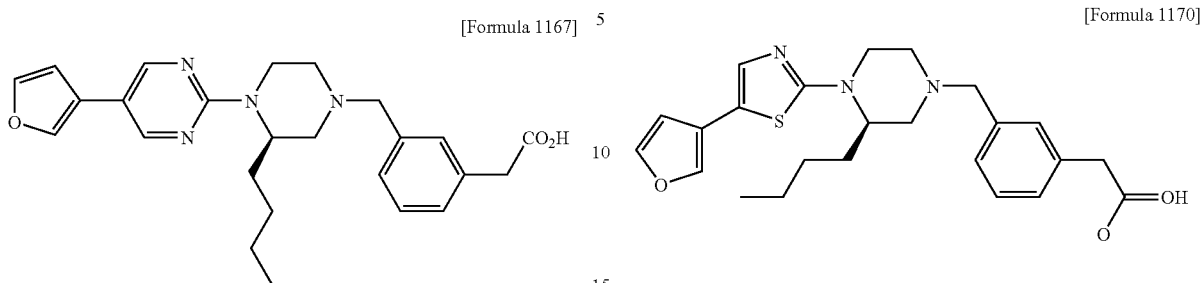
[Formula 1167]
MS (ESI) m/z 435 [M+H]+
Example 837
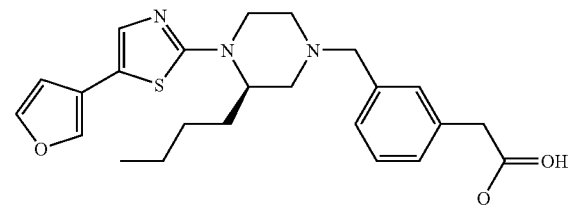
[Formula 1168]
MS (ESI) m/z 483 [M+H]+
Example 838
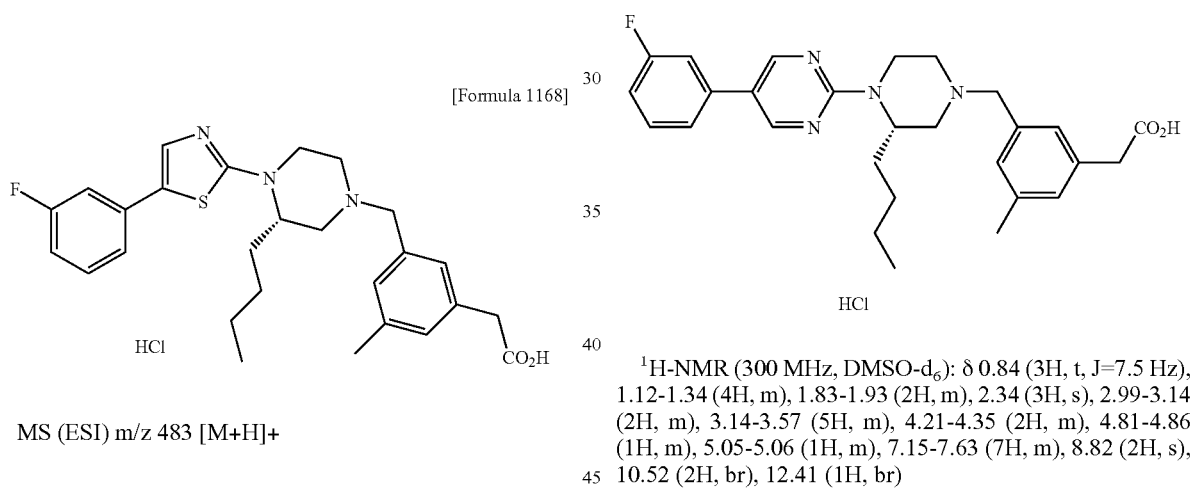
[Formula 1169]
MS (ESI) m/z 465 [M+H]+
Example 839
[Formula 1170]
1H-NMR (DMSO-d6) δ: 8.17 (1.0H, s), 7.78 (1.0H, d, J=2.01 Hz), 7.33-7.17 (4.0H, m), 6.91 (1.0H, s), 6.83 (1.0H, d, J=2.01 Hz), 4.06-0.29 (0.0H, m), 3.67-3.32 (4.0H, m), 3.19-3.16 (1.0H, m), 2.81 (1.0H, d, J=11.58 Hz), 2.67 (1.0H, d, J=11.58 Hz), 2.28-2.24 (2.0H, m), 1.95-1.92 (1.0H, br m), 1.45-1.42 (1.0H, br m), 1.28-1.08 (4.0H, m), 0.83 (3.0H, t, J=7.22 Hz).
Example 840
[Formula 1171]
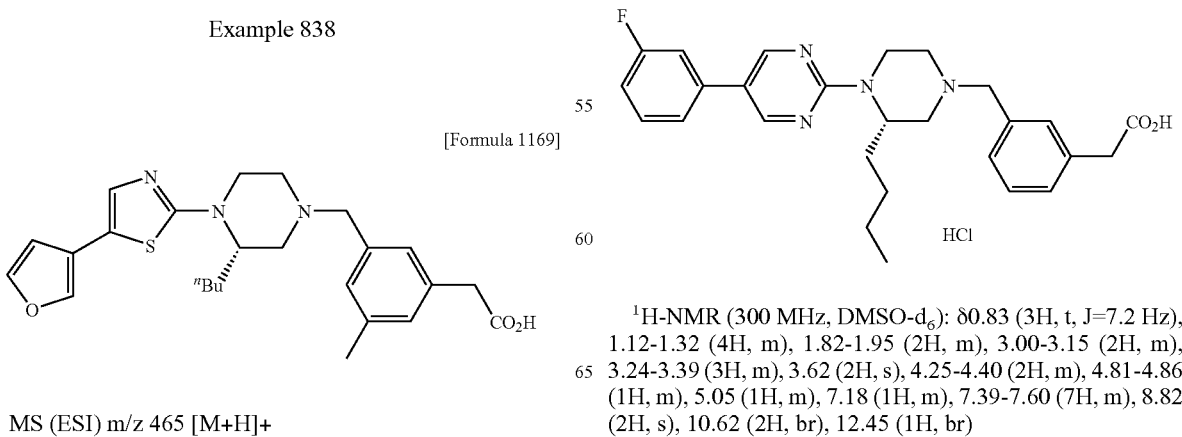
$^1$H-NMR (300 MHz, DMSO-$d_6$): δ 0.84 (3H, t, J=7.5 Hz), 1.12-1.34 (4H, m), 1.83-1.93 (2H, m), 2.34 (3H, s), 2.99-3.14 (2H, m), 3.14-3.57 (5H, m), 4.21-4.35 (2H, m), 4.81-4.86 (1H, m), 5.05-5.06 (1H, m), 7.15-7.63 (7H, m), 8.82 (2H, s), 10.52 (2H, br), 12.41 (1H, br)
Example 841
[Formula 1172]
$^1$H-NMR (300 MHz, DMSO-$d_6$): δ0.83 (3H, t, J=7.2 Hz), 1.12-1.32 (4H, m), 1.82-1.95 (2H, m), 3.00-3.15 (2H, m), 3.24-3.39 (3H, m), 3.62 (2H, s), 4.25-4.40 (2H, m), 4.81-4.86 (1H, m), 5.05 (1H, m), 7.18 (1H, m), 7.39-7.60 (7H, m), 8.82 (2H, s), 10.62 (2H, br), 12.45 (1H, br)

Example 842

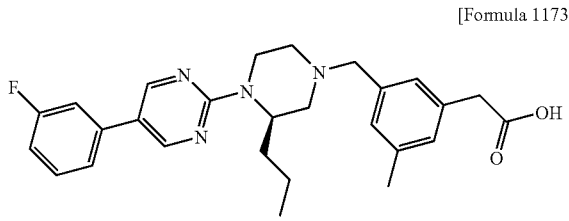
[Formula 1173]

1H-NMR (DMSO-d6) δ: 8.72 (2H, s), 7.52-7.48 (3H, m), 7.14-7.11 (1H, m), 7.03 (2H, s), 6.96 (1H, s), 4.73 (1H, s), 4.56 (1H, d, J=12.3 Hz), 3.56-3.31 (2H, m), 3.51 (2H, s), 3.19-3.15 (1H, m), 2.90 (1H, d, J=9.9 Hz), 2.79 (1H, d, J=11.0 Hz), 2.29 (3H, s), 2.03 (2H, s), 1.86-1.83 (1H, m), 1.65-1.62 (1H, m), 1.18-1.15 (2H, m), 0.88 (3H, t, J=7.1 Hz).

Example 843

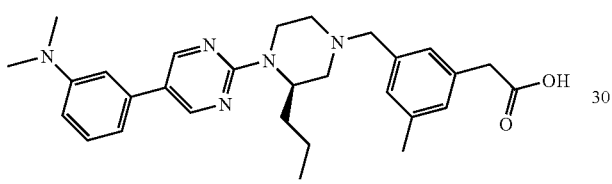
[Formula 1174]

1H-NMR (DMSO-d6) δ: 8.65 (2H, s), 7.23 (1H, t, J=8.2 Hz), 7.03 (2H, s), 6.96 (1H, s), 6.88 (1H, s), 6.87 (1H, d, J=7.8 Hz), 6.69 (1H, d, J=9.3 Hz), 4.72 (1H, s), 4.54 (1H, d, J=10.0 Hz), 3.59-3.32 (2H, m), 3.51 (2H, s), 3.15 (1H, t, J=10.0 Hz), 2.94 (6H, s), 2.91-2.88 (1H, m), 2.77 (1H, t, J=11.0 Hz), 2.29 (3H, s), 2.05-1.97 (2H, m), 1.89-1.81 (1H, m), 1.65-1.58 (1H, m), 1.18-1.14 (2H, m), 0.88 (3H, t, J=7.3 Hz).

Example 844

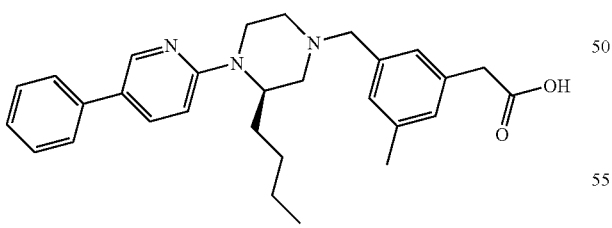
[Formula 1175]

1H-NMR (DMSO-d6) δ: 8.42 (1H, d, J=2.7 Hz), 7.82 (1H, dd, J=8.9, 2.6 Hz), 7.62 (1H, d, J=1.4 Hz), 7.59 (1H, s), 7.42 (2H, t, J=7.5 Hz), 7.29 (1H, d, J=7.4 Hz), 7.04 (2H, d, J=8.8 Hz), 6.97 (1H, s), 6.81 (1H, d, J=9.1 Hz), 4.31 (1H, s), 4.14 (1H, d, J=10.9 Hz), 3.62-3.33 (2H, m), 3.50 (2H, s), 3.14-3.06 (1H, m), 2.91 (1H, d, J=10.0 Hz), 2.80 (1H, d, J=10.0 Hz), 2.29 (3H, s), 2.09 (1H, t, J=10.0 Hz), 2.01-1.92 (2H, m), 1.47-1.38 (1H, m), 1.29-1.23 (2H, m), 1.15-1.07 (2H, m), 0.82 (3H, t, J=7.1 Hz).

Example 845

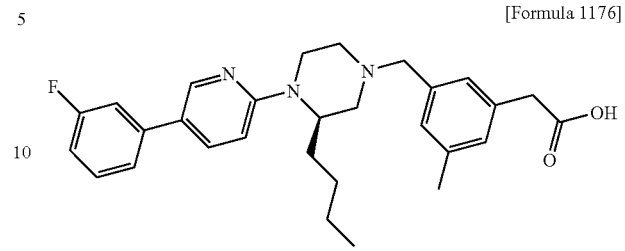
[Formula 1176]

1H-NMR (DMSO-d6) δ: 8.47 (1H, d, J=2.5 Hz), 7.87 (1H, dd, J=8.9, 2.7 Hz), 7.46 (3H, t, J=8.8 Hz), 7.05 (1H, s), 7.02 (1H, s), 6.97 (1H, s), 6.81 (1H, d, J=9.1 Hz), 4.32 (1H, s), 4.16 (1H, d, J=12.6 Hz), 3.63-3.28 (2H, m), 3.50 (2H, s), 3.10 (1H, t, J=12.6 Hz), 2.92 (1H, d, J=9.9 Hz), 2.80 (1H, d, J=10.9 Hz), 2.29 (3H, s), 2.09 (1H, t, J=9.4 Hz), 1.98-1.91 (2H, m), 1.44-1.39 (1H, m), 1.31-1.22 (2H, m), 1.15-1.06 (2H, m), 0.82 (3H, t, J=7.2 Hz).

Example 846

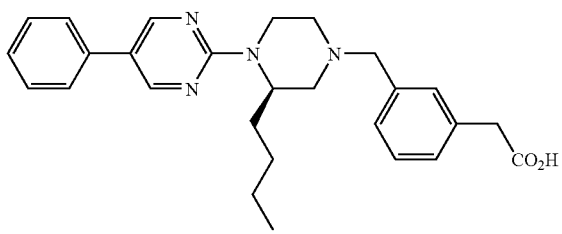
[Formula 1177]

MS (ESI); m/z 445 [M+H]+

Example 847

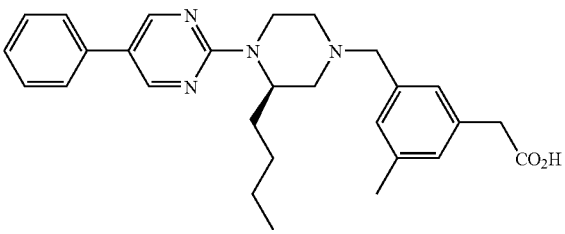
[Formula 1178]

MS (ESI) m/z 459 [M+H]+

Example 848

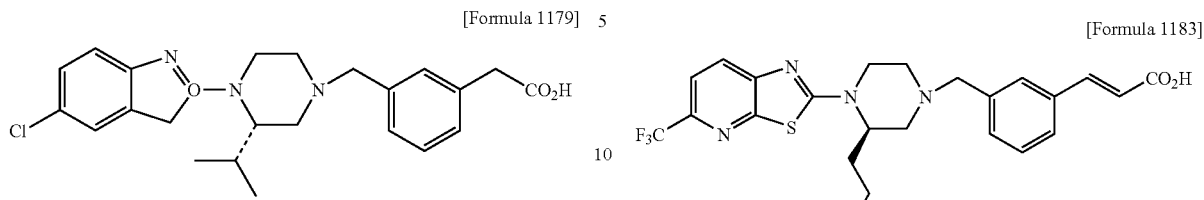

[Formula 1179]

MS (ESI) m/z 426 [M–H]–

Example 849

[Formula 1180]

MS (ESI) m/z 440 [M–H]–

Example 850

[Formula 1181]

1H-NMR (DMSO-d6) δ: 1.03 (6H, d, J=6.0 Hz), 2.27 (3H, s), 2.63-2.80 (2H, m), 2.85-2.97 (2H, m), 3.49 (2H, s), 3.69-3.78 (4H, m), 6.86-7.61 (9H, m).

Example 851

[Formula 1182]

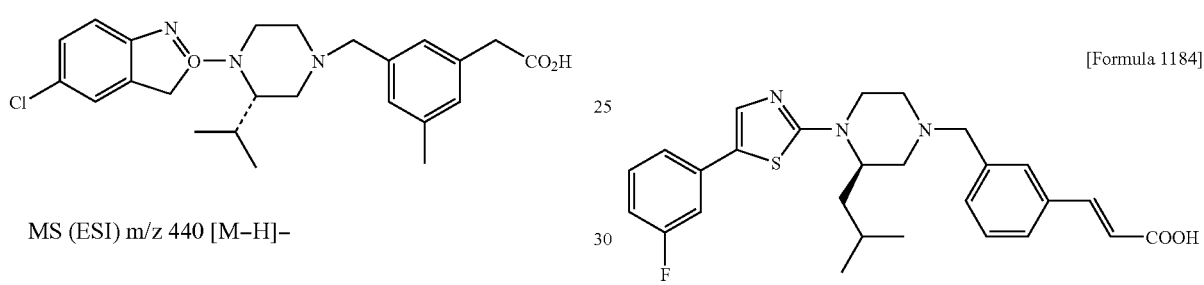

TLC R$_f$ 0.64 (hexane:AcOEt=1:1)

Example 852

[Formula 1183]

TLC R$_f$ 0.70 (hexane:AcOEt=1:1)

Example 853

[Formula 1184]

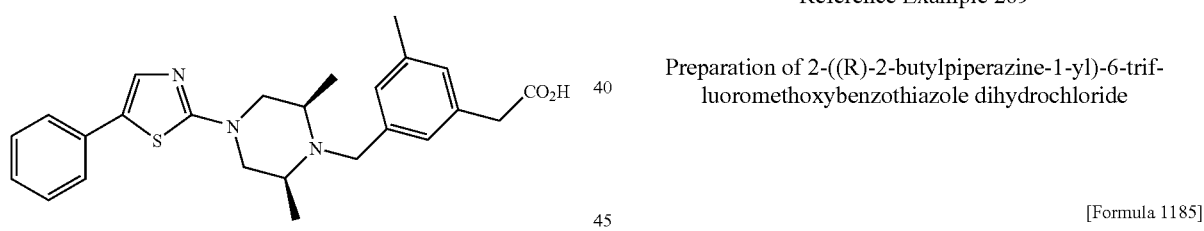

TLC: (SiO2) AcOEt-Hexane (1:1) Rf=0.34

Reference Example 269

Preparation of 2-((R)-2-butylpiperazine-1-yl)-6-trifluoromethoxybenzothiazole dihydrochloride

[Formula 1185]

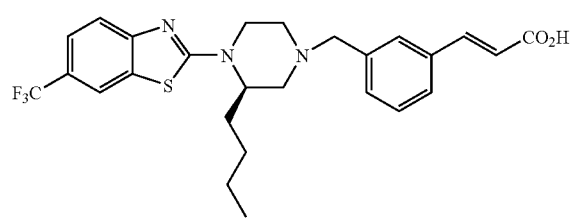

The above compound was synthesized with 2-chloro-6-trifluoromethyl benzothiazole and piperazine-1-carboxylic acid t-butyl ester as starting materials by a similar method of Reference Example 84 or 155.

$^1$H-NMR (DMSO-d$_6$) δ: 0.90 (3H, t, J=7.0 Hz), 1.31-1.37 (4H, m), 1.85-1.95 (2H, m), 3.03-3.18 (1H, m), 3.25-3.39 (3H, m), 3.42-3.55 (1H, m), 4.13-4.33 (2H, m), 7.31 (1H, dd, J=8.5, 1.8 Hz), 7.54 (1H, d, J=8.5 Hz), 7.99 (1H, d, J=1.8 Hz), 9.14 (1H, br s), 9.57 (1H, br s).

Reference Example 270

Preparation of [3-[(R)-3-butyl-4-(6-trifluoromethoxybenzothiazole-2-yl)-piperazine-1-ylmethyl]-5-methylphenoxy]acetic acid methyl ester

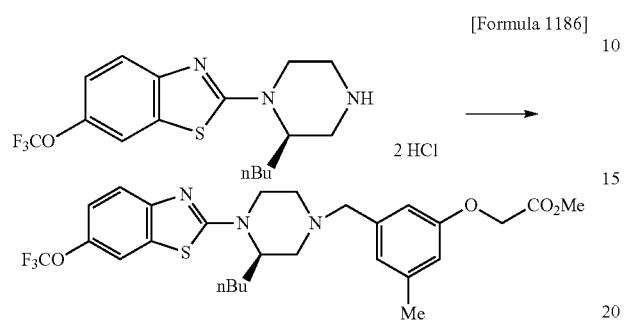

[Formula 1186]

A mixture of 2-((R)-2-butylpiperazine-1-yl)-6-trifluoromethoxybenzothiazole dihydrochloride (170 mg), (3-chloromethyl-5-methylphenoxy)acetic acid methyl ester (108 mg), potassium carbonate (270 mg), potassium iodide (65 mg) and dimethylformamide (4 mL) was stirred at room temperature for 24 hours. To the reaction solution was added water and extracted with ethyl acetate. The organic layer was washed with water and brine, and dried over magnesium sulphate. The solvent was evaporated under reduced pressure and the residue was purified by column chromatograph on silica gel to give the title compound (203 mg). Yield: 94%. TLC Rf 0.62 (AcOEt/n-hexane=1/5).

Example 854

Preparation of [3-[(R)-3-butyl-4-(6-trifluoromethoxybenzothiazole-2-yl)-piperazine-1-ylmethyl]-5-methylphenoxy]acetic acid

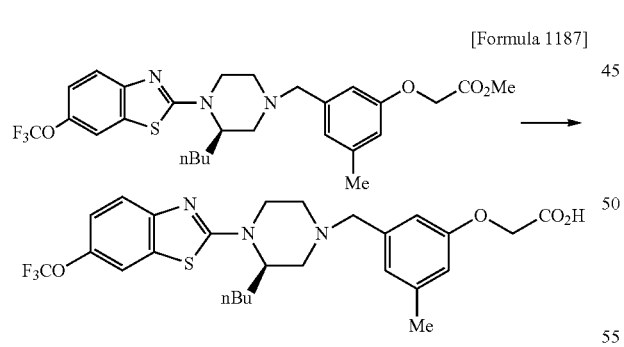

[Formula 1187]

A mixture of [3-[(R)-3-butyl-4-(6-trifluoromethoxybenzothiazole-2-yl)-piperazine-1-ylmethyl]-5-methylphenoxy]acetic acid methyl ester (203 mg), 2N sodium hydroxide (0.46 mL), tetrahydrofuran (2 mL) and methanol (2 mL) was stirred at room temperature for 16 hours. To the reaction solution were added water and chloroform. The mixture was neutralized with 2N hydrochloric acid. The reaction solution was extracted with chloroform. The organic layer was washed with brine, and dried over magnesium sulphate. The solvent was evaporated under reduced pressure to give the title compound (182 mg). Yield: 91%.

1H-NMR (DMSO-d6) δ: 7.90 (1.0H, d, J=1.65 Hz), 7.48 (1.0H, d, J=8.78 Hz), 7.25 (1.0H, dd, J=8.78, 1.65 Hz), 6.74 (1.0H, s), 6.67 (1.0H, s), 6.61 (1.0H, s), 4.48 (2.0H, s), 4.06-3.80 (1.0H, m), 3.72-3.20 (3.0H, m), 2.90 (1.0H, d, J=12.62 Hz), 2.81

The following compounds were obtained by similar methods as above.

Example 855

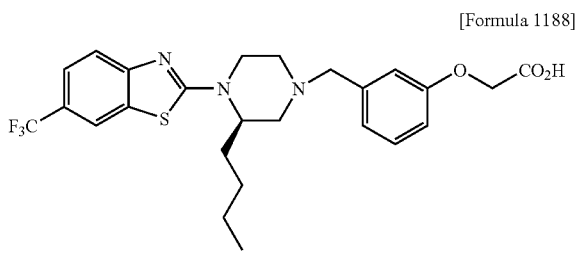

[Formula 1188]

MS (ESI) m/z 508 [M+H]+

Example 856

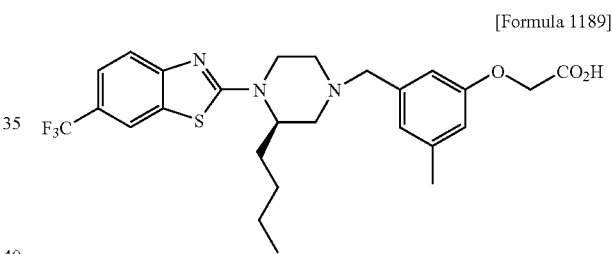

[Formula 1189]

1H-NMR (DMSO-d6) δ: 8.23 (1.0H, s), 7.58-7.54 (2.0H, m), 6.74 (1.0H, s), 6.68 (1.0H, s), 6.62 (1.0H, s), 4.48 (2.0H, s), 4.11-3.87 (1.0H, m), 3.58-3.33 (3.0H, m), 2.94 (1.0H, d, J=12.42 Hz), 2.83 (1.0H, d, J=12.42 Hz), 2.27 (3.0H, s), 2.16-2.12 (2.0H, m), 2.01-1.92 (1.0H, m), 1.80-1.76 (1.0H, m), 1.34-1.21 (4.0H, m), 0.86 (3.0H, t, J=7.22 Hz).

Example 857

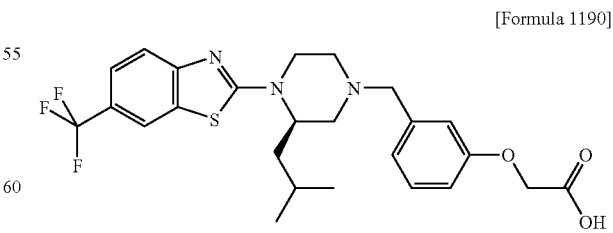

[Formula 1190]

1H-NMR (DMSO-d6) δ: 8.22 (1.0H, s), 7.59-7.49 (2.0H, m), 7.24 (1.0H, dd, J=7.72, 7.72 Hz), 6.95-6.87 (2.0H, m), 6.82-6.76 (1.0H, m), 4.60 (2.0H, s), 4.20-3.89 (2.0H, m), 3.57 (1.0H, d, J=13.76 Hz), 3.47-3.22 (2.0H, m), 2.96-2.70 (2.0H, m), 2.24-2.08 (2.0H, m), 1.93-1.79 (1.5H, br m), 1.70-1.56 (1.2H, br m), 1.52-1.37 (1.4H, br m), 0.92 (6.0H, d, J=6.55 Hz).

Example 858

[Formula 1191]

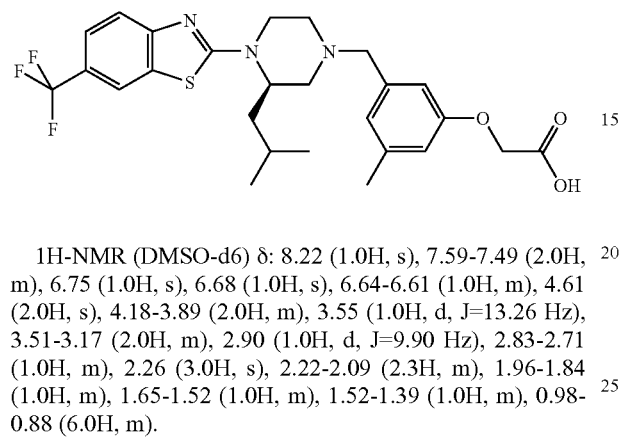

1H-NMR (DMSO-d6) δ: 8.22 (1.0H, s), 7.59-7.49 (2.0H, m), 6.75 (1.0H, s), 6.68 (1.0H, s), 6.64-6.61 (1.0H, m), 4.61 (2.0H, s), 4.18-3.89 (2.0H, m), 3.55 (1.0H, d, J=13.26 Hz), 3.51-3.17 (2.0H, m), 2.90 (1.0H, d, J=9.90 Hz), 2.83-2.71 (1.0H, m), 2.26 (3.0H, s), 2.22-2.09 (2.3H, m), 1.96-1.84 (1.0H, m), 1.65-1.52 (1.0H, m), 1.52-1.39 (1.0H, m), 0.98-0.88 (6.0H, m).

Example 859

[Formula 1192]

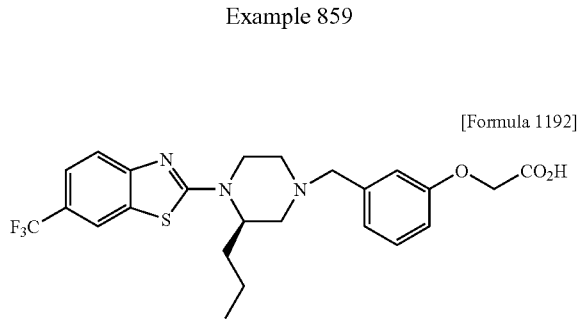

MS (ESI) m/z 492 [M−H]−

Example 860

[Formula 1193]

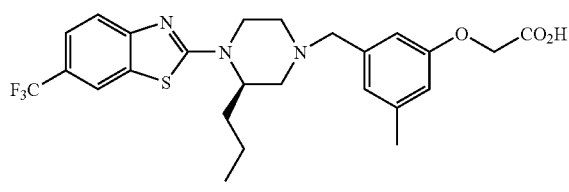

MS (ESI) m/z 506 [M−H]−

Example 861

[Formula 1194]

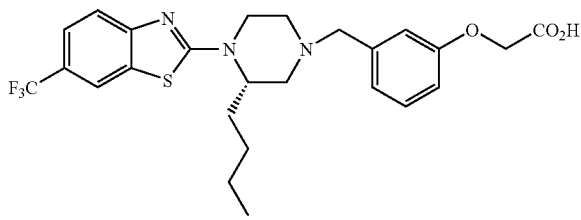

1H-NMR (300 MHz, DMSO-d6) δ 0.85 (3H, t, J=7.2 Hz), 1.16-1.36 (4H, m), 1.79-1.95 (2H, m), 2.15-2.19 (2H, m), 2.81-2.92 (2H, m), 3.34-3.60 (3H, m), 4.03 (2H, m), 4.66 (2H, s), 6.82 (1H, dd, J=7.8 Hz, 1.8 Hz), 6.91 (1H, s), 6.94 (1H, d, J=7.8 Hz), 7.26 (1H, t, J=7.8 Hz), 7.51-7.58 (2H, m), 8.22 (1H, s), 13.00 (1H, br s)

Example 862

[Formula 1195]

1H-NMR (300 MHz, DMSO-d6) δ 0.84 (3H, t, J=7.2 Hz), 1.15-1.36 (4H, m), 1.73-1.97 (2H, m), 2.11-2.16 (2H, m), 2.27 (3H, s), 2.79-2.92 (2H, m), 3.33-3.57 (3H, m), 4.02 (2H, m), 4.62 (2H, s), 6.63 (1H, s), 6.69 (1H, s), 6.76 (1H, s), 7.51-7.58 (2H, m), 8.22 (1H, s), 12.98 (1H, br s)

Example 863

[Formula 1196]

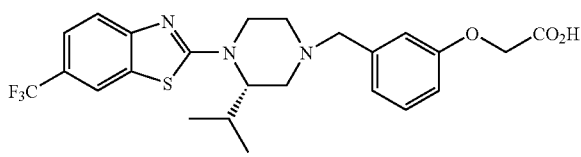

MS (ESI) 492[M−H]−

Example 864

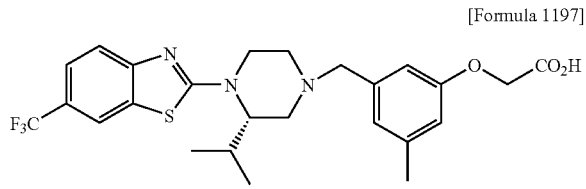

[Formula 1197]

MS (ESI) 506[M–H]–

Example 865

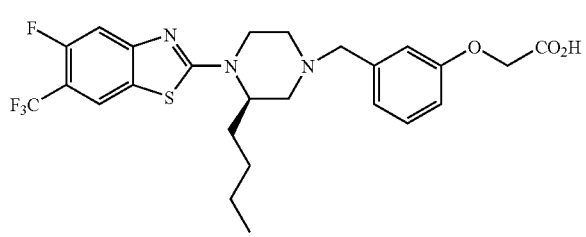

[Formula 1198]

¹H-NMR (300 MHz, DMSO-d6) δ 0.84 (3H, t, J=7.2 Hz), 1.15-1.35 (4H, m), 1.77-1.95 (2H, m), 2.10-2.18 (2H, m), 2.80-2.92 (2H, m), 3.25-3.59 (3H, m), 4.01 (2H, m), 4.61 (2H, s), 6.80 (1H, d, J=7.8 Hz), 6.89 (1H, s), 6.92 (1H, d, J=7.8 Hz), 7.25 (1H, t, J=7.8 Hz), 7.43 (1H, d, J=12.3 Hz), 8.23 (1H, d, J=7.5 Hz)

Example 866

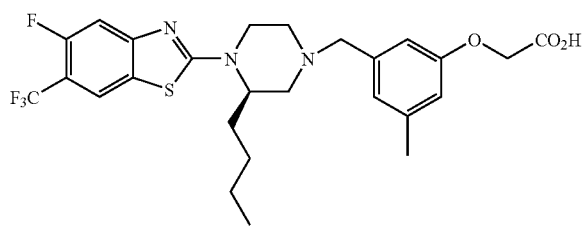

[Formula 1199]

1H-NMR (300 MHz, DMSO-d6) δ 0.84 (3H, t, J=7.2 Hz), 1.15-1.35 (4H, m), 1.74-1.99 (2H, m), 2.11-2.14 (2H, m), 2.26 (3H, s), 2.79-2.92 (2H, m), 3.33-3.57 (3H, m), 3.99 (2H, m), 4.61 (2H, s), 6.63 (1H, s), 6.69 (1H, s), 6.75 (1H, s), 7.43 (1H, d, J=12.3 Hz), 8.23 (1H, d, J=7.5 Hz)

Example 867

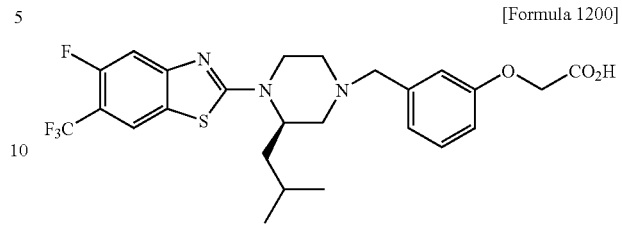

[Formula 1200]

1H-NMR (DMSO-d6) δ: 8.24 (1.0H, d, J=7.72 Hz), 7.42 (1.0H, d, J=12.59 Hz), 7.24 (1.0H, dd, J=7.72, 7.72 Hz), 6.95-6.86 (2.0H, m), 6.82-6.75 (1.0H, m), 4.55 (2.0H, s), 4.11-3.86 (2.0H, m), 3.60-3.20 (3.0H, m), 2.90 (1.0H, d, J=12.25 Hz), 2.77 (1.0H, d, J=12.25 Hz), 2.25-2.06 (2.0H, m), 1.92-1.76 (1.0H, m), 1.70-1.54 (1.0H, m), 1.53-1.35 (1.0H, m), 0.95-0.88 (6.0H, m).

Example 868

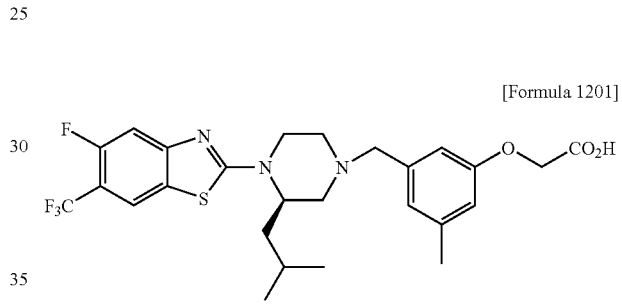

[Formula 1201]

1H-NMR (DMSO-d6) δ: 8.24 (1.0H, d, J=7.39 Hz), 7.42 (1.0H, d, J=12.59 Hz), 6.75 (1.0H, s), 6.68 (1.0H, s), 6.62 (1.0H, s), 4.61 (2.0H, s), 4.19-3.89 (2.0H, m), 3.59-3.21 (3.0H, m), 2.90 (1.0H, d, J=10.74 Hz), 2.83-2.71 (1.0H, m), 2.26 (3.0H, s), 2.21-2.08 (2.0H, m), 1.96-1.83 (1.0H, m), 1.65-1.52 (1.0H, m), 1.51-1.36 (1.0H, m), 0.95-0.88 (6.0H, m).

Example 869

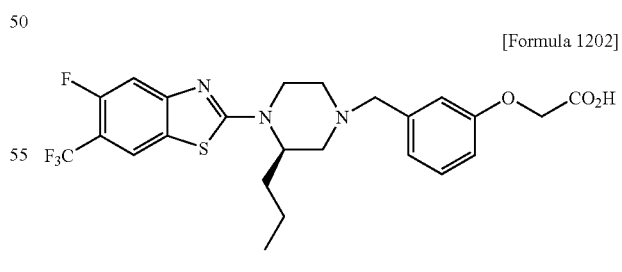

[Formula 1202]

1H-NMR (DMSO-d6) δ: 8.23 (1.0H, d, J=7.39 Hz), 7.43 (1.0H, d, J=12.42 Hz), 7.25 (1.0H, dd, J=7.72, 7.72 Hz), 6.96-6.88 (2.0H, m), 6.80 (1.0H, dd, J=8.31, 2.27 Hz), 4.64 (2.0H, s), 4.15-3.89 (2.0H, m), 3.60-3.22 (3.0H, m), 2.89 (1.0H, d, J=11.92 Hz), 2.82 (2.0H, d, J=11.92 Hz), 2.23-2.07 (2.0H, m), 1.90-1.76 (2.0H, m), 1.31-1.14 (2.0H, m), 0.90 (3.0H, t, J=7.30 Hz).

Example 870
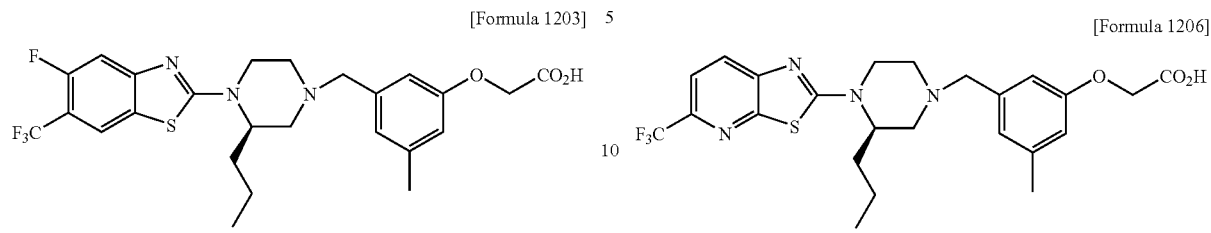
[Formula 1203]
1H-NMR (DMSO-d6) δ: 8.23 (1.0H, d, J=7.22 Hz), 7.43 (1.0H, d, J=12.42 Hz), 6.75 (1.0H, s), 6.69 (1.0H, s), 6.63 (1.0H, s), 4.62 (2.0H, s), 4.17-3.86 (2.0H, m), 3.57-3.22 (3.0H, m), 2.89 (1.0H, d, J=11.58 Hz), 2.81 (1.0H, d, J=11.58 Hz), 2.26 (3.0H, s), 2.19-2.07 (2.0H, m), 1.97-1.71 (2.0H, m), 1.31-1.15 (2.0H, m), 0.90 (3.0H, t, J=7.30 Hz).
Example 871
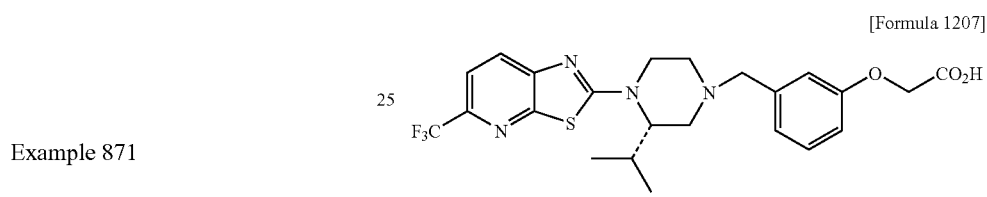
[Formula 1204]
1H-NMR (DMSO-d6) δ: 7.87 (1.0H, d, J=8.73 Hz), 7.77 (1.0H, d, J=8.39 Hz), 6.71 (1.0H, s), 6.64 (1.0H, s), 6.57 (1.0H, s), 4.28 (2.0H, s), 3.53-3.39 (6.0H, m), 3.00-2.71 (2.0H, m), 2.30-2.26 (3.0H, m), 2.18-2.15 (2.0H, m), 1.36-1.17 (4.0H, m), 0.87 (3.0H, t, J=7.13 Hz).
Example 872
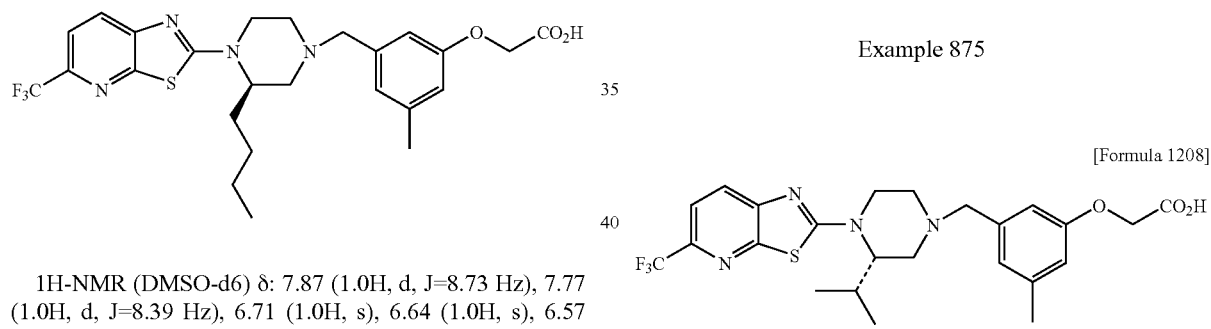
[Formula 1205]
MS (ESI) 493 [M−H]−
Example 873
[Formula 1206]
MS (ESI) 507 [M−H]−
Example 874
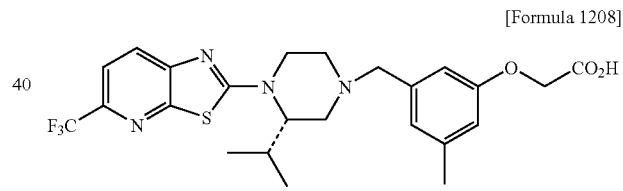
[Formula 1207]
MS (ESI) m/z 493 [M−H]−
Example 875
[Formula 1208]
MS (ESI) m/z 507 [M−H]−
Example 876
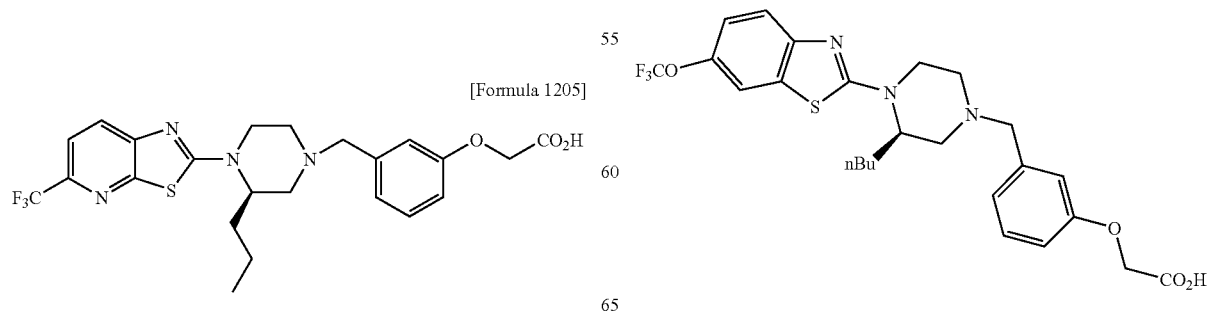
[Formula 1209]
MS (ESI) m/z 524 [M+H]+

Example 877

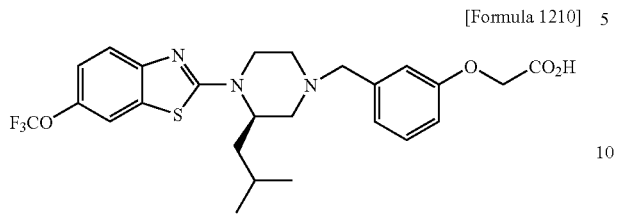

[Formula 1210]

1H-NMR (DMSO-d6) δ: 7.89 (1.0H, d, J=2.18 Hz), 7.45 (1.0H, d, J=8.73 Hz), 7.29-7.20 (2.0H, m), 6.95-6.88 (2.0H, m), 6.80 (1.0H, dd, J=8.73, 2.18 Hz), 4.64 (2.0H, s), 4.11-4.01 (1.0H, m), 3.97-3.85 (1.0H, m), 3.56 (1.0H, d, J=13.76 Hz), 3.44-3.29 (2.0H, m), 2.88 (1.0H, d, J=10.74 Hz), 2.78 (1.0H, d, J=10.74 Hz), 2.22-2.06 (2.0H, m), 1.90-1.76 (1.0H, m), 1.67-1.54 (1.0H, m), 1.50-1.37 (1.0H, m), 0.91 (6.0H, d, J=6.55 Hz).

Example 878

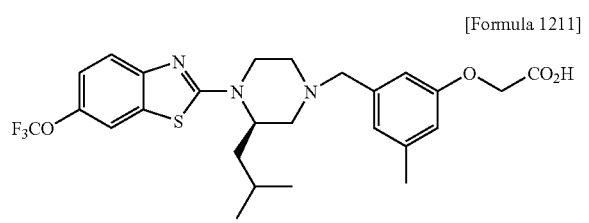

[Formula 1211]

1H-NMR (DMSO-d6) δ: 7.89 (1.0H, d, J=2.18 Hz), 7.45 (1.0H, d, J=8.73 Hz), 7.23 (1.0H, dd, J=8.73, 2.18 Hz), 6.75 (1.0H, s), 6.68 (1.0H, s), 6.62 (1.0H, s), 4.61 (2.0H, s), 4.09-4.00 (1.0H, m), 3.96-3.86 (1.0H, m), 3.55 (2.0H, d, J=13.26 Hz), 3.50-3.14 (1.0H, m), 2.89 (1.0H, d, J=11.92 Hz), 2.77 (1.0H, d, J=11.92 Hz), 2.26 (3.0H, s), 2.21-2.08 (2.0H, m), 1.96-1.83 (1.0H, m), 1.62-1.36 (2.0H, m), 0.94-0.88 (6.0H, m).

Example 879

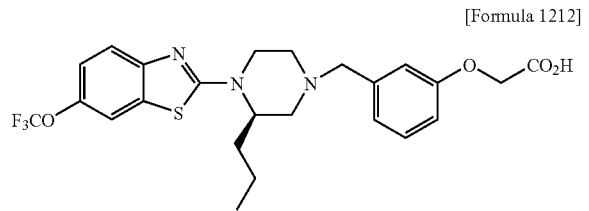

[Formula 1212]

1H-NMR (300 MHz, DMSO-d6) δ0.90 (3H, t, J=7.2 Hz), 1.14-1.28 (2H, m), 1.72-1.90 (2H, m), 2.12-2.18 (2H, m), 2.79-2.89 (2H, m), 3.33-3.58 (3H, m), 3.89-4.00 (2H, m), 4.66 (2H, s), 6.80 (1H, dd, J=8.1 Hz, 1.8 Hz), 6.90-6.94 (2H, m), 7.22-7.28 (2H, m), 7.45 (1H, d, J=8.7 Hz), 7.88 (1H, s), 12.98 (1H, br s)

Example 880

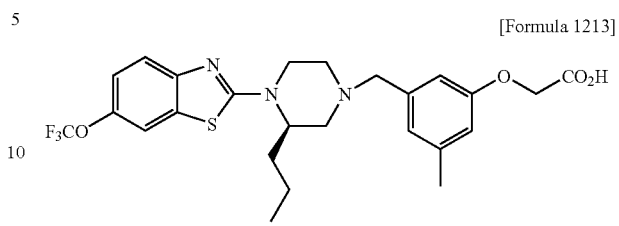

[Formula 1213]

1H-NMR (300 MHz, DMSO-d6) δ0.88 (3H, t, J=7.5 Hz), 1.21 (2H, m), 1.71-1.91 (2H, m), 2.10-2.13 (2H, m), 2.24 (3H, s), 2.76-2.88 (2H, m), 3.30-3.53 (3H, m), 3.87-3.98 (2H, m), 4.60 (2H, s), 6.61 (1H, s), 6.67 (1H, s), 6.73 (1H, s), 7.21 (1H, d, J=8.7 Hz), 7.43 (1H, d, J=8.7 Hz), 7.85 (1H, s), 13.02 (1H, br s)

Example 881

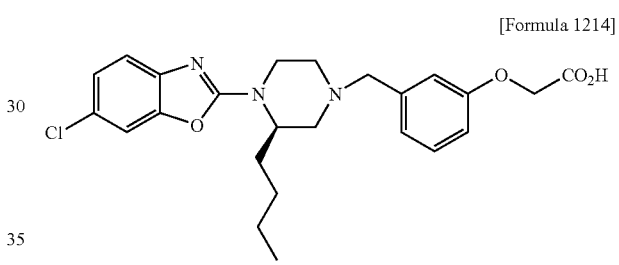

[Formula 1214]

1H-NMR (DMSO-d6) δ: 7.54 (1H, s), 7.28-7.15 (2H, m), 6.74 (1H, s), 6.94-6.89 (2H, m), 6.80 (1H, d, J=7.8 Hz), 4.64 (2H, s), 4.13 (1H, s), 3.95 (1H, m), 3.57-3.32 (3H, m), 2.90-2.76 (2H, m), 2.19-2.11 (2H, m), 1.85-1.80 (2H, m), 1.28 (2H, q, J=7.2 Hz), 1.13 (2H, q, J=7.5 Hz), 0.83 (3H, t, J=7.2 Hz).

Example 882

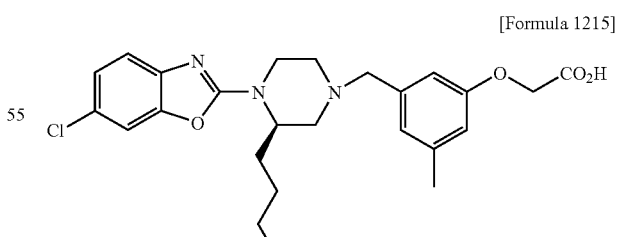

[Formula 1215]

¹H-NMR (DMSO-d6) δ: 7.54 (1H, d, J=1.85 Hz), 7.20 (2H, d, J=8.4 Hz), 6.74 (1H, s), 6.68 (1H, s), 6.62 (1H, s), 4.62 (2H, s), 4.14-3.92 (2H, m), 3.52 (1H, d, J=13.8 Hz), 2.90-2.75 2H, m), 2.26 (3H, s), 2.15-2.11 (2H, m), 1.80 (2.0H, m), 1.26 (2H, t, J=7.2 Hz), 0.85 (7.0H, t, J=5.96 Hz).

Example 883

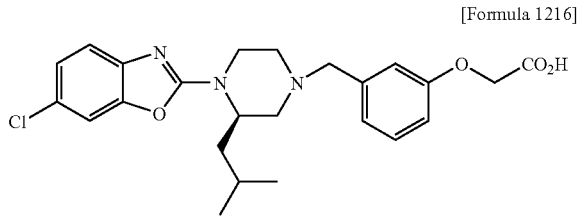

[Formula 1216]

1H-NMR (DMSO-d6) δ: 7.54 (1.0H, d, J=2.18 Hz), 7.28-7.21 (2.0H, m), 7.17 (1.0H, dd, J=8.23, 2.18 Hz), 6.94-6.87 (2.0H, m), 6.79 (1.0H, dd, J=8.23, 2.18 Hz), 4.63 (2.0H, s), 4.29-4.21 (1.0H, m), 3.94 (1.0H, d, J=13.93 Hz), 3.54 (1.0H, d, J=13.93 Hz), 3.45-3.24 (2.0H, m), 2.86 (1.0H, d, J=10.74 Hz), 2.75 (1.3H, d, J=10.74 Hz), 2.30-2.05 (2.0H, m), 1.81-1.62 (2.0H, m), 1.47-1.35 (1.0H, m), 0.93-0.86 (6.0H, m).

Example 884

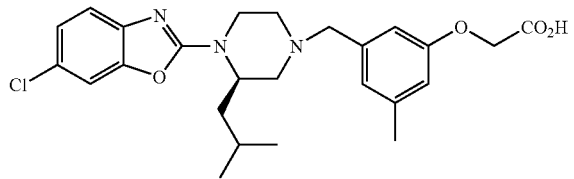

[Formula 1217]

1H-NMR (DMSO-d6) δ: 7.54 (1.0H, d, J=1.85 Hz), 7.24 (1.0H, d, J=8.56 Hz), 7.17 (1.0H, dd, J=8.56, 1.85 Hz), 6.74 (1.0H, s), 6.68 (1.0H, s), 6.62 (1.0H, s), 4.62 (2.0H, s), 4.29-4.20 (1.0H, m), 3.94 (1.0H, d, J=12.25 Hz), 3.52 (1.0H, d, J=13.76 Hz), 3.45-3.36 (2.0H, m), 2.87 (1.0H, d, J=10.58 Hz), 2.74 (1.0H, d, J=10.58 Hz), 2.26 (3.0H, s), 2.20-2.05 (2.0H, m), 1.80-1.62 (2.0H, m), 1.49-1.34 (1.0H, m), 0.90 (7.0H, t, J=5.96 Hz).

Example 885

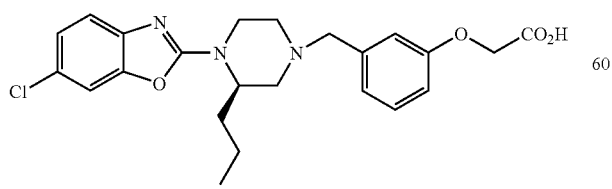

[Formula 1218]

MS (ESI) m/z 442 [M−H]−

Example 886

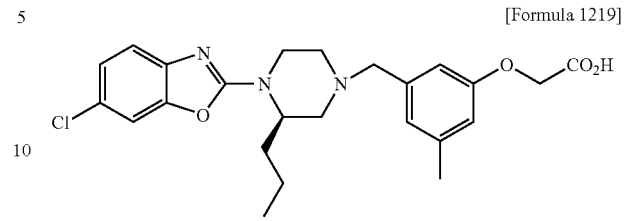

[Formula 1219]

MS (ESI) m/z 456[M−H]−

Example 887

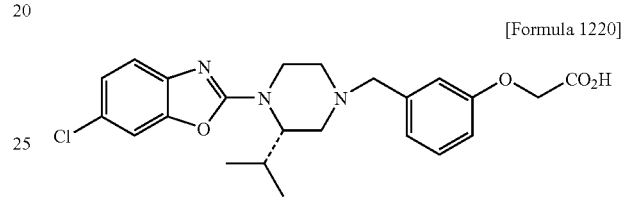

[Formula 1220]

MS (ESI) m/z 442[M−H]−

Example 888

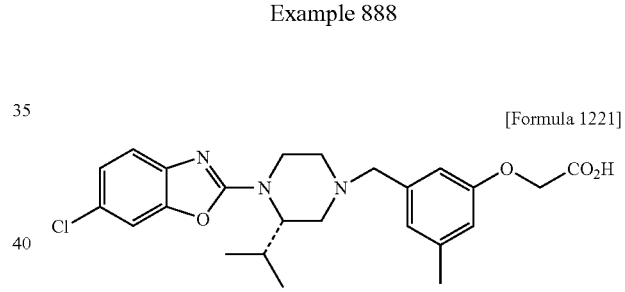

[Formula 1221]

MS (ESI) m/z 456[M−H]−

Example 889

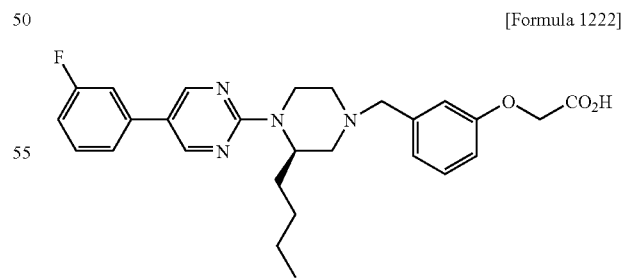

[Formula 1222]

1H-NMR (DMSO-d6) δ: 8.74 (2H, s), 7.55-7.45 (3H, m), 7.24 (1H, t, J=8.1 Hz), 7.14 (1H, m), 6.95-6.90 (2H, m), 6.80 (1H, dd, J=8.1, 2.4 Hz), 4.64 (2H, s), 4.55 (1H, m), 3.57-3.53 (2H, m), 3.15 (1H, m), 2.89-2.79 (2H, m), 2.06-2.01 (2H, m), 1.84 (1H, m), 1.68 (1H, m), 127 (2H, q, J=7.2 Hz), 117 (2H, q, J=7.2 Hz), 0.82 (3H, t, J=7.1 Hz).

Example 890

[Formula 1223]

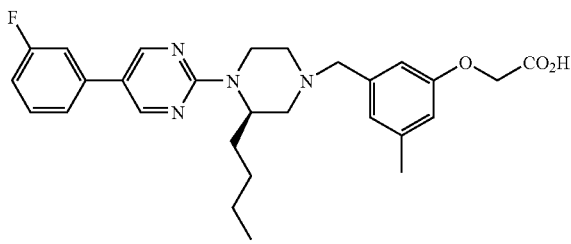

1H-NMR (DMSO-d6) δ: 8.74 (2H, s), 7.55-7.45 (3H, m), 7.24 (1H, t, J=8.1 Hz), 6.75 (1H, s), 6.68 (1H, s), 6.62 (1H, s), 4.74 (1H, s), 4.64 (2H, s), 4.55 (1H, m), 3.57-3.53 (2H, m), 3.15 (1H, m), 2.89-2.79 (2H, m), 2.25 (3H, s), 2.06-2.01 (2H, m), 1.84 (1H, m), 1.68 (1H, m), 127 (2H, q, J=7.2 Hz), 117 (2H, q, J=7.2 Hz), 0.82 (3H, t, J=7.1 Hz).

Example 891

[Formula 1224]

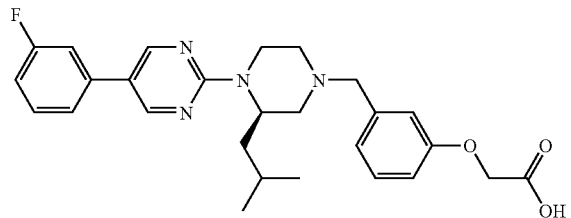

1H-NMR (DMSO-d6) δ: 8.73 (2.0H, s), 7.57-7.42 (3.0H, m), 7.25 (1.0H, dd, J=7.89, 7.89 Hz), 7.18-7.09 (1.0H, m), 6.96-6.87 (2.0H, m), 6.80 (1.0H, dd, J=7.89, 2.52 Hz), 4.92-4.83 (1.0H, m), 4.66-4.52 (3.0H, m), 3.53 (1.0H, d, J=13.60 Hz), 3.48-3.07 (2.0H, m), 2.86 (1.0H, d, J=11.25 Hz), 2.77 (1.0H, d, J=11.25 Hz), 2.11-1.94 (2.0H, m), 1.74-1.61 (2.0H, m), 1.46-1.34 (1.0H, m), 0.93-0.86 (6.0H, m).

Example 892

[Formula 1225]

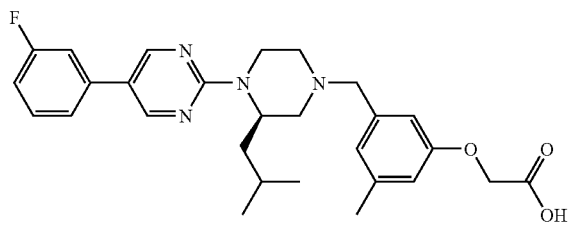

1H-NMR (DMSO-d6) δ: 8.73 (2.0H, s), 7.58-7.42 (3.0H, m), 7.18-7.09 (1.0H, m), 6.76 (1.0H, s), 6.69 (1.0H, s), 6.62 (1.0H, s), 4.91-4.81 (1.0H, m), 4.64-4.52 (3.0H, m), 3.51 (1.0H, d, J=13.60 Hz), 3.47-3.09 (2.0H, m), 2.92-2.82 (1.0H, m), 2.80-2.71 (1.0H, m), 2.26 (3.0H, s), 2.08-1.95 (2.0H, m), 1.81-1.69 (1.0H, m), 1.66-1.53 (1.0H, m), 1.49-1.35 (1.0H, m), 0.93-0.86 (6.0H, m).

Example 893

[Formula 1226]

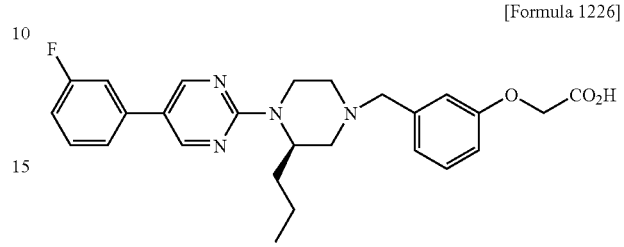

1H-NMR (DMSO-d6) δ: 8.74 (2H, s), 7.55-7.45 (3H, m), 7.25 (1H, t, J=8.0 Hz), 7.14 (1H, m), 6.94-6.90 (2H, m), 6.79 (1H, dd, J=8.1, 2.4 Hz), 4.78 (1H, s), 4.64 (2H, s), 4.59 (1H, m), 3.57-3.10 (3H, m), 2.89-2.79 (2H, m), 2.08-2.04 (2H, m), 1.77 (2H, m), 1.17 (2H, q, J=7.2 Hz), 0.87 (3H, t, J=7.1 Hz).

Example 894

[Formula 1227]

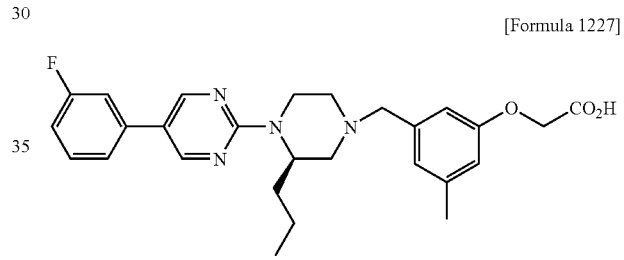

1H-NMR (DMSO-d6) δ: 8.74 (2H, s), 7.55-7.45 (3H, m), 7.25 (1H, t, J=8.0 Hz), 6.75 (1H, s), 6.68 (1H, s), 6.62 (1H, s), 4.78 (1H, s), 4.64 (2H, s), 4.59 (1H, m), 3.57-3.10 (3H, m), 2.89-2.79 (2H, m), 2.26 (3H, s), 2.08-2.04 (2H, m), 1.77 (2H, m), 1.17 (2H, q, J=7.2 Hz), 0.87 (3H, t, J=7.1 Hz).

Example 895

[Formula 1228]

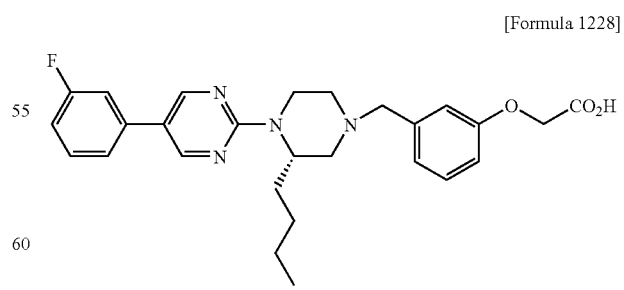

1H-NMR (300 MHz, DMSO-d6) δ0.83 (3H, t, J=7.2 Hz), 1.13-1.33 (4H, m), 1.62-1.91 (2H, m), 1.98-2.04 (2H, m), 2.79-2.90 (2H, m), 3.12-3.56 (3H, m), 4.52-4.57 (3H, m), 4.74 (1H, m), 6.77 (1H, d, J=7.8 Hz), 6.88 (1H, s), 6.91 (1H, d, J=7.8 Hz), 7.11-7.16 (1H, m), 7.23 (1H, t, J=7.8 Hz), 7.43-7.55 (3H, m), 8.73 (2H, s)

Example 896

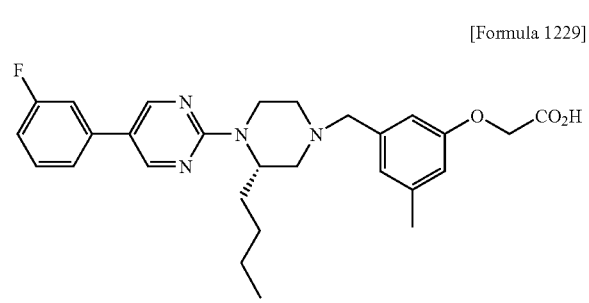

[Formula 1229]

1H-NMR (300 MHz, DMSO-d6) δ0.83 (3H, t, J=7.2 Hz), 1.06-1.33 (4H, m), 1.61-1.91 (2H, m), 1.98-2.05 (2H, m), 2.26 (3H, s), 2.78-2.90 (2H, m), 3.11-3.55 (3H, m), 4.55 (1H, d, =12.3 Hz), 4.61 (2H, s), 4.72 (1H, m), 6.62 (1H, s), 6.69 (1H, s), 6.76 (1H, s), 7.14 (1H, m), 7.45-7.55 (3H, m), 8.73 (2H, s), 12.94 (1H, br s)

Example 897

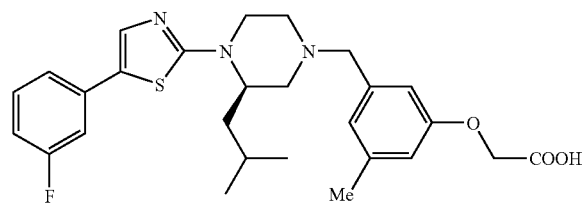

[Formula 1230]

TLC: (SiO2) AcOEt Rf=0.29

Example 898

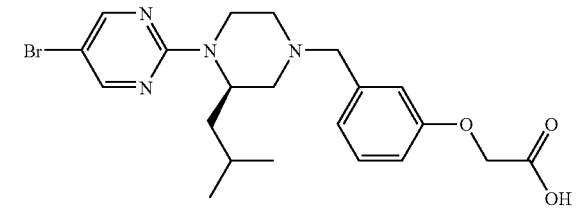

[Formula 1231]

1H-NMR (DMSO-d6) δ: 8.42 (2.0H, s), 7.24 (1.0H, dd, J=7.72, 7.72 Hz), 6.94-6.86 (2.0H, m), 6.79 (1.0H, dd, J=8.56, 1.85 Hz), 4.76-4.67 (1.0H, m), 4.64 (2.0H, s), 4.40 (1.0H, d, J=12.93 Hz), 3.51 (1.0H, d, J=13.60 Hz), 3.42-3.21 (1.0H, m), 3.18-3.05 (1.0H, m), 2.83 (1.0H, d, J=11.25 Hz), 2.74 (1.0H, d, J=11.25 Hz), 2.09-1.90 (2.0H, m), 1.72-1.52 (2.0H, m), 1.41-1.30 (1.0H, m), 0.89-0.83 (6.0H, m).

Example 899

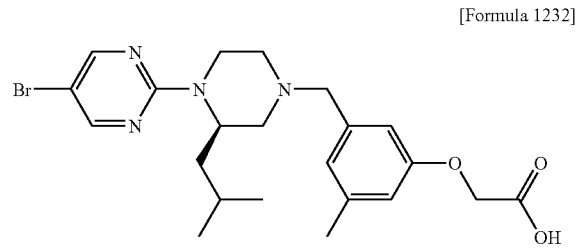

[Formula 1232]

1H-NMR (DMSO-d6) δ: 8.42 (2.0H, s), 6.74 (1.0H, s), 6.67 (1.0H, s), 6.61 (1.0H, s), 4.76-4.66 (1.0H, br m), 4.60 (2.0H, s), 4.40 (1.0H, d, J=13.26 Hz), 3.49 (1.0H, d, J=13.93 Hz), 3.45-3.20 (1.0H, m), 3.18-3.05 (1.0H, m), 2.83 (1.0H, d, J=12.09 Hz), 2.77-2.69 (1.0H, m), 2.25 (3.0H, s), 2.04-1.96 (2.0H, m), 1.77-1.65 (1.0H, m), 1.60-1.47 (1.0H, m), 1.44-1.28 (1.0H, m), 0.90-0.83 (6.0H, m).

Example 900

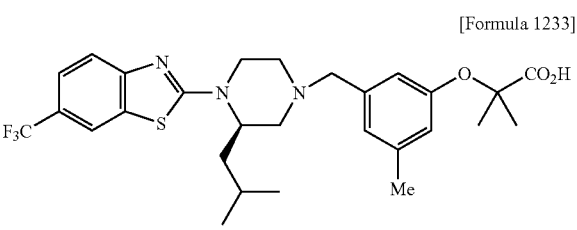

[Formula 1233]

1H-NMR (DMSO-d6) δ: 8.22 (1H, s), 7.59-7.53 (2H, m), 6.75 (1H, s), 6.68 (1H, s), 6.54 (1H, s), 4.21-3.89 (2H, m), 3.55-3.30 (3H, m), 2.92-2.75 (2H, m), 2.24 (3H, s), 2.18-2.02 (2H, m), 1.83 (1H, m), 1.65-1.38 (2H, m), 1.51 (6H, s), 0.93-0.91 (6H, m).

Example 901

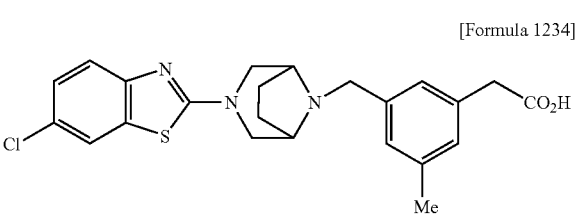

[Formula 1234]

MS (ESI) m/z 442 [M+H]+

Example 902

[Formula 1235]

MS (ESI) m/z 462 [M+H]+

Example 903

[Formula 1236]

MS (ESI) m/z 442 [M+H]+

Example 904

[Formula 1237]

1H-NMR (DMSO-d6) δ: 1.01 (6H, d, J=5.5 Hz), 2.70-2.87 (4H, m), 3.22 (3H, s), 3.47 (2H, d, J=10.2 Hz), 3.55 (2H, s), 3.71-3.83 (4H, m), 4.15-4.24 (2H, m), 7.04-7.45 (8H, m).

Example 905

[Formula 1238]

1H-NMR (DMSO-d6) δ: 1.03 (6H, d, J=5.2 Hz), 2.70-2.88 (4H, m), 3.45 (2H, d, J=11.0 Hz), 3.55 (2H, s), 3.60 (3H, s), 3.81 (2H, s), 7.04-7.42 (8H, m).

Example 906

[Formula 1239]

1H-NMR (DMSO-d6) δ: 1.04 (6H, d, J=6.0 Hz), 2.66-2.79 (2H, m), 3.01 (2H, t, J=11.7 Hz), 3.54 (3H, s), 3.76-3.88 (4H, m), 7.02-7.31 (6H, m), 7.44 (1H, d, J=8.0 Hz), 7.75 (1H, d, J=7.7 Hz).

Example 907

[Formula 1240]

1H-NMR (DMSO-d6) δ: 1.04 (6H, d, J=6.0 Hz), 2.63-2.76 (2H, m), 2.93-3.04 (2H, m), 3.53 (2H, s), 3.78 (2H, s), 3.90-3.98 (2H, m), 6.98-7.41 (8H, m).

Example 908

[Formula 1241]

1H-NMR (DMSO-d6) δ: 1.01 (6H, d, J=6.0 Hz), 2.50-2.58 (2H, m), 2.80 (2H, dd, J=12.6, 10.4 Hz), 3.52 (2H, s), 3.75 (2H, s), 4.34 (2H, dd, J=12.6, 1.6 Hz), 7.05-7.27 (4H, m), 8.44 (2H, s).

Example 909

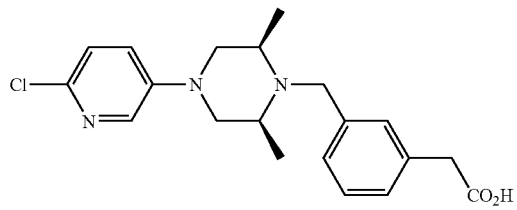

[Formula 1242]

1H-NMR (DMSO-d6) δ: 1.02 (6H, d, J=6.0 Hz), 2.47-2.55 (2H, m), 2.61-2.74 (2H, m), 3.52 (2H, s), 3.60-3.67 (2H, m), 3.76 (2H, s), 7.07-7.45 (6H, m), 8.07 (1H, d, J=3.3 Hz).

Example 910

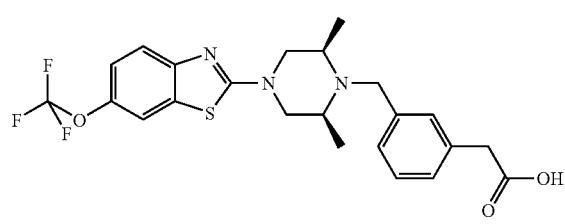

[Formula 1243]

1H-NMR (Acetone) δ: 7.76 (1.0H, s), 7.50 (1.0H, d, J=9.06 Hz), 7.41 (1.0H, s), 7.35 (1.0H, d, J=7.42 Hz), 7.30-7.22 (2.0H, m), 7.16 (1.0H, d, J=7.42 Hz), 3.94 (2.0H, dd, J=12.71, 2.33 Hz), 3.86 (2.0H, s), 3.62 (2.0H, s), 3.10 (2.0H, dd, J=12.71, 10.16 Hz), 2.87-2.77 (2.0H, m), 1.12 (6.0H, d, J=6.00 Hz).

Example 911

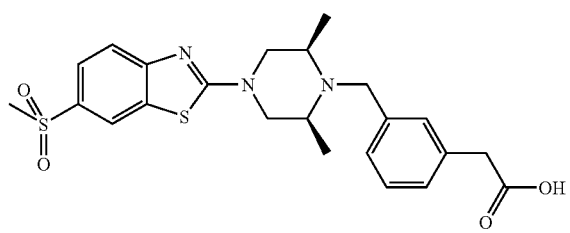

[Formula 1244]

1H-NMR (Acetone) δ: 8.27 (1.0H, d, J=1.80 Hz), 7.82 (1.0H, dd, J=8.46, 1.80 Hz), 7.58 (1.0H, d, J=8.46 Hz), 7.41 (1.0H, s), 7.35 (1.0H, d, J=7.42 Hz), 7.27 (1.0H, dd, J=7.42, 7.42 Hz), 7.17 (1.0H, d, J=7.42 Hz), 4.00 (2.0H, d, J=12.64 Hz), 3.87 (2.0H, s), 3.63 (2.0H, s), 3.21-3.07 (5.0H, m), 2.89-2.78 (2.0H, m), 1.13 (6.0H, d, J=6.32 Hz).

Example 912

[Formula 1245]

1H-NMR (Acetone) δ: 7.81 (1.0H, s), 7.47-7.33 (4.0H, m), 7.26 (1.0H, dd, J=7.54, 7.54 Hz), 7.16 (1.0H, d, J=7.54 Hz), 3.96 (2.0H, d, J=12.91 Hz), 3.86 (2.0H, s), 3.62 (2.0H, s), 3.15-3.01 (8.0H, m), 2.92-2.78 (2.0H, m), 1.12 (6.0H, d, J=6.04 Hz).

Example 913

[Formula 1246]

1H-NMR (Acetone) δ: 8.23 (1.0H, s), 7.82 (1.0H, d, J=8.52 Hz), 7.64 (1.0H, br s), 7.48-7.23 (4.0H, m), 7.16 (1.0H, d, J=7.14 Hz), 3.96 (2.0H, d, J=12.64 Hz), 3.86 (2.0H, s), 3.62 (2.0H, s), 3.11 (2.0H, dd, J=11.40, 11.40 Hz), 2.93-2.76 (5.0H, m), 1.12 (6.0H, d, J=6.32 Hz).

Example 914

[Formula 1247]

1H-NMR (Acetone) δ: 7.42-7.31 (4.0H, m), 7.26 (1.0H, dd, J=7.42, 7.42 Hz), 7.16 (1.0H, d, J=7.42 Hz), 6.90 (1.0H, dd, J=8.79, 2.75 Hz), 3.90-3.84 (4.0H, m), 3.80 (3.0H, s), 3.60 (2.0H, s), 3.01 (2.0H, dd, J=12.77, 10.30 Hz), 2.83-2.72 (2.0H, m), 1.11 (6.0H, d, J=6.00 Hz).

Example 915

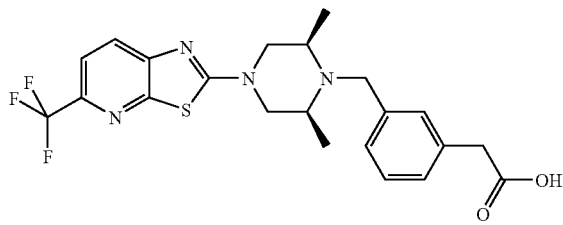

[Formula 1248]

1H-NMR (Acetone) δ: 7.83 (1.0H, d, J=8.24 Hz), 7.73 (1.0H, d, J=8.24 Hz), 7.42 (1.0H, s), 7.36 (1.0H, d, J=7.55 Hz), 7.27 (1.0H, dd, J=7.55, 7.55 Hz), 7.17 (1.0H, d, J=7.55 Hz), 4.05 (2.0H, d, J=13.05 Hz), 3.88 (2.0H, s), 3.63 (2.0H, s), 3.21 (2.0H, dd, J=13.05, 10.30 Hz), 1.14 (6.0H, d, J=6.32 Hz).

Example 916

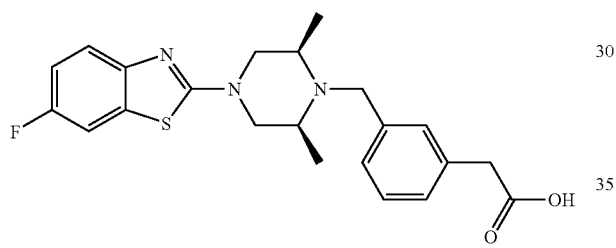

[Formula 1249]

1H-NMR (DMSO-d6) δ: 7.70 (1.0H, dd, J=8.52, 2.75 Hz), 7.43 (1.0H, dd, J=9.06, 4.94 Hz), 7.28-7.20 (3.0H, m), 7.16-7.05 (2.0H, m), 3.83-3.78 (4.0H, m), 3.52 (2.0H, s), 3.01 (2.0H, dd, J=11.54, 11.54 Hz), 2.77-2.69 (2.0H, m), 1.04 (6.0H, d, J=6.04 Hz).

Example 917

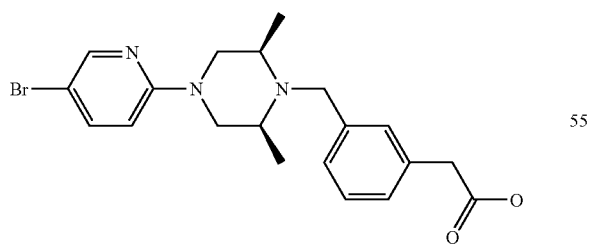

[Formula 1250]

1H-NMR (Acetone) δ: 8.30 (1.0H, d, J=5.22 Hz), 7.31 (1.0H, d, J=7.97 Hz), 7.13 (1.0H, d, J=1.92 Hz), 7.05 (1.0H, s), 6.89 (1.0H, d, J=7.97, 1.92 Hz), 6.80 (1.0H, d, J=5.22 Hz), 4.32 (2.0H, d, J=13.73 Hz), 4.16 (2.0H, dd, J=6.04, 6.04 Hz), 3.23 (2.0H, dd, J=6.04, 6.04 Hz), 2.89-2.79 (2.0H, m), 2.70-2.61 (2.0H, m), 1.25 (6.0H, d, J=6.04 Hz).

Example 918

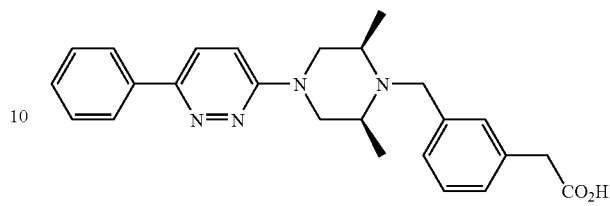

[Formula 1251]

1H-NMR (DMSO-d6) δ: 1.05 (7H, d, J=6.0 Hz), 2.58-2.87 (4H, m), 3.54 (2H, s), 3.77 (2H, s), 4.23-4.34 (2H, m), 7.05-7.53 (8H, m), 7.90-8.06 (3H, m).

Example 919

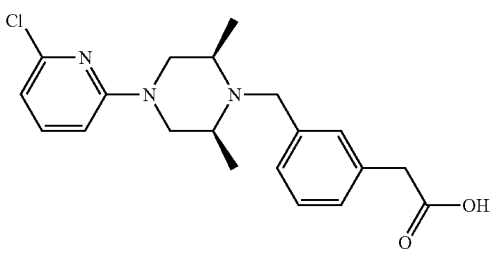

[Formula 1252]

1H-NMR (Acetone) δ: 7.50 (1.0H, dd, J=7.97, 7.97 Hz), 7.40 (1.0H, s), 7.34 (1.0H, d, J=7.42 Hz), 7.25 (1.0H, dd, J=7.42, 7.42 Hz), 7.15 (1.0H, d, J=7.42 Hz), 6.75 (1.0H, d, J=7.97 Hz), 6.59 (1.0H, d, J=7.97 Hz), 4.13 (2.0H, d, J=11.54 Hz), 3.82 (2.0H, s), 3.61 (2.0H, s), 2.80-2.62 (4.0H, m), 1.08 (6.0H, d, J=5.77 Hz).

Example 920

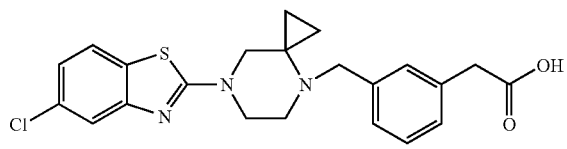

[Formula 1253]

MS (ESI) m/z 428 [M+H]+

Example 921

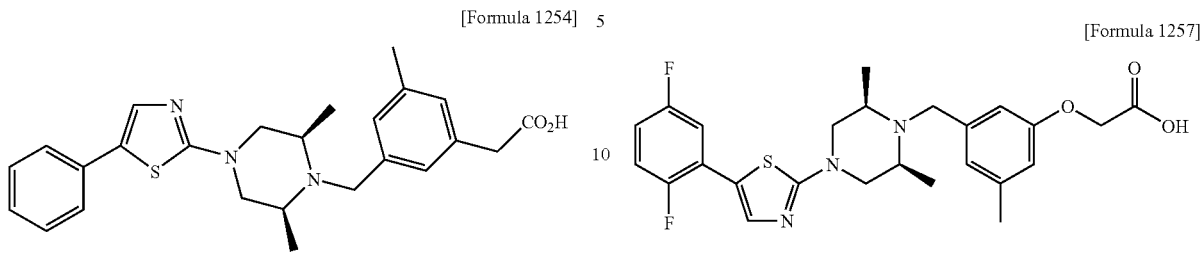

[Formula 1254]

1H-NMR (DMSO-d6) δ: 1.03 (6H, d, J=6.0 Hz), 2.27 (3H, s), 2.63-2.80 (2H, m), 2.85-2.97 (2H, m), 3.49 (2H, s), 3.69-3.78 (4H, m), 6.86-7.61 (9H, m).

Example 922

[Formula 1255]

1H-NMR (DMSO-d6) δ: 1.04 (6H, d, J=6.0 Hz), 2.52-2.62 (2H, m), 2.84 (2H, dd, J=12.9, 10.4 Hz), 3.54 (2H, s), 3.77 (2H, s), 4.44-4.52 (2H, m), 7.07-7.64 (9H, m), 8.69 (2H, s).

Example 923

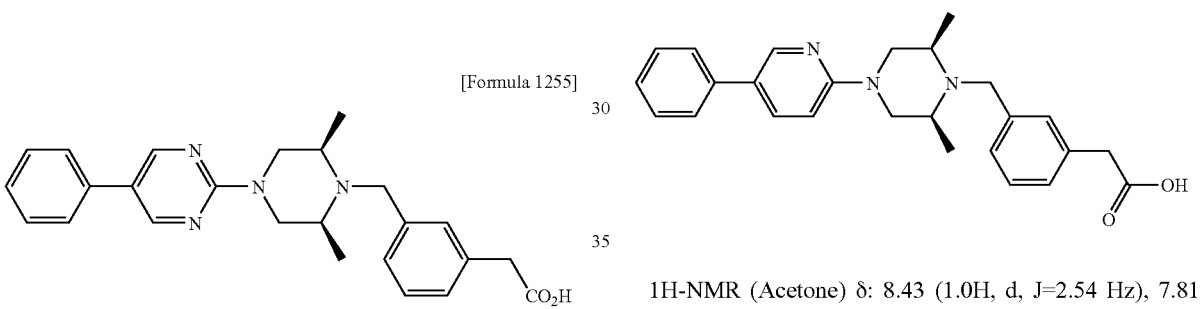

[Formula 1256]

1H-NMR (DMSO-d6)) δ: 7.77 (1H, s), 7.59-7.53 (1H, m), 7.37-7.29 (1H, m), 7.14-7.06 (3H, m), 6.89 (1H, s), 3.78-3.73 (4H, m), 3.49 (2H, s), 2.94 (2H, t, J=12.6 Hz), 2.74-2.68 (2H, m), 2.27 (3H, s), 1.0.3 (6H, d, J=6.3 Hz).

Example 924

[Formula 1257]

1H-NMR (DMSO-d6)) δ: 7.77 (1H, s), 7.59-7.53 (1H, m), 7.37-7.29 (1H, m), 7.14-7.06 (3H, m), 6.76 (2H, s), 6.54 (1H, s), 4.60 (2H, s), 3.79-3.70 (4H, m), 2.93 (2H, t, J=10.5 Hz), 2.70 (2H, brs), 2.25 (3H, s), 1.02 (6H, d, J=6.0 Hz).

Example 925

[Formula 1258]

1H-NMR (Acetone) δ: 8.43 (1.0H, d, J=2.54 Hz), 7.81 (1.0H, dd, J=9.00, 2.54 Hz), 7.61-7.58 (2.0H, m), 7.45-7.24 (6.0H, m), 7.16 (1.0H, d, J=7.69 Hz), 6.91 (1.0H, d, J=9.00 Hz), 4.25 (2.0H, d, J=11.81 Hz), 3.84 (2.0H, s), 3.63 (2.0H, s), 2.90-2.63 (4.0H, m), 1.10 (6.0H, d, J=5.22 Hz).

Example 926

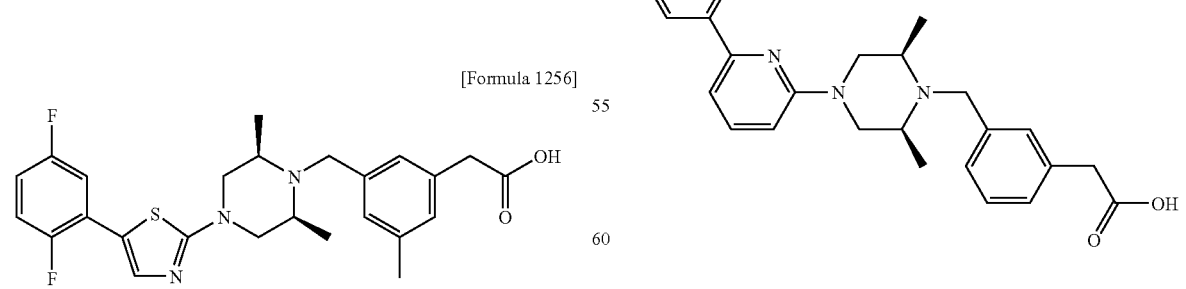

[Formula 1259]

1H-NMR (Acetone) δ: 8.09-8.07 (2.0H, m), 7.60 (1.0H, dd, J=7.76, 7.76 Hz), 7.48-7.34 (5.0H, m), 7.26 (1.0H, dd, J=7.76, 7.76 Hz), 7.20-7.13 (2.0H, m), 6.79 (1.0H, d, J=8.79 Hz), 4.32 (2.0H, d, J=11.81 Hz), 3.83 (2.0H, s), 3.62 (2.0H, s), 2.93-2.67 (4.0H, m), 1.10 (2.0H, d, J=5.70 Hz).

Example 927

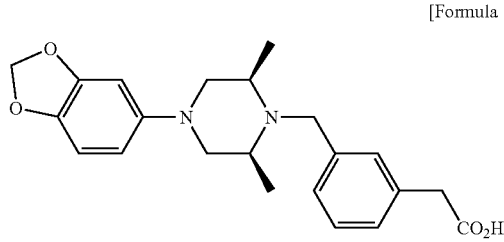

[Formula 1260]

1H-NMR (DMSO-d6) δ: 1.00 (6H, d, J=6.0 Hz), 2.35 (3H, t, J=10.7 Hz), 2.61-2.73 (2H, m), 3.53 (2H, s), 3.75 (2H, s), 5.90 (2H, s), 6.32 (1H, dd, J=8.5, 1.6 Hz), 6.65-6.78 (2H, m), 7.05-7.28 (4H, m).

Example 928

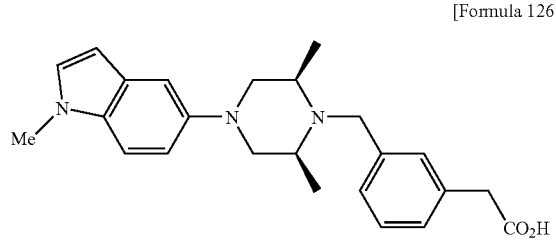

[Formula 1261]

1H-NMR (DMSO-d6) δ: 1.03 (7H, d, J=6.0 Hz), 2.35-2.46 (2H, m), 2.68-2.81 (2H, m), 3.55 (2H, s), 3.72 (3H, s), 3.79 (2H, s), 6.27 (1H, d, J=2.2 Hz), 6.90-7.31 (8H, m).

Example 929

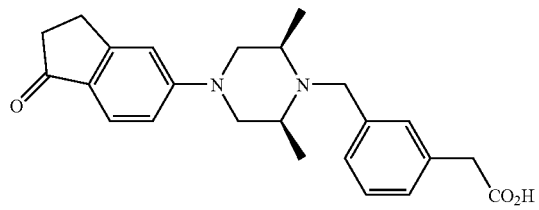

[Formula 1262]

1H-NMR (DMSO-d6) δ: 1.03 (6H, d, J=5.2 Hz), 2.61-2.76 (4H, m), 2.92-3.00 (2H, m), 3.53 (2H, s), 3.75 (2H, s), 3.83 (2H, d, J=10.7 Hz), 6.93-7.28 (6H, m), 7.42 (1H, d, J=8.5 Hz).

Example 930

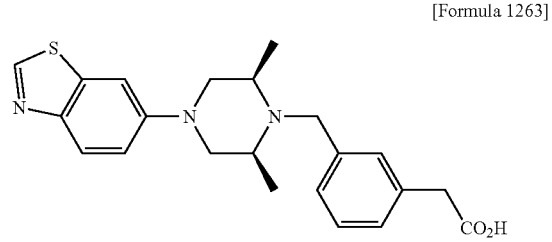

[Formula 1263]

1H-NMR (DMSO-d6) δ: 1.04 (6H, d, J=6.0 Hz), 2.50-2.58 (2H, m), 2.66-2.78 (2H, m), 3.54 (2H, s), 3.66 (2H, d, J=11.5 Hz), 3.78 (2H, s), 7.06-7.31 (5H, m), 7.59 (1H, d, J=2.2 Hz), 7.87 (1H, d, J=9.1 Hz), 9.07 (1H, s).

Example 931

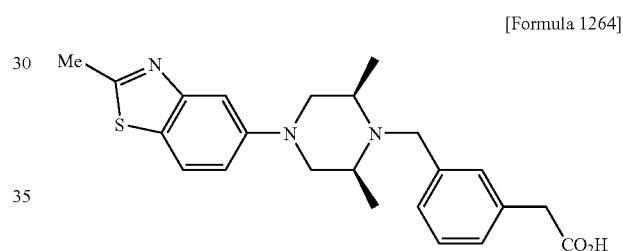

[Formula 1264]

1H-NMR (DMSO-d6) δ: 1.04 (6H, d, J=6.0 Hz), 2.45-2.75 (7H, m), 3.54 (2H, s), 3.61 (2H, d, J=10.7 Hz), 3.78 (2H, s), 7.06-7.39 (6H, m), 7.78 (1H, d, J=8.8 Hz).

Example 932

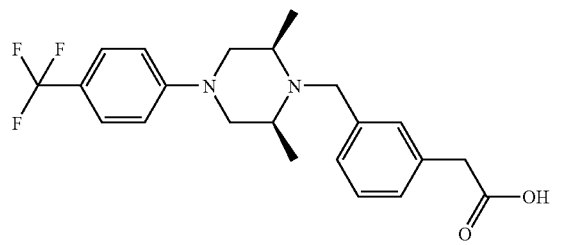

[Formula 1265]

1H-NMR (Acetone) δ: 7.49 (2.0H, d, J=8.66 Hz), 7.40 (1.0H, s), 7.35 (1.0H, d, J=7.42 Hz), 7.26 (1.0H, dd, J=7.42, 7.42 Hz), 7.16 (1.0H, d, J=7.42 Hz), 7.08 (2.0H, d, J=8.66 Hz), 3.83 (2.0H, s), 3.75 (2.0H, d, J=10.71 Hz), 3.62 (2.0H, s), 2.84-2.66 (4.0H, m), 1.09 (6.0H, d, J=5.77 Hz).

Example 933
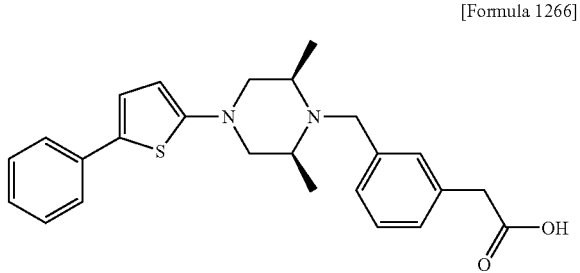
[Formula 1266]
1H-NMR (Acetone) δ: 7.53-7.49 (2.0H, m), 7.41 (1.0H, s), 7.37-7.32 (3.0H, m), 7.29 (1.0H, d, J=4.39 Hz), 7.25 (1.0H, d, J=7.42 Hz), 7.20-7.13 (3.0H, m), 6.17 (1.0H, d, J=3.85 Hz), 3.85 (2.0H, s), 3.63 (2.0H, s), 3.43 (2.0H, d, J=9.61 Hz), 2.86-2.83 (2.0H, m), 2.70-2.66 (2.0H, m), 1.09 (6.0H, d, J=6.32 Hz).
Example 934
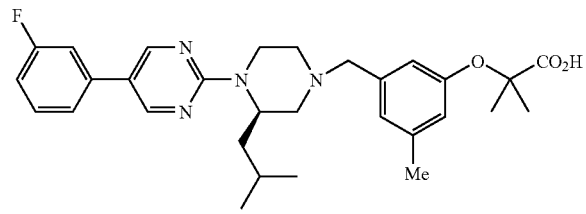
[Formula 1267]
1H-NMR (DMSO-d6) δ: 8.72 (2H, s), 7.59-7.40 (2H, m), 7.13 (1H, t, J=8.1 Hz), 6.75 (1H, s), 6.66 (1H, s), 6.54 (1H, s), 4.86 (1H, br-s), 4.56 (1H, d, J=12.9 Hz), 3.48-3.13 (3H, m), 2.86-2.72 (2H, m), 2.23 (3H, s), 2.10-1.90 (2H, m), 1.39 (1H, m), 0.91-0.87 (6H, m).
Example 935
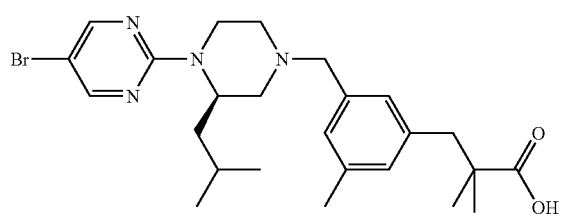
[Formula 1268]
1H-NMR (DMSO-d6) δ: 8.72 (2H, s), 6.75 (1H, s), 6.66 (1H, s), 6.54 (1H, s), 4.86 (1H, br-s), 4.56 (1H, d, J=12.9 Hz), 3.48-3.13 (3H, m), 2.86-2.72 (2H, m), 2.23 (3H, s), 2.10-1.90 (2H, m), 1.39 (1H, m), 0.91-0.87 (6H, m).
Example 936
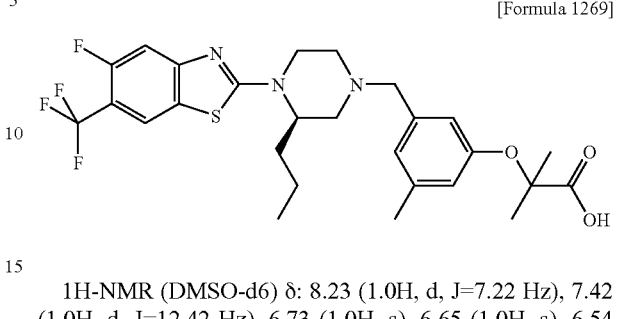
[Formula 1269]
1H-NMR (DMSO-d6) δ: 8.23 (1.0H, d, J=7.22 Hz), 7.42 (1.0H, d, J=12.42 Hz), 6.73 (1.0H, s), 6.65 (1.0H, s), 6.54 (1.0H, s), 4.15-3.86 (2.0H, m), 3.53-3.20 (3.0H, m), 2.92-2.75 (2.0H, m), 2.24 (3.0H, s), 2.20-2.05 (2.0H, m), 1.92-1.70 (2.0H, m), 1.52-1.48 (6.0H, m), 1.30-1.14 (2.0H, m), 0.90 (3.0H, t, J=7.30 Hz).
Example 937
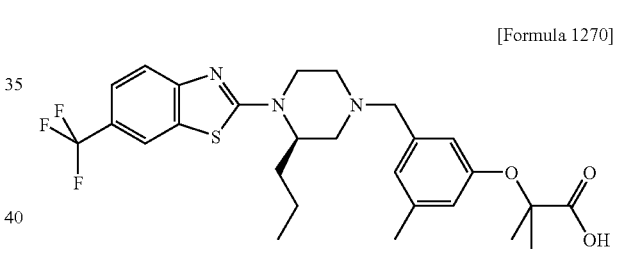
[Formula 1270]
MS (ESI) 534[M−H]−
Example 938
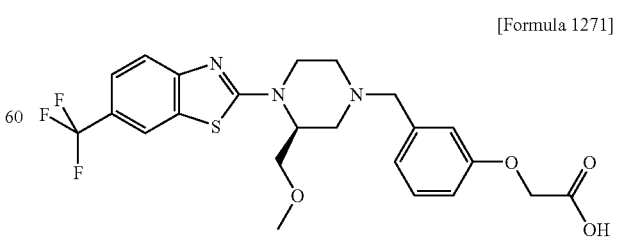
[Formula 1271]
MS (ESI) 494[M−H]−

Example 939

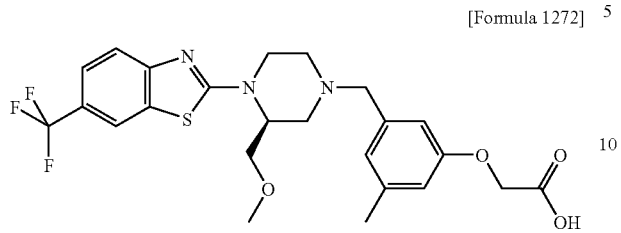

[Formula 1272]

MS (ESI) 508[M−H]−

Example 940

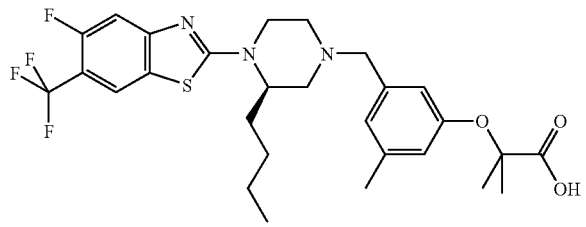

[Formula 1273]

MS (ESI) 536[M−H]−

Example 941

[Formula 1274]

1H-NMR (300 MHz, DMSO-d6) δ 0.85 (3H, t, J=7.2 Hz), 1.13-1.35 (4H, m), 1.50 (6H, s), 1.75-1.94 (2H, m), 2.12-2.17 (2H, m), 2.24 (3H, s), 2.78-2.90 (2H, m), 3.33-3.53 (3H, m), 4.02 (2H, m), 6.54 (1H, s), 6.65 (1H, s), 6.74 (1H, s), 7.43 (1H, d, J=12.0 Hz), 8.23 (1H, d, J=7.2 Hz), 12.97 (1H, br s)

Example 942

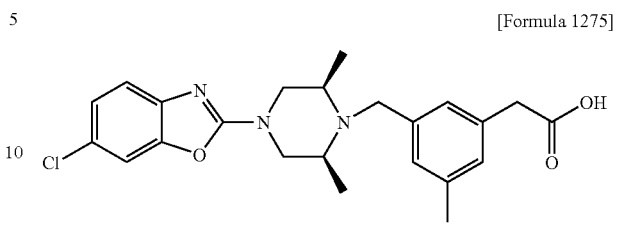

[Formula 1275]

MS (ESI) m/z 428 [M+H]+

Example 943

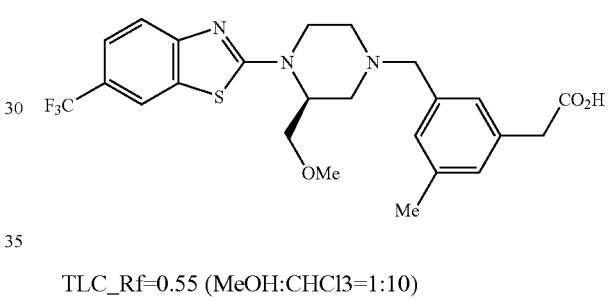

[Formula 1276]

TLC_Rf=0.55 (MeOH:CHCl3=1:10)

Example 944

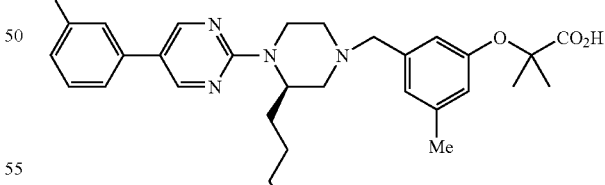

[Formula 1277]

1H-NMR (300 MHz, DMSO-d6) δ 0.83 (3H, t, J=7.2 Hz), 1.06-1.33 (4H, m), 1.51 (6H, s), 1.61-1.91 (2H, m), 1.98-2.05 (2H, m), 2.26 (3H, s), 2.78-2.90 (2H, m), 3.11-3.55 (3H, m), 4.55 (1H, d, =12.3 Hz), 4.72 (1H, m), 6.54 (1H, s), 6.66 (1H, s), 6.75 (1H, s), 7.14 (1H, m), 7.45-7.55 (3H, m), 8.72 (2H, s)

The present invention includes the following compounds synthesized by similar methods as above.

Compound I-1
[Formula 1278]
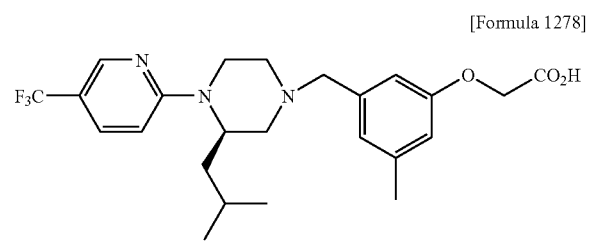
Compound I-2
[Formula 1279]
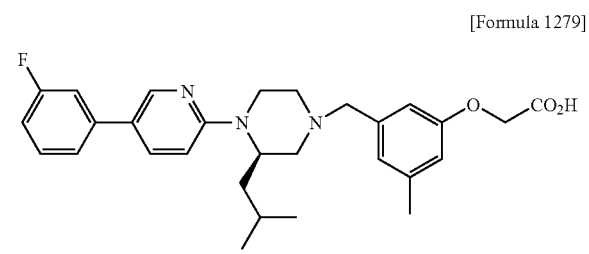
Compound I-3
[Formula 1280]
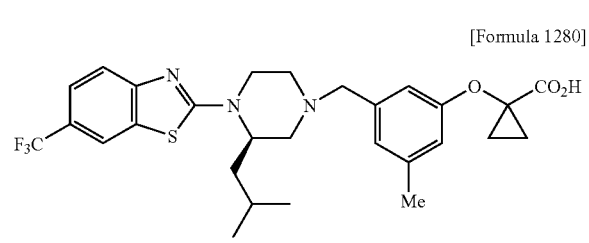
Compound I-4
[Formula 1281]
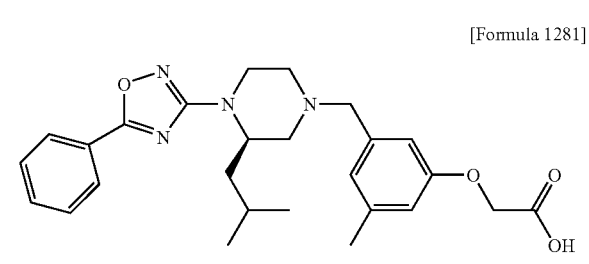
Compound I-5
[Formula 1282]
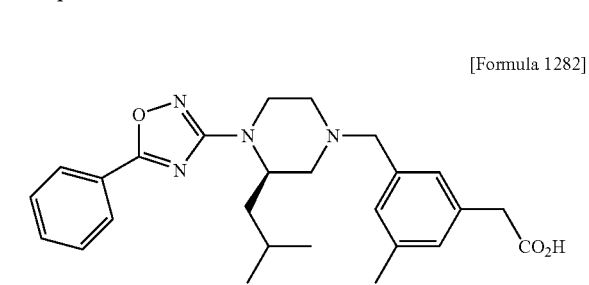
Compound I-6
[Formula 1283]
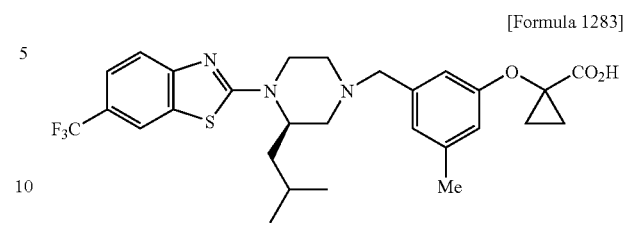
Compound I-7
[Formula 1284]
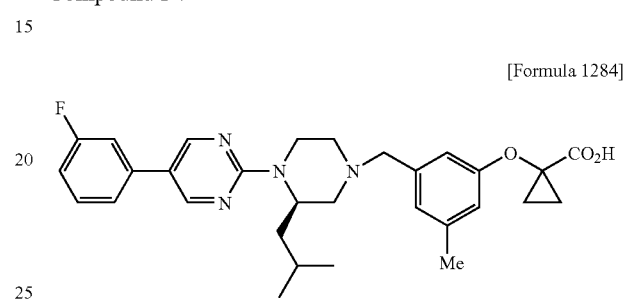
Compound I-8
[Formula 1285]
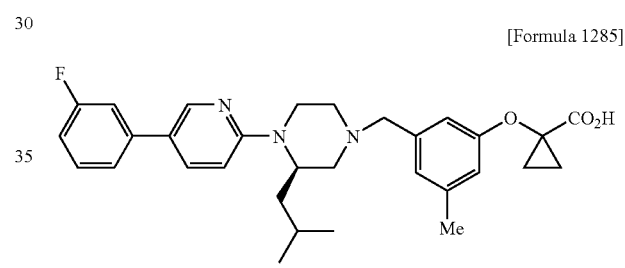
Compound I-9
[Formula 1286]
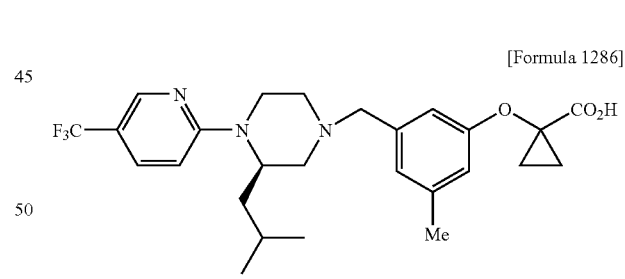
Compound I-10
[Formula 1287]
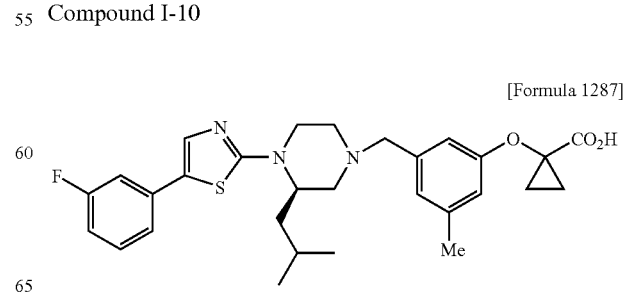

Compound I-11
[Formula 1288]
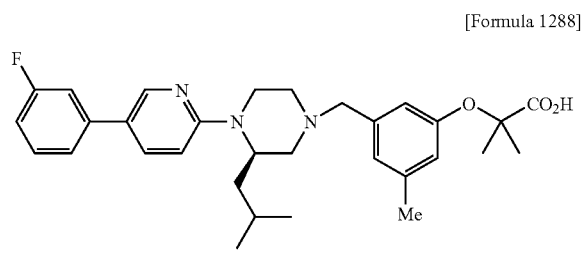
Compound I-16
[Formula 1293]
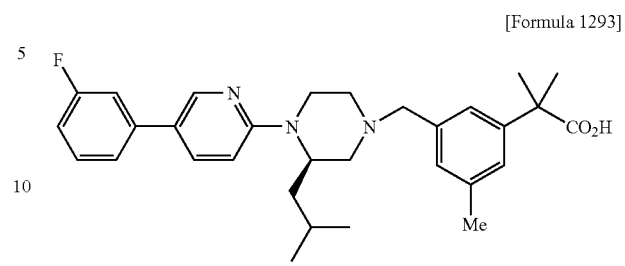
Compound I-12
[Formula 1289]
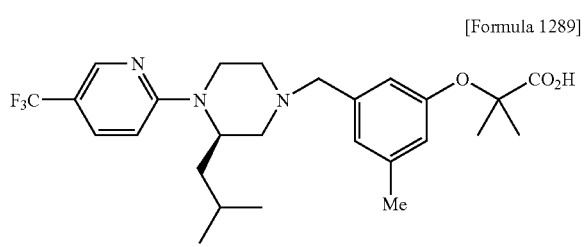
Compound I-17
[Formula 1294]
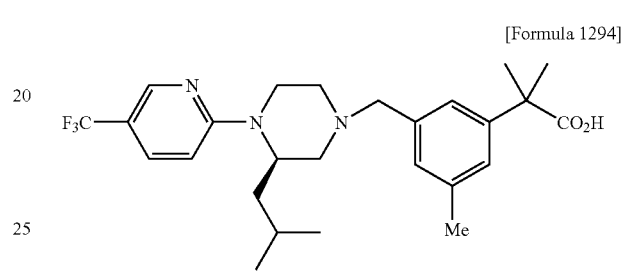
Compound I-13
[Formula 1290]
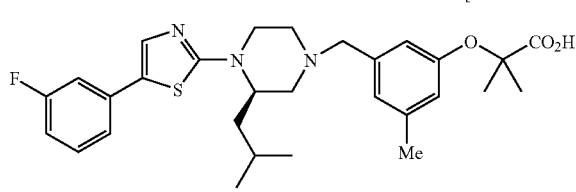
Compound I-18
[Formula 1295]
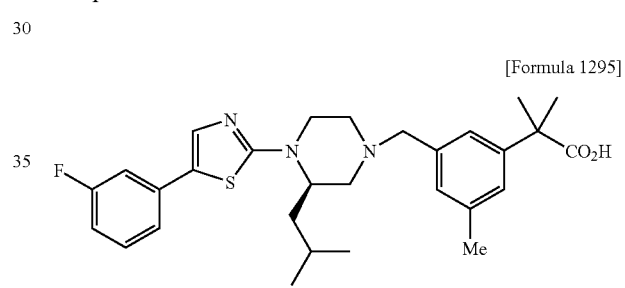
Compound I-14
[Formula 1291]
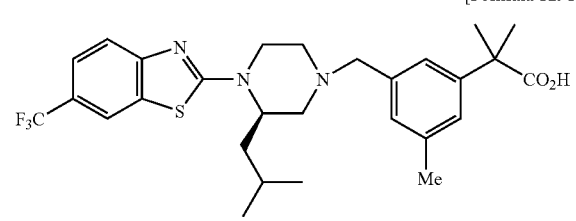
Compound I-19
[Formula 1296]
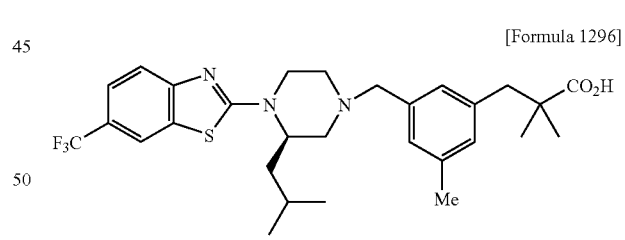
Compound I-15
[Formula 1292]
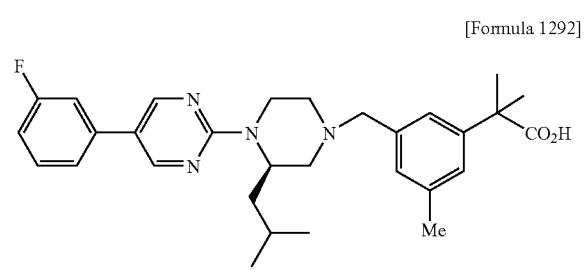
Compound I-20
[Formula 1297]
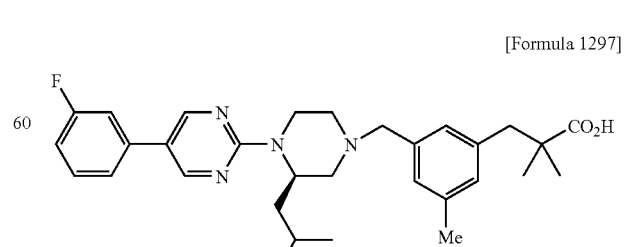

Compound I-21
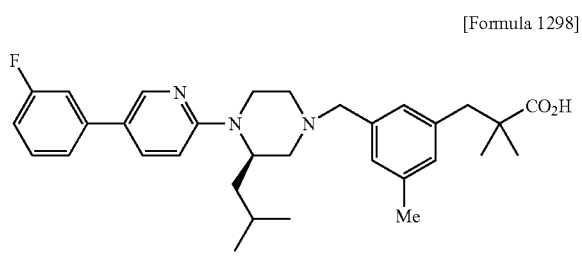
[Formula 1298]
Compound I-26
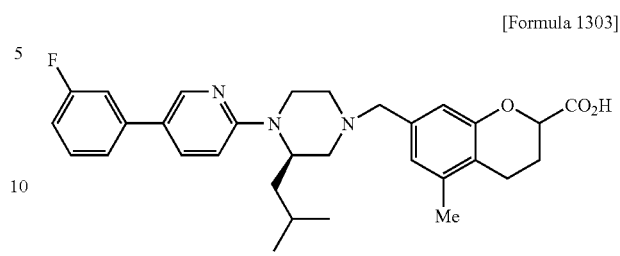
[Formula 1303]
Compound I-22
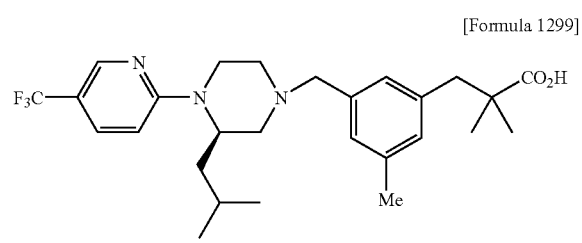
[Formula 1299]
Compound I-27
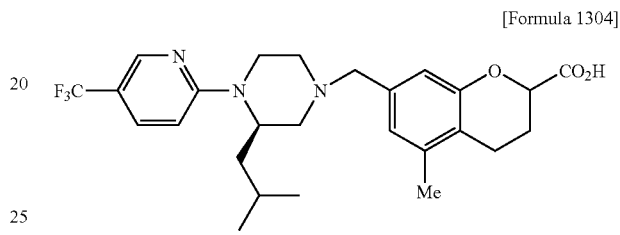
[Formula 1304]
Compound I-23
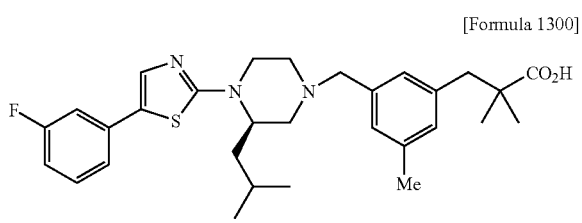
[Formula 1300]
Compound I-28
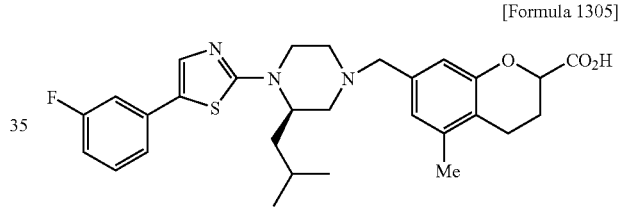
[Formula 1305]
Compound I-24
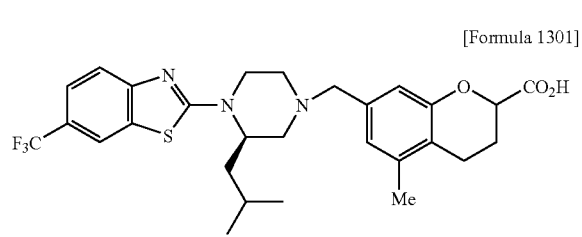
[Formula 1301]
Compound I-29
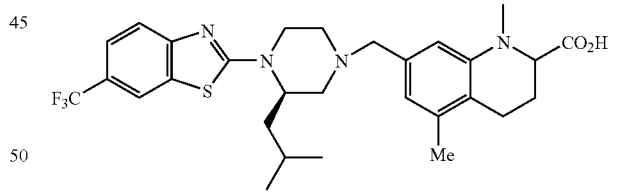
[Formula 1306]
Compound I-25
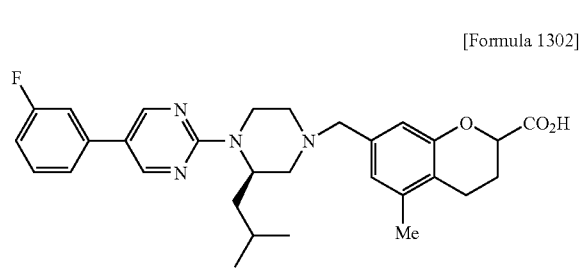
[Formula 1302]
Compound I-30
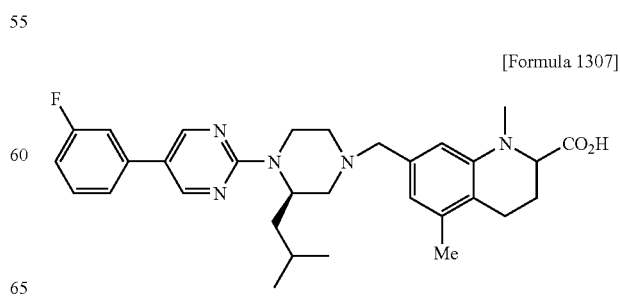
[Formula 1307]

Compound I-31
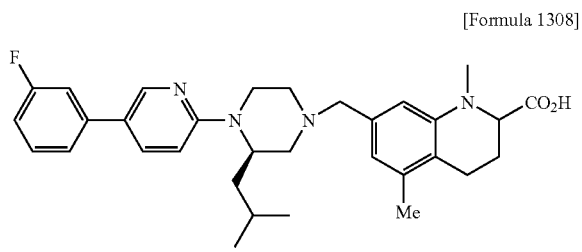
[Formula 1308]
Compound I-36
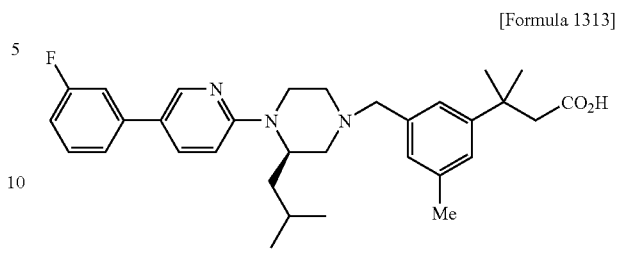
[Formula 1313]
Compound I-32
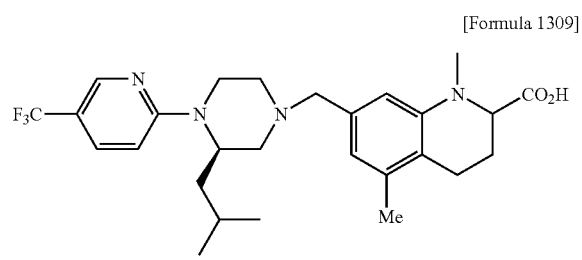
[Formula 1309]
Compound I-37
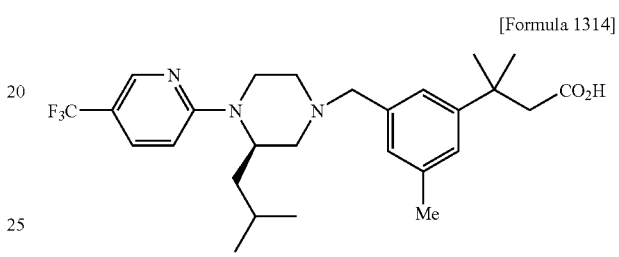
[Formula 1314]
Compound I-33
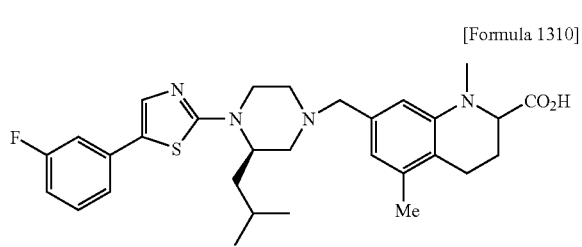
[Formula 1310]
Compound I-38
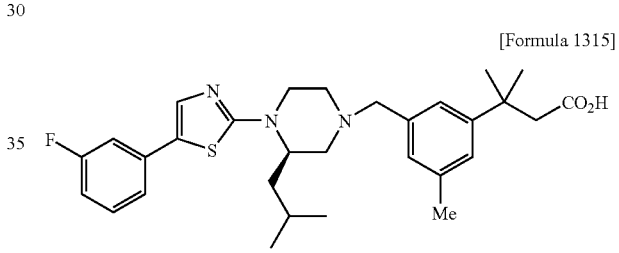
[Formula 1315]
Compound I-34
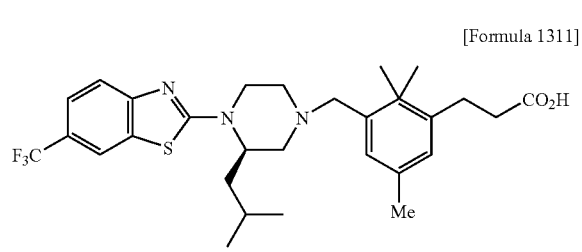
[Formula 1311]
Compound I-39
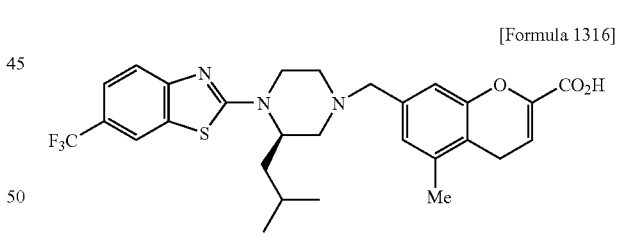
[Formula 1316]
Compound I-35
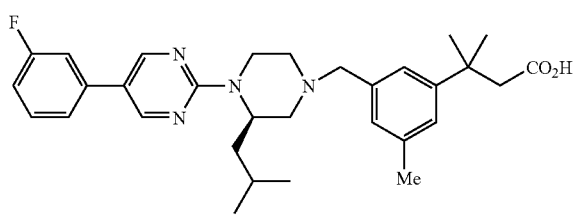
[Formula 1312]
Compound I-40
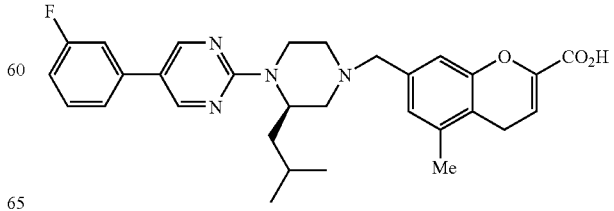
[Formula 1317]

Compound I-41
[Formula 1318]
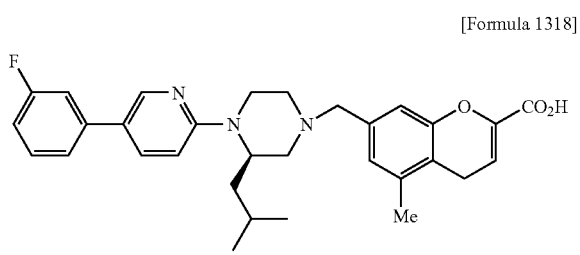
Compound I-46
[Formula 1323]
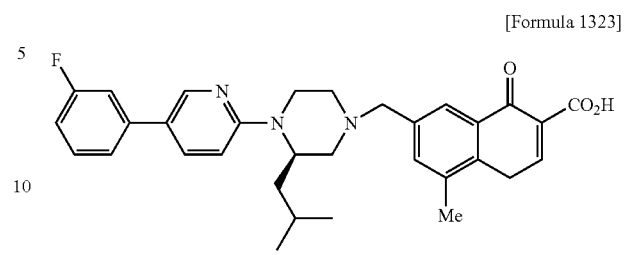
Compound I-42
[Formula 1319]
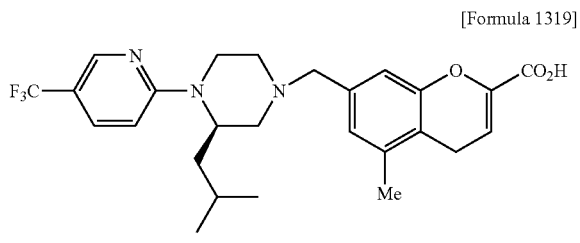
Compound I-47
[Formula 1324]
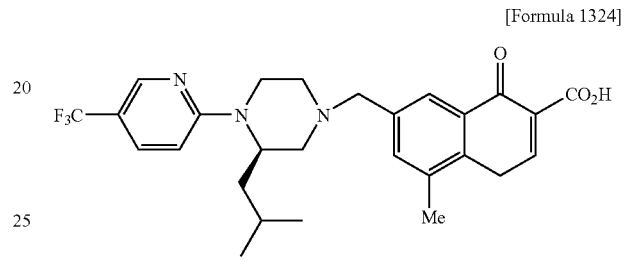
Compound I-43
[Formula 1320]
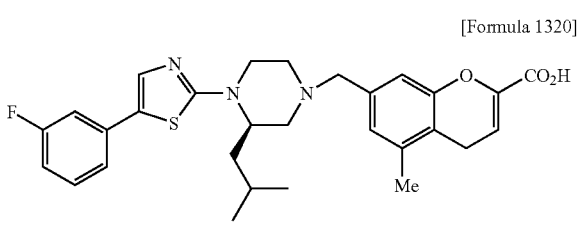
Compound I-48
[Formula 1325]
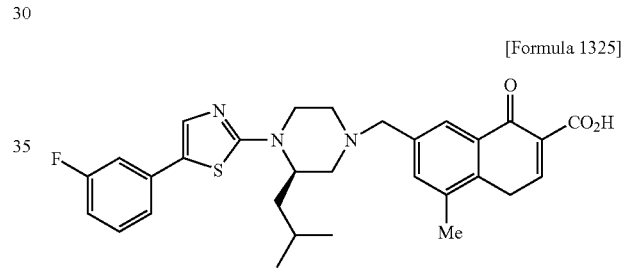
Compound I-44
[Formula 1321]
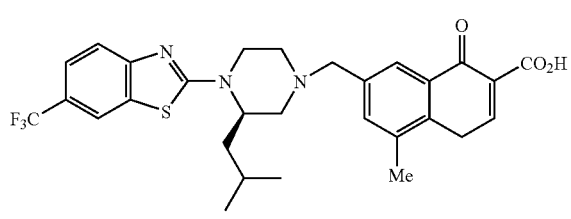
Compound I-49
[Formula 1326]
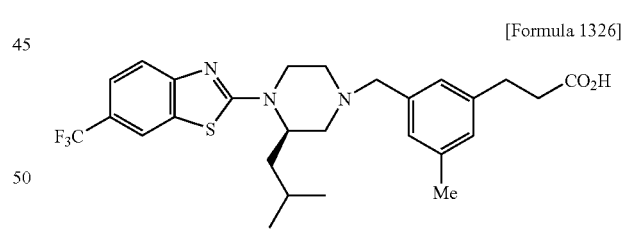
Compound I-45
[Formula 1322]
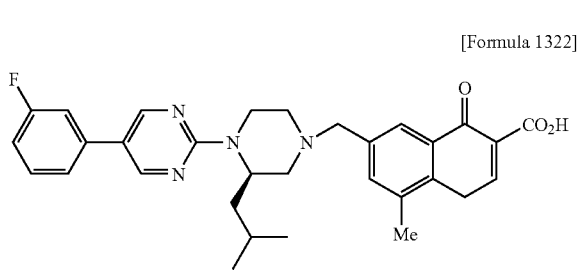
Compound I-50
[Formula 1327]
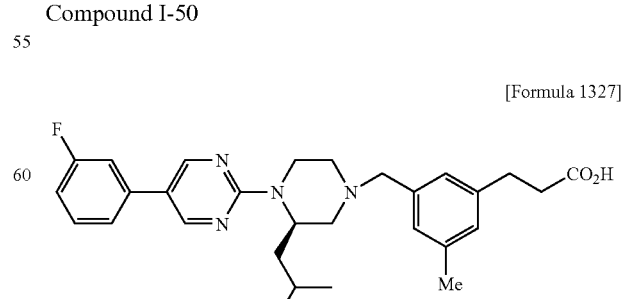

Compound I-51
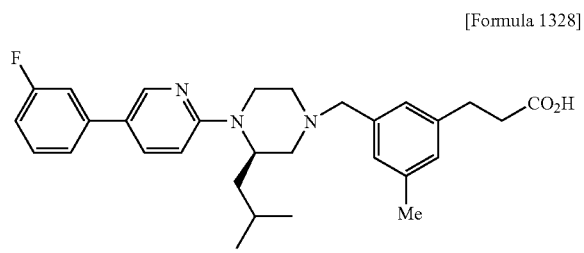
[Formula 1328]
Compound I-56
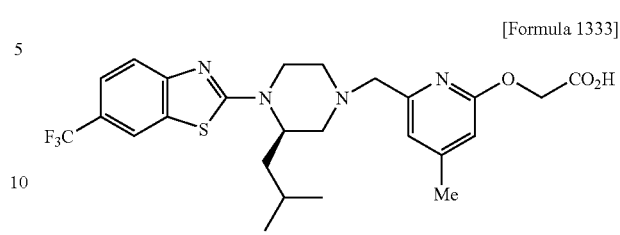
[Formula 1333]
Compound I-52
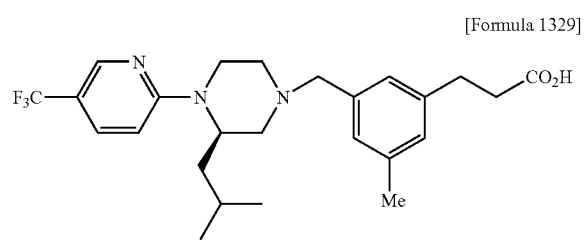
[Formula 1329]
Compound I-57
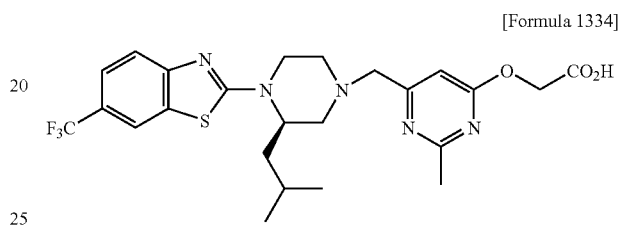
[Formula 1334]
Compound I-53
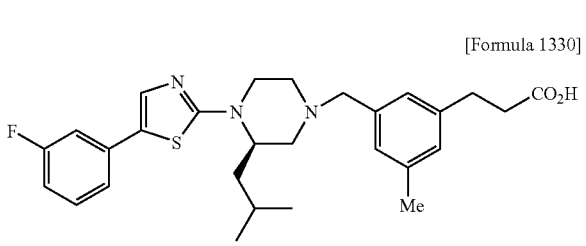
[Formula 1330]
Compound I-58
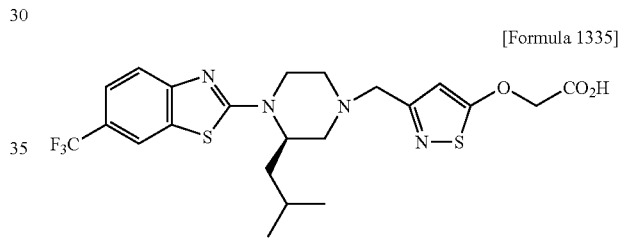
[Formula 1335]
Compound I-54
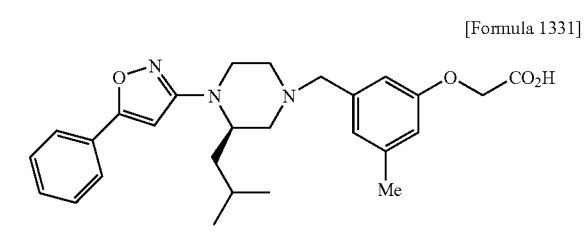
[Formula 1331]
Compound I-59
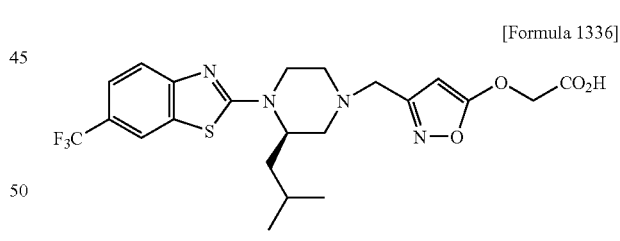
[Formula 1336]
Compound I-55
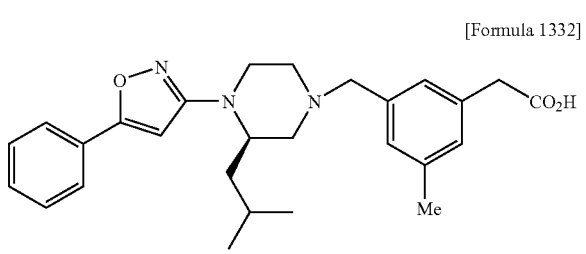
[Formula 1332]
Compound I-60
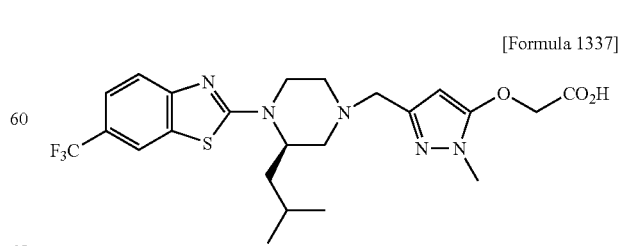
[Formula 1337]

Compound I-61
[Formula 1338]
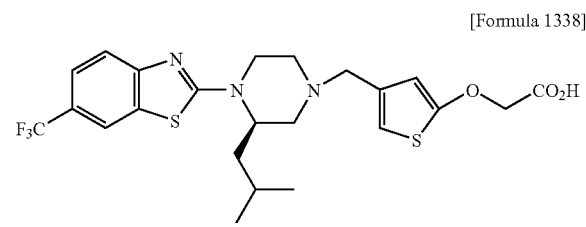
Compound I-62
[Formula 1339]
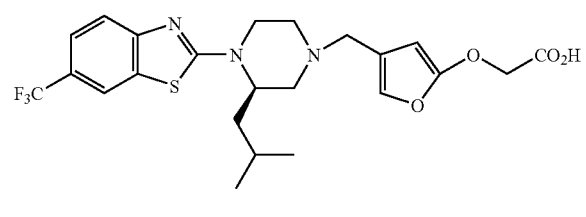
Compound I-63
[Formula 1340]
Compound I-64
[Formula 1341]
Compound I-65
[Formula 1342]
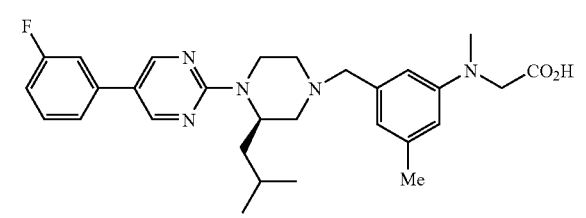
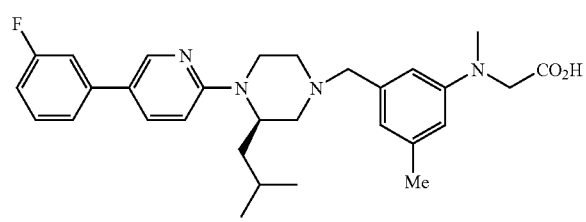
Compound I-66
[Formula 1343]
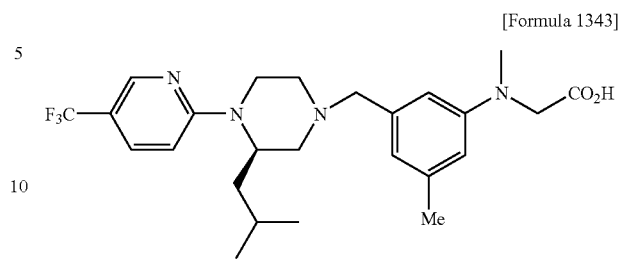
Compound I-67
[Formula 1344]
Compound I-68
[Formula 1345]
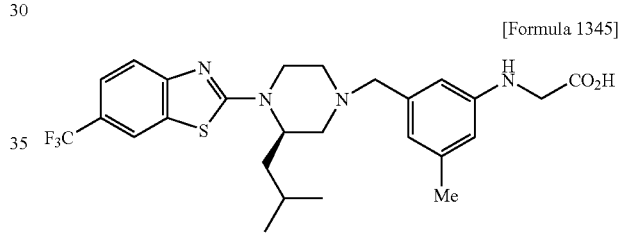
Compound I-69
[Formula 1346]
Compound I-70
[Formula 1347]
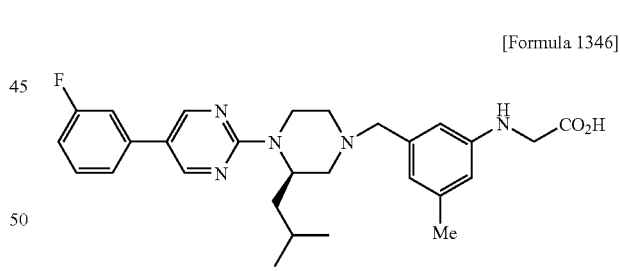
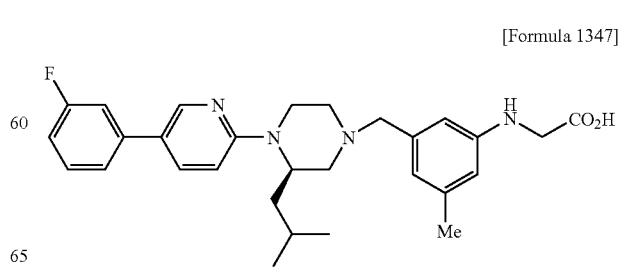

Compound I-71
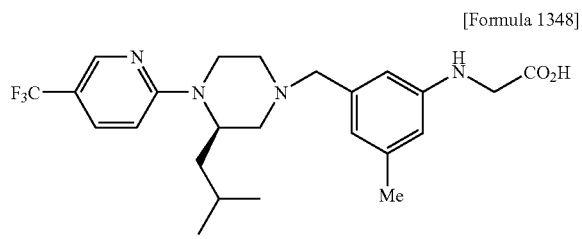
[Formula 1348]
Compound I-76
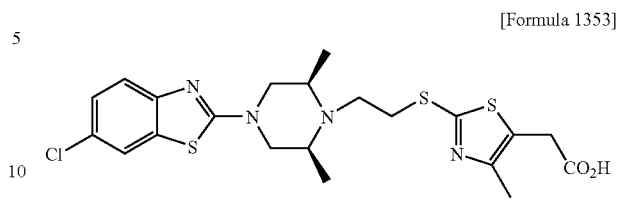
[Formula 1353]
Compound I-72
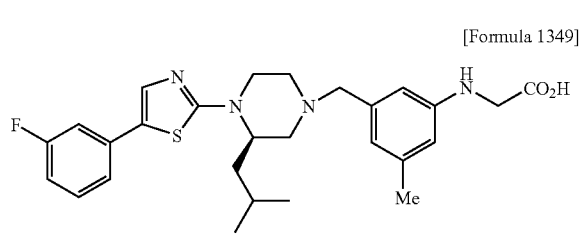
[Formula 1349]
Compound I-77
[Formula 1354]
Compound I-73
[Formula 1350]
Compound I-78
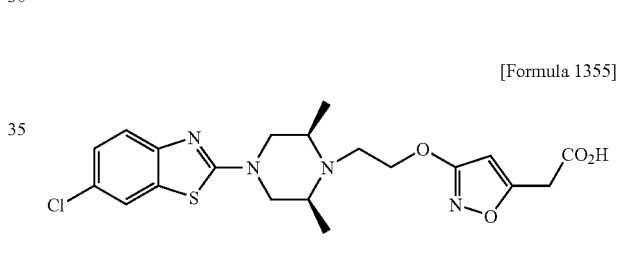
[Formula 1355]
Compound I-74
[Formula 1351]
Compound I-79
[Formula 1356]
Compound I-75
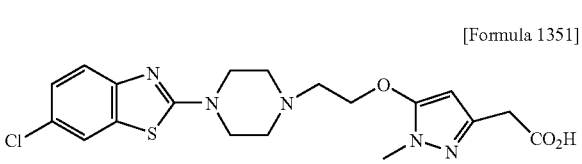
[Formula 1352]
Compound I-80
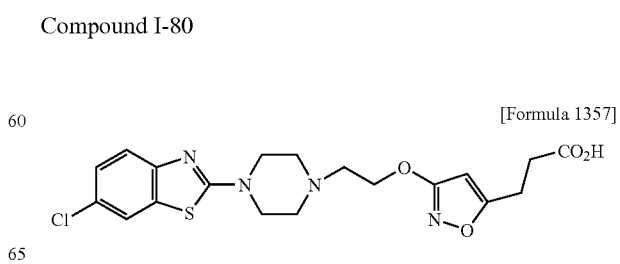
[Formula 1357]
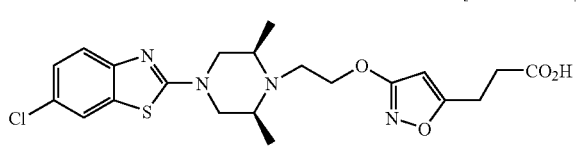

TABLE 1

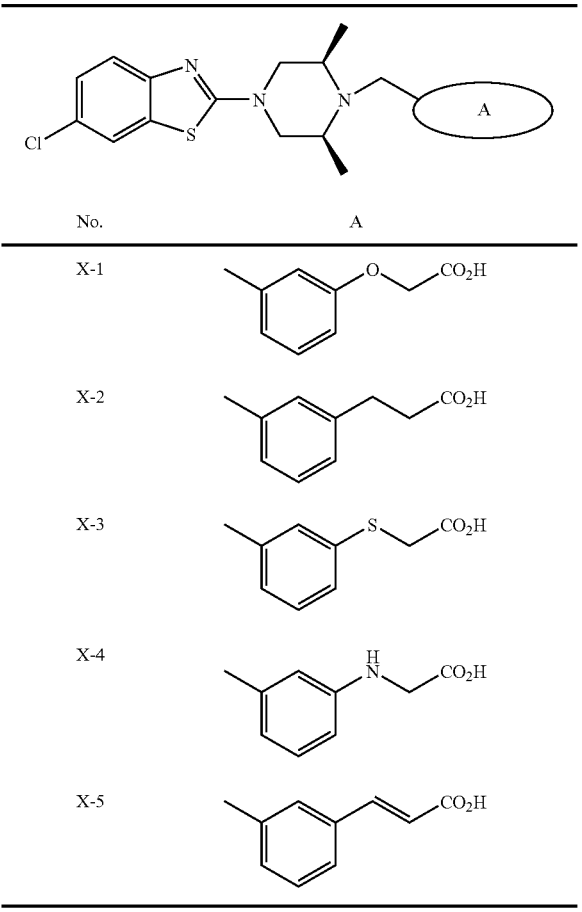

| No. | A |
|---|---|
| X-1 | 3-methylphenoxyacetic acid |
| X-2 | 3-(3-methylphenyl)propanoic acid |
| X-3 | (3-methylphenylthio)acetic acid |
| X-4 | N-(3-methylphenyl)glycine |
| X-5 | 3-(3-methylphenyl)acrylic acid |

TABLE 2

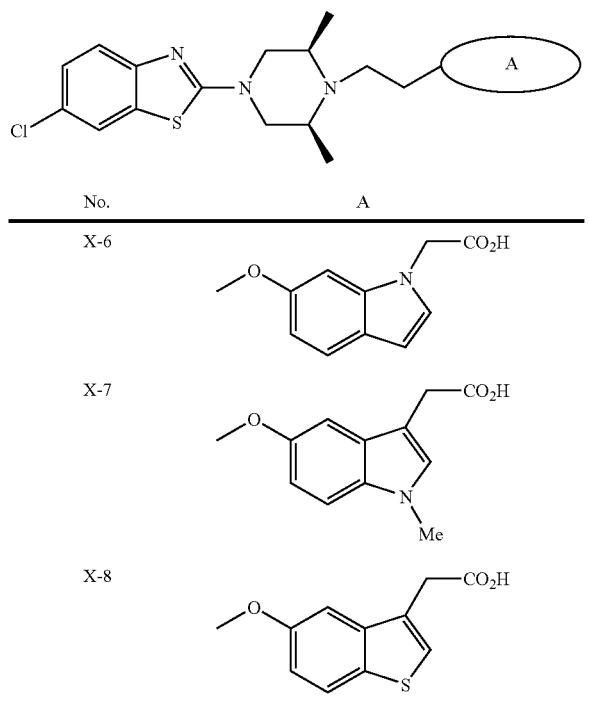

| No. | A |
|---|---|
| X-6 | (6-methoxy-1H-indol-1-yl)acetic acid |
| X-7 | (5-methoxy-1-methyl-1H-indol-3-yl)acetic acid |
| X-8 | (5-methoxybenzo[b]thiophen-3-yl)acetic acid |

TABLE 2-continued

| No. | A |
|---|---|
| X-9 | (5-methoxybenzofuran-3-yl)acetic acid |
| X-10 | (4-methyl-2-methylthiothiazol-5-yl)acetic acid |
| X-11 | (3-methoxyphenoxy)acetic acid |
| X-12 | 3-(3-methoxyphenyl)propanoic acid |
| X-13 | (3-methoxyphenylthio)acetic acid |
| X-14 | N-(3-methoxyphenyl)glycine |
| X-15 | 3-(3-methoxyphenyl)acrylic acid |

TABLE 3

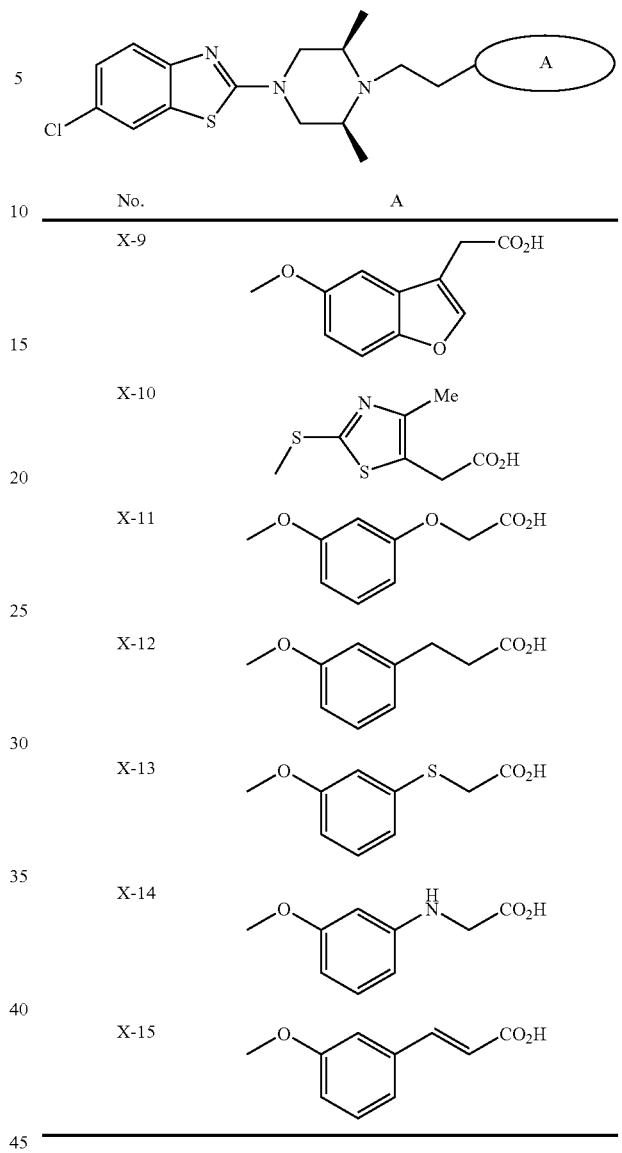

| No. | R1 | B |
|---|---|---|
| Y-1 | H | (S)-2-methylpiperazine (dimethyl) |
| Y-2 | H | (R)-2-methylpiperazine (dimethyl) |

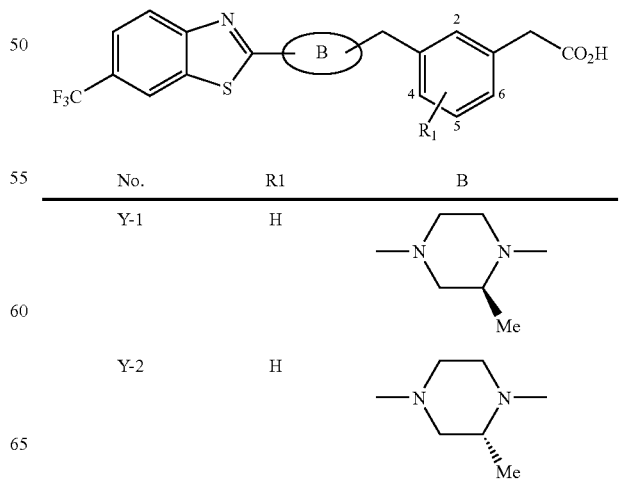

TABLE 3-continued

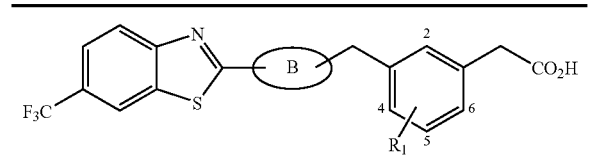

| No. | R1 | B |
|---|---|---|
| Y-3 | H | N-methylpiperazine with Et substituent |
| Y-4 | H | N-methylpiperazine with gem-diMe |
| Y-5 | H | N-methylpiperazine with Ph |
| Y-6 | H | N-methylpiperazine with Me |
| Y-7 | H | N-methylpiperazine with Me (wedge) |
| Y-8 | H | N-methylpiperazine with Me (dash) |
| Y-9 | H | N-methylpiperazine with Et |
| Y-10 | H | N-methylpiperazine with 2,6-diMe (cis) |
| Y-18 | 5-Me | N-methylpiperazine with Me |

TABLE 3-continued

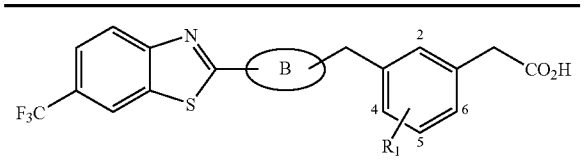

| No. | R1 | B |
|---|---|---|
| Y-19 | 5-Me | N-methylpiperazine with Me (dash) |
| Y-20 | 5-Me | N-methylpiperazine with Et |
| Y-21 | 5-Me | N-methylpiperazine with gem-diMe |
| Y-22 | 5-Me | N-methylpiperazine with Ph |
| Y-23 | 5-Me | N-methylpiperazine with Me |
| Y-24 | 5-Me | N-methylpiperazine with Me (wedge) |
| Y-25 | 5-Me | N-methylpiperazine with Me (dash) |
| Y-26 | 5-Me | N-methylpiperazine with Et |
| Y-27 | 5-Me | N-methylpiperazine with 2,6-diMe |

TABLE 4

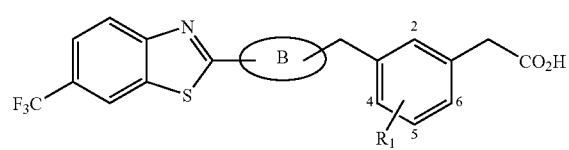

| No. | R1 | B |
|---|---|---|
| Y-11 | H | (piperazine with 2,5-Me, wedge/dash) |
| Y-12 | H | (piperazine with 2,5-Me) |
| Y-13 | H | (piperazine with 2,5-Me) |
| Y-14 | H | (piperazine with 2,5-Me) |
| Y-15 | H | (piperazine with 2,3-Me) |
| Y-16 | H | (piperazine with 2,3-Me) |
| Y-17 | H | (diazabicyclic) |
| Y-28 | 5-Me | (piperazine with 2,5-Me) |

TABLE 4-continued

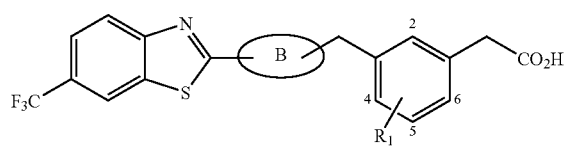

| No. | R1 | B |
|---|---|---|
| Y-29 | 5-Me | (piperazine with 2,5-Me) |
| Y-30 | 5-Me | (piperazine with 2,5-Me) |
| Y-31 | 5-Me | (piperazine with 2,5-Me) |
| Y-32 | 5-Me | (piperazine with 2,3-Me) |
| Y-33 | 5-Me | (piperazine with 2,3-Me) |
| Y-34 | 5-Me | (diazabicyclic) |

TABLE 5

| No. | R1 | B |
|---|---|---|
| Y-35 | H | (piperazine with 2-Me) |

TABLE 5-continued
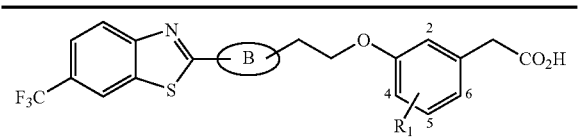
| No. | R1 | B |
|---|---|---|
| Y-36 | H | |
| Y-37 | H | |
| Y-38 | H | |
| Y-39 | H | |
| Y-40 | H | |
| Y-41 | H | |
| Y-42 | H | |
| Y-43 | H | |
| Y-44 | H | |
| Y-52 | 4-Cl | |
TABLE 5-continued
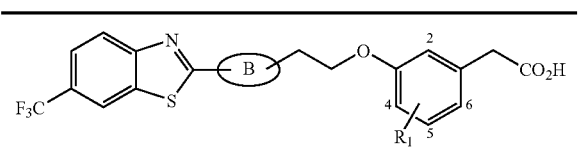
| No. | R1 | B |
|---|---|---|
| Y-53 | 4-Cl | |
| Y-54 | 4-Cl | |
| Y-55 | 4-Cl | |
| Y-56 | 4-Cl | |
| Y-57 | 4-Cl | |
| Y-58 | 4-Cl | |
| Y-59 | 4-Cl | |
| Y-60 | 4-Cl | |
| Y-61 | 4-Cl | |

TABLE 6

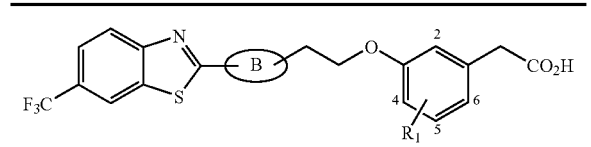

| No. | R1 | B |
|---|---|---|
| Y-45 | H | (2,6-dimethylpiperazine) |
| Y-46 | H | (2,5-dimethylpiperazine) |
| Y-47 | H | (2,5-dimethylpiperazine, alt stereo) |
| Y-48 | H | (2,5-dimethylpiperazine) |
| Y-49 | H | (2,3-dimethylpiperazine) |
| Y-50 | H | (2,3-dimethylpiperazine) |
| Y-51 | H | (2,5-diazabicyclo) |
| Y-62 | 4-Cl | (2,6-dimethylpiperazine) |

TABLE 6-continued

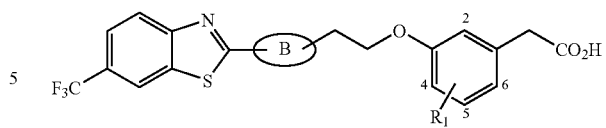

| No. | R1 | B |
|---|---|---|
| Y-63 | 4-Cl | (2,6-dimethylpiperazine) |
| Y-64 | 4-Cl | (2,5-dimethylpiperazine) |
| Y-65 | 4-Cl | (2,5-dimethylpiperazine) |
| Y-66 | 4-Cl | (2,3-dimethylpiperazine) |
| Y-67 | 4-Cl | (2,3-dimethylpiperazine) |
| Y-68 | 4-Cl | (diazabicyclo) |

TABLE 7

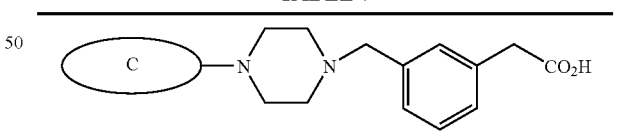

| No. | C |
|---|---|
| Z-1 | (6-chloro-1,2-dimethylbenzimidazole) |
| Z-2 | (6-chloro-3-methylbenzisoxazole) |

TABLE 7-continued
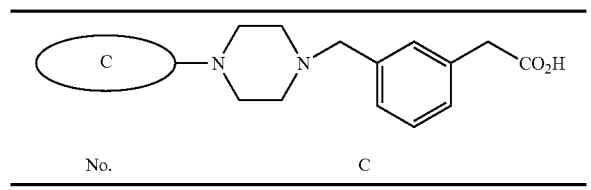
| No. | C |
|---|---|
| Z-3 | 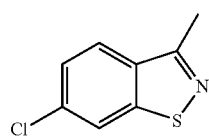 |
| Z-4 | 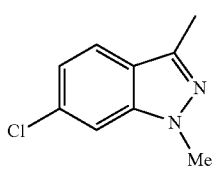 |
| Z-5 | 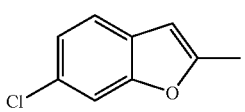 |
| Z-6 | 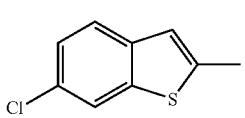 |
| Z-7 | 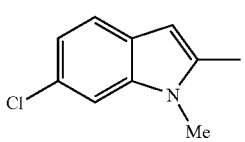 |
| Z-8 | 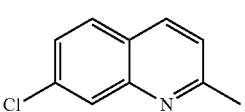 |
| Z-9 | 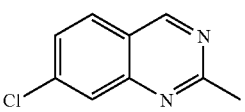 |
| Z-10 | 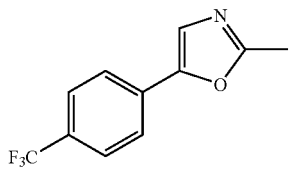 |
| Z-11 | 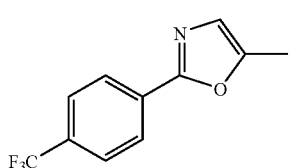 |
| Z-12 | 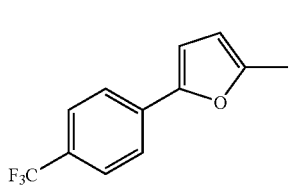 |
TABLE 7-continued
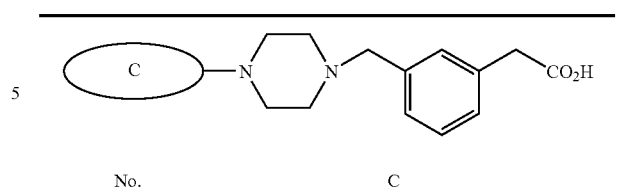
| No. | C |
|---|---|
| Z-13 | 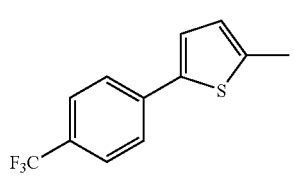 |
| Z-14 | 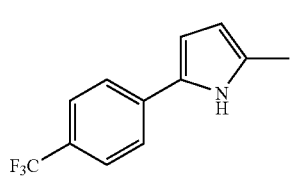 |
| Z-15 | 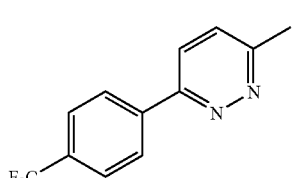 |
TABLE 8
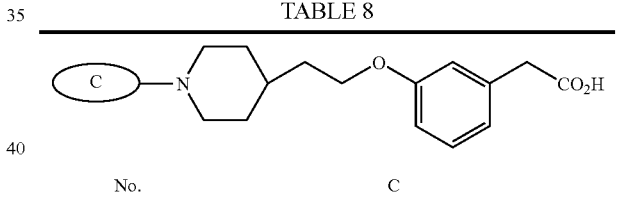
| No. | C |
|---|---|
| Z-16 | 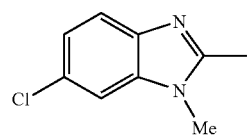 |
| Z-17 | 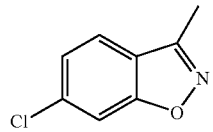 |
| Z-18 | 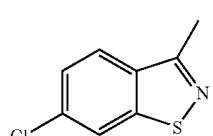 |
| Z-19 | 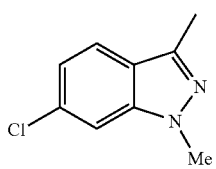 |

TABLE 8-continued

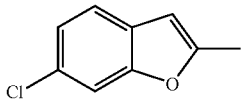

| No. | C |
|---|---|
| Z-20 | 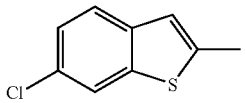 |
| Z-21 | 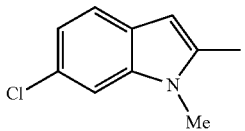 |
| Z-22 | 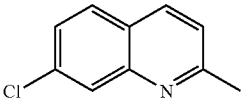 |
| Z-23 | 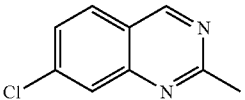 |
| Z-24 | 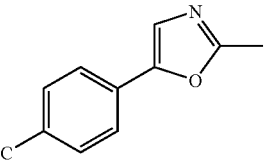 |
| Z-25 | 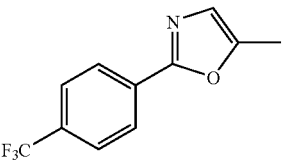 |
| Z-26 | 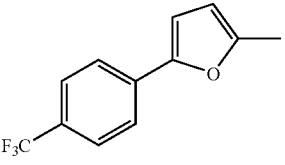 |
| Z-27 | 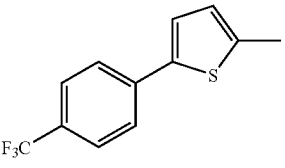 |
| Z-28 | 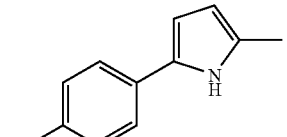 |

TABLE 8-continued

| No. | C |
|---|---|
| Z-29 | (4-trifluoromethylphenyl)-5-methyl-pyrrole |
| Z-30 | (4-trifluoromethylphenyl)-6-methyl-pyridazine |

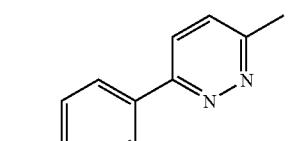

Test Example 1

Test for Transcriptional Activity of PPARδ and α

A chimeric transcription factor assay, which is commonly used to detect nuclear receptor activity, was employed to measure PPAR transcriptional activity. Specifically, two plasmids, one that expresses the fusion protein of DNA binding domain of yeast transcription factor GAL4 and a ligand binding domain of a receptor, and a reporter plasmid were transiently transfected to CHO cells. The activity of the promoter containing a recognition sequence of GAL4 coded on the reporter plasmid was used as a parameter to estimate the activity of the receptor.

Plasmid: The ligand binding domain of human PPARδ (hPPARδ) or α(hPPARα) (δ: aa 139-C-end; α: aa 167-C-end) is obtained by PCR amplification using Human Universal Quick-Clone cDNA (CLONTECH). Each amplified cDNA was subcloned into pCR2.1-TOPO vector (Invitrogen) and the identity of the cDNA clones was confirmed by the DNA sequence. Then, each obtained cDNA fragment was subcloned into pBIND vector (Promega) to construct a plasmid expressing the fusion protein with DNA binding domain of yeast transcription factor GAL4. pG5luc vector (Promega) was used as a reporter plasmid.

Cell culturing and transfection: CHO cells were cultured in 10% FBS-aMEM. With a 96-well plate (Costar), CHO cells, that were dispersed with trypsin treatment, 20000 cells per well and the two plasmids obtained by the above procedure, 25 ng per well, were transfected with FuGene Reagent (Roche) by following the instruction of the manufacture.

Measurement of the transcriptional activity: CHO cells 100 μl per well, which were transfected as above, were dispensed into the wells in which a test compound dissolved in DMSO 0.5 μl was spotted in advance. After the cells and a test compound were cultured together for 24 hours in a $CO_2$ incubator, the luciferase activity was measured by adding luciferase substrates, PicaGene LT2.0 (Toyo ink) 100 μl per well. LUMINOUS CT-9000D (DIA-IATRON) is used to measure the activity.

As to PPARδ, the concentration of a test compound which shows ½ of maximum luciferase activity was calculated using an Excel program to obtain the $EC_{50}$ value for PPARδ activity of a test compound. The result is shown in Table 9.

TABLE 9

| Example No. | $EC_{50}$ (μM) | | |
|---|---|---|---|
| | hPPARδ | hPPARα | hPPARγ |
| 474 | 0.0045 | 0.35 | 0.20 |
| 503 | 0.91 | 1.5 | >10 |
| 519 | 0.02 | 0.54 | 0.8 |
| 562 | 0.029 | >10 | 1.9 |
| 590 | 0.026 | >10 | >10 |
| 597 | 0.0075 | 0.27 | 0.69 |
| 612 | 0.049 | 0.57 | 2.2 |
| 630 | 0.023 | 2.6 | 4.2 |
| 652 | 0.28 | >10 | >10 |
| 679 | 0.013 | 0.96 | 0.58 |
| 699 | 0.041 | 1.00 | 0.76 |
| 707 | 0.019 | 2.50 | 3.30 |
| 854 | 0.0044 | >10 | >10 |

Test Example 2

Test for Inhibition of CYP2C9 Enzyme

The test for inhibition of CYP2C9 enzyme was carried out with human liver microsomes and hydration activity of 4-position of tolbutamide that is a typical reaction of CYP2C9 as a parameter.

The reaction condition was as below: A substrate, 5 μM Tolbutamide ($^{14}C$ labeled compound); the reaction time, 30 minutes; the reaction temperature, 37° C.; the protein concentration, 0.25 mg/ml (human liver microsomes, 15 pol, Lot. 210296, XenoTech).

To the HEPES Buffer (pH 7.4), was added the protein (human liver microsomes), a drug solution and a substrate with the composition as the above. NADPH, which is a coenzyme of the reaction, was added thereto to start the reaction. After reacting for the fixed hours, 2N hydrochloric acid solution was added thereto and the reaction was stopped by removing protein. The remaining substrate drug and the generating metabolite were extracted with chloroform. The solvent was removed and the residue was redissolved in methanol. This solution was spotted on TLC, developed with chloroform:methanol: acetic acid=90:10:1, contacted on the imaging plate for about 14-20 hours and analyzed by BAS2000. As to the generation activity of the metabolite, Tolbutamide 4-position hydration body, the activity in case that the solvent dissolving a drug was added to the reaction assay was used as a control (100%). The residual activity (%) in case that the test drug solution was added to the reaction was calculated to confirm the compounds of the present invention had little effect on inhibition of CYP2C9 enzyme.

Test Example 3

Test for Metabolic Stability

Test for Metabolic Stability in Hepatic Microsomes: To trishydrochloric acid buffer (pH 7.4), were added NADPH (the final concentration was 1 mM in case of oxidative metabolism), Hepatic Microsomes (the final concentration was 0.5 mg protein/ml) and each compound (the final concentration was 2 μM). The mixture was reacted at 37° C. for 0 and 30 minutes. In case of conjugated glucuronic acid, UDPGA (the final concentration is 5 mM) was added instead of NADPH. The reaction was stopped by adding acetonitrile/methanol=1/1 (v/v) which is 2 parts by volume based on 1 part by volume of the reaction solution and then compounds in the centrifugal supernatant were measured by HPLC. By comparing the values between 0 and 30 minutes the disappearance volume of the compounds by the metabolic reaction was calculated to confirm metabolic stability of the compounds of the present invention.

Test Example 4

Test for Solubility

The compounds of the present invention and test solvents (JP-2 solution, and JP-2 solution containing 20 mM sodium taurocholate) were stirred at 37° C. for 3 hours. The mixture was filtrated with a 0.45 μm filter and the concentration of the filtrate was measured with HPLC method to confirm solubility of compounds of the present invention.

Test Example 5

Test for Toxicity

The compounds of the present invention (30 to 300 mg/kg/day) were administered to rats. After administration, number of deaths, conditions, food intake and body weight of rats were checked and histopathological examination and the like were performed.

Additionally, as a hematological examination, after few days from administration, the blood was collected and PT, APTT and Fbg were measured after blood treatment. The activities of extrinsic blood coagulation factors (F-III, F-V, F-VII, F-X) and intrinsic blood coagulation factors (F-VIII, F-IX, F-XI, F-XII) were measured. The coagulation times of extrinsic or intrinsic blood coagulation factors were measured by a method for measurement of PT (extrinsic) or APTT (intrinsic) after adding plasma which is deficient a factor of each measuring object (Dade Boehringer Marburg) to plasma of rat and preincubating. Plasma of control rats was mixed and calibration curve was made with diluent which the plasma was sequentially double-diluted with Owren's Veronal Buffer as a reference material. Activity percentage was calculated with coagulation time measured by a method for coagulation time with factor deficient plasma and calibration curve and activities of each coagulation factor were evaluated by activity percentage compared to plasma of intact rat.

As the above, toxicities of compounds of the present invention were confirmed.

The invention claimed is:
1. A compound of the formula (I):

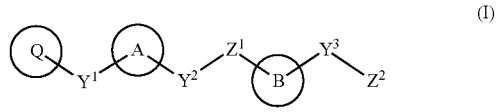

or a pharmaceutically acceptable salt thereof,
wherein
Ring Q is optionally substituted monocyclic aryl, optionally substituted monocyclic heteroaryl, optionally substituted fused aryl or optionally substituted fused heteroaryl, provided that Ring Q is not unsubstituted 11H-dibenz[b,e]-azepine-6-yl, Y¹ is a bond, —NR⁶— or —NR⁶—CO— wherein R⁶ is hydrogen or optionally substituted lower alkyl,
provided that Y¹ is —NR⁶—CO— when Ring Q is unsubstituted monocyclic aryl, and
Ring Q is phenyl substituted with alkyl halide when Ring Q is monocyclic aryl and Y¹ is a bond,
Ring A is a group of the formula:

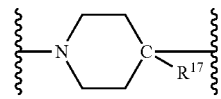

R¹⁷ is optionally substituted lower alkyl, cyano, optionally substituted nonaromatic heterocycle, optionally substituted heteroaryl, optionally substituted amino, optionally substituted lower alkoxy, aryl lower alkyl or optionally substituted cycloalkyl,
the bond from N binds with Y¹ and the bond from C binds with Y²,
a group of the formula: —Y²Z¹— is a group of the formula:

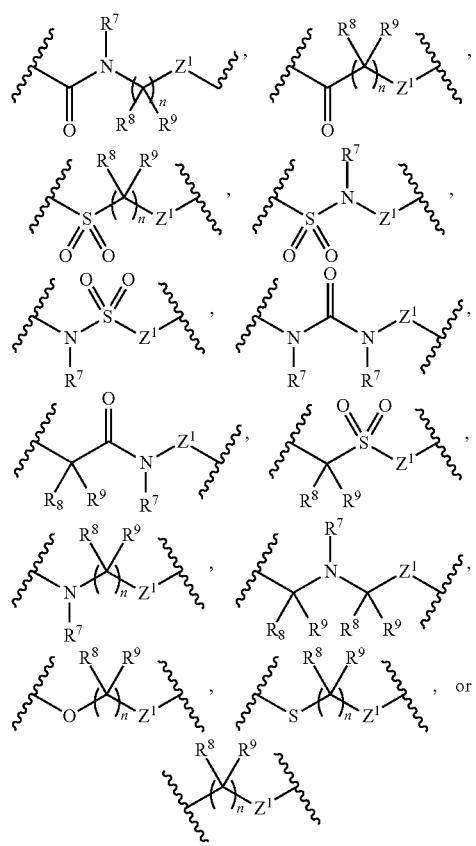

provided that a group of the formula: —Y²Z¹— is not —SO₂— and, a group of the formula: —Y²Z¹— is not —CH₂—CH₂—O— or —O— when Ring Q is unsubstituted benzothiazole-2-yl or unsubstituted benzoxazole-2-yl,
R⁷ are each independently hydrogen, optionally substituted lower alkyl or optionally substituted cycloalkyl,
R⁸ and R⁹ are each independently hydrogen or optionally substituted lower alkyl,
n is an integer between 0 and 3, Z¹ is a bond, —O—, —S— or —NR⁹— wherein R⁹ is hydrogen, optionally substituted lower alkyl, optionally substituted acyl, optionally substituted lower alkylsulfonyl or optionally substituted arylsulfonyl,
Ring B is optionally substituted aromatic carbocyclediyl or optionally substituted aromatic heterocyclediyl,
Y³ is a bond, optionally substituted lower alkylene optionally intervened by —O—, cycloalkylene optionally intervened by —O— or optionally substituted lower alkenylene,
Z² is COOR³, C(=NR³)NR¹⁴OR¹⁵, CONHCN or a group of the formula:

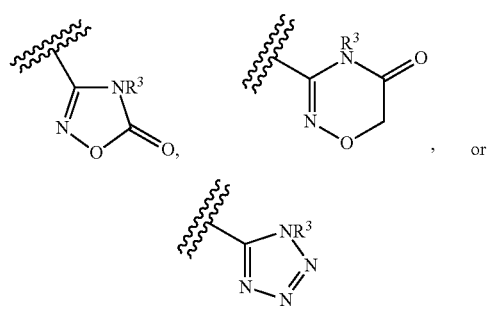

R³, R¹⁴ and R¹⁵ are each independently hydrogen, optionally substituted lower alkyl, optionally substituted lower alkenyl, optionally substituted aryl or optionally substituted heteroaryl, and
provided that a compound wherein a group of the formula: —Y²Z¹— is a group of the formula:

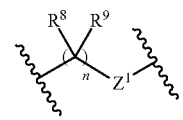

n is 0 and Z¹ is a bond is excluded.

2. The compound or pharmaceutically acceptable salt thereof according to claim 1, wherein Ring Q is substituted fused heteroaryl.

3. The compound or pharmaceutically acceptable salt thereof according to claim 1, wherein Ring Q is substituted benzofuryl, substituted benzothienyl, substituted benzopyrolyl, substituted benzoxazolyl, substituted benzoisoxazolyl, substituted benzothiazolyl, substituted benzoisothiazolyl, substituted benzoimidazolyl or substituted benzopyrazolyl.

4. The compound or pharmaceutically acceptable salt thereof according to claim 1, wherein
a group of the formula:

is a group of the formula:

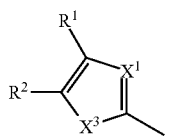

R¹ is hydrogen, halogen, hydroxy, optionally substituted lower alkyl, optionally substituted lower alkenyl, optionally substituted lower alkynyl, optionally substituted lower alkoxy or optionally substituted aryl, R² is halogen, optionally substituted alkyl, optionally substituted aryl, optionally substituted aryloxy, optionally substituted arylthio or optionally substituted heteroaryl, or R¹ and R² can be taken together with the neighboring carbon atom and 5-membered ring including X¹ and X³ as the constructive atoms to form a substituted fused heteroaryl, X¹ is N or CR¹⁰, and X³ is NR¹¹, O or S wherein R¹⁰ and R¹¹ are each independently hydrogen or optionally substituted lower alkyl.

5. The compound or pharmaceutically acceptable salt thereof according to claim 1, wherein a group of the formula:

is a group of the formula:

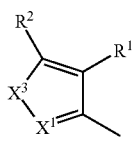

R¹ is hydrogen, halogen, hydroxy, optionally substituted lower alkyl, optionally substituted lower alkenyl, optionally substituted lower alkynyl or optionally substituted lower alkoxy, R² is halogen, optionally substituted alkyl, optionally substituted aryl, optionally substituted aryloxy, optionally substituted arylthio or optionally substituted heteroaryl, or R¹ and R² can be taken together with the neighboring carbon atom and 5-membered ring including X¹ and X³ as the constructive atoms to form a substituted fused heteroaryl, X¹ is N or CR¹², and X³ is NR¹³, O or S wherein R¹² and R¹³ are each independently hydrogen or optionally substituted lower alkyl.

6. The compound or pharmaceutically acceptable salt thereof according to claim 1, wherein a group of the formula:

is a group of the formula:

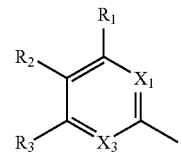

R¹ are each independently hydrogen, halogen, hydroxy, optionally substituted lower alkyl, optionally substituted lower alkenyl, optionally substituted lower alkynyl or optionally substituted lower alkoxy, R² is halogen, optionally substituted alkyl, optionally substituted aryl, optionally substituted aryloxy, optionally substituted arylthio or optionally substituted heteroaryl, X¹ is N or CR¹⁹, X³ is N or CR²⁰ wherein R¹⁹ and R²⁰ are each independently hydrogen or optionally substituted lower alkyl, and provided that either X¹ or X³ is N.

7. The compound or pharmaceutically acceptable salt thereof according to claim 1, wherein a group of the formula: —Y²Z¹— is a group of the formula:

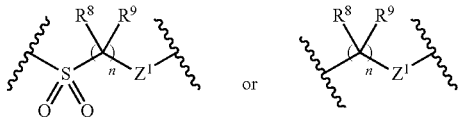

R⁸ and R⁹ are each independently hydrogen or lower alkyl, n is an integer between 0 and 2, and Z¹ is a bond, —O— or —S—.

8. The compound or pharmaceutically acceptable salt thereof according to claim 1, wherein Ring B is optionally substituted phenylene, optionally substituted indolediyl, optionally substituted benzofurandiyl, optionally substituted benzothiophenediyl, optionally substituted furandiyl or optionally substituted thiophenediyl.

9. The compound or pharmaceutically acceptable salt thereof according to claim 1, wherein Y³ is a bond, optionally substituted lower alkylene, —O-optionally substituted lower alkylene or optionally substituted lower alkenylene.

10. The compound or pharmaceutically acceptable salt thereof according to claim 1, wherein Z² is COOR³ wherein R³ is hydrogen or optionally substituted lower alkyl.

11. The compound or pharmaceutically acceptable salt thereof according to claim 1, wherein a group of the formula:

is a group of the formula:

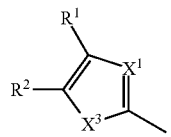

R¹ is hydrogen,
R² is optionally substituted aryl or
R¹ and R² can be taken together with the neighboring carbon atom and 5-membered ring including X¹ and X³ as the constructive atoms to form a substituted fused heteroaryl,
X¹ is N or CR¹⁰ wherein R¹⁰ is hydrogen,
X³ is O or S,
Y¹ is a bond,
a group of the formula: —Y²Z¹— is a group of the formula:

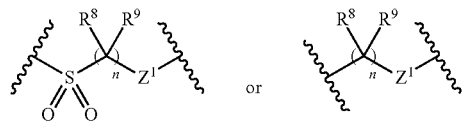

R⁸ and R⁹ are each independently hydrogen or lower alkyl,
n is an integer between 0 and 2, and
Z¹ is a bond, —O— or —S—,
Ring B is optionally substituted phenylene, optionally substituted furandiyl or optionally substituted thiophenediyl,
the substituent(s) of said phenylene, furandiyl or thiophendiyl of Ring B is/are selected from the group consisting of halogen, lower alkyl and lower alkoxy,
Y³ is a bond, optionally substituted lower alkylene, —O— optionally substituted lower alkylene or optionally substituted lower alkenylene,
the substituent(s) of said lower alkylene or lower alkenylene of Y³ is/are selected from the group consisting of halogen and lower alkylene, and
Z² is COOR³ wherein R³ is hydrogen or lower alkyl.
12. The compound or pharmaceutically acceptable salt thereof according to claim 1, wherein
a group of the formula:

is a group of the formula:

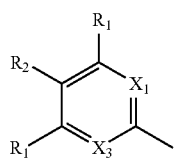

R¹ are each independently hydrogen, halogen, hydroxy, optionally substituted lower alkyl, optionally substituted lower alkenyl, optionally substituted lower alkynyl or optionally substituted lower alkoxy,
R² is optionally substituted alkyl or optionally substituted aryl,
X¹ is N or CR¹⁹,
X³ is N or CR²⁰ wherein R¹⁹ and R²⁰ are each independently hydrogen or optionally substituted lower alkyl, provided that either X¹ or X³ is N,
Y¹ is a bond,
a group of the formula: —Y²Z¹— is a group of the formula:

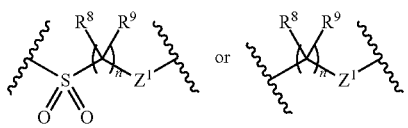

R⁸ and R⁹ are each independently hydrogen or lower alkyl,
n is an integer between 0 and 2,
Z¹ is a bond, —O— or —S—,
Ring B is optionally substituted phenylene, optionally substituted furandiyl or optionally substituted thiophendiyl,
the substituent(s) of said phenylene, furandiyl or thiophendiyl of Ring B is/are selected from the group consisting of halogen, lower alkyl and lower alkoxy,
Y³ is a bond, optionally substituted lower alkylene, —O— optionally substituted lower alkylene or optionally substituted lower alkenylene,
the substituent(s) of said lower alkylene or lower alkenylene of Y³ is/are selected from the group consisting of halogen and lower alkylene, and
Z² is COOR³ wherein R³ is hydrogen or lower alkyl.
13. The compound or pharmaceutically acceptable salt thereof according to claim 1, wherein
Y¹ is a bond,
a group of the formula: —Y²Z¹— is a group of the formula:

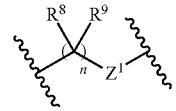

R⁸ and R⁹ are each independently hydrogen or lower alkyl,
n is 2,
Z¹ is —O—,
Ring B is optionally substituted phenylene,
Y³ is optionally substituted lower alkylene or —O— optionally substituted lower alkylene, and the substituent(s) of said lower alkylene of Y³ is/are selected from the group consisting of halogen and lower alkylene, and
Z² is COOR³ wherein R³ is hydrogen or lower alkyl.
14. A pharmaceutical composition comprising the compound or pharmaceutically acceptable salt thereof according to claim 1 as an active ingredient.

* * * * *